(12) United States Patent
Jeffrey et al.

(10) Patent No.: US 12,194,321 B2
(45) Date of Patent: Jan. 14, 2025

(54) CAMPTOTHECIN CONJUGATES

(71) Applicant: Seagen Inc., Bothell, WA (US)

(72) Inventors: Scott Jeffrey, Bothell, WA (US); Ryan Lyski, Bothell, WA (US); Uland Lau, Bothell, WA (US)

(73) Assignee: Seagen Inc., Bothell, WA (US)

( * ) Notice: Subject to any disclaimer, the term of this patent is extended or adjusted under 35 U.S.C. 154(b) by 940 days.

(21) Appl. No.: 16/972,469

(22) PCT Filed: Jun. 7, 2019

(86) PCT No.: PCT/US2019/035971
§ 371 (c)(1),
(2) Date: Dec. 4, 2020

(87) PCT Pub. No.: WO2019/236954
PCT Pub. Date: Dec. 12, 2019

(65) Prior Publication Data
US 2023/0036256 A1    Feb. 2, 2023

Related U.S. Application Data

(60) Provisional application No. 62/777,491, filed on Dec. 10, 2018, provisional application No. 62/681,847, filed on Jun. 7, 2018.

(51) Int. Cl.
| A61K 47/68 | (2017.01) |
| A61K 31/4745 | (2006.01) |
| A61K 47/54 | (2017.01) |
| A61K 47/60 | (2017.01) |
| A61P 35/00 | (2006.01) |

(52) U.S. Cl.
CPC ...... *A61K 47/6851* (2017.08); *A61K 31/4745* (2013.01); *A61K 47/545* (2017.08); *A61K 47/549* (2017.08); *A61K 47/60* (2017.08); *A61K 47/68037* (2023.08); *A61P 35/00* (2018.01)

(58) Field of Classification Search
CPC ...... A61P 35/00; A61P 35/02; A61K 31/4745; A61K 47/549; A61K 47/60; A61K 47/6803; A61K 47/68; A61K 47/68037
See application file for complete search history.

(56) References Cited

U.S. PATENT DOCUMENTS

| 4,179,337 | A | 12/1979 | Davis |
| 4,301,144 | A | 11/1981 | Iwashita |
| 4,474,893 | A | 10/1984 | Reading |
| 4,496,689 | A | 1/1985 | Mitra |
| 4,640,835 | A | 2/1987 | Shimizu |
| 4,670,417 | A | 6/1987 | Iwasaki |
| 4,676,980 | A | 6/1987 | Segal |
| 4,714,681 | A | 12/1987 | Reading |
| 4,751,180 | A | 6/1988 | Cousens et al. |
| 4,791,192 | A | 12/1988 | Nakagawa |
| 4,816,397 | A | 3/1989 | Boss |
| 4,816,567 | A | 3/1989 | Cabilly |
| 4,925,648 | A | 5/1990 | Hansen |
| 4,935,233 | A | 6/1990 | Bell et al. |
| 5,225,539 | A | 7/1993 | Winter |
| 5,342,947 | A | 8/1994 | Lackey et al. |
| 5,364,858 | A | 11/1994 | Wall et al. |
| 5,496,630 | A | 3/1996 | Hawrylko et al. |
| 5,496,830 | A | 3/1996 | Shapiro |
| 5,500,362 | A | 3/1996 | Robinson |
| 5,530,101 | A | 6/1996 | Queen |
| 5,559,235 | A | 9/1996 | Luzzio et al. |
| 5,573,920 | A | 11/1996 | Randle |
| 5,585,089 | A | 12/1996 | Queen |
| 5,601,819 | A | 2/1997 | Wong |
| 5,624,821 | A | 4/1997 | Winter |
| 5,672,662 | A | 9/1997 | Harris |
| 5,731,168 | A | 3/1998 | Carter |
| 5,757,078 | A | 5/1998 | Matsuda |
| 5,821,337 | A | 10/1998 | Carter |
| 5,834,597 | A | 11/1998 | Tso |
| 5,859,205 | A | 1/1999 | Adair |
| 6,077,939 | A | 6/2000 | Wei |
| 6,194,551 | B1 | 2/2001 | Idusogie |
| 6,407,213 | B1 | 6/2002 | Carter |
| 6,602,684 | B1 | 8/2003 | Umana |
| 6,624,821 | B1 | 9/2003 | Shin et al. |
| 6,629,995 | B1 | 10/2003 | Wrenn, Jr. et al. |
| 6,737,056 | B1 | 5/2004 | Presta |
| 6,881,557 | B2 | 4/2005 | Foote |
| 6,982,321 | B2 | 1/2006 | Winter |
| 7,087,409 | B2 | 8/2006 | Barbas, III |
| 7,090,843 | B1 | 8/2006 | Francisco et al. |

(Continued)

FOREIGN PATENT DOCUMENTS

| CA | 2087898 A1 | 7/1993 |
| EP | 0171496 A2 | 2/1986 |

(Continued)

OTHER PUBLICATIONS

U.S. Appl. No. 18/496,756, filed Oct. 27, 2023, Seagen Inc.*
U.S. Appl. No. 18/511,818, filed Nov. 16, 2023, Seagen Inc.*
Arimondo, P. B. et al. J. Biol. Chem. 2002. 277(5):3132-40. (Year: 2002).*
Xie, Z., et al., Bioorg. Med. Chem. Lett., vol. 5, No. 19, pp. 2189-2194. (Year: 1995).*
Amsberry, K.L. et al. (1990) "The Lactonizatin of 2'-Hydroxyhydrocinnamic Acid Amides: A Potential Prodrug for Amines," J. Org. Chem. 55(23):5867-5877.
Bacillieri, M. et al. (2011). "A Novel Generalized 3D-QSAR Model of Camptothecin Analogs," Molecular Informatics 30:927-938.
Beidler, C.B. et al. (Dec. 1, 1988). "Cloning and High Level Expression of a Chimeric Antibody With Specificity for Human Carcinoembryonic Antigen," J. Immunol. 141(11):4053-4060.
Better, M. et al. (May 20, 1988). "*Escherichia coli* Secretion of an Active Chimerica Antibody Fragment," Science 240:1041-1043.

(Continued)

*Primary Examiner* — Eric Olson
*Assistant Examiner* — Samuel L Galster
(74) *Attorney, Agent, or Firm* — MORRISON & FOERSTER LLP

(57) ABSTRACT

Antibody conjugates with camptothecin compounds are described, with methods of use and preparations.

43 Claims, 15 Drawing Sheets

(56) References Cited

U.S. PATENT DOCUMENTS

| | | |
|---|---|---|
| 7,332,581 B2 | 2/2008 | Presta |
| 7,361,740 B2 | 4/2008 | Hinton et al. |
| 7,371,826 B2 | 5/2008 | Presta |
| 7,521,541 B2 | 4/2009 | Eigenbrot |
| 7,527,791 B2 | 5/2009 | Adams |
| 7,659,241 B2 | 2/2010 | Senter |
| 7,745,394 B2 | 6/2010 | Doronina |
| 7,829,531 B2 | 11/2010 | Senter |
| 7,851,437 B2 | 12/2010 | Senter |
| 7,923,538 B2 | 4/2011 | Shitara |
| 7,964,566 B2 | 6/2011 | Doronina |
| 7,968,687 B2 | 6/2011 | Mcdonagh |
| 7,994,290 B2 | 8/2011 | Shitara |
| 8,038,273 B2 | 10/2011 | Frasure et al. |
| 8,263,083 B2 | 9/2012 | Oflazoglu |
| 8,288,352 B2 | 10/2012 | Doronina |
| 8,293,714 B2 | 10/2012 | Doppalapudi et al. |
| 8,470,329 B2 | 6/2013 | Oflazoglu |
| 8,512,707 B2 | 8/2013 | Doronina |
| 8,906,376 B2 | 12/2014 | Senter |
| 8,968,742 B2 | 3/2015 | Morrison |
| 9,211,319 B2 | 12/2015 | Sievers |
| 9,314,538 B2 | 4/2016 | Satpayev |
| 9,504,756 B2 | 11/2016 | Lyon |
| 9,713,648 B2 | 7/2017 | Sievers |
| 9,926,376 B2 | 3/2018 | Morrison |
| 9,962,454 B2 | 5/2018 | Satpayev |
| 9,987,374 B2 | 6/2018 | Li |
| RE47,103 E | 10/2018 | An et al. |
| 10,098,963 B2 | 10/2018 | Sievers |
| 10,391,181 B2 | 8/2019 | Li |
| 10,414,826 B2 | 9/2019 | Doronina |
| 10,478,469 B2 | 11/2019 | Sievers |
| 10,669,348 B2 | 6/2020 | Morrison |
| 10,722,549 B2 | 7/2020 | Sievers |
| 10,808,039 B2 | 10/2020 | Doronina |
| 10,894,090 B2 | 1/2021 | Satpayev |
| 10,912,813 B2 | 2/2021 | Sievers et al. |
| 10,912,842 B2 | 2/2021 | Sutherland et al. |
| 11,541,128 B2 * | 1/2023 | Levengood ............ A61K 39/00 |
| 2002/0161231 A1 | 10/2002 | Kawaguchi et al. |
| 2002/0164328 A1 | 11/2002 | Shinkawa |
| 2003/0115614 A1 | 6/2003 | Kanda |
| 2003/0157108 A1 | 8/2003 | Presta |
| 2004/0093621 A1 | 5/2004 | Shitara |
| 2004/0109865 A1 | 6/2004 | Niwa |
| 2004/0110282 A1 | 6/2004 | Kanda |
| 2004/0110704 A1 | 6/2004 | Yamane |
| 2004/0132140 A1 | 7/2004 | Satoh |
| 2005/0123546 A1 | 6/2005 | Umana |
| 2005/0256030 A1 | 11/2005 | Feng |
| 2014/0099256 A1 | 4/2014 | Zheng et al. |
| 2014/0099258 A1 | 4/2014 | Govindan |
| 2014/0107342 A1 | 4/2014 | Zhou et al. |
| 2015/0037340 A1 | 2/2015 | Beau-larvor |
| 2016/0106861 A1 | 4/2016 | Beau-larvor |
| 2016/0310612 A1 | 10/2016 | Lyon |
| 2017/0182179 A1 | 6/2017 | Ackler |
| 2017/0182181 A1 | 6/2017 | Garbaccio et al. |
| 2018/0169257 A1 | 6/2018 | Lewis |
| 2018/0326087 A1 | 11/2018 | Mcdonagh |
| 2019/0167806 A1 | 6/2019 | Moquist |
| 2019/0343828 A1 | 11/2019 | Jeffrey |
| 2020/0000932 A1 | 1/2020 | Dransfield |
| 2020/0102399 A1 | 4/2020 | Manley et al. |
| 2020/0129639 A1 | 4/2020 | Levengood |
| 2020/0239585 A1 | 7/2020 | Heiser |
| 2020/0247902 A1 | 8/2020 | Prendergast |
| 2020/0283540 A1 | 9/2020 | Kennedy |
| 2020/0306336 A1 | 10/2020 | Sievers |
| 2020/0347149 A1 | 11/2020 | Doronina |
| 2021/0138077 A1 | 5/2021 | Bindman et al. |
| 2022/0193069 A1 | 6/2022 | Jeffrey et al. |
| 2023/0087871 A1 | 3/2023 | Nicolazzi |
| 2023/0091653 A1 | 3/2023 | Bindman et al. |
| 2023/0149557 A1 | 5/2023 | Nicolazzi |
| 2023/0151088 A1 | 5/2023 | Nicolazzi |
| 2023/0181755 A1 | 6/2023 | Nicolazzi |
| 2023/0190949 A1 | 6/2023 | Ryan et al. |
| 2023/0381321 A1 * | 11/2023 | Lyski ............... A61K 47/68037 |
| 2024/0076394 A1 | 3/2024 | Heiser et al. |
| 2024/0207427 A1 | 6/2024 | Jeffrey |
| 2024/0226313 A1 | 7/2024 | Baudat |

FOREIGN PATENT DOCUMENTS

| | | |
|---|---|---|
| EP | 0173494 A2 | 3/1986 |
| EP | 0184187 A2 | 6/1986 |
| EP | 0401384 A1 | 12/1990 |
| EP | 0540099 A1 | 5/1993 |
| EP | 0556585 A2 | 8/1993 |
| EP | 0629240 A1 | 12/1994 |
| EP | 0845464 A2 | 6/1998 |
| WO | 198601533 A1 | 3/1986 |
| WO | 198702671 A1 | 5/1987 |
| WO | 199012874 A2 | 11/1990 |
| WO | 199012874 A3 | 1/1991 |
| WO | 1991000360 A1 | 1/1991 |
| WO | 199205793 A1 | 4/1992 |
| WO | 199208802 A1 | 5/1992 |
| WO | 199222653 A1 | 12/1992 |
| WO | 199308829 A1 | 5/1993 |
| WO | 199317105 A1 | 9/1993 |
| WO | 199317715 A1 | 9/1993 |
| WO | 199410308 A1 | 5/1994 |
| WO | 199730087 A1 | 8/1997 |
| WO | 199734631 A1 | 9/1997 |
| WO | 199858964 A1 | 12/1998 |
| WO | 199922764 A1 | 5/1999 |
| WO | 199951642 A1 | 10/1999 |
| WO | 200061739 A1 | 10/2000 |
| WO | 200069459 A1 | 11/2000 |
| WO | 2001029246 A1 | 4/2001 |
| WO | 200174402 A2 | 10/2001 |
| WO | 2002031140 A1 | 4/2002 |
| WO | 200240040 A1 | 5/2002 |
| WO | 200243661 A2 | 6/2002 |
| WO | 200243661 A3 | 1/2003 |
| WO | 2003011878 A2 | 2/2003 |
| WO | 200174402 A3 | 4/2003 |
| WO | 2003084570 A1 | 10/2003 |
| WO | 2003085107 A1 | 10/2003 |
| WO | 2003085119 A1 | 10/2003 |
| WO | 2004056312 A2 | 7/2004 |
| WO | 200492219 A2 | 10/2004 |
| WO | 2005035586 A1 | 4/2005 |
| WO | 2005035778 A1 | 4/2005 |
| WO | 2005053742 A1 | 6/2005 |
| WO | 2006006196 A2 | 1/2006 |
| WO | 2006036291 A2 | 4/2006 |
| WO | 2006006196 A3 | 5/2006 |
| WO | 2006113909 A2 | 10/2006 |
| WO | 2007005643 A2 | 1/2007 |
| WO | 2007005644 A2 | 1/2007 |
| WO | 2007016361 A2 | 2/2007 |
| WO | 2007016431 A2 | 2/2007 |
| WO | 2007005643 A3 | 3/2007 |
| WO | 2007044616 A2 | 4/2007 |
| WO | 2007005644 A3 | 7/2007 |
| WO | 2007016431 A3 | 7/2007 |
| WO | 2007044616 A3 | 7/2007 |
| WO | 2007112193 A2 | 10/2007 |
| WO | 2007016361 A3 | 12/2007 |
| WO | 2006113909 A3 | 1/2008 |
| WO | 2008077546 A1 | 7/2008 |
| WO | 2007112193 A3 | 11/2008 |
| WO | 2009048967 A1 | 4/2009 |
| WO | 2009089004 A1 | 7/2009 |
| WO | 2013000269 A1 | 1/2013 |
| WO | 2013173337 A2 | 11/2013 |
| WO | 2014079886 A1 | 5/2014 |
| WO | 2015057699 A2 | 4/2015 |
| WO | 2013173337 A3 | 6/2015 |
| WO | 2015095755 A1 | 6/2015 |

(56) References Cited

FOREIGN PATENT DOCUMENTS

| | | |
|---|---|---|
| WO | 2015057699 A3 | 9/2015 |
| WO | 2015155998 A1 | 10/2015 |
| WO | 2016094517 A1 | 6/2016 |
| WO | 2016149535 A1 | 9/2016 |
| WO | 2017004330 A1 | 1/2017 |
| WO | 2017165851 A1 | 9/2017 |
| WO | 2017210473 A1 | 12/2017 |
| WO | 2018112253 A1 | 6/2018 |
| WO | 2019075188 A1 | 4/2019 |
| WO | 2019089870 A1 | 5/2019 |
| WO | 2019195665 A1 | 10/2019 |
| WO | 2019236954 A1 | 12/2019 |
| WO | 2020161214 A1 | 8/2020 |
| WO | 2021055865 A1 | 3/2021 |
| WO | 2021067820 A1 | 4/2021 |
| WO | 2021067861 A1 | 4/2021 |
| WO | 2021214221 A1 | 10/2021 |
| WO | 2021214222 A1 | 10/2021 |
| WO | 2021214223 A1 | 10/2021 |
| WO | 2021214227 A1 | 10/2021 |
| WO | 2021231568 A1 | 11/2021 |
| WO | 2022048883 A1 | 3/2022 |
| WO | 2022101165 A1 | 5/2022 |
| WO | 2022120084 A1 | 6/2022 |
| WO | 2022198231 A1 | 9/2022 |
| WO | 2022198232 A1 | 9/2022 |
| WO | 2023079057 A1 | 5/2023 |
| WO | 2023099683 A1 | 6/2023 |

OTHER PUBLICATIONS

Burke, P.J. et al. (Jun. 2009). "Design, Synthesis, and Biological Evaluation of Antibody-Drug Conjugates Comprised of Potent Camptothecin Analogues," Bioconj. Chem. 20(6):1242-1250.

Chandregowda, V. et al. (2007, e-pub. Nov. 17, 2006). "One-Pot Conversion of 2-nitrobenzonitriles to Quinazolin-4 (3H)-Ones and Synthesis of Gefitinib and Erlotinib Hydrochloride," Heterocycles 71(1):39-48.

Dong, W. et al. (Apr. 1, 2019, e-pub. Feb. 7, 2019). "Antibody-Drug Conjugates of 7-ethyl-10-hydroxycamptothecin: Sacituzumab govitecan and labetuzumab govitecan," European Journal of Medicinal Chemistry (2019) 167:583-593.

Final Office Action, mailed May 27, 2021, for U.S. Appl. No. 16/376,302, filed Apr. 5, 2019, 20 pages.

Foster, A.B. (1985). "Deuterium Isotope Effects in the Metabolism of Drugs and Xenobiotics: Implications for Drug Design," Adv. Drug Res. 14:1-40, 43 pages.

Gaertner, H.F. et al. (Mar. 11, 1994). "Chemo-Enzymic Backbone Engineering of Proteins," J. Biol. Chem. 269(10):7224-7230.

Gillette, J.R. et al. (Mar. 15, 1994). "Theory for the Observed Isotope Effects on the Formation of Multiple Products by Different Kinetic Mechanisms of Cytochrome P450 Enzymes," Biochemistry 33(10):2927-2937.

Goodson, R.J. et al. (Apr. 1990). "Site-Directed Pegylation of Recombinatnt Interleukin-2 at Its Glycosylation Site," Bio/Technology 8:343-346.

Hansch, C. et al. (2007). "20-(S)-Camptothecin Analogues as DNA Topoisomerase I Inhibitors: A QSAR Study," ChemMedChem 2:1807-1813.

Hanzlik, R. et al. (1990). "Active Site Dynamics of Toluene Hydroxylation by Cytochrome P-4501," J. Org. Chem.; 55(13):3992-3997.

Hay, M.P. et al. (Aug. 2, 1999). "A 2-nitroimidazole Carbamate Prodrug of 5-amino-1-(chloromethyl)-3-[(5,6,7-trimethoxyindol-2-yl)carbonyl]-1,2-dihydro-3H-benz[e]indole (amino-seco-CBI-TMI) for Use With ADEPT and GDEPT," Bioorganic & Medicinal Chemistry Letters 9(15):2237-2242.

International Preliminary Report on Patentability, issued Dec. 8, 2020, for PCT Application No. PCT/US2019/035971, filed Jun. 7, 2019, 11 pages.

International Preliminary Report on Patentability, issued Oct. 6, 2020, for PCT Application No. PCT/US2019/025968, filed Apr. 5, 2019, 7 pages.

International Search Report and Written Opinion, dated Aug. 19, 2019, for PCT Application No. PCT/US2019/025968, filed Apr. 5, 2019, 15 pages.

International Search Report and Written Opinion, dated Jan. 15, 2021, for PCT Application No. PCT/US2020/054087, filed Oct. 2, 2020, 15 pages.

International Search Report and Written Opinion, dated Sep. 20, 2019, for PCT Application No. PCT/US2019/035971, filed Jun. 7, 2019, 18 pages.

Jarman, M. (1995) "The Deuterium Isotope Effect for the α-hydroxylation of Tamoxifen by Rat Liver Microsomes Accounts for the Reduced Genotoxicity of [D5-ethyl]tamoxifen," Carcinogenesis, 16(4):683-688.

Jeffrey, S.C. et al. (May-Jun. 2006, e-pub. May 3, 2006). "Development and Properties of Beta-Glucuronide Linkers for Monoclonal Antibody-Drug Conjugates," American Chemical Society 17(3):A-J.

Jones, P.T. et al. (May 29, 1986). "Replacing the Complementarity-Determining Regions in a Human Antibody With Those From a Mouse," Nature 321:522-525.

Kabat, E.A. et al. (Sep. 1980). "Origins of Antibody Complementarity and Specificity-Hypervariable Regions and the Minigene Hypothesis," J Immunology 125(3):961-969.

Kaneko, T. et al. (May-Jun. 1991). "New Hydrazone Derivatives of Adriamycin and Their Immunoconjugates—A Correlation Between Acid Stability and Cytotoxicity," Bioconjugate Chem. 2(3):133-141.

Kozbor, D. et al. (1983). "The Production of Monoclonal Antibodies From Human Lymphocytes," Immunology Today 4(3):72-79.

Laguzza, B.C. et al. (Mar. 1989). "New Antitumor Monoclonal Antibody-Vinca Conjugates LY203725 and Related Compounds: Design, Preparation, and Respresentative in Vivo Activity," J. Med. Chem. 32(3):548-555.

Lau, U.Y. et al. (Aug. 1, 2018). "Lactone Stabilization is Not a Necessary Feature for Antibody Conjugates of Camptothecins," Molecular Pharmaceutics 15(9):4063-4072.

Li, W. et al. (Sep. 6, 2019). "Synthesis and Evaluation of Camptothecin Antibody-Drug Conjugates," ACS Medicinal Chemistry Letters 10(10):1386-1392.

Liu, A.Y. et al. (May 1987). "Chimeric Mouse-Human IgG1 Antibody That Can Mediate Lysis of Cancer Cells," Proc. Natl. Acad. Sci. USA 84:3439-3443.

Liu, A.Y. et al. (Nov. 15, 1987). "Production of a Mouse-Human Chimeric Monoclonal Antibody to CD20 With Potent Fc-Dependent Biologic Activity," J. Immunol. 139(10):3521-3526.

Lyon, R.P. et al. (Oct. 2014, e-pub. Sep. 7, 2014). "Self-hydrolyzing Maleimides Improve the Stability and Pharmacological Properties of Antibody-Drug Conjugates," Nat Biotechnol 32(10): 1059-1062.

Malik, F. et al. (Sep. 1992). "Polyethylene glycol (PEG)-Modified Granulocyte-Macrophage Colony-Stimulating Factor (GM-CSF) With Conserved Biological Activity," Exp. Hematol. 20(8):1028-1035.

Morrison, S.L. (Sep. 1985). "Transfectomas Provide Novel Chimeric Antibodies," Science 229(4719):1202-1207.

Nishimura, Y. et al. (Feb. 15, 1987). "Recombinant Human-Mouse Chimeric Monoclonal Antibody Specific for Common Acute Lymphocytic Leukemia Antigen," Cancer. Res. 47(4):999-1005.

Non-Final Office Action, mailed Feb. 4, 2021, for U.S. Appl. No. 16/376,302, filed Apr. 5, 2019, 18 pages.

Oi, V.T. et al. (1986). "Chimeric Antibodies," Bio Techniques 4(3):214-219.

Olsson, L. et al. (1983), "Human-Human Monoclonal Antibody-Producing Hybridomas: Technical Aspects," Meth Enzymol. 92:3-16.

Reider, P.J. et al. (Jul. 1, 1987). "Synthesis of (R)-Serine-2-d and Its Conversion to the Broad-Spectrum Antibiotic Fludalanine," J. Org. Chem. 52:3326-3334.

Rodrigues, M.L. et al. (Apr. 1995). "Synthesis and β-Lactamase-Mediated Activation of a Cephalosporine-Taxol Prodrug," Chem. Biol. 2:223-227.

(56) References Cited

OTHER PUBLICATIONS

Rose, K. et al. (May-Jun. 1991). "Preparation of Well-Defined Protein Conjugates Using Enzyme-Assisted Reverse Proteolysis," Bioconjugate Chem. 2(3):154-159.
Schmidt, M.M. et al. (Oct. 2009). "A Modeling Analysis of the Effects of Molecular Size and Binding Affinity on Tumor Targeting," Mol. Cancer Ther. 8(10):2861-2871.
Schwartz, A. et al. (1990). "Enzymatic C-Terminal Biotinylation of Proteins," Methods Enzymol. 184:160-162.
Shaw, D.R. et al. (Dec. 7, 1988). "Mouse/Human Chimeric Antibodies to a Tumor-Associated Antigen: Biologic Activity of the Four Human IgG Subclasses," J. Natl. Cancer Inst. 80(19):1553-1559.
Storm, D.R. et al. (Aug. 9, 1972). "Effect of Small Changes in Orientation on Reaction Rate," Journal of the American Chemical Society 94(16):5815-5825.
Sun, L.K. et al. (Jan. 1987). "Chimeric Antibody With Human Constant Regions and Mouse Variable Regions Directed Against Carcinoma-Associated Antigen 17-1A," Proc. Natl. Acad. Sci. USA 84(1):214-218.
Teng, N.N.H. et al. (Dec. 1983). "Construction and Testing of Mouse-Human Heteromyelomas for Human Monoclonal Antibody Production," Proc. Natl. Acad. Sci. USA. 80:7308-7312.
Toki, B.E. et al. (2002, e-pub. Feb. 12, 2002). "Protease-Mediated Fragmentation of p-Amidobenzyl Ethers: A New Strategy for the Activation of Anticancer Prodrugs," J. Org. Chem. 67(6):1866-1872.
U.S. Appl. No. 16/972,469, filed Dec. 4, 2020, Jeffrey et al. (Copy not submitted herewith pursuant to the waiver of 37 C.F.R. § 1.98(a)(2)(iii) issued by the Office on Sep. 21, 2004).
Verhoeyan, M. et al. (Mar. 25, 1988). "Reshaping Human Antibodies: Grafting an Antilysozyme Activity," Science 239:1534-1536.
Veronese, F.M. (2001). "Peptide and Protein PEGylation: A Review of Problems and Solutions," Biomaterials 22:405-417.
Veronese, F.M. et al. (Apr. 1985). "Surface Modification of Proteins: Activation of Monomethoxy-Polyethylene Glycols by Phenylchloroformates and Modification of Ribonuclease and Superoxide Dismutase," Appl. Biochem. Bioechnol 11(2):141-152.
Wadkins, R.M. et al. (Sep. 15, 2004). "Hydrophilic Camptothecin Analogs That Form Extremely Stable Cleavable Complexes With DNA and Topoisomerase I," Canc. Res. 64:6679-6683.
Walker, M.A. et al. (Jan. 21, 2002). "Synthesis of an Immunoconjugate of Camptothecin," Bioorganic & Medicinal Chemistry Letters 12(2):217-219.
Wood, C.R. et al. (Apr. 4, 1985). "The Synthesis and in vivo Assembly of Functional Antibodies In Yeast," Nature 314(6010):446-449.
Xie, Z.-F. et al. (1995). "Convergent Approach to Water Soluble Camptothecin Derivatives," Bioorganic & Medicinal chemistry Letters 5(19):2189-2194.
Yao, H. et al. (Feb. 2, 2016). "Methods to Design and Synthesize Antibody Drug Conjugates (ADCs)," Int. J. Mol. Sci. 17(194):1-16.
Abdiche, Y. N. et al. (Aug. 31, 2012, e-pub. May 17, 2012). "Label-Free Epitope Binning Assays of Monoclonal Antibodies Enable the Identification of Antigen Heterogeneity," Journal of Immunological Methods 382(1-2):101-116.
Abdiche, Y. N. et al. (Mar. 20, 2014). "High-throughput Epitope Binning Assays on Label-free Array-based Biosensors can Yield Exquisite Epitope Discrimination that Facilitates the Selection of Monoclonal Antibodies with Functional Activity," PloS one, 9(3), e92451, 16 pages.
Abdiche, Y.N. et al. (Mar. 15, 2009, e-pub. Dec. 7, 2008). "Exploring Blocking Assays Using Octet, ProteOn, and Biacore Biosensors," Analytical Biochem 386(2):172-180.
Abuelgasim, K.A. et al. (2019, e-pub. Jan. 30, 2019). "Chemoimmunotherapy With Brentuximab Vedotin Combine With Ifosfamide, Gemcitabine, and Vinorelbine is Highly Active in Relapsed or Refractory Classical Hodgkin Lymphoma," Bone Marrow Transplantation 54(7):1168-1172.
Adams, D.J. et al. (2006, e-pub. Aug. 20, 2005). "Camptothecin Analogs with Enhanced Activity Against Human Breast Cancer Cells. I. Correlation of Potency with Lipophilicity and Persistence in the cleavage Complex," Cancer Chemother. Pharmacol. 57:135-144.
Akewanlop, C. et al. (May 15, 2001). "Phagocytosis of Breast Cancer Cells Mediated by Anti-MUC-1 Monoclonal Antibody, DF3, and Its Bispecific Antibody," Cancer Res. 61:4061-4065.
Al-Lazikani, B. et al. (1997). "Standard Conformations for the Canonical Structures of Immunoglobulins," J. Mol. Biol. 273:927-948.
Almagro, J.C. et al. (Jan. 1, 2008). "Humanization of Antibodies," Front. Biosci. 13:1619-1633.
Anonymous (Oct. 2, 2020). "The Fiery ADC, the Ever-Changing Three Musketeers," from the Internet https://www.pharmcube.com/index/news/article/5630, last visited Oct. 2, 2020, 9 pages.
Arimondo, P.B. et al. (Feb. 1, 2002). "Design and Optimization of Camptothecin Conjugates of Tripled Helix-Forming Oligonucleotides for Sequence-Specific DNA Cleavage by Topoisomerase I," J. Biol. Chem. 277(5):3132-3140.
Ashkenazi, A. et al. (Dec. 1991). "Protection Against Endotoxic Shock by a Tumor Necrosis Factor Receptor Immunoadhesin," Proc. Natl. Acad. Sci. USA 88:10535-10539.
Asseman, C. et al. (Oct. 4, 1999). "An Essential Role for Interleukin 10 in the Function of Regulatory T Cells That Inhibit Intestinal Inflammation," J. Exp. Med. 190(7):995-1003.
ATCC CCL 10 (No Date). "BHK-21 (C-13); Kidney; Syrian golden hamster (*Mesocricetus auratus*)," 4 pages.
ATCC CCL 2 (No Date). "HeLa; Cervical Adenocarcinoma; Human (*Homo sapiens*)," 4 pages.
ATCC CCL 34 (No Date). "MDCK (NBL-2); Kidney; Dog (*Canis familiaris*)," 4 pages.
ATCC CCL 51 (No Date). "MMT 060562," 7 pages.
ATCC CCL 61 (No Date). "CHO-K1 Ovary Chinese Hamster (*Cricetulus griseus*)," 4 pages.
ATCC CCL 70 (No Date). "CV-1; Kidney; African Green Monkey (*Cercopithecus aethiops*)," 4 pages.
ATCC CCL 75 (No Date). "WI-38; Lung Fibroblast; Human (*Homo sapiens*)," 3 pages.
ATCC CCL 1442 (No Date). "BRL 3A; Liver; Rat (*Rattus norvegicus*)," 4 pages.
ATCC CCL 1651 (No Date). "COS-7; Kidney Fibroblast; African Green Monkey (*Cercopithecus aethiops*)," 4 pages.
ATCC CRL-1587 (No Date). "Vero 76; Kidney; African Green Monkey (*Cercopithecus aethiops*)," 4 pages.
Ausubel, F. et al. (1987). Current Protocols in Molecular Biology, Greene Publishing and Wiley Interscience, New York, TOC, 7 pages.
Baca, M. et al. (Apr. 18, 1997). "Antibody Humanization Using Monovalent Phage Display," J. Biol. Chem. 272(16):10678-10684.
Barth, S. et al. (Jun. 15, 2000). "Ki-4(scFv)-ETA, a New Recombinant anti-CD30 Immunotoxin With Highly Specific Cytotoxic Activity Against Disseminated Hodgkin Tumors in SCID Mice," Blood 95(12):3909-3914.
Baudat, Y. et al. (Apr. 14-19, 2023). "A Novel Topoisomerase I Inhibitor Antibody-Drug Conjugate Targeting CEACAM5 has Potent Anti-Tumor activity in Colorectal Cancer Models," AACR, Poster # 4890, 1 page.
Belkaid, Y. (Nov. 2007, e-pub. Oct. 19, 2007). "Regulatory T Cells and Infection: A Dangerous Necessity," Nature Reviews 7:875-888.
Benoist, C. et al. (Mar. 26, 1981). "In Vivo Sequence Requirements of the SV40 Early Promotor Region," Nature 290:304-310.
Bettini, M. et al. (Dec. 2009, e-pub. Dec. 1, 2010). "Regulatory T Cells and Inhibitory Cytokines in Autoimmunity," Curr. Opin. Immunol. 21(6):612-618, 12 pages.
Bird, R.E. et al. (Oct. 21, 1988). "Single-Chain Antigen-Binding Proteins," Science 242(4877):423-426.
Bowen, M.A. et al. (Dec. 1, 1993). "Functional Effects of CD30 on a Large Granular Lymphoma Cell Line, YT. Inhibition of Cytotoxicity, Regulation of CD28 and IL-2R, and Induction of Homotypic Aggregation," J. Immunol. 151(11):5896-5906.

(56) References Cited

OTHER PUBLICATIONS

Brennan, M. et al. (Jul. 5, 1985). "Preparation of Bispecific Antibodies by Chemical Recombination of Monoclonal Immunoglobulin G1 Fragments," Science 229:81-83.
Bricogne, G. (1997). "Bayesian Statistical Viewpoint on Structure Determination: Basic Concepts and Examples," Meth Enzymol 276:361-423.
Bricogne, G. (Jan. 1, 1993). "Direct Phase Determination by Entropy Maximization and Likelihood Ranking: Status Report and Perspectives," Acta Crystallogr D Biol Crystallogr D49(Pt 1):37-60.
Brinster, R.L. et al. (Mar. 4, 1982). "Regulation of Metallothionein-Thymidine Kinase Fusion Plasmids Injected Into Mouse Eggs," Nature 296:39-42.
Byrn, R.A. et al. (Apr. 12, 1990). "Biological Properties of a CD4 Immunoadhersin," Nature 344(6267):667-670.
Capel, P.J.A. et al. (Feb. 1994). "Heterogeneity of Human IgG Fc Receptors," Immunomethods 4(1):25-34.
Cardillo, T.M. et al. (2011). "Humanized Anti-Trop-2 IgG-SN-38 Conjugate for Effective Treatment of Diverse Epithelial Cancers: Preclinical Studies in Human Cancer Xenograft Models and Monkeys," Clinical Cancer Research 17(10):3157-3169.
Carter, P. et al. (May 1992). "Humanization of an Anti-p185HER2 Antibody for Human Cancer Therapy," Proc. Natl. Acad. Sci. USA 89:4285-4289.
CAS RN149882-14-4 to RN1596548-57-0, 2 pages.
CAS RN1596548-57-0 to RN160469-20-5, 19 pages.
CAS: 55750-62-4 (No Date). "3-Maleimidopropionic Acid N-Succinimidyl Ester (CAS 55750-62-4)," 3 pages.
CAS: 955094-26-5 (No Date). "Maleimide-PEG2-NHS (CAS 955094-26-5)," 2 pages.
CAS:1174157-65-3 (No Date). "Propargyl-succinimidyl-ester (CAS 1174157-65-3)," 2 pages.
Chang, B.S. et al. (Feb. 1996). "Development of a Stable Freeze-Dried Formulation of Recombinant Human Interleukin-1 Receptor Antagonist," Pharm. Res. 13(2):243-249.
Charoentong, P. et al. (Jan. 3, 2017). "Pan-Cancer Immunogenomic Analyses Reveal Genotype-Immunophenotype Relationships and Predictors of Response to Checkpoint Blockade," Cell Reports 18:248-262.
Chayen, N.E. (Oct. 15, 1997). The Role of Oil in Macromolecular Crystallization, Structure 5(10):1269-1274.
Cheson, B.D. et al. (Sep. 20, 2014). "Recommendations for Initial Evaluation, Staging, and Response Assessment of Hodgkin and Non-Hodgkin Lymphoma: The Lugano Classification," J Clin Oncol 32(27):3059-3068.
Chothia, C. et al. (Aug. 20, 1987). "Canonical Structures for the Hypervariable Regions of Immunoglobulins," J. Mol. Biol. 196(4):901-917.
Chowdhury, P.S. (Mar. 2008. "Engineering Hot Spots for Affinity Enhancement of Antibodies," Methods Mol. Biol. 207:179-196.
Chu, G. et al. (Mar. 1981). "SV40 DNA Transfection of Cells in Suspension: Analysis of the Efficiency of Transcription and Translation of T-Antigen," Gene 13(2):197-202.
Clynes, R. et al. (Jan. 1998). "Fc Receptors are Required in Passive and Active Immunity to Melanoma," Proc. Natl. Acad. Sci. USA 95:652-656.
Coligan, J.E. et al. (1991). Current Protocols in Immunology 3.12-3.12.14.
Collison, L.W. et al. (2009). "Regulatory T Cell Suppression Is Potentiated by Target T Cells in a Cell Contact, IL-35- and IL-10-Dependent Manner," J. Immunol. 182:6121-6128.
Collison, L.W. et al. (2011, e-pub. Jan. 1, 2012). "In Vitro Treg Suppression Assays," Methods Molecular Biology 707:21-37, 18 pages.
Cromie, K.D. et al. (2015). "Nanobodies and Their Use in GPCR Drug Discovery," Curr. Top. Med. Chem. 15(24):2543-2557.
Cunningham, B.C. et al. (Jun. 2, 1989). "High-Resolution Epitope Mapping of hGH-Receptor Interactions by Alanine-Scanning Mutagenesis," Science 244:1081-1085.

Dall'Acqua, W.F. et al. (2005). "Antibody Humanization by Framework Shuffling," Methods 36:43-60.
Dannull, J. et al. (Dec. 2005). "Enhancement of Vaccine-Mediated Antitumor Immunity in Cancer Patients After Depletion of Regulatory T Cells," J Clin Invest 115(12):3623-3633.
Davies, J. et al. (Aug. 20, 2001). "Expression of GnTIII in a Recombinant Anti-CD20 CHO Production Cell Line: Expression of Antibodies With Altered Glycoforms Leads to an Increase in ADCC Through Higher Affinity for FC gamma RIII," Biotechnol. Bioeng. 74(4):288-294.
Daeron, M. (1997). "Fc Receptor Biology," Ann. Rev. Immunol. 15:203-234.
De Haas, M. et al. (1995). Fcγ Receptors of Phagocytes, J. Lab. Clin. Med. 126(4):330-341.
De Meyer, T. et al. (May 2014). "Nanobody-Based Products as Research and Diagnostic Tools," Trends Biotechnol. 32(5):263-270.
De Pascalis, R. et al. (2002). "Grafting of 'Abbreviated' Complementarity-Determining Regions Containing Specificity-Determining Residues Essential For Ligand Contact to Engineer a Less Immunogenic Humanized Monoclonal Antibody," J. Immunol. 169(6):3076-3084.
Deboer, H.A. et al. (Jan. 1983). "The Tac Promoter: a Functional Hybrid Derived From the trp and lac Promoters," Proc. Natl. Acad. Sci. U.S.A. 80(1):21-25.
Degenst, E. et al. (2006, e-pub. Jul. 11, 2005). "Antibody Repertoire Development in Camelids," Dev. Comp. Immunol. 30:187-198.
Del Poeta, M. et al. (Dec. 1999). "Comparison of in vitro Activities of Camptothecin and Nitidine Derivatives Against Fungal and Cancer Cells," Antimicrobial Agents and Chemotherapy 43(12):2862-2868.
Dieckmann, D. et al. (Jun. 4, 2001). "Ex Vivo Isolation and Characterization of CD4+ CD25+ T Cells with Regulatory Properties from Human Blood," J. Exp. Med. 193(11):1303-1310.
Dotan, E. et al. (Oct. 10, 2017). "Phase I/II Trial of Labetuzumab Govitecan (Anti-CEACAM5/SN-38 Antibody-Drug Conjugate) in Patients with Refractory or Relapsing Metastatic Colorectal Cancer," Journal of Clinical Oncology 35(29):3338-3346.
Dürkop, H. et al. (Feb. 7, 1992). "Molecular Cloning and Expression of a New Member of the Nerve Growth Factor Receptor Family That is Characteristic for Hodgkin's Disease," Cell 68:421-427.
Eisenhauer, E.A. et al. (2009) "New Response Evaluation Criteria in Solid Tumors: Revised Recist Guideline (version 1.1)," Eur. J. Cancer 45:228-247.
Endo, Y. et al. (2003). "High-Throughput, Genome-Scale Protein Production Method Based on the Wheat Germ Cell-Free Expression System," Biotechnol. Adv. 21:695-713.
Engert, A. et al. (Jan. 1, 1990). "Evaluation of Ricin A Chain-Containing Immunotoxins Directed Against the CD30 Antigen as Potential Reagents for the Treatment of Hodgkin's Disease," Cancer Research 50:84-88.
Epstein, D. (Jan. 9, 2023). "Building Oncology Leadership: Novel ADCs & Targeted Therapies," J.P. Morgan Healthcare Conference, 26 pages.
Extended European Search Report, dated Jun. 5, 2023, for European Patent Application No. 22306780.2, 9 pages.
Falini, B. et al. (May 16, 1992). "Responses of Refractory Hodgkin's Disease to Monoclonal Anti-CD30 Immunotoxin," The Lancet 339:1195-1196.
Falini, B. et al. (Sep. 1992). "In vivo Targeting of Hodgkin and Reed-Sternberg Cells of Hodgkin's Disease With Monoclonal Antibody Ber-H2 (CD30): Immunohistological Evidence," British Journal of Haematology 82(1):38-45.
Fanslow, W.C. et al. (1994). "Structural Characteristics of CD40 Ligand that Determine Biological Function," Semin. Immunol. 6:267-278.
Ferguson, W.J. et al. (May 15, 1980). "Hydrogen Ion Buffers for Biological Research," Anal. Biochem. 104(2):300-310.
Foote, J. et al. (1992). "Antibody Framework Residues Affecting the Conformation of the Hypervariable Loops," J Mol Biol. 224(2):487-499.
Francisco, J.A. et al. (Aug. 15, 2003, e-pub. May 8, 2003). "cAC10-vcMMAE, an Anti-CD30-Monomethyl Auristatin E Conjugate With Potent and Selective Antitumor Activity," Blood 102(4):1458-1465.

(56) References Cited

OTHER PUBLICATIONS

Freshney, R. I. (1987). "Culture of Specific Cell Types," Chapter 20 in Culture of Animal Cells: A Manual of Basic Techniques, Alan R. Liss & Co., New York; pp. 257-260, 270-273.
Fridman, W.H. et al. (Mar. 2012, e-pub. Apr. 2012). "The Immune Contexture in Human Tumours: Impact on Clinical Outcome," Nature Reviews Cancer 12:298-306.
Froese, P. et al. (Sep. 15, 1987). "Biochemical Characterization and Biosynthesis of the Ki-1 Antigen in Hodgkin-derived and Virus-Transformed Human B and T Lymphoid Cell Lines," J. Immunol. 139(6):2081-2087.
Gazzano-Santoro, H. et al. (1997). "A Non-Radioactive Complement-Dependent Cytotoxicity Assay for Anti-CD20 Monoclonal Antibody," J. Immunol. Methods 202:163-171.
GenBank AAA51967.1 (Nov. 1, 1994). "Carcinoembryonic Antigen [Homo sapiens]," 5 pages.
Ghetie, V. et al. (2000). "Multiple Roles for the Major Histocompatibility Complex Class I-Related Receptor FCRN," Annu. Rev. Immunol. 18:739-766, 32 pages.
Ghetie, V. et al. (2002). "Transcytosis and Catabolism of Antibody," Immunol. Res. 25(2):97-113.
Ghetie, V. et al. (Dec. 1997). "FcRn: the MHC Class I-Related Receptor That Is More Than an IgG Transporter," Immunol. Today 18(12):592-598, 7 pages.
Ghetie, V. et al. (Jul. 1997). "Increasing the Serum Persistence of an IgG Fragment by Random Mutagenesis," Nat Biotech 15:637-640.
Giegé, R. et al. (Jul. 1, 1994). Crystallogenesis of Biological Macromolecules: Facts and Perspectives, Acta Crystallogr D Biol Crystallogr D50(Pt 4):339-350.
Gold, P. et al. (1965). "Demonstration of Tumor-Specific Antigens in Human Colonic Carcinomata by Immunological Tolerance and Absorption Techniques." Freedman, J Exp Med, 121:439-462, 33 pages.
Good, N.E. et al. (1972). "Hydrogen Ion Buffers," Methods Enzymol. 24:53-68.
Good, N.E. et al. (Feb. 1966). "Hydrogen Ion Buffers for Biological Research," Biochemistry 5(2):467-477.
Govindan, S.V. et al. (Oct. 1, 2009). "CEACAM5-Targeted Therapy of Human Colonic and Pancreatic Cancer Xenografts with Potent Labetuzumab-SN-38 Immunoconjugates," Clinical Cancer Research 15(19):6052-6061.
Graham, F.L. et al. (1977). "Characteristics of a Human Cell Line Transformed by DNA from Human Adenovirus Type 5," J. Gen Virol. 36:59-72.
Graham, F.L. et al. (Apr. 1973). "A New Technique for the Assay of Infectivity of Human Adenovirus 5 DNA," Virology 52(2):456-467.
Gruber, M. et al. (1994). "Efficient Tumor Cell Lysis Mediated by a Bispecific Single Chain Antibody Expressed in *Escherichia coli*," J. Immunol. 152:5368-5374.
Guyer, R.L. et al. (Aug. 1976). "Immunoglobulin Binding by Mouse Intestinal Epithelial Cell Receptors," J. Immunol. 117(2):587-593.
Hambly, D.M. et al. (2005). "Laser Flash Photolysis of Hydrogen Peroxide to Oxidize Protein Solvent-Accessible Residues on the Microsecond Timescale," J. American Soc. Mass Spectrometry 16:2057-2063.
Herrera, A.F. et al. (Mar. 15, 2018, e-pub. Dec. 11, 2017). "Interim Results of Brentuximab Vedotin in Combination with Nivolumab in Patients With Relapsed or Refractory Hodgkin Lymphoma," Blood 131(11):1183-1194.
Hinton, P.R. et al. (Feb. 20, 2004). "Engineered Human IgG Antibodies with Longer Serum Half-lives in Primates," J. Biol. Chem. 279(8):6213-6216.
Hollenbaugh, D. et al. (May 2002). "Construction of Immunoglobulin Fusion Proteins," in Current Protocols in Immunology Chapter 10:unit 10.19.1-10.19.11, 11 pages.
Hollinger, P. et al. (Jul. 1993). "Diabodies: Small Bivalent and Bispecific Antibody Fragments," Proc. Natl. Acad. Sci. USA 90:6444-6448.

Honegger, A. et al. (Jun. 8, 2001). "Yet Another Numbering Scheme for Immunoglobulin Variable Domains: An Automatic Modeling and Analysis Tool," J. Mol. Biol. 309:657-670.
Hoogenboom, H.R. et al. (2001) "Overview of Antibody Phage-Display Technology and Its Applications," Methods in Molecular Biology 178:1-37.
Hoppe, H.-J. et al. (1994). "A Parallel Three Stranded Alpha-Helical Bundle at the Nucleation Site of Collagen Triple-Helix Formation," FEBS Lett. 344:191-195.
Huston, J.S et al. (Aug. 1988). "Protein Engineering of Antibody Binding Sites: Recovery of Specific Activity in an Anti-Digoxin Single-chain Fv Analogue Produced in *Escherichia coli*," Proc. Natl. Acad. Sci. USA 85:5879-5883.
Idusogie, E.E. et al. (2000). "Mapping of the C1q Binding Site on Rituxan, a Chimeric Antibody With a Human IgG1 Fc," J. Immunol. 164:4178-4184.
Idusogie, E.E. et al. (2001). "Engineered Antibodies With Increased Activity to Recruit Complement," J. Immunol. 166:2571-2575.
International Search Report and Written Opinion, mailed Mar. 15, 2024, for PCT Application No. PCT/US2023/080162, filed Nov. 16, 2023, 16 pages.
Iwahashi, M. et al. (Oct.-Nov. 1999). "CDR Substitutions of a Humanized Monoclonal Antibody (CC49): Contributions of Individual CDRs to Antigen Binding and Immunogenicity," Mol. Immunol. 36(15-16):1079-1091.
Japanese Notice, dated Mar. 25, 2024, for Japanese Patent Application 2020-567763, 1 page.
Japanese Third-Party Observation, dated Mar. 25, 2024, for Japanese Patent Application 2020-567763, 9 pages.
Josimovic-Alasevic, O. et al. (Janaury 1989). "Ki-1 (CD30) Antigen Is Released by Ki-1-positive Tumor Cells in vitro and in vivo. I. Partial Characterization of Soluble Ki-1 Antigen and Detection of the Antigen in Cell Culture Supernatants and in Serum by an Enzyme-Linked Immunosorbent Assay," Eur. J. Immunol. 19(1):157-162.
Kabat, E.A. (1991). Sequences of Proteins of Immunological Interest, 5th Edition, U.S. Department of Health and Human Services, NIH Publication No. 91-3242, p. 689.
Kabat, E.A. et al. (1991). Sequences of Proteins of Immunological Interest, 5th Ed. Public Health Service, National Institutes of Health, Bethesda MD., Table of Contents, 21 pages.
Kammerer, R. et al. (2010). "Coevolution of Activating and Inhibitory Receptors Within Mammalian Carcinoembryonic Antigen Families," BMC Biology, 8(12):1-21.
Kanda, Y. et al. (Jul. 5, 2006, e-pub. Apr. 11, 2006). "Comparison of Cell Line for Stable Production of Fucose-Negative Antibodies with Enhanced ADCC," Biotechnol. Bioeng. 94(4):680-688.
Kashmiri, S.V. et al. (2005). "SDR Grafting—A New Approach to Antibody Humanization," Methods 36:25-34.
Kijanka, M. et al. (2015). "Nanobody-Based Cancer Therapy of Solid Tumors," Nanomedicine 10(1):161-174.
Kim, J-K. et al. (Apr. 1994). "Localization of the Site of the Murine IgGI Molecule That is Involved in Binding to the Murine Intestinal Fc Receptor," Eur. J. Immunol. 24:2429-2434.
Klimka, A. et al. (2000). "Human Anti-CED30 Recombinant Antibodies by Guided Phage Antibody Selection Using Cell Panning," Br. J. Cancer 83(2):252-260.
Kontermann, R.E. et al. (Jul. 1997). "Complement Recruitment Using Bispecific Diabodies," Nat. Biotech. 15(7):629-631.
Kostelny, S.A. et al. (Mar. 1, 1992). "Formation of a Bispecific Antibody by the Use of Leucine Zippers," J. Immunol. 148(5):1547-1553.
Kovaleva, M. et al. (2014, e-pub. Aug. 4, 2014). "Shark Variable New Antigen Receptor Biologics—A Novel Technology Platform for Therapeutic Drug Development," Expert. Opin. Biol. Ther. 14(10):1527-1539.
Krah, S. et al. (2016). "Single-Domain Antibodies for Biomedical Applications," Immunopharmacol. Immunotoxicol. 38(1):21-28, 23 pages.
Kyte, J. et al. (1982). "A Simple Method for Displaying the Hydropathic Character of Protein," Journal of Molecular Biology 157:105-132.

(56) References Cited

OTHER PUBLICATIONS

Landschulz, W.H. et al. (Jun. 24, 1988). "The Leucine Zipper: A Hypothetical Structure Common to a New Class of DNA Binding Proteins," Science 240(4860):1759-1764.
Lazar, G.A. et al. (Mar. 14, 2006). "Engineered Antibody Fc Variants with Enhanced Effector Function," PNAS 103(11):4005-4010.
Leal, M. et al. (Jul. 16, 2015). "Preclinical Development of an Anti-5T4 Antibody-Drug Conjugate: Pharmacokinetics in Mice, Rats, and NHP and Tumor/Tissue Distribution in Mice," Bioconjugate Chemistry 26:2223-2232.
Lefranc, M.P. et al. (Jan. 2003). "IMGT Unique Numbering for Immunoglobulin and T Cell Receptor Variable Domains and Ig Superfamily V-Like Domains," Dev. Comp. Immunol. 27(1):55-77.
Li, M. et al. (2009, e-pub. Jun. 6, 2009). "7-cycloalkylcamptothecin Derivatives: Preparation and Biological Evaluation," Bioorganic & Medicinal Chemistry Letters 19:4107-4109.
Lowe, D. (Sep. 7, 2022). "Not Alphafold's Fault," Blog, 6 pages.
Lu, A.-J. et al. (Feb. 2007). "3D-QSAR Study of 20 (S)-Camptothecin Analogs," Acta Pharmacol. Sin. 28(2):307-314.
Lyski, R.D. et al. (Feb. 2021, e-pub. Dec. 3, 2020). "Development of Novel Antibody-Camptothecin Conjugates," Molecular Cancer Therapeutics 20(2):329-339.
MacCallum, R.M. et al. (1996). "Antibody-Antigen Interactions: Contact Analysis and Binding Site Topography," J. Mol. Biol. 262:732-745.
MacKenzie, A.P. (Mar. 29, 1977). "Non-Equilibrium Freezing Behaviour of Aqueous Systems," Phil Trans R Soc London, Ser B. Biol 278(959):167-189, 25 pages.
Martin, A.C. (Nov. 15, 1996). "Structural families in Loops of Homologous Proteins: Automatic Classification, Modelling and Application to Antibodies," J. Mol. Biol. 263(5):800-815.
Martin, A.C.R. et al. (Dec. 1989). "Modeling Antibody Hypervariable Loops: A Combined Algorithm," PNAS USA 86(23):9268-9272.
Mather, J.P. (1980). "Establishment and Characterization of Two Distinct Mouse Testicular Epithelial Cell Lines," Biology of Reproduction 23:243-252.
Mather, J.P. et al. (1982). "Culture of Testicular Cells in Hormone-Supplemented Serum-Free Medium," Annals New York Academy of Sciences pp. 44-68.
McCafferty, J. et al. (Dec. 6, 1990). "Phage Antibodies: Filamentous Phage Displaying Antibody Variable Domains," Nature 348:552-554.
McPherson, A. (1990). "Current Approaches to Macromolecular Crystallization," Eur J Biochem 189:1-23.
McPherson, A. (Oct. 25, 1976). "Crystallization of Proteins from Polyethylene Glycol," J Biol Chem 251(20):6300-6303.
Milstein, C. et al. (Oct. 6, 1983). "Hybrid Hybridomas and Their Use in Immunohistochemistry," Nature 305:537-540.
Morris, G.E. (1996). "Epitope Mapping Protocols," Methods in Molecular Biology 66:1-12.
Mujić-Delić, A. et al. (May 2014). "GPCR-Targeting Nanobodies: Attractive Research Tools, Diagnostics, and Therapeutics," Trends Pharmacol. Sci. 35(5):247-255.
Mullis, K.B. et al. (1994). PCR: The Polymerase Chain Reaction, Mullis et al. eds., Birkauswer Press, Boston, 5 pages.
Muyldermans, S. (Jun. 2001). "Single Domain Camel Antibodies: Current Status," Reviews in Molecular Biotechnology 74(4):277-302.
Muyldermans, S. (2013, e-pub. Mar. 13, 2013). "Nanobodies: Natural Single-Domain Antibodies," Ann. Rev. Biochem. 82:775-797.
Muyldermans, S. et al. (Apr. 2001). "Recognition of Antigens by Single-Domain Antibody Fragments: The Superfluous Luxury of Paired Domains," Trends Biochem. Sci. 26(4):230-235.
Nakada, T. et al. (2016). "Novel Antibody Drug Conjugates Containing Exatecan Derivative-Based Cytotoxic Payloads," Bioorganic & Medicinal Chemistry Letters, 4 pages.

National Comprehensive Cancer Network (NCCN). (2022-2023). Table of Contents, 3 pages.
Niwa, R. et al. (Mar. 15, 2004). "Defucosylated Chimeric Anti-CC Chemokine Receptor 4 IgG1 With Enhanced Antibody-Dependent Cellular Cytotoxicity Shows Potent Therapeutic Activity to T-Cell Leukemia and Lymphoma," Cancer Res. 64(6):2127-2133.
Okazaki, A. et al. (Mar. 5, 2004). "Fucose Depletion From Human IgG1 Oligosaccharide Enhances Binding Enthalpy and Association Rate Between IgG1 and FcγRIIIa," J. Mol. Biol. 336(5):1239-1249.
Osbourn, J. et al. (2005). "From Rodent Reagents to Human Therapeutics Using Antibody Guided Selection," Methods 36:61-68.
Padlan, E.A. (1991). "A Possible Procedure for Reducing the Immunogenicity of Antibody Variable Domains While Preserving Their Ligand-Binding Properties," Mol. Immunol. 28(4/5):489-498.
Plitas, G. et al. (Nov. 15, 2016). "Regulatory T Cells Exhibit Distinct Features in Human Breast Cancer Immunity," Immunity 45:1122-1134.
Press Release (Mar. 16, 2022). "Sanofi and Seagen Announce Collaboration to Develop and Commercialize Multiple Novel Antibody-Drug Conjugates," Sanofi, 2 pages.
Presta, L.G. et al. (Sep. 1, 1993). "Humanization of an Antibody Directed Against IgE," J. Immunol. 151(5):2623-2632.
PubChem (Apr. 18, 2015). "91668184—Labetuzumab govitecan," 12 pages.
Queen, C. et al. (Dec. 1989). "A Humanized Antibody That Binds to the Interleukin 2 Receptor," Proc. Natl Acad. Sci. USA 86:10029-10033.
Rahbarizadeh, F. et al. (2011). "Nanobody; An Old Concept and New Vehicle for Immunotargeting," Immunol. Invest. 40:299-338.
Ravetch, J.V. et al. (1991). "Fc Receptors," Annu. Rev. Immunol. 9:457-492.
Remington: The Science and Practice of Pharmacy, Lippincott Williams & Wilkins, Philadelphia, PA, 21st ed. (2006) TOC, 4 pages.
Riechmann, L. et al. (Mar. 1988). "Reshaping Human Antibodies for Therapy," Nature 332:323-329.
Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.
Rosok, M.J. et al. (Sep. 13, 1996). "A Combinatorial Library Strategy for the Rapid Humanization of Anticarcinoma BR96 Fab," J. Biol. Chem. 271(37):22611-22618.
Roversi, P. et al. (2000). "Modelling Prior Distributions of Atoms for Macro-Molecular Refinement and Completion," Acta Crystallogr D Biol Crystallogr D56:1316-1323.
Ryan, M. (Nov. 5, 2020). "Abstract 2889: SGN-CD30C, a New CD30-Directed Camptothecin Antibody-Drug Conjugate (ADC), Shows Strong Anti-Tumor Activity and Superior Tolerability in Preclinical Studies," retrieved from Internet: https://cancerres.aacrjournals.org/content/80/16_Supplement/2889, last visited Aug. 19, 2021, 4 pages.
Ryan, M. (Nov. 5, 2020). "SGN-CD30C, an Investigational CD30-Directed Camptothecin Antibody-Drug Conjugate (ADC), Shows Strong Anti-Tumor Activity and Superior Tolerability in Preclinical Studies," retrieved from the Internet https://ashpublications.org/blood/article/136/Supplement%201/41/471811/SGN-CD30C-an-Investigational-CD30-Directed, last visited Aug. 19, 2021, 6 pages.
Sambrook, J. et al. (1989). Molecular Cloning—A Laboratory Manual, 2nd Edition, Maniatis, T.(ed.) et al., Cold Spring Harbor Laboratory Press, New York, NY pp. v-xxxii, 28 pages, (Table of Contents only).
Sambrook, J. et al. (2001). "Molecular Cloning: A Laboratory Manual," 3rd edition, J.F. Sambrook and D.W. Russell, ed., Cold Spring Harbor Laboratory Press: Cold Spring Harbor, NY, 2:107 pages.
Sambrook, J. et al. (2012). Molecular Cloning: A Laboratory Manual (4 ed.), Cold Spring Harbor Laboratory Press, Cold Spring Harbor, N.Y., USA. Toc, 34 pages.
Schnell, R. et al. (Jun. 2002). "A Phase I Study with an Anti-CD30 Ricin A-Chain Immunotoxin (Ki-4.dgA) in Patients with Refractory CD30+ Hodgkin's and Non-Hodgkin's Lymphoma," Clinical Cancer Research 8(6):1779-1786.

(56) References Cited

OTHER PUBLICATIONS

Schwab, U. et al. (Sep. 2, 1982). "Production of a Monoclonal Antibody Specific for Hodgkin and Sternberg-Reed Cells of Hodgkin's Disease and a Subset of Normal Lymphoid Cells," Nature 299(5878):65-67.
Schwarting, R. et al. (Oct. 5, 1989). "BER-H2: A New Anti-Ki-1 (CD30) Monoclonal Antibody Directed at a Formol-Resistant Epitope," Blood 74(5):1678-1689.
Sela-Culang, I. et al. (Oct. 8, 2013). "The Structural Basis of Antibody-Antigen Recognition," Frontiers in Immunology 4(Article 302):1-13.
Shields, R.L. et al. (Mar. 2, 2001). "High Resolution Mapping of the Binding Site of Human IgG1 for FcyRI, FcyRII, FcyIII, and Fc Rn and Design of IgG1 Variants With Improved Binding to the FcyR," J. Biol. Chem. 9(2):6591-6604.
Shields, R.L. et al. (Jul. 26, 2002, e-pub. May 1, 2002). "Lack of Fucose on Human IgG1 N-Linked Oligosaccharide Improves Binding to Human FcyRIII and Antibody-dependent Cellular Toxicity," J. Biol. Chem. 277(30):26733-26740.
Shinkawa, T. et al. (Jan. 31, 2003). "The Absence of Fucose But Not the Presence of Galactose or Bisecting N-Acetylglucosamine of Human Lgg1 Complex-Type Oligosaccharides Shows the Critical Role of Enhancing Antibody-Dependent Cellular Cytotoxicity," Journal of Biological Chemistry 278(5):3466-3473.
Shopes, B. et al. (May 1, 1992). "A Genetically Engineered Human IgG Mutant With Enhanced Cytolytic Activity," J. Immunol. 148:2918-2922.
Sims, M.J. et al. (Aug. 15, 1993). "A Humanized CD18 Antibody Can Block Function without Cell Destruction," The Journal of Immunology 151(4):2296-2308.
Sitaraman, K. et al. (2009). "High-Throughput Protein Expression Using Cell-Free System," Methods Mol. Biol. 498:229-244.
Smith, R.I. et al. (Mar. 1, 1995). "Addition of a μ-tailpiece to IgG results in polymeric antibodies with enhanced effector functions including complement-mediated cytolysis by IgG4," J. Immunol. 154(5):2226-2236.
Spirin, A.S. (Oct. 2004). "High-Throughput Cell-Free Systems for Synthesis of Functionally Active Proteins," Trends Biotechnol. 22(10):538-545.
Takahashi, T. et al. (1998). "Immunologic Self-Tolerance Maintained by CD25+CD4+ Naturally Anergic and Suppressive T Cells: Induction of Autoimmune Disease by Breaking Their Anergic/Suppressive State," Int. Immunol. 10(12):1969-1980.
Tamura, M. et al. (Feb. 2000). "Structural Correlates of an Anticarcinoma Antibody: Identification of Specificity-Determining Residues (SDRs) and Development of a Minimally Immunogenic Antibody Variant by Retention of SDRs Only," J. Immunol. 164(3):1432-1441.
Tang, Q. et al. (Mar. 2008). "The Foxp3+ Regulatory T Cell: A Jack of All Trades, Master of Regulation," Nature Immunology 9(3):239-244, 13 pages.
Tang, X. et al. (Feb. 2004). "Design of Freeze-Drying Processes for Pharmaceuticals: Practical Advice," Pharmaceutical Research 21(2):191-200.
Thomsen, D.L. et al. (Feb. 1984). "Promoter-Regulatory Region of the Major Immediate Early Gene of Human Cytomegalovirus," Proc. Natl. Acad. Sci. U.S.A. 81:659-663.
Thornton, A.M. et al. (Jul. 20, 1998). "CD4+CD25+ Immunoregulatory T Cells Suppress Polyclonal T Cell Activation in Vitro by Inhibiting Interleukin 2 Production," J. Exp. Med. 188(2):287-296.
Traunecker, A. et al. (1991). "Bispecific Single Chain Molecules (Janusins) Target Cytotoxic Lymphocytes on HIV Infected Cells," EMBO J. 10(12):3655-3659.
Tsaknaridis, L. et al. (Oct. 15, 2003). "Functional Assay for Human CD4+CD25+ Treg Cells Reveals an Age-Dependent Loss of Suppressive Activity," J Neurosci. Res. 74(2):296-308.
Tutt, A. et al. (Jul. 1, 1991). "Trispecific F(ab')3 Derivatives that use Cooperative Signaling Via the TCR/CD3 Complex and CD2 to Activate and Redirect Resting Cytotoxic T Cells," J. Immunol. 147(1):60-69.

U.S. Appl. No. 17/766,208, filed Apr. 1, 2022, Jeffrey et al. (Copy not submitted herewith pursuant to the waiver of 37 C.F.R. § 1.98(a)(2)(iii) issued by the Office on Sep. 21, 2004).
U.S. Appl. No. 18/467,633, filed Sep. 14, 2023, Jeffrey et al. (Copy not submitted herewith pursuant to the waiver of 37 C.F.R. § 1.98(a)(2)(iii) issued by the Office on Sep. 21, 2004).
Uchida, J. et al. (Jun. 21, 2004). "The Innate Mononuclear Phagocyte Network Depletes B Lymphocytes Through Fc Receptor-Dependent Mechanisms During Anti-CD20 Antibody Immunotherapy," J. Exp. Med. 199(12):1659-1669.
Umaña, P. et al. (Feb. 1999). "Engineered Glycoforms of an Antineuro. Blastoma IgG 1 With Optimized Antibody. Dependent Cellular Cytotoxic Activity," Nat. Biotechnol. 17:176-180.
Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.
Vajdos, F.F. et al. (2002). "Comprehensive Functional Maps of the Antigen Binding Site of an Anti-ErbB2 Antibody Obtained with Shotgun Scanning Mutagenesis," J. Mol. Biol. 320:415-428.
Van Audenhove, I. et al. (2016, e-pub. Apr. 30, 2016). "Nanobodies as Versatile Tools to Understand, Diagnose, Visualize and Treat Cancer." EBioMedicine 8:40-48.
Van Bockstaele, F. et al. (Nov. 2009). "The Development of Nanobodies for Therapeutic Applications," Curr. Opin. Investig. Drugs 10(11):1212-1224.
Villa-Kamaroff, L. et al. (Aug. 1978). "A Bacterial Clone Synthesizing Proinsulin," Proc. Natl. Acad. Sci. USA 75(8):3727-3731.
Vincke, C. et al. (2012). "Introduction to Heavy Chain Antibodies and Derived Nanobodies," Methods Mol. Biol. 911:15-26.
Wagner, M.J. et al. (Mar. 1981). "Nucleotide sequence of the thymidine kinase gene of herpes simplex virus type 1," Proc. Natl. Acad. Sci. U.S.A. 78(3):1444-1445.
Watanabe, M. et al. (Feb. 1999). "Antibody Dependent Cellular Phagocytosis (ADCP) and Antibody Dependent Cellular Cytotoxicity (ADCC) of Breast Cancer Cells Mediated by Bispecific Antibody, MDX-210," Breast Cancer Res. Treat. 53(3):199-207.
Wei, H. et al. (Jan. 2014). "Hydrogen/Deuterium Exchange Mass Spectrometry for Probing Higher Order Structure of Protein Therapeutics: Methodology and Applications," Drug Discovery Today 19(1):95-102, 15 pages.
Wesolowski, J. et al. (Aug. 2009, e-pub. Jun. 16, 2009). "Single Domain Antibodies: Promising Experimental and Therapeutic Tools in Infection and Immunity," Med Microbiol Immunol 198:157-174.
Workman, C.J. et al. (2011, e-pub. Jan. 1, 2012). "In Vivo Treg Suppression Assays," Method Molecular Biology 707:119-156, 30 pages.
Wright, A. et al. (Jan. 1997). "Effect of Glycosylation on Antibody Function: Implications for Genetic Engineering," Trends Biotech. 15:26-32.
Yamamoto, T. et al. (Dec. 1980). "Identification of a functional promoter in the long terminal repeat of Rous sarcoma virus," Cell 22:787-797.
Yamane-Ohnuki, N. et al. (Sep. 5, 2004, e-pub Aug. 6, 2004). "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnology and Bioengineering 87(5):614-622.
Yu, T.Y. et al. (Apr. 23, 2020). "Prolonged Remission by Pembrolizumab and Brentuximab-Vedotin Combination Therapy in Heavily-Pretreated Relapsed/Refractory Hodgkin's Lymphoma," Journal of Hematology 9(1-2):30-32.
Zinn-Justin, S. et al. (1993). "Mapping of Two "Neutralizing" Epitopes of a Snake Curaremimetic Toxin by Proton Nuclear Magnetic Resonance Spectroscopy," Biochemistry 32:6884-6891.
Zinn-Justin, S. et al. (Nov. 24, 1992). "Three-Dimensional Solution Structure of a Curaremimetic Toxin from Naja Nigricollis Venom: A Proton NMR And Molecular Modeling Study," Biochemistry 31(46):11335-11347.
Zupnick, A. et al. (Jul. 21, 2006). "Mutational Analysis of the p53 Core Domain L1 Loop," J. Biol. Chem. 281(29):20464-20473.
International Preliminary Report on Patentability, issued Apr. 5, 2022, for PCT Application No. PCT/US2020/054087, filed Oct. 2, 2020, 7 pages.

(56) References Cited

OTHER PUBLICATIONS

International Preliminary Report on Patentability, issued Apr. 5, 2022, for PCT Application No. PCT/US2020/054137, filed Oct. 2, 2020, 8 pages.
International Search Report and Written Opinion, dated Jan. 13, 2021, for PCT Application No. PCT/US2020/054137, filed Oct. 2, 2020, 12 pages.
International Preliminary Report on Patentability, issued Nov. 15, 2022, for PCT Application No. PCT/US2021/031985, filed May 12, 2021, 11 pages.
International Search Report and Written Opinion, dated Sep. 2, 2021, for PCT Application No. PCT/US2021/031985, filed May 12, 2021, 18 pages.
International Preliminary Report on Patentability, issued May 30, 2023, for PCT Application No. PCT/US2021/061660, filed Dec. 2, 2021, 8 pages.
International Search Report and Written Opinion, dated Apr. 26, 2022, for PCT Application No. PCT/US2021/061660, filed Dec. 2, 2021, 12 pages.
Invitation to Pay Additional Fees, dated Feb. 25, 2022, for PCT Application No. PCT/US2021/061660, filed Dec. 2, 2021, 3 pages.
Meng, G. et al. (2014). "Synthesis and Cytotoxic Activities of the Amino Acid-Conjugates of 10-Hydroxycamptothecin," Chin. J. Org. Chem. 34:155-160. English Abstract, 6 pages.

\* cited by examiner

CAMPTOTHECIN CONJUGATES

CROSS-REFERENCE TO RELATED APPLICATIONS

The present application is a national stage application under 35 U.S.C. § 371 of International Application No. PCT/US2019/035971, filed internationally on Jun. 7, 2019, which claims the benefit of priority to U.S. Provisional Patent Application Ser. Nos. 62/681,847, filed Jun. 7, 2018, and 62/777,491, filed Dec. 10, 2018, which are incorporated by reference herein in their entireties for all purposes.

BACKGROUND OF THE INVENTION

Antibodies (mAbs) have been investigated for the targeted delivery of cytotoxic agents to tumor cells. While various drug classes have been evaluated for targeted delivery by antibodies, only a few drug classes have proved sufficiently active as antibody drug conjugates, while having a suitable toxicity profile and other pharmacological properties, to warrant clinical development. One drug class receiving interest is the camptothecins.

The design of Antibody Drug Conjugates (ADCs), by attaching a cytotoxic agent to antibody, typically via a linker, involves consideration of a variety of factors, including the presence of a conjugation handle on the drug for attachment to the linker and linker technology for attaching the drug to an antibody in a conditionally stable manner. The conjugation handle for the parent compound in the class is the C20 hydroxyl functional group in which the linker is attached through a carbonate functional group (e.g., see Walker, M. A. et al. *Bioorganic & Medicinal Chemistry Letters* (2002) 12(2): 217-219. However, carbonate functional groups typically suffer from hydrolytic instability, which cause premature release of free drug into systemic circulation, which can result in reduced ADC potency, insufficient immunologic specificity of the conjugate and increased toxicity. Therefore, there is a need in the art for camptothecin conjugates having improve stability to increase the amount of drug delivered to the desired sit of action. The present invention addresses those and other needs.

BRIEF SUMMARY OF THE INVENTION

The invention provides inter alia, Camptothecin Conjugates, Camptothecin-Linker Compounds and Camptothecin Compounds methods of preparing and using them, and intermediates thereof. The Camptothecin Conjugates of the present invention are stable in circulation, yet capable of inflicting cell death once free drug is released from a Conjugate in the vicinity or within tumor cells.

In one principle embodiment, a Camptothecin Conjugate is provided having a formula:

L-(Q-D)$_p$ or a salt thereof, wherein
L is a Ligand Unit;
subscript p is an integer of from 1 to 16;
Q is a Linker Unit having a formula selected from the group consisting of:

-Z-A-,-Z-A-RL-,-Z-A-RL-Y-,-Z-A-S*-RL-,-Z-A-S*-RL-Y-,

Z-A-S*-W-,-Z-A-S*-W-RL-,-Z-A-B(S*)-RL-,-Z-A-B(S*)W,

-Z-A-B(S*)-W-RL- and -Z-A-B(S*)-RL-Y-, wherein Z is a Stretcher Unit;
A is a bond or a Connecter Unit;
B is a Parallel Connector Unit;
S* is a Partitioning Agent;
RL is a Releasable Linker;
W is an Amino Acid Unit;
Y is a Spacer Unit; and
D is a Drug Unit selected from the group consisting of:

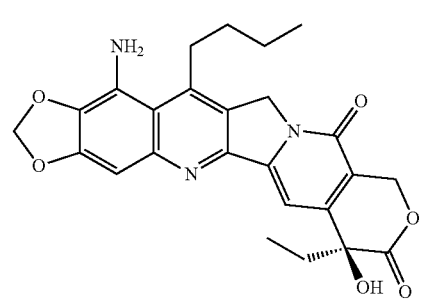

CPT1

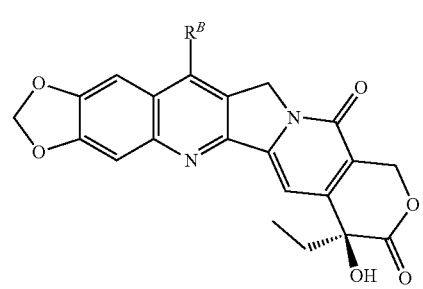

CPT2

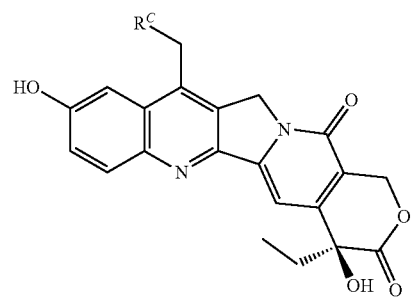

CPT3

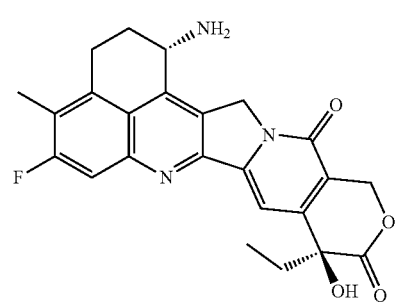

CPT4

-continued

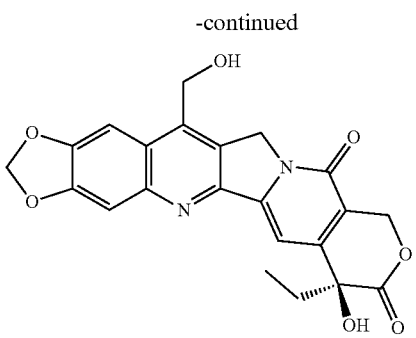
CPT5

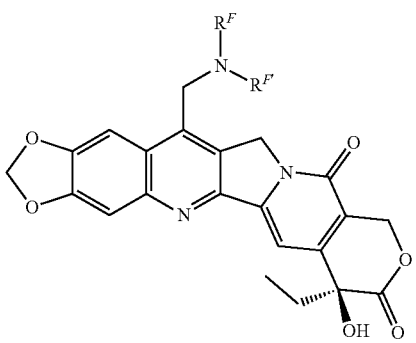
CPT6

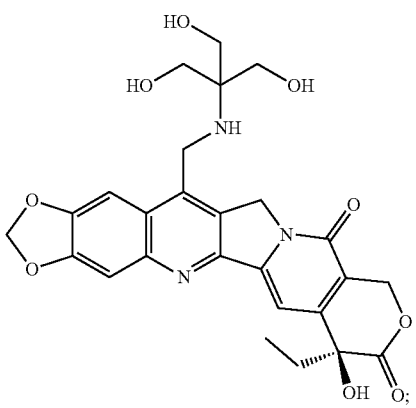
CPT7 wherein
R$^B$ is a member selected from the group consisting of H, C$_1$-C$_8$ alkyl, C$_1$-C$_8$ haloalkyl, C$_3$-C$_3$ cycloalkyl, (C$_3$-C$_8$ cycloalkyl)-C$_1$-C$_4$ alkyl-, phenyl and phenyl-C$_1$-C$_4$ alkyl-;

R$^C$ is a member selected from the group consisting of C$_1$-C$_6$ alkyl and C$_3$-C$_6$ cycloalkyl;

each R$^F$ and R$^{F'}$ is a member independently selected from the group consisting of —H, C$_1$-C$_8$ alkyl, C$_1$-C$_8$ hydroxyalkyl, C$_1$-C$_8$ aminoalkyl, (C$_1$-C$_4$alkylamino)-C$_1$-C$_8$ alkyl-, N,N—(C$_1$-C$_4$ hydroxyalkyl)(C$_1$-C$_4$ alkyl)-amino-C$_1$-C$_8$ alkyl-, N,N-di(C$_1$-C$_4$ alkyl)amino-C$_1$-C$_8$ alkyl-, N—C$_1$-C$_4$ hydroxyalkyl-C$_1$-C$_8$ aminoalkyl-, C$_1$-C$_8$ alkylC(O)—, C$_1$-C$_8$ hydroxyalkyl-C(O)—, C$_1$-C$_8$ aminoalkylC(O)—, C$_3$-C$_{10}$ cycloalkyl, (C$_3$-C$_{10}$ cycloalkyl)-C$_1$-C$_4$ alkyl-, C$_3$-C$_{10}$ heterocycloalkyl, (C$_3$-C$_{10}$ heterocycloalkyl)-C$_1$-C$_4$ alkyl-, phenyl, phenyl-C$_1$-C$_4$ alkyl-, diphenyl-C$_1$-C$_4$ alkyl-, heteroaryl and heteroaryl-C$_1$-C$_4$ alkyl-, or R$^F$ and R$^{F'}$ are combined with the nitrogen atom to which each is attached to form a 5-, 6- or 7-membered ring having 0 to 3 substituents selected from halogen, C$_1$-C$_4$ alkyl, —OH, —OC$_1$-C$_4$ alkyl, —NH$_2$, —NHC$_1$-C$_4$ alkyl and —N(C$_1$-C$_4$ alkyl)$_2$; and wherein the cycloalkyl, heterocycloalkyl, phenyl and heteroaryl moieties of R$^B$, R$^C$, R$^F$ and R$^{F'}$ are substituted with from 0 to 3 substituents selected from the group consisting of halogen, C$_1$-C$_4$ alkyl, —OH, —OC$_1$-C$_4$ alkyl, —NH$_2$, —NHC$_1$-C$_4$ alkyl and —N(C$_1$-C$_4$ alkyl)$_2$; and wherein the point of attachment of D to Q is through the heteroatom of any one of the hydroxyl or primary or secondary amine functional groups present on CPT1, CPT2, CPT3, CPT4, CPT5, CPT6 or CPT7 when Q is -Z-A-RL-, -Z-A-RL-Y-, -Z-A-S*-RL-, -Z-A-B(S*)-RL-, -Z-A-S*-RL-Y- or -Z-A-B(S*)-RL-Y- in which RL is any one of the Releasable Linkers disclosed herein, or wherein the point of attachment of D to Q is through the oxygen atom of the hydroxyl group substituent in the lactone ring of CPT1, CPT2, CPT3, CPT4, CPT5, CPT6 or CPT7 when Q is -Z-A-, -Z-A-S*-W- or -Z-A-B(S*)W, or when Q is -Z-A-S*-RL-, -Z-A-B(S*)-RL-, -Z-A-S*-W-RL-, or -Z-A-B(S*)-W-RL- in which RL is a Releasable Unit other than a Glucuronide Unit; and provided that at least one of R$^F$ and R$^{F'}$ is —H, when the point of attachment is to the nitrogen atom of the primary or secondary amino group of CPT6, provided that -Z-A- of -Z-A-RL-, -Z-A-RL-Y-, -Z A-S*-RL-, -Z-A-B(S*)-RL-, -Z-A-S*-RL-Y- and -Z-A-B(S*)-RL-Y- is other than succinimido-caproyl-β-alanyl, optionally having the succinimide ring in hydrolyzed form, when D is CPT1 having attachment through the nitrogen atom of its primary amino group.

Other principle embodiments as noted above, are Camptothecin-Linker Compounds useful as intermediates for preparing Camptothecin Conjugates, wherein the Camptothecin-Linker Compound is comprised of a Camptothecin and a Linker Unit (Q), wherein the Linker Unit is comprised of a Stretcher Unit precursor (Z') capable of forming a covalent bond to a targeting ligand that provides for a Ligand Unit, and a Releasable Linker (RL), which in some aspects of Q not having an Amino Acid Unit is a Glucuronide Unit.

In another aspect, provided herein are methods of treating cancer comprising administering to a subject in need thereof a Camptothecin Conjugate described herein.

In another aspect, provided herein are kits comprising a Camptothecin Conjugate described herein.

DETAILED DESCRIPTION OF THE INVENTION

Definitions

Figure 1A:
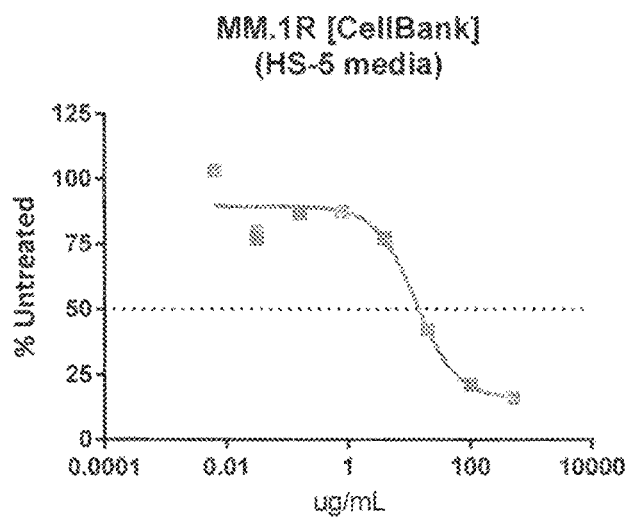
FIGS. 1A-1B show evaluations of a glucuronide-based camptothecin ADC in a multiple myeloma in vitro bystander activity model. A. Anti-Ag5 camptothecin DAR8 ADC (Ag5-(67)) dose response titration against MM.1R (Ag5+) cell line. Viability assessed by CellTitre-Glo™. B. Anti-Ag5 camptothecin DAR8 ADC (Ag5-(67)) dose response titration of a 3:1 co-culture mixture of MM.1R and MM.1R Ag5 KO (crispr cas knock out) luc+ cell lines. Viability was assessed by Bright-Glo™.

Unless stated otherwise, the following terms and phrases as used herein are intended to have the following meanings. When trade names are used herein, the trade name includes the product formulation, the generic drug, and the active pharmaceutical ingredient(s) of the trade name product, unless otherwise indicated by context.

The term "antibody" as used herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. The native form of an antibody is a tetramer and consists of two identical pairs of immunoglobulin chains, each pair having one light chain and one heavy chain. In each pair, the light and heavy chain variable regions ($V_L$ and $V_H$) are together primarily responsible for binding to an antigen. The light chain and heavy chain variable domains consist of a framework region interrupted by three hypervariable regions, also called "complementarity determining regions" or "CDRs." The constant regions may be recognized by and interact with the immune system, (see, e.g., Janeway et al, 2001, *Immunol. Biology*, 5th Ed., Garland Publishing, New York). An antibody can be of any type (e.g., IgG, IgE, IgM, IgD, and IgA), class (e.g., $IgG_1$, $IgG_2$, $IgG_3$, $IgG_4$, $IgA_1$ and $IgA_2$) or subclass thereof. The antibody can be derived from any suitable species. In some embodiments, the antibody is of human or murine origin. An antibody can be, for example, human, humanized or chimeric.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. The modifier "monoclonal" indicates the character of the antibody as being obtained from a substantially homogeneous population of antibodies and is not to be construed as requiring production of the antibody by any particular method.

An "intact antibody" is one which comprises an antigen-binding variable region as well as a light chain constant domain ($C_L$) and heavy chain constant domains, $C_H1$, $C_H2$, $C_H3$ and $C_H4$, as appropriate for the antibody class. The constant domains may be native sequence constant domains (e.g., human native sequence constant domains) or amino acid sequence variant thereof.

An "antibody fragment" comprises a portion of an intact antibody, comprising the antigen-binding or variable region thereof. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immunospecifically bind to a target antigen (e.g., a cancer cell antigen, a viral antigen or a microbial antigen).

An "antigen" is an entity to which an antibody specifically binds.

The terms "specific binding" and "specifically binds" mean that the antibody or antibody derivative will bind, in a highly selective manner, with its corresponding epitope of a target antigen and not with the multitude of other antigens. Typically, the antibody or antibody derivative binds with an affinity of at least about $1\times10^{-7}$ M, and preferably $10^{-8}$ M to $10^{-9}$ M, $10^{-10}$ M, $10^{-11}$ M, or $10^{-12}$ M and binds to the predetermined antigen with an affinity that is at least two-fold greater than its affinity for binding to a non-specific antigen (e.g., BSA, casein) other than the predetermined antigen or a closely-related antigen.

The term "inhibits" or "inhibition of" means to reduce by a measurable amount, or to prevent entirely.

The term "therapeutically effective amount" refers to an amount of a conjugate effective to treat a disease or disorder in a mammal. In the case of cancer, the therapeutically effective amount of the conjugate may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit growth and/or kill existing cancer cells, it may be cytostatic and/or cytotoxic. For cancer therapy, efficacy can, for example, be measured by assessing the time to disease progression (TTP) and/or determining the response rate (RR).

The term "substantial" or "substantially" refers to a majority, i.e. >50% of a population, of a mixture or a sample, preferably more than 50%, 55%, 60%, 65%, 70%, 75%, 80%, 85%, 90%, 91%, 92%, 93%, 94%, 95%, 96%, 97%, 98%, or 99% of a population.

The term "cytotoxic activity" refers to a cell-killing effect of a drug or Camptothecin Conjugate or an intracellular metabolite of a Camptothecin Conjugate. Cytotoxic activity may be expressed as the $IC_{50}$ value, which is the concentration (molar or mass) per unit volume at which half the cells survive.

The term "cytostatic activity" refers to an anti-proliferative effect of a drug or Camptothecin Conjugate or an intracellular metabolite of a Camptothecin Conjugate.

The term "cytotoxic agent" as used herein refers to a substance that has cytotoxic activity and causes destruction of cells. The term is intended to include chemotherapeutic agents, and toxins such as small molecule toxins or enzymatically active toxins of bacterial, fungal, plant or animal origin, including synthetic analogs and derivatives thereof.

The term "cytostatic agent" as used herein refers to a substance that inhibits a function of cells, including cell growth or multiplication. Cytostatic agents include inhibitors such as protein inhibitors, e.g., enzyme inhibitors. Cytostatic agents have cytostatic activity.

The terms "cancer" and "cancerous" refer to or describe the physiological condition or disorder in mammals that is typically characterized by unregulated cell growth. A "tumor" comprises one or more cancerous cells.

An "autoimmune disease" as used herein refers to a disease or disorder arising from and directed against an individual's own tissues or proteins.

"Patient" as used herein refers to a subject to whom is administered a Camptothecin Conjugate of the present invention. Patient includes, but are not limited to, a human, rat, mouse, guinea pig, non-human primate, pig, goat, cow, horse, dog, cat, bird and fowl. Typically, the patient is a rat, mouse, dog, human or non-human primate, more typically a human.

The terms "treat" or "treatment," unless otherwise indicated by context, refer to therapeutic treatment and prophylactic wherein the object is to inhibit or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder.

In the context of cancer, the term "treating" includes any or all of: killing tumor cells; inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

In the context of an autoimmune disease, the term "treating" includes any or all of: inhibiting replication of cells associated with an autoimmune disease state including, but not limited to, cells that produce an autoimmune antibody, lessening the autoimmune-antibody burden and ameliorating one or more symptoms of an autoimmune disease.

"Compound" as the term is used herein, refers to and encompasses the chemical compound itself, either named or represented by structure, and salt form(s) thereof, whether explicitly stated or not, unless context makes clear that such salt forms are to be excluded. The term "compound" further encompasses solvate forms of the compound, in which solvent is noncovalently associated with the compound or is reversibly associated covalently with the compound, as when a carbonyl group of the compound is hydrated to form a gem-diol. Solvate forms include those of the compound itself and its salt form(s) and are inclusive of hemisolvates, monosolvates, disolvates, including hydrates; and when a compound can be associated with two or more solvent molecules, the two or more solvent molecules may be the same or different.

In some instances, a compound of the invention will include an explicit reference to one or more of the above forms, e.g., salts and solvates, which does not imply any solid state form of the compound; however, this reference is for emphasis only, and is not to be construed as excluding any other of the forms as identified above. Furthermore, when explicit reference to a salt and/or solvate form of a compound or a Ligand Drug Conjugate composition is not made, that omission is not to be construed as excluding the salt and/or solvate form(s) of the compound or Conjugate unless context make clear that such salt and/or solvate forms are to be excluded.

The phrase "salt thereof" as the phrase is used herein, refers to a salt form of a compound (e.g., a Drug, a Drug Linker compound or a Ligand Drug Conjugate compound). A salt form of a compound is of one or more internal salt forms and/or involves the inclusion of another molecule such as an acetate ion, a succinate ion or other counterion. The counterion in a salt form of a compound is typically an organic or inorganic moiety that stabilizes the charge on the parent compound. A salt form of a compound has one or more than one charged atom in its structure. In instances where multiple charged atoms are part of the salt form, multiple counter ions and/or multiple charged counter ions are present. Hence, a salt form of a compound typically has one or more charged atoms corresponding to those of the non-salt form of the compound and one or more counterions. In some aspects, the non-salt form of a compound contains at least one amino group or other basic moeity, and accordingly in the presence of an acid, an acid addition salt with the basic moiety is obtained. In other aspects, the non-salt form of a compound contains at least one carboxylic acid group or other acidic moiety, and accordingly in the presence of a base, a carboxylate or other anionic moiety is obtained. Exemplary salts include, but are not limited to, sulfate, trifluoroacetate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

A pharmaceutically acceptable salt is a salt form of a compound that is suitable for administration to a subject as described herein and in some aspects includes counteractions or counteranions as described by P. H. Stahl and C. G. Wermuth, editors, Handbook of Pharmaceutical Salts: Properties, Selection and Use, Weinheim/Zurich: Wiley-VCH/VHCA, 2002.

A Linker Unit is a bifunctional moiety that connects a Camptothecin to a Ligand Unit in a Camptothecin Conjugate. The Linker Units of the present invention have several components (e.g., a Stretcher Unit which in some embodiments will have a Basic Unit; a Connector Unit, that can be present or absent; a Parallel Connector Unit, that can also be present or absent; a Releasable Linker; and a Spacer Unit, that can also be present or absent).

"PEG", "PEG Unit" or "polyethylene glycol" as used herein is an organic moiety comprised of repeating ethyleneoxy subunits and may be polydisperse, monodisperse or discrete (i.e., having discrete number of ethylene-oxy subunits). Polydisperse PEGs are a heterogeneous mixture of sizes and molecular weights whereas monodisperse PEGs are typically purified from heterogeneous mixtures and are therefore provide a single chain length and molecular weight. Preferred PEG Units are discrete PEGs, compounds that are synthesized in stepwise fashion and not via a polymerization process. Discrete PEGs provide a single molecule with defined and specified chain length.

The PEG Unit provided herein comprises one or multiple polyethylene glycol chains, each comprised of one or more ethyleneoxy subunits, covalently attached to each other. The polyethylene glycol chains can be linked together, for example, in a linear, branched or star shaped configuration. Typically, at least one of the polyethylene glycol chains prior to incorporation into a Camptothecin Conjugate is derivitized at one end with an alkyl moiety substituted with an electrophilic group for covalent attachment to the carbamate nitrogen of a methylene carbamate unit (i.e., represents an instance of R). Typically, the terminal ethyleneoxy subunit in each polyethylene glycol chains not involved in covalent attachment to the remainder of the Linker Unit is modified with a PEG Capping Unit, typically an optionally substituted alkyl such as —CH$_3$, —CH$_2$CH$_3$ or —CH$_2$CH$_2$CO$_2$H. A preferred PEG Unit has a single polyethylene glycol chain with 4 to 24 —CH$_2$CH$_2$O— subunits covalently attached in series and terminated at one end with a PEG Capping Unit.

Unless otherwise indicated, the term "alkyl" by itself or as part of another term refers to a substituted or unsubstituted straight chain or branched, saturated or unsaturated hydrocarbon having the indicated number of carbon atoms (e.g., "—C$_1$-C$_8$ alkyl" or "—C$_1$-C$_{10}$" alkyl refer to an alkyl group having from 1 to 8 or 1 to 10 carbon atoms, respectively). When the number of carbon atoms is not indicated, the alkyl group has from 1 to 8 carbon atoms. Representative straight chain "—C$_1$-C$_8$ alkyl" groups include, but are not limited to, -methyl, -ethyl, -n-propyl, -n-butyl, -n-pentyl, -n-hexyl, -n-heptyl and -n-octyl; while branched —C$_3$-C$_8$ alkyls include, but are not limited to, -isopropyl, -sec-butyl, -isobutyl, -tert-butyl, -isopentyl, and -2-methylbutyl; unsaturated —C$_2$-C$_8$ alkyls include, but are not limited to, -vinyl, -allyl, -1-butenyl, -2-butenyl, -isobutylenyl, -1 pentenyl, -2 pentenyl, -3-methyl-1-butenyl, -2 methyl-2-butenyl, -2,3 dimethyl-2-butenyl, -1-hexyl, 2-hexyl, -3-hexyl, -acetylenyl, -propynyl, -1 butynyl, -2 butynyl, -1 pentynyl, -2 pentynyl and -3 methyl 1 butynyl. Sometimes an alkyl group is unsubstituted. An alkyl group can be substituted with one or more groups. In other aspects, an alkyl group will be saturated.

Unless otherwise indicated, "alkylene," by itself of as part of another term, refers to a substituted or unsubstituted saturated, branched or straight chain or cyclic hydrocarbon radical of the stated number of carbon atoms, typically 1-10 carbon atoms, and having two monovalent radical centers derived by the removal of two hydrogen atoms from the same or two different carbon atoms of a parent alkane. Typical alkylene radicals include, but are not limited to: methylene (—CH$_2$—), 1,2-ethylene (—CH$_2$CH$_2$—), 1,3-propylene (—CH$_2$CH$_2$CH$_2$—), 1,4-butylene (—CH$_2$CH$_2$CH$_2$CH$_2$—), and the like. In preferred aspects, an alkylene is a branched or straight chain hydrocarbon (i.e., it is not a cyclic hydrocarbon).

Unless otherwise indicated, "aryl," by itself or as part of another term, means a substituted or unsubstituted monovalent carbocyclic aromatic hydrocarbon radical of the stated number of carbon atoms, typically 6-20 carbon atoms, derived by the removal of one hydrogen atom from a single carbon atom of a parent aromatic ring system. Some aryl groups are represented in the exemplary structures as "Ar".

Typical aryl groups include, but are not limited to, radicals derived from benzene, substituted benzene, naphthalene, anthracene, biphenyl, and the like. An exemplary aryl group is a phenyl group.

Unless otherwise indicated, an "arylene," by itself or as part of another term, is an aryl group as defined above which has two covalent bonds (i.e., it is divalent) and can be in the ortho, meta, or para orientations as shown in the following structures, with phenyl as the exemplary group:

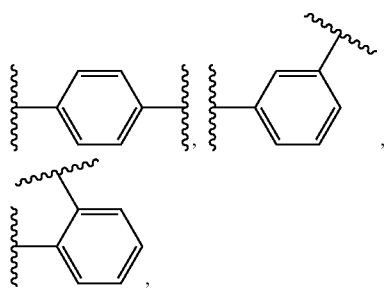

Unless otherwise indicated, a "$C_3$-$C_8$ heterocycle," by itself or as part of another term, refers to a monovalent substituted or unsubstituted aromatic or non-aromatic monocyclic or bicyclic ring system having from 3 to 8 carbon atoms (also referred to as ring members) and one to four heteroatom ring members independently selected from N, O, P or S, and derived by removal of one hydrogen atom from a ring atom of a parent ring system. One or more N, C or S atoms in the heterocycle can be oxidized. The ring that includes the heteroatom can be aromatic or nonaromatic. Heterocycles in which all the ring atoms are involved in aromaticity are referred to as heteroaryls and otherwise are referred to heterocarbocycles.

Unless otherwise noted, the heterocycle is attached to its pendant group at any heteroatom or carbon atom that results in a stable structure. As such a heteroaryl may be bonded through an aromatic carbon of its aromatic ring system, referred to as a C-linked heteroaryl, or through a non-double-bonded N atom (i.e., not =N—) in its aromatic ring system, which is referred to as an N-linked heteroaryl. Thus, nitrogen-containing heterocycles may be C-linked or N-linked and include pyrrole moieties, such as pyrrol-1-yl (N-linked) and pyrrol-3-yl (C-linked), and imidazole moieties such as imidazol-1-yl and imidazol-3-yl (both N-linked), and imidazol-2-yl, imidazol-4-yl and imidazol-5-yl moieties (all of which are C-linked).

Unless otherwise indicated, a "$C_3$-$C_8$ heteroaryl," is an aromatic $C_3$-$C_8$ heterocycle in which the subscript denotes the total number of carbons of the cyclic ring system of the heterocycle or the total number of aromatic carbons of the aromatic ring system of the heteroaryl and does not implicate the size of the ring system or the presence or absence of ring fusion. Representative examples of a $C_3$-$C_8$ heterocycle include, but are not limited to, pyrrolidinyl, azetidinyl, piperidinyl, morpholinyl, tetrahydrofuranyl, tetrahydropyranyl, benzofuranyl, benzothiophene, indolyl, benzopyrazolyl, pyrrolyl, thiophenyl (thiophene), furanyl, thiazolyl, imidazolyl, pyrazolyl, pyrimidinyl, pyridinyl, pyrazinyl, pyridazinyl, isothiazolyl, and isoxazolyl.

When explicitly given, the size of the ring system of a heterocycle or heteroaryl is indicated by the total number of atoms in the ring. For example, designation as a 5- or 6-membered heteroaryl indicates the total number or aromatic atoms (i.e., 5 or 6) in the heteroaromatic ring system of the heteroaryl but does not imply the number of aromatic heteroatoms or aromatic carbons in that ring system. Fused heteroaryls are explicitly stated or implied by context as such and are typically indicated by the number of aromatic atoms in each aromatic ring that are fused together to make up the fused heteroaromatic ring system. For example, a 5,6-membered heteroaryl is an aromatic 5-membered ring fused to an aromatic 6-membered ring in which one or both rings have aromatic heteroatom(s) or where a heteroatom is shared between the two rings.

A heterocycle fused to an aryl or heteroaryl such that the heterocycle remains non-aromatic and is part of a larger structure through attachment with the non-aromatic portion of the fused ring system is an example of an optionally substituted heterocycle in which the heterocycle is substituted by ring fusion with the aryl or heteroaryl. Likewise, an aryl or heteroaryl fused to heterocycle or carbocycle that is part of a larger structure through attachment with the aromatic portion of the fused ring system is an example of an optionally substituted aryl or heterocycle in which the aryl or heterocycle is substituted by ring fusion with the heterocycle or carbocycle.

Unless otherwise indicated, "$C_3$-$C_8$ heterocyclo," by itself or as part of another term, refers to a $C_3$-$C_8$ heterocyclic defined above wherein one of the hydrogen atoms of the heterocycle is replaced with a bond (i.e., it is divalent). Unless otherwise indicated, a "$C_3$-$C_8$ heteroarylene," by itself or as part of another term, refers to a $C_3$-$C_8$ heteroaryl group defined above wherein one of the heteroaryl group's hydrogen atoms is replaced with a bond (i.e., it is divalent).

Unless otherwise indicated, a "$C_3$-$C_8$ carbocycle," by itself or as part of another term, is a 3-, 4-, 5-, 6-, 7- or 8-membered monovalent, substituted or unsubstituted, saturated or unsaturated non-aromatic monocyclic or bicyclic carbocyclic ring derived by the removal of one hydrogen atom from a ring atom of a parent ring system. Representative —$C_3$-$C_8$ carbocycles include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl.

Unless otherwise indicated, a "$C_3$-$C_8$ carbocyclo," by itself or as part of another term, refers to a $C_3$-$C_8$ carbocycle group defined above wherein another one of the carbocycle groups' hydrogen atoms is replaced with a bond (i.e., it is divalent).

Unless otherwise indicated, the term "heteroalkyl," by itself or in combination with another term, means, unless otherwise stated, a stable straight or branched chain hydrocarbon, or combinations thereof, fully saturated or containing from 1 to 3 degrees of unsaturation, consisting of the stated number of carbon atoms and from one to ten, preferably one to three, heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group or at the position at which the alkyl group is attached to the remainder of the molecule. The heteroatom Si can be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —NH—$CH_2$—$CH_2$—NH—C(O)—$CH_2$—$CH_3$, —$CH_2$—

CH$_2$—S(O)$_2$—CH$_3$, —CH=CHO—CH$_3$, —Si(CH$_3$)$_3$, —CH$_2$—CH=NO—CH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Typically, a C$_1$ to C$_4$ heteroalkyl or heteroalkylene has 1 to 4 carbon atoms and 1 or 2 heteroatoms and a C$_1$ to C$_3$ heteroalkyl or heteroalkylene has 1 to 3 carbon atoms and 1 or 2 heteroatoms. In some aspects, a heteroalkyl or heteroalkylene is saturated.

Unless otherwise indicated, the term "heteroalkylene" by itself or in combination with another term means a divalent group derived from heteroalkyl (as discussed above), as exemplified by —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini. Still further, for alkylene and heteroalkylene linking groups, no orientation of the linking group is implied.

Unless otherwise indicated, "aminoalkyl" by itself or in combination with another term means a heteroalkyl wherein an alkyl moiety as defined herein is substituted with an amino, alkylamino, dialkylamino or cycloalkylamino group. Exemplary non-limiting aminoalkyls are —CH$_2$NH$_2$, —CH$_2$CH$_2$NH$_2$, —CH$_2$CH$_2$NHCH$_3$ and —CH$_2$CH$_2$N(CH$_3$)$_2$ and further includes branched species such as —CH(CH$_3$)NH$_2$ and —C(CH$_3$)CH$_2$NH$_2$ in the (R)- or (S)-configuration. Alternatively, an aminoalkyl is an alkyl moiety, group, or substituent as defined herein wherein a sp$^3$ carbon other than the radical carbon has been replaced with an amino or alkylamino moiety wherein its sp$^3$ nitrogen replaces the sp$^3$ carbon of the alkyl provided that at least one sp$^3$ carbon remains. When referring to an aminoalkyl moiety as a substituent to a larger structure or another moiety the aminoalkyl is covalently attached to the structure or moiety through the carbon radical of the alkyl moiety of the aminoalkyl.

Unless otherwise indicated "alkylamino" and "cycloalkylamino" by itself or in combination with another term means an alkyl or cycloalkyl radical, as described herein, wherein the radical carbon of the alkyl or cycloalkyl radical has been replaced with a nitrogen radical, provided that at least one sp$^3$ carbon remains. In those instances where the alkylamino is substituted at its nitrogen with another alkyl moiety the resulting substituted radical is sometimes referred to as a dialkylamino moiety, group or substituent wherein the alkyl moieties substituting nitrogen are independently selected.

Exemplary and non-limiting amino, alkylamino and dialkylamino substituents, include those having the structure of —N(R')$_2$, wherein R' in these examples are independently selected from hydrogen or C$_{1-6}$ alkyl, typically hydrogen or methyl, whereas in cycloalkyl amines, which are included in heterocycloalkyls, both R' together with the nitrogen to which they are attached define a heterocyclic ring. When both R' are hydrogen or alkyl, the moiety is sometimes described as a primary amino group and a tertiary amine group, respectively. When one R' is hydrogen and the other is alkyl, then the moiety is sometimes described as a secondary amino group. Primary and secondary alkylamino moieties are more reactive as nucleophiles towards carbonyl-containing electrophilic centers whereas tertiary amines are more basic.

"Substituted alkyl" and "substituted aryl" mean alkyl and aryl, respectively, in which one or more hydrogen atoms, typically one, are each independently replaced with a substituent. Typical substituents include, but are not limited to a —X, —R', —OH, —OR', —SR', —N(R')$_2$, —N(R')$_3$, =NR', —CX$_3$, —CN, —NO$_2$, —NR'C(=O)R', —C(=O)R', —C(=O)N(R')$_2$, —S(=O)$_2$R', —S(=O)$_2$NR', —S(=O)R', —OP(=O)(OR')$_2$, —P(=O)(OR')$_2$, —PO$_3$=, PO$_3$H$_2$, —C(=O)R', —C(=S)R', —CO$_2$R', —CO$_2$$^-$, —C(=S)OR', —C(=O)SR', —C(=S)SR', —C(=O)N(R')$_2$, —C(=S)N(R')$_2$, and —C(=NR)N(R')$_2$, where each X is independently selected from the group consisting of a halogen: —F, —Cl, —Br, and —I; and wherein each R' is independently selected from the group consisting of —H, —C$_1$-C$_{20}$ alkyl, —C$_6$-C$_{20}$ aryl, —C$_3$-C$_{14}$ heterocycle, a protecting group, and a prodrug moiety.

More typically substituents are selected from the group consisting of —X, —R', —OH, —OR', —SR', —N(R')$_2$, —N(R')$_3$, =NR', —NR'C(=O)R', —C(=O)R', —C(=O)N(R')$_2$, —S(=O)$_2$R', —S(=O)$_2$NR', —S(=O)R', —C(=O)R', —C(=S)R', —C(=O)N(R')$_2$, —C(=S)N(R')$_2$, and —C(=NR)N(R')$_2$, wherein each X is independently selected from the group consisting of —F and —Cl, or are selected from the group consisting of —X, —R', —OH, —OR', —N(R')$_2$, —N(R')$_3$, —NR'C(=O)R', —C(=O)N(R')$_2$, —S(=O)$_2$R', —S(=O)$_2$NR', —S(=O)R', —C(=O)R', —C(=O)N(R')$_2$, —C(=NR)N(R')$_2$, a protecting group, and a prodrug moiety, wherein each X is —F; and wherein each R' is independently selected from the group consisting of hydrogen, —C$_1$-C$_{20}$ alkyl, —C$_6$-C$_{20}$ aryl, —C$_3$-C$_{14}$ heterocycle, a protecting group, and a prodrug moiety.

In some aspects, an alkyl substituent is selected from the group consisting —N(R')$_2$, —N(R')$_3$ and —C(=NR)N(R')$_2$, wherein R' is selected from the group consisting of hydrogen and —C$_1$-C$_{20}$ alkyl. In other aspects, alkyl is substituted with a series of ethyleneoxy moieties to define a PEG Unit. Alkylene, carbocycle, carbocyclo, arylene, heteroalkyl, heteroalkylene, heterocycle, heterocyclo, heteroaryl, and heteroarylene groups as described above may also be similarly substituted.

"Protecting group" as used here means a moiety that prevents or reduces the ability of the atom or functional group to which it is linked from participating in unwanted reactions. Typical protecting groups for atoms or functional groups are given in Greene (1999), "PROTECTIVE GROUPS IN ORGANIC SYNTHESIS, 3$^{RD}$ ED.", Wiley Interscience. Protecting groups for heteroatoms such as oxygen, sulfur and nitrogen are used in some instances to minimize or avoid unwanted their reactions with electrophilic compounds. In other instances, the protecting group is used to reduce or eliminate the nucleophilicity and/or basicity of the unprotected heteroatom. Non-limiting examples of protected oxygen are given by —OR$^{PR}$, wherein R$^{PR}$ is a protecting group for hydroxyl, wherein hydroxyl is typically protected as an ester (e.g. acetate, propionate or benzoate). Other protecting groups for hydroxyl avoid interfering with the nucleophilicity of organometallic reagents or other highly basic reagents, where hydroxyl is typically protected as an ether, including alkyl or heterocycloalkyl ethers, (e.g., methyl or tetrahydropyranyl ethers), alkoxymethyl ethers (e.g., methoxymethyl or ethoxymethyl ethers), optionally substituted aryl ethers, and silyl ethers (e.g., trimethylsilyl (TMS), triethylsilyl (TES), tert-butyldiphenylsilyl (TBDPS), tert-butyldimethylsilyl (TBS/TBDMS), triisopropylsilyl (TIPS) and [2-(trimethylsilyl)ethoxy]-methylsilyl (SEM)). Nitrogen protecting groups include those for primary or secondary amines as in —NHR$^{PR}$ or —N(R$^{PR}$)$_2$—, wherein least one of R$^{PR}$ is a nitrogen atom protecting group or both R$^{PR}$ together comprise a protecting group.

A protecting group is suitable when it is capable of preventing or avoiding unwanted side-reactions or premature loss of the protecting group under reaction conditions required to effect desired chemical transformation elsewhere in the molecule and during purification of the newly formed molecule when desired, and can be removed under conditions that do not adversely affect the structure or stereochemical integrity of that newly formed molecule. By way of example and not limitation, a suitable protecting group may include those previously described for protecting functional groups. A suitable protecting group is sometimes a protecting group used in peptide coupling reactions.

"Aromatic alcohol" by itself or part of a larger structure refers to an aromatic ring system substituted with the hydroxyl functional group —OH. Thus, aromatic alcohol refers to any aryl, heteroaryl, arylene and heteroarylene moiety as described herein having a hydroxyl functional group bonded to an aromatic carbon of its aromatic ring system. The aromatic alcohol may be part of a larger moiety as when its aromatic ring system is a substituent of this moiety, or may be embedded into the larger moiety by ring fusion, and may be optionally substituted with moieties as described herein including one or more other hydroxyl substitutents. A phenolic alcohol is an aromatic alcohol having a phenol group as the aromatic ring.

"Aliphatic alcohol" by itself or part of a larger structure refers to a moiety having a non-aromatic carbon bonded to the hydroxyl functional group —OH. The hydroxy-bearing carbon may be unsubstituted (i.e., methyl alcohol) or may have one, two or three optionally substituted branched or unbranched alkyl substituents to define a primary alcohol, or a secondary or tertiary aliphatic alcohol within a linear or cyclic structure. When part of a larger structure, the alcohol may be a substituent of this structure by bonding through the hydroxy bearing carbon, through a carbon of an alkyl or other moiety as described herein to this hydroxyl-bearing carbon or through a substituent of this alkyl or other moiety. An aliphatic alcohol contemplates a non-aromatic cyclic structure (i.e., carbocycles and heterocarbocycles, optionally substituted) in which a hydroxy functional group is bonded to a non-aromatic carbon of its cyclic ring system.

"Arylalkyl" or "heteroarylalkyl" as used herein means a substituent, moiety or group where an aryl moiety is bonded to an alkyl moiety, i.e., aryl-alkyl-, where alkyl and aryl groups are as described above, e.g., $C_6H_5$—$CH_2$— or $C_6H_5$—$CH(CH_3)CH_2$—. An arylalkyl or heteroarylalkyl is associated with a larger structure or moiety through a $sp^3$ carbon of its alkyl moiety.

"Electron withdrawing group" as used herein means a functional group or electronegative atom that draws electron density away from an atom to which it is bonded either inductively and/or through resonance, whichever is more dominant (i.e., a functional group or atom may be electron withdrawing inductively but may overall be electron donating through resonance) and tends to stabilize anions or electron-rich moieties. The electron withdrawing effect is typically transmitted inductively, albeit in attenuated form, to other atoms attached to the bonded atom that has been made electron deficient by the electron withdrawing group (EWG), thus affecting the electrophilicity of a more remote reactive center. Exemplary electron withdrawing groups include, but are not limited to —C(=O), —CN, —$NO_2$, —$CX_3$, —X, —C(=O)OR', —C(=O)N(R')$_2$, —C(=O)R', —C(=O)X, —S(=O)$_2$R', —S(=O)$_2$OR', —S(=O)$_2$NHR', —S(=O)$_2$N(R')$_2$, —P(=O)(OR')$_2$, —P(=O)(CH$_3$)NHR', —NO, —N(R')$_3^+$, wherein X is —F, —Br, —Cl, or —I, and R' in some aspects is, at each occurrence, independently selected from the group consisting of hydrogen and $C_{1-6}$ alkyl, and certain O-linked moieties as described herein such as acyloxy.

Exemplary EWGs can also include aryl groups (e.g., phenyl) depending on substitution and certain heteroaryl groups (e.g., pyridine). Thus, the term "electron withdrawing groups" also includes aryls or heteroaryls that are further substituted with electron withdrawing groups. Typically, electron withdrawing groups on aryls or heteroaryls are —C(=O), —CN, —$NO_2$, —$CX_3$, and —X, wherein X independently selected is halogen, typically —F or —Cl. Depending on their substituents, an alkyl moiety may also be an electron withdrawing group.

"Leaving group ability" relates to the ability of an alcohol-, thiol-, amine- or amide-containing compound corresponding to a Camptothecin in a Camptothecin Conjugate to be released from the Conjugate as a free drug subsequent to activation of a self-immolative event within the Conjugate. That release can be variable without the benefit of a methylene carbamate unit to which its Camptothecin is attached (i.e., when the Camptothecin is directly attached to a self-immolative moiety and does not have an intervening methylene carbamate unit). Good leaving groups are usually weak bases and the more acidic the functional group that is expelled from such conjugates the weaker the conjugate base is. Thus, the leaving group ability of an alcohol-, thiol-, amine- or amide-containing free drug from a Camptothecin will be related to the pKa of the drug's functional group that is expelled from a conjugate in cases where methylene carbamate unit (i.e., one in which a Camptothecin is directly attached to a self-immolative moiety) is not used. Thus, a lower pKa for that functional group will increase its leaving group ability. Although other factors may contribute to release of free drug from conjugates not having the benefit of a methylene carbamate unit, generally a drug having a functional group with a lower pKa value will typically be a better leaving group that a drug attached via a functional group with a higher pKa value. Another consideration is that, a functional group having too low of a pKa value may result in an unacceptable activity profile due to premature loss of the Camptothecin via spontaneous hydrolysis. For conjugates employing a methylene carbamate unit, a common functional group (i.e., a carbamic acid) having a pKa value that allows for efficient release of free drug, without suffering unacceptable loss of Camptothecin, is produced upon self-immolation.

"Succinimide moiety" as used herein refers to an organic moiety comprised of a succinimide ring system, which is present in one type of Stretcher Unit (Z) that is typically further comprised of an alkylene-containing moiety bonded to the imide nitrogen of that ring system. A succinimide moiety typically results from Michael addition of a sulfhydryl group of a Ligand Unit to the maleimide ring system of a Stretcher Unit precursor (Z'). A succinimide moiety is therefore comprised of a thio-substituted succinimide ring system and when present in a Camptothecin Conjugate has its imide nitrogen substituted with the remainder of the Linker Unit of the Camptothecin Conjugate and is optionally substituted with substituent(s) that were present on the maleimide ring system of Z'.

"Acid-amide moiety" as used herein refers to succinic acid having an amide substituent that results from the thio-substituted succinimide ring system of a succinimide moiety having undergone breakage of one of its carbonyl-nitrogen bonds by hydrolysis. Hydrolysis resulting in a succinic acid-amide moiety provides a Linker Unit less likely to suffer premature loss of the Ligand Unit to which it is bonded through elimination of the antibody-thio substituent. Hydrolysis of the succinimide ring system of the thio-substituted succinimide moiety is expected to provide regiochemical isomers of acid-amide moieties that are due to differences in reactivity of the two carbonyl carbons of the succinimide ring system attributable at least in part to any substituent present in the maleimide ring system of the Stretcher Unit precursor and to the thio substituent introduced by the targeting ligand.

The term "Prodrug" as used herein refers to a less biologically active or inactive compound which is transformed within the body into a more biologically active compound via a chemical or biological process (i.e., a chemical reaction or an enzymatic biotransformation). Typically, a biologically active compound is rendered less biologically active (i.e., is converted to a prodrug) by chemically modifying the compound with a prodrug moiety. In some aspects, the prodrug is a Type II prodrug, which are bioactivated outside cells, e.g., in digestive fluids, or in the body's circulation system, e.g., in blood. Exemplary prodrugs are esters and β-D-glucopyranosides.

In many instances, the assembly of the conjugates, linkers and components described herein will refer to reactive groups. A "reactive group" or RG is a group that contains a reactive site (RS) capable of forming a bond with either the components of the Linker unit (i.e., A, W, Y) or the Camptothecin D. RS is the reactive site within a Reactive Group (RG). Reactive groups include sulfhydryl groups to form disulfide bonds or thioether bonds, aldehyde, ketone, or hydrazine groups to form hydrazone bonds, carboxylic or amino groups to form peptide bonds, carboxylic or hydroxy groups to form ester bonds, sulfonic acids to form sulfonamide bonds, alcohols to form carbamate bonds, and amines to form sulfonamide bonds or carbamate bonds.

The following table is illustrative of Reactive Groups, Reactive Sites, and exemplary functional groups that can form after reaction of the reactive site. The table is not limiting. One of skill in the art will appreciate that the noted R' and R" portions in the table are effectively any organic moiety (e.g., an alkyl group, aryl group, heteroaryl group, or substituted alkyl, aryl, or heteroaryl, group) which is compatible with the bond formation provided in converting RG to one of the Exemplary Functional Groups. It will also be appreciated that, as applied to the embodiments of the present invention, R' may represent one or more components of the self-stabilizing linker or optional secondary linker, as the case may be, and R" may represent one or more components of the optional secondary linker, Camptothecin, stabilizing unit, or detection unit, as the case may be.

| RG | RS | Exemplary Functional Groups |
| --- | --- | --- |
| 1) R'—SH | —S— | R'—S—R", R'—S—S—R" |
| 2) R'—C(=O)OH | —C(=O)— | R'—C(=O)NH—R" |
| 3) R'—C(=O)ONHS | —C(=O)— | R'—C(=O)NH—R" |
| 4) R'S(=O)$_2$—OH | —S(=O)$_2$— | R'S(=O)$_2$NH—R" |
| 5) R'—CH$_2$—X (X is Br, I, Cl) | —CH$_2$— | R'—CH$_2$—S—R" |
| 6) R'—NH$_2$ | —N— | R'—NHC(=O)R" |

EMBODIMENTS

A number of embodiments of the invention are described below, which are not meant to limit the invention in any way, are followed by a more detailed discussion of the components that make up the conjugates. One of skill in the art will understand that each of the conjugates identified and any of the selected embodiments thereof is meant to include the full scope of each component and linker.

Camptothecin Conjugates

In one principle embodiment, provided herein are camptothecin conjugates having a formula:

L-(Q-D)$_p$ or a salt thereof, wherein

L is a Ligand Unit;

the subscript p is an integer of from 1 to 16;

Q is a Linker Unit having a formula selected from the group consisting of:

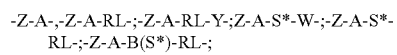

-Z-A-,-Z-A-RL-;-Z-A-RL-Y-;Z-A-S\*-W-;-Z-A-S\*-RL-;-Z-A-B(S\*)-RL-;

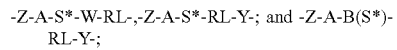

-Z-A-S\*-W-RL-,-Z-A-S\*-RL-Y-; and -Z-A-B(S\*)-RL-Y-;

wherein Z is a Stretcher Unit,

A is a bond or a Connecter Unit;

B is a Parallel Connector Unit;

S\* is a Partitioning Agent;

W is a Peptide Unit;

RL is a Releasable Unit;

Y is a Spacer Unit; and

D is a Drug Unit selected from the group consisting of:

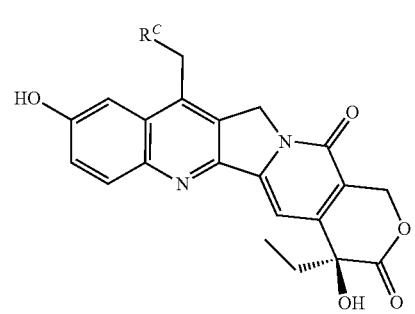

CPT3

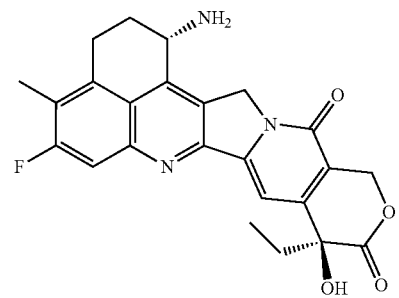

CPT4

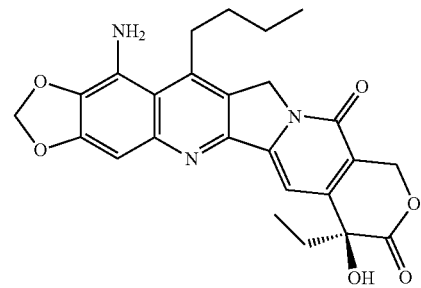

CPT1

-continued

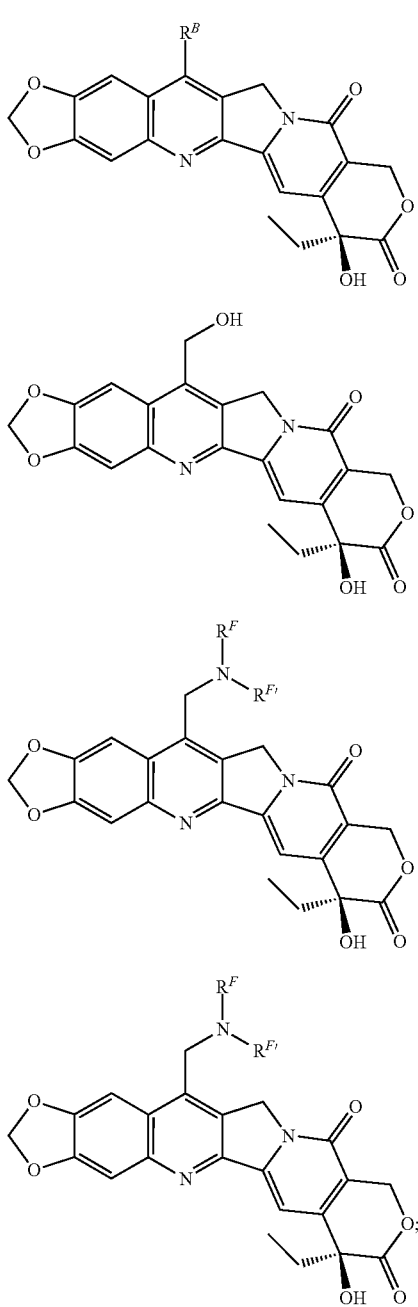

CPT2

CPT5

CPT6

CPT6 wherein $R^B$ is a member selected from the group consisting of H, $C_1$-$C_8$ alkyl, $C_1$-$C_8$ haloalkyl, $C_3$-$C_8$ cycloalkyl, ($C_3$-$C_8$ cycloalkyl)-$C_1$-$C_4$ alkyl-, phenyl and phenyl-$C_1$-$C_4$ alkyl-;
$R^C$ is a member selected from the group consisting of $C_1$-$C_6$ alkyl and $C_3$-$C_6$ cycloalkyl;
each $R^F$ and $R^{F'}$ is a member independently selected from the group consisting of —H, $C_1$-$C_8$ alkyl, $C_1$-$C_8$ hydroxyalkyl, $C_1$-$C_8$ aminoalkyl, ($C_1$-$C_4$alkylamino)-$C_1$-$C_8$ alkyl-, N,N—($C_1$-$C_4$ hydroxyalkyl)($C_1$-$C_4$ alkyl)amino-$C_1$-$C_8$ alkyl-, N,N-di($C_1$-$C_4$ alkyl)amino-$C_1$-$C_8$ alkyl-, N—($C_1$-$C_4$ hydroxyalkyl)-$C_1$-$C_8$ aminoalkyl, $C_1$-$C_8$ alkyl-C(O)—, $C_1$-$C_8$ hydroxyalkyl-C(O)—, $C_1$-$C_8$ aminoalkyl-C(O)—, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl-$C_1$-$C_4$ alkyl-, heteroaryl and heteroaryl-$C_1$-$C_4$ alkyl-, or $R^F$ and $R^{F'}$ are combined with the nitrogen atom to which each is attached to form a 5-, 6- or 7-membered ring having 0 to 3 substituents selected from the group consisting of halogen, $C_1$-$C_4$ alkyl, —OH, —O$C_1$-$C_4$ alkyl, —NH$_2$, —NH$C_1$-$C_4$ alkyl and —N($C_1$-$C_4$ alkyl)$_2$; and wherein the cycloalkyl, heterocycloalkyl, phenyl and heteroaryl portions of $R^B$, $R^C$, $R^F$ and $R^{F'}$ are substituted with from 0 to 3 substituents selected from the group consisting of halogen, $C_1$-$C_4$ alkyl, —OH, —O$C_1$-$C_4$ alkyl, —NH$_2$, —NH$C_1$-$C_4$ alkyl and —N($C_1$-$C_4$ alkyl)$_2$; and wherein the point of attachment of D to Q is through the heteroatom of any one of the hydroxyl or primary or secondary amine functional groups present on CPT1, CPT2, CPT3, CPT4, CPT5, CPT6 or CPT7 when Q is -Z-A-RL-, -Z-A-RL-Y-, -Z-A-S*—RL-, -Z-A-B(S*)-RL-, -Z-A-S*-RL-Y- or -Z-A-B(S*)-RL-Y- in which RL is any one of the Releasable Linkers disclosed herein, or wherein the point of attachment of D to Q is through the oxygen atom of the hydroxyl group substituent in the lactone ring of CPT1, CPT2, CPT3, CPT4, CPT5, CPT6 or CPT7 when Q is -Z-A-, -Z-A-S*-W- or -Z-A-B(S*)W, or when Q is -Z-A-S*-RL-, —Z-A-B(S*)-RL-, -Z-A-S*-W-RL-, or -Z-A-B(S*)-W-RL- in which RL is a Releasable Unit other than a Glucuronide Unit; and provided that at least one of $R^F$ and $R^{F'}$ is —H, when the point of attachment is to the nitrogen atom of the amino group of CPT6, and provided that -Z-A- of -Z-A-RL-, -Z-A-RL-Y-, -Z A-S*-RL-, -Z-A-B(S*)-RL-, -Z-A-S*-RL-Y- and -Z-A-B(S*)-RL-Y- is other than succinimido-caproyl-β-alanyl, optionally having the succinimide ring in hydrolyzed form, when D is CPT1 having attachment through its amino group.

In one group of embodiments, D has formula CPT5.
In one group of embodiments, D has formula CPT2.
In one group of embodiments, D has formula CPT3.
In one group of embodiments, D has formula CPT4.
In one group of embodiments, D has formula CPT1.
In one group of embodiments, D has formula CPT6.
In one group of embodiments, D has formula CPT7.
In one group of embodiments, Q has a formula selected from the group consisting of:

-Z-A-RL- and -Z-A-RL-Y-, wherein RL is a Releasable Linker that is a Glucuronide Unit and the groups Z, A and Y have the meanings provided above and in any one of the embodiments specifically recited herein.

In one group of embodiments, Q has a formula selected from the group consisting of:

-Z-A-S*-RL- and -Z-A-S*-RL-Y-, wherein RL is a Releasable Linker that is a Glucuronide Unit and the groups Z, A, S* and Y have the meanings provided above and in any one of the embodiments specifically recited herein.

In one group of embodiments, Q has a formula selected from the group consisting of:

-Z-A-B(S*)-RL- and -Z-A-B(S*)-RL-Y-, wherein RL is a Releasable Linker that is a Glucuronide Unit and the groups Z, A, S*, B and Y have the meanings provided above and in any one of the embodiments specifically recited herein.

In another group of embodiments, Q has a formula selected from the group consisting of:

-Z-A- or -Z-A-RL-, wherein RL is a Releasable Linker that is other than a Glucuronide Unit and the groups Z and A have the meanings provided above and in any one of the embodiments specifically recited herein.

In another group of embodiments, Q has a formula selected from the group consisting of:

-Z-A-S*-RL- and -Z-A-B(S*)-RL-, wherein RL is a Releasable Linker that is other than a Glucuronide Unit and the groups Z, A, S* and B have the meanings provided above and in any one of the embodiments specifically recited herein.

In another group of embodiments, Q has a formula selected from the group consisting of:

-Z-A-S*-W- and -Z-A-B(S*)W, wherein the groups Z, A, S*, B and W have the meanings provided above and in any one of the embodiments specifically recited herein.

In another group of embodiments, Q has a formula selected from the group consisting of:

-Z-A-S*-W-RL- and -Z-A-B(S*)-W-RL-, wherein RL is a Releasable Linker that is other than a Glucuronide Unit and the groups Z, A, S*, B and W have the meanings provided above and in any one of the embodiments specifically recited herein.

In one group of embodiments, the Camptothecin Conjugates in which Q has the formula of -Z-A-RL-, -Z-A-RL-Y-, -Z-A-S*-RL-, -Z-A-S*-RL-Y-, -Z-A-B(S*)-RL- or -Z-A-B(S*)-RL-Y- and are comprised of a Drug Unit having formula CPT1 are represented by formulae of:

(CPT1iN)

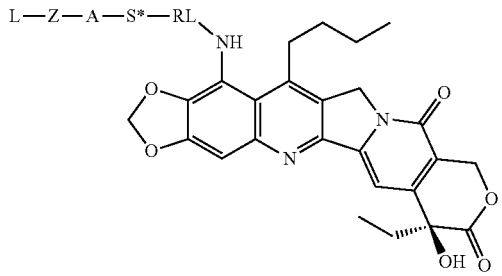

(CPT1iiN)

(CPT1iiiN)

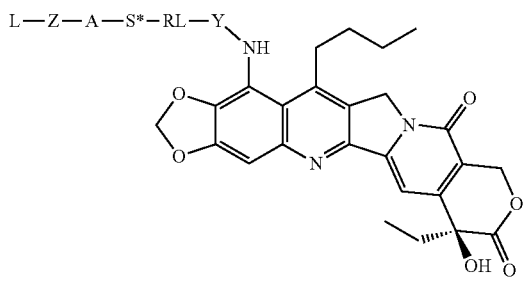

(CPT1ivN)

(CPT1vN)

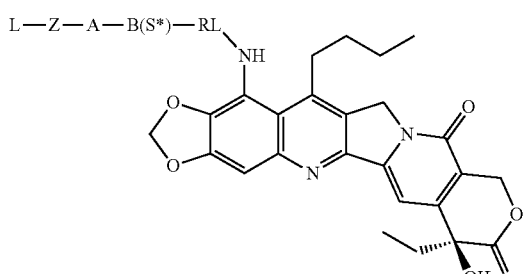

(CPT1viN)

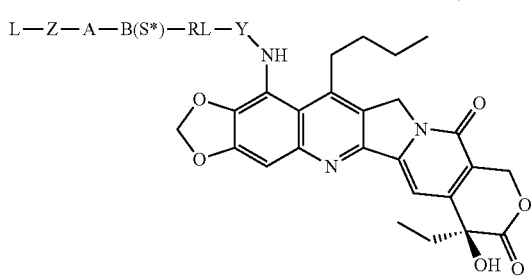

(CPT1iOa)

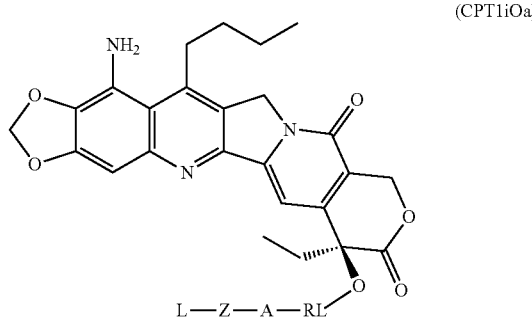

-continued

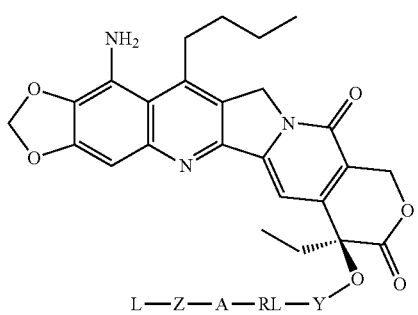
(CPT1iiOa)

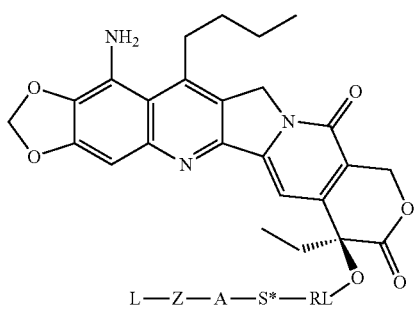
(CPT1iiiOa)

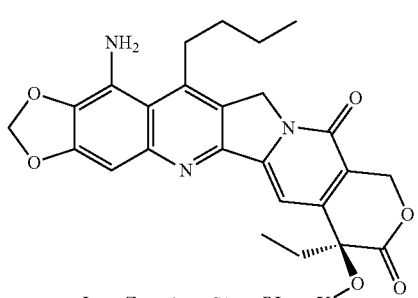
(CPT1ivOa)

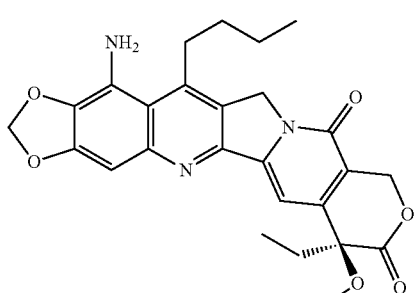
(CPT1vOa)

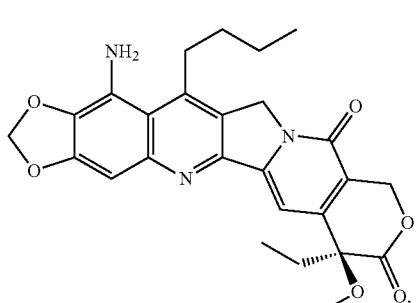
(CPT1viOa)

respectively, wherein RL is any one of the Releasable Linkers disclosed herein, preferably RL is a Glucuronide Unit, and the groups L, Z, A, S*, B and Y have the meanings provided above and in any one of the embodiments specifically recited herein provided that -Z-A- of formula CPT1iN, CPT1iiN, CPT1iiiN, CPT1ivN, CPT1vN and CPT1viN is other than succinimido-caproyl-β-alanyl, optionally having the succinimide ring in hydrolyzed form.

In other embodiments the Camptothecin Conjugates in which Q has the formula of -Z-A-, -Z-A-RL-, -Z-A-S*-W-, -Z-A-B(S*)W, -Z-A-S*-RL-, -Z-A-B(S*)—RL-, -Z-A-S*-W-RL- and -Z-A-B(S*)-W-RL- and are comprised of a Drug Unit having formula CPT1 are represented by formulae of:

(CPT1iOb)

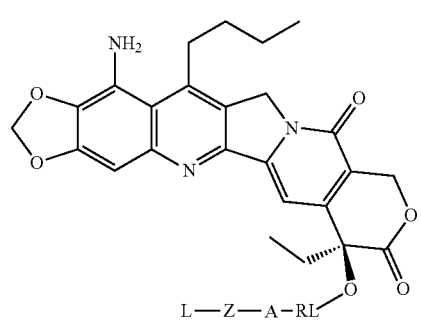

(CPT1iiOb)


(CPT1iiiOb)

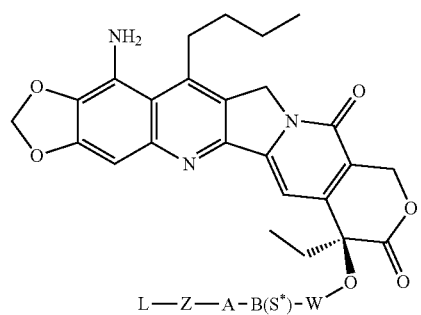

(CPT1ivOb)

(CPT1vOb)

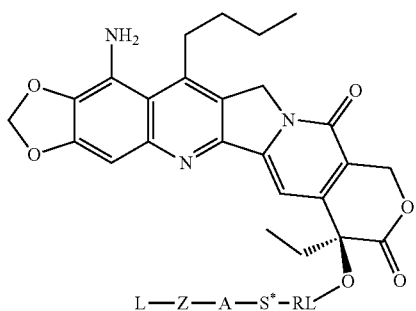

L—Z—A—S*—RL (CPT1viOb)

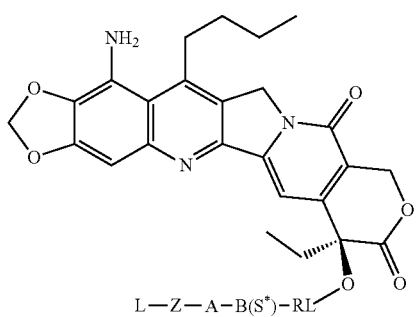

L—Z—A—B(S*)—RL (CPT1viiOb)

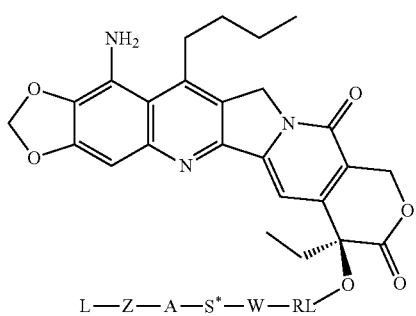

L—Z—A—S*—W—RL (CPT1viiiOb)

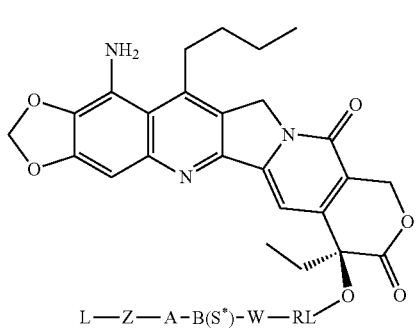

L—Z—A-B(S*)-W—RL (CPT2iOa)

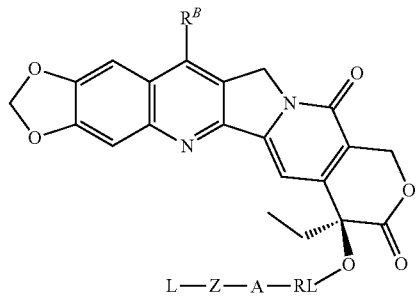

L—Z—A—RL (CPT2iiOa)

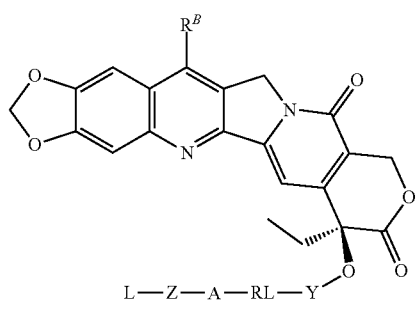

L—Z—A—RL—Y (CPT2iiiOa)

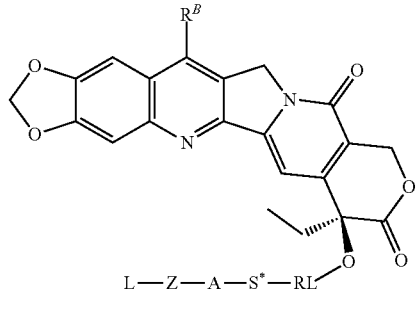

L—Z—A—S*—RL (CPT2ivOa)

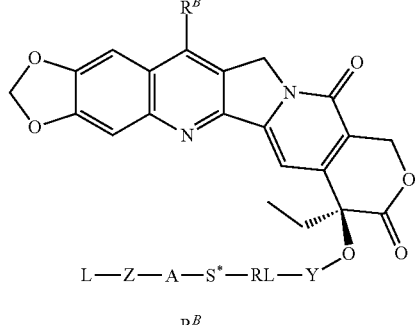

L—Z—A—S*—RL—Y (CPT2vOa)

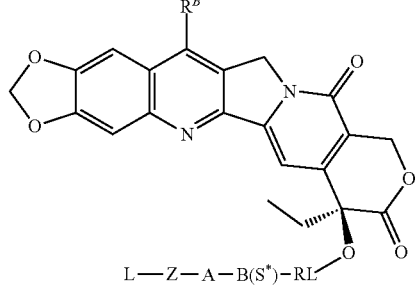

L—Z—A—B(S*)—RL respectively, wherein RL is a Releasable Linker that is other than a Glucuronide Unit and the groups L, Z, A, S*, B and W have the meanings provided above and in any one of the embodiments specifically recited herein.

In another group of embodiments, the Camptothecin Conjugates in which Q has the formula of -Z-A-RL-, -Z-A-RL-Y-, -Z-A-S*-RL-, -Z-A-S*-RL-Y-, -Z-A-B(S*)—RL- or -Z-A-B(S*)-RL-Y- and are comprised of a Drug Unit having formula CPT2 are represented by the formulae of:

(CPT2viOa)

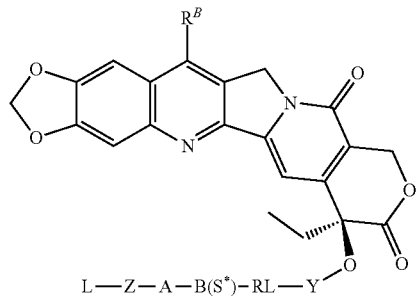

respectively, wherein RL is any one of the Releasable Linkers disclosed herein, preferably RL is a Glucuronide Unit, and the groups L, Z, A, S*, B and Y have the meanings provided above and in any one of the embodiments specifically recited herein.

In other embodiments the Camptothecin Conjugates in which Q has the formula of -Z-A-, -Z-A-RL-, -Z-A-S*-W-, -Z-A-B(S*)W, -Z-A-S*-RL-, -Z-A-B(S*)—RL-, -Z-A-S*-W-RL- and -Z-A-B(S*)-W-RL- and are comprised of a Drug Unit having formula CPT2 are represented by formulae of:

(CPT2iOb)

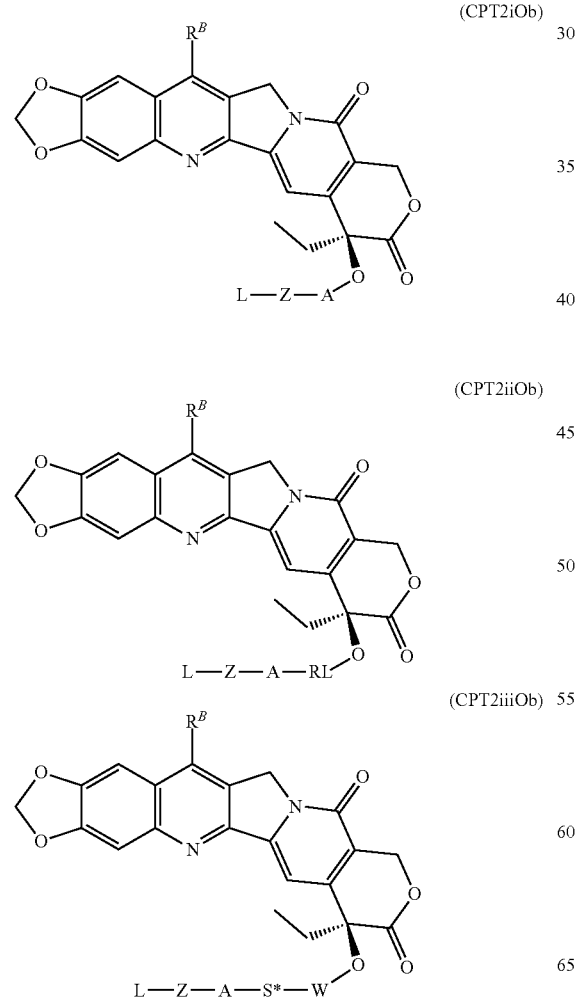

(CPT2ivOb)

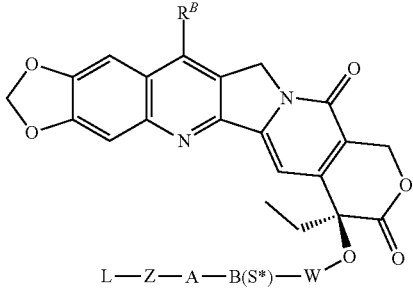

(CPT2vOb)

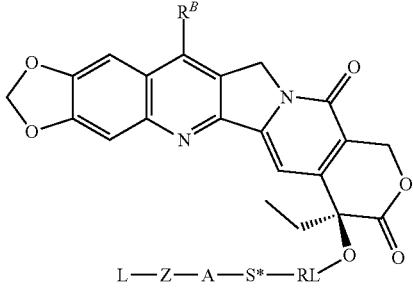

(CPT2viOb)

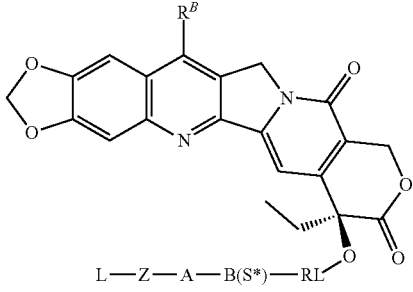

(CPT2viiOb)

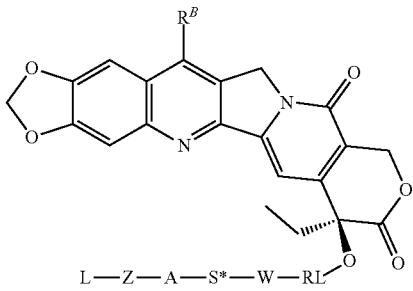

(CPT2viiiOb)

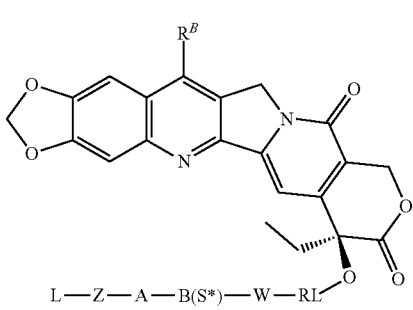

respectively, wherein RL is a Releasable Linker that is other than a Glucuronide Unit and the groups L, Z, A, S*, B and W have the meanings provided above and in any one of the embodiments specifically recited herein.

In one group of embodiments, $R^B$ in formula CPT2iOa, CPT2iiOa, CPT2iiiOa, CPT2ivOa, CPT2vOa, CPT2viOa, CPT2iOb, CPT2iiOb, CPT2iiiOb, CPT2ivOb, CPT2vOb, CPT2viOb, CPT2viiOb or CPT2viiiOb is a moiety selected from the group consisting of —H, $C_1$-$C_8$ alkyl and $C_1$-$C_8$ haloalkyl.

In one group of embodiments, $R^B$ in formula CPT2iOa, CPT2iiOa, CPT2iiiOa, CPT2ivOa, CPT2vOa, CPT2viOa, CPT2iOb, CPT2iiOb, CPT2iiiOb, CPT2ivOb, CPT2vOb, CPT2viOb, CPT2viiOb or CPT2viiiOb is a moiety selected from the group consisting of $C_3$-$C_8$ cycloalkyl, ($C_3$-$C_8$ cycloalkyl)-$C_1$-$C_4$ alkyl-, phenyl and phenyl-$C_1$-$C_4$ alkyl-, and wherein the cycloalkyl and phenyl moieties of $R^B$ are substituted with 0 to 3 substituents selected from the group consisting of halogen, $C_1$-$C_4$ alkyl, —OH, —O$C_1$-$C_4$ alkyl, —NH$_2$, —NH$C_1$-$C_4$ alkyl and —N($C_1$-$C_4$ alkyl)$_2$.

In another group of embodiments, the Camptothecin Conjugates in which Q has the formula of -Z-A-RL-, -Z-A-RL-Y-, -Z-A-S*-RL-, -Z-A-S*-RL-Y-, -Z-A-B(S*)—RL- or -Z-A-B(S*)-RL-Y- and are comprised of a Drug Unit having formula CPT3 are represented by the formulae of:

(CPT3iOa)

(CPT3iiOa)

(CPT3iiiOa)

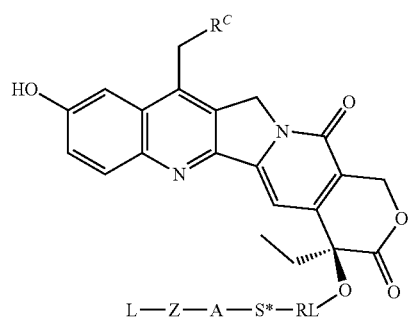

-continued (CPT3ivOa)

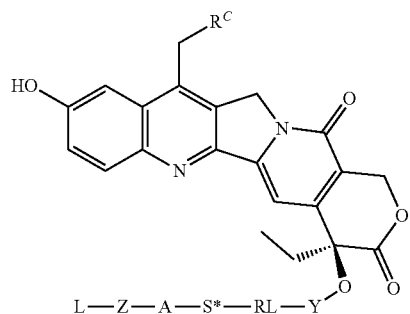

(CPT3vOa)

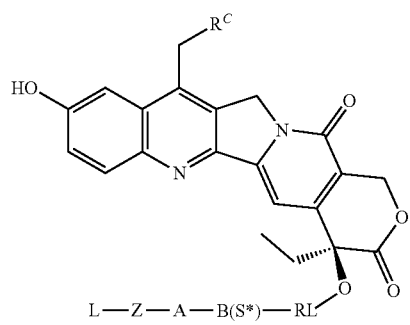

(CPT3viOa)

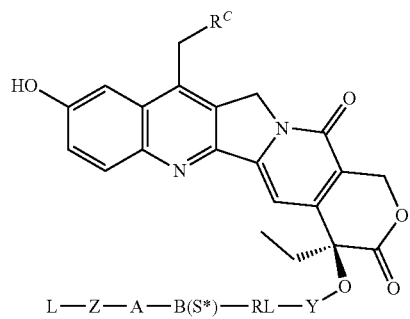

(CPT3iOa')

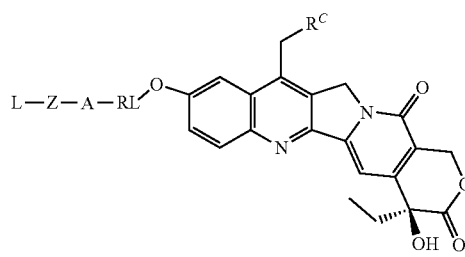

(CPT3iiOa')

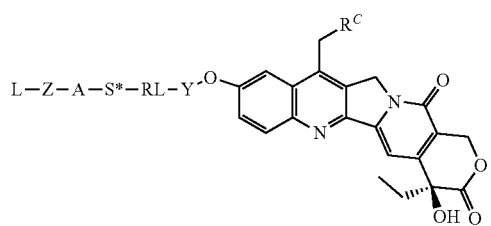

-continued (CPT3iiiO'a)
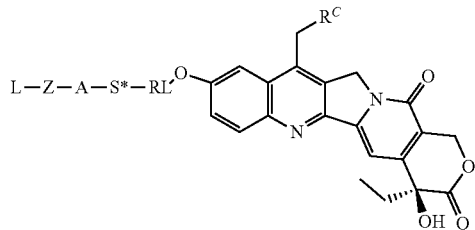

(CPT3ivO'a)
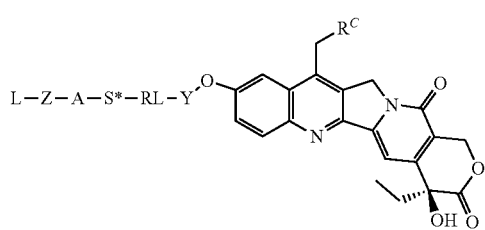

(CPT3vO'a)
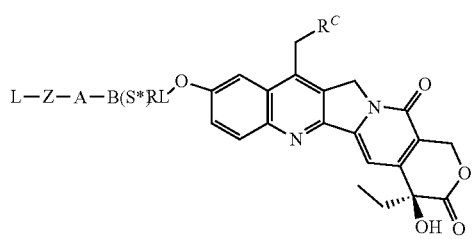

(CPT3viO'a)
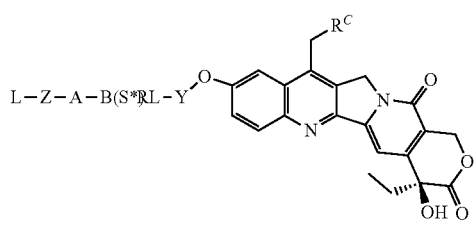

respectively, wherein RL is any one of the Releasable Linkers disclosed herein, preferably RL is a Glucuronide Unit, and the groups L, Z, A, S*, B and Y have the meanings provided above and in any one of the embodiments specifically recited herein.

In other embodiments the Camptothecin Conjugates in which Q has the formula of -Z-A-, -Z-A-RL-, -Z-A-S*-W-, -Z-A-B(S*)W, -Z-A-S*-RL-, -Z-A-B(S*)—RL-, -Z-A-S*-W-RL- and -Z-A-B(S*)-W-RL- and are comprised of a Drug Unit having formula CPT3 are represented by formulae of:

(CPT3iOb)
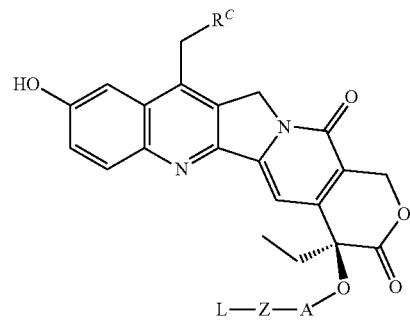

(CPT3iiOb)
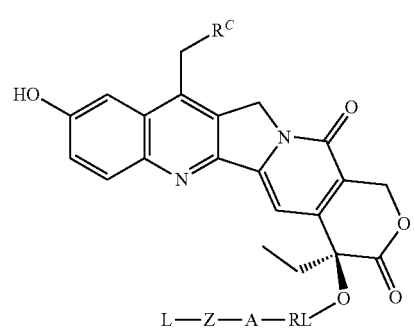

(CPT3iiiOb)
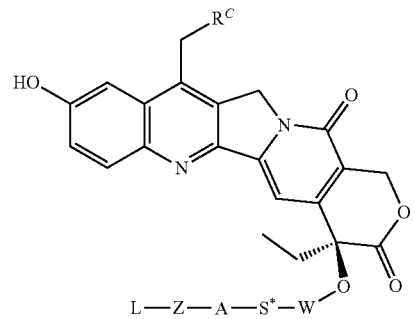

(CPT3ivOb)
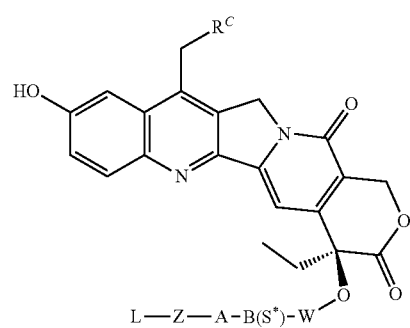

(CPT3vOb)
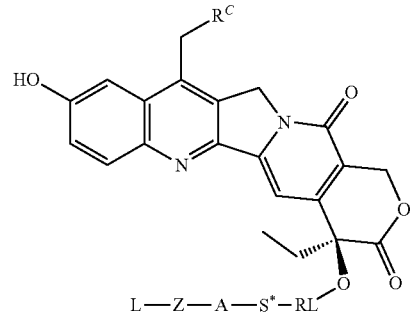

(CPT3viOb)

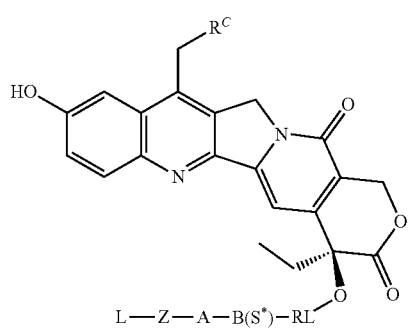

(CPT4vO)

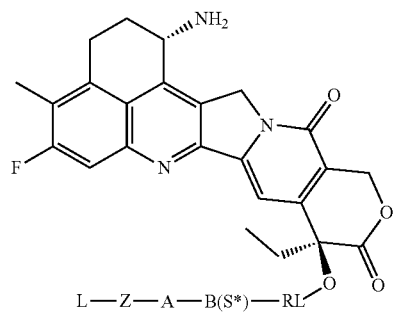

(CPT3viiOb)

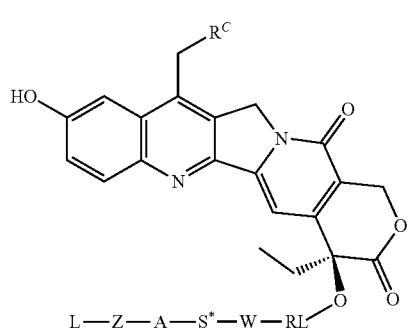

(CPT4viO)

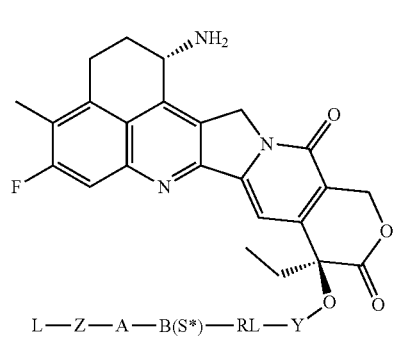

(CPT3viiiOb)

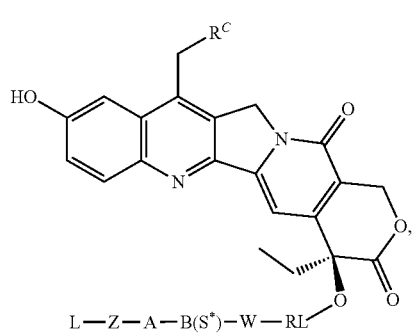

(CPT4iN)

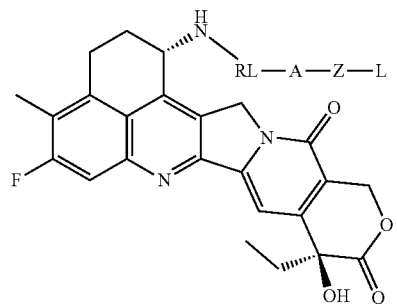

respectively, wherein RL is a Releasable Linker that is other than a Glucuronide Unit and the groups L, Z, A, S*, B and W have the meanings provided above and in any one of the embodiments specifically recited herein.

In one group of embodiments, $R^C$ in formula CPT3iOa, CPT3iiOa, CPT3iiiOa, CPT3ivOa, CPT3vOa, CPT3viOa, CPT3iO'a, CPT3iiO'a, CPT3iiiO'a, CPT3ivO'a, CPT3vO'a, CPT3viO'a, CPT3iOb, CPT3iiOb, CPT3iiiOb, CPT3ivOb, CPT3vOb, CPT3viOb, CPT3viiOb or CPT3viiiOb is $C_1$-$C_6$ alkyl.

In one group of embodiments, $R^C$ in formula CPT3iOa, CPT3iiOa, CPT3iiiOa, CPT3ivOa, CPT3vOa, CPT3viOa, CPT3iO'a, CPT3iiO'a, CPT3iiiO'a, CPT3ivO'a, CPT3vO'a, CPT3viO'a, CPT3iOb, CPT3iiOb, CPT3iiiOb, CPT3ivOb, CPT3vOb, CPT3viOb, CPT3viiOb or CPT3viiiOb is $C_3$-$C_6$ cycloalkyl.

(CPT4iiN)

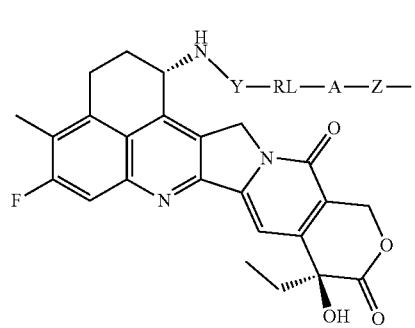

In another group of embodiments, the Camptothecin Conjugates in which Q has the formula of -Z-A-RL-, -Z-A-RL-Y-, -Z-A-S*-RL-, -Z-A-S*-RL-Y-, -Z-A-B(S*)—RL- or -Z-A-B(S*)-RL-Y- and are comprised of a Drug Unit having formula CPT4, and are represented by the formulae of:

(CPT4vN)

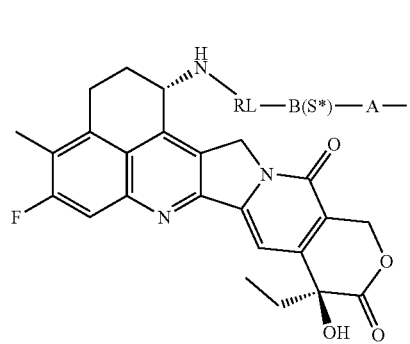

-continued

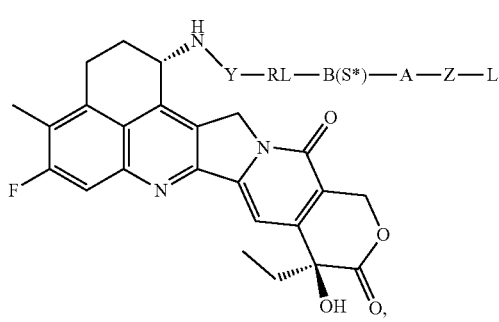
(CPT4viN)

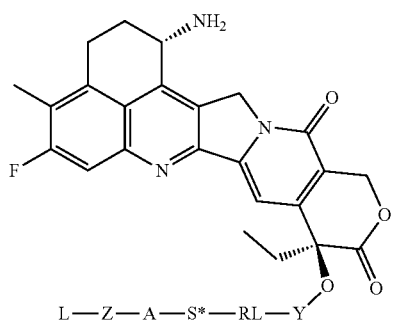
(CPT4ivO)

respectively, wherein RL is any one of the Releasable Linkers disclosed herein, preferably RL is a Glucuronide Unit, and the groups L, Z, A, S*, B and Y have the meanings provided above and in any one of the embodiments specifically recited herein.

In other embodiments the Camptothecin Conjugates in which Q has the formula of -Z-A-, -Z-A-RL-, -Z-A-S*-W-, -Z-A-B(S*)W, -Z-A-S*-RL-, -Z-A-B(S*)—RL-, -Z-A-S*-W-RL- and -Z-A-B(S*)-W-RL- and are comprised of a Drug Unit having formula CPT4 are represented by formulae of:

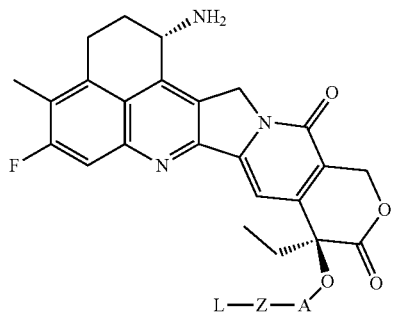
(CPT4iOb)

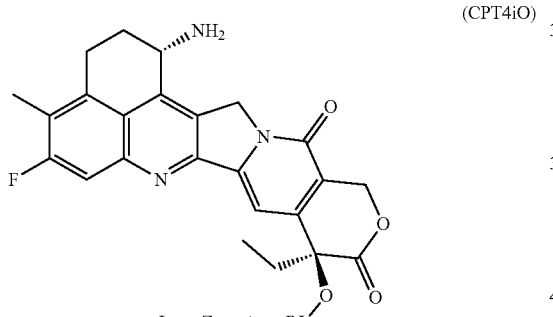
(CPT4iO)

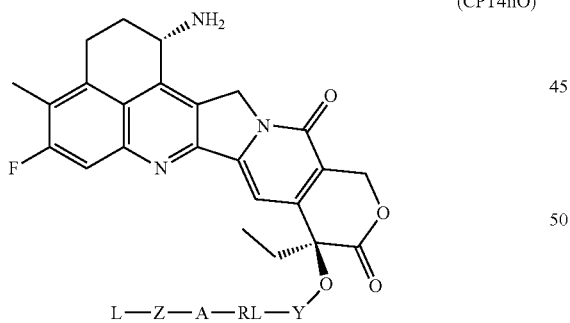
(CPT4iiO)

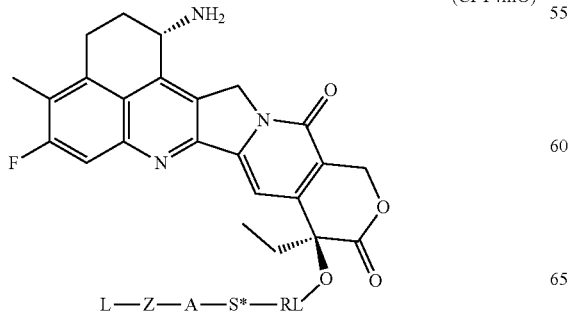
(CPT4iiiO)

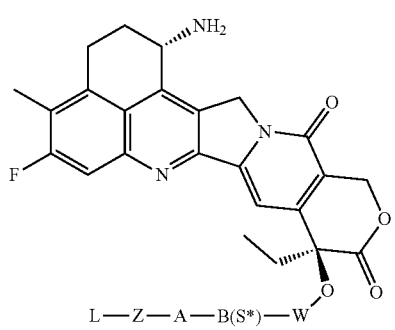
(CPT4ivOb)

(CPT4vOb)

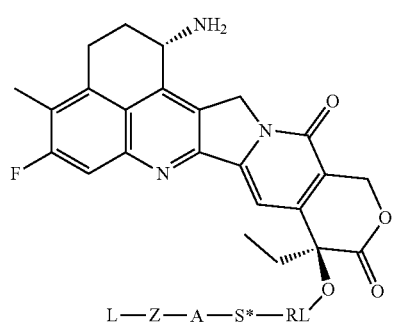

L—Z—A—S*—RL'

(CPT4viOb)

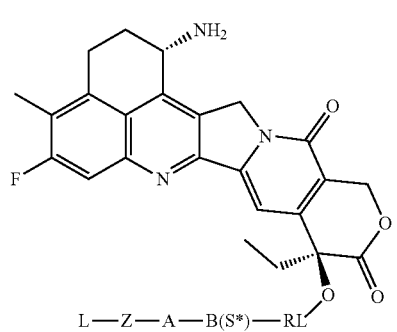

L—Z—A—B(S*)—RL'

(CPT4viiOb)

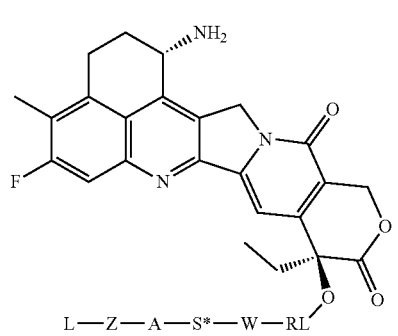

L—Z—A—S*—W—RL'

(CPT4viiiOb)

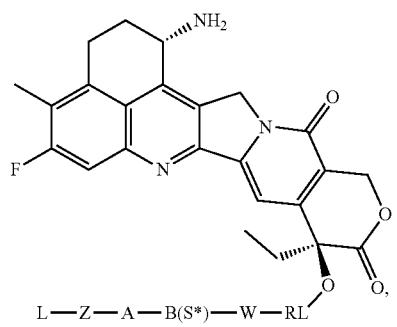

L—Z—A—B(S*)—W—RL', (CPT5iOa)

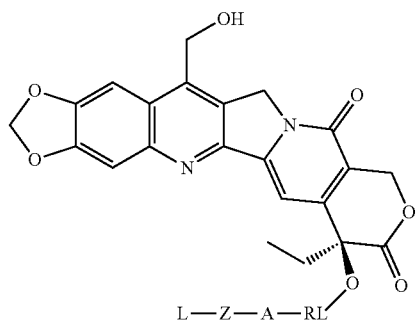

L—Z—A—RL'

(CPT5iiOa)

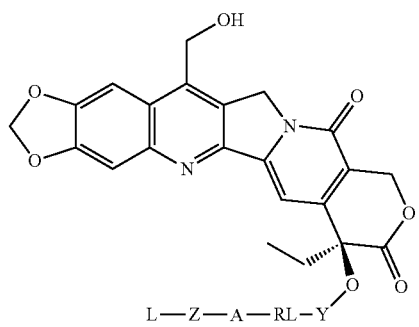

L—Z—A—RL—Y'

(CPT5iiiOa)

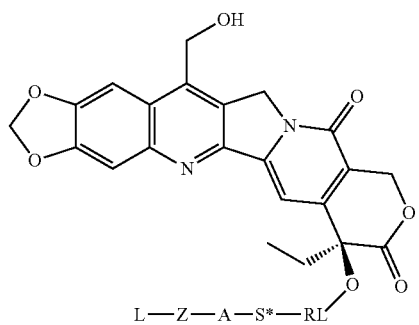

L—Z—A—S*—RL'

(CPT5ivOa)

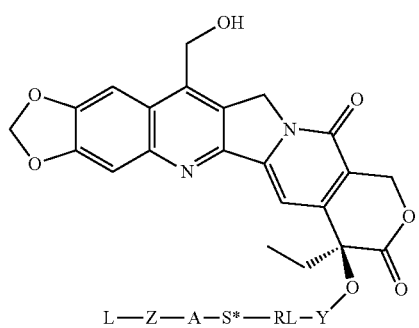

L—Z—A—S*—RL—Y'

(CPT5vOa)

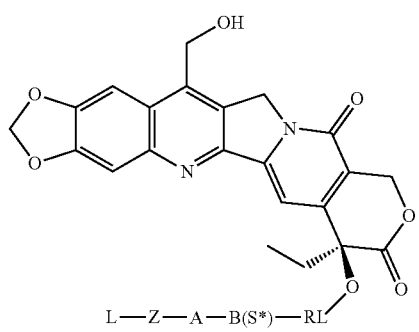

L—Z—A—B(S*)—RL' respectively, wherein RL is a Releasable Linker that is other than a Glucuronide Unit and the groups L, Z, A, S*, B and W have the meanings provided above and in any one of the embodiments specifically recited herein.

In another group of embodiments, the Camptothecin Conjugates in which Q has the formula of -Z-A-RL-, -Z-A-RL-Y-, -Z-A-S*-RL-, -Z-A-S*-RL-Y-, -Z-A-B(S*)—RL- or -Z-A-B(S*)-RL-Y- and are comprised of a Drug Unit having formula CPT5 are represented by the formulae of:

(CPT5viOa)
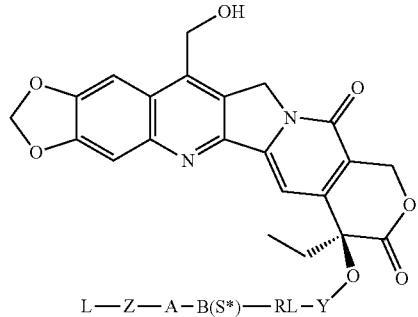

(CPT5vO'a)
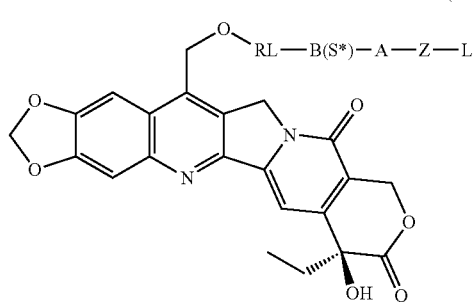

(CPT5iO'a)
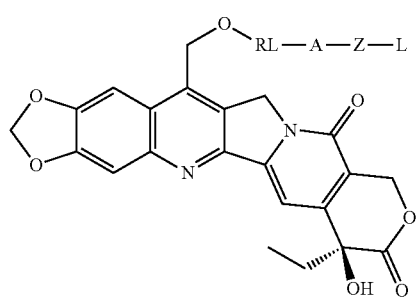

(CPT5viO'a)
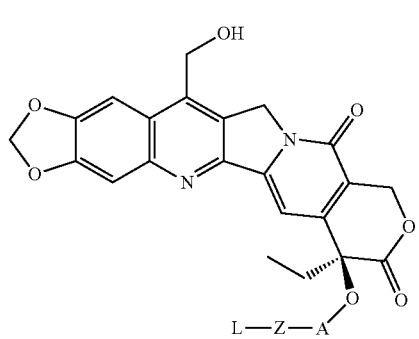

(CPT5iiO'a)
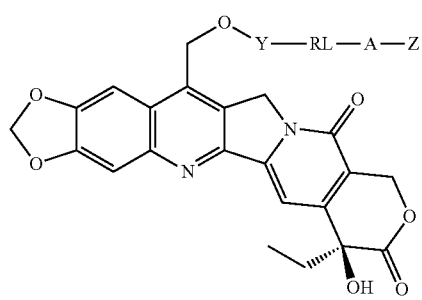

respectively, wherein RL is any one of the Releasable Linkers disclosed herein, preferably RL is a Glucuronide Unit, and the groups L, Z, A, S*, B and Y have the meanings provided above and in any one of the embodiments specifically recited herein.

In other embodiments the Camptothecin Conjugates in which Q has the formula of -Z-A-, -Z-A-RL-, -Z-A-S*-W-, -Z-A-B(S*)W, -Z-A-S*-RL-, -Z-A-B(S*)—RL-, -Z-A-S*-W-RL- and -Z-A-B(S*)-W-RL- and are comprised of a Drug Unit having formula CPT5 are represented by formulae of:

(CPT5iiiO'a)
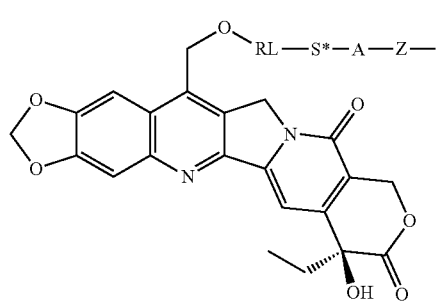

(CPT5iOb)
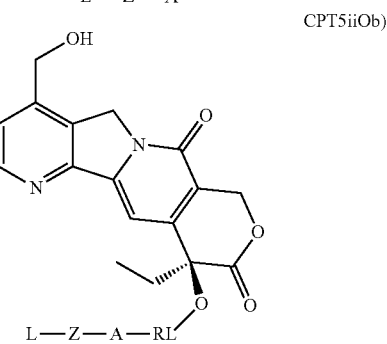

(CPT5ivO'a)
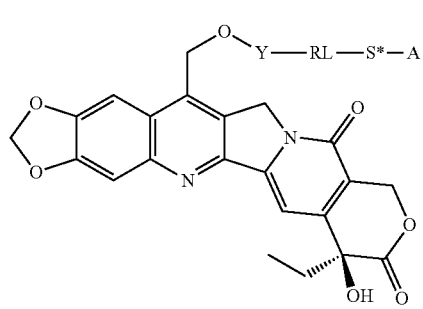

CPT5iiOb)

(CPT5iiiOa)

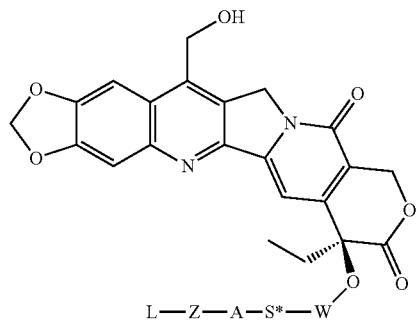

(CPT5ivOb)

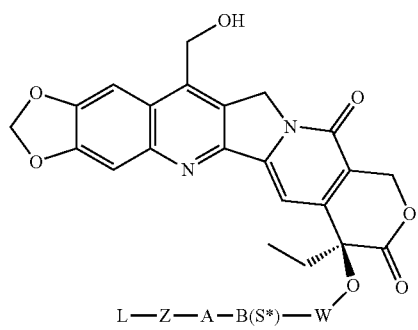

(CPT5vOb)

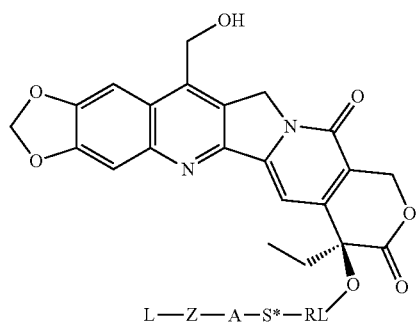

(CPT5viOb)

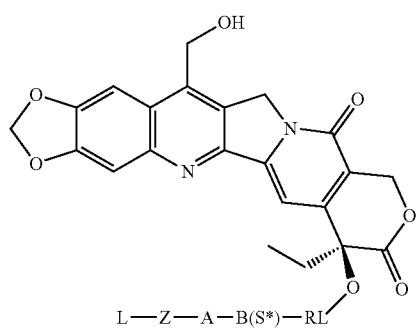

(CPT5viiOb)

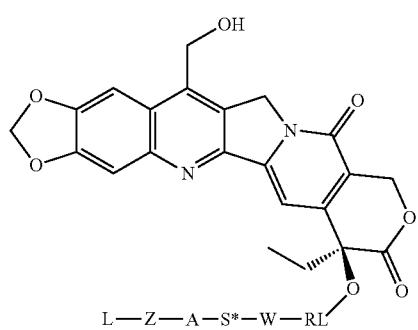

(CPT5viiiOb)

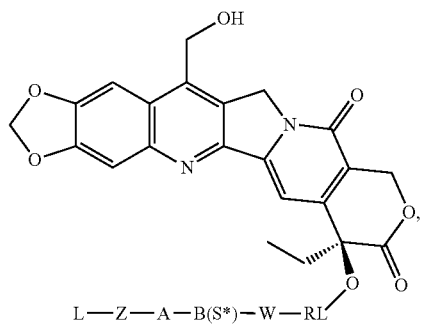

respectively, wherein RL is a Releasable Linker that is other than a Glucuronide Unit and the groups L, Z, A, S*, B and W have the meanings provided above and in any one of the embodiments specifically recited herein.

In another group of embodiments, the Camptothecin Conjugates in which Q has the formula of -Z-A-RL-, -Z-A-RL-Y-, -Z-A-S*-RL-, -Z-A-S*-RL-Y-, -Z-A-B(S*)—RL- or -Z-A-B(S*)-RL-Y- and are comprised of a Drug Unit having formula CPT6 are represented by the formulae of:

(CPT6iN)

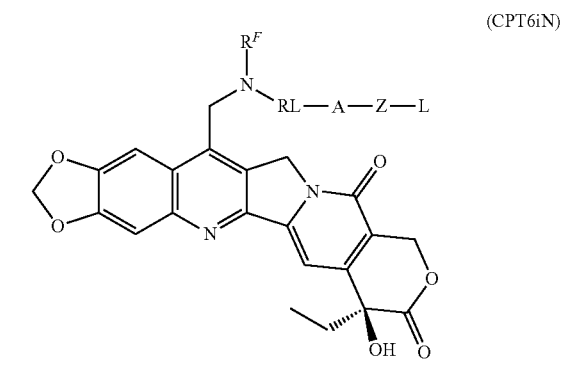

(CPT6iiN)

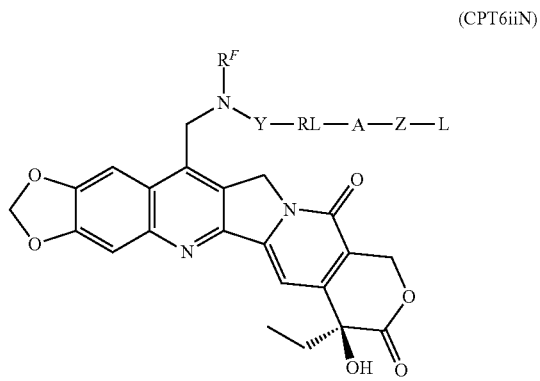

(CPT6iiiN)
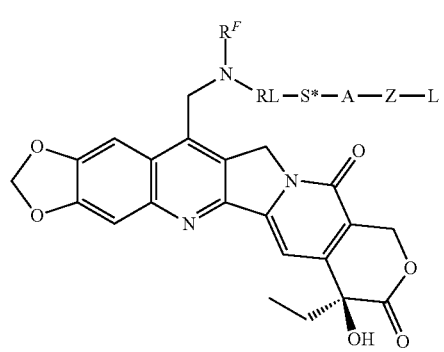
(CPT6ivN)
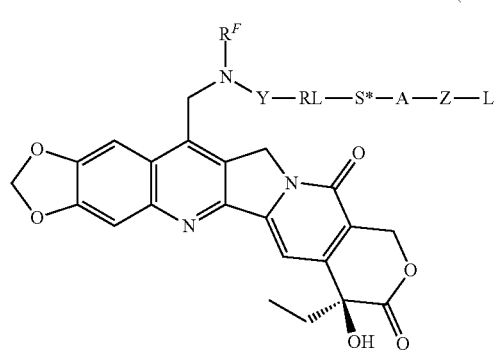
(CPT6vN)
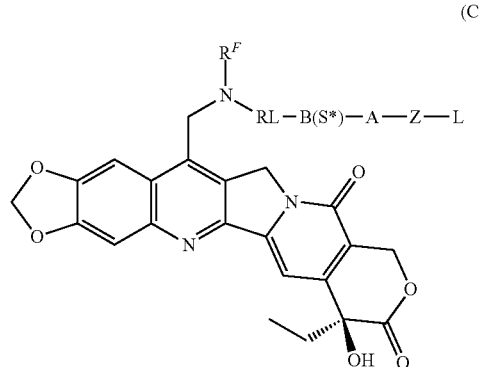
(CPT6viN)
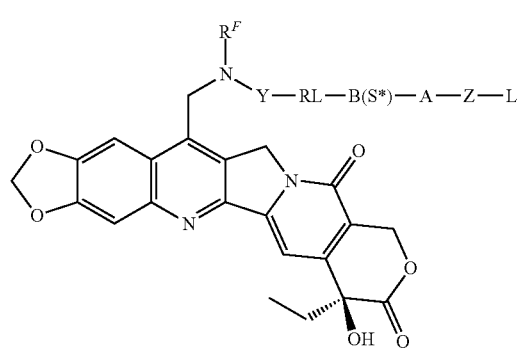
(CPT6iOa)
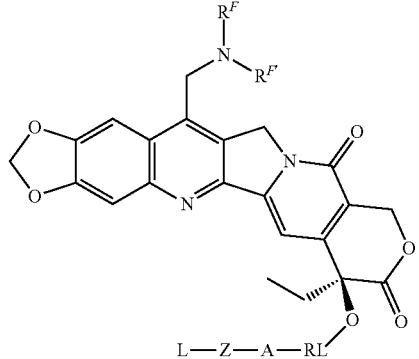
(CPT6iiOa)
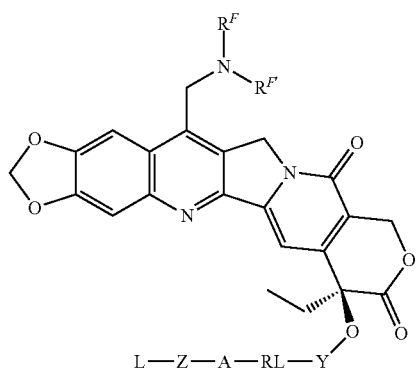
(CPT6iiiOa)
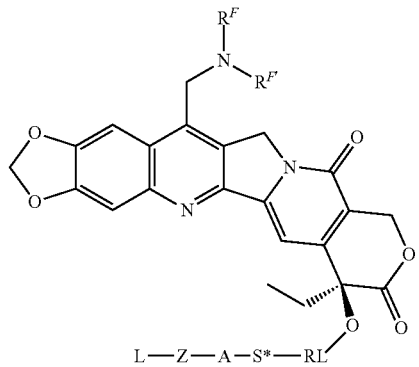
(CPT6ivOa)
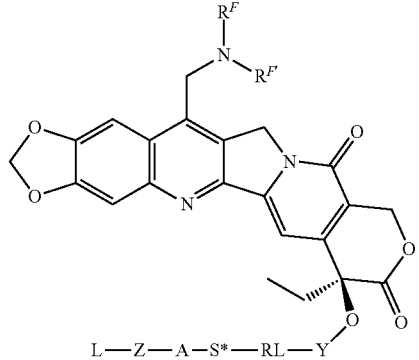

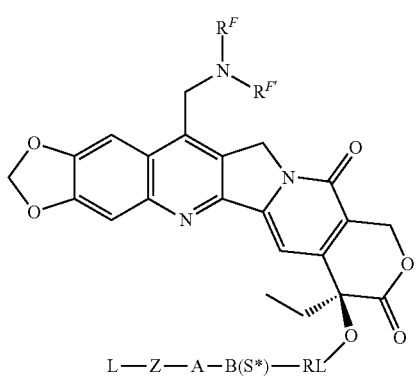
(CPT6vOa)

L—Z—A—B(S*)—RL

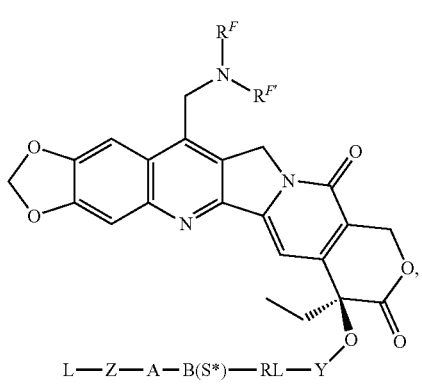
(CPT6viOa)

L—Z—A—B(S*)—RL—Y respectively, wherein RL is any one of the Releasable Linkers disclosed herein, preferably RL is a Glucuronide Unit, and the groups L, Z, A, S*, B and Y have the meanings provided above and in the any of the embodiments specifically recited herein.

In other embodiments the Camptothecin Conjugates in which Q has the formula of -Z-A-, -Z-A-RL-, -Z-A-S*-W-, -Z-A-B(S*)W, -Z-A-S*-RL-, -Z-A-B(S*)—RL-, -Z-A-S*-W-RL- and -Z-A-B(S*)-W-RL- and are comprised of a Drug Unit having formula CPT6 are represented by formulae of:

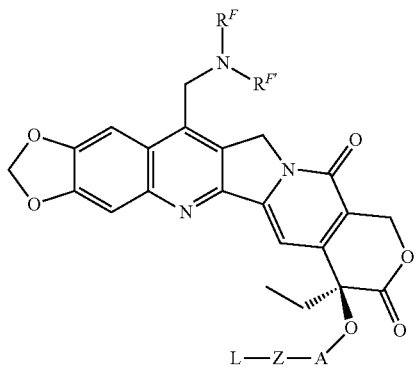
(CPT6iOb)

L—Z—A

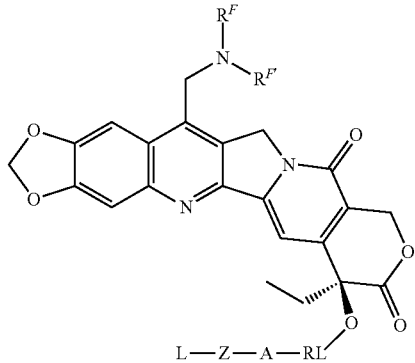
(CPT6iiOb)

L—Z—A—RL

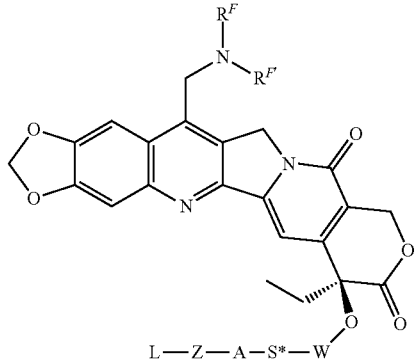
(CPT6iiiOb)

L—Z—A—S*—W

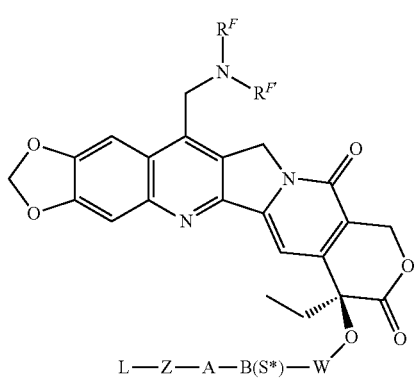
(CPT6ivOb)

L—Z—A—B(S*)—W

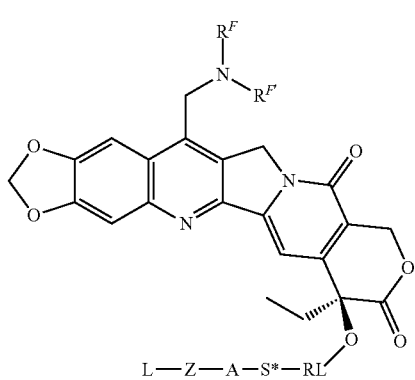
(CPT6vOb)

L—Z—A—S*—RL

-continued

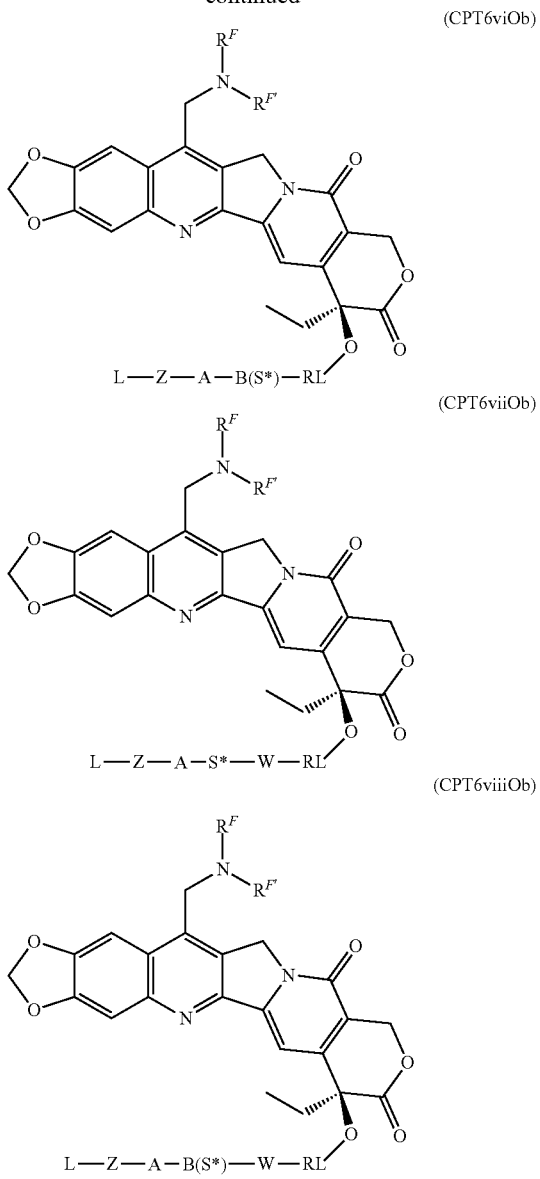

respectively, wherein RL is a Releasable Linker that is other than a Glucuronide Unit and the groups L, Z, A, S*, B and W have the meanings provided above and in any one of the embodiments specifically recited herein.

In one group of embodiments, $R^F$ in formula CPT6iN, CPT6iiN, CPT6iiiN, CPT6ivN, CPT6vN or CPT6viN is —H.

In one group of embodiments, both $R^F$ and $R^{F'}$ in formula CPT6iOa, CPT6iiOa, CPT6iiiOa, CPT6ivOa, CPT6vOa, CPT6viOa, CPT6iOb, CPT6iiOb, CPT6iiiOb, CPT6ivOb, CPT6vOb, CPT6viOb, CPT6viiOb or CPT6viiiOb is —H.

In one group of embodiments, $R^F$ in formula CPT6iN, CPT6iiN, CPT6iiiN, CPT6ivN, CPT6vN or CPT6viN is a moiety selected from the group consisting of $C_1$-$C_8$ alkyl, $C_1$-$C_8$ hydroxyalkyl, $C_1$-$C_8$ aminoalkyl, ($C_1$-$C_4$alkylamino)-$C_1$-$C_8$ alkyl-, N,N—($C_1$-$C_4$ hydroxyalkyl)($C_1$-$C_4$alkyl)amino-$C_1$-$C_8$ alkyl-, N,N-di($C_1$-$C_4$alkyl)amino-$C_1$-$C_8$ alkyl-, N—($C_1$-$C_4$ hydroxyalkyl)-$C_1$-$C_8$ aminoalkyl-, $C_1$-$C_8$ alkyl-C(O)—, $C_1$-$C_8$ hydroxyalkyl-C(O)—, and $C_1$-$C_8$ aminoalkylC(O)—.

In one group of embodiments, $R^F$ in formula CPT6iN, CPT6iiN, CPT6iiiN, CPT6ivN, CPT6vN or CPT6viN is a moiety selected from the group consisting of $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl $C_1$-$C_4$ alkyl-, heteroaryl and heteroaryl-$C_1$-$C_4$ alkyl-, and wherein cycloalkyl, heterocycloalkyl, phenyl and heteroaryl moieties of $R^F$ are substituted with from 0 to 3 substituents independently selected from the group consisting of halogen, $C_1$-$C_4$ alkyl, —OH, —O$C_1$-$C_4$ alkyl, —NH$_2$, —NH$C_1$-$C_4$ alkyl and —N($C_1$-$C_4$ alkyl)$_2$.

In one group of embodiments, $R^F$ in formula CPT6iN, CPT6iiN, CPT6iiiN, CPT6ivN, CPT6vN or CPT6viN is a moiety independently selected from the group consisting of —H, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl, phenyl, phenyl-$C_1$-$C_4$ alkyl-, diphenyl $C_1$-$C_4$ alkyl, heteroaryl and heteroaryl-$C_1$-$C_4$ alkyl-, and wherein cycloalkyl, heterocycloalkyl, phenyl and heteroaryl moieties of $R^F$ are substituted with from 0 to 3 substituents independently selected from the group consisting of halogen, $C_1$-$C_4$ alkyl, —OH, —O$C_1$-$C_4$ alkyl, —NH$_2$, —NH$C_1$-$C_4$ alkyl and —N($C_1$-$C_4$ alkyl)$_2$.

In one group of embodiments, $R^F$ and $R^{F'}$ in formula CPT6iOa, CPT6iiOa, CPT6iiiOa, CPT6ivOa, CPT6vOa, CPT6viOa, CPT6iOb, CPT6iiOb, CPT6iiiOb, CPT6ivOb, CPT6vOb, CPT6viOb, CPT6viiOb or CPT6viiiOb are combined with the nitrogen atom to which both are attached to form a 5-, 6- or 7-membered ring having 0 to 3 substituents selected independently from the group consisting of halogen, $C_1$-$C_4$ alkyl, —OH, —O$C_1$-$C_4$ alkyl, —NH$_2$, —NH$C_1$-$C_4$ alkyl and —N($C_1$-$C_4$ alkyl)$_2$.

In one group of embodiments, at least one of $R^F$ and $R^{F'}$ in formula CPT6iOa, CPT6iiOa, CPT6iiiOa, CPT6ivOa, CPT6vOa, CPT6viOa, CPT6iOb, CPT6iiOb, CPT6iiiOb, CPT6ivOb, CPT6vOb, CPT6viOb, CPT6viiOb or CPT6viiiOb is a moiety independently selected from the group consisting of $C_1$-$C_8$ alkyl, $C_1$-$C_8$ hydroxyalkyl, $C_1$-$C_8$ aminoalkyl, ($C_1$-$C_4$alkylamino)-$C_1$-$C_8$ alkyl, N,N—($C_1$-$C_4$ hydroxyalkyl)($C_1$-$C_4$ alkyl)amino-$C_1$-$C_8$ alkyl-, N,N-di($C_1$-$C_4$ alkyl)amino-$C_1$-$C_8$ alkyl-, N—($C_1$-$C_4$ hydroxyalkyl)-$C_1$-$C_8$ aminoalkyl-, $C_1$-$C_8$ alkylC(O)—, $C_1$-$C_8$ hydroxyalkyl-C(O)—, and $C_1$-$C_8$ aminoalkyl-C(O)— and the other is a moiety selected from the group consisting of —H, $C_1$-$C_8$ alkyl, $C_1$-$C_8$ hydroxyalkyl, $C_1$-$C_8$ aminoalkyl, ($C_1$-$C_4$alkylamino)-$C_1$-$C_8$ alkyl-, N,N—($C_1$-$C_4$ hydroxyalkyl)($C_1$-$C_4$alkyl)amino-$C_1$-$C_8$ alkyl-, N,N-di($C_1$-$C_4$alkyl)amino-$C_1$-$C_8$ alkyl-, N—($C_1$-$C_4$ hydroxyalkyl)-$C_1$-$C_8$ aminoalkyl-, $C_1$-$C_8$ alkyl-C(O)—, $C_1$-$C_8$ hydroxyalkyl-C(O)—, and $C_1$-$C_8$ aminoalkylC(O)—.

In one group of embodiments, each $R^F$ and $R^{F'}$ in formula CPT6iO, CPT6iiO, CPT6iiiO, CPT6ivO, CPT6vO or CPT6viO is a moiety independently selected from the group consisting of $C_1$-$C_8$ alkyl, $C_1$-$C_8$ hydroxyalkyl, $C_1$-$C_8$ aminoalkyl, ($C_1$-$C_4$ alkylamino)-$C_1$-$C_8$ alkyl-, N,N—($C_1$-$C_4$ hydroxyalkyl)($C_1$-$C_4$ alkyl)amino-$C_1$-$C_8$ alkyl-, N,N-di($C_1$-$C_4$ alkyl)amino-$C_1$-$C_8$ alkyl-, N—($C_1$-$C_4$ hydroxyalkyl)-$C_1$-$C_8$ aminoalkyl, $C_1$-$C_8$ alkyl-C(O)—, $C_1$-$C_8$ hydroxyalkyl-C(O)—, and $C_1$-$C_8$ aminoalkyl-C(O)—.

In one group of embodiments, at least one of $R^F$ and $R^{F'}$ in formula CPT6iO, CPT6iiO, CPT6iiiO, CPT6ivO, CPT6vO or CPT6viO is a moiety independently selected from the group consisting of $C_3$-$C_{10}$ cycloalkyl, $C_3$-$C_{10}$ cycloalkyl-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl, diphenyl $C_1$-$C_4$ alkyl, heteroaryl and heteroaryl-$C_1$-$C_4$ alkyl-, and wherein the cycloalkyl, heterocycloalkyl, phenyl and heteroaryl moieties of $R^F$ or $R^{F'}$ are substituted with from 0 to 3 substituents independently selected from the group consisting of halogen, $C_1$-$C_4$ alkyl, —OH, —O$C_1$-$C_4$ alkyl, —$NH_2$, —NH$C_1$-$C_4$ alkyl and —N($C_1$-$C_4$ alkyl)$_2$, and the other is a moiety selected from the group consisting of —H, $C_1$-$C_8$ alkyl, $C_1$-$C_8$ hydroxyalkyl, $C_1$-$C_8$ aminoalkyl, ($C_1$-$C_4$alkylamino)-$C_1$-$C_8$ alkyl-, N,N—($C_1$-$C_4$ hydroxyalkyl)($C_1$-$C_4$ alkyl)amino-$C_1$-$C_8$ alkyl-, N,N-di($C_1$-$C_4$alkyl)amino-$C_1$-$C_8$ alkyl-, N—($C_1$-$C_4$ hydroxyalkyl)-$C_1$-$C_8$ aminoalkyl-, $C_1$-$C_8$ alkyl-C(O)—, $C_1$-$C_8$ hydroxyalkyl-C(O)—, and $C_1$-$C_8$ aminoalkylC(O)—)$_2$.

In one group of embodiments, at least one of $R^F$ and $R^{F'}$ in formula CPT6iO, CPT6iiO, CPT6iiiO, CPT6ivO, CPT6vO or CPT6viO is a moiety independently selected from the group consisting of $C_3$-$C_{10}$ cycloalkyl, $C_3$-$C_{10}$ cycloalkyl-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl, diphenyl $C_1$-$C_4$ alkyl, heteroaryl and heteroaryl-$C_1$-$C_4$ alkyl-, and the other is a moiety selected from the group consisting of —H, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl $C_1$-$C_4$ alkyl-, heteroaryl and heteroaryl-$C_1$-$C_4$ alkyl-, wherein the cycloalkyl, heterocycloalkyl, phenyl and heteroaryl moieties of $R^F$ and $R^{F'}$ are independently substituted with from 0 to 3 substituents independently selected from the group consisting of halogen, $C_1$-$C_4$ alkyl, —OH, —O$C_1$-$C_4$ alkyl, —$NH_2$, —NH$C_1$-$C_4$ alkyl and —N($C_1$-$C_4$ alkyl)$_2$.

In one group of embodiments, each $R^F$ and $R^{F'}$ in formula CPT6iO, CPT6iiO, CPT6iiiO, CPT6ivO, CPT6vO or CPT6viO is a moiety independently selected from the group consisting of —H, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl $C_1$-$C_4$ alkyl-, heteroaryl and heteroaryl-$C_1$-$C_4$ alkyl-, and wherein the cycloalkyl, heterocycloalkyl, phenyl and heteroaryl moieties of $R^F$ and $R^{F'}$ are independently substituted with 0 to 3 substituents selected from the group consisting of halogen, $C_1$-$C_4$ alkyl, —OH, —O$C_1$-$C_4$ alkyl, —$NH_2$, —NH$C_1$-$C_4$ alkyl and —N($C_1$-$C_4$ alkyl)$_2$.

In another group of embodiments, the Camptothecin Conjugates in which Q has the formula of -Z-A-RL-, -Z-A-RL-Y-, -Z-A-S*-RL-, -Z-A-S*-RL-Y-, -Z-A-B(S*)—RL- or -Z-A-B(S*)-RL-Y- and are comprised of a Drug Unit having formula CPT7 are represented by the formulae of:

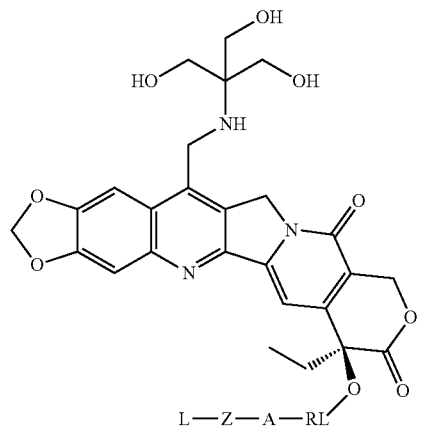
(CPT7iOa)

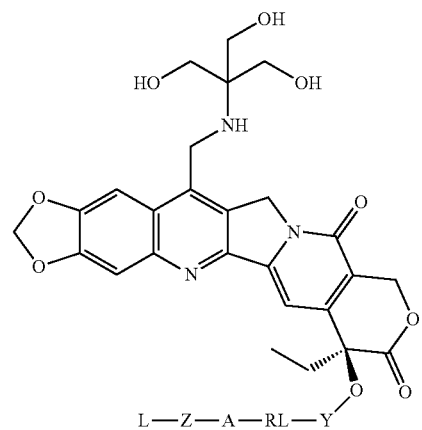
(CPT7iiOa)

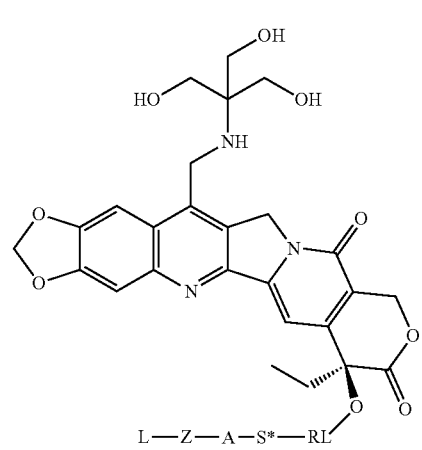
(CPT7iiiOa)

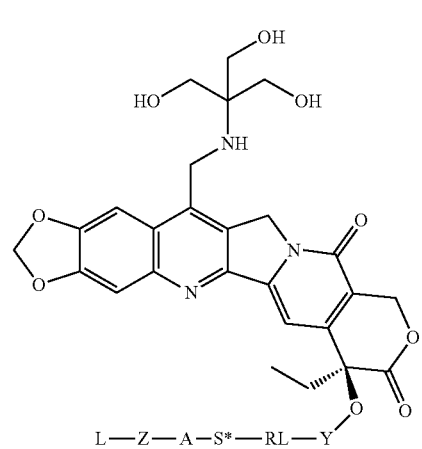
(CPT7ivOa)

51
-continued
(CPT7vOa)
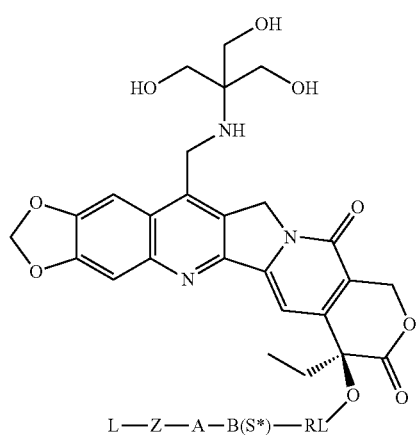
(CPTviOa)
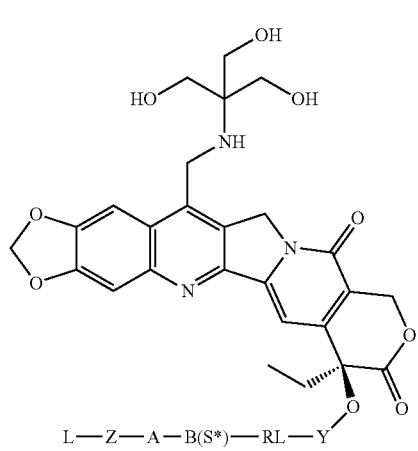
(CPT7iO'a)
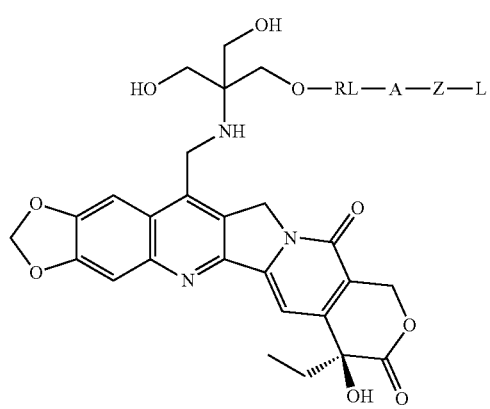
52
-continued
(CPT7iiO'a)
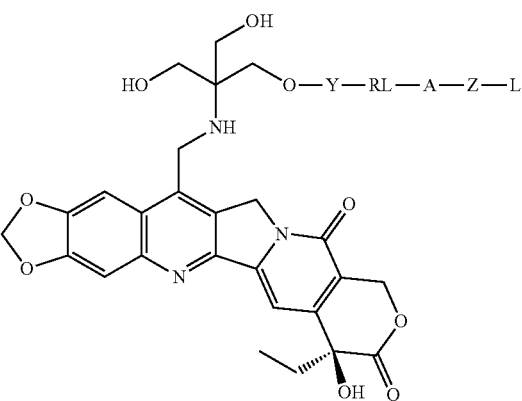
(CPT7iiiO'a)
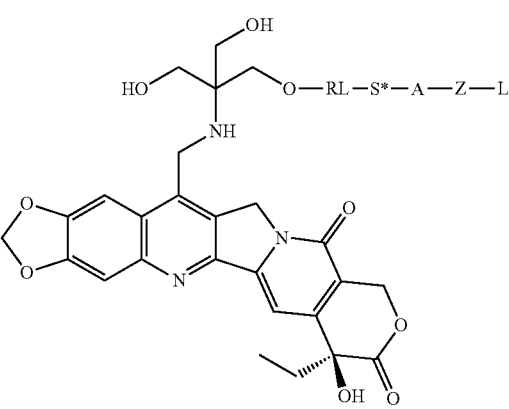
(CPT7ivO'a)

53
-continued (CPT7vO'a)
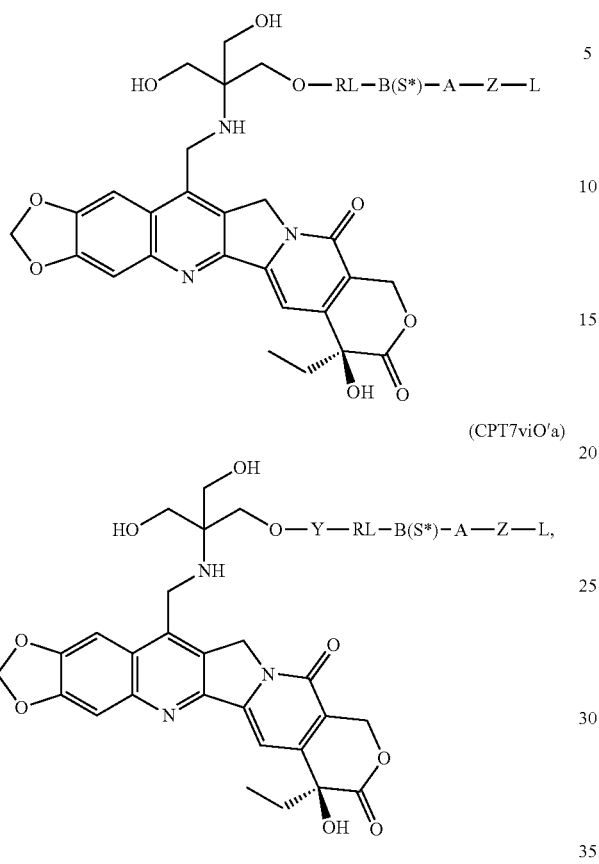

(CPT7viO'a)
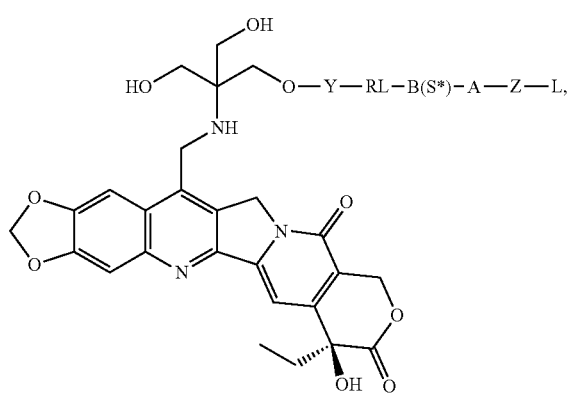

respectively, wherein RL is any one of the Releasable Linkers disclosed herein, preferably RL is a Glucuronide Unit, and the groups L, Z, A, S*, B and Y have the meanings provided above and in any one of the embodiments specifically recited herein.

In other embodiments the Camptothecin Conjugates in which Q has the formula of -Z-A-, -Z-A-RL-, -Z-A-S*-W-, -Z-A-B(S*)W, -Z-A-S*-RL-, -Z-A-B(S*)—RL-, -Z-A-S*-W-RL- and -Z-A-B(S*)-W-RL- and are comprised of a Drug Unit having formula CPT5 are represented by formulae of:

(CPT7iOb)
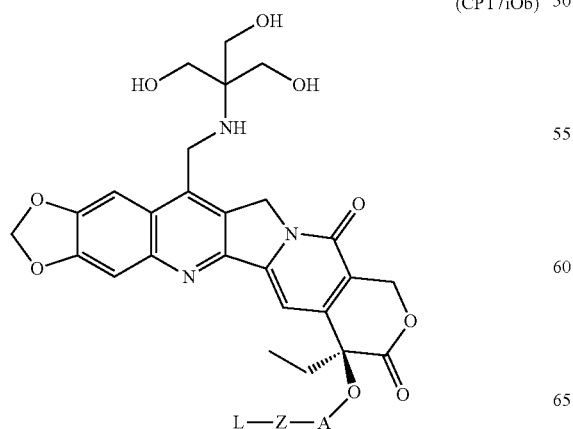

54
-continued (CPT7iiOb)
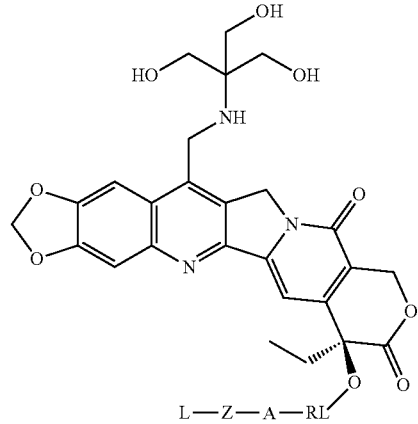

(CPT7iiiOb)
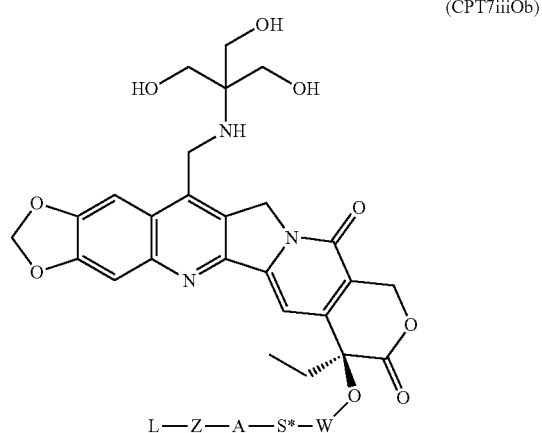

(CPT7ivOb)
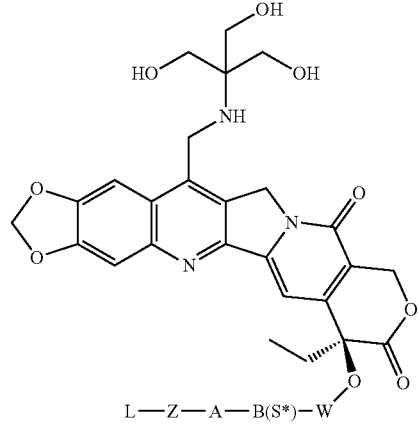

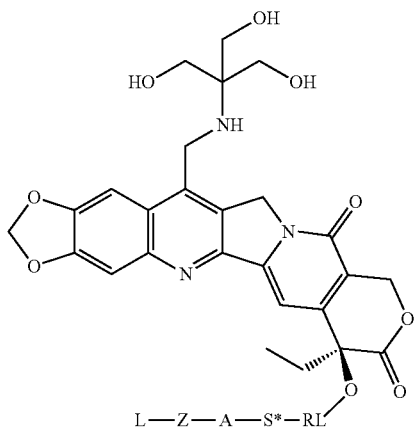
(CPT7vOb)

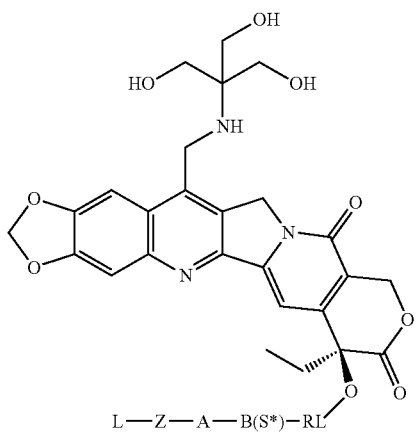
(CPT7viOb)

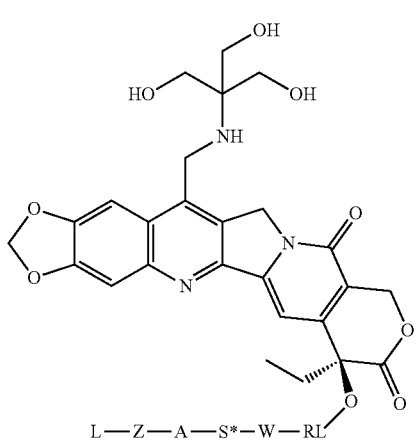
(CPT7viiOb)

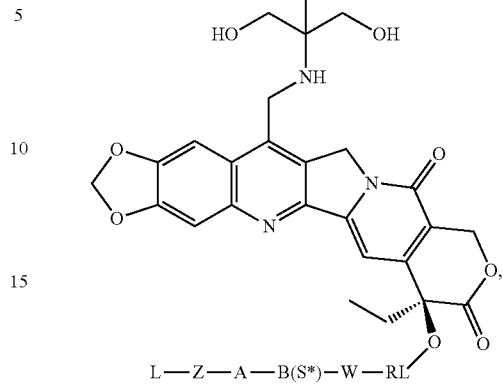
(CPT7viiiOb)

respectively, wherein RL is a Releasable Linker that is other than a Glucuronide Unit and the groups L, Z, A, S*, B and W have the meanings provided above and in any one of the embodiments specifically recited herein.

Camptothecin-Linker Compounds

In some embodiments, when preparing the Camptothecin Conjugates, it will be desirable to synthesize the full drug-linker combination prior to conjugation to a targeting agent. In such embodiments, Camptothecin-Linker Compounds as described herein, are intermediate compounds. In those embodiments, the Stretcher Unit in a Camptothecin-Linker compound is not yet covalently attached to the Ligand Unit (i.e., is a Stretcher Unit precursor, Z'), and therefore has a functional group for conjugation to a targeting ligand. In one embodiment, a Camptothecin-Linker compound is comprised of a Camptothecin compound (shown herein as formulae CPT1, CPT2, CPT3, CPT4, CPT5, CPT6 and CPT7), and a Linker Unit (Q) comprising a Glucuronide Unit as a Releasable Linker (RL) through which the Ligand Unit is connected to the Camptothecin.

In another embodiment, a Camptothecin-Linker Compound comprises a Camptothecin compound of formulae CPT1, CPT2, CPT3, CPT4, CPT5, CPT6 or CPT7, and a Linker Unit (Q) comprising a Releasable Linker (RL) that is other than a Glucuronide Unit through which the Ligand Unit is connected to the conjugated Camptothecin compound. Thus, in either embodiment the Linker Unit comprises, in addition to RL, a Stretcher Unit precursor (Z') comprising a functional group for conjugation to a targeting agent that is the precursor to the Ligand Unit and thus is capable of (directly or indirectly) connecting the RL to the Ligand Unit. In some of those embodiments a Parallel Connector Unit (B) when it is desired to add a Partitioning Agent (S*) as a side chain appendage. In any one of those embodiments, a Connector Unit (A) is present when it is desirable to add more distance between the Stretcher Unit and RL.

In one group of embodiments, a Camptothecin-Linker compound is comprised of a Camptothecin compound having formula CPT1, CPT2, CPT3, CPT4, CPT5, CPT6 or CPT7, and a Linker Unit (Q), wherein Q comprises a Releasable Linker (RL) that is a Glucuronide Unit, directly attached to a Stretcher Unit precursor (Z') or indirectly to Z' through attachment to intervening component(s) of the Camptothecin-Linker compound's Linker Unit (i.e., A, S* and/or B(S*)), wherein Z' is comprised of a functional group capable of forming a covalent bond to a targeting agent.

In another group of embodiments, a Camptothecin-Linker Compound is comprised of a Camptothecin having formula CPT1, CPT2, CPT3, CPT4, CPT5, CPT6 or CPT7, and a Linker Unit (Q), wherein Q comprises a Releasable Linker (RL) that is other than a Glucuronide Unit (RL), directly attached to a Stretcher Unit precursor (Z') or indirectly to Z' through attachment to intervening component(s) of the Camptothecin-Linker Compound's Linker Unit (i.e., A, S* and/or B(S*)), wherein Z' is comprised of a functional group capable of forming a covalent bond to a targeting agent.

In the context of the Camptothecin Conjugates and/or the Camptothecin-Linker Compounds—the assembly is best described in terms of its component groups. While some procedures are also described herein, the order of assembly and the general conditions to prepare the Conjugates and Compounds will be well understood by one of skill in the art.

Component Groups

Ligand Units:

In some embodiments of the invention, a Ligand Unit is present. The Ligand Unit (L-) is a targeting agent that specifically binds to a target moiety. In one group of embodiments, the Ligand Unit specifically and selectively binds to a cell component (a Cell Binding Agent) or to another target molecule of interest. The Ligand Unit acts to target and present the camptothecin (CPT1, CPT2, CPT3, CPT4, CPT5, CPT6 or CPT7) to the particular target cell population with which the Ligand Unit interacts due to the presence of its targeted component or molecule and allows for subsequent release of free drug within (i.e., intracellularly) or within the vicinity of the target cells (i.e., extracellularly). Ligand Units, L, include, but are not limited to, proteins, polypeptides and peptides. Suitable Ligand Units include, for example, antibodies, e.g., full-length antibodies and antigen binding fragments thereof, interferons, lymphokines, hormones, growth factors and colony-stimulating factors, vitamins, nutrient-transport molecules (such as, but not limited to, transferrin), or any other cell binding molecule or substance. In some embodiments, the Ligand Unit (L) is from an antibody or a non-antibody protein targeting agent.

In one group of embodiments a Ligand Unit is bonded to Q (a Linker Unit) which comprises a Glucuronide Releasable Linker. As noted above, still other linking components can be present in the conjugates described herein to serve the purpose of providing additional space between the Camptothecin drug compound and the Ligand Unit (e.g., a Stretcher Unit and optionally a Connector Unit, A), or providing attributes to the composition to increases solubility (e.g., a Partitioning Agent, S*). In some of those embodiments, the Ligand Unit is bonded to Z of the Linker Unit via a heteroatom of the Ligand Unit. Heteroatoms that may be present on a Ligand Unit for that bonding include sulfur (in one embodiment, from a sulfhydryl group of a targeting ligand), oxygen (in one embodiment, from a carboxyl or hydroxyl group of a targeting ligand) and nitrogen, optionally substituted (in one embodiment, from a primary or secondary amine functional group of a targeting ligand or in another embodiment from an optionally substituted amide nitrogen). Those heteroatoms can be present on the targeting ligand in the ligand's natural state, for example in a naturally occurring antibody, or can be introduced into the targeting ligand via chemical modification or biological engineering.

In one embodiment, a targeting agent that is a precursor to a Ligand Unit has a sulfhydryl functional group so that the Ligand Unit is bonded to the Linker Unit via the sulfur atom of the sulfhydryl functional group.

In another embodiment, a targeting agent that is a precursor to Ligand Unit has one or more lysine residues that are capable of reacting with activated esters (such esters include, but are not limited to, N-hydroxysuccimide, pentafluorophenyl, and p-nitrophenyl esters) of a Stretcher Unit precursor of a Camptothecin-Linker Compound intermediate and thus provides an amide bond consisting of the nitrogen atom of the Ligand Unit and the C=O group of the Linker Unit's Stretcher Unit.

In yet another aspect, a targeting agent that is a precursor to Ligand Unit has one or more lysine residues capable of chemical modification to introduce one or more sulfhydryl groups. In those embodiments, the Ligand Unit is covalently attached to the Linker Unit via the sulfhydryl functional group's sulfur atom. The reagents that can be used to modify lysines in that manner include, but are not limited to, N-succinimidyl S-acetylthioacetate (SATA) and 2-Iminothiolane hydrochloride (Traut's Reagent).

In another embodiment, a targeting agent that is a precursor to a Ligand Unit has one or more carbohydrate groups capable of modification to provide one or more sulfhydryl functional groups. The chemically modified Ligand Unit in a Camptothecin Conjugate is bonded to a Linker Unit component (e.g., a Stretcher Unit) via the sulfur atom of the sulfhydryl functional group.

In yet another embodiment, a targeting agent that is a precursor to a Ligand Unit has one or more carbohydrate groups that can be oxidized to provide an aldehyde (—CHO) functional group (see, e.g., Laguzza, et al, 1989, *J. Med Chem.* 32(3):548-55). In these embodiments, the corresponding aldehyde interacts with a reactive site on a Stretcher Unit precursor to form a bond between the Stretcher Unit and the Ligand Unit. Reactive sites on a Stretcher Unit precursor that capable of interacting with a reactive carbonyl-containing functional group on a targeting Ligand Unit include, but are not limited to, hydrazine and hydroxylamine. Other protocols for the modification of proteins for the attachment of Linker Units (Q) or related species are described in Coligan et al., *Current Protocols in Protein Science*, vol. 2, John Wiley & Sons (2002) (incorporated herein by reference).

In some aspects, a targeting agent that is a precursor to a Ligand Unit t is capable of forming a bond by interacting with a reactive functional group on a Stretcher Unit precursor (Z') to form a covalent bond between the Stretcher Unit (Z) and the Ligand Unit, which corresponds in structure to the targeting agent. The functional group of Z' having that capability for interacting with a targeting agent will depend on the nature of the targeting agent that will correspond in structure to the Ligand Unit. In some embodiments, the reactive group is a maleimide that is present on a Stretcher Unit prior to its attachment to form a Ligand Unit (i.e., a maleimide moiety of a Stretcher Unit precursor). Covalent attachment of a Ligand Unit to a Stretcher Unit is accomplished through a sulfhydryl functional group of a targeting agent that is a precursor to a Ligand Unit interacting with the maleimide functional group of Z' to form a thio-substituted succinimide. The sulfhydryl functional group can be present on the targeting agent in the targeting agent's natural state, for example, in a naturally occurring residue, or can be introduced into the targeting agent via chemical modification or by biological engineering.

In still another embodiment, the Ligand Unit is from an antibody and the sulfhydryl group is generated by reduction of an interchain disulfide of the antibody. Accordingly, in some embodiments, the Linker Unit is conjugated to a cysteine residue from reduced interchain disulfide(s).

In yet another embodiment, the Ligand Unit is from an antibody and the sulfhydryl functional group is chemically introduced into the antibody, for example, by introduction of a cysteine residue. Accordingly, in some embodiments, the Linker Unit (with or without an attached Camptothecin) is conjugated to a Ligand Unit through an introduced cysteine residue of a Ligand Unit.

It has been observed for bioconjugates that the site of drug conjugation can affect a number of parameters including ease of conjugation, drug-linker stability, effects on biophysical properties of the resulting bioconjugates, and in vitro cytotoxicity. With respect to drug-linker stability, the site of conjugation of a drug-linker moiety to a Ligand Unit can affect the ability of the conjugated drug-linker moiety to undergo an elimination reaction, in some instances, to cause premature release of free drug. Sites for conjugation on a targeting agent include, for example, a reduced interchain disulfide as well as selected cysteine residues at engineered sites. In some embodiments conjugation methods to form Camptothecin Conjugates as described herein use thiol residues at genetically engineered sites that are less susceptible to the elimination reaction (e.g., positions 239 according to the EU index as set forth in Kabat) in comparison to conjugation methods that use thiol residues from a reduced disulfide bond. In other embodiments conjugation methods to form Camptothecin Conjugates as described herein use thiol residues resulting from interchain disulfide bond reduction.

In some embodiments, a Camptothecin Conjugate comprises a non-immunoreactive protein, polypeptide, or peptide as its Ligand Unit. Accordingly, in some embodiments, the Ligand Unit is from a non-immunoreactive protein, polypeptide, or peptide. Examples include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, somatostatin, lectins and apoprotein from low density lipoprotein.

Particularly preferred Ligand Units are from antibodies. Accordingly, in any one of the embodiments described herein, the Ligand Unit is from an antibody. Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest in some embodiments is prepared by using any technique known in the art, which provides for production of antibody molecules by continuous cell lines in culture.

Useful monoclonal antibodies include, but are not limited to, human monoclonal antibodies, humanized monoclonal antibodies, or chimeric human-mouse (or other species) monoclonal antibodies. The antibodies include full-length antibodies and antigen binding fragments thereof. Human monoclonal antibodies can be made by any of numerous techniques known in the art (e.g., Teng et al., 1983, *Proc. Natl. Acad Sci. USA*. 80:7308-7312; Kozbor et al., 1983, *Immunology Today* 4:72-79; and Olsson et al., 1982, *Meth. Enzymol.* 92:3-16).

An antibody useful for practicing the invention is an intact antibody or a functionally active fragment, derivative or analog of an antibody, wherein the antibody or fragment thereof is capable of immunospecific binding to target cells (e.g., cancer cell antigens, viral antigens, or microbial antigens) or other antibodies that are bound to tumor cells or matrix. In this regard, "functionally active" means that the fragment, derivative or analog is able to immunospecifically binds to target cells. To determine which CDR sequences bind the antigen, synthetic peptides containing the CDR sequences in some embodiments are used in binding assays with the antigen by a binding assay method known in the art (e.g., the BIA core assay) (See, e.g., Rabat et al., 1991, *Sequences of Proteins of Immunological Interest*, Fifth Edition, National Institute of Health, Bethesda, Md; Rabat E et al, 1980, *J. Immunology* 125(3):961-969).

Other useful antibodies include fragments of antibodies such as, but not limited to, F(ab')$_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which in some embodiments are made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.) Such chimeric and humanized monoclonal antibodies in some embodiments are produced by recombinant DNA techniques known in the art, for example using methods described in International Publication No. WO 87/02671; European Patent Publication No. 0184187; European Patent Publication No. 0171496; European Patent Publication No. 0 173494; International Publication No. WO 86/01533; U.S. Pat. No. 4,816,567; Berter et al., *Science* (1988) 240: 1041-1043; Liu et al., *Proc. Nat'l Acad Sci. USA* (1987) 84: 3439-3443; Liu et al., *J. Immunol.* (1987) 139: 3521-3526; Sun et al., *Proc. Natl. Acad Sci. USA* (1987) 84: 214-218; Nishimura et al., *Cancer. Res*. (1987) 47: 999-1005; Wood et al., *Nature* (1985) 314: 446-449; Shaw et al, *J. Natl. Cancer Inst*. (1988) 80: 1553-1559; Morrison, *Science* (1985) 229: 1202-1207; Oi et al., *BioTechniques* (1986) 4: 214-221; U.S. Pat. No. 5,225,539; Jones et al, *Nature* (1986) 321: 552-525; Verhoeyan et al., *Science* (1988) 239: 1534-1536; and Beidler et al, *J. Immunol.* (1988) 141: 4053-4060; each of which is incorporated herein by reference in its entirety.

Completely human antibodies in some instances (e.g., when immunogenicity to a non-human or chimeric antibody may occur) are more desirable and in some embodiments are produced using transgenic mice that are incapable of expressing endogenous immunoglobulin heavy and light chains genes, but which are capable of expressing human heavy and light chain genes.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, PEGylation, phosphorylation, amidation, derivitization by known protecting/blocking groups, proteolytic cleavage, linkage to a cellular antibody unit or other protein, etc. In some embodiments one or more of those numerous chemical modifications are carried out by known techniques including, but not limited to, specific chemical cleavage, acetylation, formylation, metabolic synthesis in the presence of tunicamycin, etc. In other embodiments, an analog or derivative of an antibody contains one or more unnatural amino acids, which is sometimes in combination with one or more of the above-described chemical modifications.

In some embodiments the antibody has one or more modifications (e.g., substitutions, deletions or additions) in amino acid residues that interact with Fc receptors. Those include modifications in amino acid residues identified as involved in the interaction between the anti-Fc domain and the FcRn receptor (see, e.g., International Publication No. WO 97/34631, which is incorporated herein by reference in its entirety).

In some embodiments, antibodies immunospecific for a cancer cell antigen are obtained commercially or produced by a method known to one of skill in the art such as, recombinant expression techniques. The nucleotide sequence encoding antibodies immunospecific for a cancer cell antigen is sometimes obtained, e.g., from the GenBank database or a database like it, the literature publications, or by routine cloning and sequencing.

In a specific embodiment, a known antibody for the treatment of cancer is used.

In another specific embodiment, an antibody for the treatment of an autoimmune disease is used in accordance with the compositions and methods of the invention.

In certain embodiments, useful antibodies bind to a receptor or a receptor complex expressed on an activated lymphocyte. That receptor or receptor complex, in some embodiments, is an immunoglobulin gene superfamily member, a TNF receptor superfamily member, an integrin, a cytokine receptor, a chemokine receptor, a major histocompatibility protein, a lectin, or a complement control protein.

In some embodiments, the antibody that is incorporated into a Camptothecin Conjugate will specifically bind CD19, CD30, CD33, CD70 or LIV-1.

Camptothecin Compounds:

The Camptothecin compounds utilized in the various embodiments described herein are represented by the formulae:

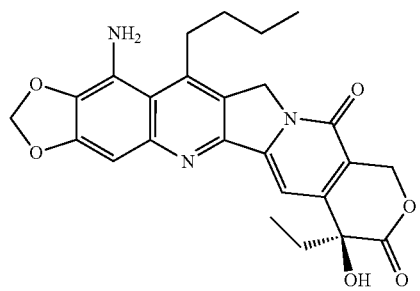

CPT1

-continued

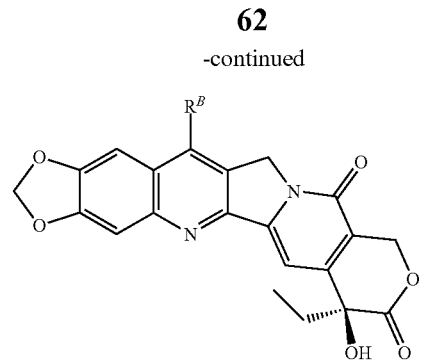

CPT2

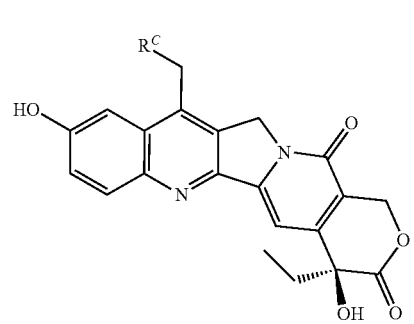

CPT3

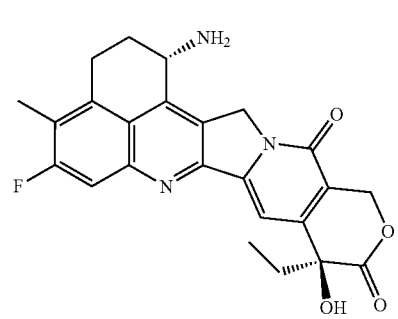

CPT4

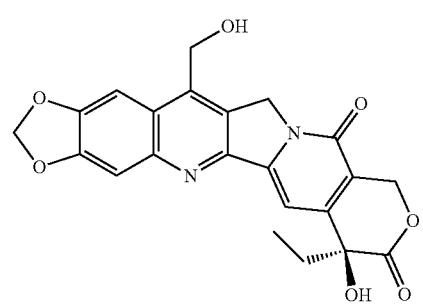

CPT5

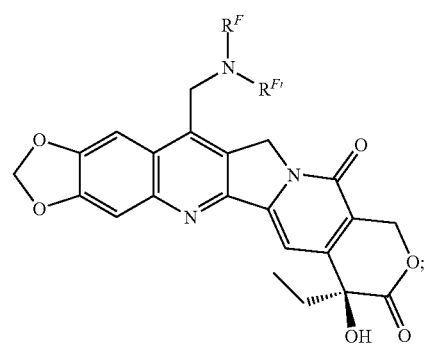

CPT6

-continued

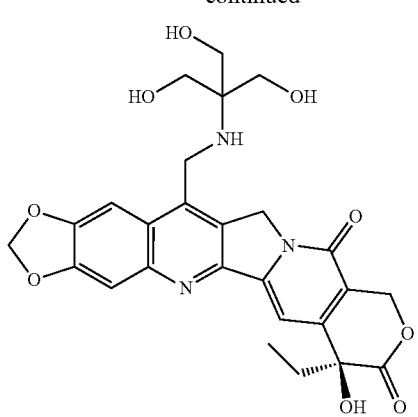

CPT7 wherein $R^B$ is a moiety selected from the group consisting of —H, $C_1$-$C_8$ alkyl, $C_1$-$C_8$ haloalkyl, $C_3$-$C_8$ cycloalkyl, ($C_3$-$C_8$ cycloalkyl)-$C_1$-$C_4$ alkyl-, phenyl and phenyl-$C_1$-$C_4$ alkyl-;

$R^C$ is a moiety selected from the group consisting of $C_1$-$C_6$ alkyl and $C_3$-$C_6$ cycloalkyl;

each $R^F$ and $R^{F'}$ is a moiety independently selected from the group consisting of —H, $C_1$-$C_8$ alkyl, $C_1$-$C_8$ hydroxyalkyl, $C_1$-$C_8$ aminoalkyl, ($C_1$-$C_4$alkylamino)-$C_1$-$C_8$ alkyl-, N,N—($C_1$-$C_4$ hydroxyalkyl)($C_1$-$C_4$alkyl)amino-$C_1$-$C_8$ alkyl-, N,N-di($C_1$-$C_4$ alkyl)amino-$C_1$-$C_8$ alkyl, N—($C_1$-$C_4$ hydroxyalkyl)-$C_1$-$C_8$ aminoalkyl-, $C_1$-$C_8$ alkylC(O)—, $C_1$-$C_8$ hydroxyalkyl-C(O)—, $C_1$-$C_8$ aminoalkyl-C(O)—, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl $C_1$-$C_4$ alkyl, heteroaryl and heteroaryl-$C_1$-$C_4$ alkyl, or $R^F$ and $R^{F'}$ are combined with the nitrogen atom to which both are attached to form a 5-, 6- or 7-membered ring having 0 to 3 substituents independently selected from the group consisting of halogen, $C_1$-$C_4$ alkyl, —OH, —O$C_1$-$C_4$ alkyl, —NH$_2$, —NH$C_1$-$C_4$ alkyl and N($C_1$-$C_4$ alkyl)$_2$, wherein the cycloalkyl, heterocycloalkyl, phenyl and heteroaryl moieties of $R^B$, $R^C$, $R^F$ and $R^{F'}$ are substituted with from 0 to 3 substituents independently selected from the group consisting of halogen, $C_1$-$C_4$ alkyl, —OH, —O$C_1$-$C_4$ alkyl, —NH$_2$, —NH$C_1$-$C_4$ alkyl and —N($C_1$-$C_4$ alkyl)$_2$.

Still other Camptothecin compounds useful in the context of the Camptothecin Conjugates and Camptothecin Linker compounds described herein are Camptothecin compounds 14a-14z of Table I and compound 18a-18r of Table J, and Camptothecin compounds that have a five- or six-ring fused framework analogs to those structures provided as formulae CPT1, CPT2, CPT3, CPT4, CPT5, CPT6, CPT7, 14a-14z and 18a-18r, which in some embodiments have an additional group including, but not limited to a hydroxyl, thiol, amine or amide functional group whose oxygen, sulfur or optionally substituted nitrogen atom is capable of incorporation into a linker, and is capable of being released from a Camptothecin Conjugate as a free drug. In some embodiments, that functional group provides the only site on the camptothecin compound available for attachment to the Linker Unit (Q). The resulting drug-linker moiety of a Camptothecin Conjugate is one that is capable of releasing active free drug at the site targeted by its Ligand Unit in order to exert a cytotoxic, cytostatic or immunosuppressive effect.

"Free drug" refers to drug, as it exists once released from the drug-linker moiety. In some embodiments, the free drug includes a fragment of the Releasable Linker or Spacer Unit (Y) group. Free drug, which includes a fragment of the Releasable Linker or Spacer Unit (Y), are released from the remainder of the drug-linker moiety via cleavage of the releasable linker or released via the cleavage of a bond in the Spacer Unit (Y) group and is biologically active after release. In some embodiments, the free drug differs from the conjugated drug in that the functional group of the free drug for attachment to the self-immolative assembly unit is no longer associated with components of the Camptothecin Conjugate (other than a previously shared heteroatom). For example, the free hydroxyl functional group of an alcohol-containing drug can be represented as D-O*H, whereas in the conjugated form the oxygen heteroatom designated by O* is incorporated into the methylene carbamate unit of a self-immolative unit. Upon activation of the self-immolative moiety and release of free drug, the covalent bond to O* is replaced by a hydrogen atom so that the oxygen heteroatom designated by O* is present on the free drug as —O—H.

Linker Unit (Q)

As noted above, is some embodiments, the Linker Unit Q has a formula selected from the group consisting of:

-Z-A-RL-;-Z-A-RL-Y-;-Z-A-S*-RL-;-Z-A-B(S*)-RL-;

-Z-A-S*-RL-Y-; and -Z-A-B(S*)-RL-Y-;

wherein Z is a Stretcher Unit; A is a bond or a Connecter Unit; B is a Branching Unit; S* is a Partitioning Agent; RL is Releasable Linker that is a Glucuronide Unit; and Y is a Spacer Unit; and wherein the point of attachment of D to Q is through any one of the heteroatoms of the hydroxyl and primary and secondary amines present on CPT1, CPT2, CPT3, CPT4, CPT5, CPT6 or CPT7 or any one of compounds 14a-14z of Table I and compounds 18a-18r of Table J.

In other embodiments, the Linker Unit Q has a formula selected from the group consisting of:

-Z-A-;-Z-A-RL-;-Z-A-S*-W-;-Z-A-B(S*)W;-Z-A-S*-RL-;-Z-A-B(S*)-RL-;

-Z-A-S*-W-RL-; and -Z-A-B(S*)-W-RL-;

wherein Z is a Stretcher Unit, A is a bond or a Connecter Unit; B is a Parallel Connector Unit; S* is a Partitioning Agent; RL is a Releasable Linker other than a Glucuronide Unit; and W is an Amino Acid Unit; and wherein the point of attachment to Q is through the hydroxyl group substituent of the lactone ring of CPT1, CPT2, CPT3, CPT4, CPT5, CPT6 or CPT7 or any one of compounds 14a-14z of Table I and compounds 18a-18r of Table J.

In one group of embodiments, Q has a formula selected from the group consisting of: -Z-A-S*-RL- and -Z-A-S*-RL-Y-.

In another group of embodiments, Q has a formula selected from the group consisting of -Z-A-B(S*)-RL- and -Z-A-B(S*)-RL-Y-.

In still another group of embodiments, Q has a formula selected from the group consisting of -Z-A-RL- and -Z-A-RL-Y-.

Stretcher Unit (Z) or (Z'):

A Stretcher Unit (Z) is a component of a Camptothecin Conjugate or a Camptothecin-Linker Compound or other Intermediate that acts to connect the Ligand Unit to the remainder of the conjugate. In that regard a Stretcher Unit, prior to attachment to a Ligand Unit (i.e. a Stretcher Unit precursor, Z'), has a functional group that can form a bond with a functional group of a targeting ligand.

In some embodiments, a Stretcher Unit precursor (Z') has an electrophilic group that is capable of interacting with a reactive nucleophilic group present on a Ligand Unit (e.g., an antibody) to provide a covalent bond between a Ligand Unit and the Stretcher Unit of a Linker Unit. Nucleophillic groups on an antibody having that capability include but are not limited to, sulfhydryl, hydroxyl and amino functional groups. The heteroatom of the nucleophilic group of an antibody is reactive to an electrophilic group on a Stretcher Unit precursor and provides a covalent bond between the Ligand Unit and Stretcher Unit of a Linker Unit or Drug-Linker moiety. Useful electrophilic groups for that purpose include, but are not limited to, maleimide, haloacetamide groups, and NHS esters. The electrophilic group provides a convenient site for antibody attachment to form a Camptothecin Conjugate or Ligand Unit-Linker intermediate.

In other embodiments, a Stretcher Unit precursor has a reactive site which has a nucleophilic group that is reactive to an electrophilic group present on a Ligand Unit (e.g., an antibody). Useful electrophilic groups on an antibody for that purpose include, but are not limited to, aldehyde and ketone carbonyl groups. The heteroatom of a nucleophilic group of a Stretcher Unit precursor can react with an electrophilic group on an antibody and form a covalent bond to the antibody. Useful nucleophilic groups on a Stretcher Unit precursor for that purpose include, but are not limited to, hydrazide, hydroxylamine, amino, hydrazine, thiosemicarbazone, hydrazine carboxylate, and arylhydrazide. The electrophilic group on an antibody provides a convenient site for antibody attachment to form a Camptothecin Conjugate or Ligand Unit-Linker intermediate.

In some embodiments, a sulfur atom of a Ligand Unit is bound to a succinimide ring system of a Stretcher Unit formed by reaction of a thiol functional group of a targeting ligand with a maleimide moiety of the corresponding Stretcher Unit precursor. In other embodiments, a thiol functional group of a Ligand Unit reacts with an alpha haloacetamide moiety to provide a sulfur-bonded Stretcher Unit by nucleophilic displacement of its halogen substituent. Representative Stretcher Units of such embodiments include those having the structures of:

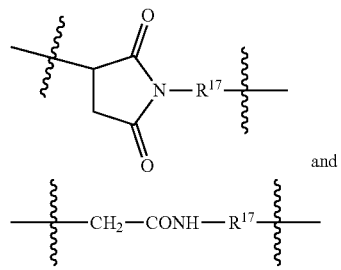

and wherein the wavy line adjacent to $R^{17}$ indicates attachment to the Parallel Connector Unit (B) or Connector Unit (A) if B is absent, or a Partitioning Agent (S*), if B is absent, the other wavy line indicates covalent attachment to a sulfur atom of a Ligand Unit and $R^{17}$ is —$C_1$-$C_{10}$ alkylene-, $C_1$-$C_{10}$ heteroalkylene-, —$C_3$-$C_8$ carbocyclo-, —O—($C_1$-$C_8$ alkylene)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$alkylene-($C_3$-$C_8$ heterocyclo)-, —($C_3$-$C_8$ heterocyclo)-$C_1$-$C_{10}$ alkylene-, —$C_1$-$C_{10}$ alkylene-C(=O)—, $C_1$-$C_{10}$ heteroalkylene-C(=O)—, —$C_3$-$C_8$ carbocyclo-C(=O)—, —O—($C_1$-$C_8$ alkylene)-C(=O)—, -arylene-C(=O)—, —$C_1$-$C_{10}$ alkylene-arylene-C(=O)—, -arylene-$C_1$-$C_{10}$ alkylene-C(=O)—, —$C_1$-$C_{10}$ alkylene-($C_3$-$C_8$ carbocyclo)-C(=O)—, —($C_3$-$C_8$ carbocyclo)-$C_1$-$C_{10}$ alkylene-C(=O)—, —$C_3$-$C_8$ heterocyclo-C(=O)—, —$C_1$-$C_{10}$ alkylene-($C_3$-$C_8$ heterocyclo)-C(=O)—, —($C_3$-$C_8$ heterocyclo)-$C_1$-$C_{10}$alkylene-C(=O)—, —$C_1$-$C_{10}$ alkylene-NH—, —$C_1$-$C_{10}$ heteroalkylene-NH—, —$C_3$-$C_8$ carbocyclo-NH—, —O—($C_1$-$C_8$ alkylene)-NH—, -arylene-NH—, —$C_1$-$C_{10}$ alkylene-arylene-NH—, -arylene-$C_1$-$C_{10}$ alkylene-NH—, —$C_1$-$C_{10}$ alkylene-($C_3$-$C_8$ carbocyclo)-NH—, —($C_3$-$C_8$ carbocyclo)-$C_1$-$C_{10}$ alkylene-NH—, —$C_3$-$C_8$ heterocyclo-NH—, —$C_1$-$C_{10}$ alkylene-($C_3$-$C_8$ heterocyclo)-NH—, —($C_3$-$C_8$ heterocyclo)-$C_1$-$C_{10}$ alkylene-NH—, —$C_1$-$C_{10}$ alkylene-S—, $C_1$-$C_{10}$ heteroalkylene-S—, —$C_3$-$C_8$ carbocyclo-S—, —O—($C_1$-$C_8$ alkylene)-S—, -arylene-S—, —$C_1$-$C_{10}$ alkylene-arylene-S—, -arylene-$C_1$-$C_{10}$ alkylene-S—, —$C_1$-$C_{10}$ alkylene-($C_3$-$C_8$ carbocyclo)-S—, —($C_3$-$C_8$ carbocyclo)-$C_1$-$C_{10}$ alkylene-S—, —$C_3$-$C_8$ heterocyclo-S—, —$C_1$-$C_{10}$alkylene-($C_3$-$C_8$ heterocyclo)-S—, or —($C_3$-$C_8$ heterocyclo)-$C_1$-$C_{10}$ alkylene-S—.

In some embodiments, the $R^{17}$ group is optionally substituted by a Basic Unit (BU) such as an aminoalkyl moiety, e.g. —$(CH_2)_xNH_2$, —$(CH_2)_xNHR^a$, and —$(CH_2)_xNR^a_2$, wherein subscript x is an integer of from 1-4 and each $R^a$ is independently selected from the group consisting of $C_{1-6}$ alkyl and $C_{1-6}$ haloalkyl, or two $R^a$ groups are combined with the nitrogen to which they are attached to form an azetidinyl, pyrrolidinyl or piperidinyl group.

An illustrative Stretcher Unit is that of Formula Za or Za-BU in which $R^{17}$ is —$C_1$-$C_{10}$ alkylene-C(=O)—, —$C_1$-$C_{10}$ heteroalkylene-C(=O)—, —$C_3$-$C_8$ carbocyclo-C(=O)—, —O—($C_1$-$C_8$ alkylene)-C(=O)—, -arylene-C(=O)—, —$C_1$-$C_{10}$ alkylene-arylene-C(=O)—, -arylene-$C_1$-$C_{10}$ alkylene-C(=O)—, —$C_1$-$C_{10}$ alkylene-($C_3$-$C_8$ carbocyclo)-C(=O)—, —($C_3$-$C_8$ carbocyclo)-$C_1$-$C_{10}$ alkylene-C(=O)—, —$C_3$-$C_8$ heterocyclo-C(=O)—, —$C_1$-$C_{10}$ alkylene-($C_3$-$C_8$ heterocyclo)-C(=O)—, or —($C_3$-$C_8$ heterocyclo)-$C_1$-$C_{10}$alkylene-C(=O)—.

Accordingly, some preferred embodiments are represented by formula Za and Za-BU:

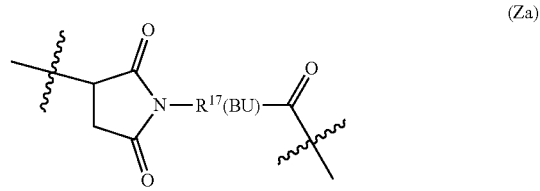

(Za)

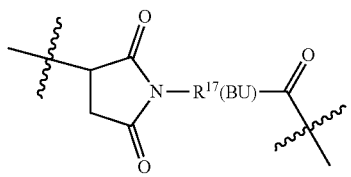
(Za-BU)

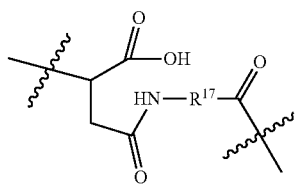
(Zb)

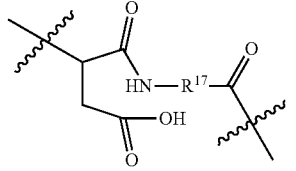
(Zc)

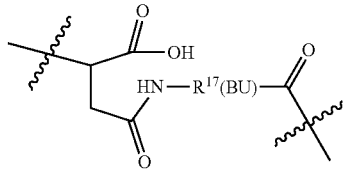
(Zb-BU)

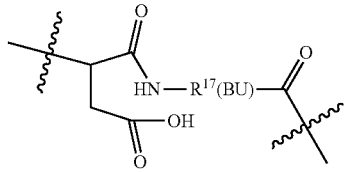
(Zc-BU)

wherein the wavy line adjacent the carbonyl carbon atom indicates attachment to B, A, or S*, in the formulae above, depending on the presence or absence of A and/or B, and the other wavy line indicates covalent bonding of the succinimide ring carbon atom to a sulfur atom of a Ligand Unit. During synthesis, the basic amino functional group of the Basic Unit (BU) can be protected by a protecting group.

More preferred embodiments of Stretcher Units of formula Za and Za-BU are as follows:

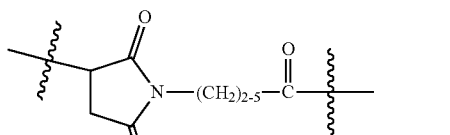

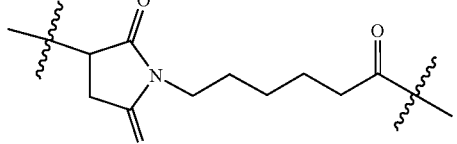

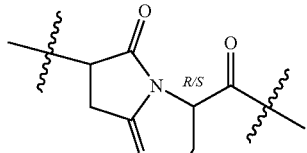

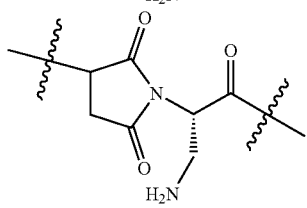

wherein the wavy line adjacent to the carbonyl carbon atom bonded to $R^{17}$ and the wavy line adjacent to the carbon atom of the acid-amide moiety is as defined for Za or Za-BU, depending on the presence or absence of A and/or B; and $R^{17}$ is $—C_1-C_5$ alkylene-, wherein in Zb-BU and Zc-BU the alkylene is substituted by a Basic Unit (BU), wherein BU is $—(CH_2)_xNH_2$, $—(CH_2)_xNHR^a$, or $—(CH_2)_xN(R^a)_2$, wherein subscript x is an integer of from 1-4 and each $R^a$ is independently selected from the group consisting of $C_{1-6}$ alkyl and $C_{1-6}$ haloalkyl, or both $R^a$ together with the nitrogen to which they are attached define an azetidinyl, pyrrolidinyl or piperidinyl group.

In more preferred embodiment, -Z-A- comprises a moiety derived from a maleimido-alkanoic acid moiety or an mDPR moiety. See, for example, see WO 2013/173337. In one group of embodiments, Z-A- is derived from a maleimido-propionyl moiety.

wherein the wavy line adjacent the carbonyl carbon atom indicates attachment to B, A, or S*, in the formulae above, depending on the presence or absence of A and/or B, and the other wavy line indicates covalent bonding of the succinimide ring carbon atom to a sulfur atom of a Ligand Unit.

It will be understood that a Ligand Unit-substituted succinimide may exist in hydrolyzed form(s). Those forms are exemplified below for hydrolysis of Za or Za-BU, wherein the structures representing the regioisomers from that hydrolysis have formula Zb and Zc or Zb-BU and Zc-BU.

Accordingly, in other preferred embodiments a Stretcher unit (Z) is comprised of a succinic acid-amide moiety represented by the following:

Accordingly in some of those more preferred embodiments, a Stretcher unit (Z) is comprised of an succinic acid-amide moiety represented by the structure of formula Zb', Zc', (R/S)-Zb'-BU, (S)-Zb'-BU, (R/S)-Zc'-BU or (S)-Zc'-BU as follows:

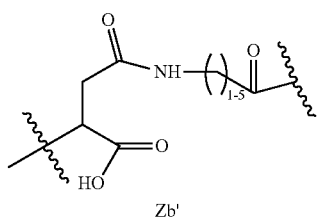
Zb'

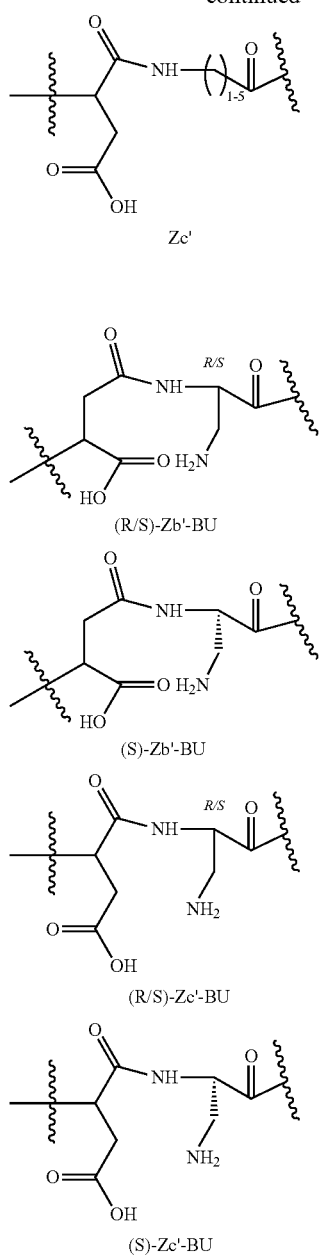

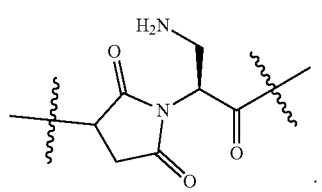 [SMILES: *C(=O)[C@H](CN)N1C(=O)CC(*)C1=O]

wherein the wavy lines are as defined for Za or Za-BU.

In particularly preferred embodiments a Stretcher unit (Z) is comprised of a succinimide moiety represented by the structure of or is comprised of a succinic acid-amide moiety represented by the structure of:

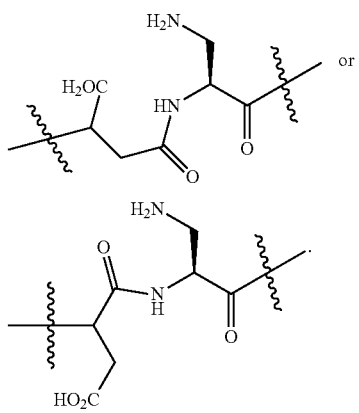

Illustrative Stretcher Units bonded to a Connector Unit (A) which are comprised of Za', Zb' or Zc', in which —$R^{17}$— of Za, Zb or Zc is —$CH_2$— or —$CH_2CH_2$—, or are comprised of Za'-BU, Zb'-BU or Zc'-BU in which —$R^{17}$(BU)- of Za-BU, Zb-BU or Zc-BU is —$CH(CH_2NH_2)$—, have the following structures:

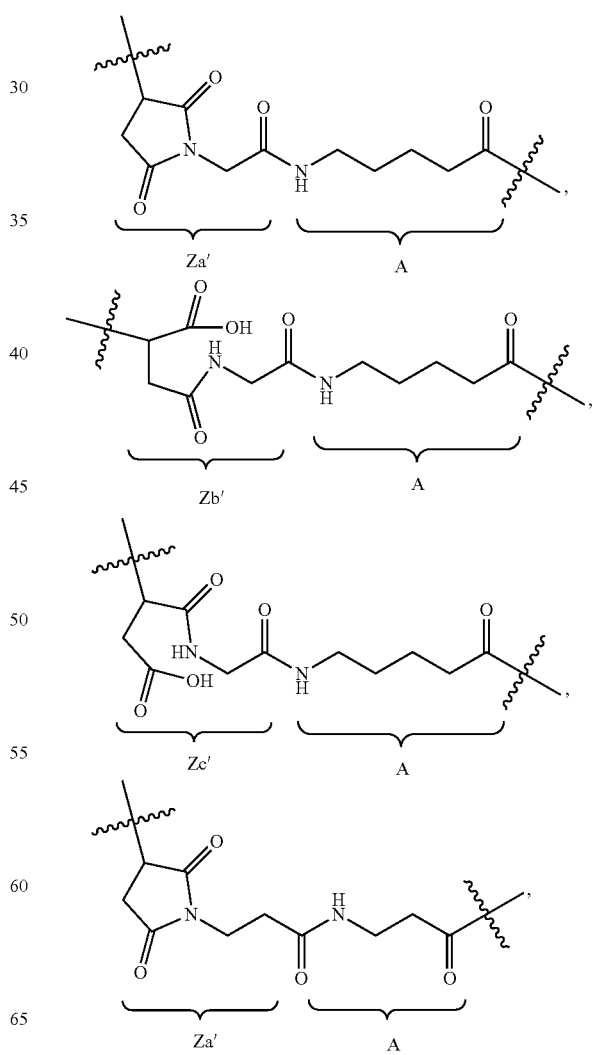

71

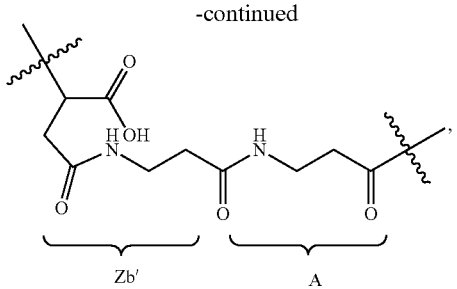

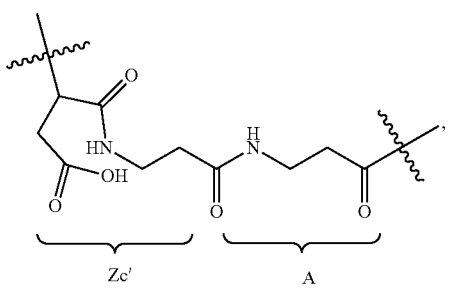

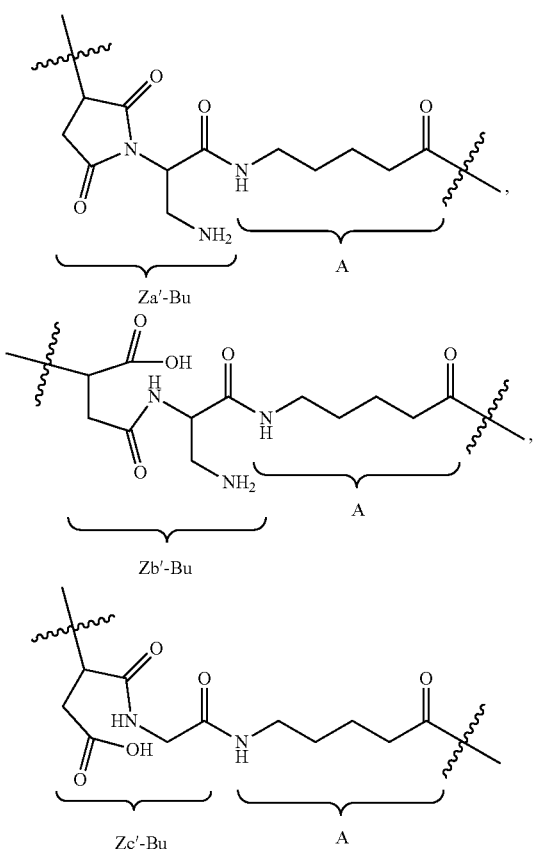

wherein the wavy lines are as defined for Za or Za-BU.

Other Stretcher Units bonded to a Ligand Unit (L) and a Connector Unit (A) have the structures above wherein A in any one of the above -Za-A-, -Za(BU)-A-, -Za'-A-, -Za'(BU)-A-, -Zb-A-, -Zb(BU)-A-, -Zb'-A-, -Zb'(BU)-, -Zc'-A- and Zc'(BU)-A- structures is replaced by a Parallel Connector Unit having the structure of:

72

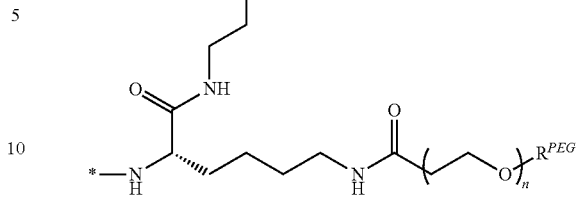

wherein subscript n ranges from 8 to 24; $R^{PEG}$ is a PEG Unit capping group, preferably —$CH_3$ or —$CH_2CH_2CO_2H$, the asterisk (*) indicates covalent attachment to a Stretcher Unit corresponding in structure to formula Za, Za', Zb' or Zc' and the wavy line indicates covalent attachment to the Releasable Linker (RL).

Illustrative Stretcher Units prior to conjugation to the Ligand Unit (i.e., Stretcher Unit precursors) are comprised of a maleimide moiety and are represented by structures including that of formula Z'a

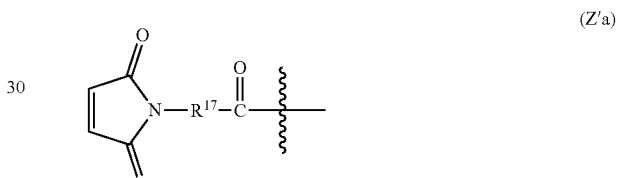

wherein the wavy line adjacent the carbonyl carbon atom indicates attachment to B, A, or S*, in the formulae above, depending on the presence or absence of A and/or B, $R^{17}$ is —$(CH_2)_{1-5}$—, optionally substituted with a Basic Unit, such as an optionally substituted aminoalkyl, e.g., —$(CH_2)_xNH_2$, —$(CH_2)_xNHR^a$, and —$(CH_2)_xN(R^a)_2$, wherein subscript x is an integer of from 1-4 and each $R^a$ is independently selected from the group consisting of $C_{1-6}$ alkyl and $C_{1-6}$ haloalkyl, or two $R^a$ groups are combined with the nitrogen to which they are attached to form an azetidinyl, pyrrolidinyl or piperidinyl group.

Other illustrative Stretcher Units prior to conjugation to the Ligand Unit (i.e., Stretcher Unit precursors) are comprised of a maleimide moiety and are represented by structures including that of formula Z'a-BU.

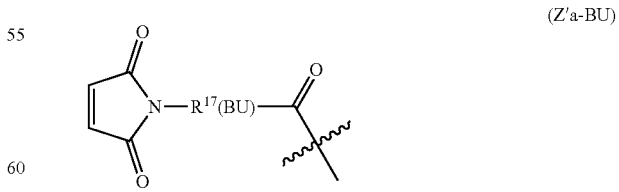

wherein the wavy line adjacent the carbonyl carbon atom indicates attachment to B, A, or S*, in the formulae above, depending on the presence or absence of A and/or B, $R^{17}$ is —$(CH_2)_{1-5}$—, substituted with a Basic Unit, such as an optionally substituted aminoalkyl, e.g., —(CH$_2$)$_x$NH$_2$, —(CH$_2$)$_x$NHR$^a$, and —(CH$_2$)$_x$N(R$^a$)$_2$, wherein subscript x is an integer of from 1-4, preferably R$^{17}$ is —CH$_2$— or —CH$_2$CH$_2$— and subscript x is 1 or 2, and each R$^a$ is independently selected from the group consisting of C$_{1-6}$ alkyl and C$_{1-6}$ haloalkyl, or two R$^a$ groups are combined with the nitrogen to which they are attached to form an azetidinyl, pyrrolidinyl or piperidinyl group.

In some preferred embodiments of formula Z'a, a Stretcher Unit precursor is represented by one of the following structures:

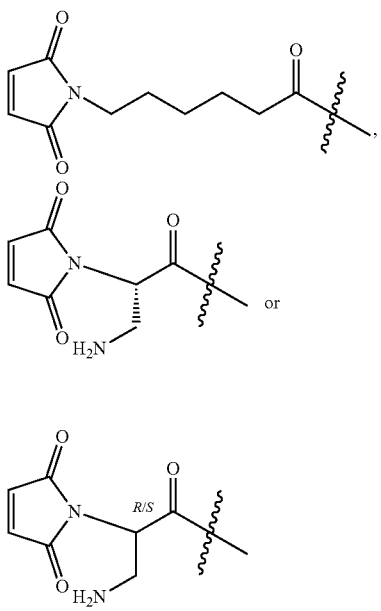

wherein the wavy line adjacent to the carbonyl is as defined for Z'a or Z'a-BU.

In more preferred embodiments the Stretcher unit precursor (Z') is comprised of a maleimide moiety and is represented by the structure of:

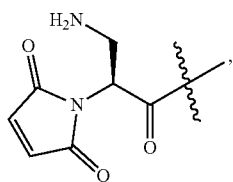 [SMILES: *C(=O)[C@H](CN)N1C(=O)C=CC1=O]

wherein the wavy line adjacent to the carbonyl is as defined for Za' and the amino group is optional protonated or protected by an amino protecting group.

In Stretcher Units having a BU moiety, it will be understood that the amino functional group of that moiety is typically protected by an amino protecting group during synthesis, e.g., an acid labile protecting group (e.g., BOC).

Illustrative Stretcher Unit precursors covalently attached to a Connector Unit that are comprised of the structure of Z'a or Z'a-BU in which —R$^{17}$— or —R$^{17}$(BU)- is —CH$_2$—, —CH$_2$CH$_2$— or —CH(CH$_2$NH$_2$)— have the following structures:

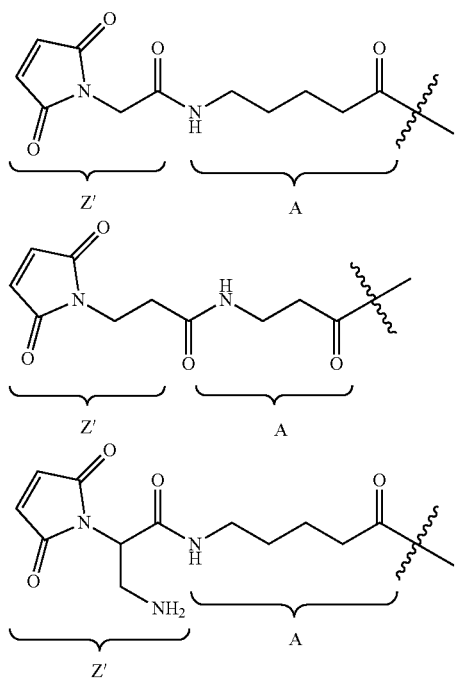

wherein the wavy line adjacent to the carbonyl is as defined for Z'a or Z'a-BU.

Other Stretcher Unit precursors bonded a Connector Unit (A) have the structures above wherein A in any one of the above Z'-A- and Z'(BU)-A- structures is replaced by a Parallel Connector Unit and Partitioning Agent (—B(S*)-) having the structure of

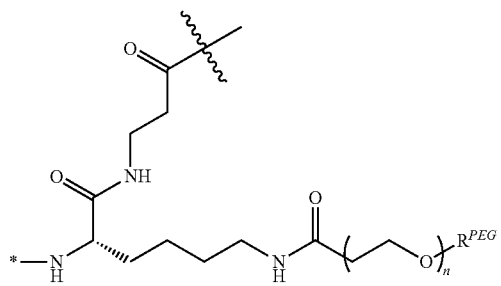

wherein subscript n ranges from 8 to 24; R$^{PEG}$ is a PEG Unit capping group, preferably -CH$_3$ or —CH$_2$CH$_2$CO$_2$H, the asterisk (*) indicates covalent attachment to the Stretcher Unit precursor corresponding in structure to formula Za or Za' and the wavy line indicates covalent attachment to RL. In instances such as those shown here, the shown PEG group is meant to be exemplary of a variety of Partitioning Agents including PEG groups of different lengths and other Partitioning Agents that can be directly attached or modified for attachment to the Parallel Connector Unit.

In another embodiment, the Stretcher Unit is attached to the Ligand Unit via a disulfide bond between a sulfur atom of the Ligand Unit and a sulfur atom of the Stretcher unit. A representative Stretcher Unit of this embodiment is depicted within the square brackets of Formula Zb:

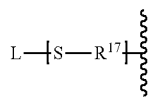

(Zb)

wherein the wavy line indicates attachment to the Parallel Connector Unit (B) or Connector Unit (A) if B is absent or a Partitioning Agent (S*), if A and B are absent and $R^{17}$ is —$C_1$-$C_{10}$ alkylene-, $C_1$-$C_{10}$ heteroalkylene-, —$C_3$-$C_8$ carbocyclo-, —O—($C_1$-$C_8$ alkylene)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$alkylene-($C_3$-$C_8$ heterocyclo)-, —($C_3$-$C_8$ heterocyclo)-$C_1$-$C_{10}$ alkylene-, —$C_1$-$C_{10}$ alkylene-C(=O)—, $C_1$-$C_{10}$ heteroalkylene-C(=O)—, —$C_3$-$C_8$ carbocyclo-C(=O)—, —O—($C_1$-$C_8$ alkylene)-C(=O)—, -arylene-C(=O)—, —$C_1$-$C_{10}$ alkylene-arylene-C(=O)—, -arylene-$C_1$-$C_{10}$ alkylene-C(=O)—, —$C_1$-$C_{10}$ alkylene-($C_3$-$C_8$ carbocyclo)-C(=O)—, —($C_3$-$C_8$ carbocyclo)-$C_1$-$C_{10}$ alkylene-C(=O)—, —$C_3$-$C_8$ heterocyclo-C(=O)—, —$C_1$-$C_{10}$ alkylene-($C_3$-$C_8$ heterocyclo)-C(=O)—, —($C_3$-$C_8$ heterocyclo)-$C_1$-$C_{10}$alkylene-C(=O)—, —$C_1$-$C_{10}$ alkylene-NH—, $C_1$-$C_{10}$ heteroalkylene-NH—, —$C_3$-$C_8$ carbocyclo-NH—, —O—($C_1$-$C_8$ alkylene)-NH—, -arylene-NH—, —$C_1$-$C_{10}$ alkylene-arylene-NH—, -arylene-$C_1$-$C_{10}$ alkylene-NH—, —$C_1$-$C_{10}$ alkylene-($C_3$-$C_8$ carbocyclo)-NH—, —($C_3$-$C_8$ carbocyclo)-$C_1$-$C_{10}$ alkylene-NH—, —$C_3$-$C_8$ heterocyclo-NH—, —$C_1$-$C_{10}$ alkylene-($C_3$-$C_8$ heterocyclo)-NH—, —($C_3$-$C_8$ heterocyclo)-$C_1$-$C_{10}$ alkylene-NH—, —$C_1$-$C_{10}$ alkylene-S—, $C_1$-$C_{10}$ heteroalkylene-S—, —$C_3$-$C_8$ carbocyclo-S—, —O—($C_1$-$C_8$ alkylene)-S—, -arylene-S—, —$C_1$-$C_{10}$ alkylene-arylene-S—, -arylene-$C_1$-$C_{10}$ alkylene-S—, —$C_1$-$C_{10}$ alkylene-($C_3$-$C_8$ carbocyclo)-S—, —($C_3$-$C_8$ carbocyclo)-$C_1$-$C_{10}$ alkylene-S—, —$C_3$-$C_8$ heterocyclo-S—, —$C_1$-$C_{10}$ alkylene-($C_3$-$C_8$ heterocyclo)-S—, or —($C_3$-$C_8$ heterocyclo)-$C_1$-$C_{10}$ alkylene-S—.

In yet another embodiment, the reactive group of a Stretcher Unit precursor contains a reactive site that can form a bond with a primary or secondary amino group of a Ligand Unit. Examples of these reactive sites include, but are not limited to, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher Units of this embodiment are depicted within the square brackets of Formulas Zci, Zcii and Zciii:

wherein the wavy line indicates attachment to the Parallel Connector Unit (B) or Connector Unit (A) if B is absent or a Partitioning Agent (S*), if A and B are absent and $R^{17}$ is —$C_1$-$C_{10}$ alkylene-, $C_1$-$C_{10}$ heteroalkylene-, —$C_3$-$C_8$ carbocyclo-, —O—($C_1$-$C_8$ alkylene)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$alkylene-($C_3$-$C_8$ heterocyclo)-, —($C_3$-$C_8$ heterocyclo)-$C_1$-$C_{10}$ alkylene-, —$C_1$-$C_{10}$ alkylene-C(=O)—, $C_1$-$C_{10}$ heteroalkylene-C(=O)—, —$C_3$-$C_8$ carbocyclo-C(=O)—, —O—($C_1$-$C_8$ alkylene)-C(=O)—, -arylene-C(=O)—, —$C_1$-$C_{10}$ alkylene-arylene-C(=O)—, -arylene-$C_1$-$C_{10}$ alkylene-C(=O)—, —$C_1$-$C_{10}$ alkylene-($C_3$-$C_8$ carbocyclo)-C(=O)—, —($C_3$-$C_8$ carbocyclo)-$C_1$-$C_{10}$ alkylene-C(=O)—, —$C_3$-$C_8$ heterocyclo-C(=O)—, —$C_1$-$C_{10}$ alkylene-($C_3$-$C_8$ heterocyclo)-C(=O)—, —($C_3$-$C_8$ heterocyclo)-$C_1$-$C_{10}$alkylene-C(=O)—, —$C_1$-$C_{10}$ alkylene-NH—, $C_1$-$C_{10}$ heteroalkylene-NH—, —$C_3$-$C_8$ carbocyclo-NH—, —O—($C_1$-$C_8$ alkylene)-NH—, -arylene-NH—, —$C_1$-$C_{10}$ alkylene-arylene-NH—, -arylene-$C_1$-$C_{10}$ alkylene-NH—, —$C_1$-$C_{10}$ alkylene-($C_3$-$C_8$ carbocyclo)-NH—, —($C_3$-$C_8$ carbocyclo)-$C_1$-$C_{10}$ alkylene-NH—, —$C_3$-$C_8$ heterocyclo-NH—, —$C_1$-$C_{10}$ alkylene-($C_3$-$C_8$ heterocyclo)-NH—, —($C_3$-$C_8$ heterocyclo)-$C_1$-$C_{10}$ alkylene-NH—, —$C_1$-$C_{10}$ alkylene-S—, $C_1$-$C_{10}$ heteroalkylene-S—, —$C_3$-$C_8$ carbocyclo-S—, —O—($C_1$-$C_8$ alkylene)-S—, -arylene-S—, —$C_1$-$C_{10}$ alkylene-arylene-S—, -arylene-$C_1$-$C_{10}$ alkylene-S—, —$C_1$-$C_{10}$ alkylene-($C_3$-$C_8$ carbocyclo)-S—, —($C_3$-$C_8$ carbocyclo)-$C_1$-$C_{10}$ alkylene-S—, —$C_3$-$C_8$ heterocyclo-S—, —$C_1$-$C_{10}$ alkylene-($C_3$-$C_8$ heterocyclo)-S—, or —($C_3$-$C_8$ heterocyclo)-$C_1$-$C_{10}$ alkylene-S—.

In still other embodiments, the reactive group of the Stretcher Unit precursor contains a reactive nucleophile that is capable of reacting with an electrophile present on, or introduced to, a Ligand Unit. For example, a carbohydrate moiety on a targeting ligand can be mildly oxidized using a reagent such as sodium periodate and the resulting electrophilic functional group (—CHO) of the oxidized carbohydrate can be condensed with a Stretcher Unit precursor that contains a reactive nucleophile such as a hydrazide, an oxime, a primary or secondary amine, a hydrazine, a thiosemicarbazone, a hydrazine carboxylate, or an arylhydrazide such as those described by Kaneko, T. et al. (1991) Bioconjugate Chem. 2:133-41. Representative Stretcher Units of this embodiment are depicted within the square brackets of Formulas Zdi, Zdii, and Zdiii:

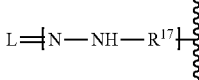

(Zci)

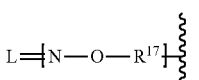

(Zcii)

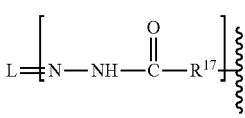

(Zciii)

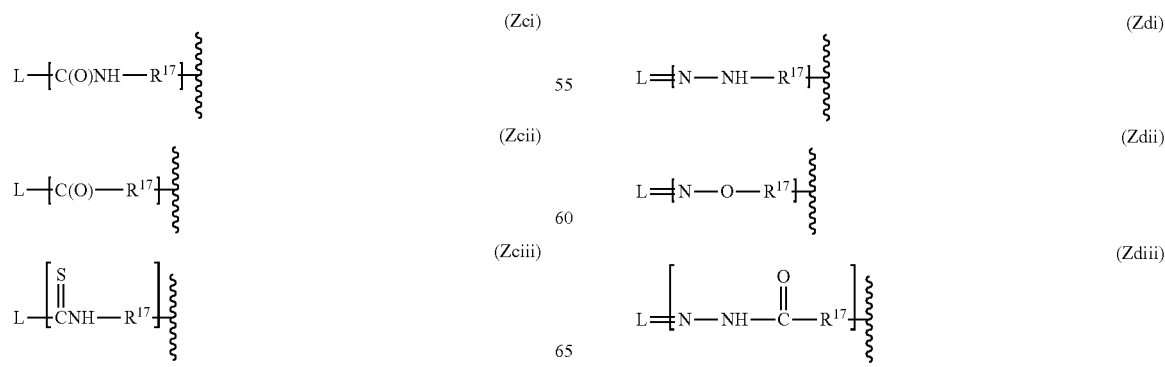

(Zdi)

(Zdii)

(Zdiii)

wherein the wavy line indicates attachment to the Parallel Connector Unit (B) or Connector Unit (A), or a Partitioning Agent (S*), if A and B are absent and $R^{17}$ is —$C_1$-$C_{10}$ alkylene-, $C_1$-$C_{10}$ heteroalkylene-, —$C_3$-$C_8$ carbocyclo-, —O—($C_1$-$C_8$ alkylene)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$C_1$-$C_{10}$ alkylene-C(=O)—, $C_1$-$C_{10}$ heteroalkylene-C(=O)—, —$C_3$-$C_8$ carbocyclo-C(=O)—, —O—($C_1$-$C_8$ alkylene)-C(=O)—, -arylene-C(=O)—, —$C_1$-$C_{10}$ alkylene-arylene-C(=O)—, -arylene-$C_1$-$C_{10}$ alkylene-C(=O)—, —$C_1$-$C_{10}$ alkylene-($C_3$-$C_8$ carbocyclo)-C(=O)—, —($C_3$-$C_8$ carbocyclo)-$C_1$-$C_{10}$ alkylene-C(=O)—, —$C_3$-$C_8$ heterocyclo-C(=O)—, —$C_1$-$C_{10}$ alkylene-($C_3$-$C_8$ heterocyclo)-C(=O)—, —($C_3$-$C_8$ heterocyclo)-$C_1$-$C_{10}$alkylene-C(=O)—, —$C_1$-$C_{10}$ alkylene-NH—, $C_1$-$C_{10}$ heteroalkylene-NH—, —$C_3$-$C_8$ carbocyclo-NH—, —O—($C_1$-$C_8$ alkylene)-NH—, -arylene-NH—, —$C_1$-$C_{10}$ alkylene-arylene-NH—, -arylene-$C_1$-$C_{10}$ alkylene-NH—, —$C_1$-$C_{10}$ alkylene-($C_3$-$C_8$ carbocyclo)-NH—, —($C_3$-$C_8$ carbocyclo)-$C_1$-$C_{10}$ alkylene-NH—, —$C_3$-$C_8$ heterocyclo-NH—, —$C_1$-$C_{10}$ alkylene-($C_3$-$C_8$ heterocyclo)-NH—, —($C_3$-$C_8$ heterocyclo)-$C_1$-$C_{10}$ alkylene-NH—, —$C_1$-$C_{10}$ alkylene-S—, $C_1$-$C_{10}$ heteroalkylene-S—, $C_3$-$C_8$ carbocyclo-S—, —O—($C_1$-$C_8$ alkylene)-S—, -arylene-S—, —$C_1$-$C_{10}$ alkylene-arylene-S—, -arylene-$C_1$-$C_{10}$ alkylene-S—, —$C_1$-$C_{10}$ alkylene-($C_3$-$C_8$ carbocyclo)-S—, —($C_3$-$C_8$ carbocyclo)-$C_1$-$C_{10}$ alkylene-S—, —$C_3$-$C_8$ heterocyclo-S—, —$C_1$-$C_{10}$ alkylene-($C_3$-$C_8$ heterocyclo)-S—, or —($C_3$-$C_8$ heterocyclo)-$C_1$-$C_{10}$ alkylene-S—.

In some aspects of the prevent invention the Stretcher Unit has a mass of no more than about 1000 daltons, no more than about 500 daltons, no more than about 200 daltons, from about 30, 50 or 100 daltons to about 1000 daltons, from about 30, 50 or 100 daltons to about 500 daltons, or from about 30, 50 or 100 daltons to about 200 daltons.

Connector Unit (A)

In some embodiments, a Connector Unit (A), is included in a Camptothecin Conjugate or Camptothecin-Linker Compound in instances where it is desirable to add additional distance between the Stretcher Unit (Z) or precursor thereof (Z') and the Releasable Linker. In some embodiments, the extra distance will aid with activation within RL. Accordingly, the Connector Unit (A), when present, extends the framework of the Linker Unit. In that regard, a Connector Unit (A) is covalently bonded with the Stretcher Unit (or its precursor) at one terminus and is covalently bonded to the optional Parallel Connector Unit or the Partitioning Agent (S*) at its other terminus.

The skilled artisan will appreciate that the Connector Unit can be any group that serves to provide for attachment of the Releasable Linker to the remainder of the Linker Unit (Q). The Connector Unit can be, for example, comprised of one or more (e.g., 1-10, preferably, 1, 2, 3, or 4) natural or non-natural amino acid, amino alcohol, amino aldehyde, diamino residues. In some embodiments, the Connector Unit is a single natural or non-natural amino acid, amino alcohol, amino aldehyde, or diamino residue. An exemplary amino acid capable of acting as Connector units is β-alanine.

In some of those embodiments, the Connector Unit has the formula denoted below:

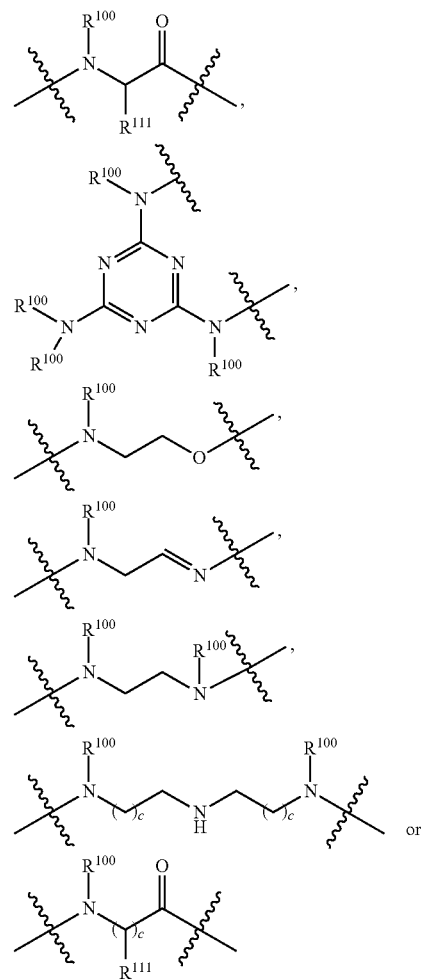

wherein the wavy lines indicate attachment of the Connector Unit within the Camptothecin Conjugate or Camptothecin Linker Compound; and wherein $R^{111}$ is independently selected from the group consisting of hydrogen, p-hydroxybenzyl, methyl, isopropyl, isobutyl, sec-butyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-,

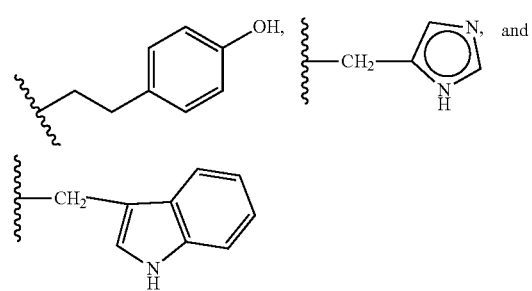

and each $R^{100}$ is independently selected from hydrogen or —$C_1$-$C_3$ alkyl, preferably hydrogen or $CH_3$; and subscript c is an independently selected integer from 1 to 1510, preferably 1 to 3.

A representative Connector Unit having a carbonyl group for attachment to the Partitioning Agent (S*) or to —B(S*)- is as follows:

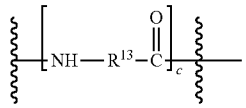

wherein in each instance $R^{13}$ is independently selected from the group consisting of —$C_1$-$C_6$ alkylene-, —$C_3$-$C_8$carbocyclo-, -arylene-, —$C_1$-$C_{10}$ heteroalkylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$carbocyclo)-, —($C_3$-$C_8$carbocyclo)-$C_1$-$C_{10}$alkylene-, —$C_1$-$C_{10}$alkylene-($C_3$-$C_8$ heterocyclo)-, and —($C_3$-$C_8$ heterocyclo)-$C_1$-$C_{10}$ alkylene-, and the subscript c is an integer ranging from 1 to 4. In some embodiments $R^{13}$ is —$C_1$-$C_6$ alkylene and c is 1.

Another representative Connector Unit having a carbonyl group for attachment to Partitioning Agent (S*) or to —B(S*)- is as follows:

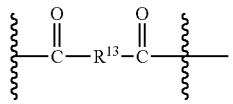

wherein $R^{13}$ is —$C_1$-$C_6$ alkylene-, —$C_3$-$C_8$carbocyclo-, -arylene-, —$C_1$-$C_{10}$ heteroalkylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$carbocyclo)-, —($C_3$-$C_8$carbocyclo)-$C_1$-$C_{10}$ alkylene-, —$C_1$-$C_{10}$alkylene-($C_3$-$C_8$ heterocyclo)-, or —($C_3$-$C_8$ heterocyclo)-$C_1$-$C_{10}$ alkylene-. In some embodiments $R^{13}$ is —$C_1$-$C_6$ alkylene.

A representative Connector Unit having a NH moiety that attaches to Partitioning Agent (S*) or to —B(S*)- is as follows:

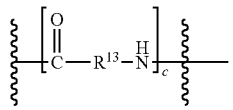

wherein in each instance, $R^{13}$ is independently selected from the group consisting of —$C_1$-$C_6$ alkylene-, —$C_3$-$C_8$carbocyclo-, -arylene-, —$C_1$-$C_{10}$ heteroalkylene-, —$C_3$-$C_8$heterocyclo-, —$C_1$-$C_{10}$ alkylene-arylene-, -arylene-$C_1$-$C_{10}$alkylene-, —$C_1$-$C_{10}$alkylene-($C_3$-$C_8$carbocyclo)-, —($C_3$-$C_8$carbocyclo)-$C_1$-$C_{10}$alkylene-, —$C_1$-$C_{10}$alkylene-($C_3$-$C_8$ heterocyclo)-, and —($C_3$-$C_8$ heterocyclo)-$C_1$-$C_{10}$ alkylene-, and subscript c is from 1 to 14. In some embodiments $R^{13}$ is —$C_1$-$C_6$ alkylene and subscript c is 1.

Another representative Connector Unit having a NH moiety that attaches to Partitioning Agent (S*) or to —B(S*)- is as follows:

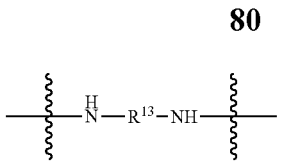

wherein $R^{13}$ is —$C_1$-$C_6$ alkylene-, —$C_3$-$C_8$carbocyclo-, -arylene-, —$C_1$-$C_{10}$ heteroalkylene-, —$C_3$-$C_8$heterocyclo-, —$C_1$-$C_{10}$ alkylene-arylene-, -arylene-$C_1$-$C_{10}$alkylene-, —$C_1$-$C_{10}$alkylene-($C_3$-$C_8$carbocyclo)-, —($C_3$-$C_8$carbocyclo)-$C_1$-$C_{10}$alkylene-, —$C_1$-$C_{10}$alkylene-($C_3$-$C_8$ heterocyclo)-, —($C_3$-$C_8$ heterocyclo)-$C_1$-$C_{10}$ alkylene-, —C(=O)$C_1$-$C_6$ alkylene- or —$C_1$-$C_6$ alkylene-C(=O)—$C_1$-$C_6$ alkylene.

Selected embodiments of Connector Units include those having the following structure of:

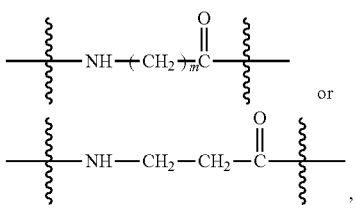

wherein the wavy line adjacent to the nitrogen indicates covalent attachment a Stretcher Unit (Z) (or its precursor Z'), and the wavy line adjacent to the carbonyl indicates covalent attachment to Partitioning Agent (S*) or to —B(S*)-; and m is an integer ranging from 1 to 6, preferably 2 to 6, more preferably 2 to 4.

Releasable Linker (RL)

A Glucuronide Unit is one type of Releasable Linker that provides a mechanism for separation of the Camptothecin from the Ligand Unit and other components of the Linker Unit through activation of a self-immolation cascade within the Linker Unit. In such embodiments, a self-immolation cascade is activated by operation of a glycosidase on a carbohydrate moiety of the Glucuronide Unit. A number of sugars are useful in the embodiments described herein. Particular carbohydrate moieties include those of Galactose, Glucose, Mannose, Xylose, Arabinose, Mannose-6-phosphate, Fucose, Rhamnose, Gulose, Allose, 6-deoxy-glucose, Lactose, Maltose, Cellobiose, Gentiobiose, Maltotriose, GlcNAc, GalNAc and maltohexaose.

A glycoside unit typically comprises a sugar moiety (Su) linked via an oxygen glycosidic bond to a self-immolative spacer. Cleavage of the oxygen glycosidic bond initiates the self-immolation reaction sequence that result in release of free drug. In some embodiments, the self-immolation sequence is activated from cleavage by β-glucuronidase of a Glucuronide Unit, which is an exemplary glycoside unit. The Glucuronide unit comprises an activation unit and a self-immolative Spacer Unit. The Glucuronide unit comprises a sugar moiety (Su) linked via an oxygen glycosidic bond to a self-immolative Spacer Unit.

In some embodiments, a Glucuronide Unit comprises a sugar moiety (Su) linked via an oxygen glycoside bond (—O'—) to a Self-immolative Unit (SP) of the formula:

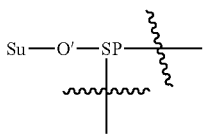

wherein the wavy lines indicate covalent attachment to the Drug Unit of any one of formulae CPT1, CPT2, CPT3, CPT4, CPT5 CPT6 and CPT7, or to a Spacer Unit that is attached to the Drug Unit (a Camptothecin Compound), and to the Stretcher Unit (Z) or its precursor (Z'), either directly or indirectly through the Connector Unit (A) or Parallel Connector Unit (B), Partitioning Agent (S*) or combinations of the Connector Unit and Parallel Connector Unit, as the case may be.

The oxygen glycosidic bond (—O'—) is typically a β-glucuronidase-cleavage site (i.e., Su is from glucuronide), such as a glycoside bond cleavable by human, lysosomal β-glucuronidase.

In some embodiments, the Glucuronide Unit can be represented by formula Ga or Gb:

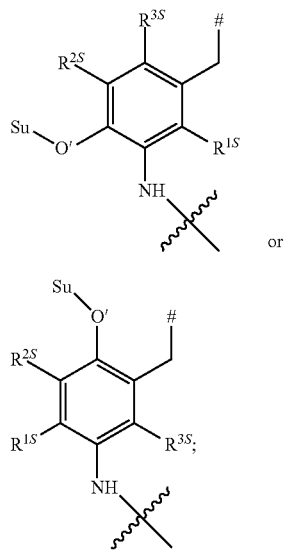

wherein Su is a Sugar moiety, —O'— represents an oxygen glycosidic bond; $R^{1S}$, $R^{2S}$ and $R^{3S}$ independently are hydrogen, a halogen, —CN, —NO$_2$, or other electron withdrawing group, or an electron donating group; and wherein the wavy line indicates attachment to a Stretcher Unit (Z) (or its precursor (Z'), either directly or indirectly through a Connector Unit or Parallel Connector Unit or Connector unit and Parallel Connector Unit); and # indicates attachment to the Camptothecin or to a Spacer (either directly or indirectly via an intervening functional group or other moiety).

In preferred embodiments $R^{1S}$, $R^{2S}$ and $R^{3S}$ are independently selected from hydrogen, halogen, —CN, or —NO$_2$. In other preferred embodiments, $R^{1S}$, $R^{2S}$ and $R^{3S}$ are each hydrogen. In other preferred embodiments $R^{2S}$ is an electron withdrawing group, preferably NO$_2$, and $R^{1S}$ and $R^{3S}$ are each hydrogen.

In some such aspects the activatable self-immolative group capable of glycosidase cleavage to initiate the self-immolative reaction sequence is represented by the formula Gc:

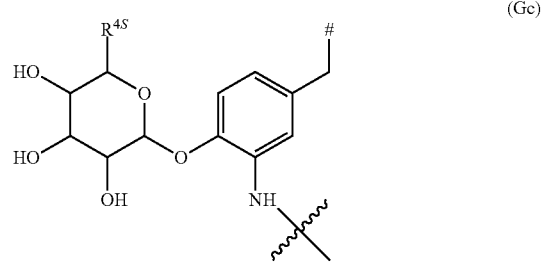

wherein $R^{4S}$ is CH$_2$OH or —CO$_2$H, the wavy line indicates covalent attachment to a Stretcher Unit (Z) (or its precursor Z'), either directly or indirectly through a Connector Unit or Parallel Connector Unit or Connector unit and Parallel Connector Unit, and the hash mark (#) indicates covalent attachment to the methylene carbamate unit.

In some embodiments wherein the activatable self-immolative moiety is comprised of a Glucuronide Unit, it is represented by the following formula Gd:

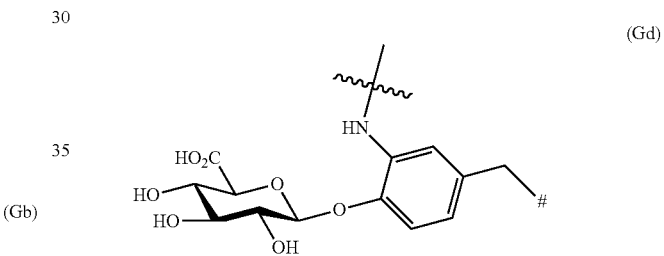

wherein the wavy line indicates covalent attachment to a Stretcher Unit (Z) (or its precursor Z'), either directly or indirectly through a Connector Unit or Parallel Connector Unit or Connector unit and Parallel Connector Unit and the hash mark (#) indicates covalent attachment of the benzylic carbon of a Spacer or functional group attached to the Camptothecin.

Another type of Releasable Linker that provides a mechanism for separation of the Camptothecin from the Ligand Unit and other components of the Linker Unit through activation of a self-immolation cascade within the Linker Unit is comprised of a p-aminobenzyloxycarbonyl (PAB) moiety whose phenylene component is substituted with $J_m$ wherein the subscript m indicating the number of substituents is an integer ranging from 0-4, and each J is independently —C$_1$-C$_8$ alkyl, —O—(C$_1$-C$_8$ alkyl), -halogen, -nitro or -cyano.

In some embodiments, RL is a self-immolative group capable of releasing -D without the need for a separate hydrolysis step or subsequent self-immolative event. In some embodiments, -RL- is a PAB moiety that is linked to the carbonyl of —W- via the amino nitrogen atom of the PAB group, and connected directly to -D via a carbonate group. In related embodiments, -RL- is comprised of a PAB moiety that is linked to the carbonyl of -A-, -S*- or -B- via the amino nitrogen atom of the PAB group, and connected directly to -D via a carbonate group. Without being bound by any particular theory or mechanism, a possible mechanism of Drug release from RL comprised of a PAB moiety in which RL is attached directly to -D via a carbonate group is shown in Toki et al. (2002) J Org. Chem. 1067:1866-1872.

In some embodiments, RL units containing a PAB moiety are represented by the formula:

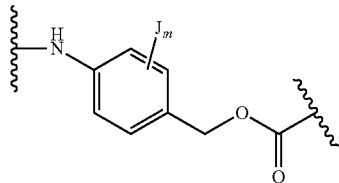

wherein subscript m is an integer ranging from 0-4, and each J is independently —$C_1$-$C_8$ alkyl, —O—($C_1$-$C_8$ alkyl), -halogen, -nitro or -cyano.

Other examples of self-immolative groups include, but are not limited to, aromatic compounds that are electronically similar to the PAB moiety such as 2-aminoimidazol-5-methanol derivatives (Hay et al. (1999) Bioorg. Med. Chem. Lett. 9:2237) and ortho or para-aminobenzylacetals. Other RLs undergo cyclization upon amide bond hydrolysis, such as substituted and unsubstituted 4-aminobutyric acid amides (Rodrigues et al., Chemistry Biology, 1995, 2, 223), appropriately substituted bicyclo[2.2.1] and bicyclo[2.2.2] ring systems (Storm, et al., J. Amer. Chem. Soc., 1972, 94, 5815) and 2-aminophenylpropionic acid amides (Amsberry, et al, J. Org. Chem., 1990, 55, 5867).

In one embodiment, RL is a branched bis(hydroxymethyl) styrene (BHMS) unit.

In some embodiments, RL has the formula:

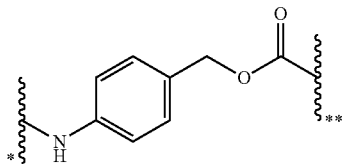 [SMILES: *Nc1ccc(COC(*)=O)cc1]

wherein the wavy line marked with ** indicates the site of attachment to D; and the wavy line marked with * indicates the point of attachment to additional linker components of Q.

In some embodiments, RL comprises a heterocyclic "self-immolating moiety" of Formulas I, II or III bound to the drug and incorporates an amide group that upon hydrolysis by an intracellular protease initiates a reaction that ultimately cleaves the self-immolative moiety from the drug such that the drug is released from the conjugate in an active form. The linker moiety further comprises a peptide sequence adjacent to the self-immolative moiety that is a substrate for an intracellular enzyme, for example an intracellular protease such as a cathepsin (e.g., cathepsin B), that cleaves the peptide at the amide bond shared with the self-immolative moiety. For embodiments disclosed herein, a PAB-containing RL is directly attached to the tertiary hydroxyl of the lactone ring present in each of CPT1-CPT7, in each of compound 14-14z of Table I or in each of compounds 18a-18r of Table J.

In some embodiments, a heterocyclic self-immolating group (RL) is selected from Formulas I, II and III:

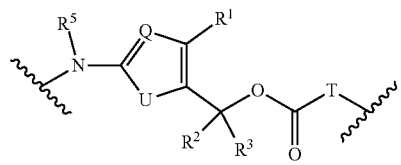

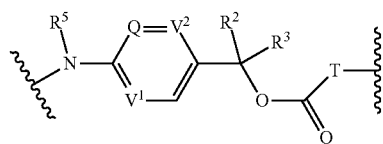

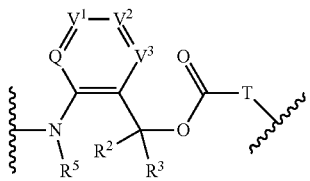

wherein the wavy lines indicate the covalent attachment sites to the cell-specific ligand and the drug moiety, and wherein U is O, S or $NR^6$; Q is $CR^4$ or N; $V^1$, $V^2$ and $V^3$ are independently $CR^4$ or N provided that for formula II and III at least one of Q, $V^1$ and $V^2$ is N;T is O pending from CPT1, CPT2, CPT3, CPT4, CPT5, CPT6 or CPT7;

$R^1$, $R^2$, $R^3$ and $R^4$ are independently selected from the group consisting of H, F, Cl, Br, I, OH, —$N(R^5)_2$, —$N(R^5)_3^+$, $C_1$-$C_8$ alkylhalide, carboxylate, sulfate, sulfamate, sulfonate, —$SO_2R^5$, —$S(=O)R^5$, —$SR^5$, —$SO_2N(R^5)_2$, —$C(=O)R^5$, —$CO_2R^5$, —$C(=O)N(R^5)_2$, —CN, —$N_3$, —$NO_2$, $C_1$-$C_8$ alkoxy, $C_1$-$C_8$ halo-substituted alkyl, polyethyleneoxy, phosphonate, phosphate, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle; or when taken together, $R^2$ and $R^3$ form a carbonyl (=O), or spiro carbocyclic ring of 3 to 7 carbon atoms; and $R^5$ and $R^6$ are independently selected from H, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle;

wherein $C_1$-$C_8$ substituted alkyl, $C_2$-$C_8$ substituted alkenyl, $C_2$-$C_8$ substituted alkynyl, $C_6$-$C_{20}$ substituted aryl, and $C_2$-$C_{20}$ substituted heterocycle are independently substituted with one or more substituents selected from the group consisting of F, Cl, Br, I, OH, —$N(R^5)_2$, —$N(R^5)_3^+$, $C_1$-$C_8$ alkylhalide, carboxylate, sulfate, sulfamate, sulfonate, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —$SO_2R^5$, —$S(=O)R^5$, —$SR^5$, —$SO_2N(R^5)_2$, —$C(=O)R^5$, —$CO_2R^5$, —$C(=O)N(R^5)_2$, —CN, —$N_3$, —$NO_2$, $C_1$-$C_8$ alkoxy, $C_1$-$C_8$ trifluoroalkyl, $C_1$-$C_8$ alkyl, $C_3$-$C_{12}$ carbocycle, $C_6$-$C_{20}$ aryl, $C_2$-$C_{20}$ heterocycle, polyethyleneoxy, phosphonate, and phosphate.

The conjugate is stable extracellularly, or in the absence of an enzyme capable of cleaving the amide bond of the self-immolative moiety. However, upon entry into a cell, or exposure to a suitable enzyme, an amide bond is cleaved initiating a spontaneous self-immolative reaction resulting in the cleavage of the bond covalently linking the self-immolative moiety to the drug, to thereby effect release of the drug in its underivatized or pharmacologically active form.

The self-immolative moiety in conjugates of the invention either incorporates one or more heteroatoms and thereby provides improved solubility, improves the rate of cleavage and/or decreases propensity for aggregation of the conjugate. These improvements of the heterocyclic self-immolative linker constructs of the present invention over non-heterocyclic, PAB-type linkers in some instances result in surprising and unexpected biological properties such as increased efficacy, decreased toxicity, and/or improvements in one or more desirable pharmacokinetic and/or pharmacodynamic properties.

It is understood that T in Formulae I-III is O, as it is derived from the tertiary hydroxyl (—OH) on the lactone ring portion of any one of CPT1, CPT2, CPT3, CPT4, CPT5, CPT6, CPT7, compounds 14a-14z of Table I and compounds 18a-18r of Table J.

Not to be limited by theory or any particular mechanism, the presence of electron-withdrawing groups on the heterocyclic ring of formula I, II or III linkers sometimes moderate the rate of cleavage.

In one embodiment, the self-immolative moiety is the group of formula I in which Q is N, and U is O or S. Such a group has a non-linearity structural feature which improves solubility of the conjugates. In this context R is sometimes H, methyl, nitro, or $CF_3$. In one embodiment, Q is N and U is O thereby forming an oxazole ring and R is H. In another embodiment, Q is N and U is S thereby forming a thiazole ring optionally substituted at R with an Me or $CF_3$ group.

In another exemplary embodiment, the self-immolative moiety is the group of formula II in which Q is N and $V^1$ and $V^2$ are independently N or CH. In another embodiment, Q, $V^1$ and $V^2$ are each N. In another embodiment, Q and $V^1$ are N while $V^2$ is CH. In another embodiment, Q and $V^2$ are both CH and $V^2$ is N. In another embodiment, Q is N while $V^1$ and $V^2$ are both CH.

In another embodiment, the self-immolative moiety is the group of formula III in which Q, $V^1$, $V^2$ and $V^3$ are each independently N or CH. In another embodiment Q is N while $V^1$, $V^2$ and $V^3$ are each N. In another embodiment, Q $V^1$, and $V^2$ are each CH while $V^3$ is N. In another embodiment Q, $V^2$ and $V^3$ are each CH while $V^1$ is N. In another embodiment, Q, $V^1$ and $V^3$ are each CH while $V^2$ is N. In another embodiment, Q and $V^2$ are both N while $V^1$ and $V^3$ are both CH. In another embodiment Q and $V^2$ are both CH while $V^1$ and $V^3$ are both N. In another embodiment, Q and $V^3$ are both N while $V^1$ and $V^2$ are both CH.

Without being bound by theory, Scheme 1a depicts a mechanism of free drug release from a Camptothecin Drug Unit attached through a nitrogen atom of an amine substituent from the free drug to a Releasable Linker that is a Glucuronide Unit.

Scheme 1a

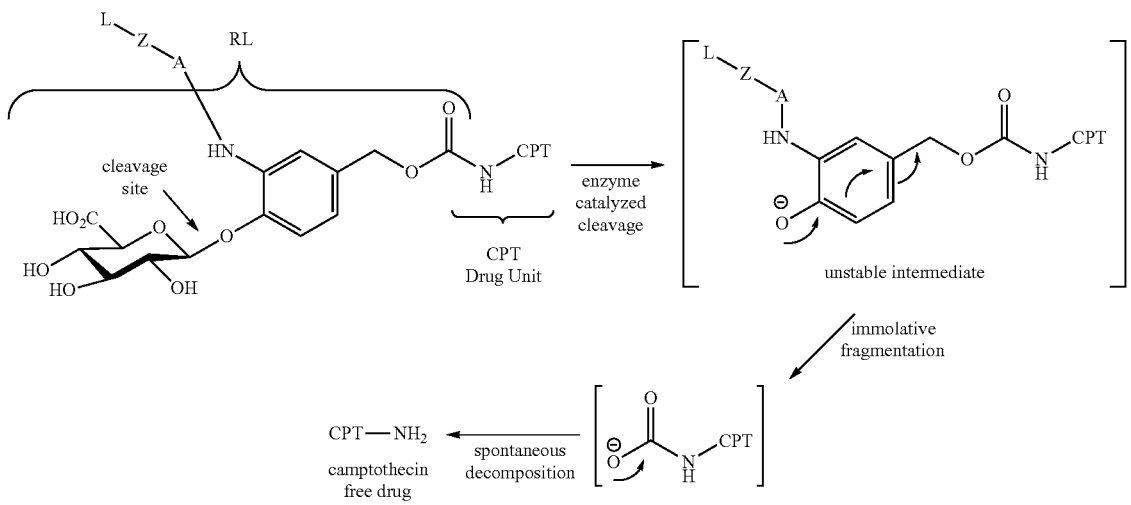

Partitioning Agent (S*):

The Camptothecin Conjugates described herein can also include a Partitioning Agent (S*). The Partitioning Agent portions are useful, for example, to mask the hydrophobicity of particular Camptothecin Drug Units or Linking Unit components.

Representative Partitioning Agents include polyethylene glycol (PEG) units, cyclodextrin units, polyamides, hydrophilic peptides, polysaccharides and dendrimers.

When the polyethylene glycol (PEG) units, cyclodextrin units, polyamides, hydrophilic peptides, polysaccharides or dendrimers are included in Q, the groups may be present as an 'in line' component or as a side chain or branched component. For those embodiments in which a branched version is present, the Linker Units will typically include a lysine residue (or Parallel Connector Unit, B) that provides simple functional conjugation of, for example, the PEG unit, to the remainder of the Linking Unit.

Polyethylene Glycol Unit (PEG)

Polydisperse PEGS, monodisperse PEGS and discrete PEGs can be used to make the Compounds of the present invention. Polydisperse PEGs are a heterogeneous mixture of sizes and molecular weights whereas monodisperse PEGs are typically purified from heterogeneous mixtures and are therefore provide a single chain length and molecular weight. Preferred PEG Units are discrete PEGs, compounds that are synthesized in stepwise fashion and not via a polymerization process. Discrete PEGs provide a single molecule with defined and specified chain length.

The PEG Unit provided herein comprises one or multiple polyethylene glycol chains. In some embodiments the polyethylene glycol chains are linked together, for example, in a linear, branched or star shaped configuration. Typically, at least one of the PEG chains is derivitized at one end for covalent attachment to an appropriate site on a component of the Linker Unit (e.g. B) or can be used as an in-line (e.g., bifunctional) linking group within to covalently join two of the Linker Unit components (e.g., Z-A-S*—RL-, Z-A-S*-RL-Y-). Exemplary attachments within the Linker Unit are by means of non-conditionally cleavable linkages or via conditionally cleavable linkages. Exemplary attachments are via amide linkage, ether linkages, ester linkages, hydrazone linkages, oxime linkages, disulfide linkages, peptide linkages or triazole linkages. In some embodiments, attachment within the Linker Unit is by means of a non-conditionally cleavable linkage. In some embodiments, attachment within the Linker Unit is not via an ester linkage, hydrazone linkage, oxime linkage, or disulfide linkage. In some embodiments, attachment within the Linker Unit is not via a hydrazone linkage.

A conditionally cleavable linkage refers to a linkage that is not substantially sensitive to cleavage while circulating in the plasma but is sensitive to cleavage in an intracellular or intratumoral environment. A non-conditionally cleavable linkage is one that is not substantially sensitive to cleavage in any biological environment. Chemical hydrolysis of a hydrazone, reduction of a disulfide, and enzymatic cleavage of a peptide bond or glycosidic linkage are examples of conditionally cleavable linkages.

In some embodiments, the PEG Unit will be directly attached to a Parallel Connector Unit B. The other terminus (or termini) of the PEG Unit will be free and untethered and may take the form of a methoxy, carboxylic acid, alcohol or another suitable functional group. The methoxy, carboxylic acid, alcohol or other suitable functional group acts as a cap for the terminal PEG subunit of the PEG Unit. By untethered, it is meant that the PEG Unit will not be attached at that untethered site to a Camptothecin, to an antibody, or to another linking component. The skilled artisan will understand that the PEG Unit in addition to comprising repeating polyethylene glycol subunits may also contain non-PEG material (e.g., to facilitate coupling of multiple PEG chains to each other). Non-PEG material refers to the atoms in the PEG Unit that are not part of the repeating —$CH_2CH_2O$— subunits. In some embodiments provided herein, the PEG Unit comprises two monomeric PEG chains attached to each other via non-PEG elements. In other embodiments provided herein, the PEG Unit comprises two linear PEG chains attached to a central core or Parallel Connector Unit (i.e., the PEG Unit itself is branched).

There are a number of PEG attachment methods available to those skilled in the art, [see, e.g., Goodson, et al. (1990) *Bio/Technology* 8:343 (PEGylation of interleukin-2 at its glycosylation site after site-directed mutagenesis); EP 0401384 (coupling PEG to G-CSF); Malik, et al., (1992) *Exp. Hematol.* 20:1028-1035 (PEGylation of GM-CSF using tresyl chloride); PCT Pub. No. WO 90/12874 (PEGylation of erythropoietin containing a recombinantly introduced cysteine residue using a cysteine-specific mPEG derivative); U.S. Pat. No. 5,757,078 (PEGylation of EPO peptides); U.S. Pat. No. 5,672,662 (Poly(ethylene glycol) and related polymers monosubstituted with propionic or butanoic acids and functional derivatives thereof for biotechnical applications); U.S. Pat. No. 6,077,939 (PEGylation of an N-terminal .alpha.-carbon of a peptide); Veronese et al., (1985) *Appl. Biochem. Biotechnol* 11:141-142 (PEGylation of an N-terminal α-carbon of a peptide with PEG-nitrophenylcarbonate ("PEG-NPC") or PEG-trichlorophenylcarbonate); and Veronese (2001) *Biomaterials* 22:405-417 (Review article on peptide and protein PEGylation)].

For example, PEG may be covalently bound to amino acid residues via a reactive group. Reactive groups are those to which an activated PEG molecule may be bound (e.g., a free amino or carboxyl group). For example, N-terminal amino acid residues and lysine (K) residues have a free amino group; and C-terminal amino acid residues have a free carboxyl group. Thiol groups (e.g., as found on cysteine residues) are also useful as a reactive group for attaching PEG. In addition, enzyme-assisted methods for introducing activated groups (e.g., hydrazide, aldehyde, and aromatic-amino groups) specifically at the C-terminus of a polypeptide have been described (see Schwarz, et al. (1990) *Methods Enzymol.* 184:160; Rose, et al. (1991) *Bioconjugate Chem.* 2:154; and Gaertner, et al. (1994) *J. Biol. Chem.* 269:7224].

In some embodiments, PEG molecules may be attached to amino groups using methoxylated PEG ("mPEG") having different reactive moieties. Non-limiting examples of such reactive moieties include succinimidyl succinate (SS), succinimidyl carbonate (SC), mPEG-imidate, para-nitrophenylcarbonate (NPC), succinimidyl propionate (SPA), and cyanuric chloride. Non-limiting examples of such mPEGs include mPEG-succinimidyl succinate (mPEG-SS), mPEG$_2$-succinimidyl succinate (mPEG$_2$-SS); mPEG-succinimidyl carbonate (mPEG-SC), mPEG$_2$-succinimidyl carbonate (mPEG$_2$-SC); mPEG-imidate, mPEG-para-nitrophenylcarbonate (mPEG-NPC), mPEG-imidate; mPEG$_2$-para-nitrophenylcarbonate (mPEG$_2$-NPC); mPEG-succinimidyl propionate (mPEG-SPA); mPEG$_2$-succinimidyl propionate (mPEG$_2$-SPA); mPEG-N-hydroxy-succinimide (mPEG-NHS); mPEG$_2$-N-hydroxy-succinimide (mPEG$_2$-NHS); mPEG-cyanuric chloride; mPEG$_2$-cyanuric chloride; mPEG$_2$-Lysinol-NPC, and mPEG$_2$-Lys-NHS.

Generally, at least one of the PEG chains that make up the PEG Unit is functionalized so that it is capable of covalent attachment to other Linker Unit components.

Functionalization includes, for example, via an amine, thiol, NHS ester, maleimide, alkyne, azide, carbonyl, or some other functional group. In some embodiments, the PEG Unit further comprises non-PEG material (i.e., material not comprised of —$CH_2CH_2O$—) that provides coupling to other Linker Unit components or to facilitate coupling of two or more PEG chains.

The presence of the PEG Unit (or other Partitioning Agent) in the Linker Unit can have two potential impacts upon the pharmacokinetics of the resulting Camptothecin Conjugate. The desired impact is a decrease in clearance (and consequent increase in exposure) that arises from the reduction in non-specific interactions induced by the exposed hydrophobic elements of the Camptothecin Conjugate or to the Camptothecin itself. The second impact is undesired and is a decrease in volume and rate of distribution that sometimes arises from the increase in the molecular weight of the Camptothecin Conjugate.

Increasing the number of PEG subunits increases the hydrodynamic radius of a conjugate, typically resulting in decreased diffusivity. In turn, decreased diffusivity typically diminishes the ability of the Camptothecin Conjugate to penetrate a tumor (Schmidt and Wittrup, *Mol Cancer Ther* 2009; 8:2861-2871). Because of these two competing pharmacokinetic effects, it is desirable to use a PEG that is sufficiently large to decrease the Camptothecin Conjugate clearance thus increasing plasma exposure, but not so large as to greatly diminish its diffusivity, to an extent that it interferes with the ability of the Camptothecin Conjugate to reach the intended target cell population. See the examples (e.g., examples 1, 18, and 21) of US2016/0310612, which are incorporated by reference herein, for methodology for selecting an optimal PEG size for a particular drug-linker.

In one group of embodiments, the PEG Unit comprises one or more linear PEG chains each having at least 2 subunits, at least 3 subunits, at least 4 subunits, at least 5 subunits, at least 6 subunits, at least 7 subunits, at least 8 subunits, at least 9 subunits, at least 10 subunits, at least 11 subunits, at least 12 subunits, at least 13 subunits, at least 14 subunits, at least 15 subunits, at least 16 subunits, at least 17 subunits, at least 18 subunits, at least 19 subunits, at least 20 subunits, at least 21 subunits, at least 22 subunits, at least 23 subunits, or at least 24 subunits. In preferred embodiments, the PEG Unit comprises a combined total of at least 4 subunits, at least 6 subunits, at least 8 subunits, at least 10 subunits, or at least 12 subunits. In some such embodiments, the PEG Unit comprises no more than a combined total of about 72 subunits, preferably no more than a combined total of about 36 subunits.

In another group of embodiments, the PEG Unit comprises a combined total of from 4 to 72, 4 to 60, 4 to 48, 4 to 36 or 4 to 24 subunits, from 5 to 72, 5 to 60, 5 to 48, 5 to 36 or 5 to 24 subunits, from 6 to 72, 6 to 60, 6 to 48, 6 to 36 or from 6 to 24 subunits, from 7 to 72, 7 to 60, 7 to 48, 7 to 36 or 7 to 24 subunits, from 8 to 72, 8 to 60, 8 to 48, 8 to 36 or 8 to 24 subunits, from 9 to 72, 9 to 60, 9 to 48, 9 to 36 or 9 to 24 subunits, from 10 to 72, 10 to 60, 10 to 48, 10 to 36 or 10 to 24 subunits, from 11 to 72, 11 to 60, 11 to 48, 11 to 36 or 11 to 24 subunits, from 12 to 72, 12 to 60, 12 to 48, 12 to 36 or 12 to 24 subunits, from 13 to 72, 13 to 60, 13 to 48, 13 to 36 or 13 to 24 subunits, from 14 to 72, 14 to 60, 14 to 48, 14 to 36 or 14 to 24 subunits, from 15 to 72, 15 to 60, 15 to 48, 15 to 36 or 15 to 24 subunits, from 16 to 72, 16 to 60, 16 to 48, 16 to 36 or 16 to 24 subunits, from 17 to 72, 17 to 60, 17 to 48, 17 to 36 or 17 to 24 subunits, from 18 to 72, 18 to 60, 18 to 48, 18 to 36 or 18 to 24 subunits, from 19 to 72, 19 to 60, 19 to 48, 19 to 36 or 19 to 24 subunits, from 20 to 72, 20 to 60, 20 to 48, 20 to 36 or 20 to 24 subunits, from 21 to 72, 21 to 60, 21 to 48, 21 to 36 or 21 to 24 subunits, from 22 to 72, 22 to 60, 22 to 48, 22 to 36 or 22 to 24 subunits, from 23 to 72, 23 to 60, 23 to 48, 23 to 36 or 23 to 24 subunits, or from 24 to 72, 24 to 60, 24 to 48, 24 to 36 or 24 subunits.

Illustrative linear PEG Units that can be used in any of the embodiments provided herein are as follows:

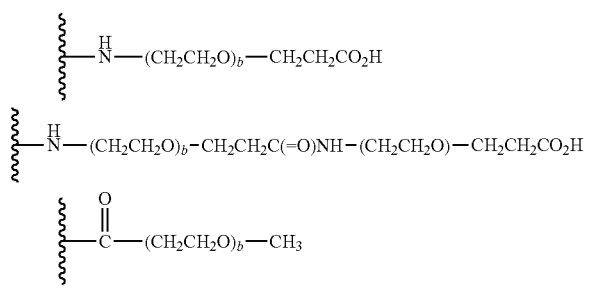

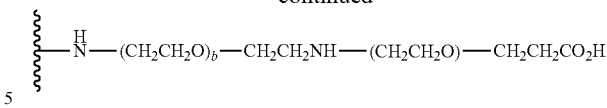

wherein the wavy line indicates site of attachment to the Parallel Connector Unit (B), and each n is independently selected from 4 to 72, 6 to 72, 8 to 72, 10 to 72, 12 to 72, 6 to 24, or 8 to 24. In some embodiments, subscript b is about 4, about 8, about 12, or about 24.

As described herein, the PEG unit is selected such that it improves clearance of the resultant Camptothecin Conjugate but does not significantly impact the ability of the Conjugate to penetrate into the tumor. In embodiments, the PEG unit to be selected for use will preferably have from 4 subunits to about 24 subunits, more preferably about 4 subunits to about 12 subunits.

In preferred embodiments of the present disclosure the PEG Unit is from about 300 daltons to about 5 kilodaltons; from about 300 daltons, to about 4 kilodaltons; from about 300 daltons, to about 3 kilodaltons; from about 300 daltons, to about 2 kilodaltons; or from about 300 daltons, to about 1 kilodalton. In some such aspects, the PEG Unit has at least 6 subunits or at least 8, 10 or 12 subunits. In some such aspects, the PEG Unit has at least 6 subunits or at least 8, 10 or 12 subunits but no more than 72 subunits, preferably no more than 36 subunits.

It will be appreciated that when referring to PEG subunits, and depending on context, the number of subunits can represent an average number, e.g., when referring to a population of Camptothecin Conjugates or Camptothecin-Linker Compounds using polydisperse PEGs.

Parallel Connector Unit (B):

In some embodiments, the Camptothecin Conjugates and Camptothecin Linker Compounds will comprise a Parallel Connector Unit to provide a point of attachment to a Partitioning Agent (shown in the Linker Units as —B(S*)—). As a general embodiment, the PEG Unit can be attached to a Parallel Connector Unit such as lysine as shown below wherein the wavy line and asterisks indicate covalent linkage within the Linker Unit of a Camptothecin Conjugate or Camptothecin Linker Compound:

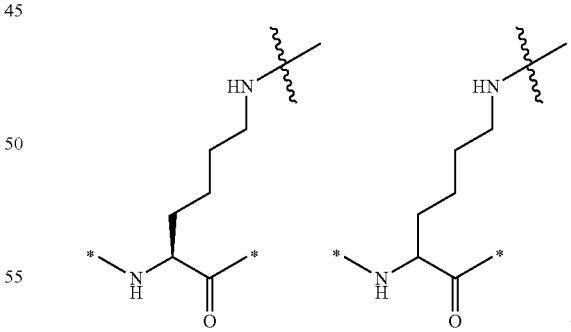

Spacer Unit (Y):

In some embodiments, the Camptothecin Conjugates provided herein will have a Spacer (Y) between the Releasable Linker (RL) and the Camptothecin. The Spacer Unit can be a functional group to facilitate attachment of RL to the Camptothecin, or it can provide additional structural components to further facilitate release of the Camptothecin Unit from the remainder of the Conjugate (e.g., a methylene carbamate unit).

In those embodiments to further facilitate release of the Camptothecin Unit as free drug exemplary Spacer Units are represented by the formulae:

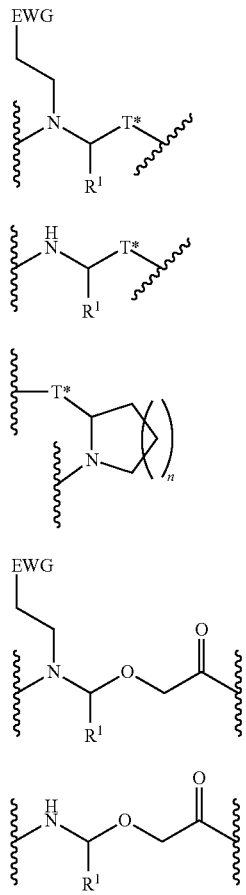

(a)

(a')

(a")

(b)

(b')

of Table I or any one of compounds 18a-18r of Table J and wherein the wavy line adjacent to T* is the point of covalent attachment to the remainder of the Camptothecin Drug Unit corresponding in structure to the camptothecin compound.

In still other embodiments, Spacer Units that are methylene carbamate units are represented by the formulae:

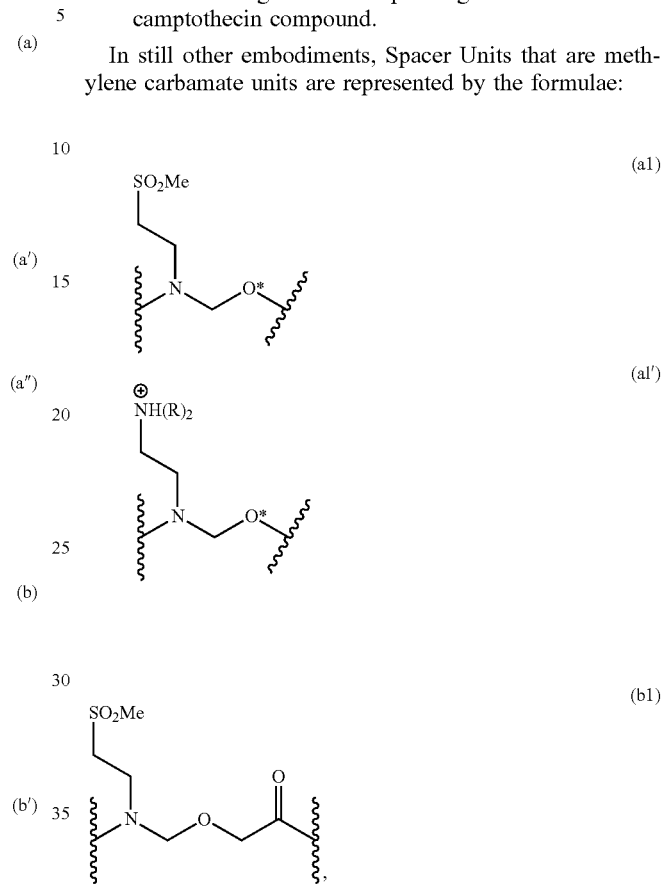

(a1)

(a1')

(b1)

wherein EWG represents an electron-withdrawing group, $R^1$ is —H or $C_1$-$C_4$ alkyl and subscript n is 1 or 2. In some embodiments, EWG is selected from the group consisting of —CN, —$NO_2$, —$CX_3$, —X, C(=O)OR', —C(=O)N(R')$_2$, —C(=O)R', —C(=O)X, —S(=O)$_2$R', —S(=O)$_2$OR', —S(=O)$_2$NHR', —S(=O)$_2$N(R')$_2$, —P(=O)(OR')$_2$, —P(=O)($CH_3$)NHR', —NO, —N(R')$_3^+$, wherein X is —F, —Br, —Cl, or —I, and R is independently selected from the group consisting of hydrogen and $C_1$-$C_6$ alkyl, and wherein the wavy line adjacent to the nitrogen atom in each of formula (a), (a'), (a"), (b) and (b') is the point of covalent attachment to RL and the wavy line adjacent to the carbonyl carbon atom of formula (b) and formula (b') is the point of covalent attachment to a heteroatom of a hydroxyl or primary or secondary amine of a camptothecin compound of formula CPT1, CPT2, CPT3, CPT4, CPT5, CPT 6 or CPT7, or of any one of compounds 14a-14z of Table I or any one of compounds 18a-18r of Table J and wherein formula (a), formula (a') and formula (a") represents exemplary methylene carbamate units in which T* is the heteroatom from a hydroxyl or primary or secondary amine functional group of a camptothecin compound of formula CPT1, CPT2, CPT3, CPT4, CPT5, CPT 6 or CPT7 or of any one of compounds 14a-14z wherein formula (a1) and formula (a1') in which each R is independently —H or $C_1$-$C_4$ alkyl represents methylene carbamate units in which O* is the oxygen atom from the hydroxyl substituent to the lactone ring of the camptothecin compound of formula CPT1, CPT2, CPT3, CPT4, CPT5, CPT 6 or CPT7 or of any one of compounds 14a-14z of Table I or any one of compounds 18a-18r of Table J, or from the another hydroxyl substituent of the camptothecin compound of formula CPT5 or CPT7 or from the hydroxyl substituents of $R^F$ or $R^{F'}$ of CPT6, when at least one of $R^F$ and $R^{F'}$ is $C_1$-$C_8$ hydroxyalkyl N,N—($C_1$-$C_4$ hydroxyalkyl)($C_1$-$C_4$ alkyl)-amino-$C_1$-$C_8$ alkyl- or N—$C_1$-$C_4$ hydroxyalkyl-$C_1$-$C_8$ aminoalkyl-, $C_1$-$C_8$ alkylC(O)—, and the wavy lines of formula (a1), formula (a1') and formula (b1) retain their previous meanings from formulae (a), (a') and (b), respectively. In formula (a1') the —$CH_2CH_2N^+(R)_2$ moiety represents exemplary Basic Units in protonated form.

Without being bound by theory, Scheme 1b depicts a mechanism of free drug release from a Camptothecin attached to a methylene carbamate unit in a Camptothecin Conjugate having a self-immolative moiety. In that scheme, T* is a heteroatom from the hydroxyl or primary or secondary amine of a Camptothecin compound that is incorporated into the methylene carbamate unit.

Scheme 1b

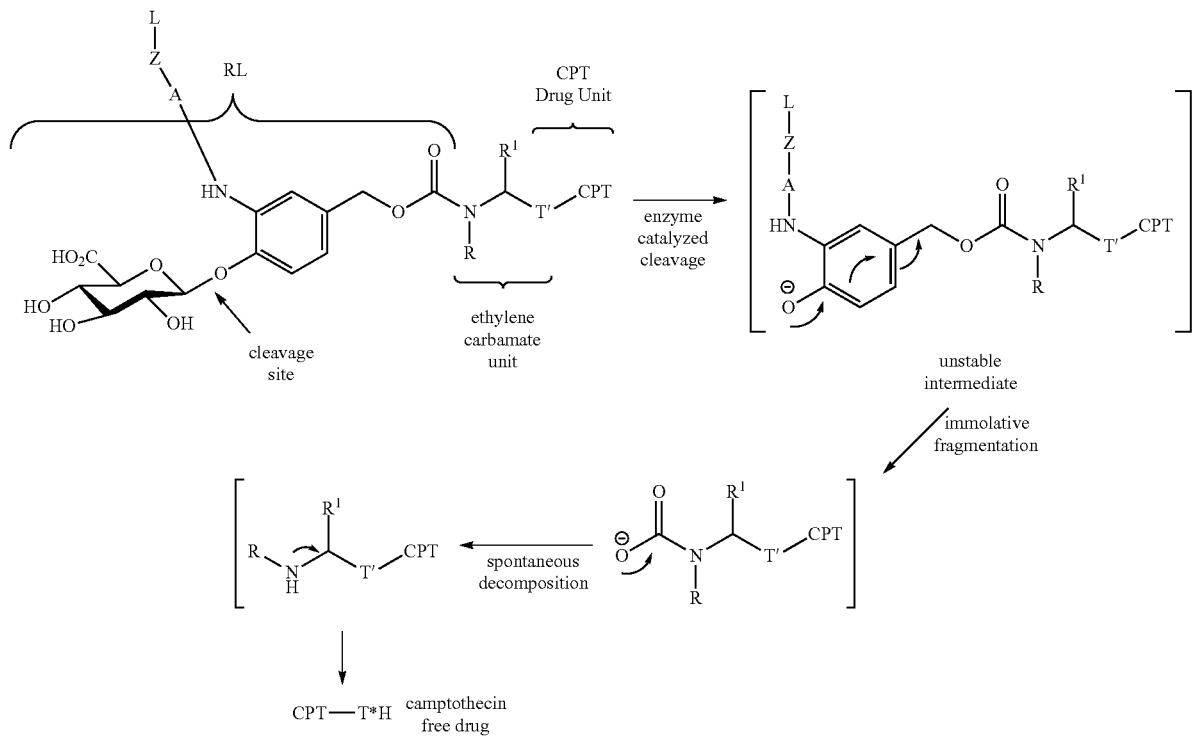

Subscript "p"

In one group of embodiments of the invention, subscript p represents the number of Drug Linker moieties on a Ligand Unit of an individual Camptothecin Conjugate and is an integer preferably ranging from 1 to 16, 1 to 12, 1 to 10, or 1 to 8. Individual Camptothecin Conjugates can be also be referred to as a Camptothecin Conjugate compound. In that group of embodiments there are 1, 2, 3, 4, 5, 6, 7, 8, 9, 10, 11, 12, 13, 14, 15, or 16 Drug Linker moieties conjugated to a Ligand Unit of an individual Camptothecin Conjugate. In another group of embodiments of the invention, a Camptothecin Conjugate describes a population of individual Camptothecin Conjugate compounds substantially identical except for the number of Camptothecin drug linker moieties bound to each Ligand Unit (i.e., a Camptothecin Conjugate composition) so that subscript p represents the average number of Camptothecin drug linker moieties bound to the Ligand Units of the Camptothecin Conjugate composition. In that group of embodiments, subscript p is a number ranging from 1 to about 16, 1 to about 12, 1 to about 10, or 1 to about 8, from 2 to about 16, 2 to about 12, 2 to about 10, or 2 to about 8. In some embodiments, the value of subscript p refers to the average drug loading as well as the drug loading of the predominate ADC in the composition.

In some embodiments, conjugation will be via the interchain disulfides and there will from 1 to about 8 Camptothecin Linker Compound molecules conjugated to a targeting agent that becomes a Ligand Unit. In some embodiments, conjugation will be via an introduced cysteine residue as well as interchain disulfides and there will be from 1 to 10 or 1 to 12 or 1 to 14 or 1 to 16 Camptothecin Linker Compound moieties conjugated to a Ligand Unit. In some embodiments, conjugation will be via an introduced cysteine residue and there will be 2 or 4 Camptothecin Linker Compound molecules conjugated to a Ligand Unit.

| | | Camptothecin Drug-Linker Compounds | | | |
|---|---|---|---|---|---|
| Drug Linker Number | Z'-A | S* or B(S*) | RL | Y | Camptothecin (N or O link) |
| | | Glucuronide Drug-Linker Compounds | | | |
| 67 | mDPr-β-Ala | — | Glucuronide | — | CPT1 (N) |
| 72 | mDPr- | Lys (PEG24)-β-Ala | Glucuronide | — | CPT1 (N) |
| 51 | mPr-β-Ala | — | Glucuronide | — | " |
| 29 | mPr-β-Ala | — | Glucuronide | — | CPT4 (N) |
| 48 | mPr-β-Ala | — | Glucuronide | — | 13b (N) |
| 100 | mDPr-MeGly- | — | Glucuronide | — | CPT4 (N) |
| 55 | mPr-MeGly- | — | Glucuronide | (a1) | CPT2 (O) |
| 34 | mPr-MeGly- | — | Glucuronide | (a1) | CPT5 (O) |
| 42 | mPr-MeGly- | — | Glucuronide | (b1) | CPT4 (N) |
| 103 | mPr-β-Ala | — | Glucuronide | — | CPT6 (N) |
| 109a | mPr-MeGly- | — | Glucuronide | — | CPT1 (N) |

Camptothecin Drug-Linker Compounds

| Drug Linker Number | Z'-A | S* or B(S*) | RL | Y | Camptothecin (N or O link) |
|---|---|---|---|---|---|
| 109b | mPr-MeGly- | — | Glucuronide | — | 18q (N) |
| 58 | mPr-MeGly- | — | Glucuronide | (a1) | CPT3 (O) |
| 61 | mPr-MeGly- | — | Glucuronide | (a1) | CPT3 (O') |
| 150 | mPr-MeGly | — | Glucuronide | (a1) | CPT7 (O') |
| 135 | mPr-β-Ala | — | Glucuronide | — | 14a (N) |
| 138a | mPr-β-Ala | — | Glucuronide | — | 18q (N) |
| 138b | mPr-β-Ala | — | Glucuronide† | — | 18r (N) |
| 141 | mPr-MeGly | — | Glucuronide | (a1) | 18m (O) |
| 113 | mPr-MeGly | — | Glucuronide | — | 18m (O) |
| 114a | mPr-MeGly | — | Glucuronide | — | 18h (O) |
| 114b | mPr-MeGly | — | Glucuronide | — | 6 (O) |
| 150 | mPr-MeGly | — | Glucuronide | (a) | CPT7 (O') |
| Click Drug Linker Compounds | | | | | |
| 86 | PropargOPr-MeGly- | — | Glucuronide | (a1) | CPT4 (O') |
| 82 | PropargOPr-MeGly- | — | Glucuronide | — | CPT4 (N) |
| 87 | PropargOPr-MeGly- | — | Glucuronide | (a1) | CPT4 (O') |
| 63 | PropargOPr-MeGly- | — | Glucuronide | (a1) | CPT3 (O') |
| 62 | PropargOPr-MeGly- | — | Glucuronide | (a1) | CPT3 (O) |
| 144 | PropargOPr-MeGly- | — | Glucuronide | (a1) | CPT6 (N) |

†Glucuronic acid residue replaced by mannose mDPR=maleimido-aminopropionyl:

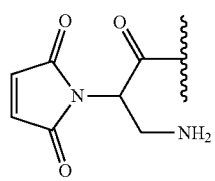 [SMILES: *C(=O)C(CN)N1C(=O)C=CC1=O]

mPR=Maleimido-propionyl:

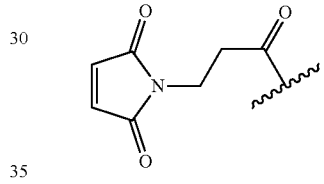

PropargOPr=—(C=O)CH$_2$CH$_2$OCH$_2$C≡CH

Other Camptothecin Drug Linker Compounds

| Drug Linker Number | General Formula | Compound Structure |
|---|---|---|
| 120 | Z'-A-D | 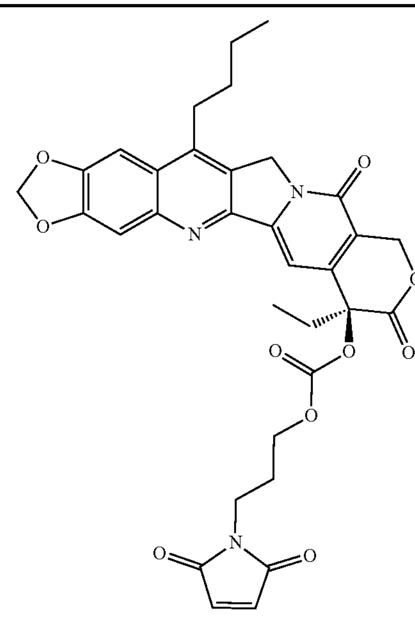 |

Other Camptothecin Drug Linker Compounds
| Drug Linker Number | General Formula | Compound Structure |
|---|---|---|
| 124 | Z'-A-D | 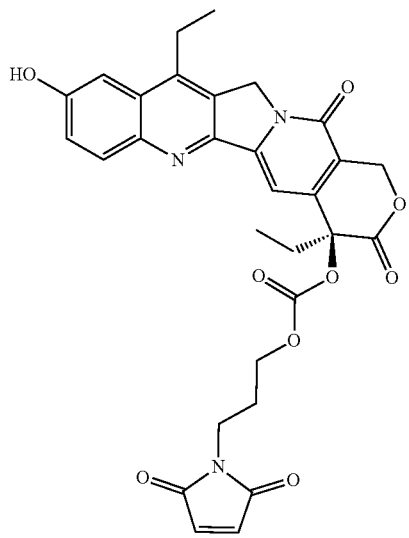 [SMILES: CCc1c2c(nc3ccc(O)cc13)-c1cc3c(c(=O)n1C2)COC(=O)[C@@]3(CC)OC(=O)OCCCN1C(=O)C=CC1=O] |
| 120 | Z'-A-S*-W-D | 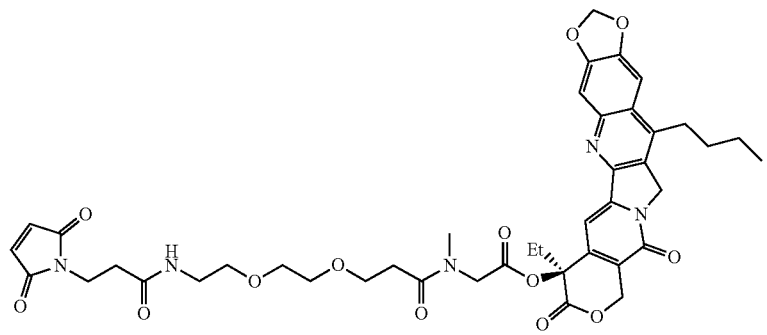 [SMILES: CCCCc1c2c(nc3cc4c(cc13)OCO4)-c1cc3c(c(=O)n1C2)COC(=O)[C@@]3(CC)OC(=O)CN(C)C(=O)CCOCCOCCNC(=O)CCN1C(=O)C=CC1=O] |
| 133 | Z'-A-S*-W-RL-D | 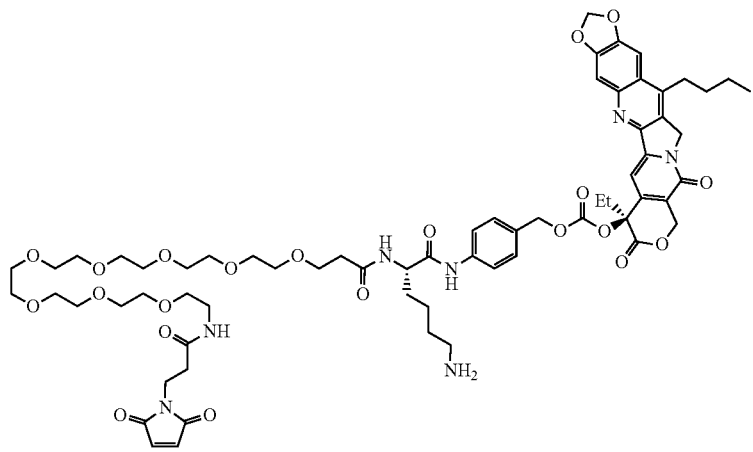 |

Other Camptothecin Drug Linker Compounds

| Drug Linker Number | General Formula | Compound Structure |
|---|---|---|
| 129 | Z'-A-S*-W-RL-D | 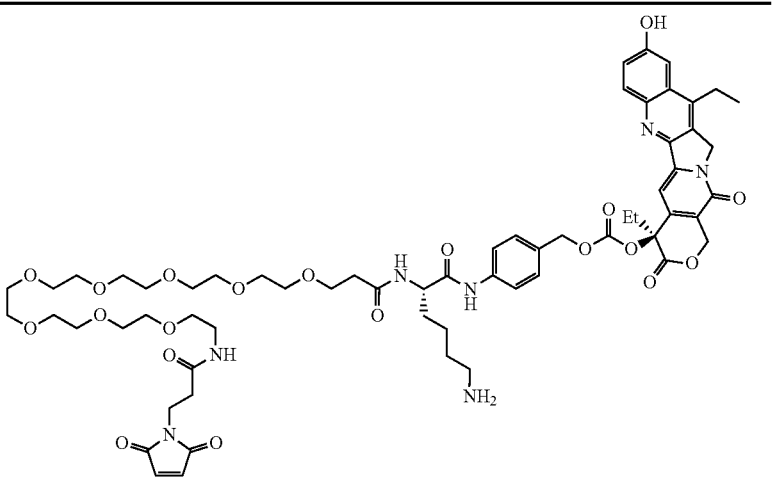 |

Camptothecin Conjugate Mixtures and Compositions

The present invention provides Camptothecin Conjugate mixtures and pharmaceutical compositions comprising any of the Camptothecin Conjugates described herein. The mixtures and pharmaceutical compositions comprise a plurality of conjugates. In some embodiments, each of the conjugates in the mixture or composition is identical or substantially identical, however, the distribution of drug-linkers on the ligands in the mixture or compositions may vary as well as the drug loading. For example, the conjugation technology used to conjugate drug-linkers to antibodies as the targeting agent in some embodiments results in a composition or mixture that is heterogeneous with respect to the distribution of Camptothecin Linker Compounds on the antibody (Ligand Unit) within the mixture and/or composition. In some of those embodiments, the loading of Camptothecin Linker Compounds on each of the antibody molecules in a mixture or composition of such molecules is an integer that ranges from 1 to 16.

In those embodiments, when referring to the composition as a whole, the loading of drug-linkers is a number ranging from 1 to about 16. Within the composition or mixture, there sometimes is a small percentage of unconjugated antibodies. The average number of drug-linkers per Ligand Unit in the mixture or composition (i.e., average drug-load) is an important attribute as it relates to the maximum amount of drug that can be delivered to the target cell. Typically, the average drug load is 1, 2 or about 2, 3 or about 3, 4 or about 4, 5 or about 5, 6 or about 6, 7 or about 7, 8 or about 8, 9 or about 9, 10 or about 10, 11 or about 11, 12 or about 12, 13 or about 13, 14 or about 14, 15 or about 15, 16 or about 16.

In some embodiments, the mixtures and pharmaceutical compositions comprise a plurality (i.e., population) of conjugates, however, the conjugates are identical or substantially identical and are substantially homogenous with respect to the distribution of drug-linkers on the ligand molecules within the mixture and/or composition and with respect to loading of drug-linkers on the ligand molecules within the mixture and/or composition. In some such embodiments, the loading of drug-linkers on an antibody Ligand Unit is 2 or 4. Within the composition or mixture, there may also be a small percentage of unconjugated antibodies. The average drug load in such embodiments is about 2 or about 4. Typically, such compositions and mixtures result from the use of site-specific conjugation techniques and conjugation is due to an introduced cysteine residue.

The average number of Camptothecins or Camptothecin-Linker Compounds per Ligand Unit in a preparation from a conjugation reaction is typically characterized by conventional means such as mass spectrometry, ELISA assay, HPLC (e.g., HIC). In those instances, the quantitative distribution of Camptothecin Conjugates in terms of subscript p is typically determined. In other instances, separation, purification, and characterization of homogeneous Camptothecin Conjugates is typically achieved by conventional means such as reverse phase HPLC or electrophoresis.

In some embodiments, the compositions are pharmaceutical compositions comprising the Camptothecin Conjugates described herein and a pharmaceutically acceptable carrier. In some of those embodiments, the pharmaceutical composition is in liquid form. In other of those embodiments, the pharmaceutical composition is a lyophilized powder.

The compositions, including pharmaceutical compositions, can be provided in purified form. As used herein, "purified" means that when isolated, the isolate contains at least 95%, and in other embodiments at least 98%, of Conjugate by weight of the isolate.

Methods of Use
Treatment of Cancer

The Camptothecin Conjugates are useful for inhibiting the multiplication of a tumor cell or cancer cell, causing apoptosis in a tumor or cancer cell, or for treating a cancer in a patient. The Camptothecin Conjugates are used accordingly in a variety of settings for the treatment of cancers. The Camptothecin Conjugates are intended to deliver a drug to a tumor cell or cancer cell. Without being bound by theory, in one embodiment, the Ligand Unit of a Camptothecin Conjugate binds to or associates with a cancer-cell or a tumor-cell-associated antigen, and the Camptothecin Conjugate is taken up (internalized) inside the tumor cell or cancer cell through receptor-mediated endocytosis or other internalization mechanism. In some embodiments, the antigen is attached to a tumor cell or cancer cell or is an extracellular matrix protein associated with the tumor cell or cancer cell. Once inside the cell, via activation of the Activation Unit, the drug is released within the cell. In an alternative embodiment, the free drug is released from the Camptothecin Conjugate outside the tumor cell or cancer cell, and the free drug subsequently penetrates the cell.

In one embodiment, the Ligand Unit binds to the tumor cell or cancer cell.

In another embodiment, the Ligand Unit binds to a tumor cell or cancer cell antigen which is on the surface of the tumor cell or cancer cell.

In another embodiment, the Ligand Unit binds to a tumor cell or cancer cell antigen that is an extracellular matrix protein associated with the tumor cell or cancer cell.

The specificity of the Ligand Unit for a particular tumor cell or cancer cell is an important consideration for determining the tumors or cancers that are most effectively treated. For example, Camptothecin Conjugates that target a cancer cell antigen present on hematopoietic cancers are useful treating hematologic malignancies (e.g., anti-CD30, anti-CD70, anti-CD19, anti-CD33 binding Ligand Unit (e.g., antibody) are useful for treating hematologic malignancies). Camptothecin Conjugates that target a cancer cell antigen present on solid tumors in some embodiments are useful treating such solid tumors.

Cancers that are intended to be treated with a Camptothecin Conjugate include, but are not limited to, hematopoietic cancers such as, for example, lymphomas (Hodgkin Lymphoma and Non-Hodgkin Lymphomas) and leukemias and solid tumors. Examples of hematopoietic cancers include, follicular lymphoma, anaplastic large cell lymphoma, mantle cell lymphoma, acute myeloblastic leukemia, chronic myelocytic leukemia, chronic lymphocytic leukemia, diffuse large B cell lymphoma, and multiple myeloma. Examples of solid tumors include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, neuroblastoma, and retinoblastoma.

In preferred embodiments, the treated cancer is any one of the above-listed lymphomas and leukemias.

Multi-Modality Therapy for Cancer

Cancers, including, but not limited to, a tumor, metastasis, or other disease or disorder characterized by uncontrolled cell growth are intended to be treated or inhibited by administration of an effective amount of a Camptothecin Conjugate.

In one group of embodiments, methods for treating cancer are provided, including administering to a patient in need thereof an effective amount of a Camptothecin Conjugate and a chemotherapeutic agent. In one embodiment the chemotherapeutic agent is one in which treatment of the cancer has not been found to be refractory to that agent. In another embodiment, the chemotherapeutic agent one in which the treatment of cancer has been found to be refractory to that agent.

In another group of embodiments, the Camptothecin Conjugates is administered to a patient that has also undergone surgery as treatment for the cancer. In such embodiments a chemotherapeutic agent is typically administered over a series of sessions, or one or a combination of the chemotherapeutic agents, such a standard of care chemotherapeutic agent(s), is administered.

In either group of embodiments, the patient also receives an additional treatment, such as radiation therapy. In a specific embodiment, the Camptothecin Conjugate is administered concurrently with the chemotherapeutic agent or with radiation therapy. In another specific embodiment, the chemotherapeutic agent or radiation therapy is administered prior or subsequent to administration of a Camptothecin Conjugate.

Additionally, methods of treatment of cancer with a Camptothecin Conjugate are provided as an alternative to chemotherapy or radiation therapy where the chemotherapy or the radiation therapy has proven or can prove too toxic, e.g., results in unacceptable or unbearable side effects, for the subject being treated. The patient being treated is optionally treated with another cancer treatment such as surgery, radiation therapy or chemotherapy, depending on which treatment is found to be acceptable or bearable.

Treatment of Autoimmune Diseases

The Camptothecin Conjugates are intended to be useful for killing or inhibiting the unwanted replication of cells that produce an autoimmune disease or for treating an autoimmune disease.

The Camptothecin Conjugates are used accordingly in a variety of settings for the treatment of an autoimmune disease in a patient. The Camptothecin Conjugates are typically used to deliver a camptothecin drug to a target cell. Without being bound by theory, in one embodiment, the Camptothecin Conjugate associates with an antigen on the surface of a pro-inflammatory or inappropriately stimulated immune cell, and the Camptothecin Conjugate is then taken up inside the targeted cell through receptor-mediated endocytosis. Once inside the cell, the Linker Unit is cleaved, resulting in release of the Camptothecin Drug Unit as free drug. The Camptothecin free drug is then able to migrate within the cytosol and induce a cytotoxic or cytostatic activity. In an alternative embodiment, the Camptothecin Drug Unit is cleaved from the Camptothecin Conjugate outside the target cell, and the Camptothecin free drug resulting from that release subsequently penetrates the cell.

In one embodiment, the Ligand Unit binds to an autoimmune antigen. In one such embodiment, the antigen is on the surface of a cell involved in an autoimmune condition.

In one embodiment, the Ligand Unit binds to activated lymphocytes that are associated with the autoimmune disease state.

In a further embodiment, the Camptothecin Conjugate kills or inhibits the multiplication of cells that produce an autoimmune antibody associated with a particular autoimmune disease.

Particular types of autoimmune diseases intended to be treated with the Camptothecin Conjugates include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); and activated B lymphocyte-related disorders (e.g., systemic lupus erythematosus, Goodpasture's syndrome, rheumatoid arthritis, and type I diabetes).

Multi-Drug Therapy of Autoimmune Diseases

Methods for treating an autoimmune disease are also disclosed including administering to a patient in need thereof an effective amount of a Camptothecin Conjugate and another therapeutic agent known for the treatment of an autoimmune disease.

Compositions and Methods of Administration

The present invention provides pharmaceutical compositions comprising the Camptothecin Conjugates described herein and at least one pharmaceutically acceptable carrier. The pharmaceutical composition is in any form that allows the compound to be administered to a patient for treatment of a disorder associated with expression of the antigen to which the Ligand unit binds. For example, the conjugates are in the form of a liquid or solid. The preferred route of administration is parenteral. Parenteral administration includes subcutaneous injections, intravenous, intramuscular, intrasternal injection or infusion techniques. In one embodiment, the pharmaceutical compositions is administered parenterally. In one embodiment, the conjugates are administered intravenously. Administration is by any convenient route, for example by infusion or bolus injection.

Pharmaceutical compositions are formulated to allow a Camptothecin Conjugate to be bioavailable upon administration of the composition to a patient. Compositions sometimes take the form of one or more dosage units.

Materials used in preparing the pharmaceutical compositions are preferably non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the compound, the manner of administration, and the composition employed.

The composition in some embodiments is in the form of a liquid. The liquid in some of those embodiments is useful for delivery by injection. In some embodiments a composition for administration by injection, in addition to the Camptothecin Conjugate, contains one or more excipients selected from the group consisting of a surfactant, preservative, wetting agent, dispersing agent, suspending agent, buffer, stabilizer and isotonic agent.

The liquid compositions, whether they are solutions, suspensions or other like form, in some embodiments include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as amino acids, acetates, citrates or phosphates; detergents, such as nonionic surfactants, polyols; and agents for the adjustment of tonicity such as sodium chloride or dextrose. A parenteral composition is sometimes enclosed in ampoule, a disposable syringe or a multiple-dose vial made of glass, plastic or other material. Physiological saline is an exemplary adjuvant. An injectable composition is preferably sterile.

The amount of the conjugate that is effective in the treatment of a particular disorder or condition will depend on the nature of the disorder or condition, which in some embodiments is determined by standard clinical techniques. In addition, in vitro or in vivo assays are optionally employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a Camptothecin Conjugate such that a suitable dosage amount will be obtained. Typically, that amount is at least about 0.01% of a compound by weight of the composition.

For intravenous administration, the pharmaceutical composition typically comprises from about 0.01 to about 100 mg of a Camptothecin Conjugate per kg of the animal's body weight. In one embodiment, the composition can include from about 1 to about 100 mg of a Camptothecin Conjugate per kg of the animal's body weight. In another aspect, the amount administered will be in the range from about 0.1 to about 25 mg/kg of body weight of a compound. Depending on the drug used, the dosage can be even lower, for example, 1.0 µg/kg to 5.0 mg/kg, 4.0 mg/kg, 3.0 mg/kg, 2.0 mg/kg or 1.0 mg/kg, or 1.0 µg/kg to 500.0 µg/kg of the subject's body weight.

Generally, the dosage of a conjugate administered to a patient is typically about 0.01 mg/kg to about 100 mg/kg of the subject's body weight or from 1.0 µg/kg to 5.0 mg/kg of the subject's body weight. In some embodiments, the dosage administered to a patient is between about 0.01 mg/kg to about 15 mg/kg of the subject's body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight. In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight. In some embodiments, the dosage administered is between about 0.1 to 4 mg/kg, even more preferably 0.1 to 3.2 mg/kg, or even more preferably 0.1 to 2.7 mg/kg of the subject's body weight over a treatment cycle.

The term "carrier" refers to a diluent, adjuvant or excipient, with which a compound is administered. Such pharmaceutical carriers in some embodiments is a liquid, such as water and oils, including those of petroleum, animal, vegetable or synthetic origin, such as peanut oil, soybean oil, mineral oil, sesame oil. Other carriers include saline, gum acacia, gelatin, starch paste, talc, keratin, colloidal silica, urea. In addition, auxiliary, stabilizing, thickening, lubricating and coloring agents are sometimes used. In one embodiment, when administered to a patient, the Camptothecin Conjugate or compositions thereof and pharmaceutically acceptable carriers are sterile.

Water is an exemplary carrier when the compounds are administered intravenously. Saline solutions and aqueous dextrose and glycerol solutions are often employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol. The present compositions, if desired, also contain minor amounts of wetting or emulsifying agents, or pH buffering agents.

In an embodiment, the conjugates are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions include a solubilizing agent. Compositions for intravenous administration optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachets indicating the quantity of active agent. Where a conjugate is to be administered by infusion, it is typically dispensed, for example, with an infusion bottle containing sterile pharmaceutical grade water or saline. Where the conjugate is administered by injection, an ampoule of sterile water for injection or saline is sometimes provided so that the ingredients can be mixed prior to administration.

The pharmaceutical compositions are generally formulated as sterile, substantially isotonic and in full compliance with all Good Manufacturing Practice (GMP) regulations of the U.S. Food and Drug Administration.

Methods of Preparing Camptothecin Conjugates

The Camptothecin Conjugates described herein are prepared in either a serial construction of antibodies, linkers, and drug units, or in a convergent fashion by assembling portions followed by a completed assembly step. The Curtius Rearrangement or a Chloramine synthesis can be used to provide a methylene carbamate linker (Spacer) which is useful in a number of embodiments of the Conjugates described herein.

Scheme 2: Preparation of Exemplary Camptothecin Drug-Linker compounds of formula Z'-A-RL-Y-D, Z'-A-S*-RL-Y-D or Z'-A-B(S*)-RL-Y-D wherein Y has formula (a') using the Curtius Rearrangement Reaction

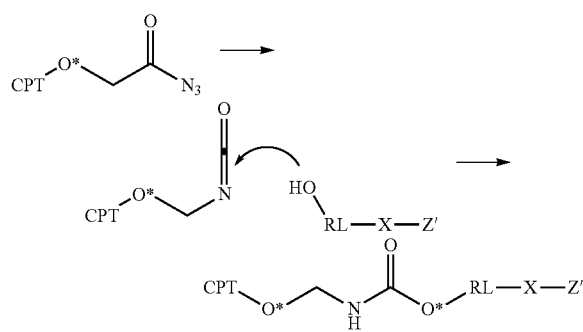

Scheme 2 illustrates a synthetic strategy involving a Curtius rearrangement of an acyl azide derivative of the free drug, wherein CPT is a Camptothecin Drug Unit corresponding in structure to a Camptothecin compound having a hydroxyl functional group whose oxygen atom, which is represented by O*, is incorporated into the methylene carbamate unit formed as a consequence of the rearrangement, Z' is a Stretcher Unit precursor, RL is a Releasable Linker and X is -A-, -A-S*- or -A-B(S*)- wherein A is a Connector Unit, S* is a Partitioning agent and B is a Parallel Connector Unit. That strategy may be applied to Camptothecin drugs containing multiple alcohols, or other heteroatoms, as a means for acquiring regioselectivity, as there a many complementary methods of alkylation to form an acyl azide such as: halo ester alkylation, halo acid alkylation or metal carbene insertion with ethyl or methyl diazoacetate, see Doyle, M. et al. Modern Catalytic Methods for Organic Synthesis with Diazo Compounds; Wiley: New York, 1998. The acyl azide is then heated with at least a stoichiometric amount of alcohol-containing Linker Unit intermediate of formula Z'—X-RL-OH.

Scheme 3: Alternative preparation of exemplary Camptothecin Drug-Linker compounds of formula Z'-A-RL-Y-D, Z'-A-S*-RL-Y-D or Z'-A-B(S*)-RL-Y-D wherein Spacer Unit Y is a methylene carbamate unit of formula (a) or formula (a') via N-chloromethylamine synthesis

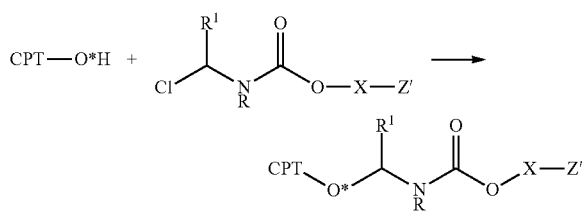

wherein $R^1$ is hydrogen or $C_1$-$C_4$ alkyl, R is —H or —$CH_2CH_2SO_2Me$ and the other the variable groups have their meanings from Scheme 2.

The N-chloromethylamine synthesis is an alternative to the Curtius rearrangement in that it allows for the introduction of an unmodified alcohol or other heteroatom containing Camptothecin compound, whose use may not be compatible with the conditions required to form the acyl azide of Scheme 2, and proceeds by condensation with a reactive N-chloromethylamine. That methodology is also more appropriate for introducing certain types of methylene carbamate units as shown for example by Scheme 4.

Scheme 4 demonstrates synthesis of exemplary Camptothecin-Linker Compounds of formula Z'-A-RL-Y-D, Z'-A-S*-RL-Y-D or Z'-A-B(S*)-RL-Y-D wherein the Spacer Unit (Y) is a methylene carbamate unit of formula (a''). Reaction of the p-nitro-phenyl carbonate with the cyclic aminol provides a carbamate, which is then converted to the chlorcycloalkylamine for alkylation with a nucleophile from the thiol, hydroxyl, amine or amide functional group of free camptothecin drug. Alternatively, the carbamate can be treated with acid in the presence of the drug moiety to assemble the drug-linker intermediate shown. The alkylation product is deprotected followed by condensation of the resulting free amine with 3-maleimidopropionic acid N-hydroxysuccimide ester, which introduces a Stretcher Unit precursor covalently attached to a Connector Unit thus providing Camptothecin-Linker Compounds. The resulting Camptothecin-Linker Compounds are then condensed with a thiol-containing targeting agent to provide Camptothecin Conjugates having a Spacer Unit comprising a self-immolative moiety and the methylene carbamate unit of formula a''.

Scheme 4: Preparation of exemplary Camptothecin Drug-Linker compounds of formula
Z'—A—RL—Y—D wherein Spacer Unit Y is a formula (a″) methylene unit.

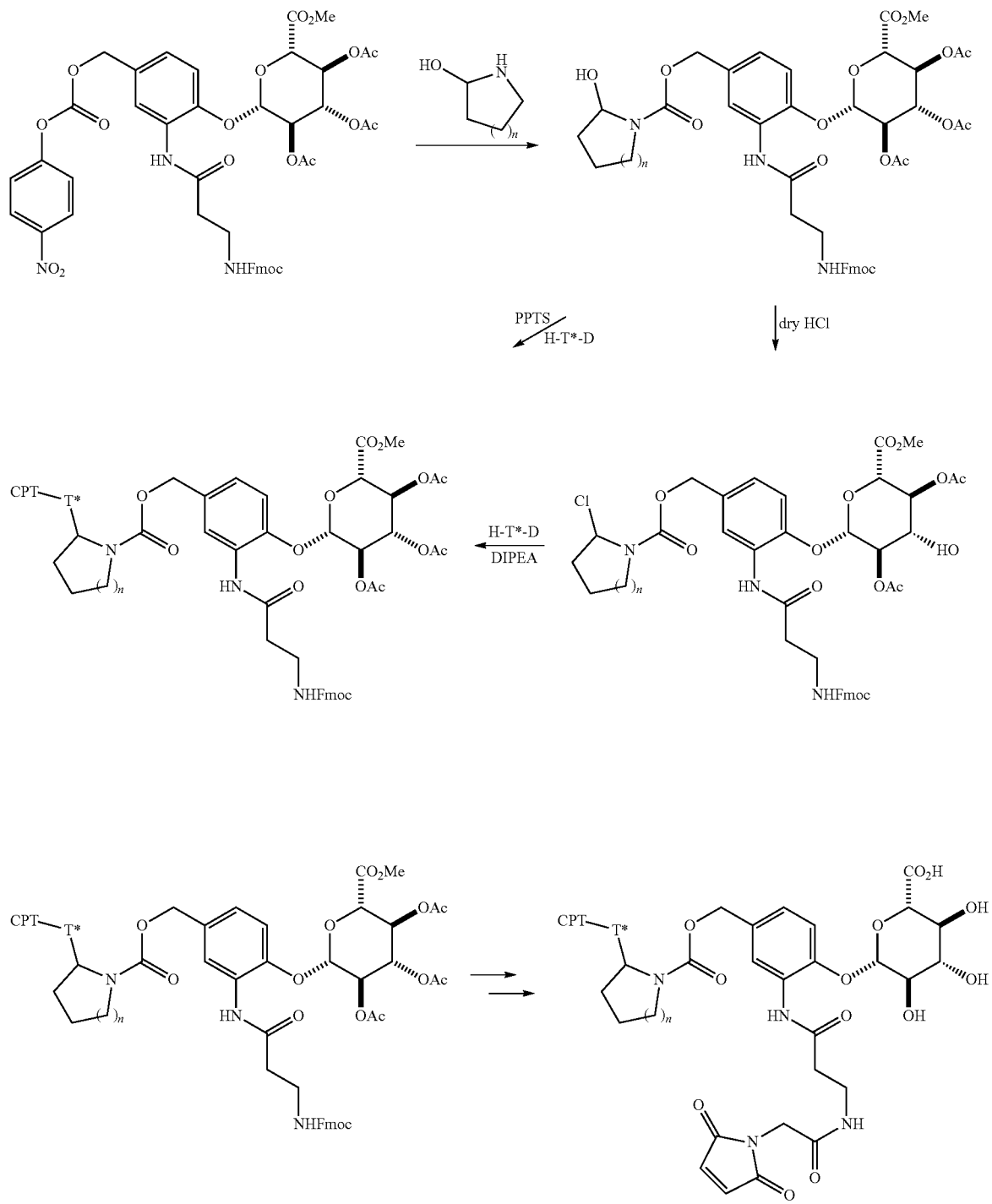

For Camptothecin-Linker Compounds and Camptothecin Conjugates having a methylene carbamate unit wherein T* is the nitrogen atom from a primary or secondary amine substituent of a Camptothecin compound direct alkylation with a chlormethylamine following the generalized procedures provided by Scheme 3 or Scheme 4 may not be suitable due to excessive or undesired over-alkylation of the nitrogen heteroatom from the amine functional group of free drug. In those instances, the method embodied by Scheme 105 may be used.

Scheme 5

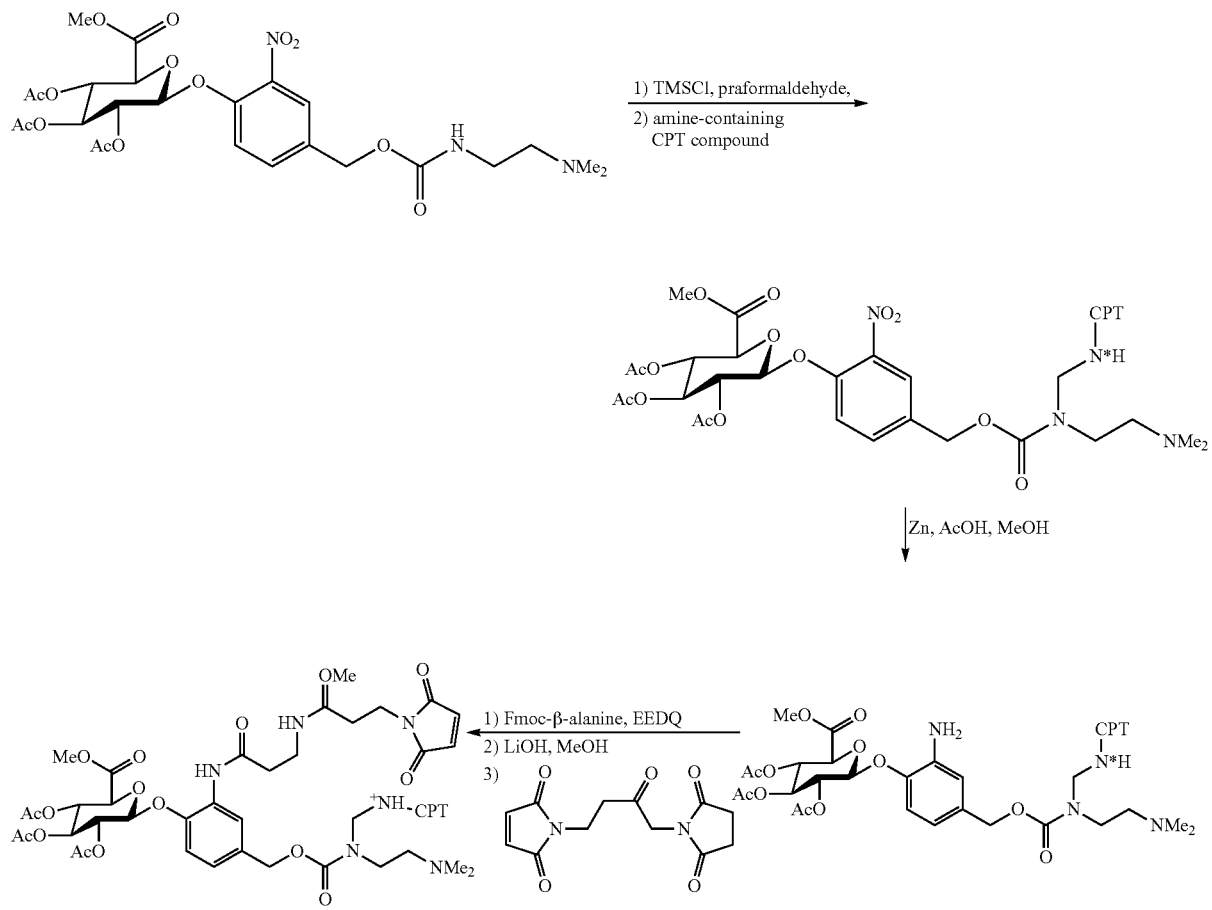

In Scheme 5 an intermediate carbamate is prepared already having a Basic Unit (i.e., the dimethylaminoethyl moiety) as the R substituent for a formula (a1') methylene carbamate unit. The nitrogen of that carbamate is condensed with formaldehyde and the resulting intermediate quenched with the amine functional group of an aliphatic amine-containing camptothecin drug. N* represents the nitrogen atom from that functional group. That condensation forms the methylene carbamate of formula (a1') covalently attached to a Camptothecin Drug Unit, wherein $R^1$ is hydrogen and R is dimethylaminoethyl. The phenyl nitro group is then reduced to an amine in order to provide a handle for sequential introduction of a Connector Unit (A) and a Stretcher Unit precursor (Z').

NUMBERED EMBODIMENTS

The following numbered embodiments describes various non-limiting aspects of the invention.

1. A Camptothecin Conjugate having the formula of L-(Q-D)$_p$, or a salt thereof, wherein L is a Ligand Unit; subscript p is an integer ranging from 1 to 16; Q is a Linker Unit having a formula selected from the group consisting of -Z-A-, -Z-A-RL, -Z-A-RL-Y-, -Z-A-S*-RL-, -Z-A-S*-RL-Y-, -Z-A-S*-W-, -Z-A-S*-W-RL-, -Z-A-B(S*)-RL-, —Z-A-B(S*)W, -Z-A-B(S*)-W-RL- and -Z-A-B(S*)-RL-Y-, wherein Z is a Stretcher Unit; A is a bond or a Connecter Unit; B is a Parallel Connector Unit; S* is a Partitioning Agent; RL is a Releasable Linker; W is an Amino Acid Unit; Y is a Spacer Unit; and D is a Drug Unit selected from the group consisting of CPT1, CPT2, CPT3, CPT4, CPT5, CPT6 and CPT7 as follows:

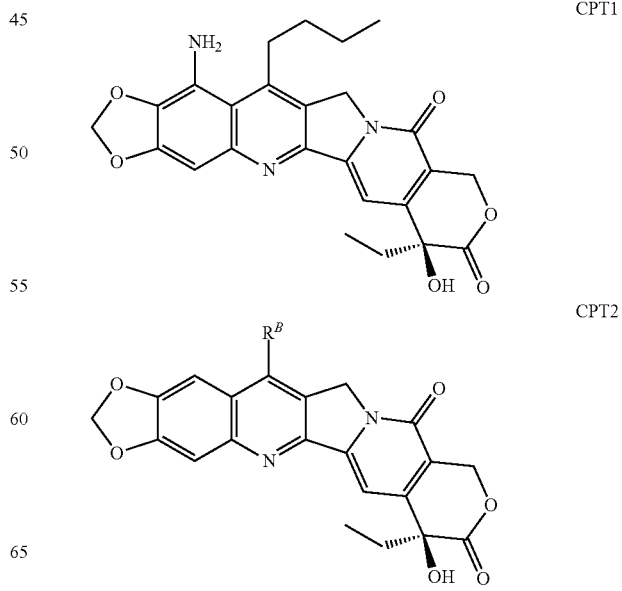

-continued

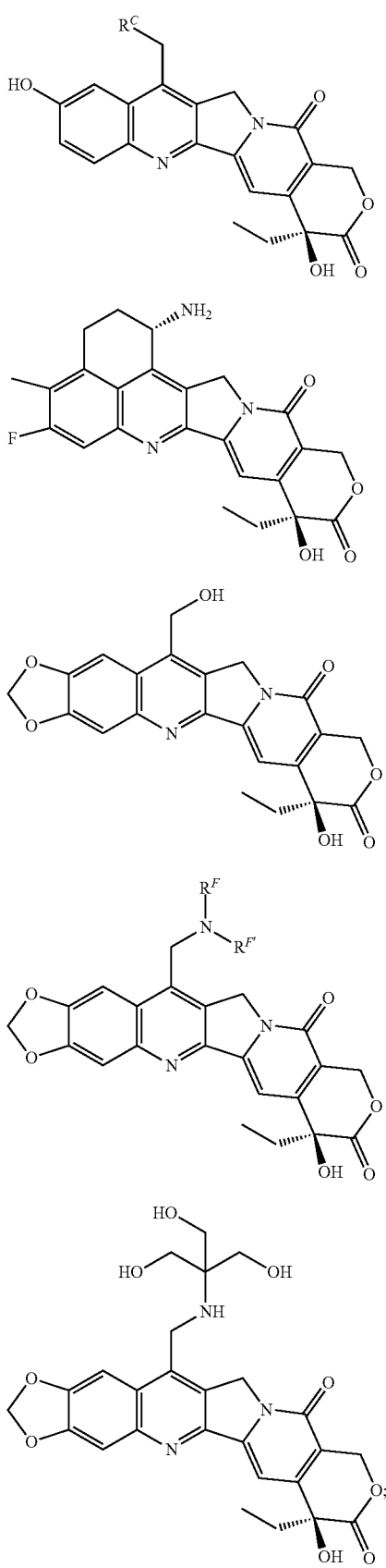

CPT3

CPT4

CPT5

CPT6

CPT7 wherein $R^B$ is a member selected from the group consisting of H, $C_1$-$C_8$ alkyl, $C_1$-$C_8$ haloalkyl, $C_3$-$C_8$ cycloalkyl, ($C_3$-$C_8$ cycloalkyl)$C_1$-$C_4$ alkyl-, phenyl and phenyl-$C_1$-$C_4$ alkyl-; $R^C$ is a member selected from the group consisting of $C_1$-$C_6$ alkyl and $C_3$-$C_6$ cycloalkyl; each $R^F$ and $R^{F'}$ is a member independently selected from the group consisting of —H, $C_1$-$C_8$ alkyl, $C_1$-$C_8$ hydroxyalkyl, $C_1$-$C_8$ aminoalkyl, ($C_1$-$C_4$alkylamino)-$C_1$-$C_8$ alkyl-, N,N—($C_1$-$C_4$ hydroxyalkyl)($C_1$-$C_4$ alkylamino-$C_1$-$C_8$ alkyl-, N,N-di($C_1$-$C_4$ alkyl)amino-$C_1$-$C_8$ alkyl-, N—($C_1$-$C_4$ hydroxyalkyl)-$C_1$-$C_8$ aminoalkyl-, $C_1$-$C_8$ alkylC(O)—, $C_1$-$C_8$ hydroxyalkyl-C(O)—, $C_1$-$C_8$ aminoalkylC(O)—, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl-$C_1$-$C_4$ alkyl-, heteroaryl and heteroaryl-$C_1$-$C_4$ alkyl-, or $R^F$ and $R^{F'}$ are combined with the nitrogen atom to which each is attached to form a 5-, 6- or 7-membered ring having 0 to 3 substituents selected from halogen, $C_1$-$C_4$ alkyl, —OH, —O$C_1$-$C_4$ alkyl, —$NH_2$, —NH$C_1$-$C_4$ alkyl and —N($C_1$-$C_4$ alkyl)$_2$; and wherein the cycloalkyl, heterocycloalkyl, phenyl and heteroaryl moieties of $R^B$, $R^C$, $R^F$ and $R^{F'}$ are substituted with from 0 to 3 substituents selected from the group consisting of halogen, $C_1$-$C_4$ alkyl, —OH, —O$C_1$-$C_4$ alkyl, —$NH_2$, —NH$C_1$-$C_4$ alkyl and —N($C_1$-$C_4$ alkyl)$_2$, or D is a Drug Unit selected from the group consisting of 13a-13c of Table H, 14a-14z of Table I and 18a-18r of Table J;

and wherein the point of covalent attachment of D is to the heteroatom of any one of the hydroxyl or aliphatic primary or secondary amino substituents of any one of CPT1, CPT2, CPT3, CPT4, CPT5, CPT6 and CPT7 or of any one of 13a-13c of Table H, 14a-14z of Table I and 18a-18r of Table J when Q is -Z-A-RL-, -Z-A-RL-Y-, -Z-A-S*—RL-, -Z-A-B(S*)-RL-, -Z-A-S*-RL-Y- or -Z-A-B(S*)-RL-Y-, or wherein the point of covalent attachment of D is to the oxygen atom of the hydroxyl substituent on the lactone ring of any one of CPT1, CPT2, CPT3, CPT4, CPT5, CPT6 or CPT7 or any one of 13a-13c of Table H, 14a-14z of Table I and 18a-18r of Table J when Q is -Z-A-, -Z-A-S*-W- or -Z-A- B(S*)W, or when Q is -Z-A-S*-RL-, —Z-A-B(S*)-RL-, -Z-A-S*-W-RL-, or -Z-A-B(S*)-W-RL- in which RL is a Releasable Unit other than a Glucuronide Unit; and provided that at least one of $R^F$ and $R^{F'}$ is —H, when the point of covalent attachment is to the nitrogen atom of the primary or secondary aliphatic amino substituent of CPT6; and provided that -Z-A- of -Z-A-RL-, -Z-A-RL-Y-, -Z-A-S*-RL-, -Z-A-B(S*)—RL-, -Z-A-S*-RL-Y- and -Z-A-B(S*)-RL-Y- is other than succinimidocaproyl-β-alanyl moiety, optionally having the succinimide ring in hydrolyzed form as a succinic acid amide moiety, when D is compound CPT1 having covalent attachment through the nitrogen atom of its amino substituent.

2. The Camptothecin Conjugate of embodiment 1, wherein Q is a Linker Unit having the formula selected from the group consisting of -Z-A-RL-, -Z-A-RL-Y-, -Z-A-S*—RL-, -Z-A-B(S*)-RL-, -Z-A-S*-RL-Y- and -Z-A-B(S*)-RL-Y-, wherein A is a Connector Unit and RL is a Glucuronide Unit.

3. The Camptothecin Conjugate of embodiment 1 or 2, wherein the point of covalent attachment of D is through the oxygen atom of the hydroxyl substituent on the lactone ring of any one of CPT1, CPT2, CPT3, CPT4, CPT5, CPT6 and CPT7.

4. The Camptothecin Conjugate of embodiment 1 or 2, wherein the point of covalent attachment of D is through the oxygen atom of the hydroxyl substituent on the lactone ring of any one of 13a-13c of Table H, 14a-14z of Table I or 18a-18r of Table J.

5. The Camptothecin Conjugate of embodiment 1 or 2, wherein the point of covalent attachment of D is through the oxygen atom of the hydroxyl substituent of $R^F$ or $R^{F'}$ of CPT6, when at least one of $R^F$ and $R^{F'}$ is $C_1$-$C_8$ hydroxyalkyl N,N—($C_1$-$C_4$ hydroxyalkyl)($C_1$-$C_4$ alkyl)-amino-$C_1$-$C_8$ alkyl-, N—$C_1$-$C_4$ hydroxyalkyl-$C_1$-$C_8$ aminoalkyl-, $C_1$-$C_8$ alkylC(O)—, 6. The Camptothecin Conjugate of embodiment 1 or 2, wherein the point of covalent attachment of D is through the nitrogen atom of the amine substituent of $R^F$ or $R^{F'}$ of CPT6, when at least one of $R^F$ and $R^{F'}$ is $C_1$-$C_8$ aminoalkyl, ($C_1$-$C_4$ alkylamino)-$C_1$-$C_8$ alkyl-, N—($C_1$-$C_4$ hydroxyalkyl)-$C_1$-$C_8$ aminoalkyl- or $C_1$-$C_8$ aminoalkylC(O)—, 7. The Camptothecin Conjugate of embodiment 1 or 2, wherein the point of covalent attachment of D is through the nitrogen atom of the amino substituent of CPT1 provided that -Z-A- is other than succinimido-caproyl-3-alanyl, optionally having the succinimide ring in hydrolyzed form as a succinic acid amide moiety.

8. The Camptothecin Conjugate of embodiment 1 or 2, wherein the point of covalent attachment of D is to the nitrogen atom of the amino substituent on CPT4.

9. The Camptothecin Conjugate of embodiment 1 or 2, wherein the point of covalent attachment is through the nitrogen atom of the substituent on CPT6 provided that least one of $R^F$ and $R^{F'}$ is —H.

10. The Camptothecin Conjugate of any one of embodiments 1-9, wherein Q is a Linker Unit having the formula selected from the group consisting of -Z-A-RL- and -Z-A-RL-Y-.

11. The Camptothecin Conjugate of any one of embodiments 1-9, wherein Q is a Linker Unit having the formula selected from the group consisting of -Z-A-S*—RL- and -Z-A-S*-RL-Y-.

12. The Camptothecin Conjugate of any one of embodiments 1-9, wherein Q is a Linker Unit having the formula selected from the group consisting of -Z-A-B(S*)—RL- and -Z-A-B(S*)-RL-Y-.

13. The Camptothecin Conjugate of any one of embodiments 1-3 and 7, wherein D is CPT1.

14. The Camptothecin Conjugate of any one of embodiments 1-3, wherein D is CPT2.

15. The Camptothecin Conjugate of any one of embodiments 1-3, wherein D is CPT3.

16. The Camptothecin Conjugate of any one of embodiments 1-3 and 8, wherein D is CPT4.

17. The Camptothecin Conjugate of any one of embodiments 1-3, wherein D is CPT5.

18. The Camptothecin Conjugate of any one of embodiments 1-3, 5, 6 and 9, wherein D is CPT6.

18. The Camptothecin Conjugate of any one of embodiments 1-3, wherein D is CPT7.

19. The Camptothecin Conjugate of any one of embodiments 2-18, wherein RL is a Glucuronide Unit having the formula of:

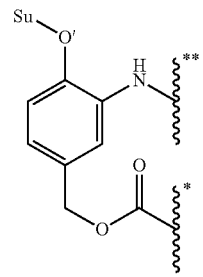

wherein Su is a hexose form of a monosaccharide, in particular a glucuronic acid or mannose residue; O' represents the oxygen atom of a glycosidic bond that is capable of cleavage by a glycosidase; the wavy line marked with a single asterisk (*) indicates the site of covalent attachment to the nitrogen atom of the primary or secondary aliphatic amino substituent of CPT1, CPT4, CPT6 in which at least one of $R^F$ and $R^{F'}$ is —H, or of any one of 13b and 13c of Table H, 14a-14f and 14i-14o, 14s and 14u-14z of Table I and 18q and 18r of Table J, or to a Spacer Unit (Y), or indicates the site of covalent attachment to the oxygen atom of the hydroxyl substituent on the lactone ring of CPT1, CPT2, CPT3, CPT4, CPT5, CPT6 or CPT7 or of any one of 13a-13c of Table H and 14a-14z of Table I or 18a-18r of Table J; and the wavy line marked with a double asterisk (**) indicates the site of covalent attachment to the remainder of Q.

20. The Camptothecin Conjugate of embodiment 19, wherein Q is a Linker Unit having the formula of -Z-A-RL-Y-, -Z-A-S*-RL-Y- or -Z-A-B(S*)-RL-Y-; and Spacer Unit (Y) has the formula of:

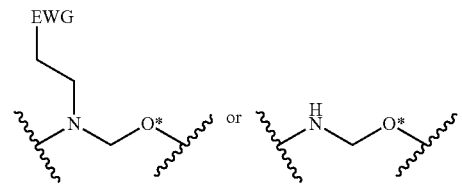

wherein EWG is an electron-withdrawing group; O* represent the oxygen atom from a hydroxy substituent of D; the wavy line adjacent to the nitrogen atom indicates the site of covalent attachment to the carbonyl carbon atom of the Glucuronide Unit; and the wavy line adjacent to O* indicates the site of covalent attachment to the remainder of D.

21. The Camptothecin Conjugate of embodiment 19, wherein Q is a Linker Unit having the formula of -Z-A-RL-Y-, -Z-A-S*-RL-Y- or -Z-A-B(S*)-RL-Y-; D is selected from the group consisting of CPT1, CPT4 and CPT6 in which each of $R^F$ and $R^{F'}$ is —H; and the Spacer Unit (Y) has the formula of:

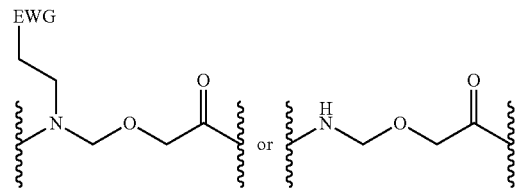

wherein EWG is an electron-withdrawing group; the wavy line adjacent to the nitrogen atom indicates the site of covalent attachment to the carbonyl carbon atom of the Glucuronide Unit; and the wavy line adjacent to the carbonyl carbon atom indicates the site of covalent attachment to the nitrogen atom of the amino substituent of CPT1, CPT4 or CPT6 in which each of $R^F$ and $R^{F'}$ is —H.

22. The Camptothecin Conjugate of embodiment 19, wherein Q is a Linker Unit having the formula of -Z-A-RL-Y-, -Z-A-S*-RL-Y- or -Z-A-B(S*)-RL-Y-; D is selected from the group consisting of CPT1, CPT4 and CPT6 in which each of $R^F$ and $R^{F'}$ is —H; and the Spacer Unit (Y) has the formula of:

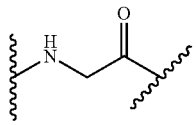 [SMILES: *NCC(*)=O]

wherein EWG is an electron-withdrawing group; the wavy line adjacent to the nitrogen atom indicates the site of covalent attachment to the carbonyl carbon atom of the Glucuronide Unit; and the wavy line adjacent to the carbonyl carbon atom indicates the site of covalent attachment to the nitrogen atom of the amino substituent of CPT1, CPT4 or CPT6 in which each of $R^F$ and $R^{F'}$ is —H.

23. The Camptothecin Conjugate of any one of embodiments 1-22, wherein A is a Connector Unit, wherein the Connector Uni is comprised of a triazolyl moiety, wherein the triazole moiety is optionally formed from 1,3-dipolar cycloaddition of an azido substituent from a chemically modified targeting agent that is the precursor to the Ligand Unit of the Conjugate to an alkynyl moiety of a Drug Linker compound.

24. The Camptothecin Conjugate of any one of embodiments 1-22, wherein -Z-A- is comprised of a succinimidoalkanoyl moiety or succinimido and triazolyl moieties, each optionally having the succinimide ring in hydrolyzed form as a succinic acid amide moiety, or a succinic acid amide moiety derivable from an mDPR moiety of a Camptothecin-Linker Compound, provided that -Z-A- is comprised of succinimido and triazolyl moieties, optionally having the succinimide ring in hydrolyzed form as a succinic acid amide moiety, or the succinic acid amide moiety derivable from the mDPR moiety when CPT1 has covalent attachment through the nitrogen atom of its amino substituent.

25. The Camptothecin Conjugate of any one of embodiments 1-22, wherein -Z-A- is comprised of a succinimidoalkanoyl-β-alanyl moiety, optionally having the succinimide ring in hydrolyzed form as a succinic acid amide moiety, provided that D has covalent attachment to the oxygen atom of the hydroxyl substituent on its lactone ring when D is CPT1.

26. The Camptothecin Conjugate of any one of embodiments 1-22, wherein -Z-A- is comprised of a succinic acid amide moiety derivable from an mDPR moiety of a Camptothecin-Linker Compound.

27. The Camptothecin Conjugate of embodiment 26, wherein Q has the formula:

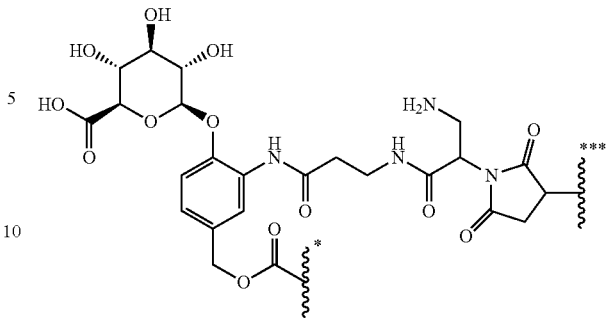

or a salt thereof, wherein the succinimide ring is in hydrolyzed form as a succinic acid amide moiety; the wavy line marked with a single asterisk (*) indicates the site of covalent attachment to the nitrogen atom of CPT1, CPT4 or CPT6 in which $R^F$ and $R^{F'}$ is —H, or to a Spacer Unit; and the wavy line marked with a triple asterisk (***) indicates the point of covalent attachment to a sulfur atom of L.

28. The Camptothecin Conjugate of any one of embodiments 2-26, wherein RL is a Glucuronide Unit having the structure of:

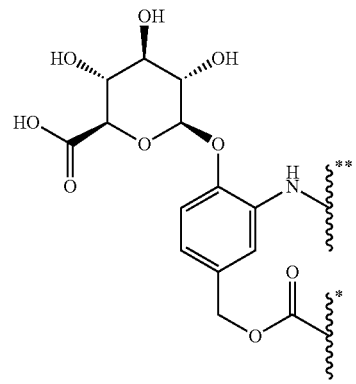 [SMILES: *Nc1cc(COC(*)=O)ccc1O[C@H]1O[C@@H](C(=O)O)[C@H](O)[C@@H](O)[C@@H]1O]

wherein the wavy line marked with a single asterisk (*) indicates the point of covalent attachment to the oxygen atom of a hydroxyl substituent on the lactone ring of CPT1, CPT2, CPT3, CPT4, CPT5, CPT6 or CPT7, or to the nitrogen atom of an amino substituent of CPT1 CPT 4 or CPT6 in which each of $R^F$ and $R^{F'}$ are —H, or to a Spacer Unit (Y); and the wavy line marked with a double asterisk (**) indicates the point of covalent attachment to A, B, S* or Z.

29. The Camptothecin Conjugate of embodiment 28, wherein Q is a Linker Unit having the formula selected from the group consisting of -Z-A-S*-RL-; -Z-A-B(S*)—RL-; -Z-A- S*-RL-Y-; and -Z-A-B(S*)-RL-Y-, wherein -Z-A- is comprised of a succinimido-propionyl moiety.

30. The Camptothecin Conjugate of embodiment 29, wherein Q is -Z-A-S*—RL- having the formula of:

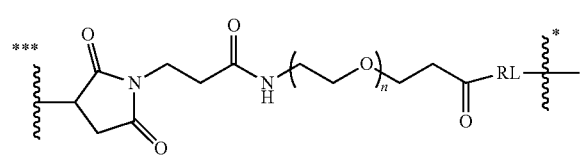

wherein subscript n is an integer ranging from 1 to 50; the wavy line marked with a single asterisk (*) indicates the site of covalent attachment to D, or to a Spacer Unit (Y); and the wavy line marked with a triple asterisk (***) indicates the point of covalent attachment to a sulfur atom of L.

31. The Camptothecin Conjugate of embodiment 30, wherein subscript n is 4.

32. The Camptothecin Conjugate of embodiment 2, wherein -Q-D has the structure of:

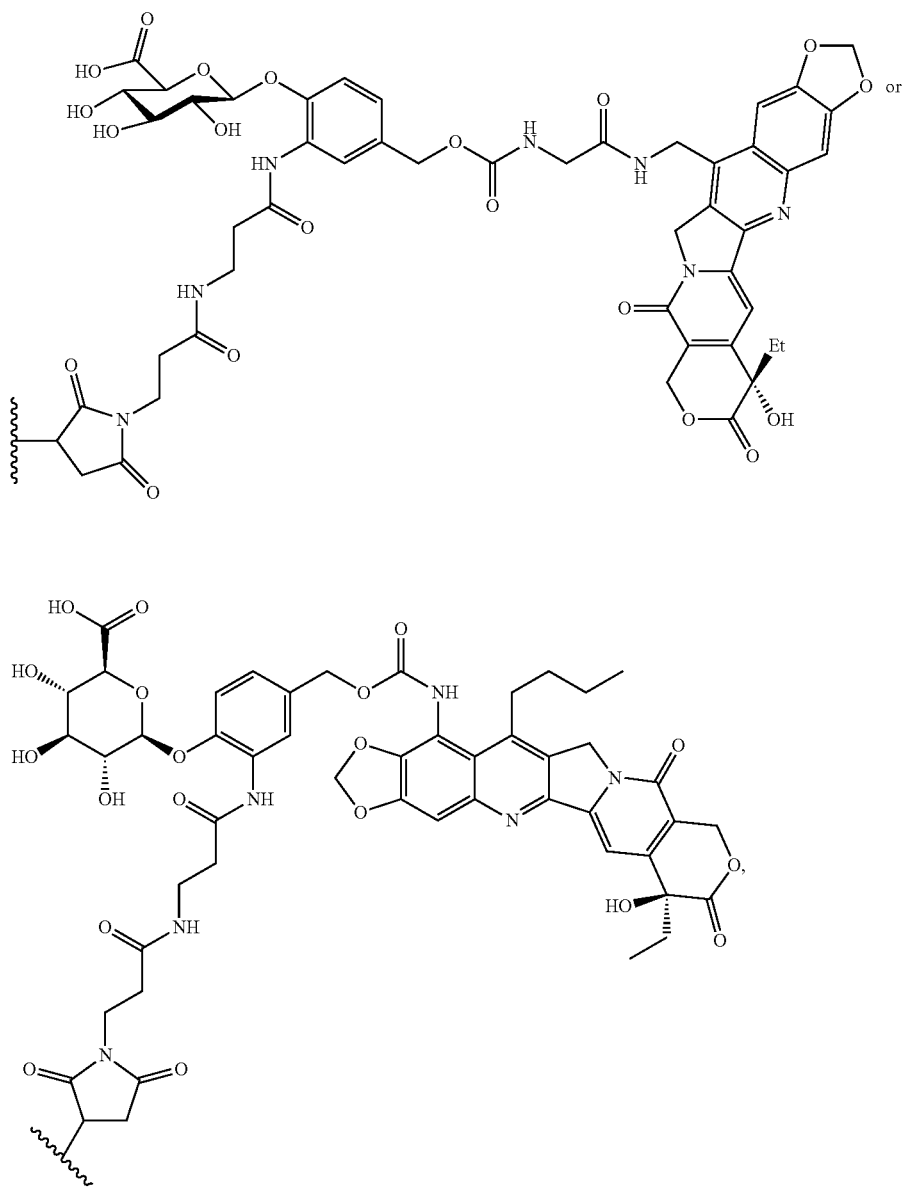

or a salt thereof, optionally having the succinimide ring in hydrolyzed form as a succinic acid amide moiety, wherein the wavy line indicates covalent attachment to a sulfur atom of the Ligand Unit.

33. The Camptothecin Conjugate of embodiment 2, wherein -Q-D has the structure of:

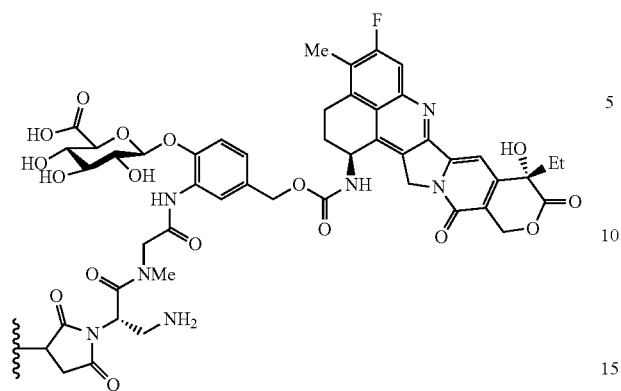
or a salt thereof, wherein the wavy line indicates covalent attachment to a sulfur atom of the Ligand Unit and the succinimide ring is in hydrolyzed form as a succinic acid amide moiety.
34. The Camptothecin Conjugate of embodiment 2, wherein -Q-D has the structure of:
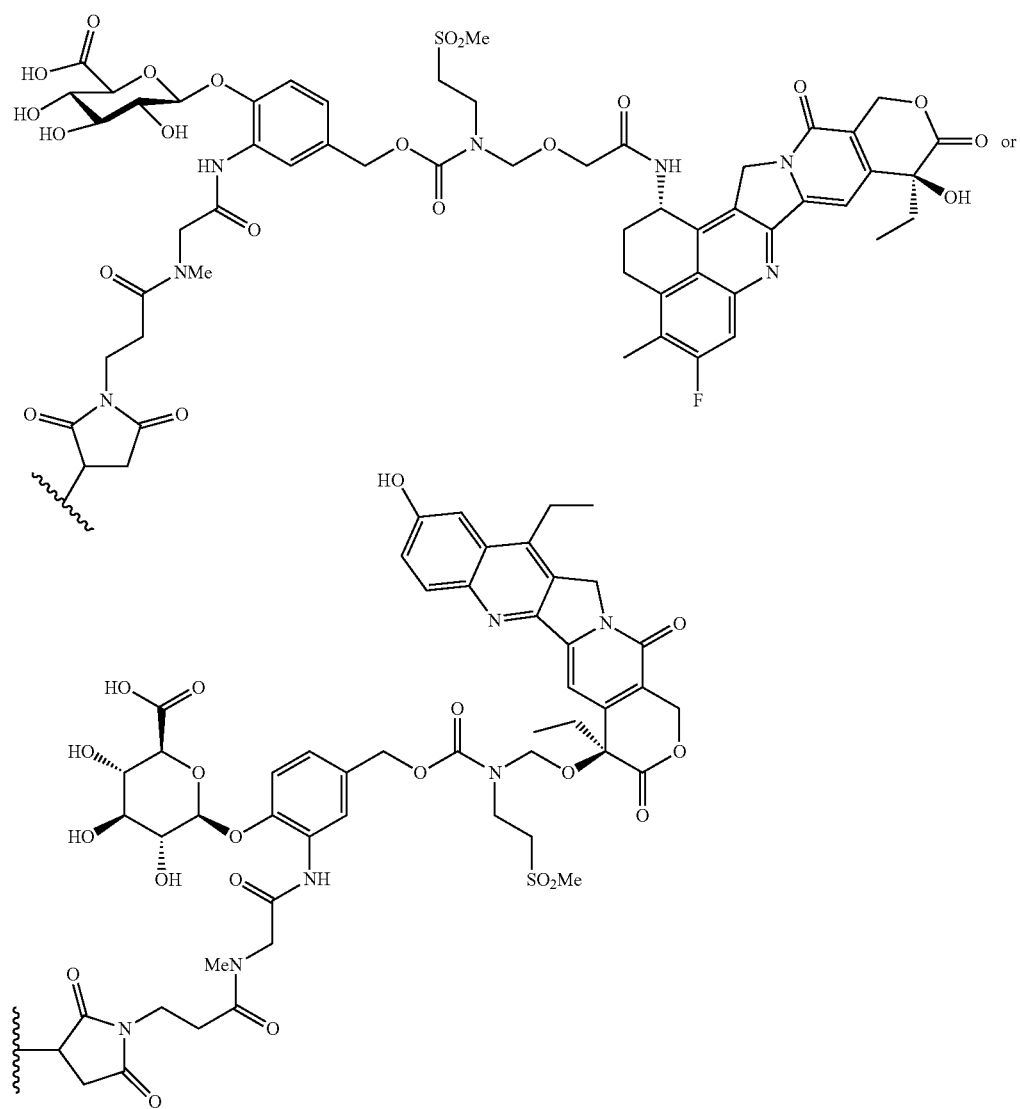

or a salt thereof, optionally having the succinimide ring in hydrolyzed form as a succinic acid amide moiety, wherein the wavy line indicates covalent attachment to a sulfur atom of the Ligand Unit.

35. The Camptothecin Conjugate of any one of embodiments 1-34, wherein L is from an antibody.

36. The Camptothecin Conjugate of embodiment 35, wherein the antibody specifically binds to an antigen selected from the group consisting of CD19, CD30, CD33, CD70 and LIV-1.

37. The Camptothecin Conjugate of embodiment 1, wherein Q is a Linker Unit having a formula selected from the group consisting of -Z-A-, -Z-A-S*-W- and -Z-A-B(S*)W, wherein A is a Connector Unit, or Q is a Linker Unit having a formula selected from the group consisting of -Z-A-RL-, -Z-A-S*-RL-, -Z-A-B(S*)-RL-, -Z-A-S*-W-RL-, and -Z-A-B(S*)-W-RL, wherein A is a Connector Unit and RL is a Releasable linker other than a Glucuronide Unit.

38. The Camptothecin Conjugate of embodiment 37, wherein Q is a Linker Unit having the formula of -Z-A-S*-W- or -Z-A-S*-W-RL-.

39. The Camptothecin Conjugate of embodiment 37, wherein Q is a Linker Unit having the formula of -Z-A-RL- or -Z-A-S*-RL-.

40. The Camptothecin Conjugate of embodiment 37, wherein Q is a Linker Unit having the formula of -Z-A-.

41. The Camptothecin Conjugate of any one of embodiments 37-40, wherein D is CPT2.

42. The Camptothecin Conjugate of any one of embodiments 37-40, wherein D is CPT3.

43. The Camptothecin Conjugate of any one of embodiments 37-40, wherein D is CPT1.

44. The Camptothecin Conjugate of any one of embodiments 37-40, wherein D is CPT4.

45. The Camptothecin Conjugate of any one of embodiments 37-40, wherein D is CPT5.

46. The Camptothecin Conjugate of any one of embodiments 37-40, wherein D is CPT6.

47. The Camptothecin Conjugate of any one of embodiments 37-40, wherein D is CPT7.

48. The Camptothecin Conjugate of any one of embodiments 37-47, wherein Q is a Linker Unit having the formula selected from the group consisting of -Z-A-RL-, -Z-A-S*-RL- and -Z-A-S*-W-RL-, wherein RL has the formula:

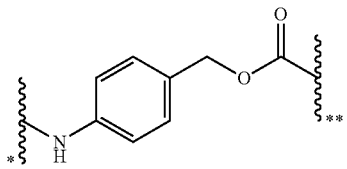 [SMILES: *Nc1ccc(COC(*)=O)cc1]

wherein the wavy line marked with a double asterisk (**) indicates the site of covalent attachment to D; and the wavy line marked with a single asterisk (*) indicates the point of covalent attachment to A, S* or W.

49. The Camptothecin Conjugate of embodiment 48, wherein -Q-D has the formula of -Z-A-S*-W-RL-D, wherein D is CPT1, CPT4 or CPT6 in which each of $R^F$ and $R^{F'}$ is —H having covalent attachment to the nitrogen atom of the amine substituent; and W is an Amino Acid Unit selected from the group consisting of N-methyl-glycine (sarcosine), N-methyl-alanine, N-methyl-3-alanine, valine, N-methyl-valine, or D is CPT1, CPT2, CPT3, CPT4, CPT5, CPT6 or CPT7 having covalent attachment to the oxygen atom of the hydroxyl substituent on the lactone ring; and W is an Amino Acid Unit selected from the group consisting glutamic acid or lysine.

50. The Camptothecin Conjugate of any one of embodiments 37-49, wherein -Z-A- is comprised of a succinimidoalkanoyl moiety or succinimido and triazole moieties, each optionally having the succinimide ring in hydrolyzed form as a succinic acid amide moiety, or a succinic acid amide moiety derivable from mDPR of a Camptothecin-Linker Compound.

51. The Camptothecin Conjugate of any one of embodiments 37-49, wherein -Z-A- is comprised of a succinimidoalkanoyl moiety optionally having the succinimide ring in hydrolyzed form as a succinic acid amide moiety.

52. The Camptothecin Conjugate of any one of embodiments 37-49, wherein -Z-A- is comprised of a succinic acid amide moiety derivable from an mDPR moiety of a Camptothecin-Linker Compound.

53. The Camptothecin Conjugate of any one of embodiments 37-49, wherein Q is a Linker Unit having the formula selected from the group consisting of -Z-A-S*—RL- and -Z-A-S*-W-RL-, wherein -Z-A- has a formula selected from the group consisting of:

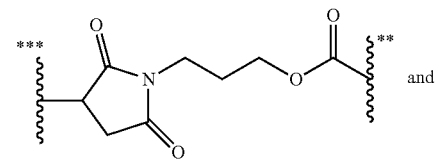 and

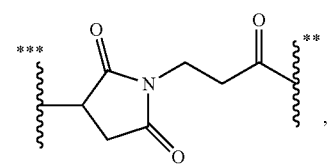, optionally having the succinimide ring in hydrolyzed form as a succinic acid amide moiety, wherein the wavy line marked with a double asterisk (**) indicates the site of covalent attachment to S*; and the wavy line marked with a triple asterisk (***) indicates the point of covalent attachment to a sulfur atom of L.

54. The Camptothecin Conjugate of any one of claims 37-49, wherein Q is a Linker Unit having the formula selected from the group consisting of -Z-A-S*-RL- and —Z-A-S*-W-RL-, wherein S* has the formula of:

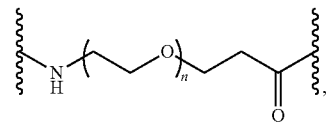

wherein subscript n is an integer ranging from 2 to 36.

55. The Camptothecin Conjugate of any one of claims 37-49, wherein -Z A- has the formula of:

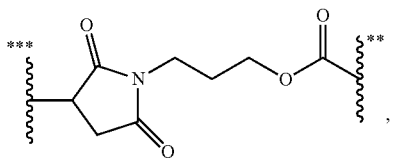 [SMILES: *C(=O)OCCCN1C(=O)CC(*)C1=O]

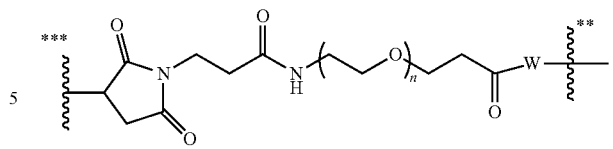

optionally having the succinimide ring in hydrolyzed form as a succinic acid amide moiety, wherein the wavy line marked with a double asterisk (**) indicates the site of covalent attachment to S*; and the wavy line marked with a triple asterisk (***) indicates the point of covalent attachment to a sulfur atom of L.

56. The Camptothecin Conjugate of any one of claims 37-49, wherein Q is a Linker Unit of formula -Z-A-S*-W- or -Z-A-S—W-RL-, wherein RL is other than a Glucuronide Unit, wherein -Z-A-S*-W- in either formula has the formula of:

optionally having the succinimide ring in hydrolyzed form as a succinic acid amide moiety, wherein subscript n is an integer ranging from 2 to 10; the wavy line marked with a double asterisk () indicates the site of covalent attachment to D or RL; and the wavy line marked with a triple asterisk (*) indicates the point of covalent attachment to a sulfur atom of L.

57. The Camptothecin Conjugate of embodiment 56, wherein subscript n is an integer ranging from 2 to 4.

58. The Camptothecin Conjugate of embodiment 49, wherein -Q-D has PGP-459 ci the structure of:

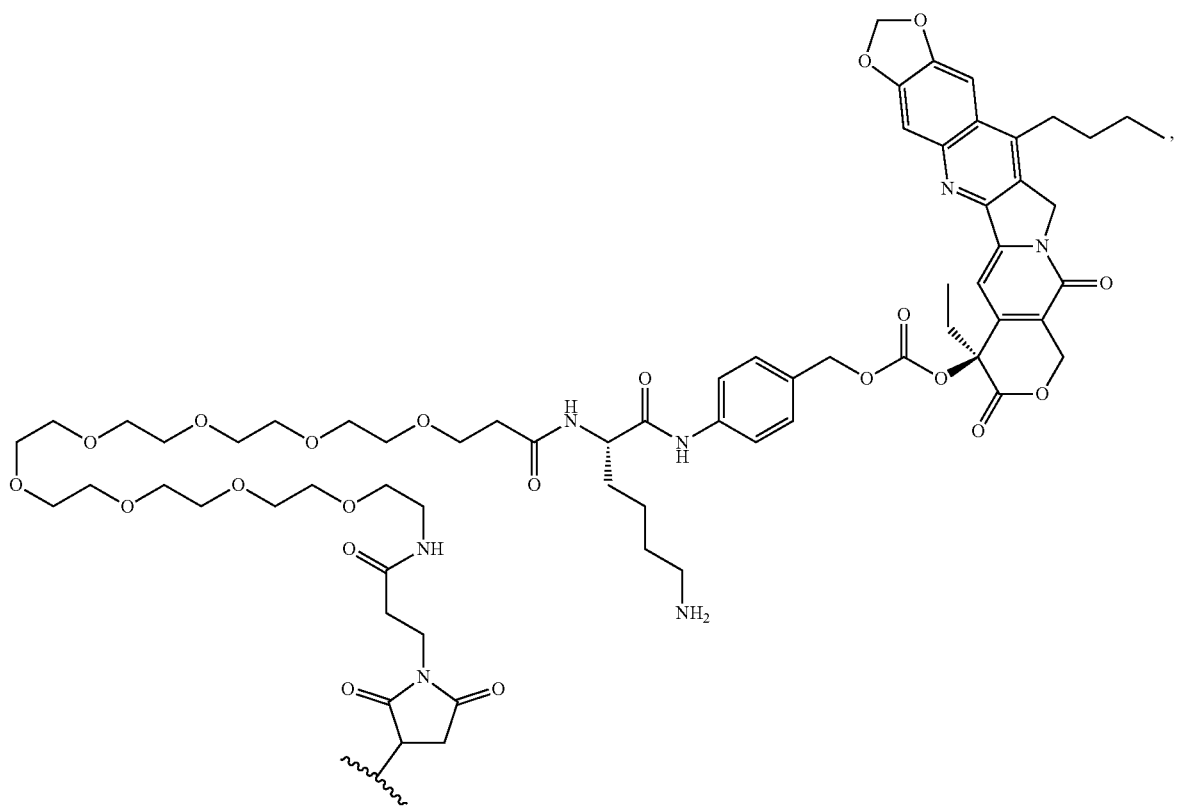 [SMILES: *C1CC(=O)N(CCC(=O)NCCOCCOCCOCCOCCOCCOCCOCCOCCC(=O)N[C@@H](CCCCN)C(=O)Nc2ccc(COC(=O)O[C@]3(CC)C(=O)OCc4c3cc3n(c4=O)Cc4c-3nc3cc5c(cc3c4CCCC)OCO5)cc2)C1=O]

or salt thereof, optionally having the succinimide ring in hydrolyzed form as a succinic acid amide moiety, wherein the wavy line indicates the point of covalent attachment to a sulfur atom of the Ligand Unit.

59. The Camptothecin Conjugate of embodiment 49, wherein -Q-D has the structure of:

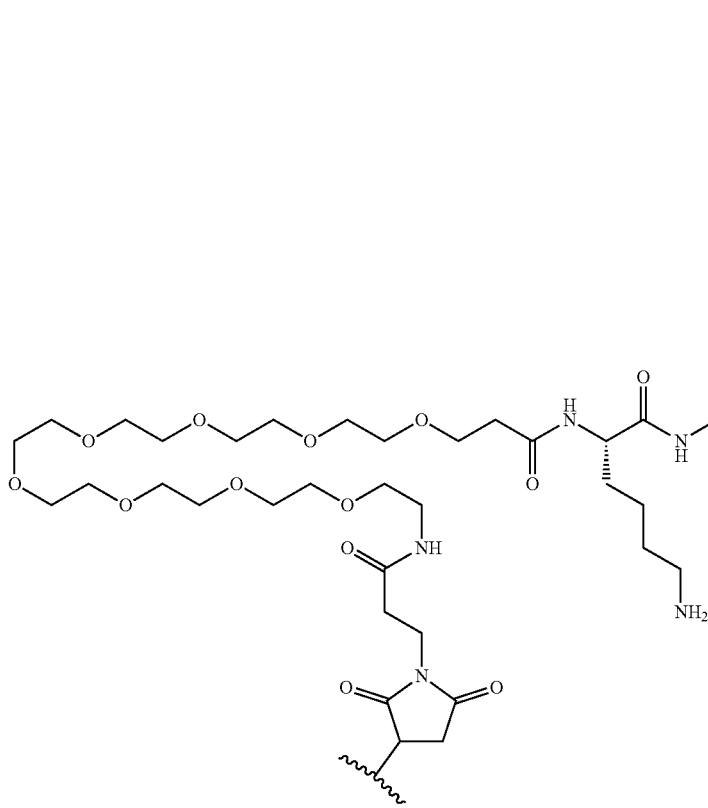

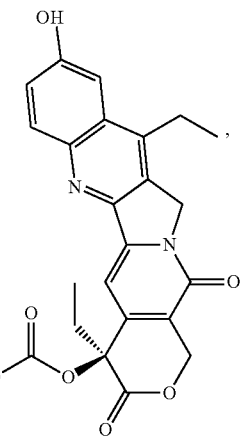

or salt thereof, optionally having the succinimide ring in hydrolyzed form as a succinic acid amide moiety, wherein the wavy line indicates the point of covalent attachment to a sulfur atom of the Ligand Unit.

60. The Camptothecin Conjugate of any one of embodiments 37-59, wherein L is of an antibody.

61. The Camptothecin Conjugate of embodiment 60, wherein the antibody specifically binds to an antigen selected from the group consisting of CD19, CD30, CD33, CD70 and LIV-1.

62. A Camptothecin-Linker Compound having a formula selected from the group consisting of Z'-A-RL-D (i), Z'-A-RL-Y-D (ii), Z'-A-S*-RL-D (iii), -Z'-A-S*-RL-Y-D (iv), Z'-A-B(S*)-RL-D (v), Z'-A-B(S*)-RL-Y-D (vi), Z'-A-D (vii), Z'-A-S*-W-D (viii), Z'-A-B(S*)-W-D (ix), Z'-A-S*-W-RL-D (x) and Z'-A-B(S*)-W-RL-D (xi), wherein in each of the formula Z' is a Stretcher Unit precursor; A is a bond or a Connecter Unit; B is a Parallel Connector Unit; S* is a Partitioning Agent; RL is a Releasable Linker; Y is a Spacer Unit; and D is a Camptothecin Compound selected from the group consisting of CPT1, CPT2, CPT3, CPT4, CPT5, CPT6 and CPT7 as follows:

CPT1

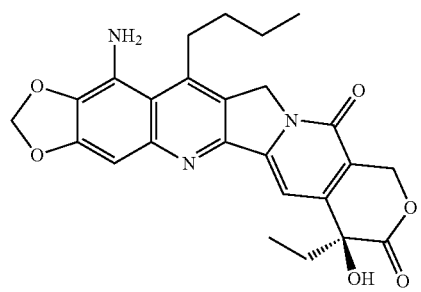

-continued

CPT2

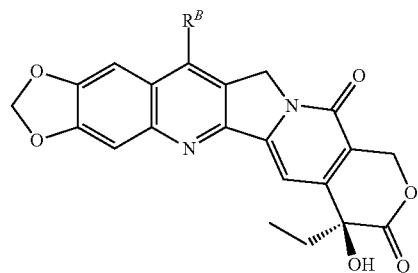

CPT3

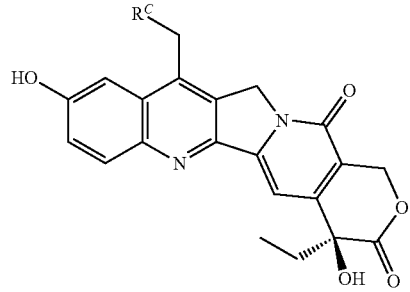

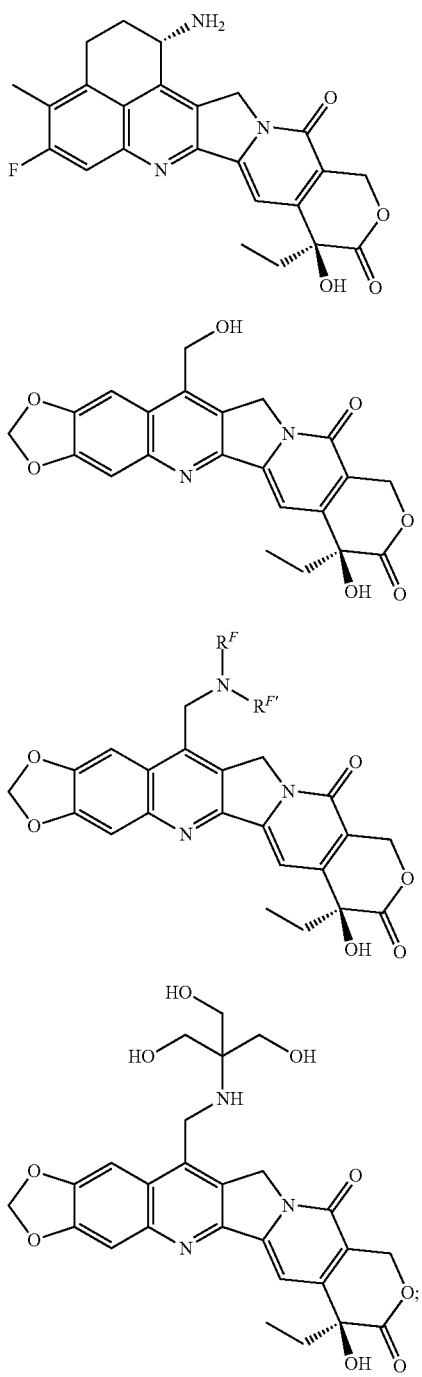

wherein $R^B$ is a member selected from the group consisting of —H, $C_1$-$C_8$ alkyl, $C_1$-$C_8$ haloalkyl, $C_3$-$C_8$ cycloalkyl, ($C_3$-$C_8$ cycloalkyl)$C_1$-$C_4$ alkyl-, phenyl and phenyl-$C_1$-$C_4$ alkyl-; $R^C$ is a moiety selected from the group consisting of $C_1$-$C_6$ alkyl and $C_3$-$C_6$ cycloalkyl; each $R^F$ and $R^{F'}$ is a moiety independently selected from the group consisting of —H, $C_1$-$C_8$ alkyl, $C_1$-$C_8$ hydroxyalkyl, $C_1$-$C_8$ aminoalkyl, ($C_1$-$C_4$alkylamino)-$C_1$-$C_8$ alkyl-, N,N—($C_1$-$C_4$ hydroxyalkyl)($C_1$-$C_4$ alkyl)-amino-$C_1$-$C_8$ alkyl-, N,N-di($C_1$-$C_4$ alkyl)amino-$C_1$-$C_8$ alkyl-, N—$C_1$-$C_4$ hydroxyalkyl-$C_1$-$C_8$ aminoalkyl-, $C_1$-$C_8$ alkylC(O)—, $C_1$-$C_8$ hydroxyalkyl-C(O)—, $C_1$-$C_8$ aminoalkylC(O)—, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl-$C_1$-$C_4$ alkyl-, heteroaryl and heteroaryl-$C_1$-$C_4$ alkyl-, or $R^F$ and $R^{F'}$ are combined with the nitrogen atom to which each is attached to form a 5-, 6- or 7-membered ring having 0 to 3 substituents selected from halogen, $C_1$-$C_4$ alkyl, —OH, —O$C_1$-$C_4$ alkyl, —$NH_2$, —NH$C_1$-$C_4$ alkyl and —N($C_1$-$C_4$ alkyl)$_2$; and wherein the cycloalkyl, heterocycloalkyl, phenyl and heteroaryl moieties of $R^B$, $R^C$, $R^F$ and $R^{F'}$ are substituted with from 0 to 3 substituents selected from the group consisting of halogen, $C_1$-$C_4$ alkyl, —OH, —O$C_1$-$C_4$ alkyl, —$NH_2$, —NH$C_1$-$C_4$ alkyl and —N($C_1$-$C_4$ alkyl)$_2$, or D is a Drug Unit selected from the group consisting of 13a-13c of Table H, 14a-14z of Table I and 18a-18r of Table J;

and wherein the point of covalent attachment of D is to the heteroatom of any one of the hydroxyl or aliphatic primary or secondary amino substituents of any one of CPT1, CPT2, CPT3, CPT4, CPT5, CPT6 and CPT7 or of any one of 13a-13c of Table H, 14a-14z of Table I and 18a-18r of Table J when Q is -Z-A-RL-, -Z-A-RL-Y-, -Z-A-S*-RL-, -Z-A-B(S*)-RL-, -Z-A-S*-RL-Y- or -Z-A-B(S*)-RL-Y-, or wherein the point of covalent attachment of D is to the oxygen atom of the hydroxyl substituent on the lactone ring of any one of CPT1, CPT2, CPT3, CPT4, CPT5, CPT6 or CPT7 or any one of 13a-13c of Table H, 14a-14z of Table I and 18a-18r of Table J when Q is -Z-A-, -Z-A-S*-W- or -Z-A- B(S*)W, or when Q is -Z-A-S*-RL-, —Z-A-B(S*)-RL-, -Z-A-S*-W-RL-, or -Z-A-B(S*)-W-RL- in which RL is a Releasable Unit other than a Glucuronide Unit; and provided that at least one of $R^F$ and $R^{F'}$ is —H, when the point of covalent attachment is to the nitrogen atom of the amino substituent on CPT6; and provided that Z'-A- of the Camptothecin-Linker compound of formula (i), formula (ii), formula (iii), formula (iv), formula (v), and formula (vi) is other than maleimido-caproyl-β-alanyl moiety when D is CPT1 having covalent attachment through the nitrogen atom of its amino substituent.

63. The Camptothecin-Linker Compound of embodiment 62 having the formula selected from the group consisting of formula (i), formula (ii); formula (iii), formula (iv), formula (v) and formula (vi), wherein A is a Connector Unit and RL is a Glucuronide Unit.

64. The Camptothecin-Linker Compound of embodiment 62 or 63, wherein the point of covalent attachment of D is through the oxygen atom of the hydroxyl substituent on the lactone ring of CPT1, CPT2, CPT3, CPT4, CPT5, CPT6 or CPT7.

65. The Camptothecin-Linker Compound of embodiment 62 or 63, wherein the point of covalent attachment of D is through the oxygen atom of the hydroxyl substituent on the lactone ring of any one of 13a-13c of Table H, 14a-14z of Table I and 18a-18n of Table J.

66. The Camptothecin-Linker Compound of embodiment 62 or 63, wherein the point of covalent attachment of D is through the oxygen atom of the hydroxyl substituent of $R^F$ or $R^{F'}$ of CPT6, when at least one of $R^F$ and $R^{F'}$ is $C_1$-$C_8$ hydroxyalkyl N,N—($C_1$-$C_4$ hydroxyalkyl)($C_1$-$C_4$alkyl)-amino-$C_1$-$C_8$ alkyl-, N—$C_1$-$C_4$ hydroxyalkyl-$C_1$-$C_8$ aminoalkyl-, $C_1$-$C_8$ alkylC(O)—, 67. The Camptothecin-Linker Compound of embodiment 62 or 63, wherein the point of covalent attachment of D is through the nitrogen atom of the amine substituent of $R^F$ or $R^{F'}$ of CPT6, when at least one of $R^F$ and $R^{F'}$ is $C_1$-$C_8$ aminoalkyl, $(C_1$-$C_4$alkylamino)-$C_1$-$C_8$ alkyl-, N—$(C_1$-$C_4$ hydroxyalkyl)-$C_1$-$C_8$ aminoalkyl- or $C_1$-$C_8$ aminoalkylC(O)—, 68. The Camptothecin-Linker Compound of embodiment 62 or 63, wherein the point of attachment of D is through the nitrogen atom of the amino substituent on CPT1, provided that Z'-A- is other than maleimido-caproyl-β-alanyl.

69. The Camptothecin-Linker Compound of embodiment 62 or 63, wherein the point of attachment of D is to the nitrogen atom of the amino substituent on CPT4.

70. The Camptothecin-Linker Compound of embodiment 62 or 63, wherein the point of attachment of D is through the nitrogen atom of the substituent on CPT6 provided that least one of $R^F$ and $R^{F'}$ is —H.

71. The Camptothecin-Linker Compound of any one of embodiments 62-70 having formula (i) or (ii).

72. The Camptothecin-Linker Compound of any one of embodiments 62-70 having formula (iii) or (iv).

73. The Camptothecin-Linker Compound of any one of embodiments 62-70 having formula (v) or (vi).

74. The Camptothecin-Linker Compound of any one of embodiments 62-70 having formula (i).

75. The Camptothecin-Linker Compound of any one of embodiments 62-70 having formula (ii).

76. The Camptothecin-Linker Compound of any one of embodiments 62-64, 66, 67 and 70-75, wherein D is CPT6.

77. The Camptothecin-Linker Compound of any one of embodiments 62-64, 69 and 71-75, wherein D is CPT4.

78. The Camptothecin-Linker Compound of any one of embodiments 62-64 and 71-75, wherein D is selected from the group consisting of CPT1, CPT2, CPT3 and CPT5.

79. The Camptothecin-Linker Compound of any one of embodiments 62-78, wherein Z' is a maleimido moiety.

80. The Camptothecin-Linker Compound of any one of embodiments 62-78, wherein Z'-A- is maleimidopropionyl, maleimidopropionyl-β-alanyl or mDPR, the basic nitrogen of which is optionally protonated or protected with an acid-labile protecting group, provided that Z'-A- is other than maleimido-caproyl-β-alanyl moiety when D is CPT1 having covalent attachment through the nitrogen atom of its amino substituent.

81. The Camptothecin-Linker Compound of any one of embodiments 62-70 having formula (iii), formula (iv), formula (v) and formula (vi), wherein S* is a PEG group.

82. The Camptothecin-Linker Compound of any one of embodiments 63-81, wherein RL is a Glucuronide Unit having the structure of:

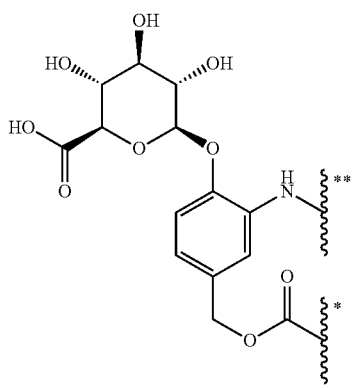 [SMILES: *Nc1cc(COC(*)=O)ccc1O[C@H]1O[C@@H](C(=O)O)[C@H](O)[C@@H](O)[C@@H]1O]

wherein the wavy line marked with a single asterisk (*) indicates the site of covalent attachment to D or to a Spacer Unit (Y); and the wavy line marked with a double asterisk (**) indicates the point of covalent attachment to A, B or S*.

83. The Camptothecin-Linker Compound of embodiment 82 having formula (ii), formula (iv) or formula (vi), wherein Spacer Unit (Y) has the formula of:

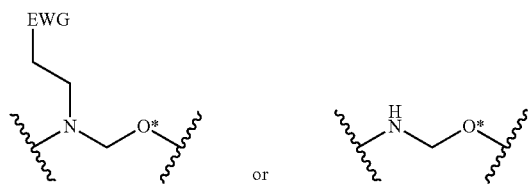

wherein EWG is an electron-withdrawing group; O* represent the oxygen atom from a hydroxy substituent of D; the wavy line adjacent to the nitrogen atom indicates the site of covalent attachment to the carbonyl carbon atom of the Glucuronide Unit; and the wavy line adjacent to O* indicates the site of covalent attachment to the remainder of D.

84. The Camptothecin-Linker Compound of embodiment 82 having formula (ii), formula (iv) or formula (vi), wherein D is selected from the group consisting of CPT1, CPT4 and CPT6 in which each of $R^F$ and $R^{F'}$ is —H; and Spacer Unit (Y) has the formula of:

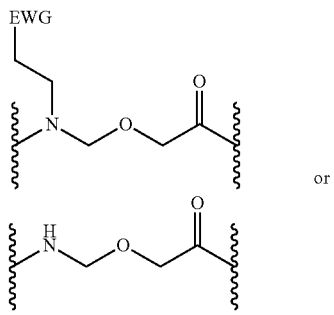

wherein EWG is an electron-withdrawing group; the wavy line adjacent to the nitrogen atom indicates the site of covalent attachment to the carbonyl carbon atom of the Glucuronide Unit; and the wavy line adjacent to the carbonyl carbon atom indicates the site of covalent attachment to the nitrogen atom of the amino substituent of CPT1, CPT4 or CPT6 in which each of $R^F$ and $R^{F'}$ is —H.

85. The Camptothecin-Linker Compound of embodiment 82 having formula (ii), formula (iv) or formula (vi), wherein D is selected from the group consisting of CPT1, CPT4 and CPT6 in which each of $R^F$ and $R^{F'}$ is —H; and the Spacer Unit (Y) has the formula of:

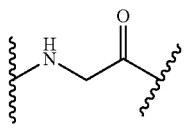 [SMILES: *NCC(*)=O]

wherein EWG is an electron-withdrawing group; the wavy line adjacent to the nitrogen atom indicates the site of covalent attachment to the carbonyl carbon atom of the Glucuronide Unit; and the wavy line adjacent to the carbonyl carbon atom indicates the site of covalent attachment to the nitrogen atom of the amino substituent of CPT1, CPT4 or CPT6 in which each of $R^F$ and $R^{F'}$ is —H.

86. The Camptothecin-Linker Compound of any one of embodiments 62-85, wherein A is comprised of an alkynyl moiety capable of undergoing a 1,3-dipolar cycloaddition with an azido substituent from a chemically modified targeting agent that is the precursor to a Ligand Unit of a Camptothecin Conjugate so as to provide the Conjugate having a Connector Unit comprised of a triazolyl moiety.

87. The Camptothecin-Linker Compound of any one of embodiments 62-85, wherein Z'-A- is comprised of a maleimido-alkanoyl moiety or maleimido and triazolyl moieties provided that Z'-A- is comprised of maleimido and triazolyl moieties when CPT1 has covalent attachment through the nitrogen atom of its amino substituent.

88. The Camptothecin-Linker Compound of any one of embodiments 62-85, wherein Z'-A- is comprised of a maleimido-alkanoyl-β-alanyl moiety provided that D has covalent attachment to the oxygen atom of the hydroxyl substituent on its lactone ring when D is CPT1.

89. The Camptothecin-Linker Compound of any one of embodiments 58-79, wherein Z'-A- is comprised of mDPR, the basic nitrogen atom of which is optionally protonated or protected by an acid-labile protecting group.

90. The Camptothecin-Linker Compound of embodiment 62 having formula (vii), formula (viii) or formula (ix), wherein A is a Connector Unit, or having formula (i), formula (iii), formula (x) or formula (xi), wherein A is a Connector Unit and RL is a Releasable linker other than a Glucuronide Unit.

91. The Camptothecin-Linker Compound of embodiment 62 or 90 having formula (viii) or formula (x).

92. The Camptothecin-Linker Compound of embodiment 62 or 90 having formula (i) or formula (iii).

93. The Camptothecin-Linker Compound of embodiment 62 or 90 having formula (vii).

94. The Camptothecin-Linker Compound of any one of embodiments 62 and 90-93, wherein D has formula CPT2.

95. The Camptothecin-Linker Compound of any one of embodiments 62 and 90-93, wherein D has formula CPT3.

96. The Camptothecin-Linker Compound of any one of embodiments 62 and 90-93, wherein D has formula CPT1.

97. The Camptothecin-Linker Compound of any one of embodiments 62 and 90-93, wherein D has formula CPT4.

98. The Camptothecin-Linker Compound of any one of embodiments 62 and 90-93, wherein D has formula CPT5.

99. The Camptothecin-Linker Compound of any one of embodiments 62 and 90-93, wherein D has formula CPT6.

100. The Camptothecin-Linker Compound of any one of embodiments 62 and 90-99 having formula (i), formula (iii) or formula (x), wherein RL has the formula:

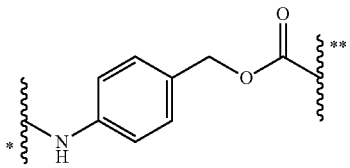 [SMILES: *Nc1ccc(COC(*)=O)cc1]

wherein the wavy line marked with a double asterisk (**) indicates the site of covalent attachment to D; and the wavy line marked with a single asterisk (*) indicates the point of covalent attachment to A, S* or W.

101. The Camptothecin-Linker Compound of embodiment 100 having formula (x) wherein W is an Amino Acid Unit selected from the group consisting of N-methyl-glycine (sarcosine), N-methyl-alanine, N-methyl-3-alanine, valine and N-methyl-valine.

102. The Camptothecin-Linker Compound of any one of embodiments 62-20101, wherein Z'-A- is comprised of a maleimido-alkanoyl moiety, maleimide and triazole moieties, or mDPR, the basic nitrogen atom of which is optionally protonated or protected by an acid-labile protecting group.

102. The Camptothecin-Linker Compound of any one of embodiments 62-101, wherein Z'-A- is comprised of a maleimido-alkanoyl moiety.

103. The Camptothecin-Linker Compound of any one of embodiments 62-101, wherein Z'-A- is comprised of mDPR.

104. The Camptothecin-Linker Compound of embodiment 62-70 having formula (iii) or formula (x), wherein Z'-A- has a formula selected from the group consisting of:

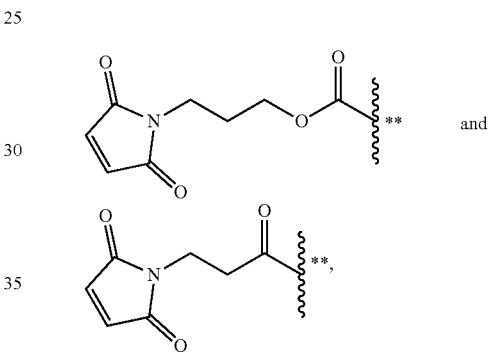

wherein the wavy line marked with a double asterisk (**) indicates the site of covalent attachment to S*.

105. The Camptothecin-Linker Compound of any one of embodiments 62-570 and 94-104 having formula (iii) or formula (x), wherein S* has the formula of:

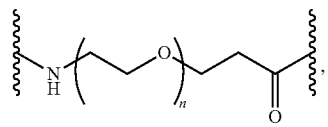

wherein subscript n is an integer ranging from 2 to 36.

106. The Camptothecin-Linker Compound of any one of embodiments 62-70 and 94-105 wherein Z'-A- has the formula of:

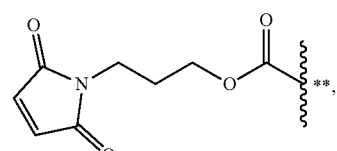

wherein the wavy line marked with a double asterisk (**) indicates the site of covalent attachment to S*.

107. The Camptothecin-Linker Compound of any one of embodiments 62-70 and 94-105 having formula (viii) or formula (x) in which Z'-A-S*-W- has the formula of:

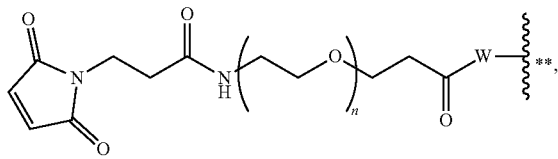

wherein subscript n is an integer ranging from 2 to 10; the wavy line marked with a double asterisk () indicates the site of covalent attachment to D or RL; and the wavy line marked with a triple asterisk (*) indicates the point of covalent attachment to a sulfur atom of L.

108. The Camptothecin-Linker Compound of embodiment 107, wherein subscript n is an integer ranging from 2 to 4.

109. The Camptothecin-Linker Compound of embodiment 62 having the structure of:

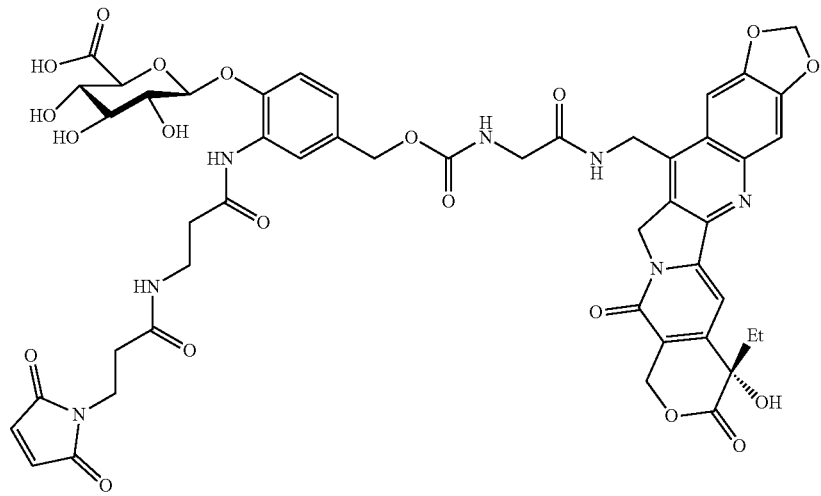

or

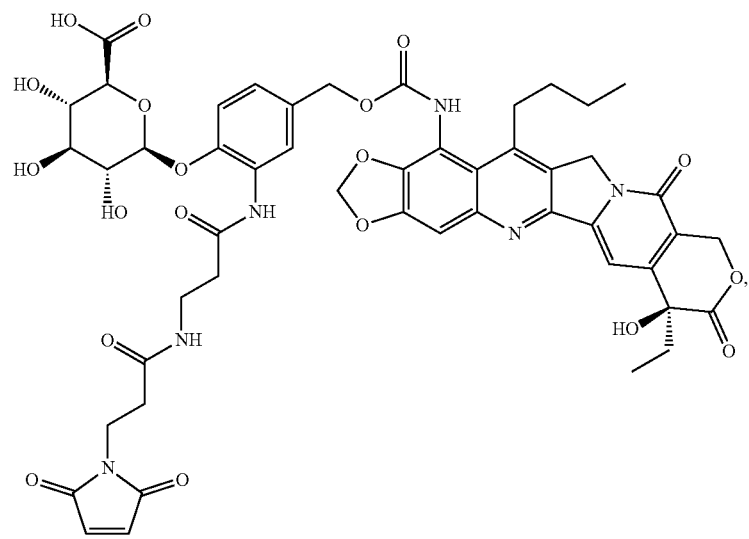

or a salt thereof.

110. The Camptothecin-Linker Compound of embodiment 62 having the structure of:
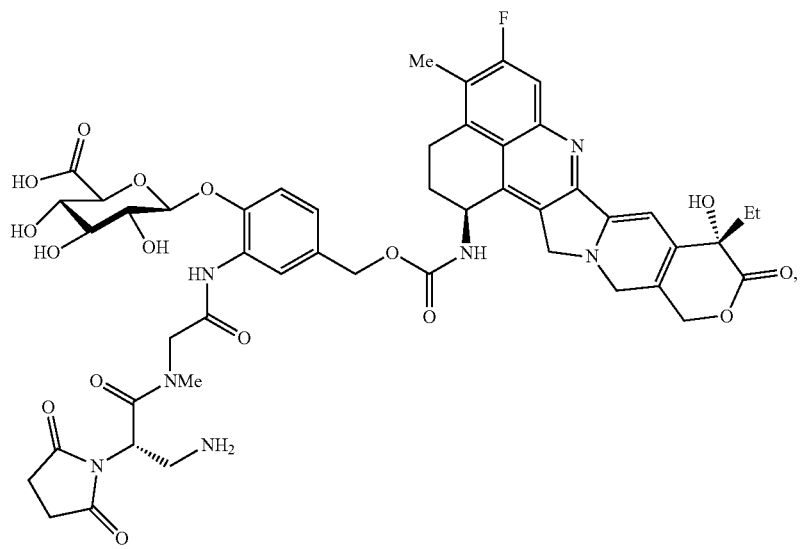
or a salt thereof.
111. The Camptothecin-Linker Compound of embodiment 62 having the structure of:
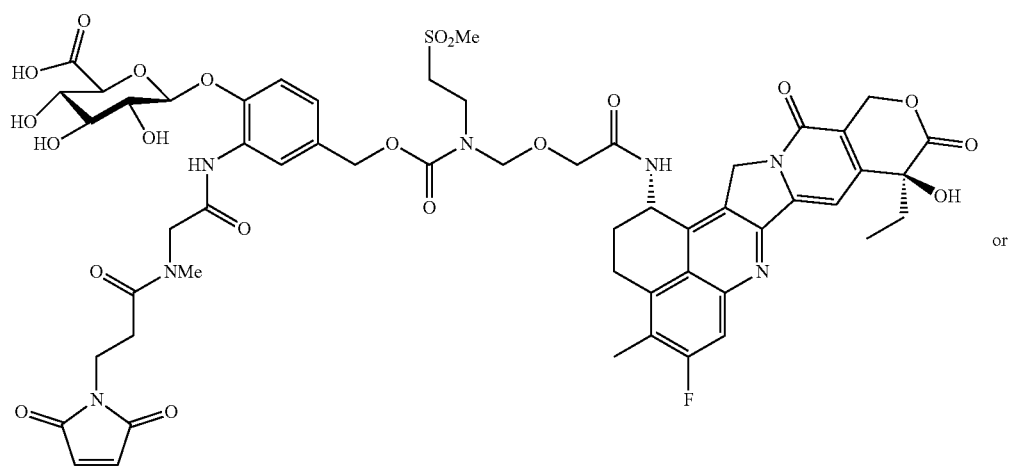
or

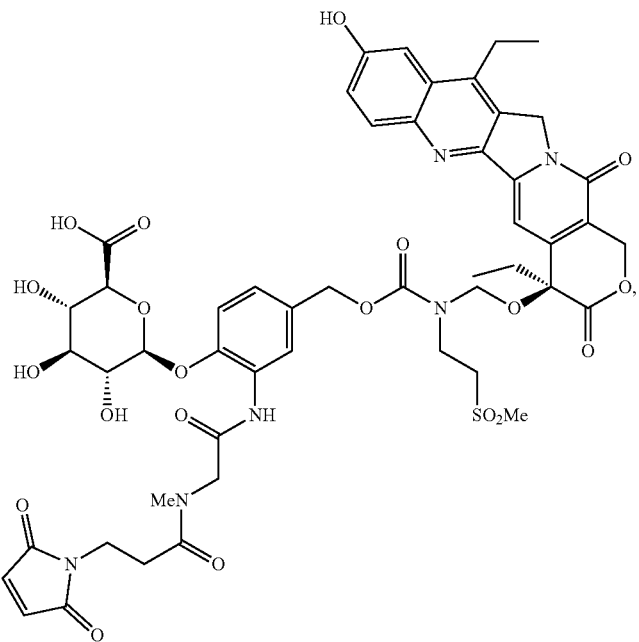
or a salt thereof.
112. The Camptothecin-Linker Compound of embodiment 62 having the structure of:
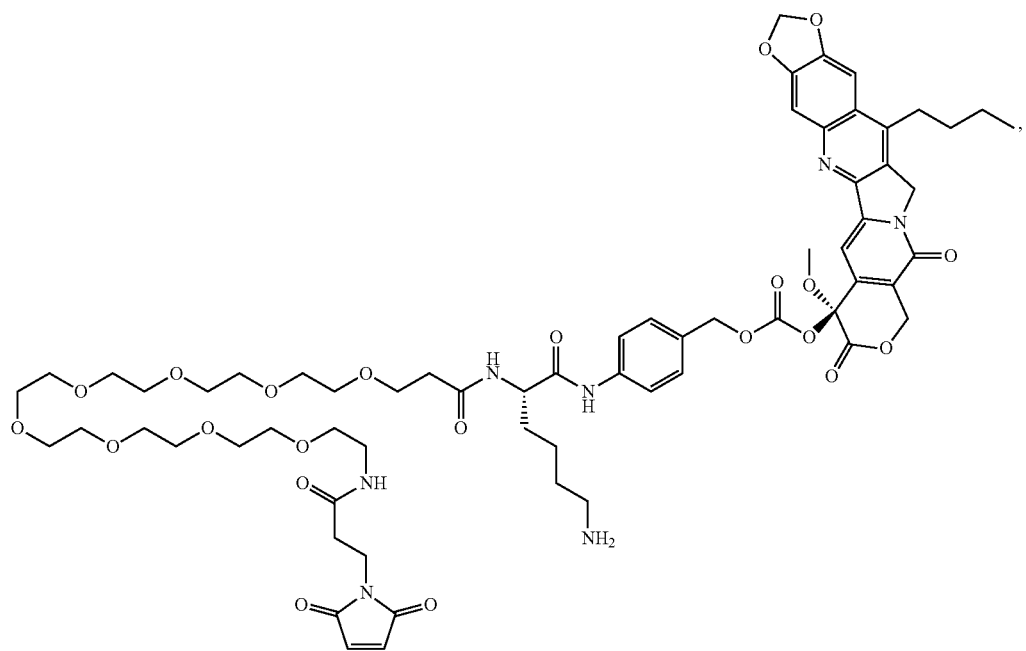 [SMILES: CCCCc1c2c(nc3cc4c(cc13)OCO4)-c1cc3c(c(=O)n1C2)COC(=O)[C@@]3(OC)OC(=O)OCc1ccc(NC(=O)[C@H](CCCCN)NC(=O)CCOCCOCCOCCOCCOCCOCCOCCOCCNC(=O)CCN2C(=O)C=CC2=O)cc1]
or a salt thereof.

113. The Camptothecin-Linker Compound of embodiment 62 having the structure of:

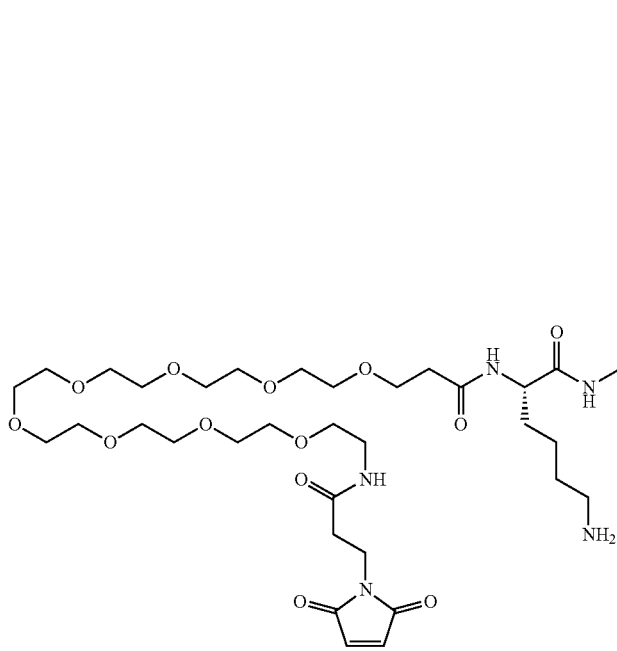

or a salt thereof.

114. Use of a Camptothecin Conjugate in preparation of a mendicant for treatment of a cancer in a subject, wherein the Camptothecin Conjugate has the formula of any one embodiments 1-113.

115. The use according to embodiment 114, wherein said cancer is selected from the group consisting of lymphomas, leukemias, and solid tumors.

116. The use according to embodiment 114, wherein said cancer is a lymphoma or a leukemia.

117. Use of a Camptothecin Conjugate in preparation of a medicant for treatment of an autoimmune disease in a subject, wherein the Camptothecin Conjugate has the formula of any one embodiments 1-113 and the autoimmune disease is selected from the group consisting of Th2 lymphocyte related disorders, Th1 lymphocyte-related disorders, and activated B lymphocyte-related disorders.

118. A method of preparing a Camptothecin Conjugate of any one of embodiments 1-61, said method comprising the step of contacting an antibody having a functional group reactive towards Z' of a Camptothecin-Linker Compound of any one of embodiments 62-113.

1A. A Camptothecin Conjugate having a formula L-(Q-D)$_p$, or a salt thereof, wherein L is a Ligand Unit; Q is a Linker Unit having a formula selected from the group consisting of -Z-A-RL-, -Z-A-RL-Y-, -Z-A-S*-RL-, -Z-A-B(S*)-RL-, -Z-A-S*-RL-Y— and -Z-A-B(S*)-RL-Y-, wherein Z is a Stretcher Unit, A is a bond or a Connecter Unit; B is a Parallel Connector Unit; S* is a Partitioning Agent; RL is a Glucuronide Unit; and Y is a Spacer Unit; D is a Drug Unit selected from the group consisting of:

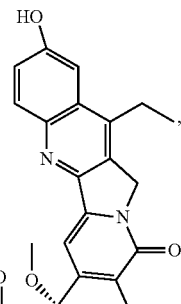

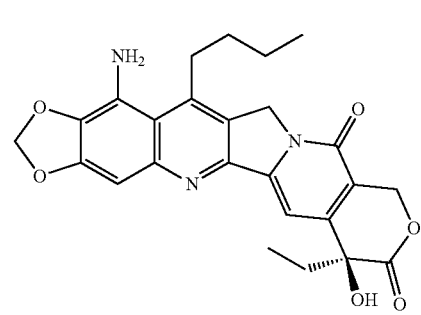
CPT1

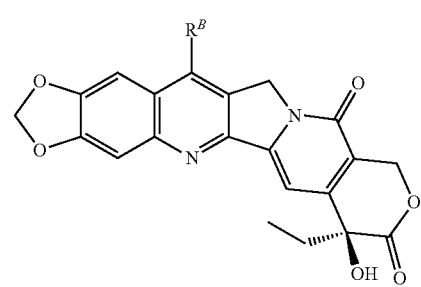
CPT2

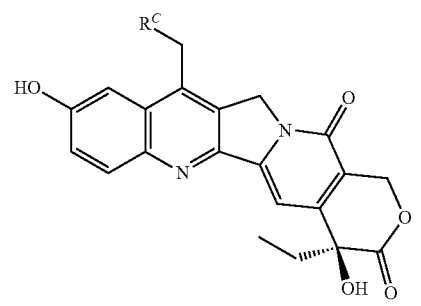
CPT3

CPT4

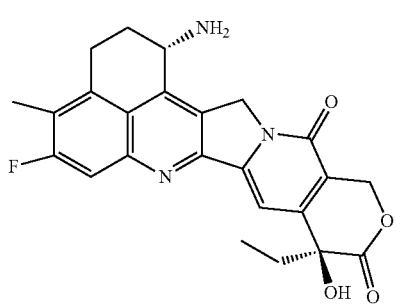

CPT5

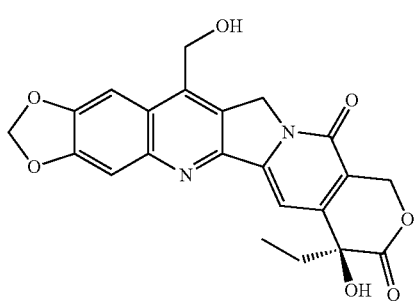

CPT6

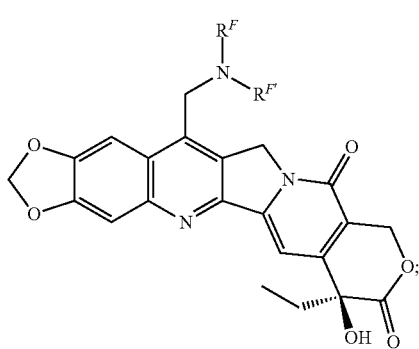

wherein $R^B$ is a member selected from the group consisting of H, $C_1$-$C_8$ alkyl, $C_1$-$C_8$ haloalkyl, $C_3$-$C_8$ cycloalkyl, $C_3$-$C_8$ cycloalkyl$C_1$-$C_4$ alkyl, phenyl and phenyl$C_1$-$C_4$ alkyl; $R^C$ is a member selected from the group consisting of $C_1$-$C_6$ alkyl and $C_3$-$C_6$ cycloalkyl; each $R^F$ and $R^{F'}$ is a member independently selected from the group consisting of H, $C_1$-$C_8$ alkyl, $C_1$-$C_8$ hydroxyalkyl, $C_1$-$C_8$ aminoalkyl, $C_1$-$C_4$alkylamino$C_1$-$C_8$ alkyl, ($C_1$-$C_4$ hydroxyalkyl)($C_1$-$C_4$alkyl)amino$C_1$-$C_8$ alkyl, di($C_1$-$C_4$alkyl)amino$C_1$-$C_8$ alkyl, $C_1$-$C_4$ hydroxyalkyl$C_1$-$C_8$ aminoalkyl, $C_1$-$C_8$ alkylC(O)—, $C_1$-$C_8$ hydroxyalkylC(O)—, $C_1$-$C_8$ aminoalkylC(O)—, $C_3$-$C_{10}$ cycloalkyl, $C_3$-$C_{10}$ cycloalkyl$C_1$-$C_4$ alkyl, $C_3$-$C_{10}$ heterocycloalkyl, $C_3$-$C_{10}$ heterocycloalkyl$C_1$-$C_4$ alkyl, phenyl, phenyl$C_1$-$C_4$ alkyl, diphenyl$C_1$-$C_4$ alkyl, heteroaryl and heteroaryl$C_1$-$C_4$ alkyl; or $R^F$ and $R^{F'}$ are combined with the nitrogen atom to which each is attached to form a 5-, 6- or 7-membered ring having 0 to 3 substituents selected from halogen, $C_1$-$C_4$ alkyl, —OH, —O$C_1$-$C_4$ alkyl, —NH$_2$, —NH$C_1$-$C_4$ alkyl and —N($C_1$-$C_4$ alkyl)$_2$; and wherein cycloalkyl, heterocycloalkyl, phenyl and heteroaryl portions of $R^B$, $R^C$, $R^F$ and $R^{F'}$ are substituted with from 0 to 3 substituents selected from halogen, $C_1$-$C_4$ alkyl, —OH, —O$C_1$-$C_4$ alkyl, —NH$_2$, —NH$C_1$-$C_4$ alkyl and —N($C_1$-$C_4$ alkyl)$_2$; subscript p is an integer of from 1 to 16; and wherein Q is attached through any of the hydroxyl and amine groups present on CPT1, CPT2, CPT3, CPT4, CPT5, or CPT6; and wherein when D is CPT1, with attachment through the amino group of CPT1, then -Z-A- is other than maleimido-caproyl-β-alanyl.

2A. A Camptothecin Conjugate of embodiment 1A, wherein Q is a Linker Unit having a formula selected from the group consisting of -Z-A-RL- and -Z-A-RL-Y-.

3A. A Camptothecin Conjugate of embodiment 1A, wherein Q is a Linker Unit having a formula selected from the group consisting of -Z-A-S*-RL- and -Z-A-S*-RL-Y-.

4A. A Camptothecin Conjugate of embodiment 1A, wherein Q is a Linker Unit having a formula selected from the group consisting of -Z-A-B(S*)-RL- and -Z-A-B(S*)—RL-Y-.

5A. A Camptothecin Conjugate of any one of embodiments 1A to 4A, wherein D has formula CPT1.

6A. A Camptothecin Conjugate of any one of embodiments 1A to 4A, wherein D has formula CPT2.

7A. A Camptothecin Conjugate of any one of embodiments 1A to 4A, wherein D has formula CPT3.

8A. A Camptothecin Conjugate of any one of embodiments 1A to 4A, wherein D has formula CPT4.

9A. A Camptothecin Conjugate of any one of embodiments 1A to 4A, wherein D has formula CPT5.

10A. A Camptothecin Conjugate of any one of embodiments 1A to 4A, wherein D has formula CPT6.

11A. A Camptothecin Conjugate of any one of embodiments 1A to 4A, wherein L is an antibody.

12A. A Camptothecin Conjugate of embodiment 1A, wherein Q comprises a Glucuronide Unit (RL) having the formula:

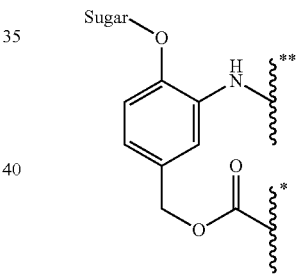

wherein Sugar is a hexose form of a natural or non-natural monosaccharide, and wherein RL is attached to the primary amine of any of CPT1, CPT4 or CPT6, wherein the wavy line marked with a single * indicates the site of attachment to the primary amine of CPT1, CPT4 or CPT6, or to a Spacer Unit (Y); and the wavy line marked with ** indicates the point of attachment to additional linker components of Q.

13A. A Camptothecin Conjugate of embodiment 12A, wherein the Spacer Unit (Y) is present and comprises:

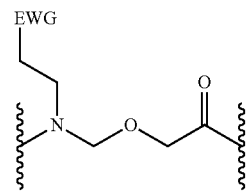

wherein EWG is an electron-withdrawing group.

14A. A Camptothecin Conjugate of embodiment 12A, wherein A comprises a triazole formed from an alkyne and an azide under using Click chemistry.

15A. A Camptothecin Conjugate of embodiment 12A, wherein -Z-A-comprises a maleimido-alkanoic acid component, a maleimido and triazole components, or an mDPR component.

16A. A Camptothecin Conjugate of embodiment 12A, wherein -Z-A-comprises a maleimido-alkanoyl-β-alanyl component.

17A. A Camptothecin Conjugate of embodiment 12A, wherein Z-A-comprises an mDPR component.

18A. A Camptothecin Conjugate of embodiment 12A, wherein Q has the formula:

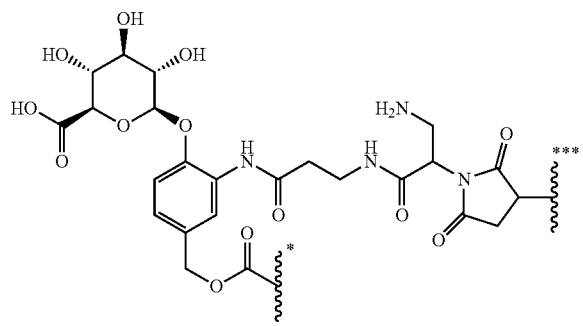 [SMILES: *C(=O)OCc1ccc(O[C@H]2O[C@@H](C(=O)O)[C@H](O)[C@@H](O)[C@@H]2O)c(NC(=O)CCNC(=O)C(CN)N2C(=O)CC(*)C2=O)c1]

wherein the wavy line marked with a single * indicates the site of attachment to the primary amine of CPT1, CPT4 or CPT6, or to a Spacer Unit; and the wavy line marked with *** indicates the point of attachment to a sulfur atom of L.

19A. A Camptothecin Conjugate of embodiment 1A, wherein the Glucuronide Unit has the formula:

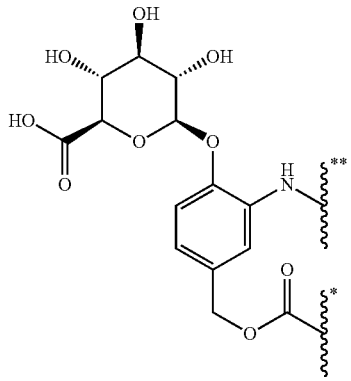 [SMILES: *Nc1cc(COC(*)=O)ccc1O[C@H]1O[C@@H](C(=O)O)[C@H](O)[C@@H](O)[C@@H]1O]

wherein the wavy line marked with a single * indicates the point of attachment to a hydroxyl of CPT1, CPT2, CPT3, CPT4, CPT5 or CPT6, or to a Spacer Unit (Y); and the wavy line marked with ** indicates the point of attachment to A, B, S* or Z.

20A. A Camptothecin Conjugate of embodiment 19A, wherein the Spacer Unit is present and comprises:

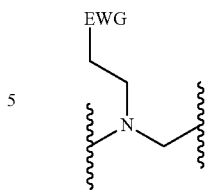

wherein EWG is an electron-withdrawing group.

21A. A Camptothecin Conjugate of embodiment 19A, wherein the Spacer Unit is present and comprises:

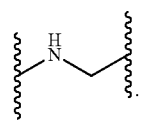 [SMILES: *CN*]

22A. A Camptothecin Conjugate of claim 19A, wherein A comprises a triazole formed from an alkyne and an azide under using Click chemistry.

23A. A Camptothecin Conjugate of claim 19A, wherein -Z-A- comprises a maleimido-alkanoic acid component, a maleimido and triazole components, or an mDPR component.

24A. A Camptothecin Conjugate of embodiment 19A, wherein -Z-A-comprises a maleimido-alkanoyl-β-alanyl component.

25A. A Camptothecin Conjugate of embodiment 19A, wherein -Z-A-comprises an mDPR component.

26A. A Camptothecin Conjugate of embodiment 19A, wherein —Z-A- comprises a maleimidopropionyl component and a Partitioning Agent (S*) is present in said Linker Unit.

27A. A Camptothecin Conjugate of embodiment 19A, wherein Q has the formula:

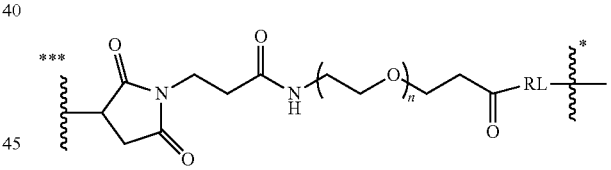

wherein n is an integer from 1 to 50; the wavy line marked with a single * indicates the site of attachment to D, or to a Spacer Unit (Y); and the wavy line marked with *** indicates the point of attachment to a sulfur atom of L.

28A. A Camptothecin Conjugate of embodiment 27A, wherein n is 4.

29A. A Camptothecin Conjugate of any one of embodiments 1A to 28A, wherein L is an antibody that specifically binds to an antigen selected from the group consisting of CD19, CD30, CD33, CD70 and LIV-1.

30A. A Camptothecin-Linker Compound having a formula selected from the group consisting of Z'-A-RL-D (i), Z'-A-RL-Y-D (ii), Z'-A-S*-RL-D (iii), Z'-A-S*-RL-Y-D (iv), Z'-A-B(S*)-RL-D (v) and Z'-A-B(S*)-RL-Y-D (vi), wherein Z' is a Stretcher Unit, A is a bond or a Connecter Unit; B is a Parallel Connector Unit; S* is a Partitioning Agent; RL is a Glucuronide Unit; Y is a Spacer Unit; and D is a Camptothecin Compound selected from the group consisting of:

CPT1

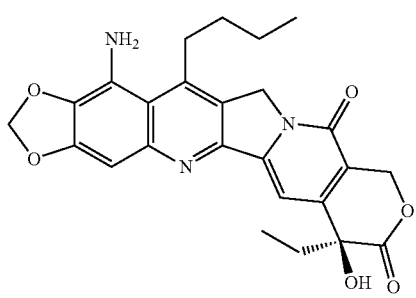

CPT2

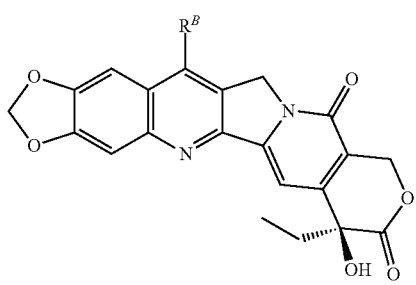

CPT3

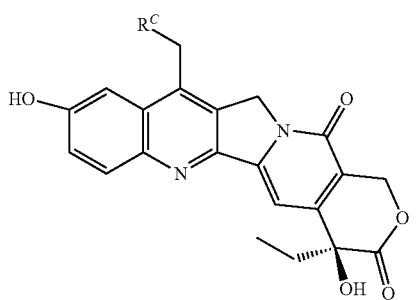

CPT4

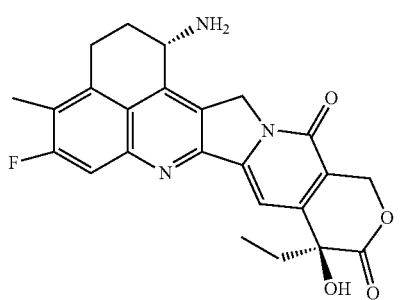

CPT5

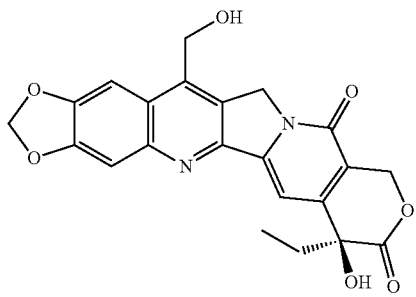

CPT6

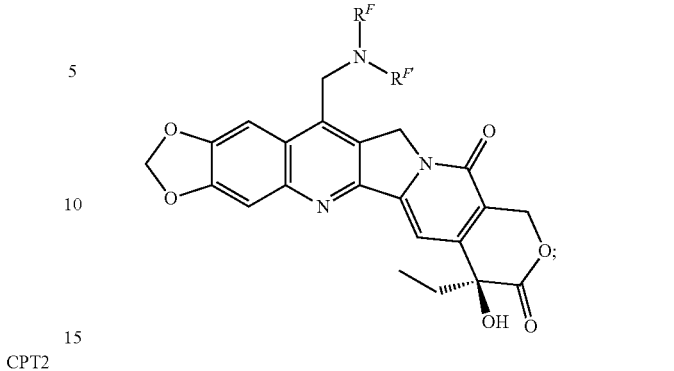

$R^B$ is a member selected from the group consisting of H, $C_1$-$C_8$ alkyl, $C_1$-$C_8$ haloalkyl, $C_3$-$C_8$ cycloalkyl, $C_3$-$C_8$ cycloalkyl$C_1$-$C_4$ alkyl, phenyl and phenyl$C_1$-$C_4$ alkyl; $R^C$ is a member selected from the group consisting of $C_1$-$C_6$ alkyl and $C_3$-$C_6$ cycloalkyl; each $R^F$ and $R^{F'}$ is a member independently selected from the group consisting of —H, $C_1$-$C_8$ alkyl, $C_1$-$C_8$ hydroxyalkyl, $C_1$-$C_8$ aminoalkyl, $C_1$-$C_4$alkylamino$C_1$-$C_8$ alkyl, ($C_1$-$C_4$ hydroxyalkyl)($C_1$-$C_4$alkyl)amino$C_1$-$C_8$ alkyl, di($C_1$-$C_4$alkyl)amino$C_1$-$C_8$ alkyl, $C_1$-$C_4$ hydroxyalkyl$C_1$-$C_8$ aminoalkyl, $C_1$-$C_8$ alkylC(O)—, $C_1$-$C_8$ hydroxyalkyl-C(O)—, $C_1$-$C_8$ aminoalkylC(O)—, $C_3$-$C_{10}$ cycloalkyl, $C_3$-$C_{10}$ cycloalkyl$C_1$-$C_4$ alkyl, $C_3$-$C_{10}$ heterocycloalkyl, $C_3$-$C_{10}$ heterocycloalkyl$C_1$-$C_4$ alkyl, phenyl, phenyl$C_1$-$C_4$ alkyl, diphenyl$C_1$-$C_4$ alkyl, heteroaryl and heteroaryl$C_1$-$C_4$ alkyl; or $R^F$ and $R^{F'}$ are combined with the nitrogen atom to which each is attached to form a 5-, 6- or 7-membered ring having 0 to 3 substituents selected from halogen, $C_1$-$C_4$ alkyl, —OH, —O$C_1$-$C_4$ alkyl, —NH$_2$, NH$C_1$-$C_4$ alkyl and N($C_1$-$C_4$ alkyl)$_2$; and wherein cycloalkyl, heterocycloalkyl, phenyl and heteroaryl portions of $R^B$, $R^C$, $R^F$ and $R^{F'}$ are substituted with from 0 to 3 substituents selected from halogen, $C_1$-$C_4$ alkyl, OH, O$C_1$-$C_4$ alkyl, NH$_2$, NH$C_1$-$C_4$ alkyl and N($C_1$-$C_4$ alkyl)$_2$;

subscript p is an integer of from 1 to 16; and wherein Q is attached through any of the hydroxyl and amine groups present on CPT1, CPT2, CPT3, CPT4, CPT5, or CPT6; and wherein when D is CPT1, with attachment through the amino group of CPT1, then -Z-A- is other than maleimido-caproyl-β-alanyl.

31A. A Camptothecin-Linker Compound of embodiment 30A having formula (i) or (ii).

32A. A Camptothecin-Linker Compound of embodiment 30A having formula (iii) or (iv).

33A. A Camptothecin-Linker Compound of embodiment 30A having formula (v) or (vi).

34A. A Camptothecin-Linker Compound of embodiment 30A having formula (i).

35A. A Camptothecin-Linker Compound of embodiment 30A having formula (ii).

36A. A Camptothecin-Linker Compound of any one of embodiments 30A to 34A, wherein D is CPT6.

37A. A Camptothecin-Linker Compound of any one of embodiments 30A to 34A, wherein D is CPT4.

38A. A Camptothecin-Linker Compound of any one of embodiments 30A to 34A, wherein D is selected from the group consisting of CPT1, CPT2, CPT3 and CPT5.

39A. A Camptothecin-Linker Compound of any one of embodiments 30A to 34A, wherein Z' is a maleimido group.

40A. A Camptothecin-Linker Compound of any one of embodiments 30A to 34A, wherein Z'-A- is maleimidopropionyl, mDPR or maleimidopropionyl-3-Alanyl.

41A. A Camptothecin-Linker Compound of any one of embodiments 30A, and 32A to 34A, wherein S* is a PEG group.

42A. A Camptothecin-Linker Compound of embodiment 30A, wherein said Glucuronide Unit has the formula:

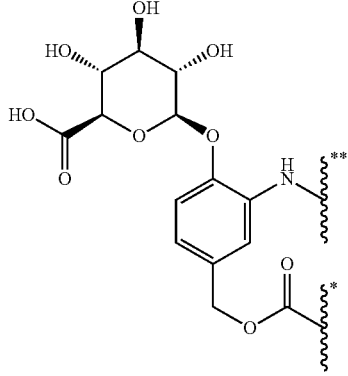 [SMILES: *Nc1cc(COC(*)=O)ccc1O[C@H]1O[C@@H](C(=O)O)[C@H](O)[C@@H](O)[C@@H]1O]

wherein the wavy line marked with a single * indicates the site of attachment to D or to a Spacer Unit (Y); and the wavy line marked with ** indicates the point of attachment to additional linker components, A, B, S* or Z' of the Camptothecin-Linker Compound.

42A. A Camptothecin-Linker Compound of embodiment 30A, wherein the Spacer Unit is present and comprises:

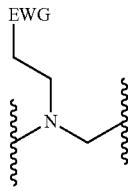

wherein EWG is an electron-withdrawing group.

43A. A Camptothecin-Linker Compound of embodiment 42A, wherein the Spacer Unit is present and comprises:

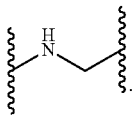

44A. A Camptothecin-Linker Compound of embodiment 42A, wherein A comprises a triazole formed from an alkyne and an azide under using Click chemistry.

45A. A Camptothecin-Linker Compound of embodiment 42A, wherein Z'-A- comprises a maleimido-alkanoic acid component, a maleimido and triazole components, or an mDPR component.

46A. A Camptothecin-Linker Compound of embodiment 42A, wherein Z'-A- comprises a maleimido-alkanoyl-β-alanyl component.

47A. A Camptothecin-Linker Compound of embodiment 42A, wherein Z'-A- comprises an mDPR component.

48A. A Camptothecin-Linker Compound of embodiment 42A, wherein Z'-A- comprises a maleimidopropionyl component and a Partitioning Agent (S*) is present in said Linker Unit.

49A. A Camptothecin-Linker Compound of embodiment 30A, wherein formulae (i) and (ii) comprise the formula:

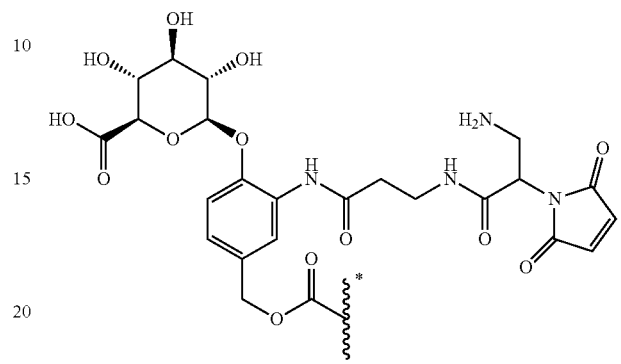

wherein the wavy line marked with a single * indicates the site of attachment to the primary amine of CPT1, CPT4 or CPT6, or to a Spacer Unit.

50A. A method of treating cancer in a subject in need thereof, said method comprising administering to the subject a Camptothecin Conjugate of any one of embodiments 1A to 29A.

51A. The method of embodiment 50A, wherein said cancer is selected from the group consisting of lymphomas, leukemias, and solid tumors.

52A. The method of embodiment 50A, wherein said cancer is a lymphoma or a leukemia.

53A. The method of any one of embodiments 50A to 53A, further comprising an additional therapeutic agent.

54A. The method of embodiment 53A, wherein said additional therapeutic agent is one or more chemotherapeutic agents or radiation therapy.

55A. A method of treating an autoimmune disease in a subject in need thereof, said method comprising administering the subject a Camptothecin Conjugate of any one of embodiments 1A to 29A.

56A. The method of embodiment 55A, wherein said autoimmune disease is selected from the group consisting of Th2 lymphocyte related disorders, Th1 lymphocyte-related disorders, and activated B lymphocyte-related disorders.

57A. A method of preparing a Camptothecin Conjugate of any one of embodiments 1A to 29A, said method comprising reacting an antibody with a Camptothecin-Linker Compound of any one of embodiments 30A to 49A.

58A. A kit comprising a Camptothecin Conjugate of any one of embodiments 1A to 29A.

59A. The kit of embodiment 58A, further comprising an additional therapeutic agent.

1B. A Camptothecin Conjugate having a formula L-(Q-D)$_p$, or a salt thereof, wherein L is a Ligand Unit; Q is a Linker Unit having a formula selected from the group consisting of -Z-A-, -Z-A-RL-, -Z-A-S*-W-, -Z-A-B(S*)W, -Z-A-S*-RL-, -Z-A-B(S*)—RL-, -Z-A-S*-W-RL- and -Z-A-B(S*)-W-RL-, wherein Z is a Stretcher Unit, A is a bond or a Connecter Unit; B is a Parallel Connector Unit; S* is a Partitioning Agent; RL is a Releasable Linker; and W is an Amino Acid Unit; D is a Drug Unit selected from the group consisting of:

CPT1

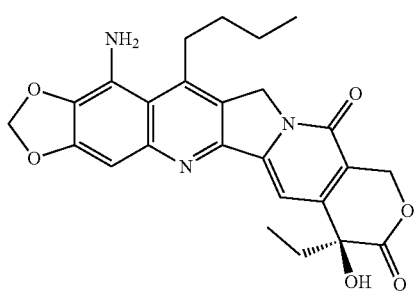

CPT2

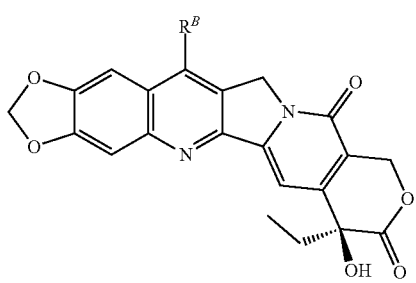

CPT3

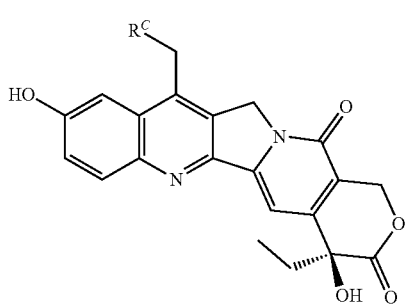

CPT4

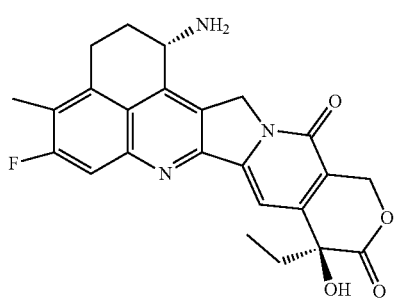

CPT5

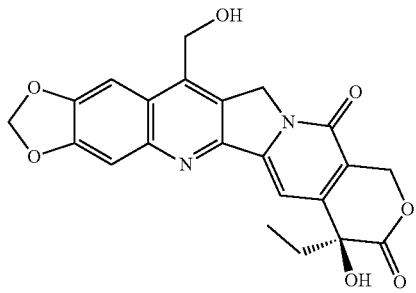

CPT6

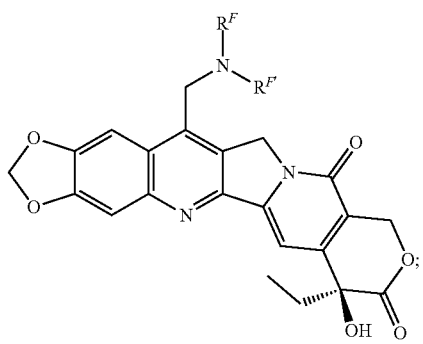

wherein $R^B$ is a member selected from the group consisting of H, $C_1$-$C_8$ alkyl, $C_1$-$C_8$ haloalkyl, $C_3$-$C_8$ cycloalkyl, $C_3$-$C_8$ cycloalkyl$C_1$-$C_4$ alkyl, phenyl and phenyl$C_1$-$C_4$ alkyl; $R^C$ is a member selected from the group consisting of $C_1$-$C_6$ alkyl and $C_3$-$C_6$ cycloalkyl; each $R^F$ and $R^{F'}$ is a member independently selected from the group consisting of —H, $C_1$-$C_8$ alkyl, $C_1$-$C_8$ hydroxyalkyl, $C_1$-$C_8$ aminoalkyl, $C_1$-$C_4$alkylamino$C_1$-$C_8$ alkyl, (Ci-CU hydroxyalkyl)($C_1$-$C_4$ alkyl)amino$C_1$-$C_8$ alkyl, di($C_1$-$C_4$ alkyl)amino$C_1$-$C_8$ alkyl, $C_1$-$C_4$ hydroxyalkyl$C_1$-$C_8$ aminoalkyl, $C_1$-$C_8$ alkylC(O)—, $C_1$-$C_8$ hydroxyalkylC(O)—, $C_1$-$C_8$ aminoalkylC(O)—, $C_3$-$C_{10}$ cycloalkyl, $C_3$-$C_{10}$ cycloalkyl$C_1$-$C_4$ alkyl, $C_3$-$C_{10}$ heterocycloalkyl, $C_3$-$C_{10}$ heterocycloalkyl$C_1$-$C_4$ alkyl, phenyl, phenyl$C_1$-$C_4$ alkyl, diphenyl$C_1$-$C_4$ alkyl, heteroaryl and heteroaryl$C_1$-$C_4$ alkyl; or $R^F$ and $R^{F'}$ are combined with the nitrogen atom to which each is attached to form a 5-, 6- or 7-membered ring having 0 to 3 substituents selected from halogen, $C_1$-$C_4$ alkyl, —OH, —O$C_1$-$C_4$ alkyl, —$NH_2$, NH$C_1$-$C_4$ alkyl and N($C_1$-$C_4$ alkyl)$_2$; and wherein cycloalkyl, heterocycloalkyl, phenyl and heteroaryl portions of $R^B$, $R^C$, $R^F$ and $R^{F'}$ are substituted with from 0 to 3 substituents selected from halogen, $C_1$-$C_4$ alkyl, OH, O$C_1$-$C_4$ alkyl, $NH_2$, NH$C_1$-$C_4$ alkyl and N($C_1$-$C_4$ alkyl)$_2$; and wherein the point of attachment of D to Q is through the oxygen atom of the hydroxyl substituent of the lactone ring of CPT1, CPT2, CPT3, CPT4, CPT5, or CPT6.

2B. The Camptothecin Conjugate of embodiment 1B, wherein Q is a Linker Unit having the formula -Z-A-S*-W-.

3B. The Camptothecin Conjugate of embodiment 1B, wherein Q is a Linker Unit having the formula -Z-A-S*-W-RL-.

4B. The Camptothecin Conjugate of embodiment 1B, wherein Q is a Linker Unit having the formula -Z-A-.

5B. The Camptothecin Conjugate of any one of embodiments 1B to 4B, wherein D has formula CPT2.

6B. The Camptothecin Conjugate of any one of embodiments 1B to 4B, wherein D has formula CPT3.

7B. The Camptothecin Conjugate of any one of embodiments 1B to 4B, wherein D has formula CPT1.

8B. The Camptothecin Conjugate of any one of embodiments 1B to 4B, wherein D has formula CPT4.

9B. The Camptothecin Conjugate of any one of embodiments 1B to 4B, wherein D has formula CPT5.

10B. The Camptothecin Conjugate of any one of embodiments 1B to 4B, wherein D has formula CPT6.

11B. The Camptothecin Conjugate of any one of embodiments 1B to 4B, wherein L is an antibody.

12B. The Camptothecin Conjugate of embodiment 3B, wherein RL has the formula:

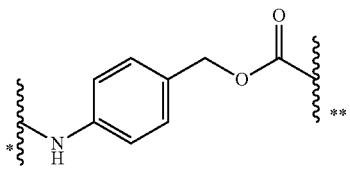 [SMILES: *Nc1ccc(COC(*)=O)cc1]

wherein the wavy line marked with ** indicates the site of attachment to D; and the wavy line marked with * indicates the point of attachment to another linker component of Q.

13B. The Camptothecin Conjugate of embodiment 12B, wherein W is an Amino Acid Unit selected from the group consisting of N-methyl glycine, N-methyl alanine, N-methyl β-alanine, valine and N-methyl valine.

14B. The Camptothecin Conjugate of embodiment 12B, wherein -Z-A-comprises a maleimido-alkanoyl moiety, or a maleimido and triazole moieties, or an mDPR moiety.

15B. The Camptothecin Conjugate of embodiment 12B, wherein -Z-A-comprises a maleimido-alkanoyl moiety.

16B. The Camptothecin Conjugate of embodiment 12B, wherein -Z-A- has a formula selected from the group consisting of:

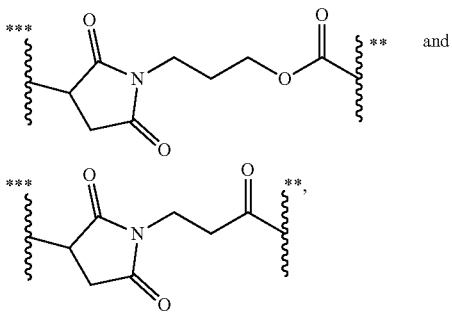

wherein the wavy line marked with ** indicates the site of attachment to S*; and the wavy line marked with *** indicates the point of attachment to a sulfur atom of L.

17B. The Camptothecin Conjugate of embodiment 12B, wherein S* has the formula:

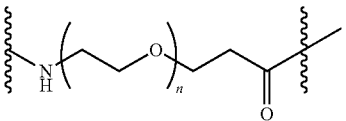

and the subscript n is an integer from 2 to 36.

18B. The Camptothecin Conjugate of embodiment 2B, wherein W is an Amino Acid Unit selected from the group consisting of N-methyl glycine, N-methyl alanine, N-methyl β-alanine, valine and N-methyl valine.

19B. The Camptothecin Conjugate of embodiment 12B, wherein -Z-A-comprises a maleimido-alkanoyl moiety, or a maleimido and triazole moieties, or an mDPR moiety.

20B. The Camptothecin Conjugate of embodiment 2B, wherein -Z-A-comprises a maleimido-alkanoyl moiety.

21B. The Camptothecin Conjugate of embodiment 2B, wherein -Z-A- has a formula selected from the group consisting of:

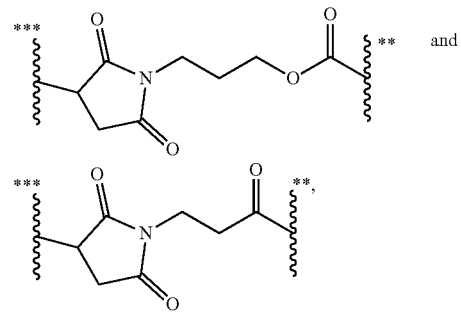

wherein the wavy line marked with ** indicates the site of attachment to S*; and the wavy line marked with *** indicates the point of attachment to a sulfur atom of L.

22B. The Camptothecin Conjugate of embodiment 2B, wherein S* has the formula:

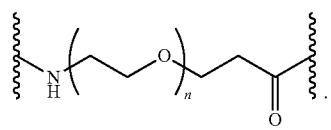

23B. The Camptothecin Conjugate of embodiment 18B, wherein -Z-A- is

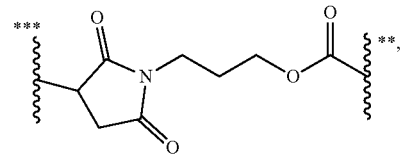 [SMILES: *C(=O)OCCCN1C(=O)CC(*)C1=O]

wherein the wavy line marked with ** indicates the site of attachment to S*; and the wavy line marked with *** indicates the point of attachment to a sulfur atom of L.

24B. The Camptothecin Conjugate of embodiment 18B, wherein Q has the formula:

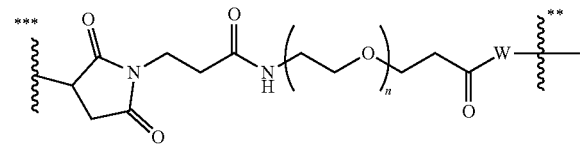

wherein n is an integer from 2 to 10; the wavy line marked with  indicates the site of attachment to D; and the wavy line marked with * indicates the point of attachment to a sulfur atom of L.

25B. The Camptothecin Conjugate of embodiment 27B, wherein n is 2 to 4.

26B. The Camptothecin Conjugate of any one of embodiments 1B to 25B, wherein L is an antibody that selectively binds to an antigen selected from the group consisting of CD19, CD30, CD33, CD70 and LIV-1.

27B. A Camptothecin-Linker Compound having a formula selected from the group consisting of: Z'-A-D (i), Z'-A-RL-D (ii), Z'-A-S*-W-D (iii), Z'-A-S*-W-RL-D (iv), Z'-A-B(S*)-RL-D (v) and Z'-A-B(S*)-W-RL-D, wherein Z' is a Stretcher Unit, A is a bond or a Connecter Unit; B is a Parallel Connector Unit; S* is a Partitioning Agent; RL is a Releasable Linker Unit; and D is a Drug Unit selected from the group consisting of:

CPT1
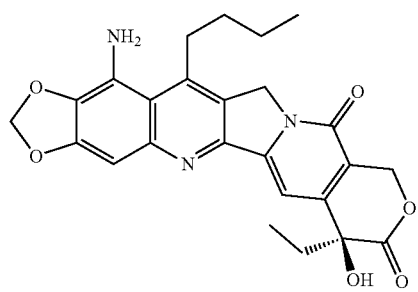

CPT2
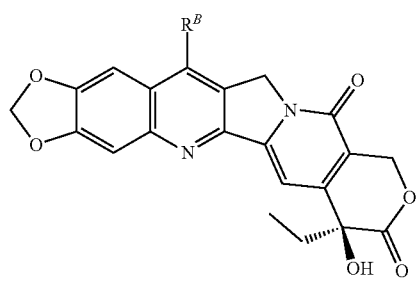

CPT3
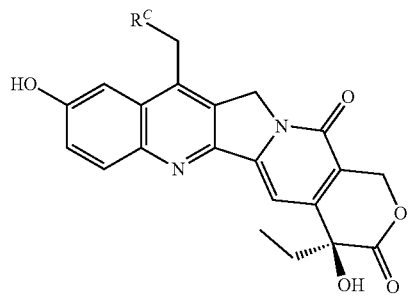

CPT4
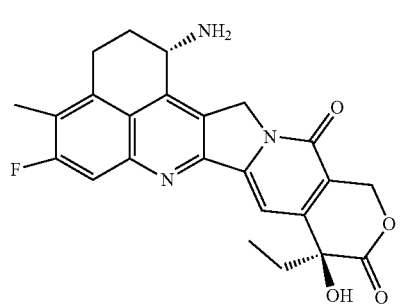

CPT5
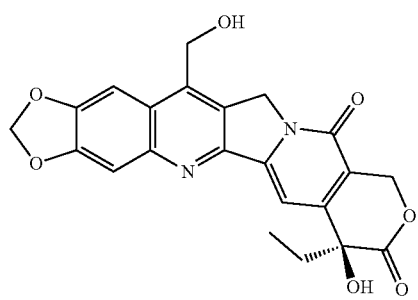

CPT6
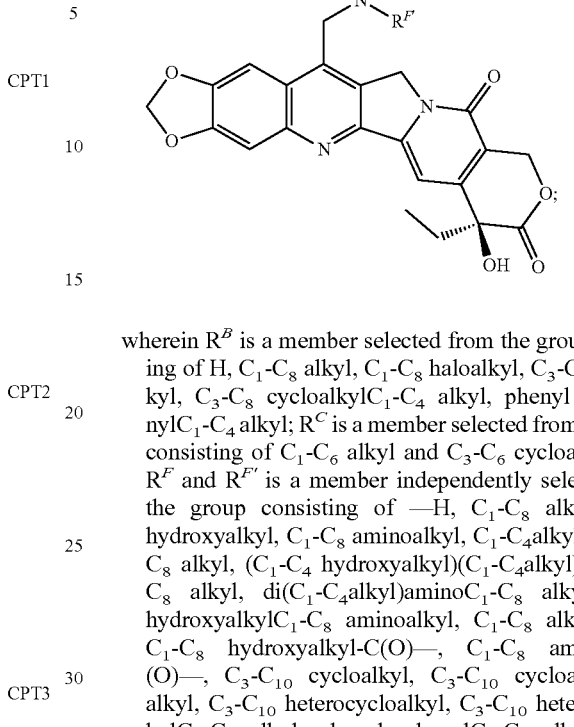

wherein $R^B$ is a member selected from the group consisting of H, $C_1$-$C_8$ alkyl, $C_1$-$C_8$ haloalkyl, $C_3$-$C_8$ cycloalkyl, $C_3$-$C_8$ cycloalkyl$C_1$-$C_4$ alkyl, phenyl and phenyl$C_1$-$C_4$ alkyl; $R^C$ is a member selected from the group consisting of $C_1$-$C_6$ alkyl and $C_3$-$C_6$ cycloalkyl; each $R^F$ and $R^{F'}$ is a member independently selected from the group consisting of —H, $C_1$-$C_8$ alkyl, $C_1$-$C_8$ hydroxyalkyl, $C_1$-$C_8$ aminoalkyl, $C_1$-$C_4$alkylamino$C_1$-$C_8$ alkyl, ($C_1$-$C_4$ hydroxyalkyl)($C_1$-$C_4$alkyl)amino$C_1$-$C_8$ alkyl, di($C_1$-$C_4$alkyl)amino$C_1$-$C_8$ alkyl, $C_1$-$C_4$ hydroxyalkyl$C_1$-$C_8$ aminoalkyl, $C_1$-$C_8$ alkylC(O)—, $C_1$-$C_8$ hydroxyalkyl-C(O)—, $C_1$-$C_8$ aminoalkylC(O)—, $C_3$-$C_{10}$ cycloalkyl, $C_3$-$C_{10}$ cycloalkyl$C_1$-$C_4$ alkyl, $C_3$-$C_{10}$ heterocycloalkyl, $C_3$-$C_{10}$ heterocycloalkyl$C_1$-$C_4$ alkyl, phenyl, phenyl$C_1$-$C_4$ alkyl, diphenyl$C_1$-$C_4$ alkyl, heteroaryl and heteroaryl$C_1$-$C_4$ alkyl, or $R^F$ and $R^{F'}$ are combined with the nitrogen atom to which each is attached to form a 5-, 6- or 7-membered ring having 0 to 3 substituents selected from halogen, $C_1$-$C_4$ alkyl, —OH, —O$C_1$-$C_4$ alkyl, —$NH_2$, NH$C_1$-$C_4$ alkyl and N($C_1$-$C_4$ alkyl)$_2$; and wherein cycloalkyl, heterocycloalkyl, phenyl and heteroaryl moieties of $R^B$, $R^C$, $R^F$ and $R^{F'}$ are substituted with from 0 to 3 substituents selected from halogen, $C_1$-$C_4$ alkyl, OH, O$C_1$-$C_4$ alkyl, $NH_2$, NH$C_1$-$C_4$ alkyl and N($C_1$-$C_4$ alkyl)$_2$; and wherein the cycloalkyl, heterocycloalkyl, phenyl and heteroaryl moieties of $R^B$, $R^C$, $R^F$ and $R^{F'}$ are substituted with from 0 to 3 substituents selected from the group consisting of halogen, $C_1$-$C_4$ alkyl, OH, O$C_1$-$C_4$ alkyl, $NH_2$, NH$C_1$-$C_4$ alkyl and N($C_1$-$C_4$ alkyl)$_2$; and wherein the point of attachment of D to Q is through the oxygen atom of the hydroxyl substituent of the lactone ring of CPT1, CPT2, CPT3, CPT4, CPT5, or CPT6.

28B. The Camptothecin-Linker Compound of embodiment 27B having formula (i) or (ii).

29B. The Camptothecin-Linker Compound of embodiment 27B having formula (iii) or (iv).

30B. The Camptothecin-Linker Compound of embodiment 27B having formula (v) or (vi).

31B. The Camptothecin-Linker Compound of embodiment 27B having formula (i).

32B. The Camptothecin-Linker Compound of embodiment 27B having formula (ii).

33B. The Camptothecin-Linker Compound of any one of embodiments 27B to 31B, wherein D is CPT2.

34B. The Camptothecin-Linker Compound of any one of embodiments 27B to 31B, wherein D is CPT3.

35B. The Camptothecin-Linker Compound of any one of embodiments 27B to 31B, wherein D is selected from the group consisting of CPT1, CPT4, CPT5 and CPT6.

36B. The Camptothecin-Linker Compound of any one of embodiments 27B to 31B, wherein Z' is a maleimido group.

37B. The Camptothecin-Linker Compound of any one of embodiments 27B to 31B, wherein Z'-A- is maleimidopropionyl, mDPR or maleimidopropionyl-β-alanyl.

38B. The Camptothecin-Linker Compound of any one of embodiments 27B and 29B to 31B, wherein S* is a PEG group.

39B. The Camptothecin-Linker Compound of embodiment 27B, wherein RL has the formula:

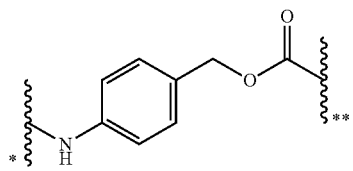 [SMILES: *Nc1ccc(COC(*)=O)cc1]

wherein the wavy line marked with ** indicates the site of attachment to D; and the wavy line marked with * indicates the point of attachment to another linker component of Q.

40B. The Camptothecin-Linker Compound of embodiment 39B, wherein Z'-A- comprises a maleimido-alkanoic acid moiety, or a maleimido and triazole moieties, or a mDPR moiety.

41B. The Camptothecin-Linker Compound of embodiment 39B, wherein Z'-A- comprises a maleimido-alkanoyl-β-alanyl component.

42B. The Camptothecin-Linker Compound of embodiment 39B, wherein Z'-A- comprises a mDPR moiety.

43B. The Camptothecin-Linker Compound of embodiment 39B, wherein Z'-A- comprises a maleimidopropionyl moiety and wherein a Partitioning Agent (S*) is present.

44B. The Camptothecin-Linker Compound of embodiment 39B having the formula:

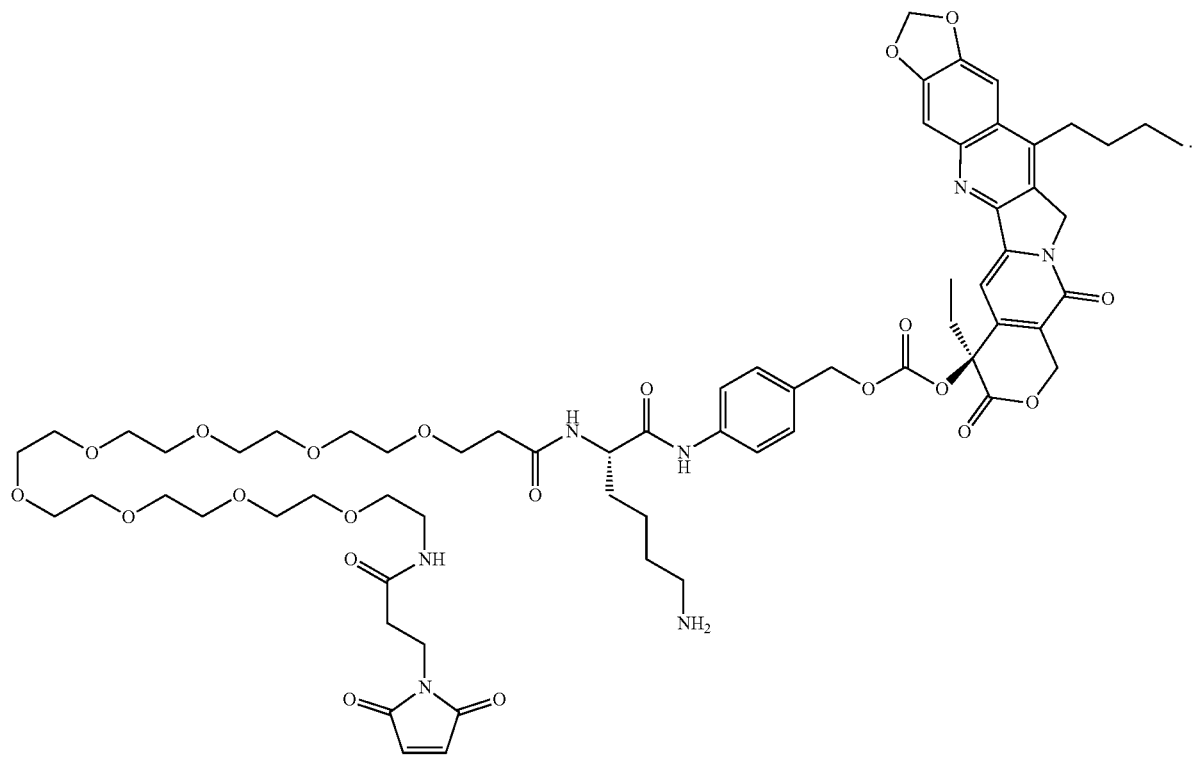 [SMILES: CCCCc1c2c(nc3cc4c(cc13)OCO4)-c1cc3c(c(=O)n1C2)COC(=O)[C@@]3(CC)OC(=O)OCc1ccc(NC(=O)[C@H](CCCCN)NC(=O)CCOCCOCCOCCOCCOCCOCCOCCOCCNC(=O)CCN2C(=O)C=CC2=O)cc1]

45B. The Camptothecin-Linker Compound of embodiment 39B having the formula:

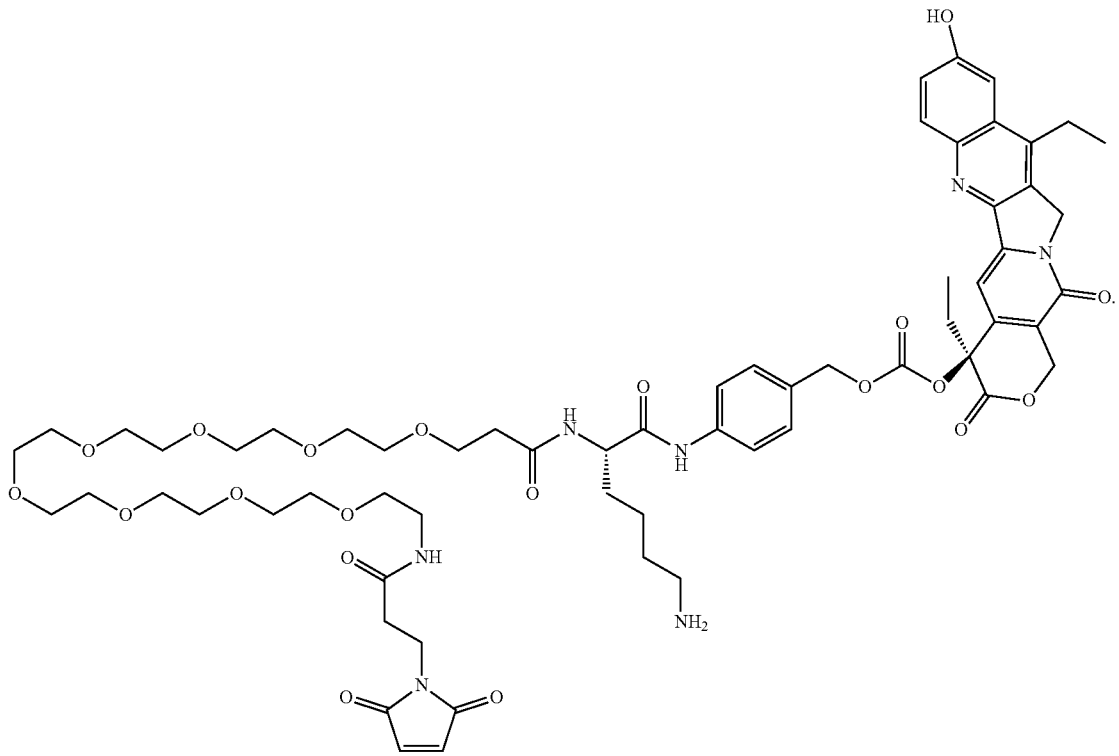 [SMILES: CCc1c2c(nc3ccc(O)cc13)-c1cc3c(c(=O)n1C2)COC(=O)[C@@]3(CC)OC(=O)OCc1ccc(NC(=O)[C@H](CCCCN)NC(=O)CCOCCOCCOCCOCCOCCOCCOCCOCCNC(=O)CCN2C(=O)C=CC2=O)cc1]

46B. A method of treating cancer in a subject in need thereof, said method comprising administering to the subject a Camptothecin Conjugate of any one of embodiments 1B to 29B.

47B. The method of embodiment 46B, wherein said cancer is selected from the group consisting of lymphomas, leukemias, and solid tumors.

48B. The method of embodiment 46B, wherein said cancer is a lymphoma or a leukemia.

49B. The method of any one of embodiments 46B to 48B, further comprising administering an additional therapeutic agent.

50B. The method of embodiment 39B, wherein said additional therapeutic agent is one or more chemotherapeutic agents or radiation therapy.

51B. A method of treating an autoimmune disease in a subject in need thereof, said method comprising administering to the subject a Camptothecin Conjugate of any one of embodiments 1B to 26B.

52B. The method of embodiment 51B, wherein said autoimmune disease is selected from the group consisting of Th2 lymphocyte related disorders, Th1 lymphocyte-related disorders, and activated B lymphocyte-related disorders.

53B. A method of preparing a Camptothecin Conjugate of any one of embodiments 1B to 26B, said method comprising reacting an antibody having a free thiol with a Camptothecin-Linker Compound of any one of embodiments 27B to 43B.

54B. A kit comprising a Camptothecin Conjugate of any one of embodiments 1B to 26B.

55B. The kit of embodiment 54B, further comprising an additional therapeutic agent.

1C. A Camptothecin Conjugate having the formula of

L-(Q-D)$_p$ or a salt thereof, wherein L is a Ligand Unit from a targeting agent, in particular, from an antibody that selectively binds to a cancer cell antigen; subscript p is an integer ranging from 1 to 16; Q is a Linker Unit having a formula selected from the group consisting of: -Z-A-, -Z-A-RL-, -Z-A-RL-Y-, -Z-A-S*-RL-, -Z-A-S*-RL-Y-, -Z-A-S*-W-, -Z-A-S*-W-RL-, -Z-A-B(S*)-RL-, -Z-A-B(S*)W, and -Z-A-B(S*)-W-RL- and -Z-A-B(S*)-RL-Y-, wherein Z is a Stretcher Unit; A is a bond or a Connecter Unit; B is a Parallel Connector Unit; S* is a Partitioning Agent; RL is a Releasable Linker; W is an Amino Acid Unit; Y is a Spacer Unit; and D is a Drug Unit selected from the group consisting of CPT1, CPT2, CPT3, CPT4, CPT5, CPT6 and CPT7 as follows:

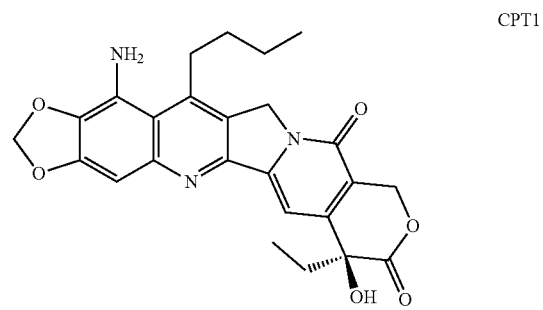

CPT1

-continued

CPT2
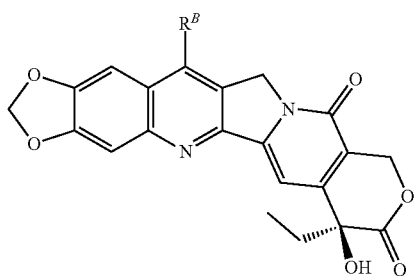

CPT3
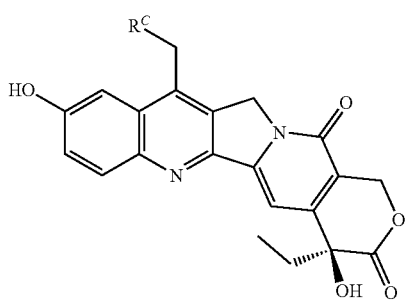

CPT4
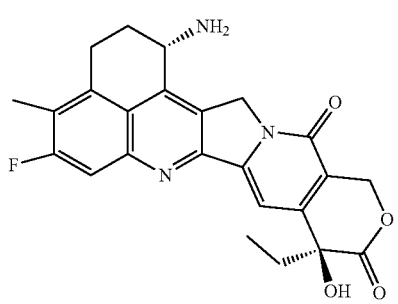

CPT5
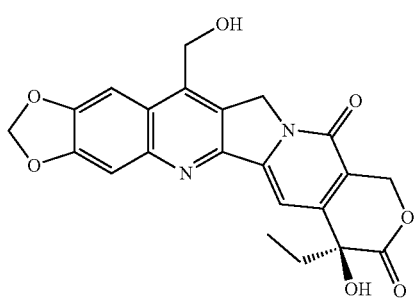

CPT6
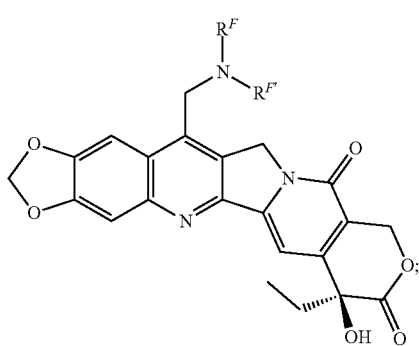

-continued

CPT7
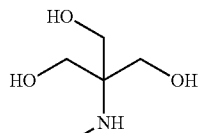
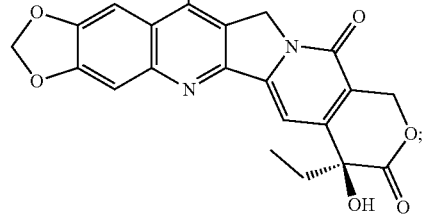

wherein $R^B$ is a member selected from the group consisting of H, $C_1$-$C_8$ alkyl, $C_1$-$C_8$ haloalkyl, $C_3$-$C_8$ cycloalkyl, ($C_3$-$C_8$cycloakyl)-$C_1$-$C_4$ alkyl-, phenyl and phenyl-$C_1$-$C_4$ alkyl-; $R^C$ is a member selected from the group consisting of $C_1$-$C_6$ alkyl and $C_3$-$C_6$ cycloalkyl; each $R^F$ and $R^{F'}$ is a member independently selected from the group consisting of —H, $C_1$-$C_8$ alkyl, $C_1$-$C_8$ hydroxyalkyl, $C_1$-$C_8$ aminoalkyl, ($C_1$-$C_4$alkylamino)-$C_1$-$C_8$ alkyl-, NA-($C_1$-$C_4$ hydroxyalkyl)($C_1$-$C_4$ alkyl)-amino-$C_1$-$C_8$ alkyl-, NA-di($C_1$-$C_4$ alkyl)amino-$C_1$-$C_8$ alkyl-, N—$C_1$-$C_4$ hydroxyalkyl-$C_1$-$C_8$ aminoalkyl-, $C_1$-$C_8$ alkylC(O)—, $C_1$-$C_8$ hydroxyalkyl-C(O)—, $C_1$-$C_8$ aminoalkylC(O)—, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl-$C_1$-$C_4$ alkyl-, heteroaryl and heteroaryl-$C_1$-$C_4$ alkyl-, or $R^F$ and $R^{F'}$ are combined with the nitrogen atom to which each is attached to form a 5-, 6- or 7-membered ring having 0 to 3 substituents selected from halogen, $C_1$-$C_4$ alkyl, —OH, —O$C_1$-$C_4$ alkyl, —NH$_2$, —NH$C_1$-$C_4$ alkyl and —N($C_1$-$C_4$ alkyl)$_2$; and wherein the cycloalkyl, heterocycloalkyl, phenyl and heteroaryl moieties of $R^B$, $R^C$, $R^F$ and $R^{F'}$ are substituted with from 0 to 3 substituents selected from the group consisting of halogen, $C_1$-$C_4$ alkyl, —OH, —O$C_1$-$C_4$ alkyl, —NH$_2$, —NH$C_1$-$C_4$ alkyl and —N($C_1$-$C_4$ alkyl)$_2$, or wherein D is a camptothecin compound of any one of 13a-13c of Table H, 14a-14a of Table I and 18a-18r of Table J; and wherein the point of covalent attachment of D is to the heteroatom of any one of the hydroxyl or amino substituents on CPT1, CPT2, CPT3, CPT4, CPT5 CPT6 or CPT7 or any one of 13a-13c of Table H, 14a-14a of Table I and 18a-18r of Table J when Q is —Z-A-RL-, -Z-A-RL-Y-, -Z-A-S*-RL-, -Z-A-B(S*)-RL-, -Z-A-S*-RL-Y- or -Z-A-B(S*)—RL-Y-, or wherein the point of covalent attachment of D is to the oxygen atom of the hydroxyl substituent on the lactone ring of CPT1, CPT2, CPT3, CPT4, CPT5 CPT6 or CPT7 or any one of 13a-13c of Table H, 14a-14a of Table I and 18a-18r of Table J, when Q is -Z-A-, -Z-A-S*-W- or -Z-A- B(S*)W, or when Q is -Z-A-S*-RL-, -Z-A-B(S*)—RL-, -Z-A-S*-W-RL-, or -Z-A-B(S*)-W-RL- in which RL is a Releasable Unit other than a Glucuronide Unit; and provided that at least one of $R^F$ and $R^{F'}$ is —H, when the point of covalent attachment is to the nitrogen atom of the amino substituent on CPT6; and provided that -Z-A- of -Z-A-RL-, -Z-A-RL-Y-, -Z-A-S*-RL-, -Z-A-B(S*)-RL-, -Z-A-S*-RL-Y- and -Z-A-B(S*)-RL-Y- is other than succinimido-caproyl-β-alanyl moiety, optionally having the succinimide ring in hydrolyzed form, when D is CPT1 having covalent attachment through the nitrogen atom of its amino substituent.

2C. The Camptothecin Conjugate of embodiment 1C, wherein Q is a Linker Unit having the formula selected from the group consisting of: -Z-A-RL-; -Z-A-RL-Y-; -Z-A-S*-RL-; -Z-A-B(S*)-RL-; -Z-A-S*-RL-Y-; and -Z-A-B(S*)-RL-Y-, wherein A is a Connector Unit and RL is a Glucuronide Unit.

3C. The Camptothecin Conjugate of embodiment 2C, wherein the point of covalent attachment of D is through the oxygen atom of the hydroxyl substituent on the lactone ring of any one of CPT1-CPT7.

4C. The Camptothecin Conjugate of embodiment 2C, wherein D is CPT1, CPT4, CPT6 or CPT7, wherein the point of covalent attachment to CPT1 is through the nitrogen atom of its amine functional group provided that -Z-A- is other than succinimido-caproyl-β-alanyl, optionally having the succinimide ring in hydrolyzed form as a succinic acid amide moiety, wherein the point of covalent attachment to CPT4 is through the nitrogen atom of its amine functional group, wherein the point of covalent attachment to CPT6 is through the nitrogen atom of its amine functional group provided that least one of $R^F$ and $R^{F'}$ is —H, and wherein the point of covalent attachment to CPT7 is through the oxygen atom of one of its primary hydroxyl functional groups.

5C. The Camptothecin Conjugate of embodiment 2C, 3C or 4C, wherein the Glucuronide Unit has the formula of:

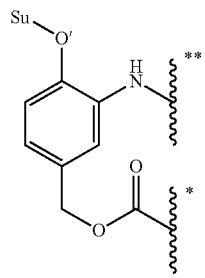

wherein Su is a hexose form of a monosaccharide; O' represents the oxygen atom of a glycosidic bond that is capable of cleavage by a glycosidase; the wavy line marked with a single asterisk (*) indicates the site of covalent attachment to the nitrogen atom of the amino substituent on CPT1, CPT4 or CPT6 in which at least one of $R^F$ and $R^{F'}$ is —H, or to a Spacer Unit (Y), or indicates the site of covalent attachment to the oxygen atom of the hydroxyl substituent on the lactone ring of any one of CPT1-CPT7; and the wavy line marked with a double asterisk (**) indicates the site of covalent attachment to the remainder of Q, in particular the Glucuronide Unit has the formula of:

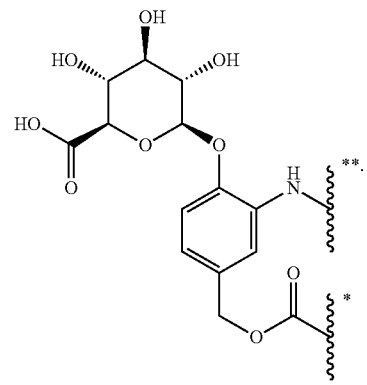 [SMILES: *Nc1cc(COC(*)=O)ccc1O[C@H]1O[C@@H](C(=O)O)[C@H](O)[C@@H](O)[C@@H]1O]

6C. The Camptothecin Conjugate of embodiment 5C, wherein Q is a Linker Unit having the formula of -Z-A-RL-Y-, -Z-A-S*-RL-Y- or -Z-A-B(S*)-RL-Y-; and Spacer Unit (Y) has the formula of:

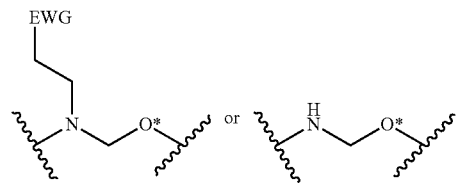

wherein EWG is an electron-withdrawing group; O* represent the oxygen atom from a hydroxy substituent of D; the wavy line adjacent to the nitrogen atom indicates the site of covalent attachment to the carbonyl carbon atom of the Glucuronide Unit; and the wavy line adjacent to O* indicates the site of covalent attachment to the remainder of D, or the Spacer Unit (Y) has the formula of:

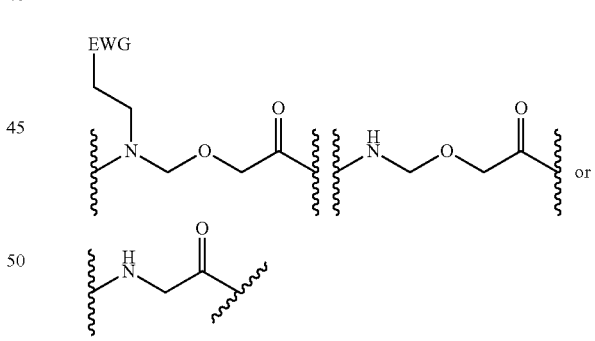

when D is CPT1, CPT4 or CPT6 in which each of $R^F$ and $R^{F'}$ is —H; and wherein EWG is an electron-withdrawing group; the wavy line adjacent to the nitrogen atom indicates the site of covalent attachment to the carbonyl carbon atom of the Glucuronide Unit; and the wavy line adjacent to the carbonyl carbon atom indicates the site of covalent attachment to the nitrogen atom of the amino substituent of CPT1, CPT4 or CPT6.

7C. The Camptothecin Conjugate of embodiment 5C, wherein -Z-A- is comprised of a succinimido-alkanoyl moiety or succinimido and triazolyl moieties, each optionally having the succinimide ring in hydrolyzed form as a succinic acid amide moiety, wherein the triazole moiety is optionally formed from 1,3-dipolar cycloaddition of an azido substituent from a chemically modified targeting agent to an alkynyl moiety of a Drug Linker compound, wherein the targeting agent is the precursor to the Ligand Unit of the Conjugate, or -Z-A- is comprised of a succinic acid amide moiety derivable from an mDPR moiety of a Camptothecin-Linker Compound or is comprised of a succinimido-propionyl moiety, optionally having it succinimide ring in hydrolyzed form, provided that D has covalent attachment through the nitrogen atom of its amino substituent and -Z-A- is comprised of succinimido and triazolyl moieties, optionally having the succinimide ring in hydrolyzed form as a succinic acid amide moiety, or is comprised of the succinic acid amide moiety derivable from the mDPR moiety when D is CPT1, or provided that D has covalent attachment to the oxygen atom of the hydroxyl substituent on its lactone ring and -Z-A- is comprised of a succinimido-alkanoyl-β-alanyl moiety, optionally having the succinimide ring in hydrolyzed form as a succinic acid amide moiety when D is CPT1.

8C. The Camptothecin Conjugate of embodiment 7C, wherein Q has the formula of:

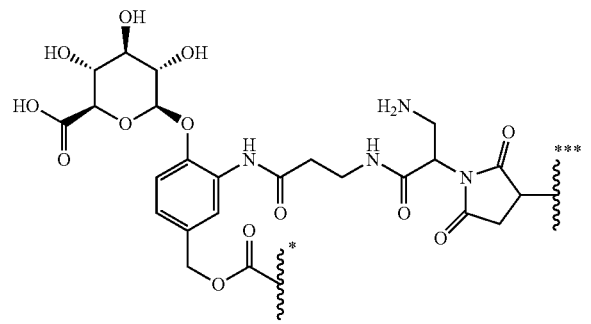 [SMILES: *C(=O)OCc1ccc(O[C@H]2O[C@@H](C(=O)O)[C@H](O)[C@@H](O)[C@@H]2O)c(NC(=O)CCNC(=O)C(CN)N2C(=O)CC(*)C2=O)c1]

or a salt thereof, in which -Z-A- is a succinimido-alkanoyl-β-alanyl moiety, preferably having its succinimide ring is in hydrolyzed form as a succinic acid amide moiety, wherein the succinimide ring is derivable from the mDPR moiety of a Camptothecin-Linker Compound; the wavy line marked with a single asterisk (*) indicates the site of covalent attachment to the oxygen atom of the hydroxyl functional group substituting the lactone ring of any one of CPT1-CPT7, to the nitrogen atom of the amine functional group of CPT1, CPT4 or CPT6 in which $R^F$ and $R^{F'}$ is —H, or to a Spacer Unit; and the wavy line marked with a triple asterisk (***) indicates the point of covalent attachment to a sulfur atom of L, or Q has the formula of:

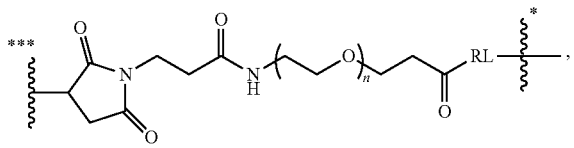

optionally having the succinimide ring in hydrolyzed form as a succinic acid amide moiety, when Q is -Z-A-S*-RL wherein subscript n is an integer ranging from 1 to 50, preferably 4; the wavy line marked with a single asterisk (*) indicates the site of covalent attachment to the heteroatom of a hydroxy or amine functional group of any one of CPT1-CPT7, or to a Spacer Unit (Y); and the wavy line marked with a triple asterisk (***) indicates the point of covalent attachment to a sulfur atom of L.

9C. The Camptothecin Conjugate of embodiment 6C, wherein -Q-D has the structure of:

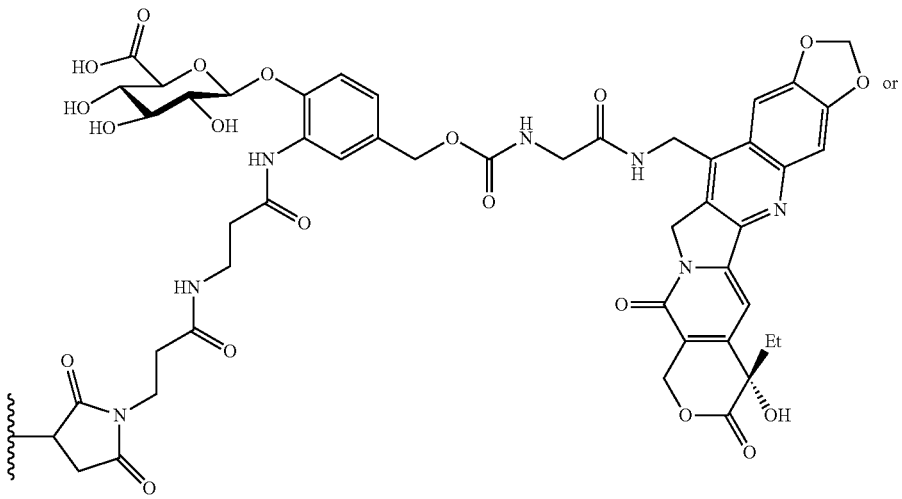

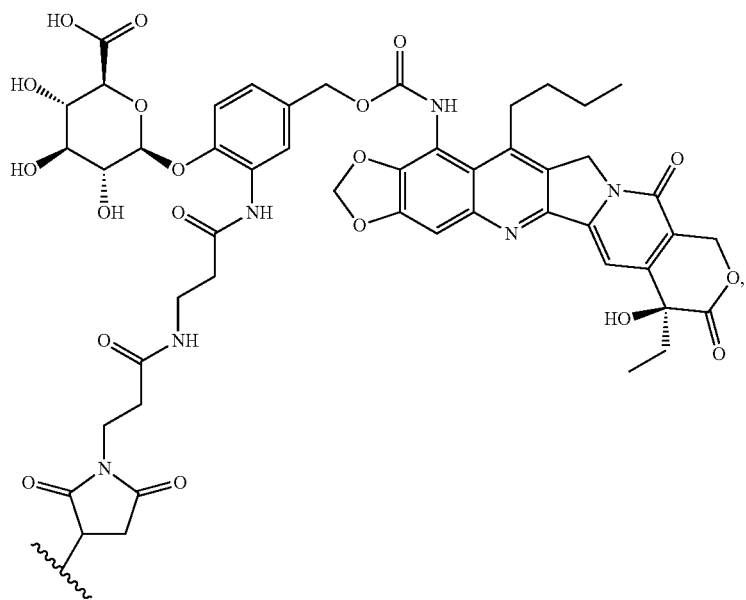
or a salt thereof, optionally having the succinimide ring in hydrolyzed form as a succinic acid amide moiety, wherein the wavy line indicates the site of covalent attachment of the succinimide ring to a sulfur atom of the Ligand Unit or
-Q-D has the structure of:
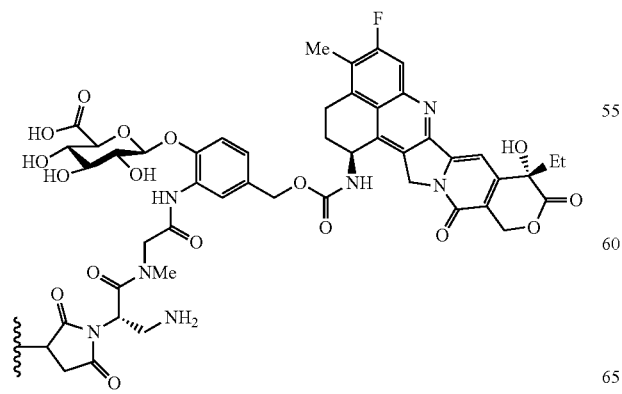

or a salt thereof, or -Q-D has the structure of:

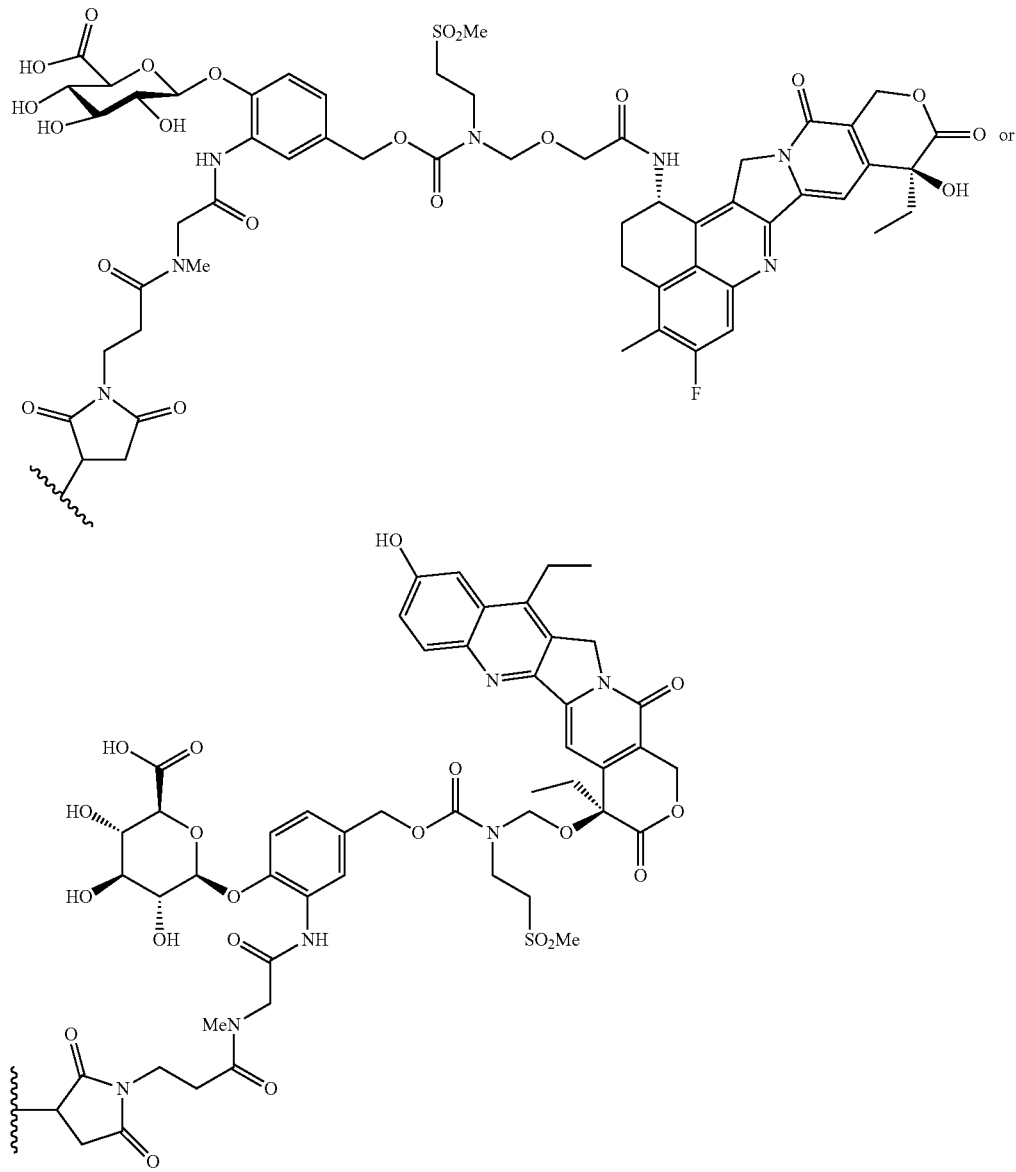

or a salt thereof, and wherein the wavy line indicates the site of covalent attachment of the succinimide ring to a sulfur atom of the Ligand Unit wherein the succinimide ring is in hydrolyzed form as a succinic acid amide moiety.

10C. The Camptothecin Conjugate of embodiment 1C, wherein Q is a Linker Unit having a formula selected from the group consisting of: -Z-A-; -Z-A-S*-W- and -Z-A-B(S*)W, wherein A is a Connector Unit, or Q is a Linker Unit having a formula selected from the group consisting of: -Z-A-RL-, -Z-A-S*-RL-; -Z-A-B(S*)-RL-, -Z-A-S*-W-RL-, and -Z-A-B(S*)-W-RL-, wherein A is a Connector Unit and RL is a Releasable linker other than a Glucuronide Unit.

11C. The Camptothecin Conjugate of embodiment 10C, wherein Q is a Linker Unit having the formula selected from the group consisting of -Z-A-RL-, -Z-A-S*—RL- and -Z-A-S*-W-RL-, wherein RL has the formula:

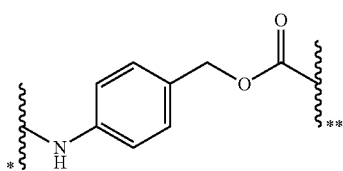 [SMILES: *Nc1ccc(COC(*)=O)cc1]

wherein the wavy line marked with a double asterisk (**) indicates the site of covalent attachment to D; and the wavy line marked with a single asterisk (*) indicates the point of covalent attachment to A, S* or W.

12C. The Camptothecin Conjugate of embodiment 10C or 11C, wherein -Q-D has the formula of -Z-A-S*-W-RL-D, wherein D is CPT1, CPT4 or CPT6 in which each of $R^F$ and $R^{F'}$ is —H, each having covalent attachment to the nitrogen atom of the amine functional group; and W is an Amino Acid Unit selected from the group consisting of N-methyl-glycine (sarcosine), N-methyl-alanine, N-methyl-3-alanine, valine, N-methyl-valine, or D is any one of CPT1-CPT7 having covalent attachment to the oxygen atom of the hydroxyl substituent on the lactone ring; and W is an Amino Acid Unit selected from the group consisting glutamic acid or lysine.

13C. The Camptothecin Conjugate of embodiment 12C, wherein -Z-A- is comprised of a succinimido-alkanoyl moiety or succinimido and triazole moieties, each optionally having the succinimide ring in hydrolyzed form as a succinic acid amide moiety, or a succinic acid amide moiety derivable from mDPR of a Camptothecin-Linker Compound, or wherein -Z-A- has the formula of:

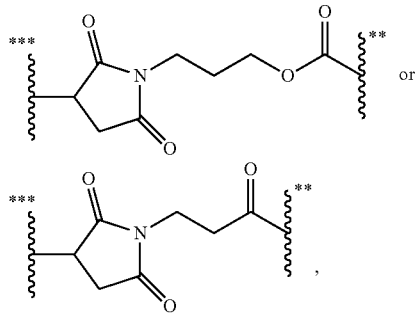

or

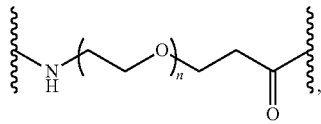

, optionally having the succinimide ring in hydrolyzed form as a succinic acid amide moiety, wherein the wavy line marked with a double asterisk (**) indicates the site of covalent attachment to S*; and the wavy line marked with a triple asterisk (***) indicates the point of covalent attachment to a sulfur atom of L.

14C. The Camptothecin Conjugate of embodiment 11C, wherein Q is a Linker Unit having the formula selected from the group consisting of -Z-A-S*-RL- and —Z-A-S*-W-RL-, wherein S* has the formula of:

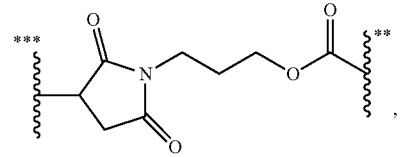 [SMILES: *C(=O)OCCCN1C(=O)CC(*)C1=O]

wherein subscript n is an integer ranging from 2 to 36, the wavy line adjacent to the nitrogen atom indicates the site of covalent attachment to a carbonyl carbon atom of A, and the wavy adjacent to the carbonyl carbon atom indicates the site of covalent attachment to the nitrogen atom of the amine functional group of RL of -Z-A-S*-RL- or W of -Z-A-S*-W-RL-, in particular, -Z A- in either formula of Q has the formula of:

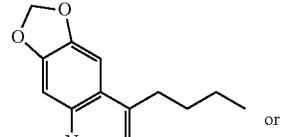

, wherein the wavy line marked with a double asterisk (**) indicates the site of covalent attachment to the nitrogen atom of the amine functional group of S*; and the wavy line marked with a triple asterisk (***) indicates the point of covalent attachment to a sulfur atom of L.

15C. The Camptothecin Conjugate of embodiment 11C, wherein Q is a Linker Unit of formula -Z-A-S*-W- or -Z-A-S—W-RL-, wherein -Z-A-S*-W- in either formula has the formula of:

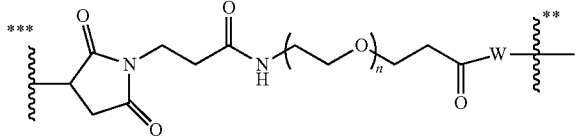

optionally having the succinimide ring in hydrolyzed form as a succinic acid amide moiety, wherein subscript n is an integer ranging from 2 to 10, preferably ranging from 2 to 4; the wavy line marked with a double asterisk () indicates the site of covalent attachment to D or RL; and the wavy line marked with a triple asterisk (*) indicates the point of covalent attachment to a sulfur atom of L.

16C. The Camptothecin Conjugate of embodiment 10C, wherein -Q-D has the structure of:

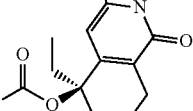

or

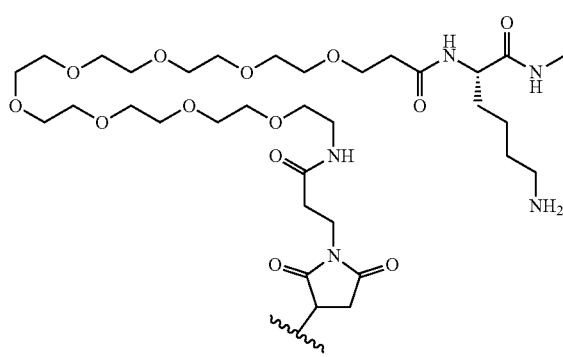

-continued

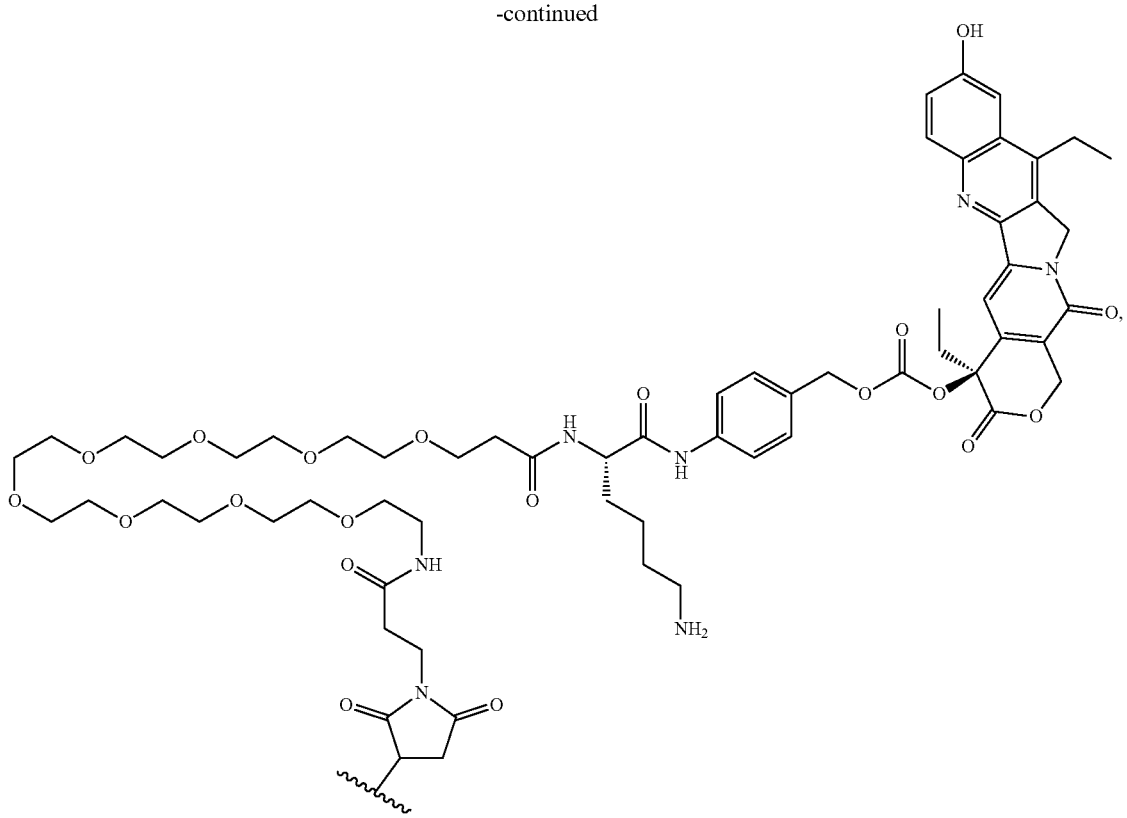

or salt thereof, wherein the wavy line indicates the point of covalent attachment of the succinimide ring, optionally in hydrolyzed form as a succinic acid amide moiety, to a sulfur atom of the Ligand Unit.

17C. A Camptothecin-Linker compound having a formula selected from the group consisting of:

Z'-A-RL-D;                    (i)

Z'-A-RL-Y-D;                  (ii)

Z'-A-S*-RL-D;                 (iii)

Z'-A-S*-RL-Y-D;               (iv)

Z'-A-B(S*)-RL-D;              (v)

Z'-A-B(S*)-RL-Y-D;            (vi)

Z'-A-D                        (vii)

Z'-A-S*-W-D                   (viii)

Z'-A-B(S*)-W-D                (ix)

Z'-A-S*-W-RL-D; and           (x)

Z'-A-B(S*)-W-RL-D             (xi)

wherein Z' is a Stretcher Unit precursor; A is a bond or a Connecter Unit; B is a Parallel Connector Unit; S* is a Partitioning Agent; RL is a Releasable Linker; Y is a Spacer Unit; and D is a Camptothecin compound selected from the group consisting of CPT1, CPT2, CPT3, CPT4, CPT5, CPT6 and CPT7 as follows:

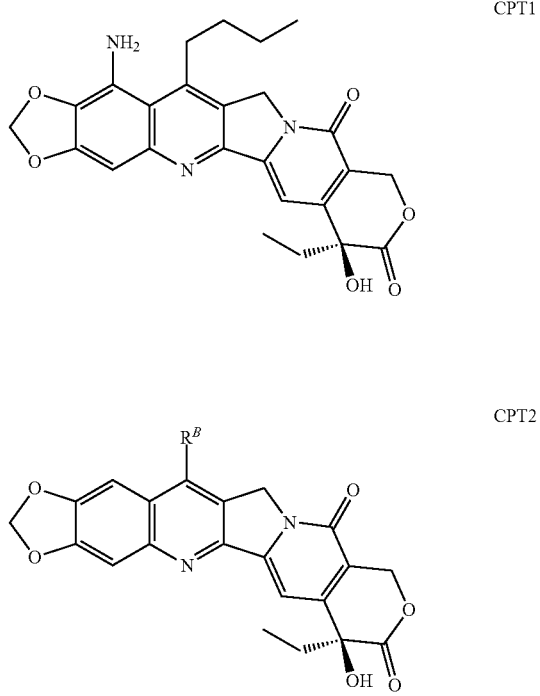

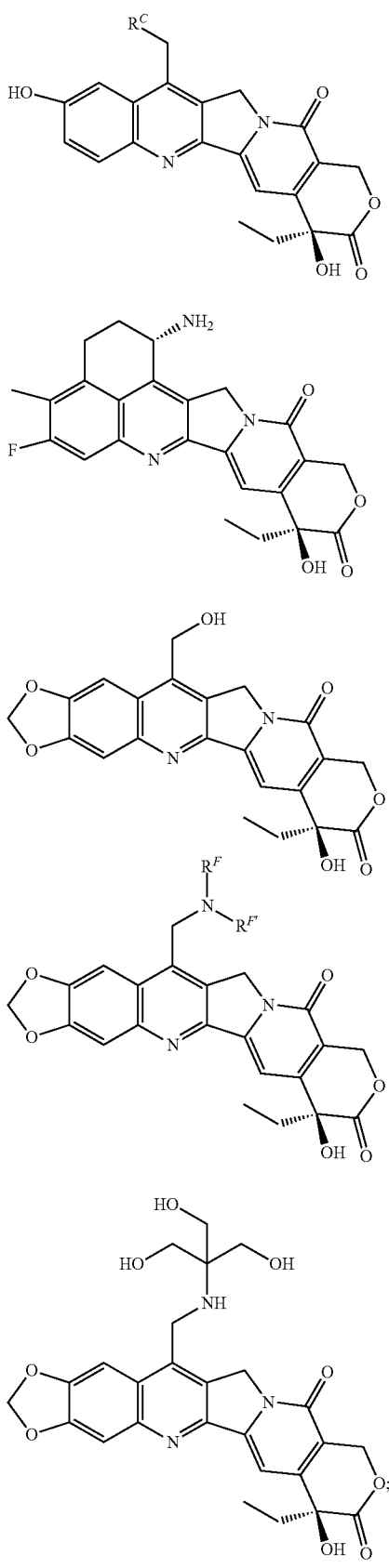

$R^B$ is a moiety selected from the group consisting of —H, $C_1$-$C_8$ alkyl, $C_1$-$C_8$ haloalkyl, $C_3$-$C_8$ cycloalkyl, ($C_3$-$C_8$ cycloalkyl)-$C_1$-$C_4$ alkyl-, phenyl and phenyl-$C_1$-$C_4$ alkyl-; $R^C$ is a moiety selected from the group consisting of $C_1$-$C_6$ alkyl and $C_3$-$C_6$ cycloalkyl; each $R^F$ and $R^{F'}$ is a member independently selected from the group consisting of —H, $C_1$-$C_8$ alkyl, $C_1$-$C_8$ hydroxyalkyl, $C_1$-$C_8$ aminoalkyl, ($C_1$-$C_4$alkylamino)-$C_1$-$C_8$ alkyl-, N,N—($C_1$-$C_4$ hydroxyalkyl)($C_1$-$C_4$ alkyl)-amino-$C_1$-$C_8$ alkyl-, N,N-di($C_1$-$C_4$ alkyl)amino-$C_1$-$C_8$ alkyl-, N—$C_1$-$C_4$ hydroxyalkyl-$C_1$-$C_8$ aminoalkyl-, $C_1$-$C_8$ alkylC(O)—, $C_1$-$C_8$ hydroxyalkyl-C(O)—, $C_1$-$C_8$ aminoalkylC(O)—, $C_3$-$C_{10}$ cycloalkyl, ($C_3$-$C_{10}$ cycloalkyl)-$C_1$-$C_4$ alkyl-, $C_3$-$C_{10}$ heterocycloalkyl, ($C_3$-$C_{10}$ heterocycloalkyl)-$C_1$-$C_4$ alkyl-, phenyl, phenyl-$C_1$-$C_4$ alkyl-, diphenyl-$C_1$-$C_4$ alkyl-, heteroaryl and heteroaryl-$C_1$-$C_4$ alkyl-, or $R^F$ and $R^{F'}$ are combined with the nitrogen atom to which each is attached to form a 5-, 6- or 7-membered ring having 0 to 3 substituents selected from halogen, $C_1$-$C_4$ alkyl, —OH, —O$C_1$-$C_4$ alkyl, —$NH_2$, —NH$C_1$-$C_4$ alkyl and —N($C_1$-$C_4$ alkyl)$_2$; and wherein the cycloalkyl, heterocycloalkyl, phenyl and heteroaryl moieties of $R^B$, $R^C$, $R^F$ and $R^{F'}$ are substituted with from 0 to 3 substituents selected from the group consisting of halogen, $C_1$-$C_4$ alkyl, —OH, —O$C_1$-$C_4$ alkyl, —$NH_2$, —NH$C_1$-$C_4$ alkyl and —N($C_1$-$C_4$ alkyl)$_2$; and wherein the point of covalent attachment of D is to the heteroatom of any one of the hydroxyl or amino substituents on any one of CPT1-CPT7 when the Camptothecin-Linker compound is of formula (i), formula (ii), formula (iii), formula (iv), formula (v), or formula (vi), or wherein the point of covalent attachment of D is to the oxygen atom of the hydroxyl substituent on the lactone ring of any one of CPT1-CPT7 when the Camptothecin-Linker compound is of formula (vii), formula (viii) or formula (ix), or when the Camptothecin-Linker compound is of formula (iii), formula (iv), formula (x), or formula (xi) in which RL is a Releasable Unit other than a Glucuronide Unit; and provided that at least one of $R^F$ and $R^{F'}$ is —H, when the point of covalent attachment is to the nitrogen atom of the amino substituent on CPT6; and provided that Z'-A- of the Camptothecin-Linker compound of formula (i), formula (ii), formula (iii), formula (iv), formula (v), and formula (vi) is other than maleimido-caproyl-β-alanyl moiety when D is CPT1 having covalent attachment through the nitrogen atom of its amino substituent.

18C. The Camptothecin-Linker compound of embodiment 17C having the formula selected from the group consisting of formula (i), formula (ii); formula (iii), formula (iv), formula (v) and formula (vi), wherein A is a Connector Unit; and RL is a Glucuronide Unit, in particular, having the structure of:

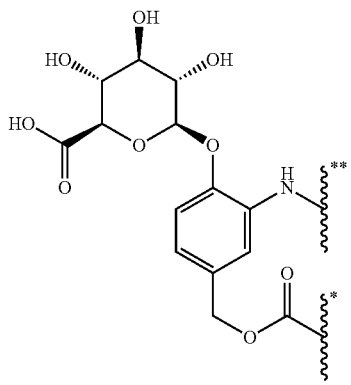 [SMILES: *Nc1cc(COC(*)=O)ccc1O[C@H]1O[C@@H](C(=O)O)[C@H](O)[C@@H](O)[C@@H]1O]

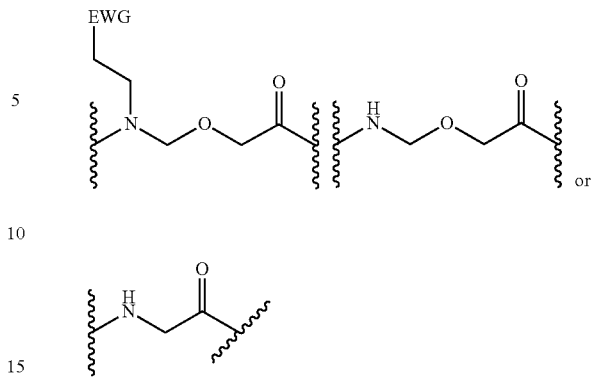

wherein the wavy line marked with a single asterisk (*) indicates the site of covalent attachment to D or to a Spacer Unit (Y); and the wavy line marked with a double asterisk (**) indicates the point of covalent attachment to A, B or S*.

19C. The Camptothecin-Linker compound of embodiment 18C, wherein the point of covalent attachment of D is through the oxygen atom of the hydroxyl substituent on the lactone ring of any one of CPT1-CPT7.

20C. The Camptothecin-Linker compound of embodiment 18C, wherein D is CPT1, CPT4, or CPT6, wherein the point of attachment of CPT1 is through the nitrogen atom of its amine functional group, provided that Z'-A- is other than maleimido-caproyl-β-alanyl, the point of attachment of CPT4 is to the nitrogen atom of its amine functional group, and the point of attachment of CPT6 is through the nitrogen atom of its amine functional group provided that least one of $R^F$ and $R^{F'}$ is —H.

21C. The Camptothecin-Linker compound of embodiment 17C having formula (iii), formula (iv), formula (v) and formula (vi), wherein S* is a PEG group.

22C. The Camptothecin-Linker compound of embodiment 18C having formula (ii), formula (iv) or formula (vi), wherein D is any one of CPT1-CPT7; and Spacer Unit (Y) has the formula of:

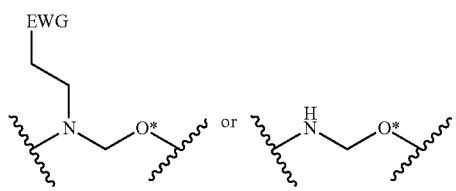

wherein EWG is an electron-withdrawing group; O* represent the oxygen atom from a hydroxy functional group of D; the wavy line adjacent to the nitrogen atom indicates the site of covalent attachment to the carbonyl carbon atom of the Glucuronide Unit; and the wavy line adjacent to O* indicates the site of covalent attachment to the remainder of D, or D is selected from the group consisting of CPT1, CPT4 and CPT6 in which each of $R^F$ and $R^{F'}$ is —H; and Spacer Unit (Y) has the formula of:

wherein EWG is an electron-withdrawing group; the wavy line adjacent to the nitrogen atom indicates the site of covalent attachment to the carbonyl carbon atom of the Glucuronide Unit; and the wavy line adjacent to the carbonyl carbon atom indicates the site of covalent attachment to the nitrogen atom of the amine functional group of CPT1, CPT4 or CPT6 in which each of $R^F$ and $R^{F'}$ is —H.

23C. The Camptothecin-Linker compound of any one of embodiments 17C-22C, wherein A is comprised of an alkynyl moiety capable of undergoing a 1,3-dipolar cycloaddition with an azido substituent from a chemically modified targeting agent that is the precursor to a Ligand Unit of a Camptothecin Conjugate so as to provide the Conjugate having a Connector Unit comprised of a triazolyl moiety.

23C. The Camptothecin-Linker Compound of any one of embodiments 17C-22C, wherein Z'-A- is comprised of a maleimido-alkanoyl moiety or mDPR, the basic nitrogen atom of which is optionally protonated or protected by an acid-labile protecting group, provided that Z'-A- is comprised of mDPR when D is CPT1 having covalent attachment through the nitrogen atom of its amino substituent, in particular Z'-A- is comprised of mDPR or a maleimido-alkanoyl-β-alanyl moiety provided that D has covalent attachment to the oxygen atom of the hydroxyl substituent on its lactone ring when D is CPT1.

24C. The Camptothecin-Linker Compound of embodiment 17C having formula (vii), formula (viii) or formula (ix), wherein A is a Connector Unit, or having formula (i), formula (iii), formula (x) or formula (xi), wherein A is a Connector Unit and RL is a Releasable linker other than a Glucuronide Unit.

25C. The Camptothecin-Linker Compound of embodiment 24C having formula (i), formula (iii) or formula (x), wherein RL has the formula:

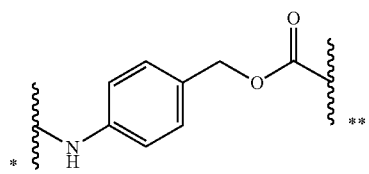 [SMILES: *Nc1ccc(COC(*)=O)cc1]

wherein the wavy line marked with a double asterisk (**) indicates the site of covalent attachment to D; and the wavy line marked with a single asterisk (*) indicates the point of covalent attachment to A, S* or W.

26C. The Camptothecin-Linker Compound of embodiment 25C having formula (x) wherein W is an Amino Acid Unit selected from the group consisting of N-methyl-glycine (sarcosine), N-methyl-alanine, N-methyl-β-alanine, valine and N-methyl-valine.

27C. The Camptothecin-Linker Compound of embodiment 24C, 25C or 26C wherein Z'-A- is comprised of a maleimido-alkanoyl moiety or mDPR, the basic nitrogen atom of which is optionally protonated or protected by an acid-labile protecting group.

28C. The Camptothecin-Linker Compound of embodiment 24C, 25C or 26C having formula (iii) or formula (x), wherein Z'-A- has a formula selected from the group consisting of:

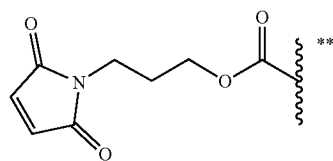

and

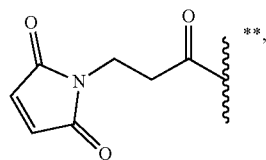

wherein the wavy line marked with a double asterisk (**) indicates the site of covalent attachment to S*.

29C. The Camptothecin-Linker Compound of embodiment 24C, 25C or 26C having formula (iii) or formula (x), wherein S* has the formula of:

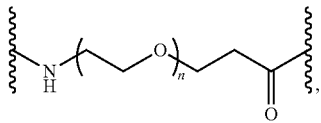

wherein subscript n is an integer ranging from 2 to 36.

30C. The Camptothecin-Linker Compound of embodiment 24C or 25C of formula (viii) or formula (x) in which Z'-A-S*-W- has the formula of:

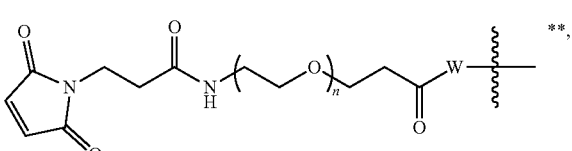

wherein subscript n is an integer ranging from 2 to 10, preferably ranging from 2 to 4; the wavy line marked with a double asterisk (**) indicates the site of covalent attachment to D or RL.

31C. The Camptothecin-Linker Compound of embodiment 17C having the structure of:

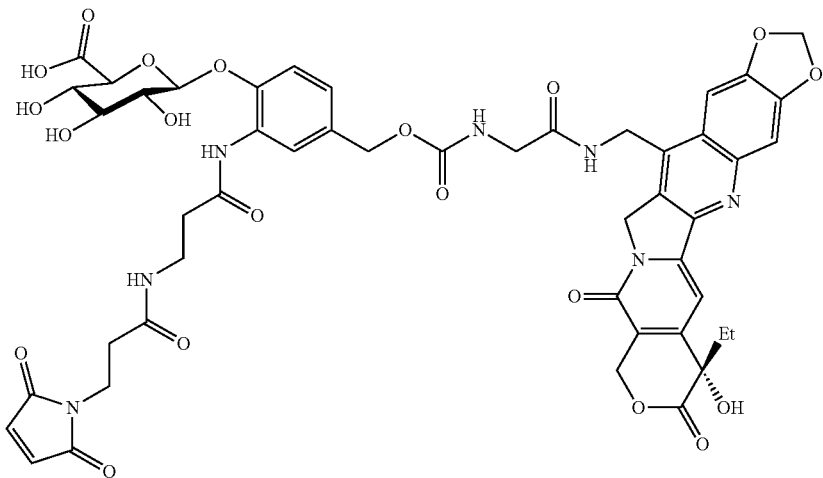

-continued
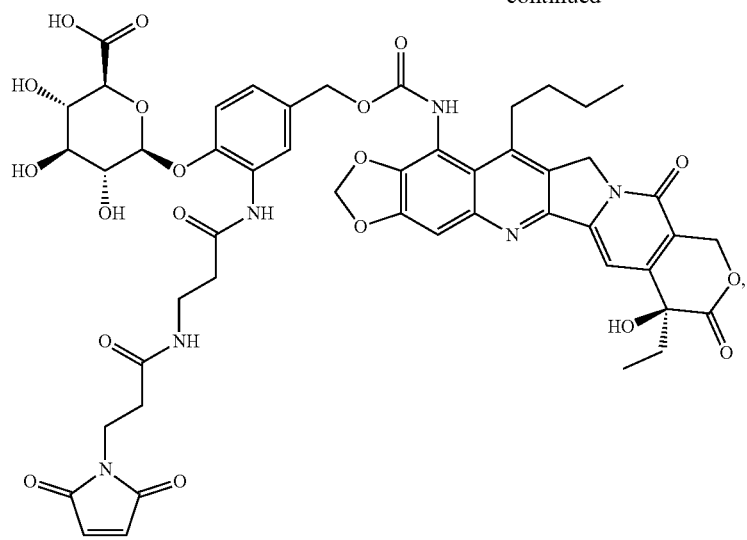
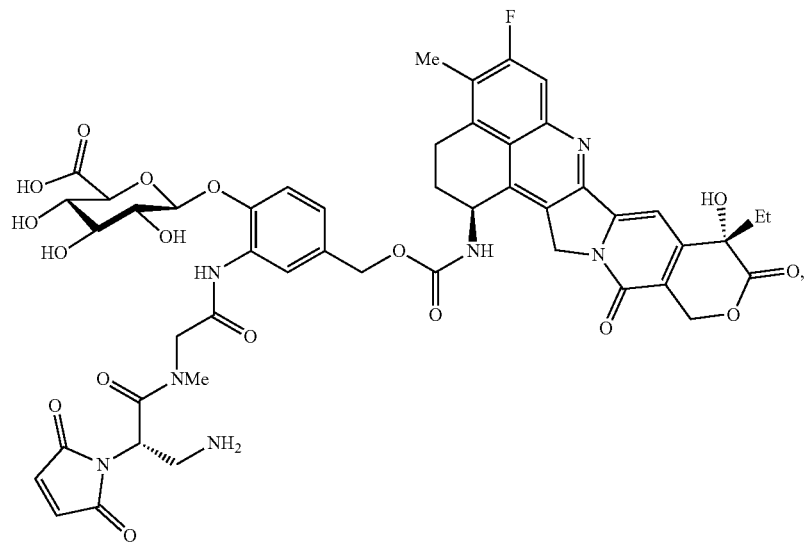
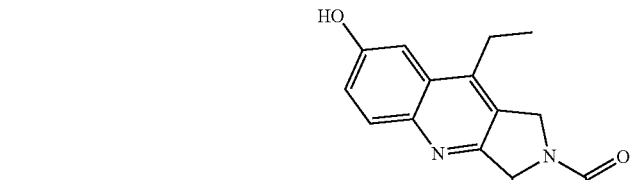
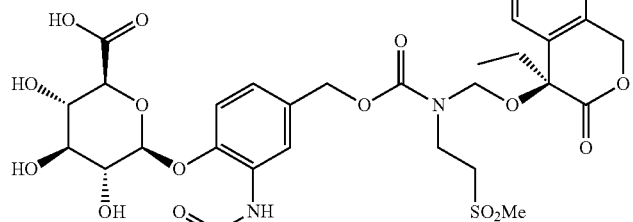
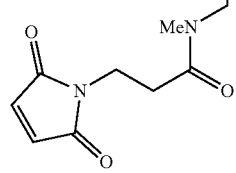

181 182
-continued
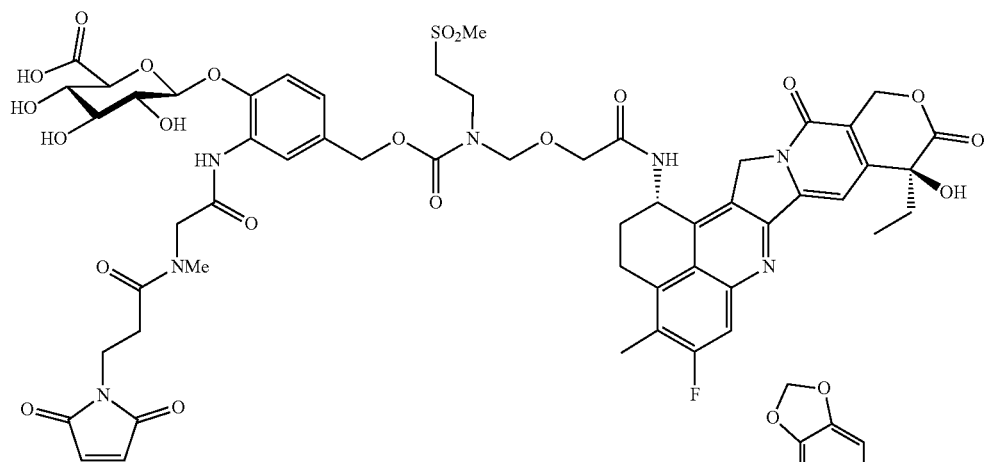
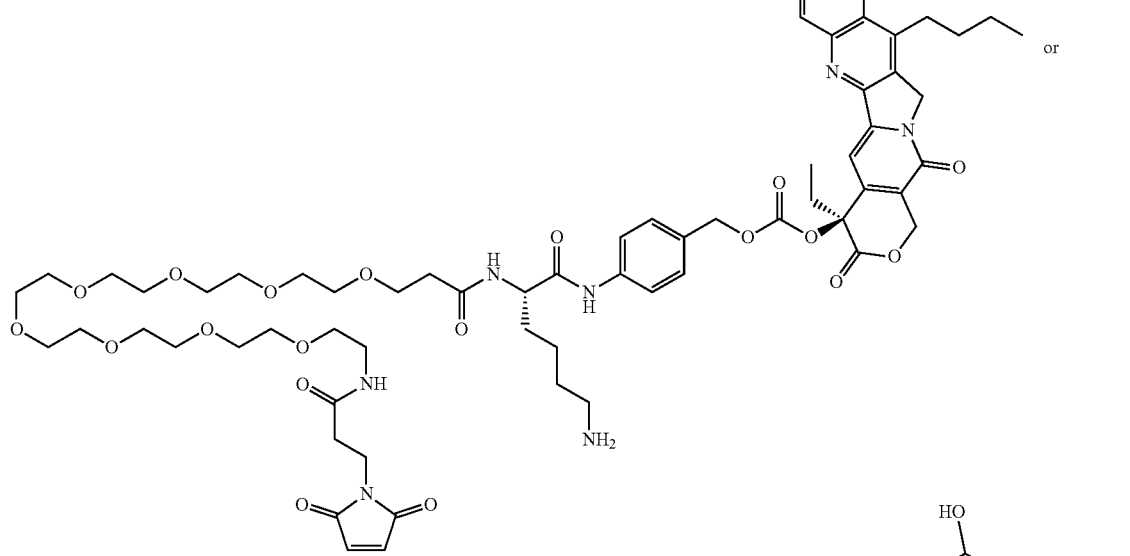
or
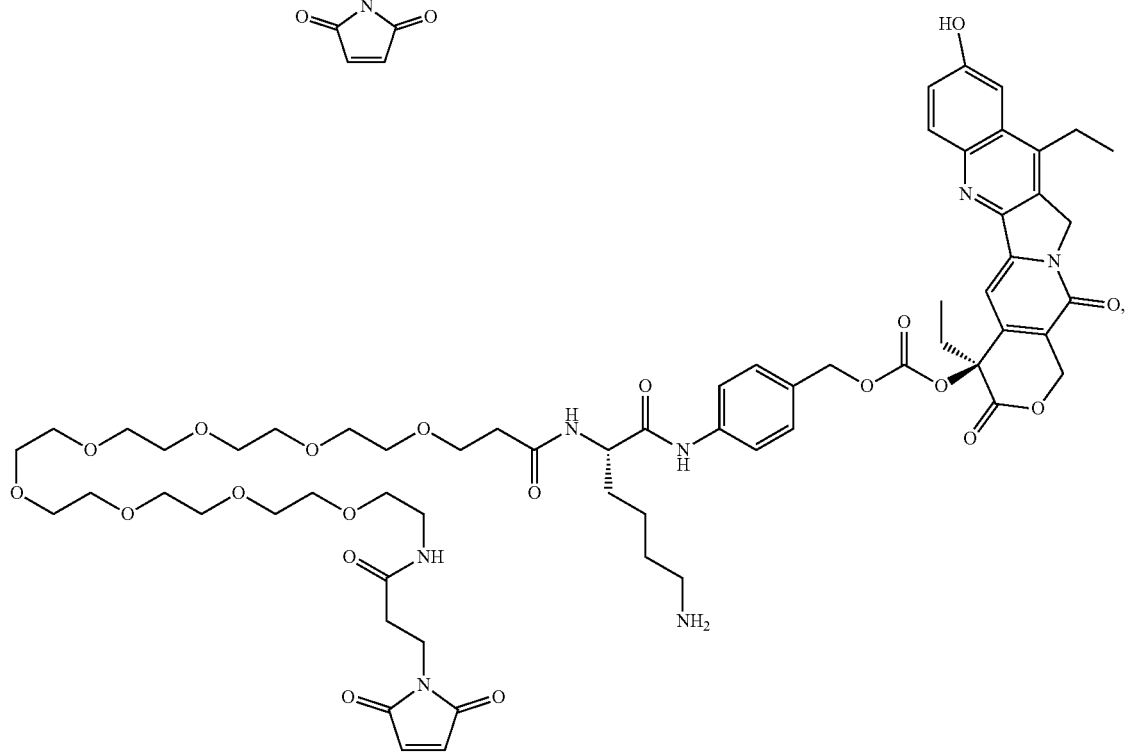

or a salt thereof.

32C. Use of a Camptothecin Conjugate in preparation of a medicament for treatment of a cancer in a subject, wherein the Camptothecin Conjugate has the formula of embodiment 1C, in particular, said cancer is selected from the group consisting of lymphomas, leukemias, and solid tumors, preferably a lymphoma or a leukemia.

33C. A pharmaceutically acceptable composition comprising a Camptothecin Conjugate of embodiment 1C and at least one pharmaceutically acceptable excipient.

34C. A composition for treatment of a cancer in a subject in need thereof, wherein the composition is comprised of an effective amount of a Camptothecin Conjugate of embodiment 1C, in particular, said cancer is selected from the group consisting of lymphomas, leukemias, and solid tumors, preferably a lymphoma or a leukemia.

35C. A method of preparing a Camptothecin Conjugate of embodiment 1, said method comprising the step of contacting a targeting agent having a functional group reactive towards Z' of a Camptothecin-Linker Compound of claim 17 thereby forming a covalent between the Ligand Unit and Stretcher Unit (Z) of the Camptothecin Conjugate, which corresponds in structure to the targeting agent and Z', respectively, in particular the targeting agent is an antibody having at least one cysteine residue in which the reactive functional group is thiol and Z' is comprised of a maleimide moiety, or the targeting agent is antibody modified to have an azide-containing residue as the reactive functional group and Z' is comprised of an alkyne functional group, wherein said azide and alkyne functional groups are capable of undergoing a 1,3-dipolar cycloaddition to form a triazole ring system.

EXAMPLES

Materials and Methods

The following materials and methods are applicable to the synthetic procedures described in this section unless indicated otherwise. All commercially available anhydrous solvents were used without further purification. Starting materials, reagents and solvents were purchased from commercial suppliers (SigmaAldrich and Fischer). Products were purified by flash column chromatography utilizing a Biotage Isolera One™ flash purification system (Charlotte, NC). UPLC-MS was performed on a Waters single quad detector mass spectrometer interfaced to a Waters Acquity™ UPLC system using UPLC methods shown in Tables A-F. Preparative HPLC was carried out on a Waters 2454 Binary Gradient Module solvent delivery system configured with a Wasters 2998 PDA detector. Products were purified Phenomenex Max-RP 4 μm Synergi™ 80 Å 250 mm reverse phase column of appropriate diameter eluting with 0.05% trifluoroacetic acid in water and 0.05% trifluoroacetic acid in acetonitrile unless otherwise specified.

TABLE A

Column - Waters Acuity UPLC BEH C18 2.1 × 50 mm, 1.7 μm, reversed-phase column, Solvent A - 0.1% aqueous formic acid, Solvent B - acetonitrile with 0.1% formic acid (Method A).

| Time (min) | Flow (mL/min) | A % | B % | Gradient |
|---|---|---|---|---|
| Initial | 0.5 | 97 | 3 | |
| 1.70 | 0.5 | 40 | 60 | Linear |
| 2.00 | 0.5 | 5 | 95 | Linear |
| 2.50 | 0.5 | 5 | 95 | Linear |

TABLE A-continued

Column - Waters Acuity UPLC BEH C18 2.1 × 50 mm, 1.7 μm, reversed-phase column, Solvent A - 0.1% aqueous formic acid, Solvent B - acetonitrile with 0.1% formic acid (Method A).

| Time (min) | Flow (mL/min) | A % | B % | Gradient |
|---|---|---|---|---|
| 2.80 | 0.5 | 97 | 3 | Linear |
| 3.00 | 0.5 | 97 | 3 | Linear |

TABLE B

Column - Waters Acuity UPLC BEH C18 2.1 × 50 mm, 1.7 μm, reversed-phase column, Solvent A - 0.1% aqueous formic acid, Solvent B - acetonitrile with 0.1% formic acid (Method B).

| Time (min) | Flow (mL/min) | A % | B % | Gradient |
|---|---|---|---|---|
| Initial | 0.6 | 97 | 3 | |
| 1.50 | 0.6 | 5 | 95 | Linear |
| 2.40 | 0.6 | 5 | 95 | Linear |
| 2.50 | 0.6 | 97 | 3 | Linear |
| 2.80 | 0.6 | 97 | 3 | Linear |

TABLE C

Column - Kinetex F5 1.7 μm 100 Å, 2.1 × 50 mm, reversed-phase column, Solvent A - 0.1% aqueous formic acid, Solvent B - acetonitrile with 0.1% formic acid (Method C).

| Time (min) | Flow (mL/min) | A % | B % | Gradient |
|---|---|---|---|---|
| Initial | 0.5 | 97 | 3 | |
| 2.50 | 0.5 | 40 | 95 | Linear |
| 3.50 | 0.5 | 5 | 95 | Linear |
| 3.75 | 0.5 | 97 | 3 | Linear |
| 4.00 | 0.5 | 97 | 3 | Linear |

TABLE D

Column - Waters CORTECS C18 1.6 μm, 2.1 × 50 mm, reversed-phase column, Solvent A - 0.1% aqueous formic acid, Solvent B - acetonitrile with 0.1% formic acid (Method D).

| Time (min) | Flow (mL/min) | A % | B % | Gradient |
|---|---|---|---|---|
| Initial | 0.6 | 97 | 3 | |
| 1.70 | 0.6 | 40 | 60 | Linear |
| 2.00 | 0.6 | 5 | 95 | Linear |
| 2.50 | 0.6 | 5 | 95 | Linear |
| 2.80 | 0.6 | 97 | 3 | Linear |
| 3.00 | 0.6 | 97 | 3 | Linear |

TABLE E

Column - Waters CORTECS C18 1.6 μm, 2.1 × 50 mm, reversed-phase column, Solvent A - 0.1% aqueous formic acid, Solvent B - acetonitrile with 0.1% formic acid (Method E).

| Time (min) | Flow (mL/min) | A % | B % | Gradient |
|---|---|---|---|---|
| Initial | 0.6 | 97 | 3 | |
| 1.50 | 0.6 | 5 | 95 | Linear |
| 2.40 | 0.6 | 5 | 95 | Linear |
| 2.50 | 0.6 | 97 | 3 | Linear |
| 2.80 | 0.6 | 97 | 3 | Linear |

TABLE F

Column - Waters CORTECS C8 1.6 μm, 2.1 × 50 mm,
reversed-phase column, Solvent A - 0.1% aqueous formic
acid, Solvent B - acetonitrile with 0.1% formic acid (Method F).

| Time (min) | Flow (mL/min) | A % | B % | Gradient |
|---|---|---|---|---|
| Initial | 0.6 | 97 | 3 | |
| 1.50 | 0.6 | 5 | 95 | Linear |
| 2.40 | 0.6 | 5 | 95 | Linear |
| 2.50 | 0.6 | 97 | 3 | Linear |
| 2.80 | 0.6 | 97 | 3 | Linear |

TABLE G

List of Abbreviations

| | |
|---|---|
| AcOH | acetic acid |
| Boc | tert-butyloxycarbonyl protecting group |
| DCM | dichloromethane |
| DIPEA | N,N-diisopropylethylamine |
| DMA | N,N-dimethyacetamide |
| DMF | N,N-dimethylformamide |
| EtOAc | ethyl acetate |
| EtOH | ethanol |
| Fmoc | 9-fluorenylmethyl carbamates |
| HATU | 1-[bis(dimethylamino)methylene]-1H-1,2,3-triazolo[4,5-b]pyridinium 3-oxid hexafluorophosphate |
| Hex | hexanes |
| HPLC | high performance liquid chromatography |
| MeCN | acetonitrile |
| MeOH | methanol |
| MP | 3-maleimidopropyl |
| MS | Mass spectrometry |
| OSu | N-hydroxysuccinimide |
| PEG | polyethylene glycol |
| PPTS | pyridinium para-toluene sulfonic acid |
| Prep | preparative |
| TFA | trifluoroacetic acid |
| TSTU | N,N,N',N'-tetramethyl-O-(N-succinimidyl)uronium tetrafluoroborate |
| UPLC | Ultra Performance Liquid Chromatography |

Camptothecin Compound Preparations

The Camptothecin Compounds provided in the following Examples can be used in preparing Camptothecin-Linker Compounds as well as Camptothecin Conjugates as described herein.

Example 1

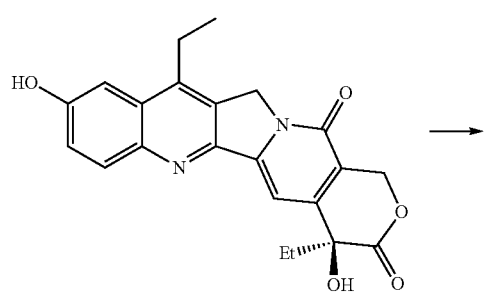

1

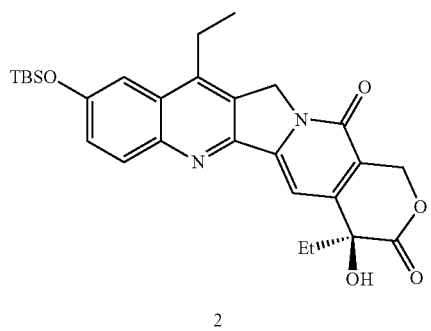

2

SN-38 (compound 1, 160.0 mg, 0.4077 mmol), purchased from MedChemExpress, was suspended in anhydrous DCM (2 mL). DIPEA (0.22 mL, 1.3 mmol) was added followed by TBSCl (154 mg, 1.02 mmol). The reaction was stirred for 30 minutes until compound 1 becomes soluble and complete conversion was observed by UPLC-MS. The reaction was quenched with MeOH, filtered through plug of silica, and concentrated in vacuo. The colorless oil obtained was triturated with Hex. The product precipitated out of solution. The precipitate was collected by filtration and rinsed with Hex to afford compound 2 (TBS-SN-38) as an off-white solid (200 mg, 0.395 mmol, 97%). LC-MS (Method B): $t_R$=1.86 min; MS (m/z) [M+H]$^+$ calc. for $C_{28}H_{35}N_2O_5Si$ 5507.23, found 506.96.

Example 2

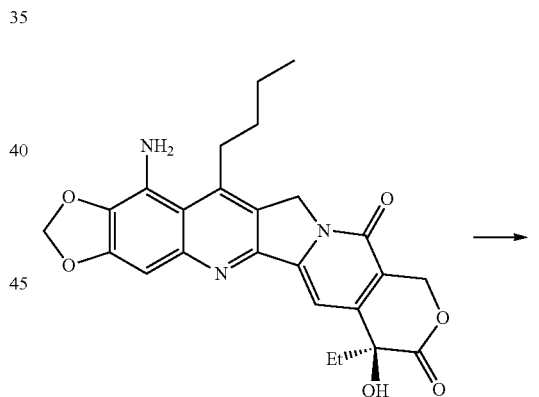

3

4

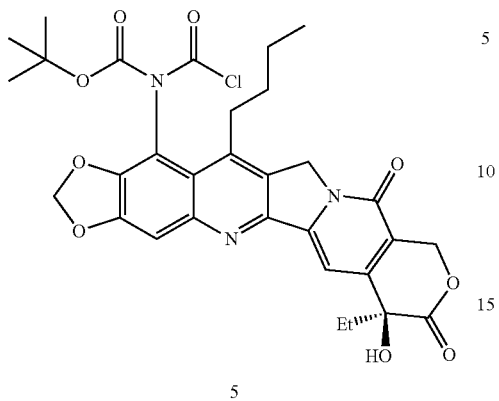

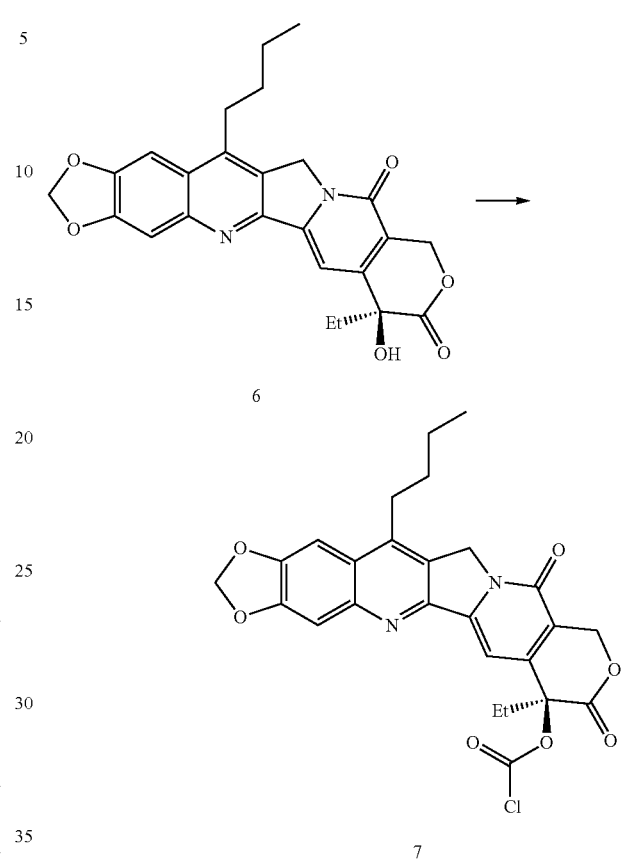

Compound 3 was synthesized according to the procedure described by *Bioconjugate Chem.* 2009, 20, 1242-1250. Compound 3 (50 mg, 0.108 mmol) dissolved in DCM (1 mL). DMAP (13 mg, 0.11 mmol) was added to the reaction followed by Boc$_2$O (24 mg, 0.11 mmol). The reaction was stirred for 5 minutes at which time complete conversion to the desired product was observed. The protected product was purified by column chromatography 10G Biotage Ultra 0-5% MeOH in DCM. Fractions containing the desired product were concentrated in vacuo to afford compound 4 as a yellow solid (49 mg, 0.087 mmol, 80%). LC-MS (Method A): $t_R$=2.24 min; MS (m/z) [M+H]$^+$ calc. for $C_{30}H_{34}N_3O_8$ 564.23, found 564.10.

Compound 4 (49 mg, 0.087 mmol) was dissolved in anhydrous DCM (2 mL). DMAP (37 mg, 0.304 mmol) was added and the reaction was cooled to 0° C. Triphosgene (12 mg, 0.039 mmol) dissolved 10 mg/mL in DCM was added dropwise to the reaction over 15 minutes. A 2 µL aliquot was quenched into 98 µL MeOH diluent and injected onto the UPLC-MS. Complete conversion to the MeOH adduct was observed by UPLC-MS. The reaction mixture (compound 5) can be used directly in coupling steps with suitable linkers. LC-MS (Method A): $t_R$=2.09 min; MS (m/z) [M+H]$^+$ calc. for $C_{32}H_{36}N_3O_{10}$ 622.24, found 622.02.

Example 3

Compound 6 (150 mg, 0.334 mmol), synthesized according to the procedure described in *Bioconjugate Chem.* (2009) 20: 1242-1250, was dissolved in anhydrous DCM (2 mL). DMAP (143 mg, 1.17 mmol) was added. Triphosgene (45 mg, 0.15 mmol) dissolved in anhydrous DCM (50 mg/mL) was added dropwise over 5 minutes. The reaction was stirred for 30 minutes at room temperature. A 2 µL aliquot of the reaction mixture was quenched in 98 µL MeOH diluent. Nearly complete conversion to MeOH carbonate observed indicating chloroformate formation. Compound 7 so obtained is used without further purification in coupling steps with suitable linkers. LC-MS (Method A): $t_R$=1.55 min; MS (m/z) [M+H]$^+$ calc. for $C_{27}H_{27}N_2O_8$ 507.18, found 507.06.

Example 4

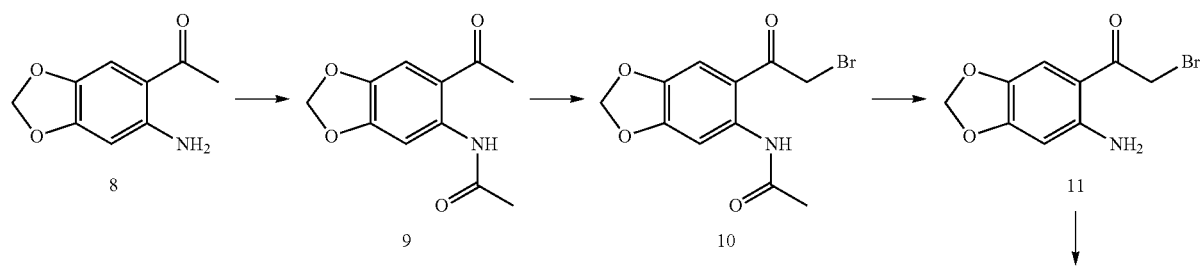

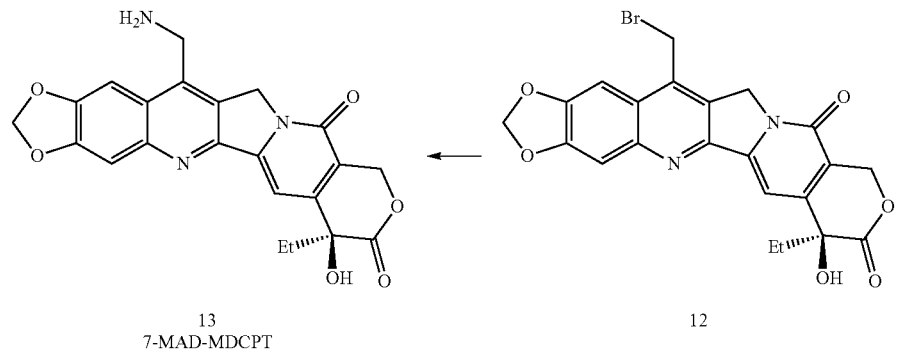

13
7-MAD-MDCPT

12

6-Amino-3,4-(methylenedioxy)-acetophenone (8, 5.00 g, 27.9 mmol), obtained from TCI Research Chemicals (Cat. No. A1356), was dissolved in DCM (100 mL). The reaction was cooled to 0° C. and DIPEA (7.29 mL, 41.9 mmol) was added followed by slow addition of acetyl chloride (2.49 mL, 34.9 mL). The reaction was allowed to warm to room temperature and stirred for 30 minutes. Complete conversion was observed by UPLC-MS. The reaction was quenched with MeOH (5 mL), and the reaction was concentrated in vacuo to afford compound 9 as a white solid used in the next step without further purification. LC-MS (Method A): $t_R$=1.37; MS (m/z) [M+H]$^+$ calc. for $C_{11}H_{12}NO_4$ 222.08, found 222.11.

Compound 9 (27.9 mmol) was dissolved in AcOH (100 mL). HBr 33% w/w in AcOH (9.78 mL, 55.8 mmol) was added slowly. Bromine (1.44 mL, 27.9 mmol) was added dropwise over 15 minutes. The reaction was stirred for 30 minutes at which time conversion to desired product was observed. The reaction was poured over ice water and the precipitate was collected by filtration and washed with water. The filtrate was dried to afford a yellow powder which was a mixture of the desired product compound 10 with starting material and dibrominated product impurities which was used in the next step without further purification (7.2 g, 24 mmol, 86%). LC-MS (Method A): $t_R$=1.58 min; MS (m/z) [M+H]$^+$ calc. for $C_{11}H_{11}BrNO_4$ 299.99, found 299.90.

Compound 10 (7.2 g, 24 mmol) was dissolved in EtOH (100 mL). Concentrated HBr (5 mL) was added and the reaction was heated to reflux for 60 minutes. Nearly complete conversion to the deprotected product was observed. The reaction was concentrated in vacuo, diluted with DCM (200 mL) and H$_2$O (200) mL. The aqueous phase was extracted with DCM (3×200 mL), the collected organic phases were dried with MgSO$_4$, filtered and concentrated in vacuo. The crude product was purified by column chromatography 0-10% MeOH in DCM. Fractions containing the desired product with minor impurity were concentrated to afford compound 11 as a yellow powder (4.05 g, 15.7 mmol, 65%). LC-MS (Method A): $t_R$=1.57 min; MS (m/z) [M+H]$^+$ calc. for $C_9H_9BrNO_3$ 257.98, found 257.71.

Example 5

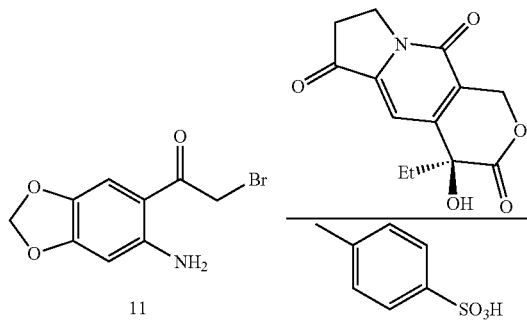

11

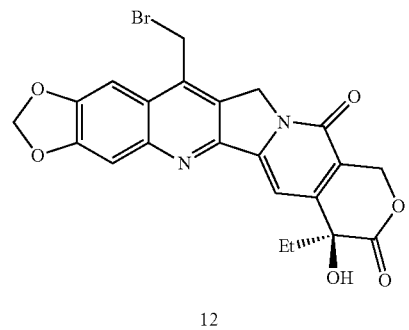

12

Compound 11 (1.00 g, 3.87 mmol), p-TSA (667 mg, 3.87 mmol), and 4-Ethyl-4-hydroxy-7,8-dihydro-1H-pyrano[3,4-f]indolizine-3,6,10(4H)-trione (1.02 g, 3.87 mmol, obtained from Avra Laboratories Pvt. Ltd.) were charged in a flask. DCM (5 mL) was added to homogenize the solids, and then evaporated under nitrogen. The neat solids were then heated to 120° C. under high vacuum (1 mbar) for 60 minutes. Reaction was cooled to room temperature, the crude product precipitated with H$_2$O, filtered and washed with H$_2$O. The precipitate was purified by column chromatography 0-10%

MeOH in DCM. Fractions containing the desired product were concentrated in vacuo to afford compound 12 as a brown solid (989 mg, 2.04 mmol, 53%). LC-MS (Method A): $t_R$=1.62 min (General Method UPLC); MS (m/z) [M+H]$^+$ calc. for $C_{22}H_{17}BrN_2O_6$ 485.03, found 484.95.

Example 6

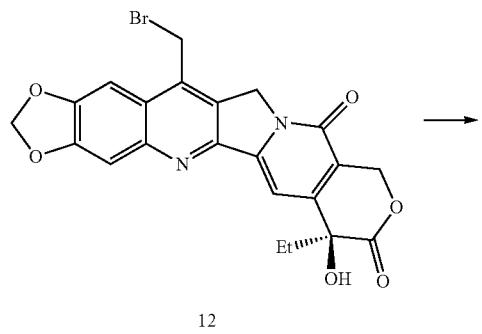

12

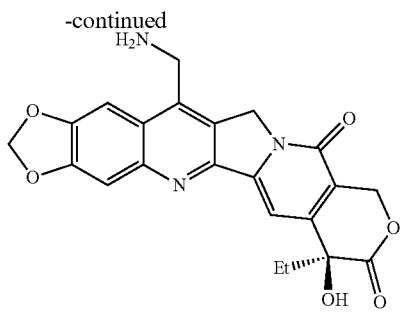

13
7-MAD-MDCPT

Compound 12 (188 mg, 0.387 mmol) was dissolved in EtOH (5 mL). Hexamethylenetetramine (163 mg, 1.16 mmol) was added and the reaction as stirred at reflux for 90 minutes. The reaction was cooled and aq. conc. HCl (0.1 mL) was added. The reaction was concentrated and purified by prep-HPLC. Fractions containing the desired product were lyophilized to afford compound 13 as an off white solid (109 mg, 0.259 mmol, 67%). LC-MS (Method A): $t_R$=0.89; MS (m/z) [M+H]$^+$ calc. for $C_{22}H_{20}N_3O_6$ 422.14, found 422.16.

TABLE H

Camptothecin compounds prepared from compound 13 (7-MAD-MDCPT)

| No. | Structure | Parent Exact Mass | Calc'd MS (m/z) [M + H]$^+$ | Observed MS (m/z) | $t_R$ |
|---|---|---|---|---|---|
| 13a | 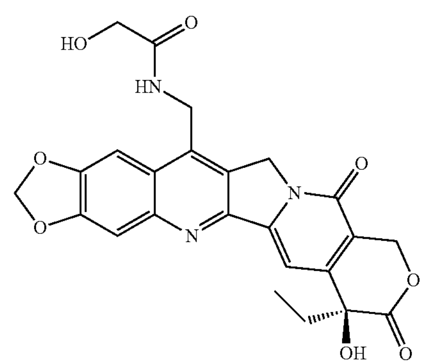 [SMILES: CC[C@@]1(O)C(=O)OCc2c1cc1n(c2=O)Cc2c-1nc1cc3c(cc1c2CNC(=O)CO)OCO3] | 479.13 | 480.14 | 480.08 | 1.20 |
| 13b | 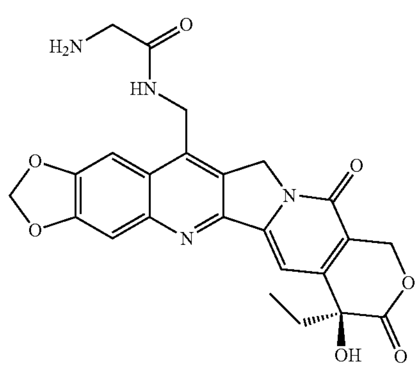 [SMILES: CC[C@@]1(O)C(=O)OCc2c1cc1n(c2=O)Cc2c-1nc1cc3c(cc1c2CNC(=O)CN)OCO3] | 478.15 | 479.16 | 479.11 | 1.05 |

TABLE H-continued

Camptothecin compounds prepared from compound 13 (7-MAD-MDCPT)

| No. | Structure | Parent Exact Mass | Calc'd MS (m/z) [M + H]+ | Observed MS (m/z) | $t_R$ |
|---|---|---|---|---|---|
| 13c | 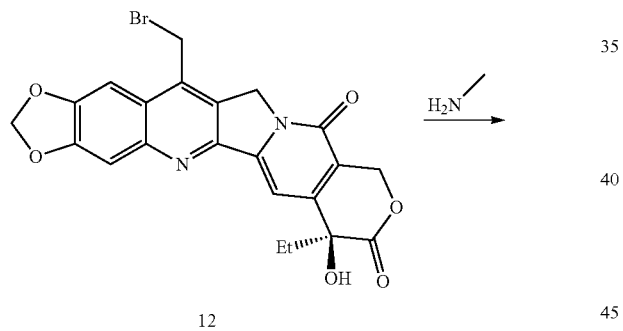 | 492.16 | 493.17 | 493.00 | 1.4 |

The Camptothecin compounds of Table H are exemplary compounds of formula W-CPT that are incorporated into Camptothecin Conjugates of Camptothecin in which Q-D is of formula -Z-A-S*-W-D or -Z-A-B(S*)-W-D or are incorporated into Drug Linker compounds of formula Z'-A-S*-W-D or Z'-A-B(S*)-W-D through covalent attachment to the oxygen atom or nitrogen atom of the primary hydroxy or amine functional group, respectively.

Example 7

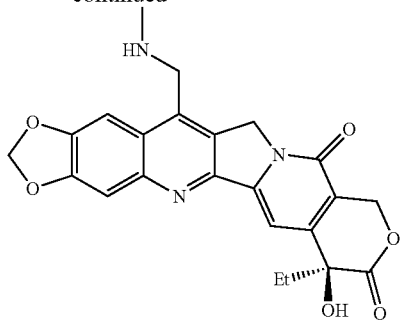

Compound 12 (10.0 mg, 20.6 μmol) from Example 4 was dissolved in anhydrous DMF (0.25 mL). Methylamine (2M in THF, 0.031 mL, 62 μmol) was added. The reaction was stirred for 30 minutes, then quenched with AcOH (20 μL). The reaction was purified by prep-HPLC. Fractions containing the desired product (14) were lyophilized to afford a yellow solid (3.27 mg, 7.51 μmol, 36%). LC-MS (Method D): $t_R$=151.57 min; MS (m/z) [M+H]+ calc. for $C_9H_9BrNO_3$ 257.98, found 257.71. $t_R$=0.93 min (Method A); MS (m/z) [M+H]+ calc. for $C_{23}H_{22}N_3O_6$ 436.15, found 435.78.

TABLE I

Other camptothecin compounds prepared according Example 7.

| No. | Structure | Parent Exact Mass | Calc'd MS (m/z) [M + H] | Obsv'd MS (m/z) | $t_R$* |
|---|---|---|---|---|---|
| 14a | 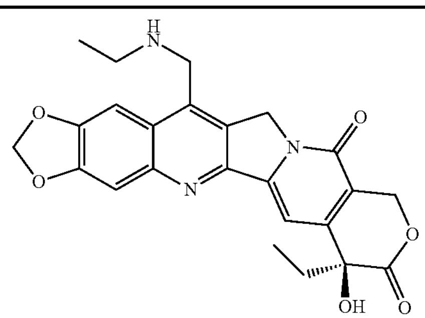 | 449.158685 | 450.17 | 450.14 | 1.19 |

TABLE I-continued

Other camptothecin compounds prepared according Example 7.

| No. | Structure | Parent Exact Mass | Calc'd MS (m/z) [M + H] | Obsv'd MS (m/z) | $t_R$* |
|---|---|---|---|---|---|
| 14b | 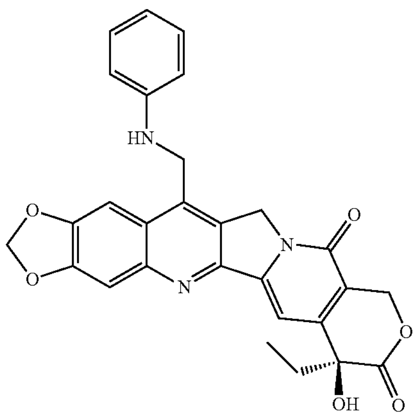 [SMILES: CC[C@@]1(O)C(=O)OCc2c1cc1n(c2=O)Cc2c-1nc1cc3c(cc1c2CNc1ccccc1)OCO3] | 497.158685 | 498.17 | 498.05 | 1.22 |
| 14c | 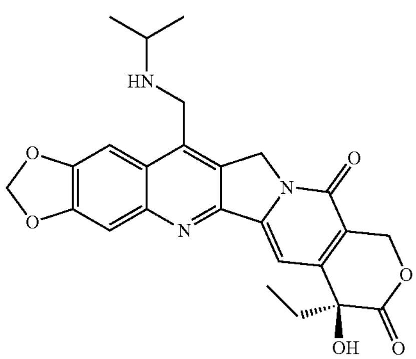 [SMILES: CC[C@@]1(O)C(=O)OCc2c1cc1n(c2=O)Cc2c-1nc1cc3c(cc1c2CNC(C)C)OCO3] | 463.174336 | 464.18 | 464.00 | 0.98 |
| 14d | 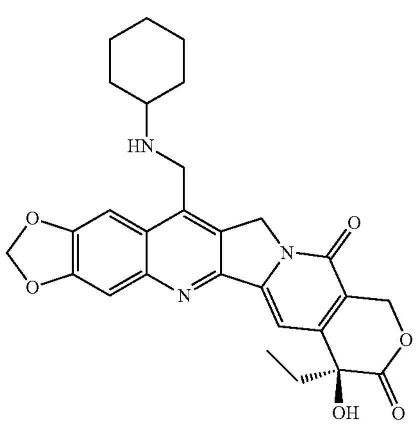 [SMILES: CC[C@@]1(O)C(=O)OCc2c1cc1n(c2=O)Cc2c-1nc1cc3c(cc1c2CNC1CCCCC1)OCO3] | 503.205636 | 504.22 | 504.16 | 1.16 |

TABLE I-continued

Other camptothecin compounds prepared according Example 7.

| No. | Structure | Parent Exact Mass | Calc'd MS (m/z) [M + H] | Obsv'd MS (m/z) | $t_R$* |
|---|---|---|---|---|---|
| 14e | 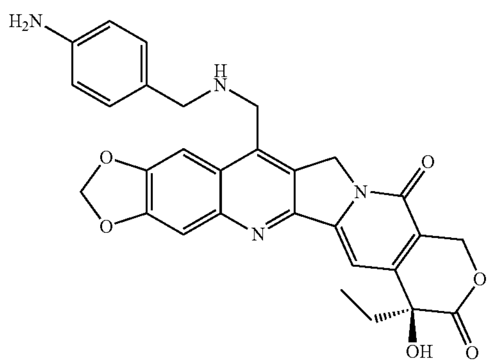 [SMILES: CC[C@@]1(O)C(=O)OCc2c1cc1n(c2=O)Cc2c-1nc1cc3c(cc1c2CNCc1ccc(N)cc1)OCO3] | 526.185235 | 527.20 | 526.08 | 1.11 |
| 14f | 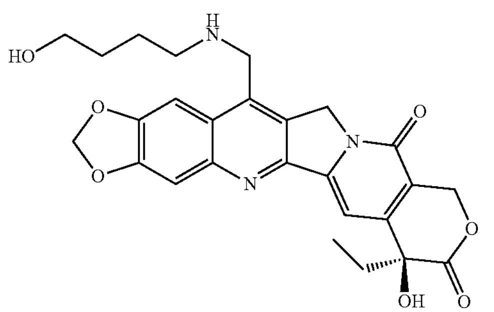 [SMILES: CC[C@@]1(O)C(=O)OCc2c1cc1n(c2=O)Cc2c-1nc1cc3c(cc1c2CNCCCCO)OCO3] | 493.1849 | 494.19 | 493.88 | 1.03 |
| 14g | 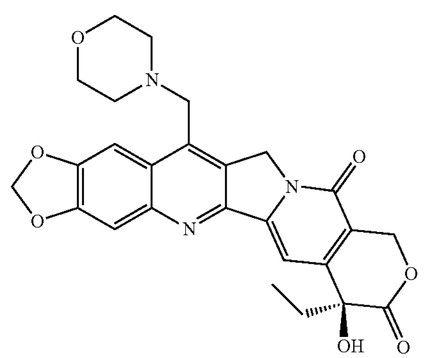 [SMILES: CC[C@@]1(O)C(=O)OCc2c1cc1n(c2=O)Cc2c-1nc1cc3c(cc1c2CN1CCOCC1)OCO3] | 491.16925 | 492.18 | 491.74 | 1.19 |
| 14h | 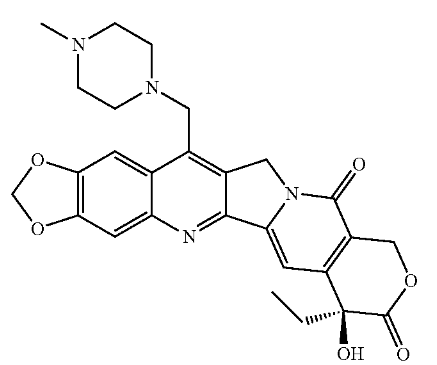 [SMILES: CC[C@@]1(O)C(=O)OCc2c1cc1n(c2=O)Cc2c-1nc1cc3c(cc1c2CN1CCN(C)CC1)OCO3] | 504.200885 | 505.21 | 504.93 | 1.10 |

TABLE I-continued

Other camptothecin compounds prepared according Example 7.

| No. | Structure | Parent Exact Mass | Calc'd MS (m/z) [M + H] | Obsv'd MS (m/z) | $t_R$* |
|---|---|---|---|---|---|
| 14i | 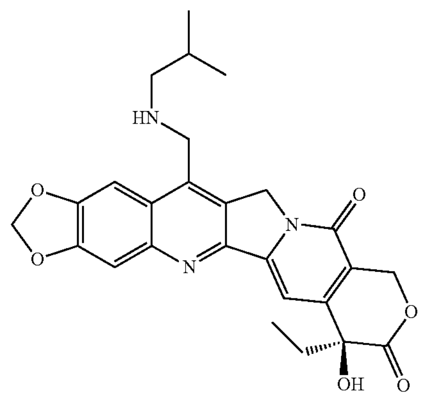 [SMILES: CC[C@@]1(O)C(=O)OCc2c1cc1n(c2=O)Cc2c-1nc1cc3c(cc1c2CNCC(C)C)OCO3] | 477.189986 | 478.20 | 478.26 | 1.30 |
| 14j | 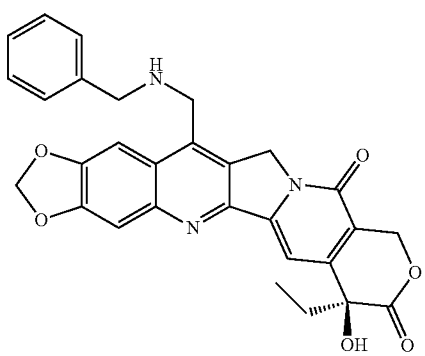 [SMILES: CC[C@@]1(O)C(=O)OCc2c1cc1n(c2=O)Cc2c-1nc1cc3c(cc1c2CNCc1ccccc1)OCO3] | 511.174336 | 512.18 | 512.21 | 1.20 |
| 14k | 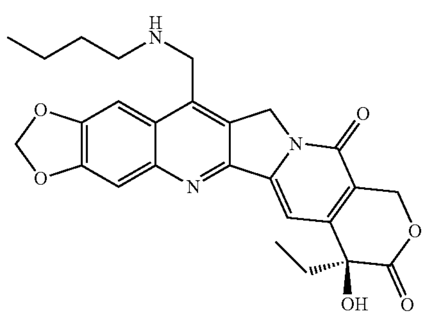 [SMILES: CCCCNCc1c2c(nc3cc4c(cc13)OCO4)-c1cc3c(c(=O)n1C2)COC(=O)[C@]3(O)CC] | 477.189986 | 478.20 | 477.68 | 1.13 |
| 14l | 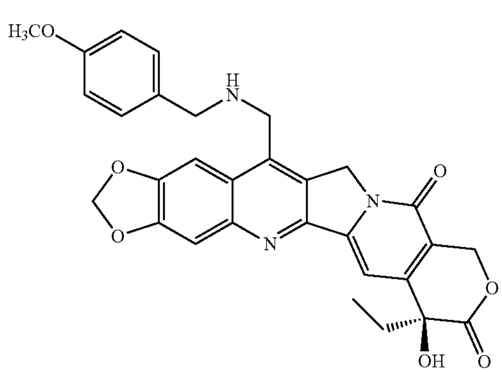 [SMILES: CC[C@@]1(O)C(=O)OCc2c1cc1n(c2=O)Cc2c-1nc1cc3c(cc1c2CNCc1ccc(OC)cc1)OCO3] | 541.1849 | 542.19 | 542.37 | 1.30 |

TABLE I-continued

Other camptothecin compounds prepared according Example 7.

| No. | Structure | Parent Exact Mass | Calc'd MS (m/z) [M + H] | Obsv'd MS (m/z) | $t_R$* |
|---|---|---|---|---|---|
| 14m | 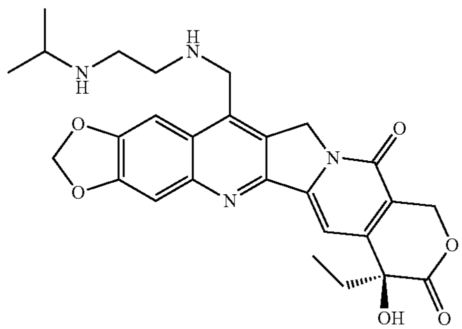 [SMILES: CC[C@@]1(O)C(=O)OCc2c1cc1n(c2=O)Cc2c-1nc1cc3c(cc1c2CNCCNC(C)C)OCO3] | 506.216535 | 507.23 | 507.94 | 0.76 |
| 14n | 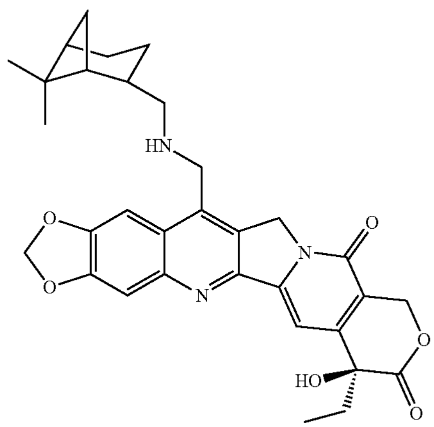 [SMILES: CC[C@@]1(O)C(=O)OCc2c1cc1n(c2=O)Cc2c-1nc1cc3c(cc1c2CNCC1CCC2CC1C2(C)C)OCO3] | 557.252586 | 558.26 | 557.89 | 1.51 |
| 14o | 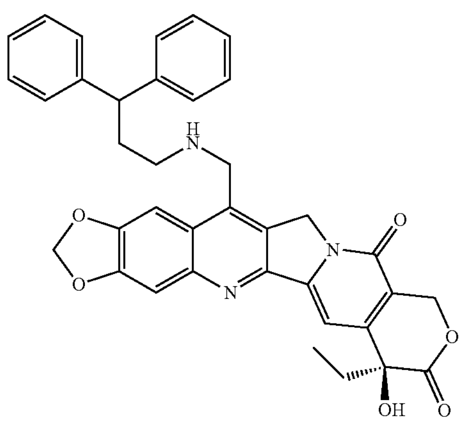 [SMILES: CC[C@@]1(O)C(=O)OCc2c1cc1n(c2=O)Cc2c-1nc1cc3c(cc1c2CNCCC(c1ccccc1)c1ccccc1)OCO3] | 615.236936 | 616.25 | 615.60 | 1.56 |
| 14p | 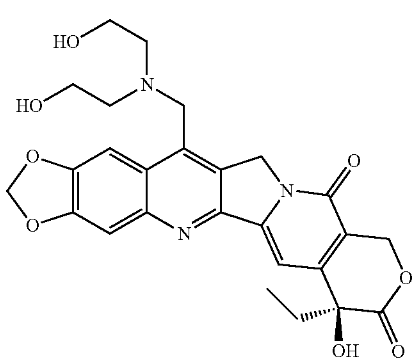 [SMILES: CC[C@@]1(O)C(=O)OCc2c1cc1n(c2=O)Cc2c-1nc1cc3c(cc1c2CN(CCO)CCO)OCO3] | 509.179815 | 510.19 | 509.69 | 1.09 |

TABLE I-continued

Other camptothecin compounds prepared according Example 7.

| No. | Structure | Parent Exact Mass | Calc'd MS (m/z) [M + H] | Obsv'd MS (m/z) | $t_R$* |
|---|---|---|---|---|---|
| 14q | 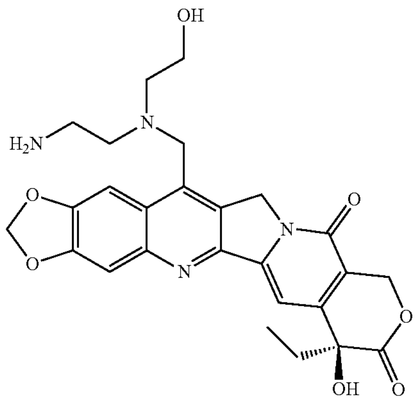 [SMILES: CC[C@@]1(O)C(=O)OCc2c1cc1n(c2=O)Cc2c-1nc1cc3c(cc1c2CN(CCN)CCO)OCO3] | 508.195799 | 509.21 | 508.91 | 1.11 |
| 14r | 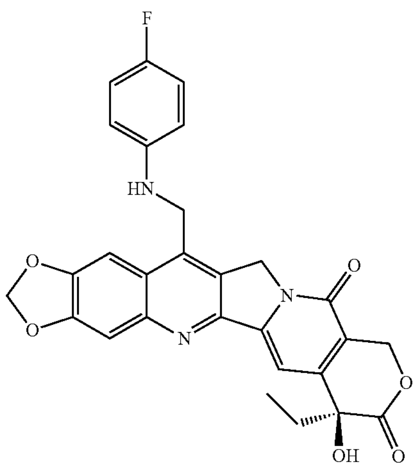 [SMILES: CC[C@@]1(O)C(=O)OCc2c1cc1n(c2=O)Cc2c-1nc1cc3c(cc1c2CNc1ccc(F)cc1)OCO3] | 515.149264 | 516.16 | 515.09 | 1.33 |
| 14s | 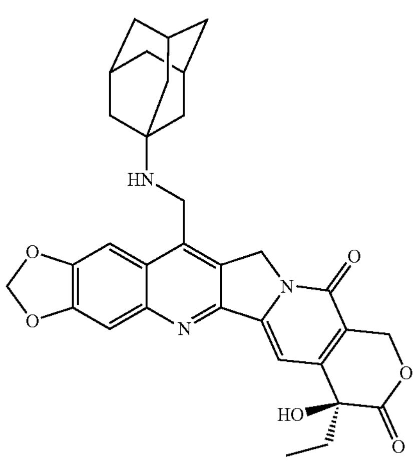 [SMILES: CC[C@@]1(O)C(=O)OCc2c1cc1n(c2=O)Cc2c-1nc1cc3c(cc1c2CNC12CC4CC(CC(C4)C1)C2)OCO3] | 555.236936 | 556.25 | 555.85 | 1.49 |

TABLE I-continued

Other camptothecin compounds prepared according Example 7.

| No. | Structure | Parent Exact Mass | Calc'd MS (m/z) [M + H] | Obsv'd MS (m/z) | $t_R$* |
|---|---|---|---|---|---|
| 14t | 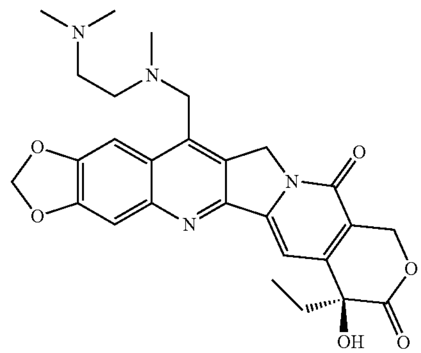 [SMILES: CC[C@@]1(O)C(=O)OCc2c1cc1n(c2=O)Cc2c-1nc1cc3c(cc1c2CN(C)CCN(C)C)OCO3] | 506.216535 | 507.23 | 506.58 | 1.17 |
| 14u | 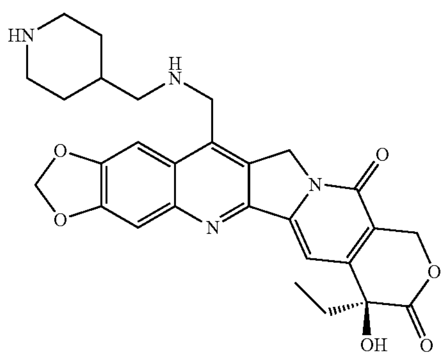 [SMILES: CC[C@@]1(O)C(=O)OCc2c1cc1n(c2=O)Cc2c-1nc1cc3c(cc1c2CNCC1CCNCC1)OCO3] | 518.216535 | 519.23 | 519.09 | 1.00 |
| 14v | 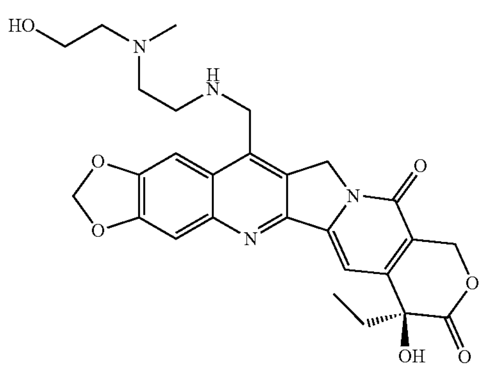 [SMILES: CC[C@@]1(O)C(=O)OCc2c1cc1n(c2=O)Cc2c-1nc1cc3c(cc1c2CNCCN(C)CCO)OCO3] | 522.211449 | 523.22 | 522.68 | 1.04 |
| 14w | 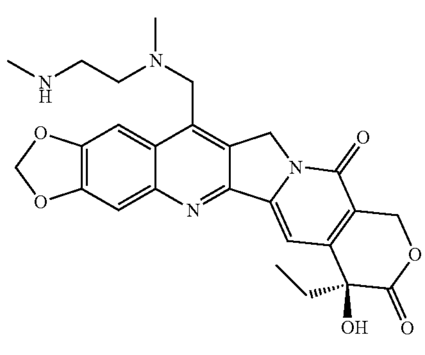 [SMILES: CC[C@@]1(O)C(=O)OCc2c1cc1n(c2=O)Cc2c-1nc1cc3c(cc1c2CN(C)CCNC)OCO3] | 492.200885 | 493.21 | 492.71 | 1.07 |

TABLE I-continued

Other camptothecin compounds prepared according Example 7.

| No. | Structure | Parent Exact Mass | Calc'd MS (m/z) [M + H] | Obsv'd MS (m/z) | $t_R$* |
|-----|-----------|-------------------|--------------------------|-----------------|--------|
| 14x | 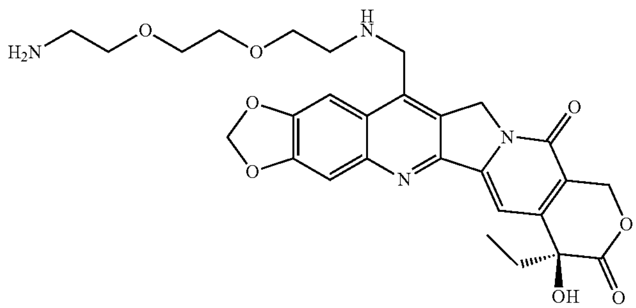 [SMILES: CC[C@@]1(O)C(=O)OCc2c1cc1n(c2=O)Cc2c-1nc1cc3c(cc1c2CNCCOCCOCCN)OCO3] | 552.222014 | 553.23 | 553.14 | 1.08 |
| 14y | 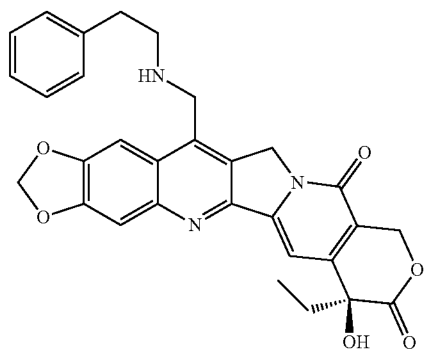 [SMILES: CC[C@@]1(O)C(=O)OCc2c1cc1n(c2=O)Cc2c-1nc1cc3c(cc1c2CNCCc1ccccc1)OCO3] | 525.189986 | 526.20 | 525.59 | 1.31 |
| 14z | 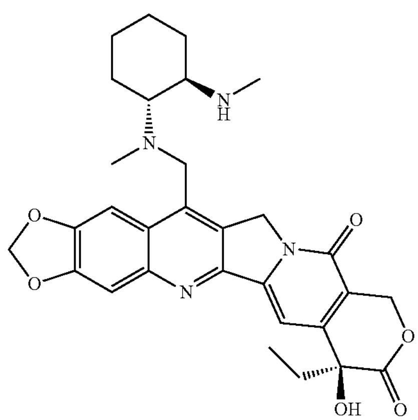 [SMILES: CC[C@@]1(O)C(=O)OCc2c1cc1n(c2=O)Cc2c-1nc1cc3c(cc1c2CN(C)[C@@H]1CCCC[C@H]1NC)OCO3] | 546.247835 | 547.26 | 546.64 | 1.26 |

*LC-MS Method A

Example 8

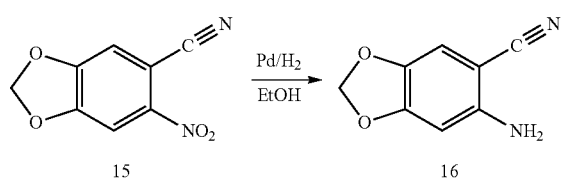 [SMILES: "EtOH" ; N#Cc1cc2c(cc1[N+](=O)[O-])OCO2 ; N#Cc1cc2c(cc1N)OCO2]

As described in *Heterocycles*, (2007) 71: 39-48) 6-nitro-1,3-benzodioxole-5-carbonitrile (compound 15, 2.00 g, 10.4 mmol) was prepared and then dissolved in EtOH (50 mL). Reaction was placed under nitrogen atmosphere. Pd/C (2.22 g, 10% w/w, 2.08 mmol) added to the reaction, which was placed under hydrogen atmosphere. The reaction was stirred for 2 hours. The reaction was filtered through a bed of Celite, then rinsed with MeOH. The eluent was concentrated in vacuo and purified by flash chromatography 0-10% DCM in MeOH. Fractions containing the desired product were concentrated to afford compound 16 as a red solid (1.46 g, 9.00 mmol, 87%). LC-MS (Method D): $t_R$=1.14 min; MS (m/z) [M+H]$^+$ calc. for $C_8H_7N_2O_2$ 163.05, found 162.37.

Example 9

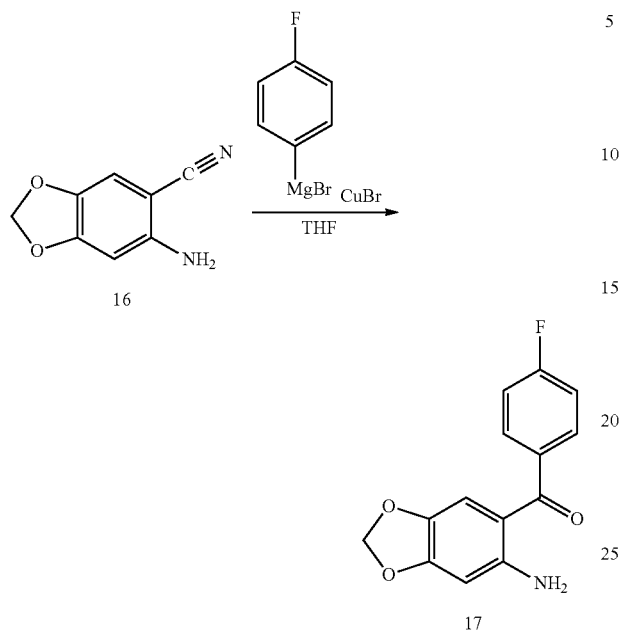

6-amino-1,3-benzodioxole-5-carbonitrile (compound 16, 50 mg, 0.31 mmol) was placed under nitrogen atmosphere and dissolved in anhydrous THF (1 mL). CuBr (1.5 mg, 0.010 mmol) was added followed by 4-fluorophenylmagnesium bromide 1M in THF (1.23 mL). The reaction was heated to 60° C. for 30 minutes, and then cooled to room temperature. A solution of 15% $H_2SO_4$ was added to the reaction slowly, then stirred for 30 minutes. The reaction was poured into sat. $NaHCO_3$ (50 mL), then extracted with EtOAc (3×50 mL). The organic was dried with $MgSO_4$, filtered and concentrated in vacuo. The crude product was purified by column chromatography 10G Biotage Ultra 0-10% EtOAc in Hex. Fractions containing the desired product were concentrated in vacuo to afford compound 17 as a red solid (46.2 mg, 0.178 mmol, 58%). LC-MS (Method D): $t_R$=1.81 min; MS (m/z) $[M+H]^+$ calc. for $C_{14}H_{11}FNO_3$ 260.07, found 259.46.

Example 10

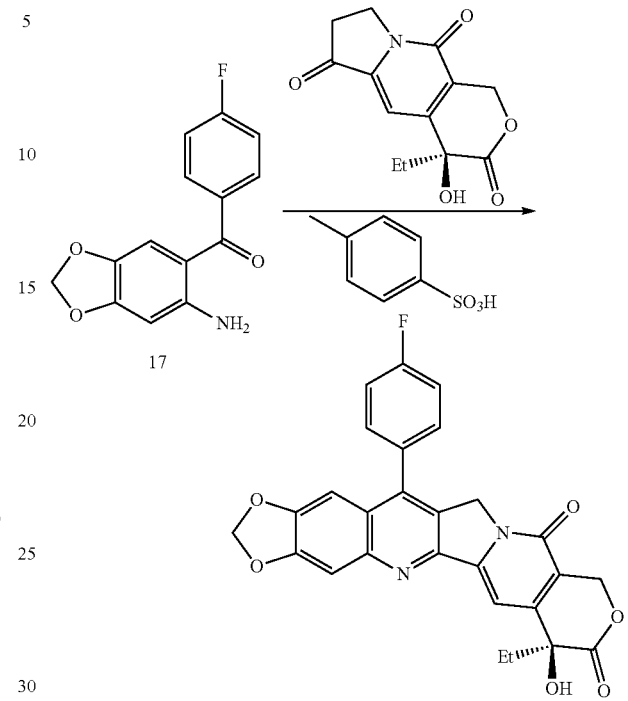

Compound 17 (46.2 mg, 0.178 mmol), p-TSA (30.7 mg, 0.178 mmol), and 4-Ethyl-4-hydroxy-7,8-dihydro-1H-pyrano[3,4-f]indolizine-3,6,10(4H)-trione (46.9 mg, 0.178 mmol, obtained from Avra Laboratories Pvt. Ltd.) were charged in a scintillation vial. DCM (1 mL) was added to homogenate the solids. The solvent was concentrated under nitrogen. The neat solids were the heated to 120° C. under high vacuum (1 mbar) for 60 minutes. The reaction was reconstituted in DCM (50 mL), washed with $H_2O$, the organic phase wash dried with $MgSO_4$, filtered and concentrated in vacuo. The crude product was purified by column chromatography 10G Biotage Ultra 0-10% MeOH in DCM. Fractions containing the desired product (18) were concentrated in vacuo to afford a red solid (32.9 mg, 0.0676 mmol, 38%). LC-MS (Method D): $t_R$=1.81 min; MS (m/z) $[M+H]^+$ calc. for $C_{27}H_{20}FN_2O_6$ 487.13, found 487.19.

TABLE J

Other camptothecin compounds prepared according to the procedures of Examples 9 and 10.

| No. | Structure | Parent Exact Mass | Calc'd MS (m/z) $[M + H]^+$ | Observed MS (m/z) | $t_R$* |
|---|---|---|---|---|---|
| 18a | 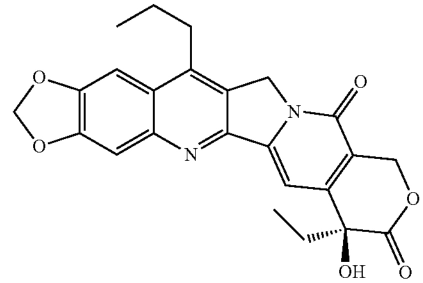 [SMILES: CCCc1c2c(nc3cc4c(cc13)OCO4)-c1cc3c(c(=O)n1C2)COC(=O)[C@]3(O)CC] | 434.147786 | 435.16 | 434.81 | 1.62 |

TABLE J-continued

Other camptothecin compounds prepared according to the procedures of Examples 9 and 10.

| No. | Structure | Parent Exact Mass | Calc'd MS (m/z) [M + H]+ | Observed MS (m/z) | t$_R$* |
|---|---|---|---|---|---|
| 18b | 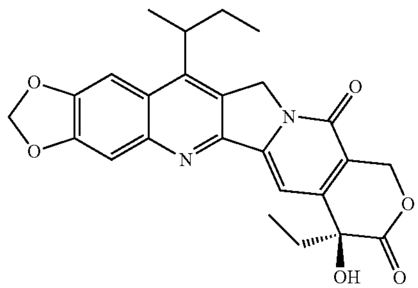 [SMILES: CCC(C)c1c2c(nc3cc4c(cc13)OCO4)-c1cc3c(c(=O)n1C2)COC(=O)[C@]3(O)CC] | 448.163437 | 449.17 | 448.78 | 1.71 |
| 18c | 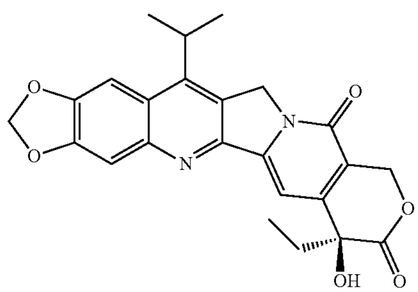 [SMILES: CC[C@@]1(O)C(=O)OCc2c1cc1n(c2=O)Cc2c-1nc1cc3c(cc1c2C(C)C)OCO3] | 434.147786 | 435.16 | 434.81 | 1.59 |
| 18d | 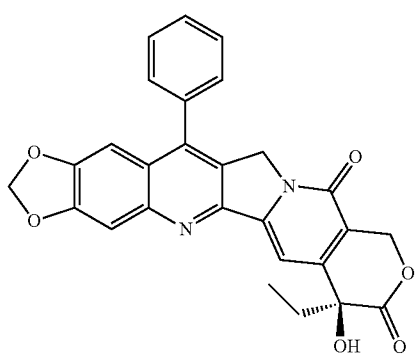 [SMILES: CC[C@@]1(O)C(=O)OCc2c1cc1n(c2=O)Cc2c-1nc1cc3c(cc1c2-c1ccccc1)OCO3] | 468.132136 | 469.14 | 469.15 | 1.77 |
| 18e | 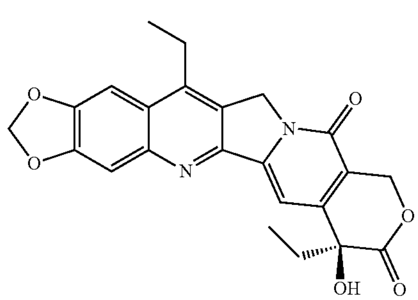 [SMILES: CCc1c2c(nc3cc4c(cc13)OCO4)-c1cc3c(c(=O)n1C2)COC(=O)[C@]3(O)CC] | 420.132136 | 421.14 | 420.85 | 1.48 |

TABLE J-continued

Other camptothecin compounds prepared according to the procedures of Examples 9 and 10.

| No. | Structure | Parent Exact Mass | Calc'd MS (m/z) [M + H]$^+$ | Observed MS (m/z) | $t_R$* |
|---|---|---|---|---|---|
| 18f | 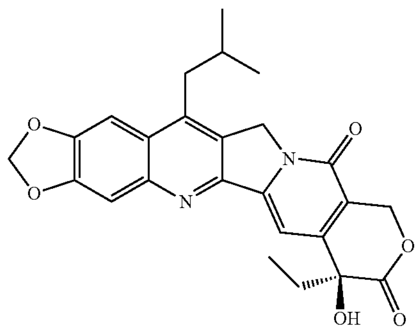 [SMILES: CC[C@@]1(O)C(=O)OCc2c1cc1n(c2=O)Cc2c-1nc1cc3c(cc1c2CC(C)C)OCO3] | 448.163437 | 449.17 | 448.78 | 1.76 |
| 18g | 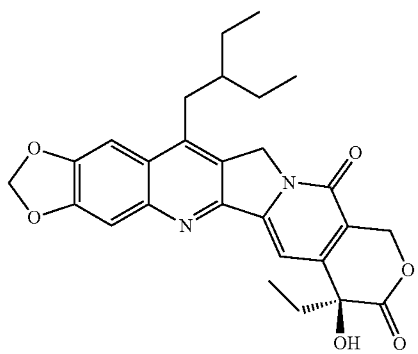 [SMILES: CCC(CC)Cc1c2c(nc3cc4c(cc13)OCO4)-c1cc3c(c(=O)n1C2)COC(=O)[C@]3(O)CC] | 476.194737 | 477.20 | 476.81 | 2.00 |
| 18h | 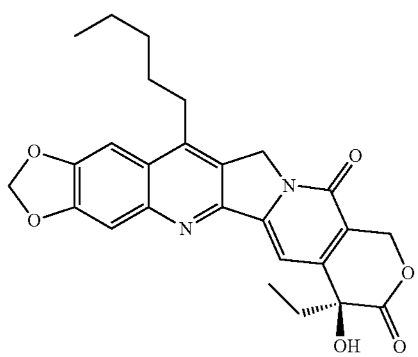 [SMILES: CCCCCc1c2c(nc3cc4c(cc13)OCO4)-c1cc3c(c(=O)n1C2)COC(=O)[C@]3(O)CC] | 462.179087 | 463.19 | 462.94 | 1.93 |
| 18i | 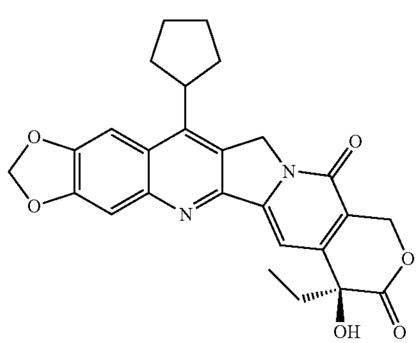 [SMILES: CC[C@@]1(O)C(=O)OCc2c1cc1n(c2=O)Cc2c-1nc1cc3c(cc1c2C1CCCC1)OCO3] | 460.163437 | 461.17 | 460.80 | 1.79 |

TABLE J-continued

Other camptothecin compounds prepared according to the procedures of Examples 9 and 10.

| No. | Structure | Parent Exact Mass | Calc'd MS (m/z) [M + H]$^+$ | Observed MS (m/z) | t$_R$* |
|---|---|---|---|---|---|
| 18j | 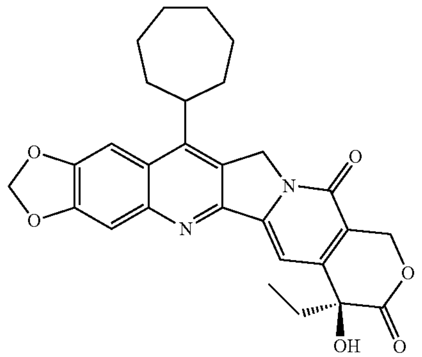 [SMILES: CC[C@@]1(O)C(=O)OCc2c1cc1n(c2=O)Cc2c-1nc1cc3c(cc1c2C1CCCCCC1)OCO3] | 488.194737 | 489.20 | 489.12 | 2.03 |
| 18k | 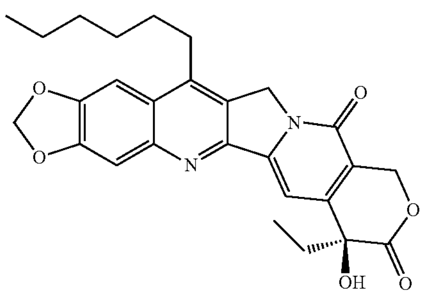 [SMILES: CCCCCCc1c2c(nc3cc4c(cc13)OCO4)-c1cc3c(c(=O)n1C2)COC(=O)[C@]3(O)CC] | 476.194737 | 477.20 | 478.07 | 2.06 |
| 18l | 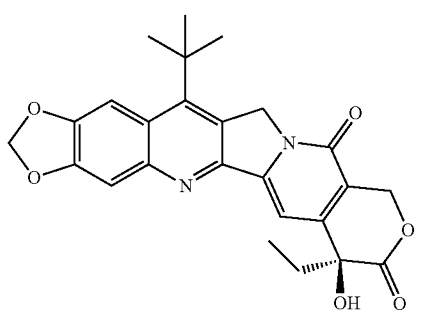 [SMILES: CC[C@@]1(O)C(=O)OCc2c1cc1n(c2=O)Cc2c-1nc1cc3c(cc1c2C(C)(C)C)OCO3] | 448.163437 | 449.17 | 448.87 | 1.69 |
| 18m | 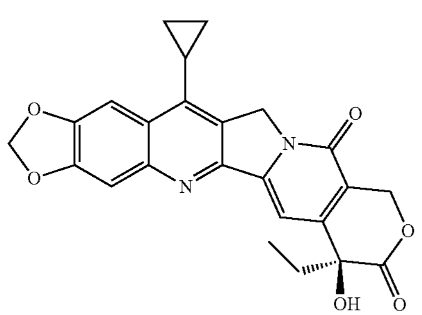 [SMILES: CC[C@@]1(O)C(=O)OCc2c1cc1n(c2=O)Cc2c-1nc1cc3c(cc1c2C1CC1)OCO3] | 432.132136 | 433.14 | 433.16 | 1.56 |

TABLE J-continued

Other camptothecin compounds prepared according to the procedures of Examples 9 and 10.

| No. | Structure | Parent Exact Mass | Calc'd MS (m/z) [M + H]+ | Observed MS (m/z) | $t_R$* |
|---|---|---|---|---|---|
| 18n | 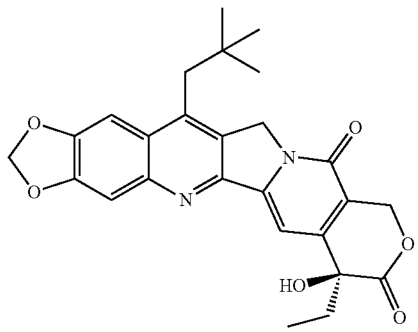 [SMILES: CC[C@@]1(O)C(=O)OCc2c1cc1n(c2=O)Cc2c-1nc1cc3c(cc1c2CC(C)(C)C)OCO3] | 462.179087 | 463.19 | 463.04 | 1.83 |
| 18o | 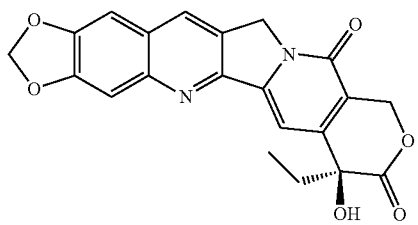 [SMILES: CC[C@@]1(O)C(=O)OCc2c1cc1n(c2=O)Cc2cc3cc4c(cc3nc2-1)OCO4] | 392.100836 | 393.11 | 393.01 | 1.31 |
| 18p | 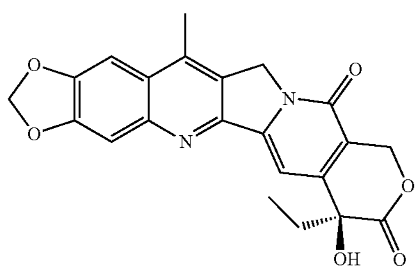 [SMILES: CC[C@@]1(O)C(=O)OCc2c1cc1n(c2=O)Cc2c-1nc1cc3c(cc1c2C)OCO3] | 406.12 | 407.13 | 407.07 | 1.42 |
| 18q | 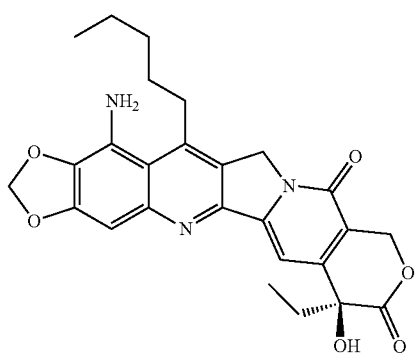 [SMILES: CCCCCc1c2c(nc3cc4c(c(N)c13)OCO4)-c1cc3c(c(=O)n1C2)COC(=O)[C@]3(O)CC] | 477.18999 | 478.20 | 478.17 | 1.26 |
| 18r | 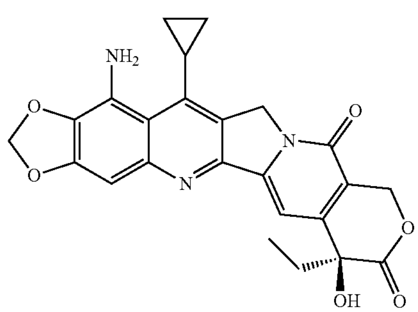 [SMILES: CC[C@@]1(O)C(=O)OCc2c1cc1n(c2=O)Cc2c-1nc1cc3c(c(N)c1c2C1CC1)OCO3] | 447.14304 | 448.15 | 448.00 | 1.33 |

*LC-MS Method A except 18q (Method E) and 18r (Method D)

Example 11

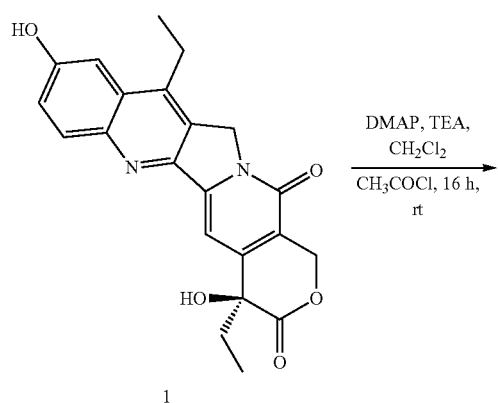

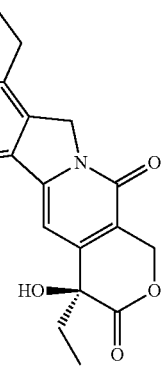

SN-38 (compound 1, 76.0 mg, 0.19 mmol), obtained from MedChemExpress, was dissolved in dichloromethane, followed by addition of triethylamine (128 μL, 0.92 mmol) and DMAP (2.60 mg, 0.02 mmol). Mixture was cooled to 0° C. in an ice bath, followed by dropwise addition of acetyl chloride (15.9 μL, 0.22 mmol). The reaction mixture was stirred at room temperature for 16 h. The reaction was diluted with dichloromethane, washed with saturated NH$_4$Cl, water, and brine. The organic phase was then dried over MgSO$_4$, filtered, concentrated and purified over silica via Biotage flash column chromatography (CH$_2$Cl$_2$/MeOH 0-15%) to yield acetylated SN-38 (19). MS (m/z) calculated 435.15 (M+H)$^+$, found 435.07.

TABLE K

Camptothecin compounds prepared as described herein:

| Ex. No. | Structure | Parent Exact Mass | Calc'd MS (m/z) [M + H]$^+$ | Observed MS (m/z) | $t_R$ |
|---|---|---|---|---|---|
| 20a | 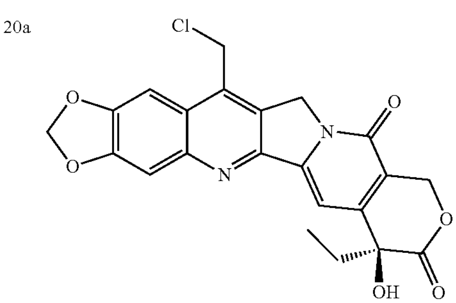 | 440.077514 | 441.09 | 441.02 | 1.49 |
| 20b | 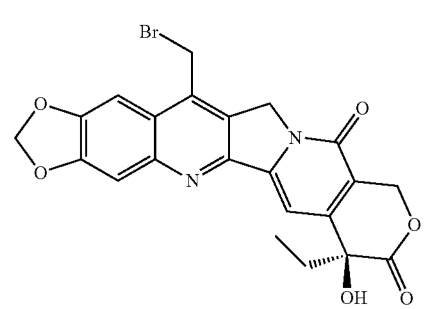 [SMILES: CC[C@@]1(O)C(=O)OCc2c1cc1n(c2=O)Cc2c-1nc1cc3c(cc1c2CBr)OCO3] | 484.026999 | 485.04 | 484.95 | 1.53 |

TABLE K-continued

Camptothecin compounds prepared as described herein:

| Ex. No. | Structure | Parent Exact Mass | Calc'd MS (m/z) [M + H]+ | Observed MS (m/z) | $t_R$ |
|---|---|---|---|---|---|
| 20c | 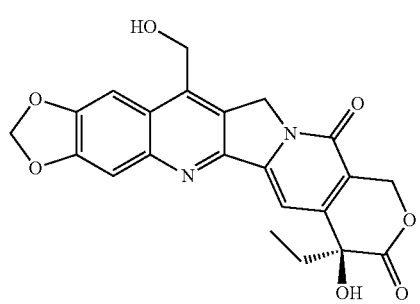 [SMILES: CC[C@@]1(O)C(=O)OCc2c1cc1n(c2=O)Cc2c-1nc1cc3c(cc1c2CO)OCO3] | 422.11 | 423.12 | 423.04 | 1.29 |

Example 12

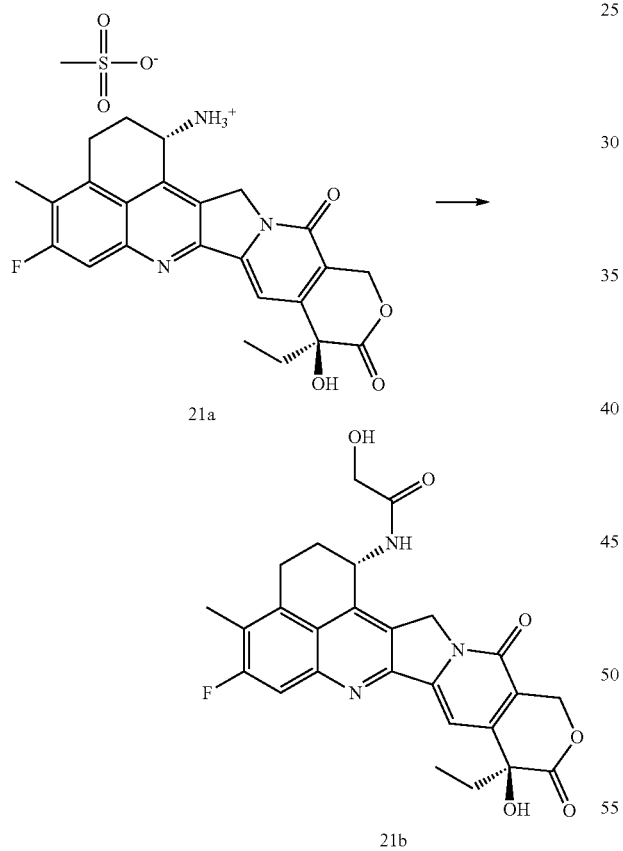

Exatecan mesylate (compound 21a) 20.0 mg, 0.0376 mmol, obtained from MedChemExpress Cat. No.: HY-13631A) was suspended in anhydrous DCM (1 mL). DIPEA (20.0 µL, 0.0146 mmol) was added followed by acetoxyacetyl chloride (5.0 µL, 0.046 mmol). The reaction was stirred for 30 minutes, then quenched with MeOH, and concentrated in vacuo. The reaction mixture was re-dissolved in MeOH (1 mL). LiOH (20 mg) added. Complete deprotection of acetate observed. Quenched AcOH. Purified by Prep-HPLC 10 mm 10-95% MeCN in H$_2$O 0.05% TFA. Fractions containing the desired product were concentrated in vacuo to afford compound 21b as a yellow solid (15.3 mg, 0.0310 mmol, 82%). LC-MS (Method A): $t_R$=1.46 min; MS (m/z) [M+H]+ calc. for C$_{26}$H$_{25}$N$_3$O$_6$ 494.17, found 494.05.

Example 13

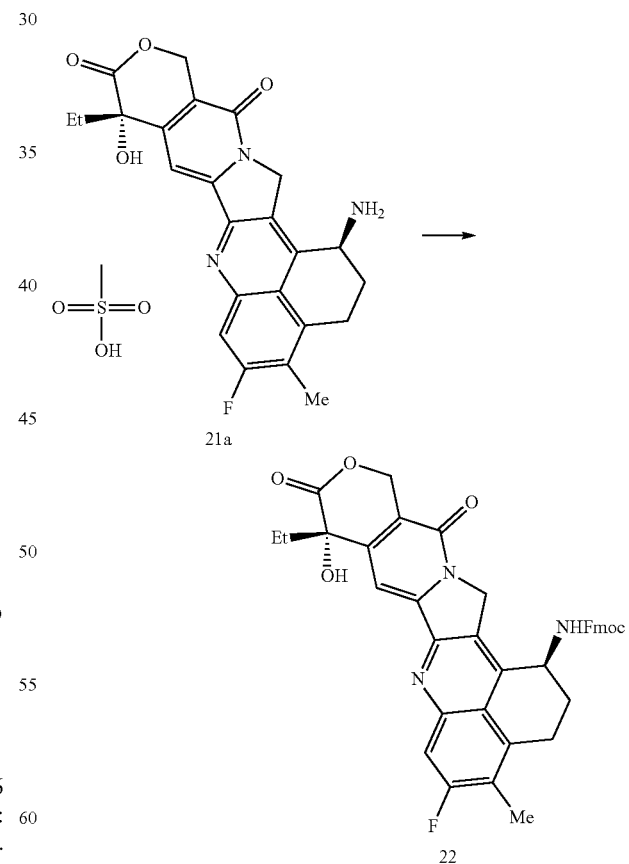

Exatecan mesylate (compound 21a, 20.0 mg, 0.0376 mol) was dissolved in MeCN (1 mL) and NaHCO$_3$ 0.75M in H$_2$O. Fmoc-OSu (19.0 mg, 0.0564 mmol) was added and the reaction was stirred for 2 hours 30 minutes. The reaction was

223 diluted with H₂O (50 mL), the pH was adjusted to neutral and extracted with DCM (3×50 mL). The organic phase was dried with MgSO₄, filter and concentrated in vacuo. The crude product was purified by prep-TLC 0-5% MeOH in DCM. The band containing the desired product was scraped, filtered washing with 10% MeOH in DCM, and the eluent was concentrated in vacuo to afford compound 22 as an orange solid (19.1 mg, 0.0290 mmol, 77%). LC-MS (Method A): $t_R$=2.23 min; MS (m/z) [M+H]⁺ calc. for $C_{39}H_{33}FN_3O_6$ 658.24, found 10658.09.

Example 14

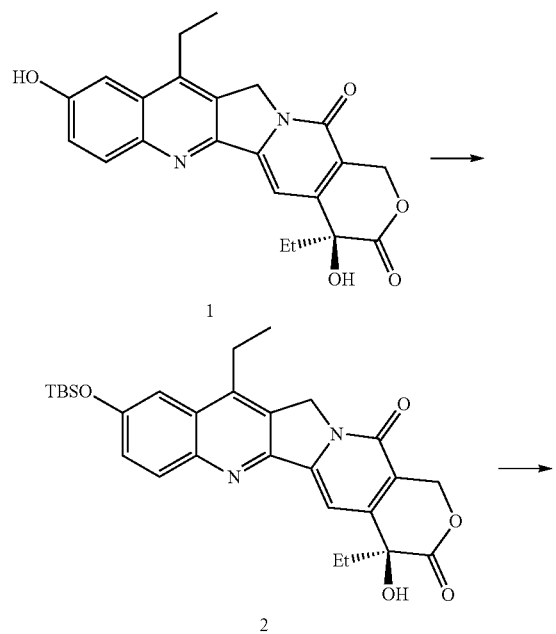

224

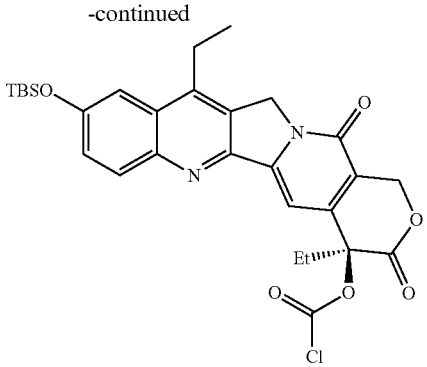

Compound 2 (132 mg, 0.260 mmol), prepared according to Example 1, was dissolved in 2 mL anhydrous DCM. DMAP (111 mg, 0.911 mmol) was added. Triphosgene (34.8 mg, 0.117 mmol) dissolved 50 mg/mL in anhydrous DCM, and the solution was added dropwise to stirred reaction solution over 5 minutes. A 2 µL aliquot of the reaction solution was quenched into 98 µL MeOH diluent. Nearly complete conversion was observed to the Me-carbonate by UPLC-MS after 15 minutes. Reaction mixture containing compound 24 was used immediately in coupling reactions described herein.

Camptothecin Drug Linker Compound Preparations

Example 15

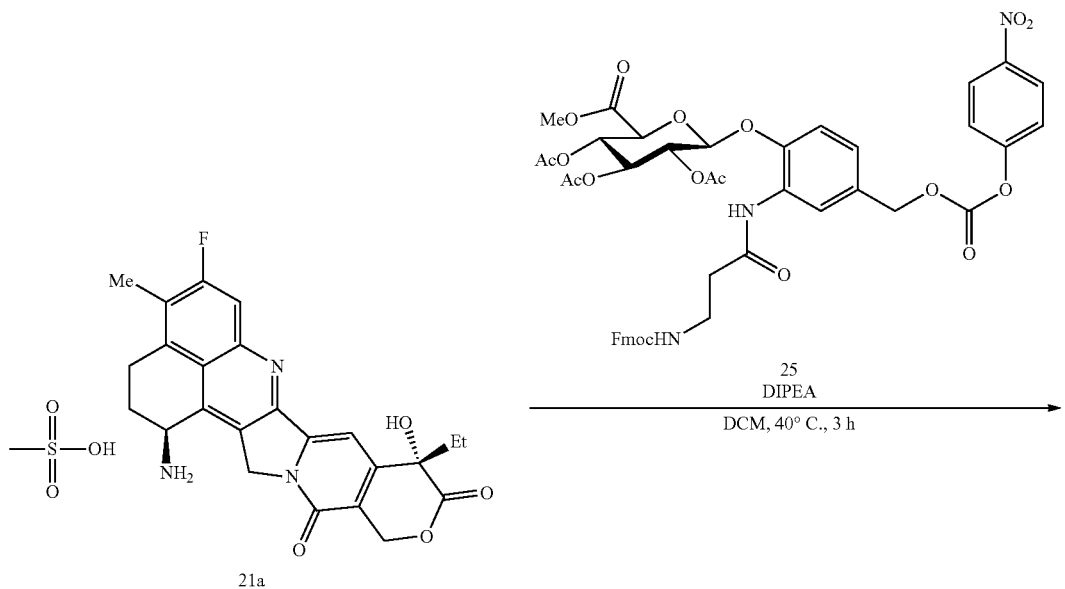

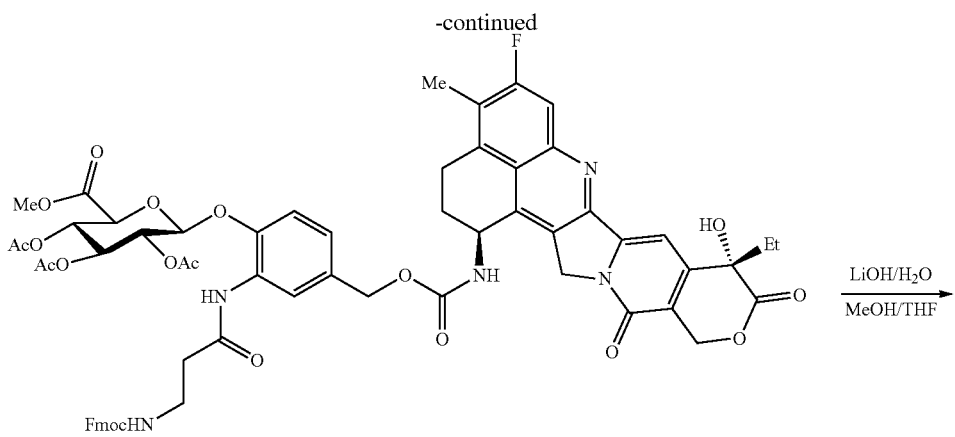

26

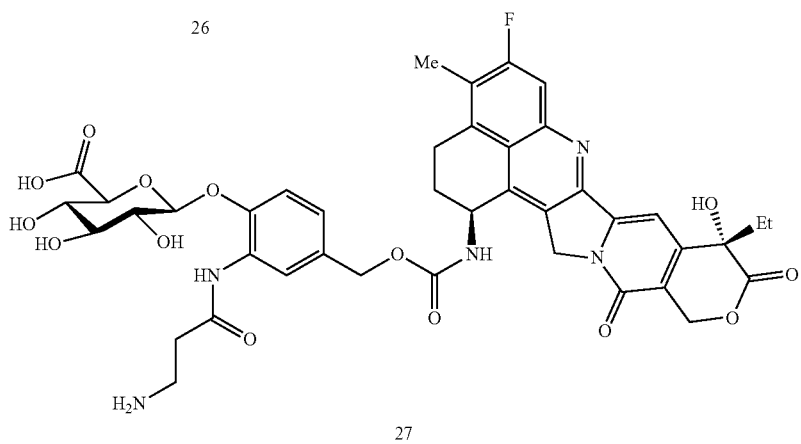

27

Exatecan mesylate (compound 21a, 5.00 mg, 9.41 μmol) was dissolved in anhydrous DCM. DIPEA (5.0 μL, 28 μmol) was added followed by compound 25 (17.2 mg, 18.8 μmol) previously described by *Bioconjugate Chem.* (2006) 17: 831-840. The reaction was stirred at 40° C. for 3 hours. The reaction was quenched with MeOH and concentrated in vacuo. The crude reaction mixture was used in the next step. LC-MS (Method A): $t_R$=2.32 min; MS (m/z) [M+H]$^+$ calc. for $C_{63}H_{61}FN_5O_{19}$ 1210.39, found 1210.08.

Crude compound 26 (9.41 μmol) from the previous step was dissolved in THF (1 mL), and 1M LiOH in MeOH (1 mL). The reaction was stirred for 5 minutes, then H$_2$O was added and stirred for an additional 5 minutes. The reaction was quenched with AcOH (100 μL), concentrated in vacuo and purified by prep-HPLC 21 mm 5-60-95% MeCN in H$_2$O 0.05% TFA. Fractions containing the desired product were lyophilized to afford compound 27 as a yellow powder (1.1 mg, 1.3 μmol). LC-MS (Method A): $t_R$=1.29 min; MS (m/z) [M+H]$^+$ calc. for $C_{41}H_{43}FN_5O_{14}$ 848.28, found 848.03.

Example 16

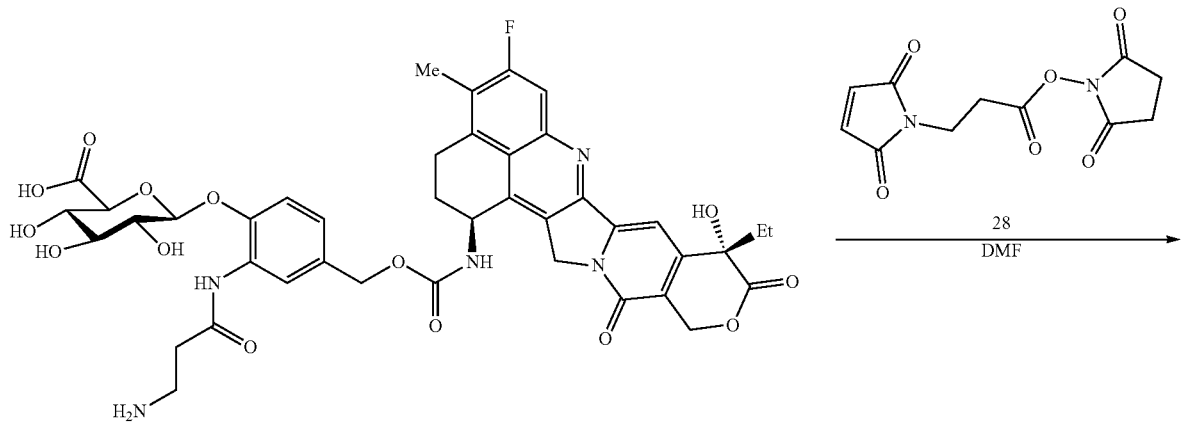

27

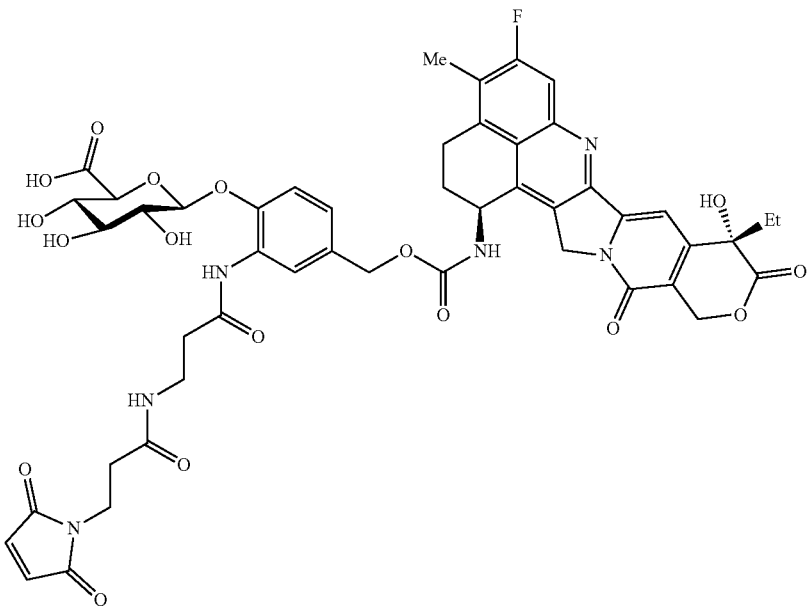

29

Compound 27 (1.1 mg, 1.3 μmol) was dissolved in anhydrous DMF (0.5 mL). DIPEA (1 μL) was added followed by N-Succinimidyl 3-Maleimidopropionate (28, 0.63 mg, 2.4 μmol) purchased from TCI (CAS: 55750-62-4). The reaction was stirred for 5 minutes. Complete conversion was observed by UPLC-MS. The reaction was quenched with AcOH (10 μL), then purified by prep-HPLC 10 mm 5-60-95% MeCN in H$_2$O 0.05% TFA. Fractions containing the desired product were lyophilized to afford compound 29 as a yellow powder (1.21 mg, 1.21 μmol, 93%). LC-MS (Method A): t$_R$=1.52 min; MS (m/z) [M+H]$^+$ calc. for C$_{48}$H$_{48}$FN$_6$O$_{17}$ 999.31, found 999.07.

Example 17

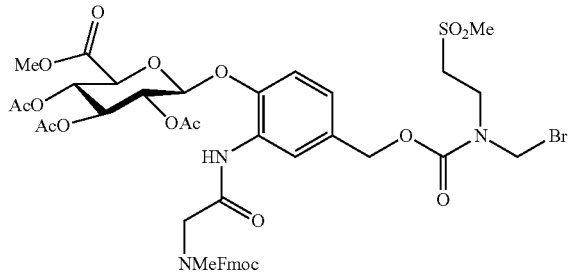

31

Compound 30 (210 mg, 0.234 mmol), prepared as described by Examples 21 and 22, was dissolved in bench DCM (3 mL). Paraformaldehyde (300-600 mg, xs) was added. Stirring vigorously, TMSBr (0.1 mL) was added. Reaction stirred for 10 minutes at which time complete conversion was observed by UPLC-MS. Reaction mixture was filtered through syringe filter, rinsed DCM (2×3 mL), toluene (3 mL) was added to azeotrope the final mixture. Concentrated in vacuo to afford a white solid. Used in next step without further purification. MeOH diluent was used to observe MeOH quenched adduct by UPLC-MS. LC-MS (Method A): t$_R$=2.19 min; MS (m/z) [M+Na]$^+$ calc. for C$_{44}$H$_{51}$N$_3$NaO$_{18}$S 964.28, found 965.17.

Example 18

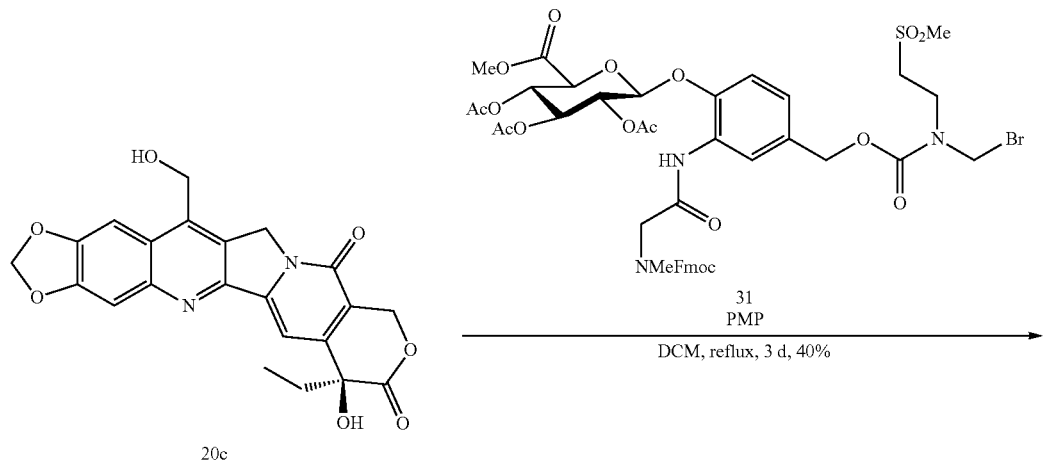

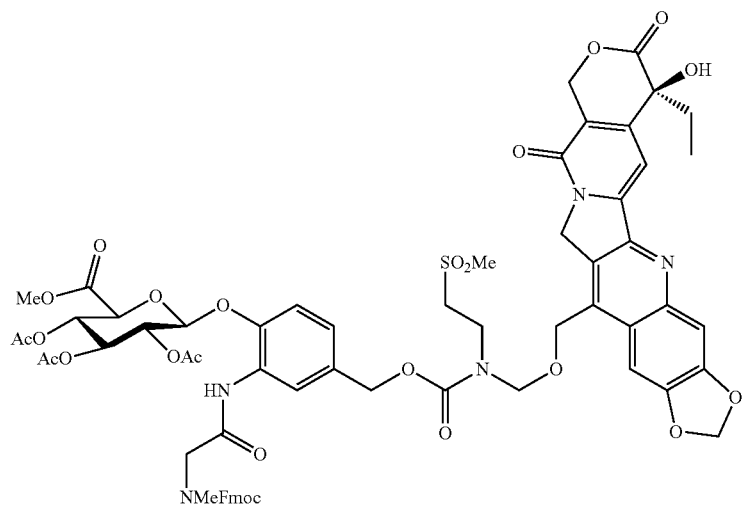

Compound 20c (20 mg, 0.047 mmol), referred to as 7-BAD-MDCPT, was azeotroped 3 times with toluene and dried under high vacuum prior to use. Crude compound 31 (231 mg, 0.234 mmol) from Example 16 was dissolved in anhydrous DCM, and 1,2,2,6,6-pentamethylpiperidine (PMP, 51.4 µL, 0.284 mmol) was added. Minimal hydrolysis of compound 31 in solution was observed by UPLC-MS after base addition. The solution of compound 31 was added directly to the drug reaction vessel, then heated to reflux. Compound 20c is only slightly soluble in DCM. Reaction was monitored by UPLC-MS for completion, which required heating at reflux for 3 days. Afterwards, the reaction was quenched with MeOH, concentrated in vacuo, and purified by FCC Biotage 10G Ultra 0-10% MeOH in DCM. Fractions containing the desired product (compound 32) were concentrated to afford a yellow solid (50 mg, ~50% w/w, 0.019 mmol, 40%) as an approximately 50% w/w mixture with dimerized hydrolyzed linker. $t_R$=1.46 min (General Method UPLC); MS (m/z) [M+H]$^+$ calc. for $C_{65}H_{66}N_5O_{24}S$ 1332.38, found 1332.54.

Example 19

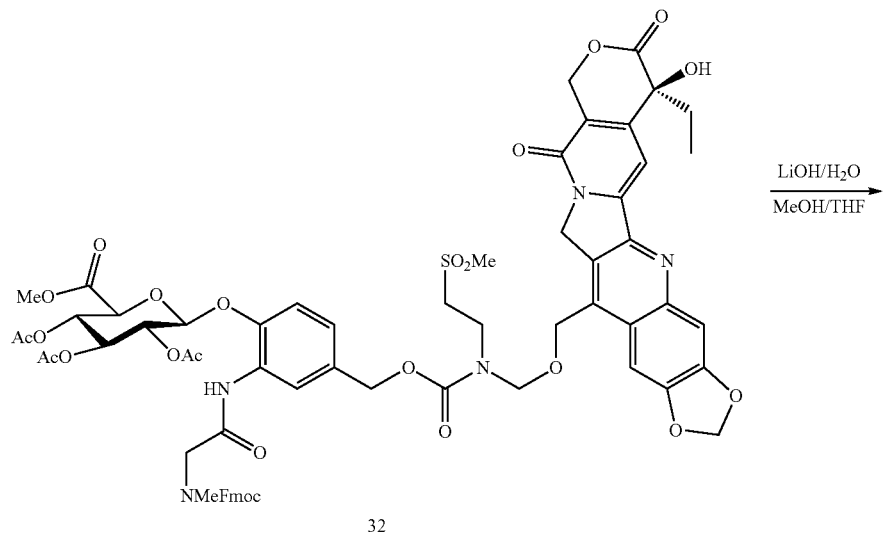

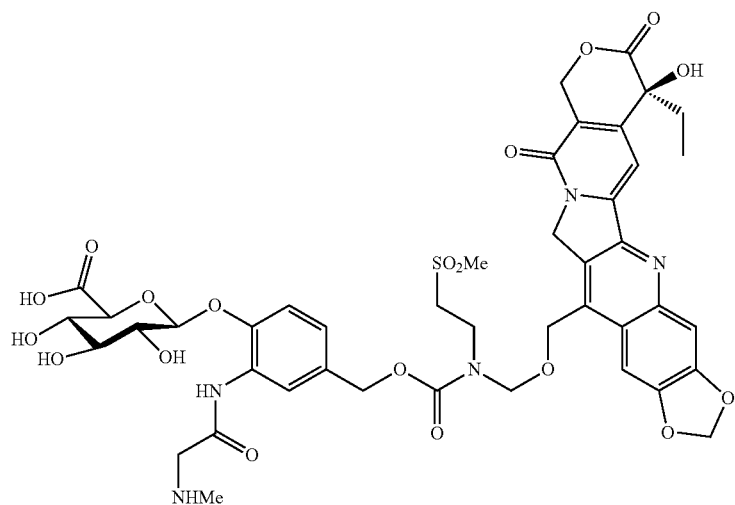

Compound 32 (50 mg, 50% w/w, 0.019 mmol) was dissolved in MeOH:THF 1:1 (1 mL). LiOH (20 mg, 0.84 mmol) was added and stirred for 60 minutes. Water (0.5 mL) was added. Complete conversion was observed by UPLC-MS. Reaction was quenched with AcOH, concentrated in vacuo, and purified by Prep-HPLC. Fractions containing the desired product were lyophilized to afford the desired product, compound 33, as a yellow solid (5 mg, 0.005 mmol, 27%). LC-MS (Method A): $t_R$=0.84 min; MS (m/z) [M+H]$^+$ calc. for $C_{43}H_{48}N_5O_{19}S$ 970.27, found 969.92.

Example 20

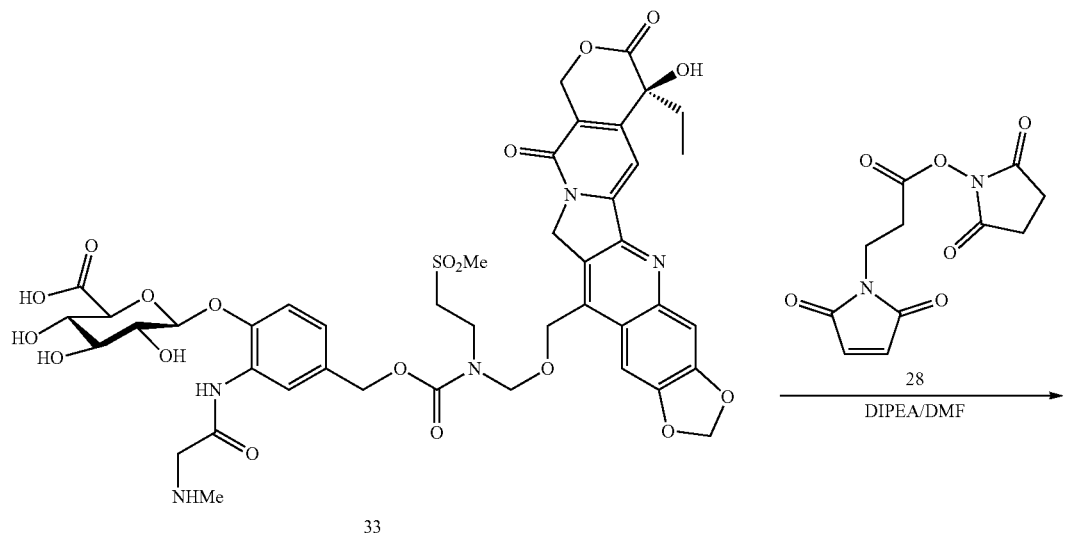

33

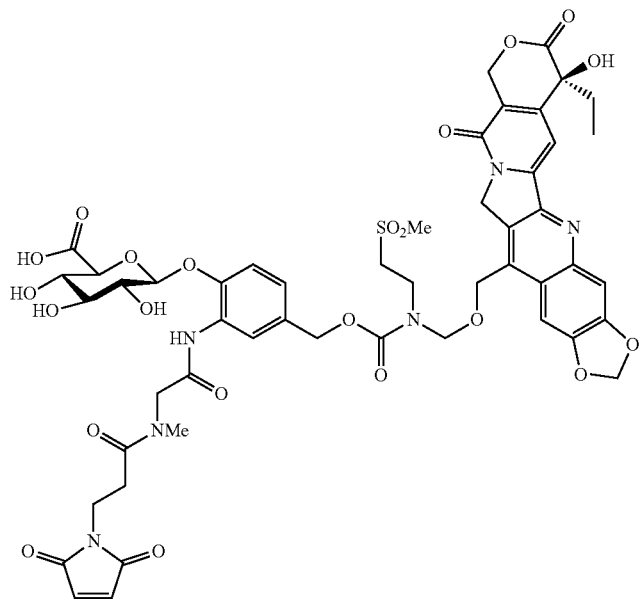

34

Compound 33 (5 mg, 0.005 mmol) was dissolved in DMF (0.5 mL). DIPEA (10 μL) added followed by 3-(maleimido)-propionic acid N-hydroxysuccinimide ester (28, 4.1 mg, 0.016 mmol) and stirred for 45 minutes at which point complete conversion was observed by UPLC-MS. The reaction was quenched with AcOH (20 μL) and purified by Prep-HPLC 10 mm Max-RP C125-60-95% MeCN in $H_2O$. Fractions containing the desired product compound 34 were lyophilized to afford a yellow powder (2.33 mg, 2.08 μmol, 40.3%). LC-MS (Method A): $t_R$=1.35 min; MS (m/z) [M+H]$^+$ calc. for $C_{50}H_{53}N_6O_{22}S$ 1121.29, found 1121.25.

Example 21

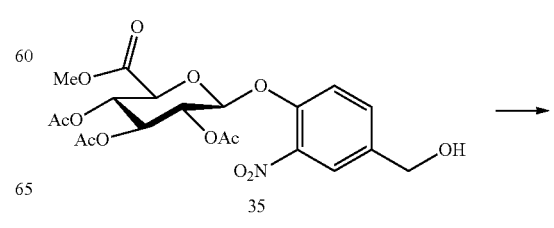

35

-continued

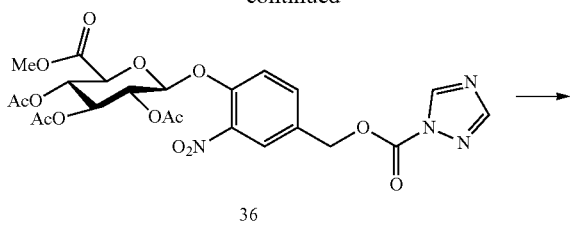

36

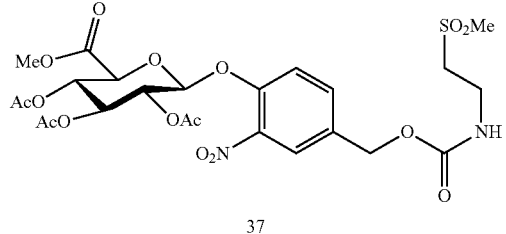

37

Compound 35 (2.00 g, 4.12 mmol), prepared according to the procedure in *Bioconjugate Chem.* (2006) 17: 831-840, was dissolved in anhydrous DCM (20 mL). DIPEA (3.59 mL, 20.60 mmol) was added followed by 1,1'-Carbonyl-di-(1,2,4-triazole) (744 mg, 4.53 mmol). The reaction was stirred for 5 minutes, and the reaction mixture containing compound 36 was used in the next step.

To the reaction mixture containing compound 36 (4.12 mmol) was added 2-(methylsulfonyl)-ethanamine (0.61 mL, 6.2 mmol). The reaction as stirred for 5 minutes at which time complete conversion was observed by UPLC-MS. The reaction was concentrated in vacuo and purified by column chromatography KP-Sil 100G 10-100% EtOAc in Hex. Fractions containing the desired product were concentrated in vacuo to afford compound 37 as a colorless solid (2.40 g, 3.78 mmol, 92%). LC-MS (Method A): $t_R$=1.71 min; MS (m/z) [M+Na]$^+$ calc. for $C_{24}H_{30}N_2NaO_{16}S$ 657.12, found 656.93.

Example 22

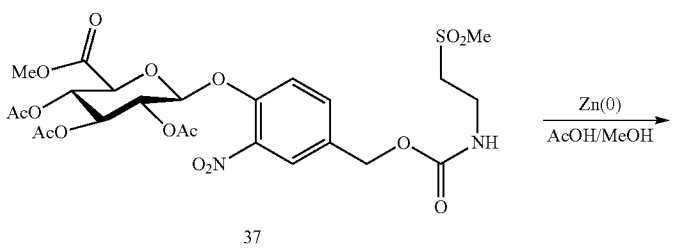

37

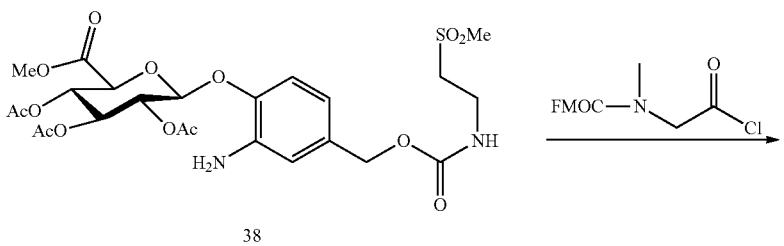

38

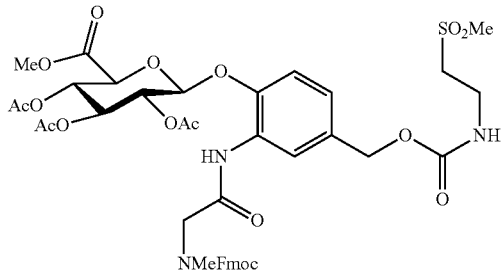

30

Compound 37 (2.40 g, 3.78 mmol) was dissolved in MeOH (20 mL). AcOH (10 mL) was added to the reaction followed by zinc dust (7.42 g, 113 mmol). The reaction was stirred for 20 minutes at which time complete conversion was observed by UPLC-MS. The reaction was filtered through silica eluting with 20% MeOH in DCM. The eluent was concentrated and used in the next step.

Crude compound 38 (3.78 mmol) was dissolved in anhydrous DCM (10 ml). DIPEA (3.30 mL, 18.9 mmol) was added followed by Fmoc-Sar-Cl (2.50 g, 7.58 mmol). The reaction was stirred for 5 minutes at which point complete conversion was observed by UPLC-MS. The reaction was quenched MeOH, concentrated in vacuo and purified by column chromatography KP-Sil 100G 10-100% EtOAc in Hex. Fractions containing the desired product were concentrated in vacuo to afford compound 30 as a colorless solid. LC-MS (Method A): $t_R$=2.17 min; MS (m/z) [M+H]$^+$ calc. for $C_{42}H_{48}N_3O_{17}S$ 898.27, found 898.09.

Example 23

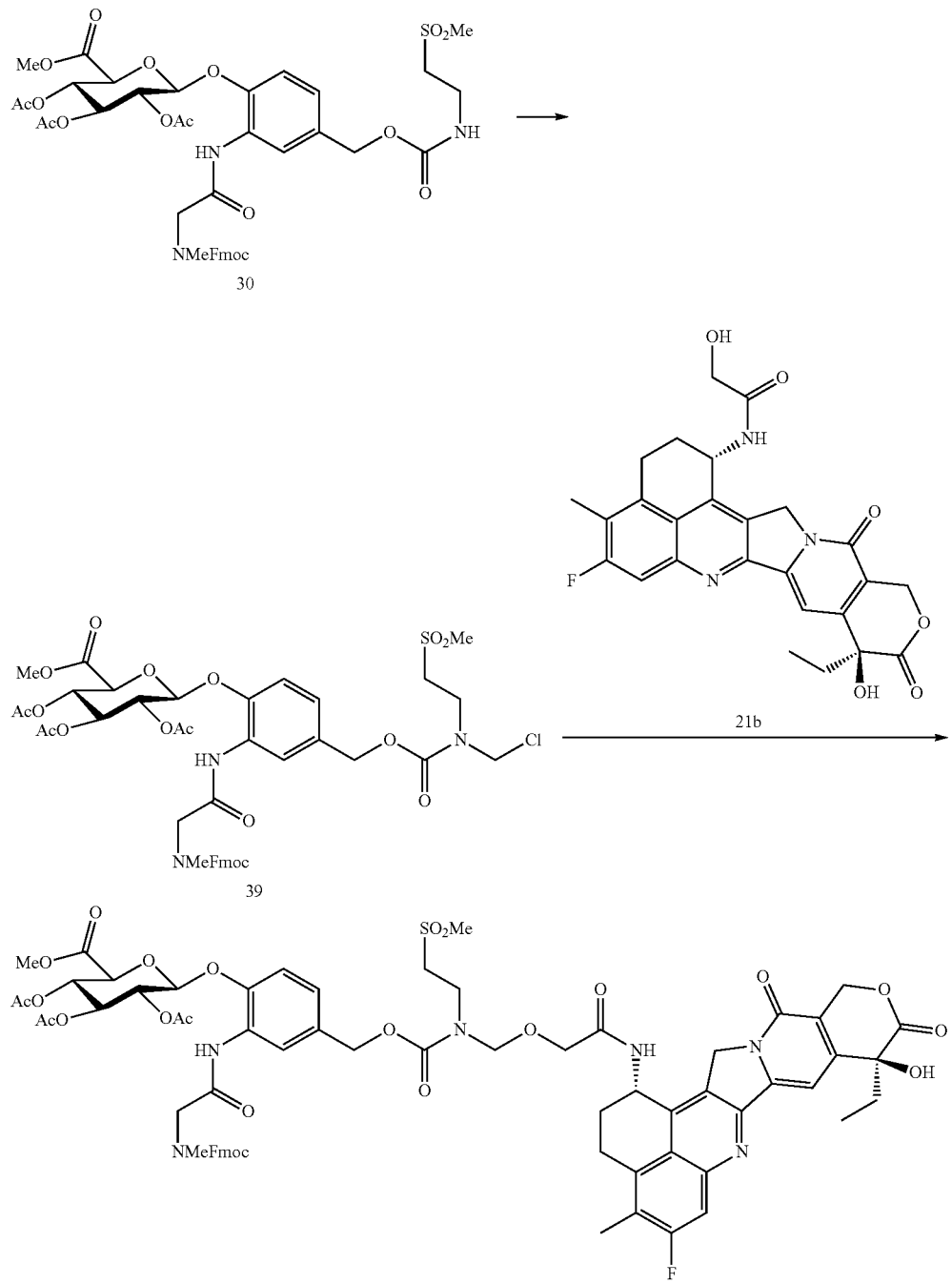

Compound 30 (200 mg, 0.223 mmol) was dissolved in DCM (2 mL). Paraformaldehyde (200 mg, 6.68 mmol) was added, followed by TMSCl (1 mL). The reaction was stirred for 15 minutes, then filtered, rinsed DCM (2×2 mL), and toluene (2 mL) was added to azeotrope the final mixture. The eluent was concentrated to afford a white solid. The crude compound 39 was used immediately in the next step.

Crude compound 39 (0.223 mmol) was dissolved in anhydrous DCM (1 mL). DIPEA (0.047 mL, 0.27 mmol) was added to the reaction. The reaction solution was added directly to the solid compound 21-b (22 mg, 0.045 mmol). The reaction was stirred for 120 minutes. The reaction was quenched with MeOH, concentrated in vacuo and purified by column chromatography 0-10% MeOH in DCM. Fractions containing the desired product and minor impurity concentrated in vacuo to afford compound 40 as a white solid (30 mg, 80% w/w, 0.021 mmol, 48%). LC-MS (Method A): $t_R$=2.25 min; MS (m/z) [M+H]$^+$ calc. for $C_{69}H_{72}FN_6O_{23}S$ 1403.44, found 1404.03.

Example 24

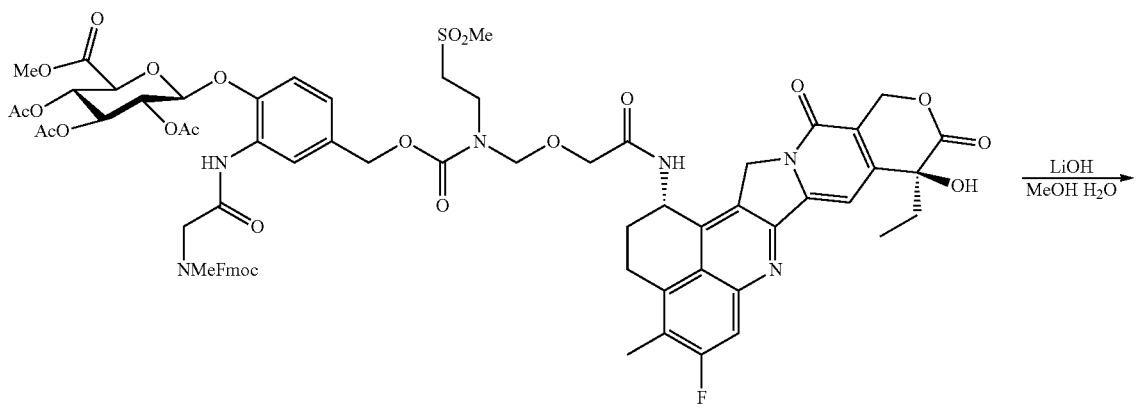

40

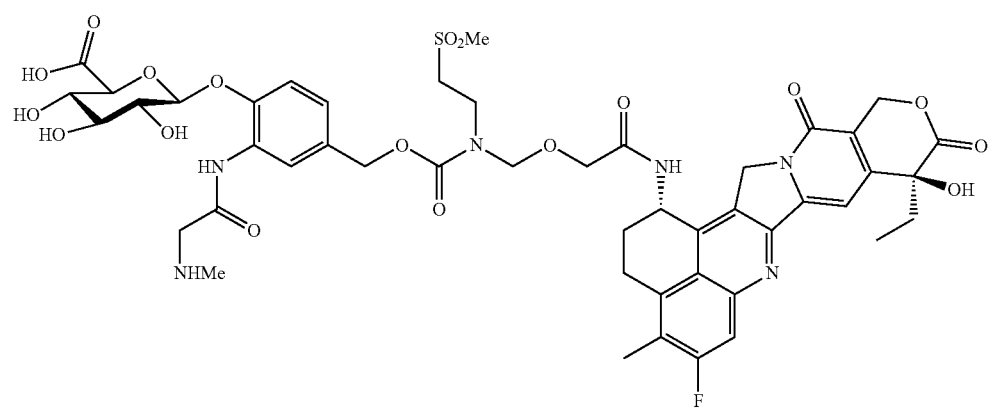

41

Compound 40 (30 mg, 0.021 mmol) was dissolved in MeOH (1 mL). LiOH (25 mg, 1.1 mmol) was added to the reaction, and the reaction was sonicated to aid in dissolution. The reaction was stirred for 10 minutes then H$_2$O (1 mL) was added. The reaction was stirred an additional 20 minutes then quenched with AcOH. The reaction was concentrated in vacuo and purified by prep-HPLC 21 mm 5-60-95% MeCN in H$_2$O 0.05% TFA. Fractions containing the desired product were purified to afford compound 41 as a white solid (14.5 mg, 0.0139 mmol, 65%). LC-MS (Method A): $t_R$=1.29 min; MS (m/z) [M+H]$^+$ calc. for $C_{47}H_{54}FN_6O_{18}S$ 1041.32, found 1041.24.

Example 25

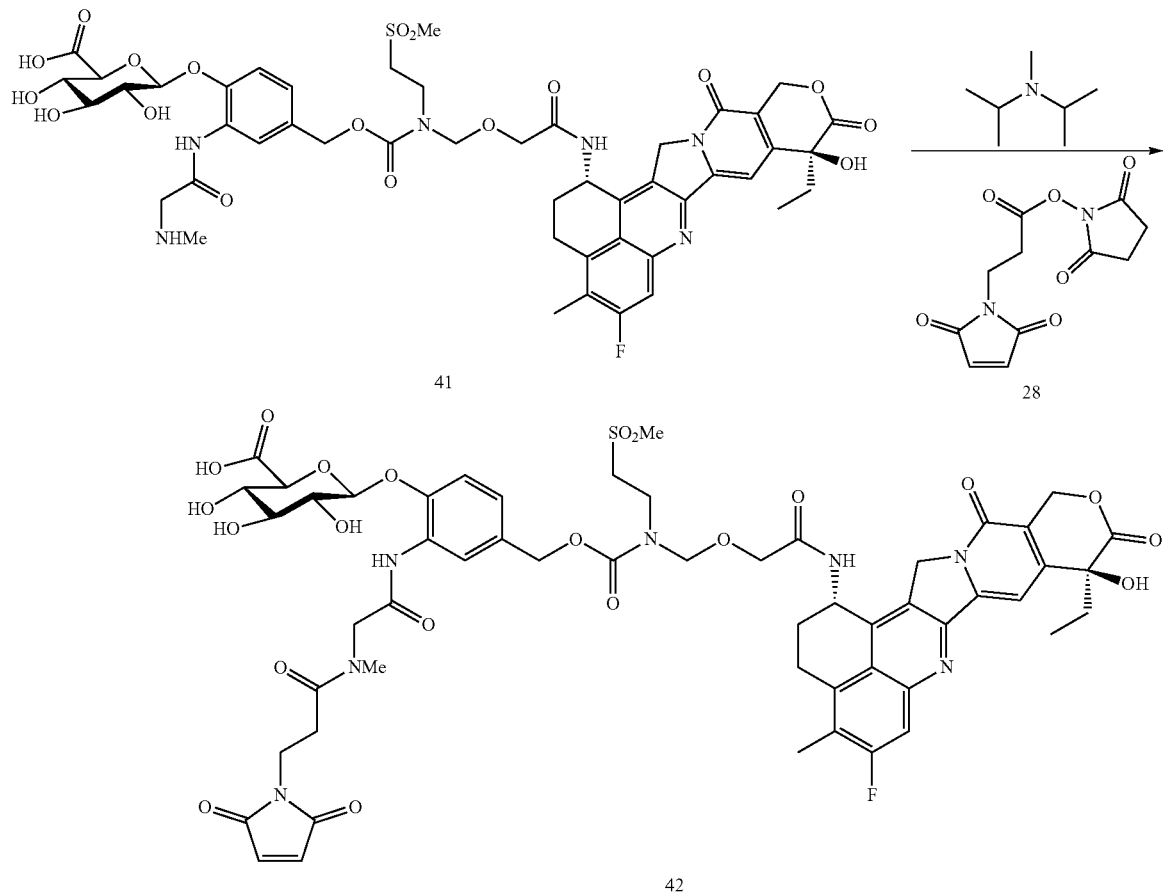

Compound 41 (14.5 mg, 0.0139 mmol) was dissolved in anhydrous DMF (0.5 mL). DIPEA (15 μL, 0.084 mmol) was added followed by 3-(maleimido)-propionic acid N-hydroxysuccinimide ester (28, 11 mg, 0.042 mmol). The reaction was stirred at room temperature for 80 minutes. The reaction was quenched with AcOH and purified by prep-HPLC 10 mm 5-60-95% MeCN in H$_2$O 0.05% TFA. Fractions containing the desired product were lyophilized to afford compound 42 as a yellow solid (2.24 mg, 1.88 μmol, 13%). LC-MS (Method A): t$_R$=1.49 min; MS (m/z) [M+H]$^+$ calc. for C$_{54}$H$_{59}$FN$_7$O$_{21}$S 1192.35, found 1192.31.

Example 26

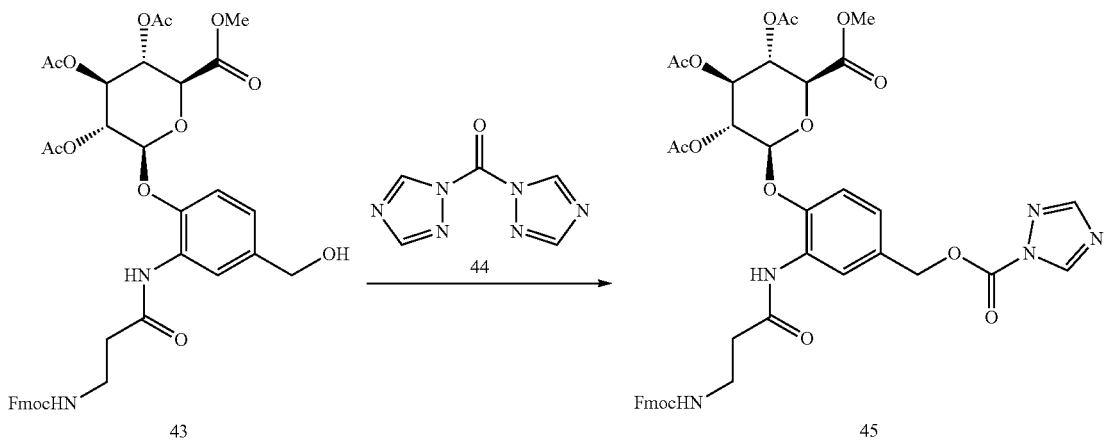

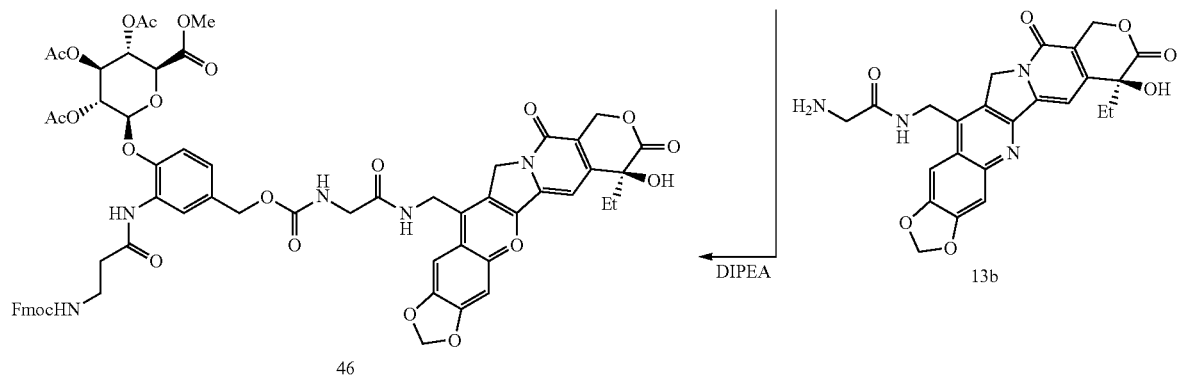

46

Compound 43 (200 mg, 0.267 mmol), prepared according to the procedure of *Bioconjugate Chem.* (2006) 17: 831-840), was dissolved in DCM (1 mL). Carbonyl ditriazole (44, 131.52 mg, 0.801 mmol) was added and the reaction was stirred for 30 minutes. Complete conversion was observed by UPLC-MS. The reaction was diluted with EtOAc (50 mL), and washed $H_2O$ (3×50 mL). The organic was dried with $MgSO_4$, filtered and concentrated in vacuo to afford compound 45 as a white solid (209 mg, 0.248 mmol, 93%). LC-MS (Method D): $t_R$=2.07 min; MS (m/z) $[M+H]^+$ calc. for $C_{41}H_{42}N_5O_{15}$ 844.27, found 844.02. The product was used in the next step without further purification.

Compound 45 (100 mg, 0.119 mmol) and compound 13b (18 mg, 0.039 mmol), referred to as H-Gly-7-MAD-MDCPT, were dissolved in DMF (0.5 mL). DIPEA (0.1 mL) was added and the reaction was stirred at room temperature. Approximately 50% conversion observed to the desired product, compound 46, with hydrolysis of compound 45 was observed after 15 minutes. Note: Compound 46 and hydrolysis product had the same retention time by UPLC-MS. Reaction was quenched AcOH and concentrated in vacuo, then purified by column chromatography 0-5% MeOH in DCM. Fractions containing compound 46 with 50% compound 13b impurity were concentrated to afford a white solid (46 mg, 50% w/w, 0.018 mmol, 46%). LC-MS (Method E): $t_R$=1.32 min; MS (m/z) $[M+H]^+$ calc. for $C_{63}H_{61}N_6O_{22}$ 1253.38, found 1253.47.

Example 27

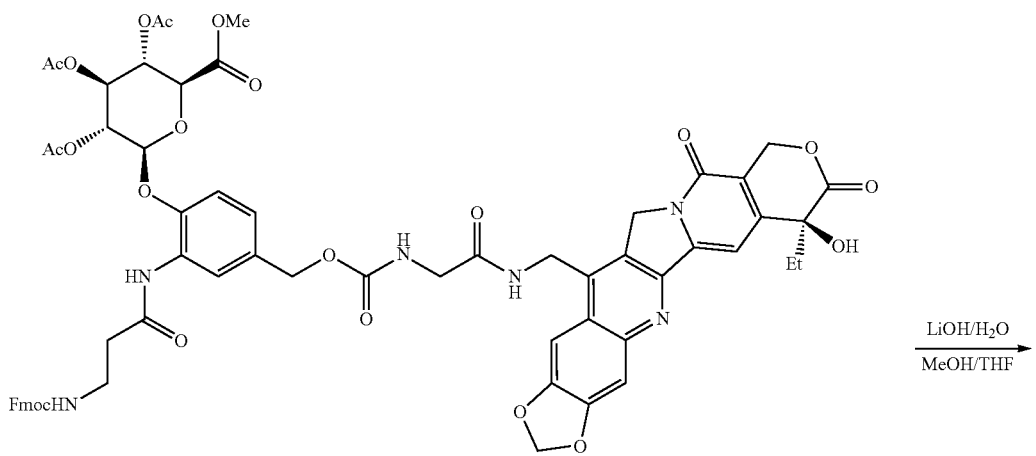

46

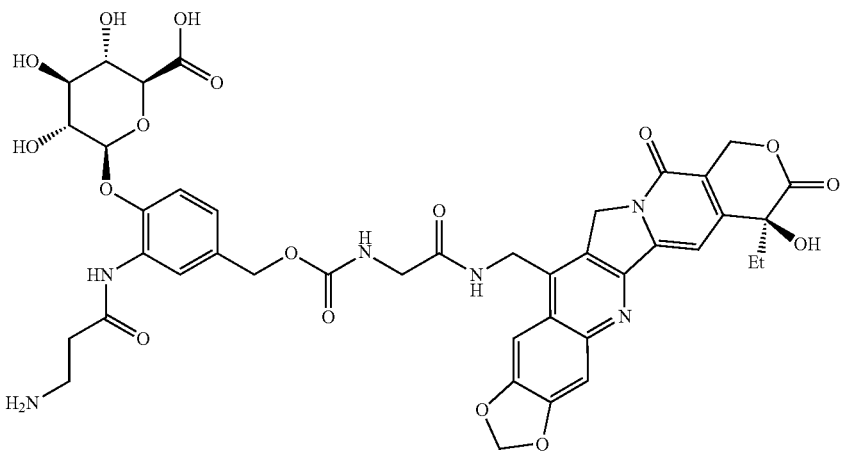

47

Compound 46 (0.018 mmol) was dissolved in MeOH (0.5 mL) and THF (0.5 mL). LiOH (25 mg, 1.0 mmol) was added. The reaction was sonicated to solubilize LiOH and stirred. After 10 minutes water was added (0.5 mL). Complete conversion was observed by UPLC-MS after 100 minutes. The reaction was quenched with AcOH (0.2 mL). The reaction was concentrated, then purified by Prep-HPLC using a 10 mm Max-RP with a 5-60-95 MeCN in H$_2$O 0.05% TFA gradient. Fractions containing the desired product compound 47 were concentrated in vacuo to afford a yellow solid (8.4 mg, 9.4 μmol, 51%). LC-MS (Method D): $t_R$=0.92 min; MS (m/z) [M+H]$^+$ calc. for C$_{41}$H$_{43}$N$_6$O$_{17}$ 891.27, found 891.06.

Example 28

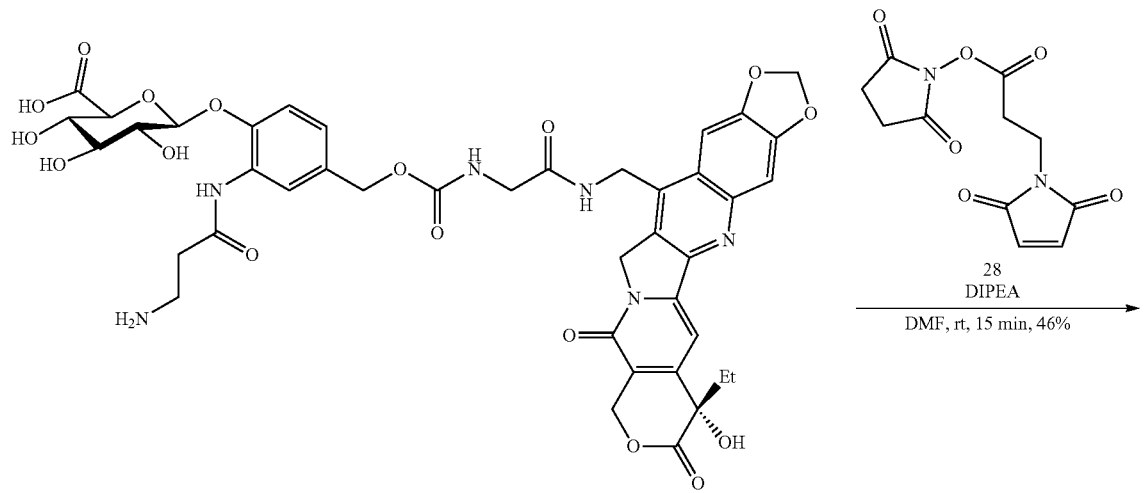

47

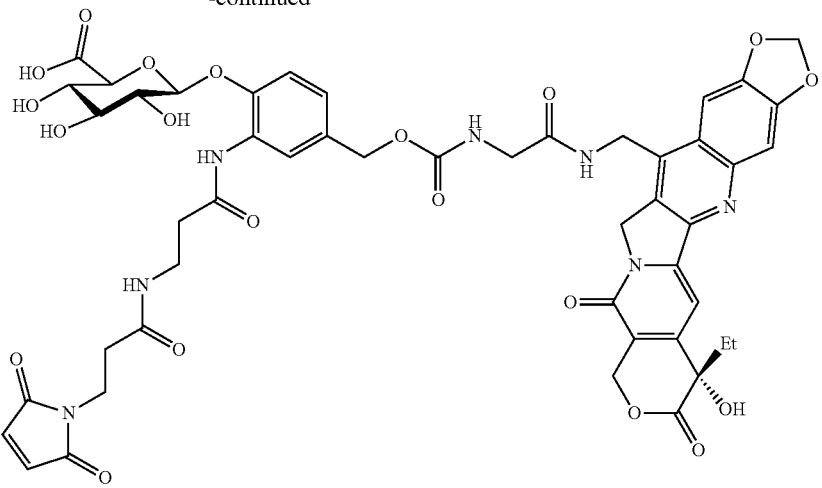

48

Compound 47 (8.4 mg, 9.4 μmol) was dissolved in DMF (0.2 mL). 3-(Maleimido)propionic acid N-hydroxysuccinimide ester (28, 7.5 mg, 0.028 mmol) was added. DIPEA (9 μL, 0.05 mmol) was added. The reaction was stirred for 5 minutes at which point complete conversion was observed by UPLC-MS. The reaction was quenched with AcOH (0.05 mL), the purified by Prep-HPLC 10 mm Max RP C12. Fractions containing the desired product were lyophilized to afford a yellow powder with 10% impurity. The crude lyophilized product was re-purified by Prep-HPLC 10 mm Max-RP C12 fractions containing the desired product were lyophilized to afford compound 48 as a yellow solid (1.33 mg, 1.28 μmol, 13.5%). LC-MS (Method D): $t_R$=1.08 min; MS (m/z) [M+H]$^+$ calc. for $C_{48}H_{48}N_7O_{20}$ 1042.30, found 1042.19.

Example 29

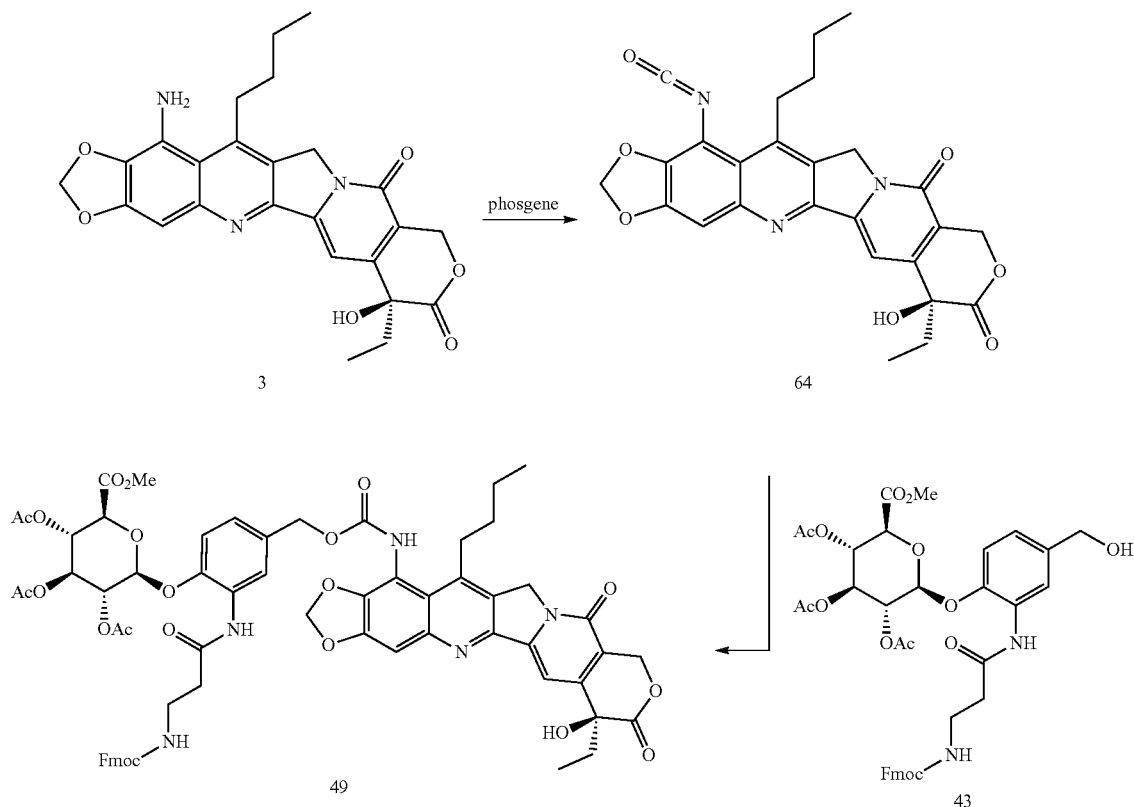

A flame dried flask was charged with compound 3 (30 mg, 65 µmol) and flushed with N₂. Anhydrous DCM (3.25 mL) was added followed by phosgene (20% in toluene, 1.2 mL). The reaction was capped and stirred for 24 h. Isocyanate formation was confirmed by spiking reaction mixture into MeOH and observing methyl carbamate adduct. LC-MS (Method A): $t_R$=1.58 min, MS m/z (ES+) found 522.32. The reaction was stirred to dryness under N₂ stream, placed under high vacuum for 1 h to provide compound 64, which was carried forward without further purification.

Compound 43 (103 mg, 138 µmol), prepared according to the procedure of *Bioconjugate Chem.* (2006) 17: 831-840, was solubilized in anhydrous DMF (1.5 mL) and added to a flask charged with compound 64 (32 mg, 65 µmol). The reaction was stirred under N₂ for 24h then concentrated in vacuo to dryness. Crude mixture was loaded onto a 1 mM chromatotron plate and eluted with DCM/MeOH (1%, 2%, 3% MeOH gradient) to yield compound 49 (25 mg, 31%). LC-MS (Method A): $t_R$=2.23 min; MS (m/z) calculated 1238.22 (M+H)⁺, found 1238.40.

Example 30

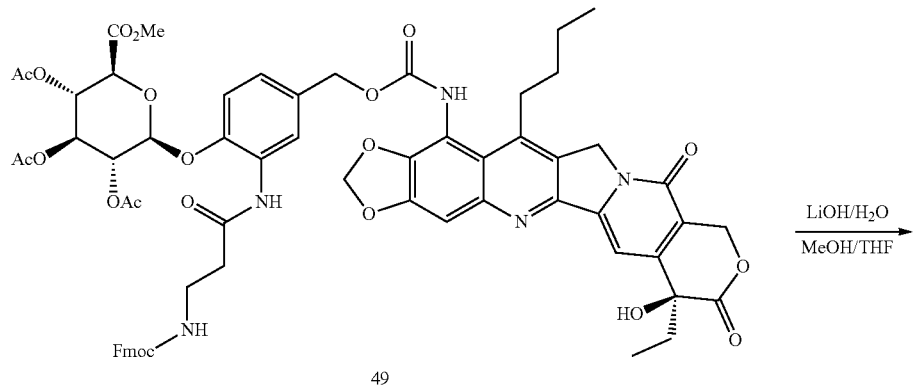

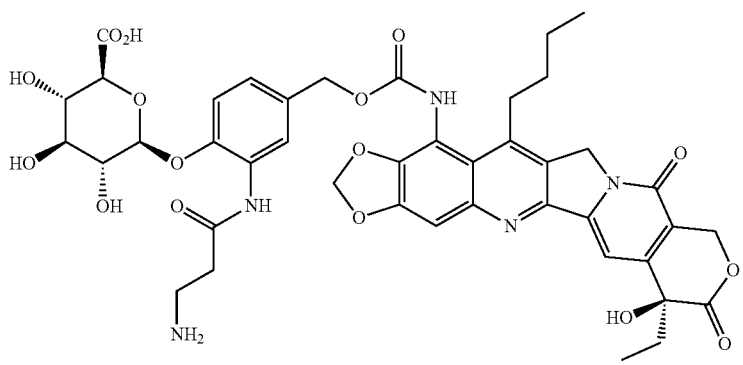

Compound 49 (3, 41 mg, 33 µmol) was solubilized in MeOH (1.1 mL) and THF (1.1 mL) then cooled to 0° C. LiOH monohydrate (14 mg, 333 µmol) was taken up in H₂O (1.1 mL) then added to the reaction dropwise with stirring. The reaction was allowed to warm to RT and stopped after 4.5 h. MeOH and THF were removed in vacuo, DMSO was added to solubilize, then the reaction was purified by preparative HPLC to provide compound 50 (9 mg, 31%). LC-MS (Method A): $t_R$=1.16 min; MS m/z (ES+) found 876.23.

Example 31

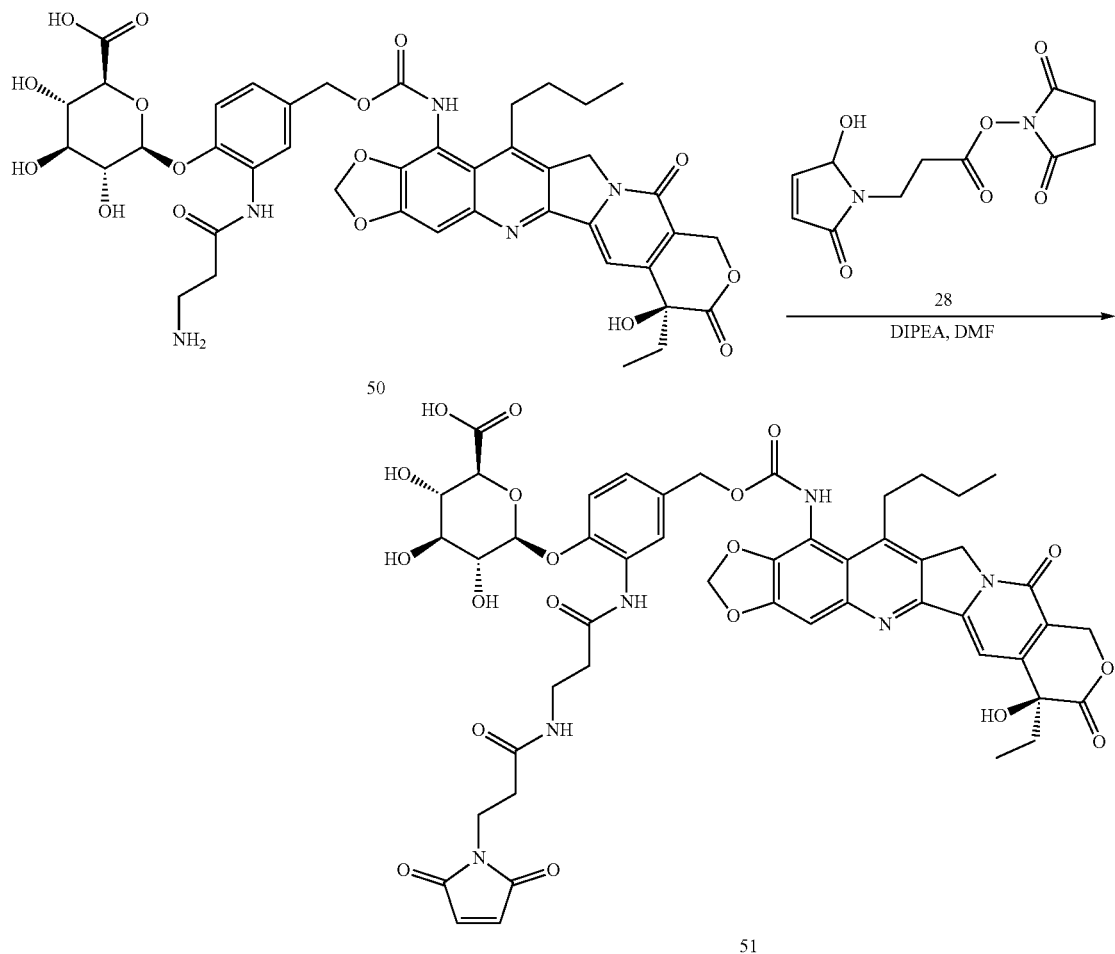

3-(Maleimido)propionic acid N-hydroxysuccinimide ester (28) was dissolved in anhydrous DMF and added to compound 50 to a final concentration of 30 mM, followed by addition of DIPEA. The reaction was monitored by LC-MS. Upon completion, the solution was neutralized with acetic acid, concentrated, and then purified by preparative HPLC to yield compound 51. LC-MS (Method A): $t_R$=1.36 min, MS (m/z) calculated 1026.96 (M+H)$^+$, found 1027.21.

Example 32

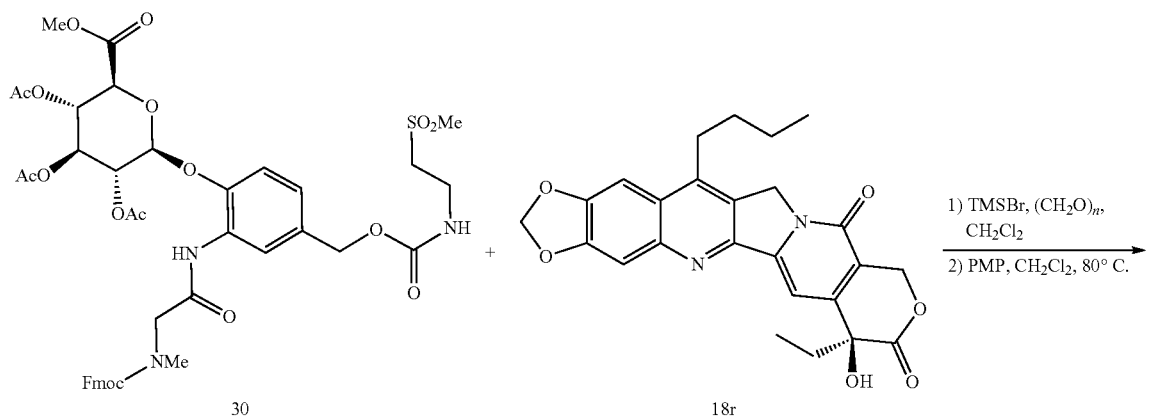

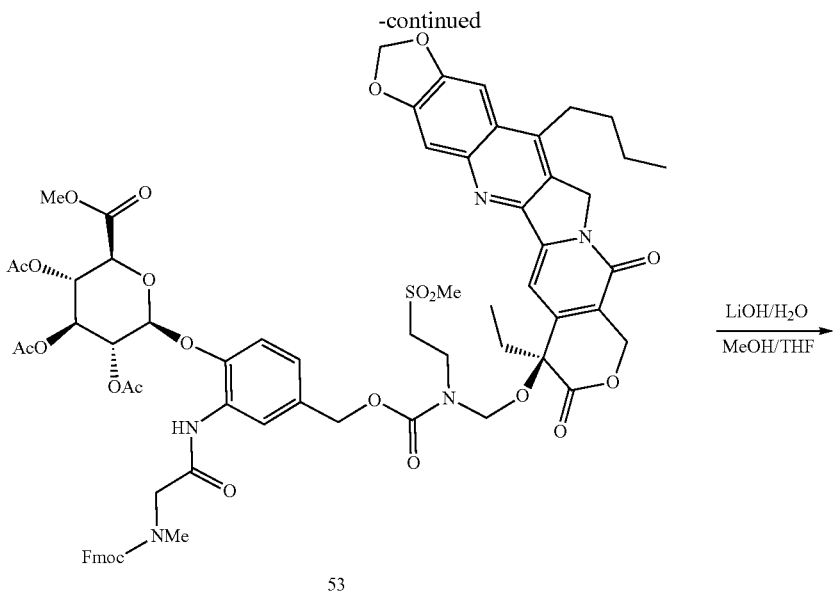

53

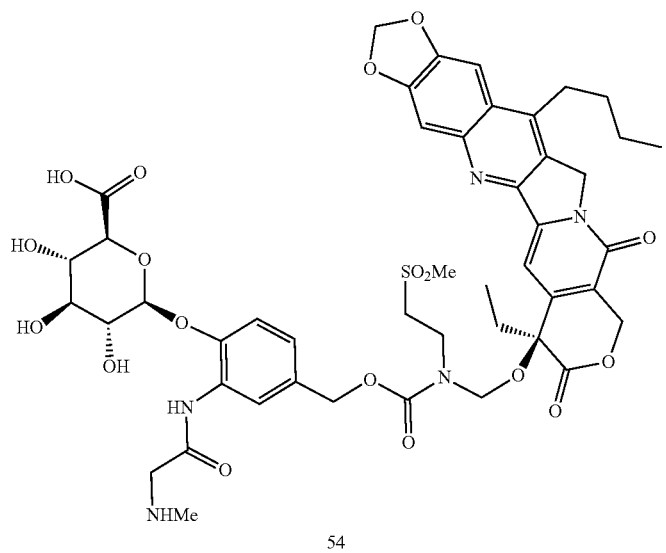

54

In an oven dried flask, compound 30 (162 mg, 180 μmol), prepared as described in Example 21, was dissolved in anhydrous dichloromethane (1 mL), followed by the addition of paraformaldehyde (10.8 mg, 0.36 mmol) and TMSBr (250 μL, 1.40 mmol). The solution was stirred at room temperature for 10 min with monitoring by quenching with methanol and observing the formation of the methanol adduct by LC-MS. The reaction was filtered, washed with anhydrous toluene and dichloromethane, and dried in vacuo for 3 cycles to yield the crude product, which was used in the subsequent reaction without further purification. The crude compound was re-dissolved in anhydrous dichloromethane and added to compound 18r (32.3 mg, 72 μmol), prepared according to the procedure in Bioconjugate Chem. (2009) 20: 1242-1250, followed by 1,2,2,6,6-pentamethylpiperidine (PMP, 200 μL, 0.96 mmol). The reaction was capped, microwaved at 80° C. for 2 h, and monitored by LC-MS. Upon completion, the solvent was removed and purified by preparative HPLC to yield the desired product, compound 53. MS (m/z) calculated 1358.39 (M+H)$^+$, found 1358.03.

Crude compound 53 was dissolved in MeOH and THF, and cooled to 0° C. LiOH in H$_2$O was slowly added to the reaction flask to a final concentration of 10 mM. The reaction was warmed to room temperature, and monitored by LC-MS. Upon completion, the solution was neutralized with acetic acid, concentrated, and then purified by preparative HPLC to yield compound 54. MS (m/z) calculated 996.01 (M+H)$^+$, found 996.36.

Example 33

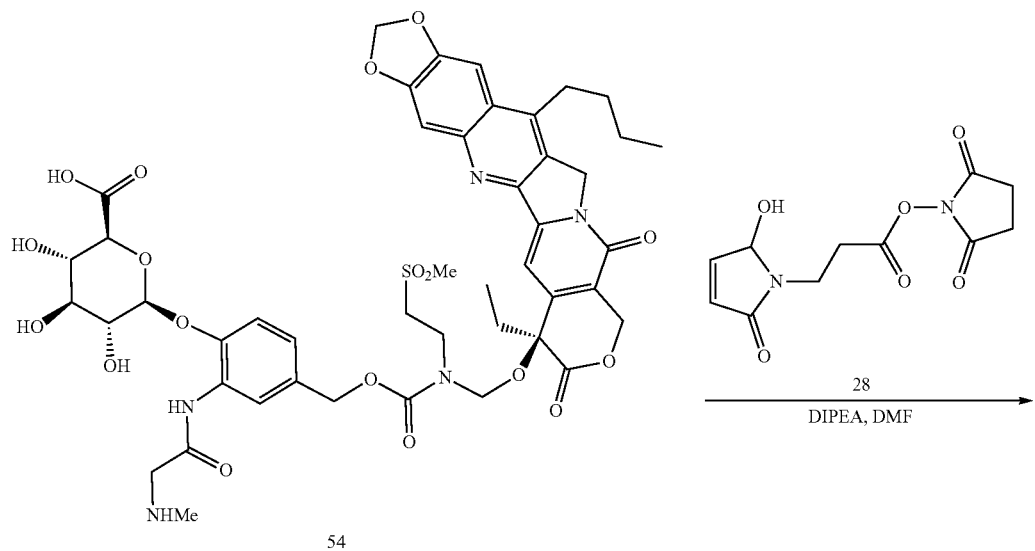

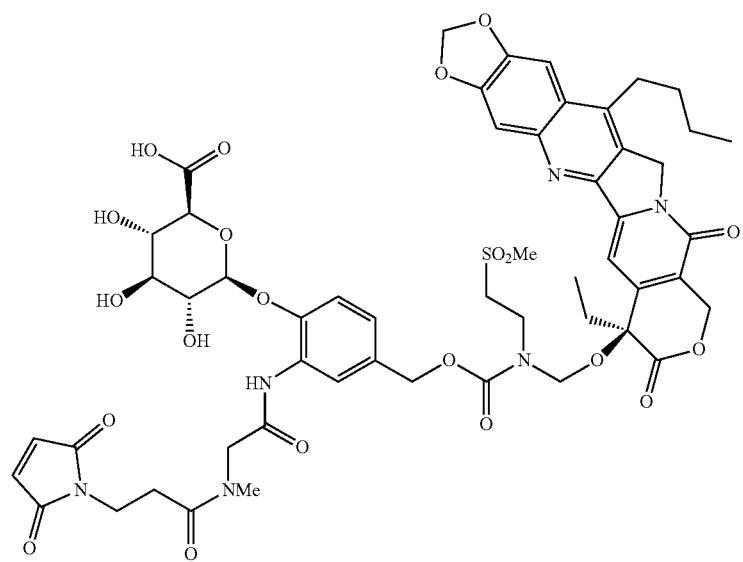

3-(Maleimido)propionic acid N-hydroxysuccinimide ester (28) was dissolved in anhydrous DMF and added to compound 54 to a final concentration of 30 mM, followed by addition of DIPEA. The reaction was monitored by LC-MS. Upon completion, the solution was neutralized with acetic acid, concentrated, and then purified by preparative HPLC to yield compound 55. LC-MS (Method A): $t_R$=1.75 min, MS (m/z) calculated 1147.13 (M+H)$^+$, found 1147.02.

Example 34

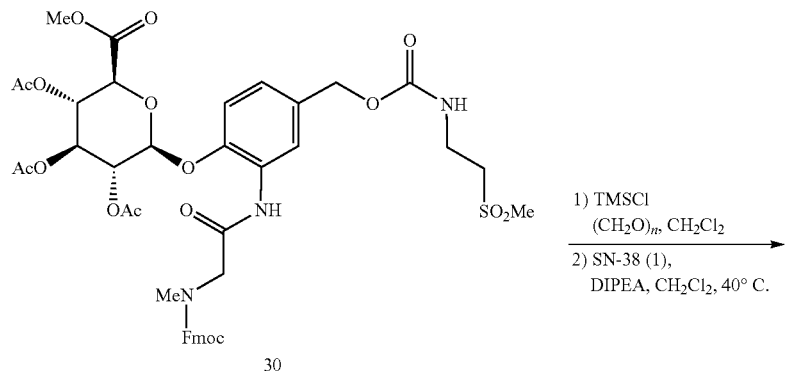

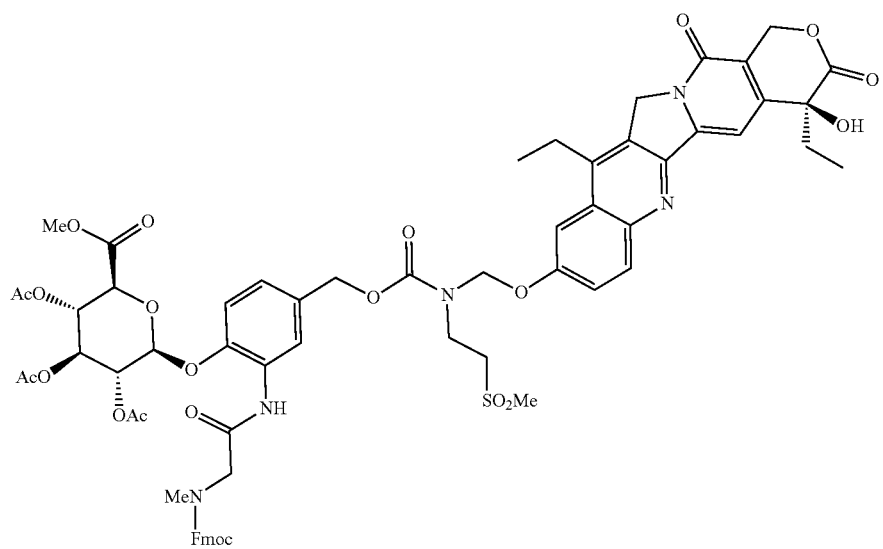

In an oven dried flask compound 30 (1235 mg, 1.38 mmol), prepared as described in Example 21, was dissolved in anhydrous dichloromethane (5 mL), followed by the addition of paraformaldehyde (13.8 mg, 0.46 mmol) and TMSCl (1.0 mL, 7.88 mmol). The solution was stirred at room temperature for 30 min with monitoring by quenching with methanol and observing the formation of the methanol adduct by LC-MS. MS (m/z) calculated for the methanol adduct 942.29 (M+H)$^+$, found 942.28. The reaction was filtered, washed with anhydrous toluene and dichloromethane, and dried in vacuo for 103 cycles. The crude product was dissolved in anhydrous dichloromethane (6 mL) and DIPEA (359 μL, 2.06 mmol), and added to the flask containing SN-38 (compound 1, 90 mg, 0.23 mmol). The reaction was capped and stirred at 40° C. for 18 h. The reaction mixture was purified over silica via Biotage flash column chromatography (CH$_2$Cl$_2$/MeOH, 0-10%) to yield compound 56. MS (m/z) calculated 1302.40 (M+H)$^+$, found 1302.36.

Example 35
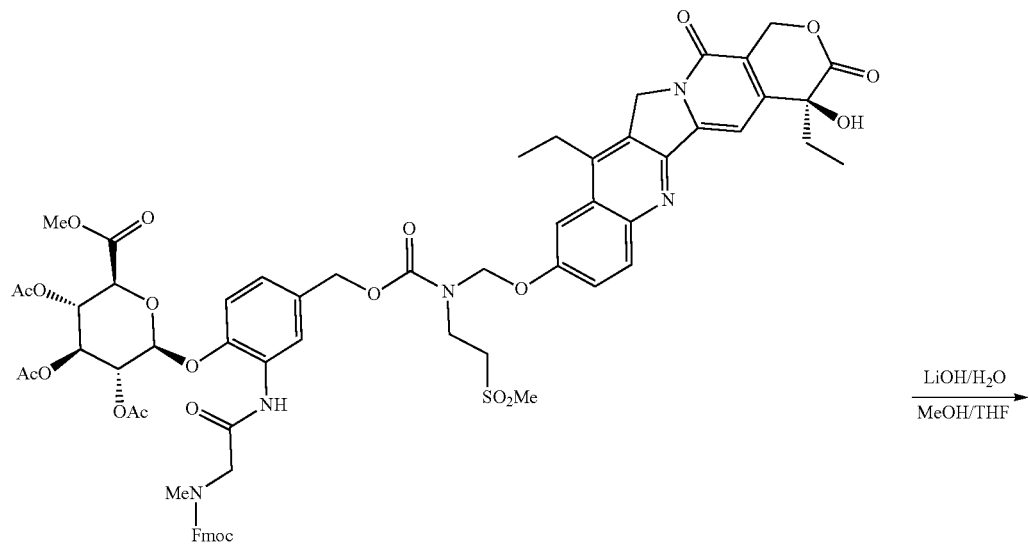
Compound 56 (282.6 mg, 0.22 mmol) was dissolved in THF and MeOH and cooled to 0° C. in an ice bath. LiOH (91.1 mg, 2.17 mmol) was dissolved in $H_2O$ and added dropwise. The reaction was stirred at room temperature and was complete within 45 min. The reaction was neutralized with acetic acid, concentrated, and directly purified by preparative HPLC to yield compound 57.

Example 36

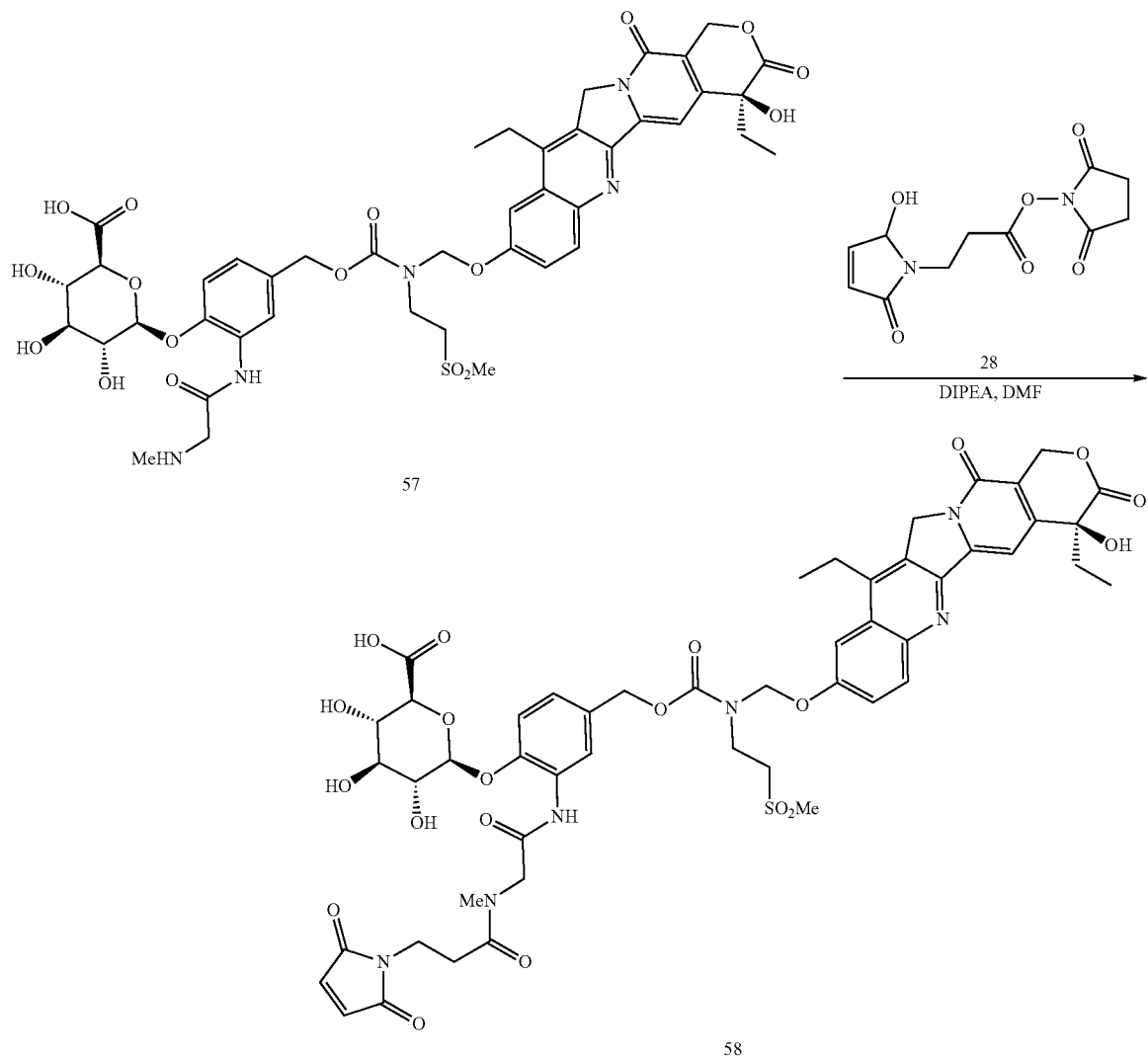

3-(Maleimido)propionic acid N-hydroxysuccinimide ester (28) was dissolved in DMF and DIPEA, and added to compound 57. The reaction was stirred for 3 h until completion as monitored by LC-MS. The reaction mixture was neutralized with acetic acid and directly purified by preparative HPLC to yield compound 58. LC-MS (Method A): $t_R$=1.40 min; MS (m/z) calculated 1091.31 (M+H)$^+$, found 1091.47.

Example 37

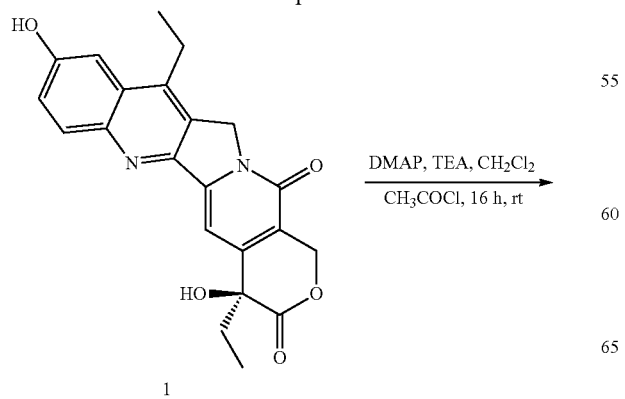

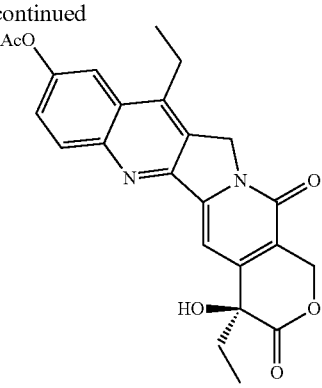

19

SN-38 (1, 76.0 mg, 0.19 mmol, purchased from MedChemExpress) was dissolved in dichloromethane, followed by addition of triethylamine (128 μL, 0.92 mmol) and DMAP (2.60 mg, 0.02 mmol). Mixture was cooled to 0° C. in an ice bath, followed by dropwise addition of acetyl chloride (15.9 μL, 0.22 mmol). The reaction mixture was stirred at room temperature for 16 h. The reaction was diluted with dichloromethane, washed with saturated NH$_4$Cl, water, and brine. The organic phase was then dried over MgSO$_4$, filtered, concentrated and purified over silica via Biotage flash column chromatography (CH$_2$Cl$_2$/MeOH 0-15%) to provide compound 19 (Ac-SN-38). MS (m/z) calculated 435.15 (M+H)$^+$, found 435.07.

Example 38

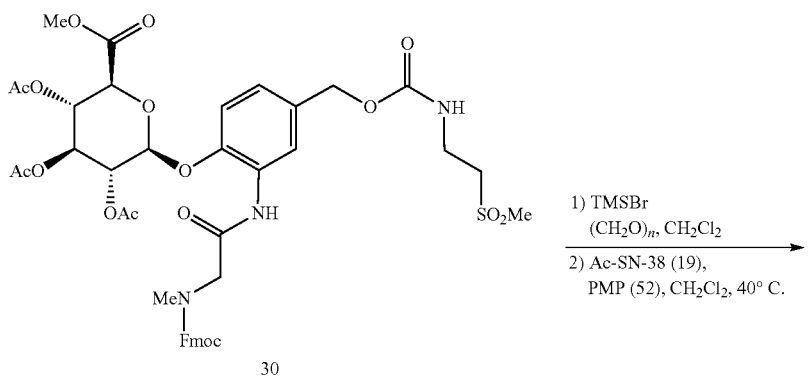

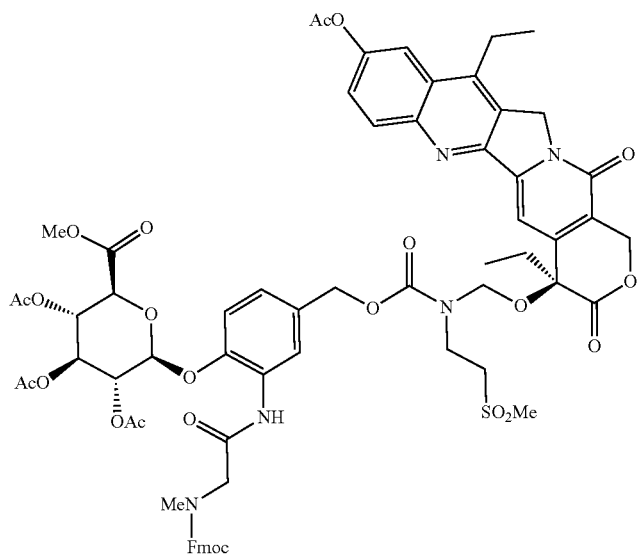

In an oven dried flask, Compound 30 (1.12 g, 1.24 mmol) was dissolved in anhydrous dichloromethane (5 mL), followed by the addition of paraformaldehyde (12.4 mg, 0.41 mmol) and TMSBr (300 µL, 1.68 mmol). The solution was stirred at room temperature for 10 min with monitoring by quenching with methanol and observing the formation of the methanol adduct by LC-MS. The reaction was filtered, washed with anhydrous toluene and dichloromethane, and dried in vacuo for 3 cycles. The crude product was dissolved in anhydrous dichloromethane and added to compound 19 (90.0 mg, 0.21 mmol), followed by 1,2,2,6,6-pentamethylpiperidine (3.90 mL, 1.86 mmol). The reaction was capped and stirred at 40° C. for 18 h. The reaction mixture was purified over silica via Biotage flash column chromatography (CH$_2$Cl$_2$/MeOH, 0-10%) to yield compound 59. MS (m/z) calculated 1344.41 (M+H)$^+$, found 1344.46.

Example 39

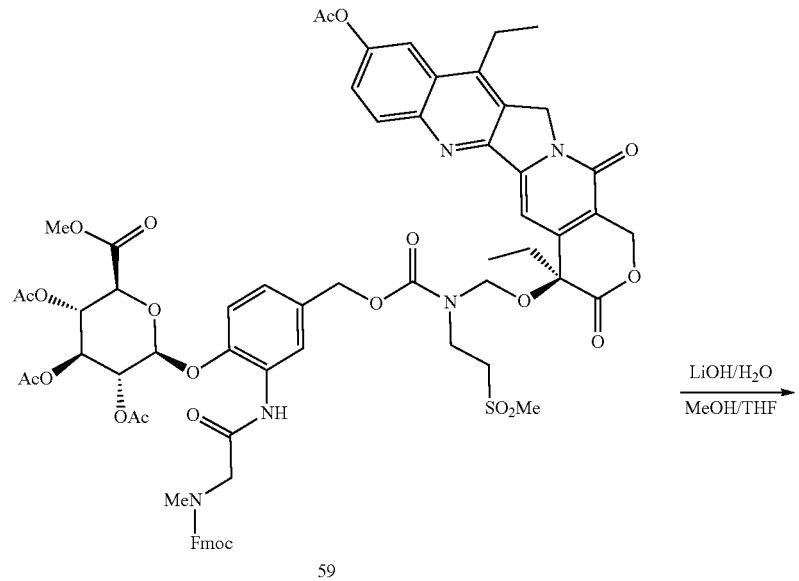

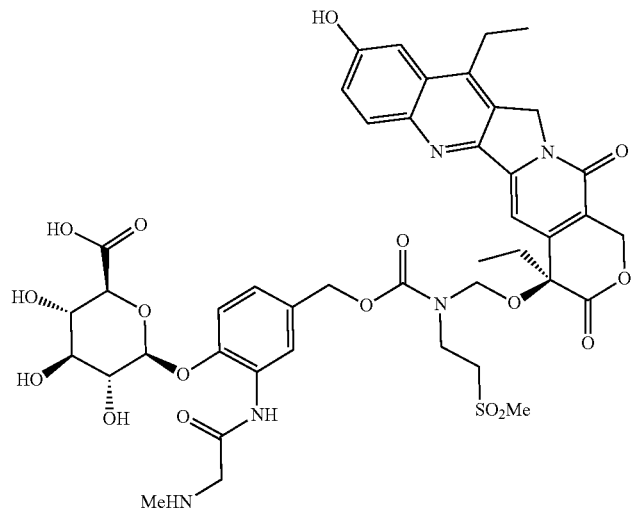

Compound 59 (290.0 mg, 0.22 mmol) was dissolved in THF and MeOH and cooled to 0° C. in an ice bath. LiOH (90.5 mg, 2.16 mmol) was dissolved in $H_2O$ and added dropwise. The reaction was stirred at room temperature and was complete within 45 min. The reaction was neutralized with acetic acid, concentrated, and directly purified by preparative HPLC to yield the deprotected intermediate compound 60.

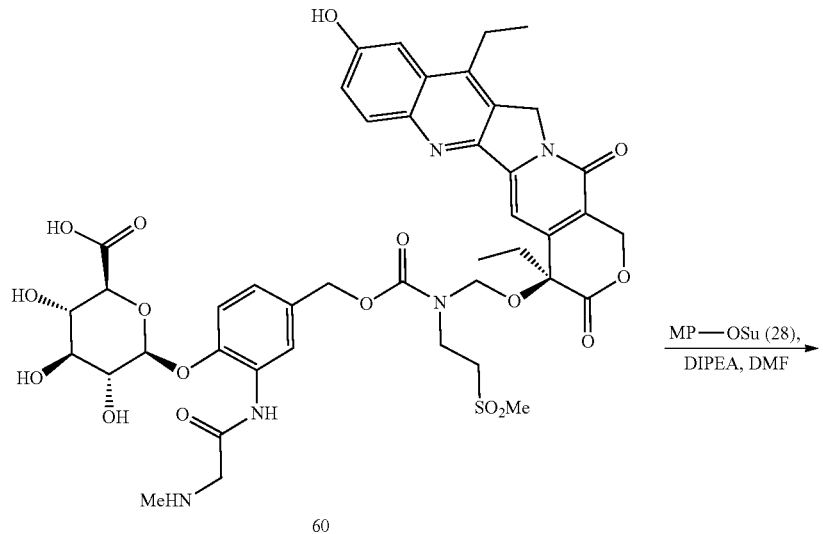

60

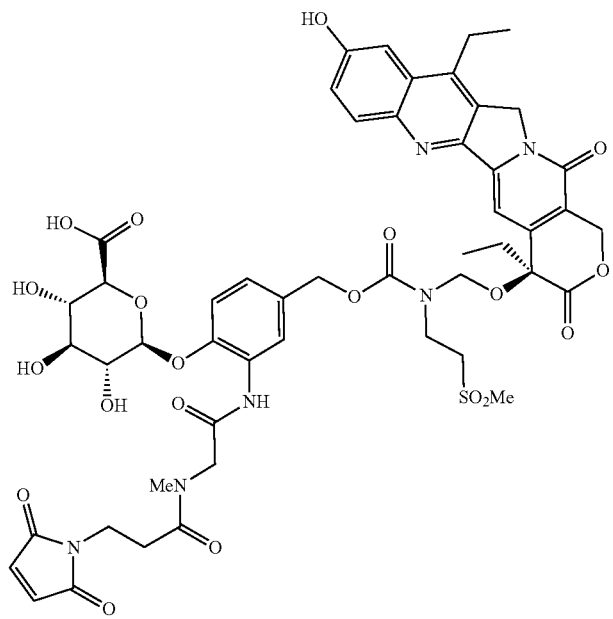

61

3-(Maleimido)propionic acid N-hydroxysuccinimide ester (28), referred to as MP-OSu, was dissolved in DMF and DIPEA, and added to compound 60. The reaction was stirred for 3 h until completion as monitored by LC-MS. The reaction mixture was neutralized with acetic acid and directly purified by preparative HPLC to yield compound 61. LC-MS (Method A): $t_R$=1.42 min, MS (m/z) calculated 1091.31 $(M+H)^+$, found 1091.31.

Example 40
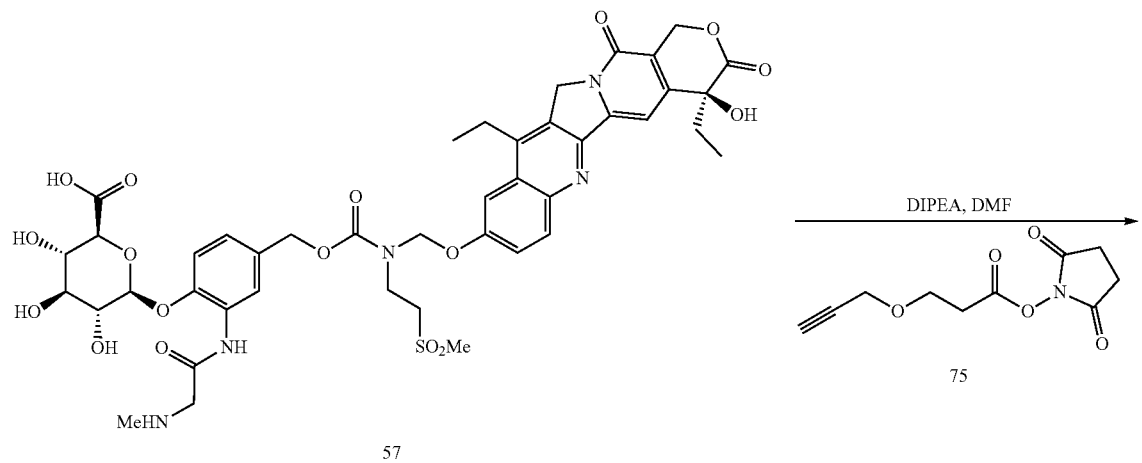
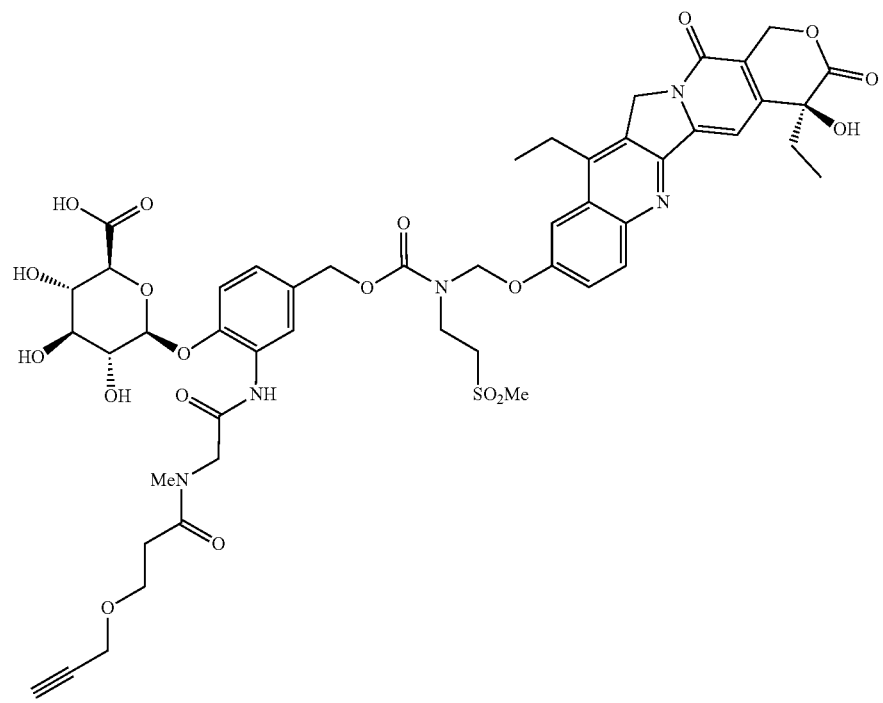
Compound 75 (3 eq), purchased from Click Chemistry Tools (CAS: 1174157-65-3), was dissolved in DMF and DIPEA, and added to compound 57. The reaction was stirred for 3 h until completion as monitored by LC-MS. The reaction mixture was neutralized with acetic acid and directly purified by preparative HPLC to yield compound 62. LC-MS (Method A): $t_R$=1.43 min, MS (m/z) calculated 1050.06 (M+H)$^+$, found 1050.07.

Example 41
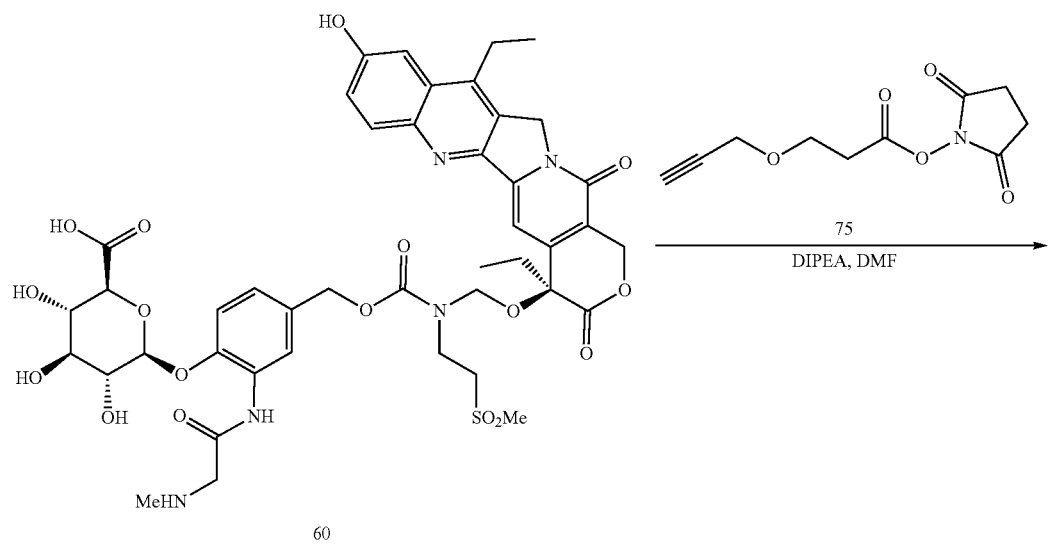
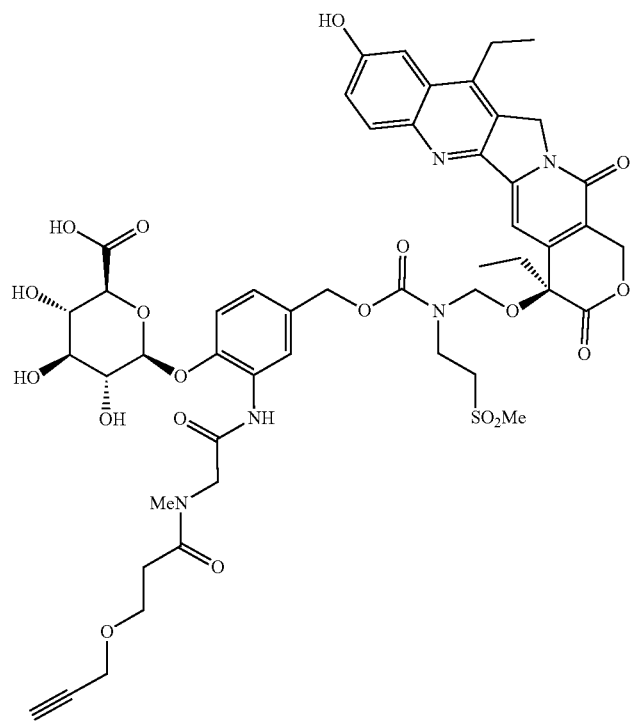
Compound 63 was prepared according to the procedure of Example 37. LC-MS (Method A); $t_R$=1.44 min; MS (m/z) calculated 1050.06 (M+H)$^+$, found 1050.

Example 42

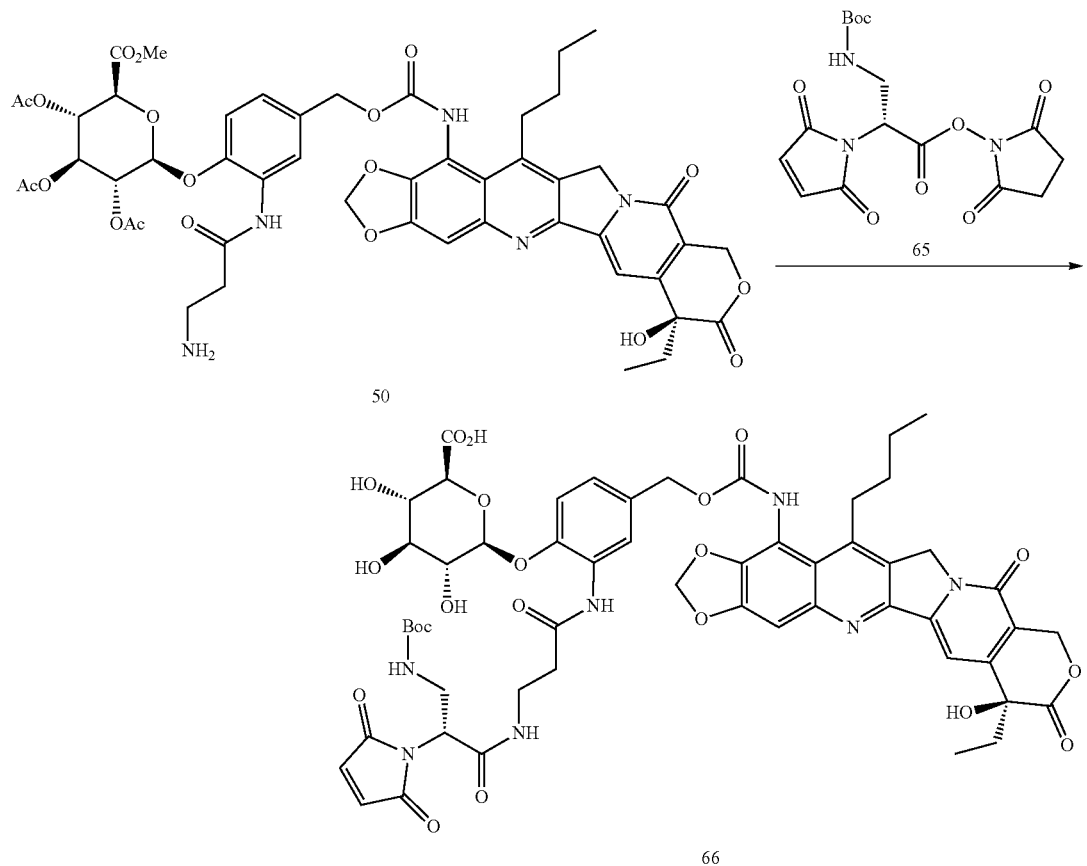

Compound 65 (6 mg, 16 μmol), referred to as mDPR (Boc)-OSu, prepared according to procedure of *Nature Biotechnology* (2014) 32: 1059-1065), was dissolved in anhydrous DMF (0.25 mL) and added to flask containing compound 50 (9 mg, 10 μmol), prepared according to the procedure of Example 30. The reaction was stirred as DIPEA (9 μL) was added, and the reaction was complete in 1.5 h. The reaction was then quenched with AcOH (9 μL), diluted in DMSO, then purified by preparative HPLC to provide compound 66 (7 mg, 61%). LC-MS (Method A): $t_R$=1.57 min; MS m/z (ES+) found 1143.51.

Example 43

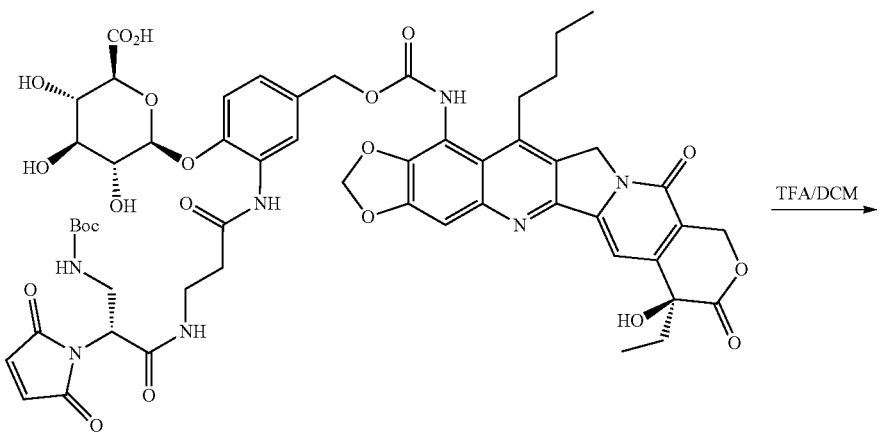

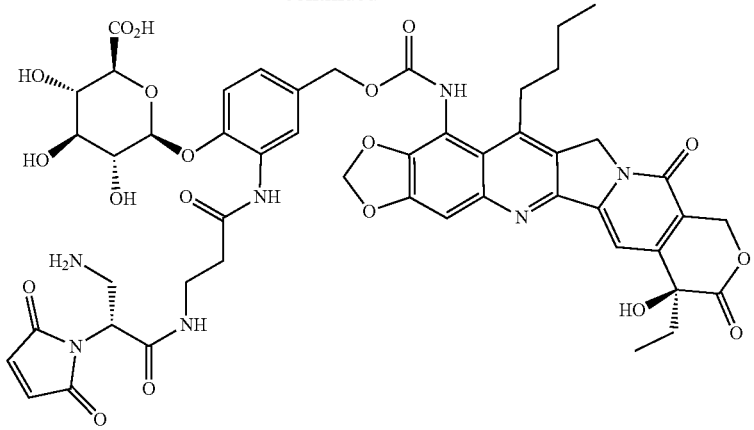
67
Compound 66 (7 mg, 6 μmol) was stirred at 0° C. in anhydrous DCM (0.54 mL) followed by dropwise addition of TFA (0.06 mL). The reaction was complete in 2.5 h. The reaction was diluted in DMSO, DCM removed in vacuo, then purified by preparative HPLC to provide compound 67 (4 mg, 64%). LC-MS (Method A): $t_R$=1.18 min; MS m/z (ES+) found 1041.22.
Example 44
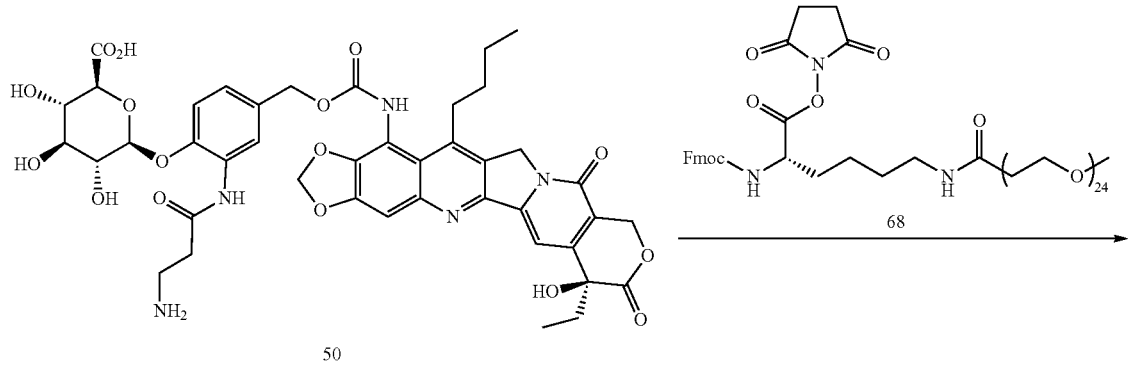
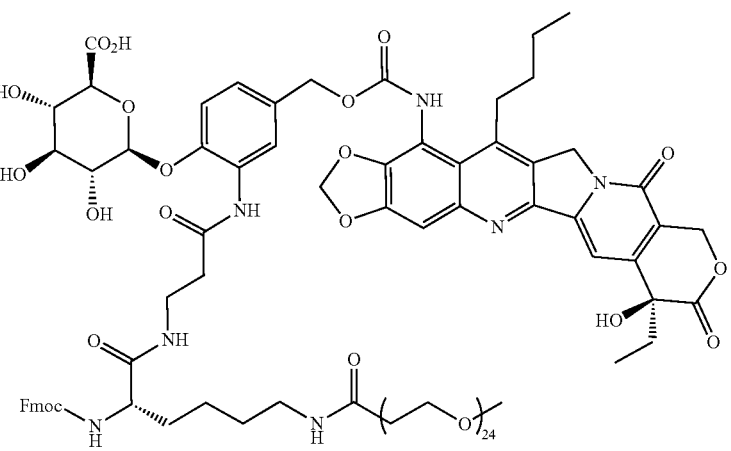

Compound 68 (86 mg, 56 μmol), referred to as Fmoc-Lys(PEG24)-OSu and prepared according to the procedure of WO 2017165851 was taken up into anhydrous DMF (0.93 mL) and added to a flask charged with compound 50 (32 mg, 37 μmol), prepared according to the procedure of Example 30. DIPEA (32 μL) was added, the reaction was stirred for 1 h, the diluted in DMSO and purified by preparative HPLC to provide compound 69 (25 mg, 29%). LC-MS (Method A): $t_R$=1.68 min; MS m/z (ES+) found 1163.50 (½ mass).

Example 45

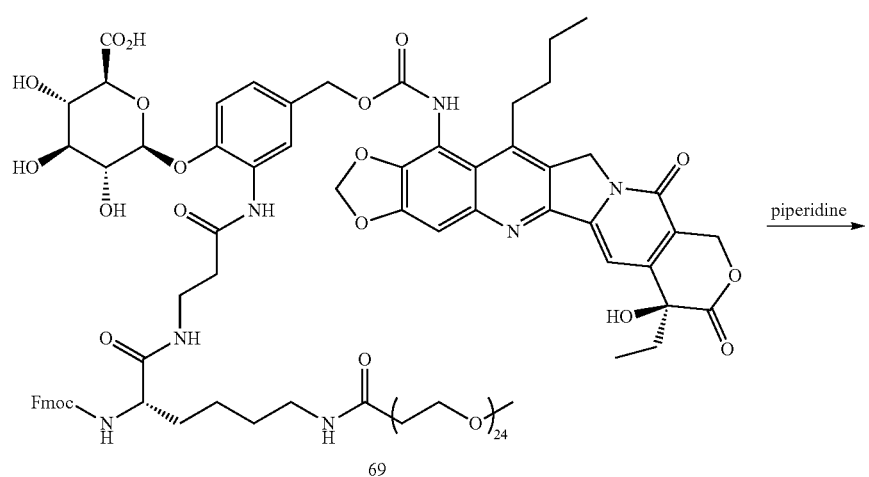

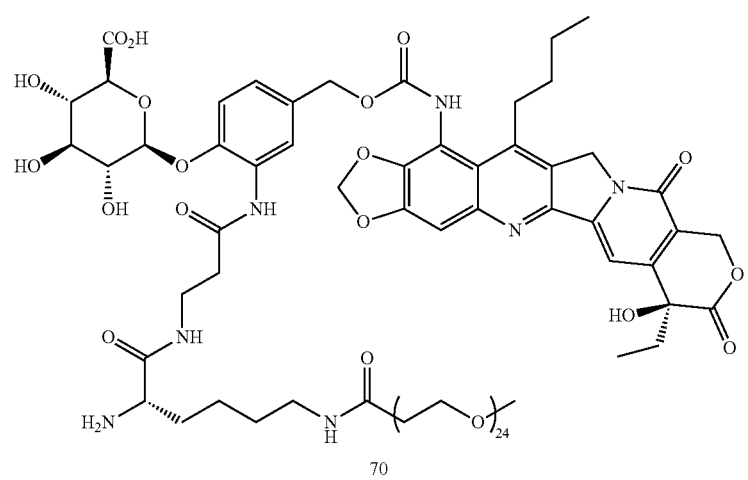

Compound 69 (10, 25 mg, 11 μmol) was taken up in 20% piperidine in DMF (0.55 mL) and stirred for 1 h. The reaction was then diluted in DMSO and purified by preparative HPLC to provide compound 70 (22 mg, 95%). LC-MS (Method A): $t_R$=1.31 min, MS m/z (ES+) found 1052.41 (½ mass).

Example 46
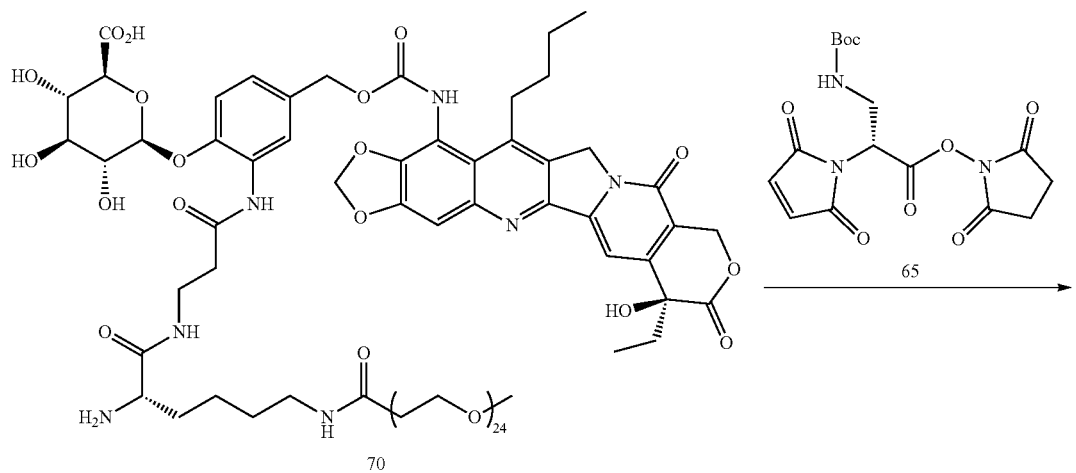
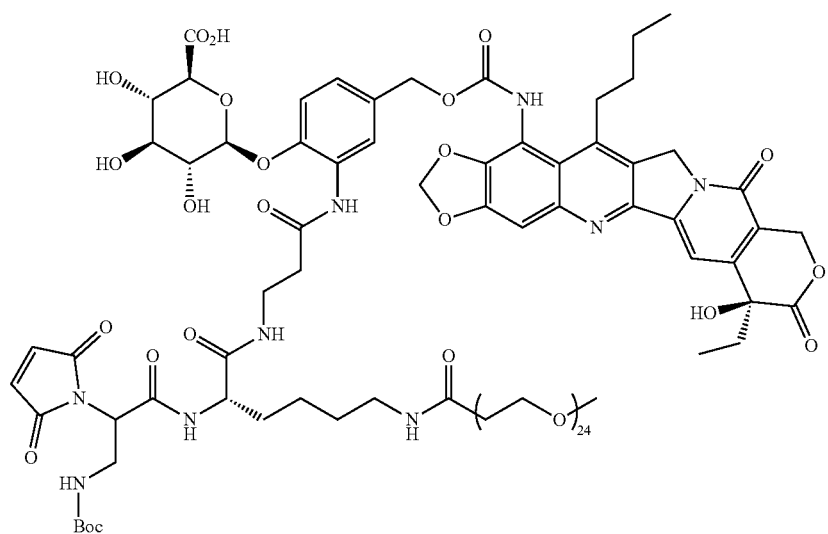
Compound 65 (8 mg, 21 µmol), referred to as mDPr(Boc)-OSu was solubilized in DMF (0.2 mL) then transferred to a flask containing compound 70 (11, 22 mg, 10 µmol) followed by DIPEA (9 µL). The reaction was stirred for 3 h, quenched with AcOH (9 µL), diluted in DMSO, and purified by preparative HPLC to provide compound 71 (12 mg, 51%). LC-MS (Method A): $t_R$=1.58 min; MS m/z (ES+) found 1185.52 (½ mass).

Example 47

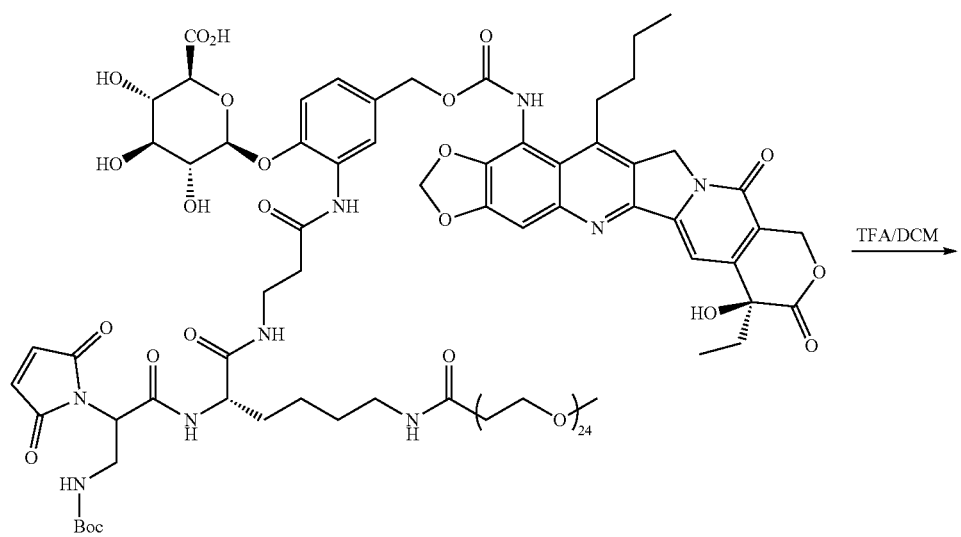

Compound 71 was solubilized in anhydrous DCM (0.45 mL) and cooled to 0° C. TFA (0.05 mL) was added and the reaction was stirred for 3 h. The reaction was then diluted with DMSO, DCM was removed in vacuo, then purified by preparative HPLC to provide compound 72 (10 mg, 88%). LC-MS (Method A): $t_R$=1.32 min; MS m/z (ES+) found 1135.85 (½ mass).

Example 48

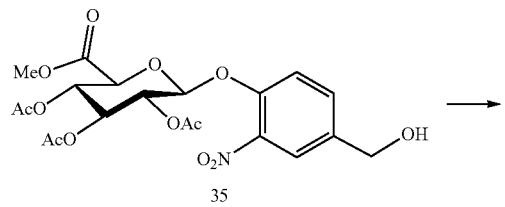

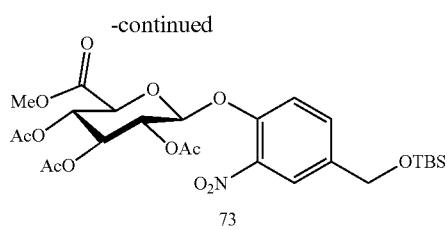

Compound 35 (660 mg, 1.36 mmol), prepared according to the procedure in *Bioconjugate Chem.* (2006) 17: 831-840, was dissolved in DCM (5 mL). DIPEA (0.71 mL, 4.1 mmol) was added followed by slow addition of TBSOTf (0.34 mL, 1.5 mmol). The reaction was stirred for 5 minutes, quenched with MeOH and concentrated in vacuo. The crude product was purified by column chromatography 25G KP-Sil 10-80% EtOAc in Hex. Fractions containing the desired product were concentrated in vacuo to afford compound 73 as a colorless solid (731 mg, 1.22 mmol, 90%). LC-MS (Method A): $t_R$=2.44 min; MS (m/z) [M+Na]$^+$ calc. for $C_{26}H_{37}NNaO_{13}Si$ 622.19, found 622.10.

Example 49

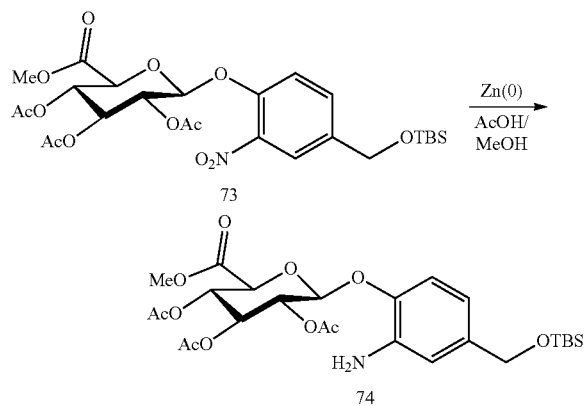

Compound 73 (731 mg, 1.22 mmol) was dissolved in 5:1 MeOH:AcOH (10 mL). Zinc dust (2.39 g, 36.6 mmol) was added to reaction. The reaction was stirred for 10 minutes them filter through a bed of Celite and rinsed with MeOH. The eluent was concentrated and purified by column chromatography 25G KP-Sil 10-100% EtOAc in Hex. Fractions containing the desired product were concentrated to afford compound 74 as a colorless solid (693 mg, 1.22 mmol, 99%). LC-MS (Method A): $t_R$=2.40 min; MS (m/z) [M+H]$^+$ calc. for $C_{26}H_{40}NO_{11}Si$ 570.24, found 571.08.

Example 50

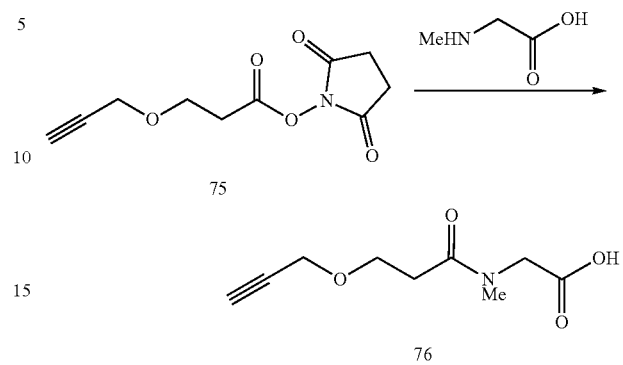

Compound 75 (1.05 g, 4.66 mmol), referred to as PropargOPr and obtained from Click Chemistry Tools (CAS: 1174157-65-3), was dissolved in DMF (10 mL). H-Sar-OH (831 mg, 9.33 mmol), which is N-methyl glycine, and DIPEA (2.4 mL, 14 mmol) were added. The reaction was stirred for 45 minutes, quenched AcOH, and purified by prep-HPLC. Fractions containing the desired product were concentrated to afford compound 76 as a colorless solid (821.3 mg, 4.12 mmol, 88%). LC-MS (Method A): $t_R$=0.81 min; MS (m/z) [M+H]$^+$ calc. for $C_9H_{14}NO_4$ 200.09, found 199.72.

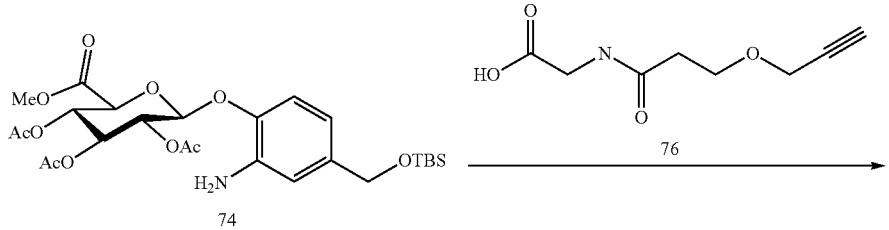

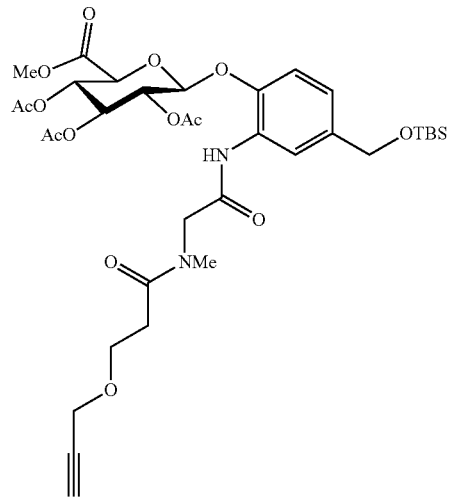

Example 51

Compound 74 (636 mg, 1.22 mmol) from Example 49 was dissolved in DMF (5 mL). DIPEA (1.06 mL, 6.08 mmol), compound 76 (727 mg, 3.65 mmol) from Example 50 and HATU (1.38 g, 3.65 mmol) were added to the reaction. The reaction was stirred for 1590 minutes then diluted in EtOAc (200 mL), washed with sat NaHCO$_3$ (200 mL), and H$_2$O (2×200 mL). The organic portion was dried with MgSO$_4$, filtered, and concentrated in vacuo. The crude product was purified by column chromatography 10-80% EtOAc in Hex. Fractions containing the desired product were concentrated to afford compound 77 as a colorless solid (823 mg, 1.10 mmol, 90%). LC-MS (Method A): $t_R$=2.34 min; MS (m/z) [M+H]$^+$ calc. for C$_{35}$H$_{51}$N$_2$O$_{14}$Si 751.31, found 751.22.

Example 52

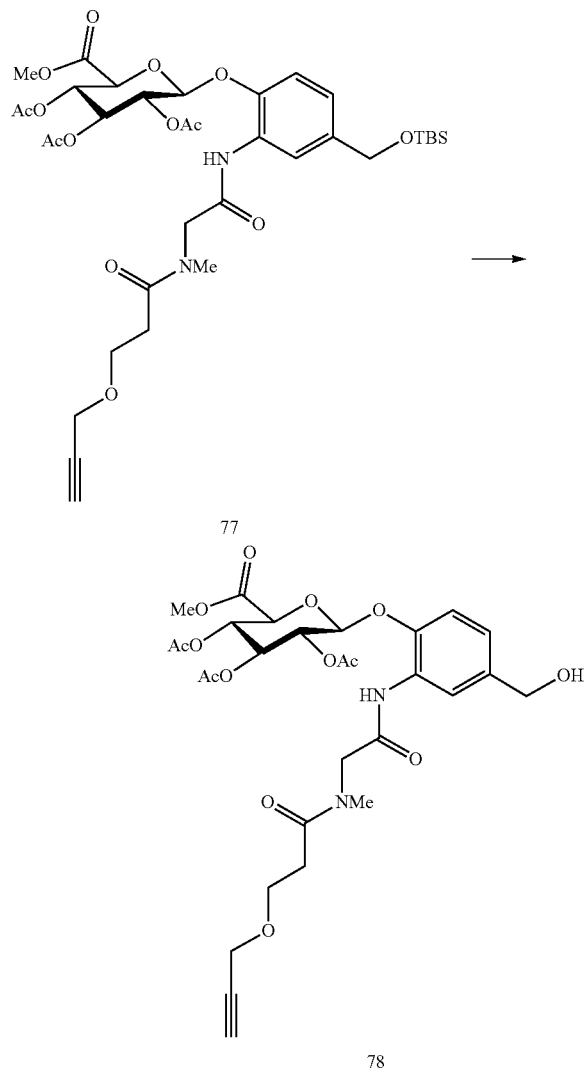

Compound 77 (823 mg, 1.10 mmol) was dissolved in 1:1:1 THF:H$_2$O:AcOH and stirred at room temperature for 24 hours. The reaction was concentrated in vacuo, diluted EtOAc (200 mL), washed with sat. NaHCO3 (3×200 mL), dried MgSO$_4$, filtered and concentrated in vacuo to afford compound 78 as a colorless solid (601 mg, 0.944 mmol, 86%). LC-MS (Method A): $t_R$=1.55 min; MS (m/z) [M+H]$^+$ calc. for C$_{29}$H$_{37}$N$_2$O$_{14}$ 637.22, found 637.04.

Example 53

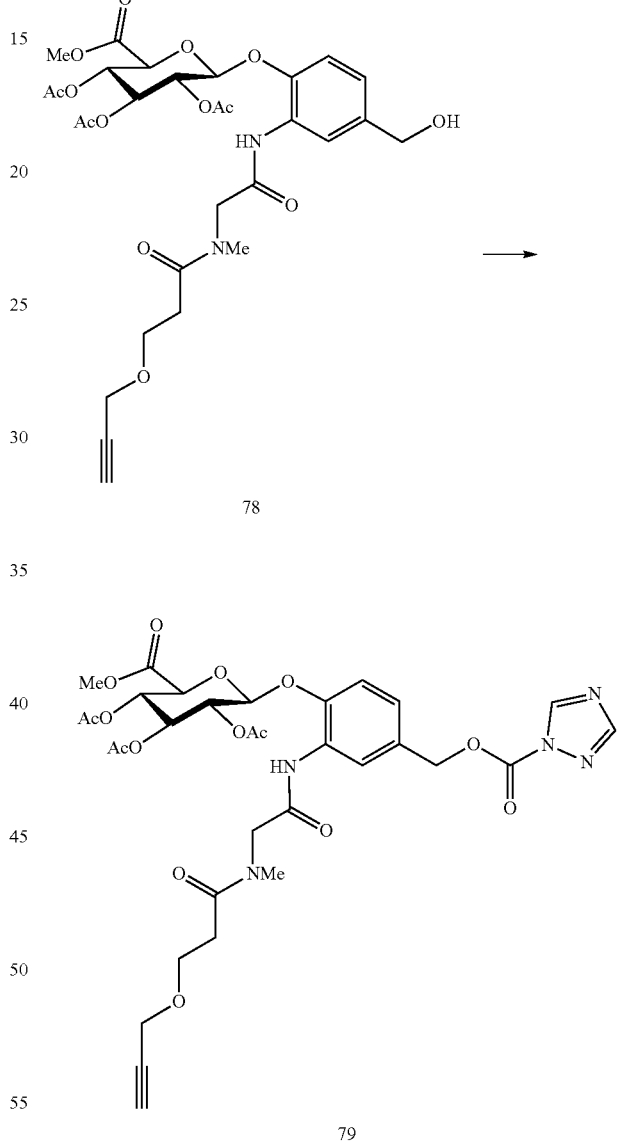

Compound 78 (300 mg, 0.47 mmol) was dissolved in DCM (2 mL). 1,1'-Carbonyl-di-(1,2,4-triazole) (232 mg, 1.41 mmol) was added. The reaction was stirred for 30 minutes then diluted into EtOAc (50 mL), washed with H$_2$O (3×50 mL), dried MgSO$_4$, filtered and concentrated in vacuo to afford compound 79 as a colorless solid (340 mg, 0.465 mmol, 99%), which was used in subsequent steps without purification. LC-MS (Method A): $t_R$=1.68 min; MS (m/z) [M+H]$^+$ calc. for C$_{32}$H$_{38}$N$_5$O$_{15}$ 732.24, found 732.11.

Example 54

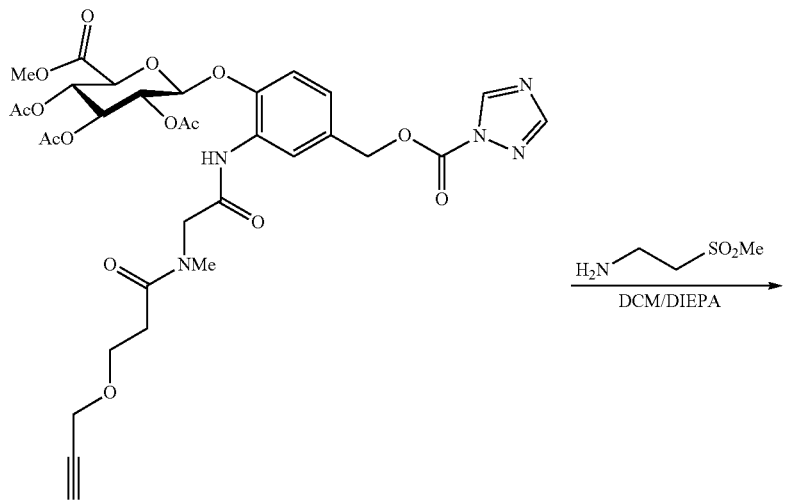

Compound 79 (200 mg, 0.273 mmol) was dissolved in DCM (2 mL). 2-(methylsulfonyl)-ethanamine (54 µL, 0.547 mmol) purchased from Enamine and DIPEA (0.14 mL, 0.82 mmol) were added to the reaction. The reaction was stirred for 10 minutes then diluted into EtOAc (50 mL), washed with 1M HCl (3×50 mL), H$_2$O (50 mL), dried MgSO$_4$, filtered, and concentrated in vacuo to afford compound 80 as a colorless solid (210 mg, 0.267 mmol, 98%). LC-MS (Method A); t$_R$=1.64 min; MS (m/z) [M+H]$^+$ calc. for C$_{33}$H$_{44}$N$_3$O$_{17}$S 786.24, found 786.14.

Example 55

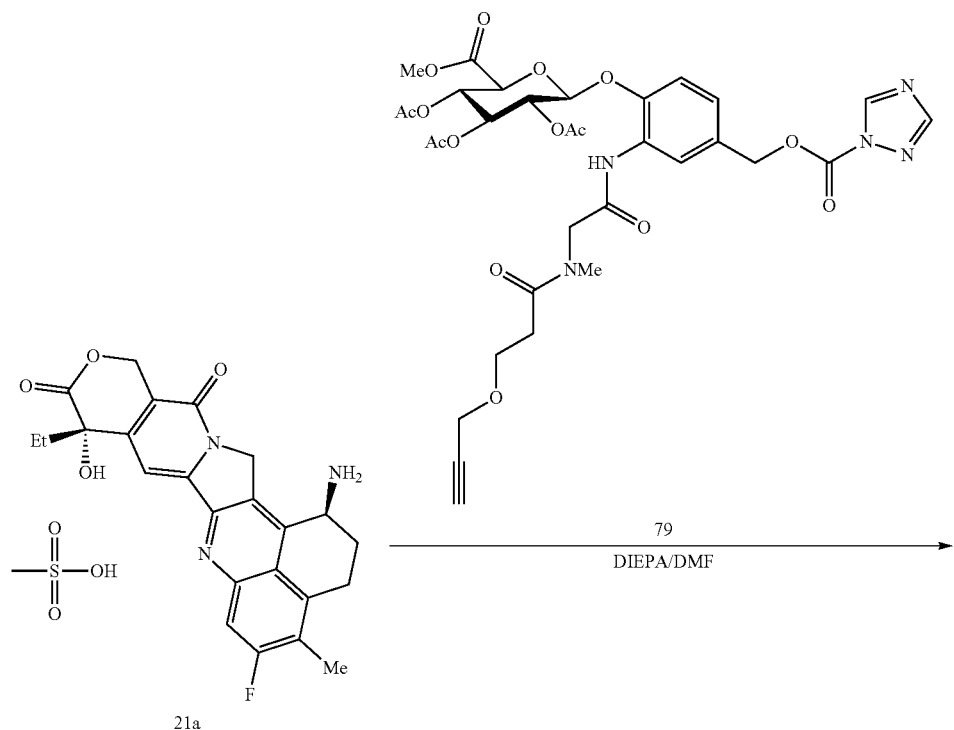

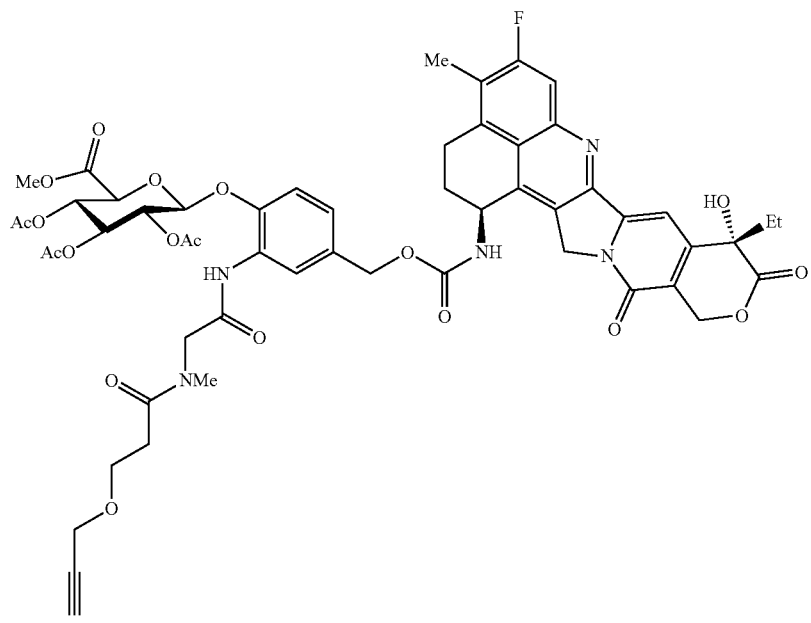

Exatecan mesylate (21a, 10.0 mg, 0.0188 mmol) was dissolved in anhydrous DMF (0.5 mL). DIPEA (16 μL, 0.094 mmol) and compound 79 (41.3 mg, 0.0.564 mmol) were added to the reaction. The reaction was heated at 60° C. for 5h. The reaction was quenched with AcOH and purified by prep-HPLC. Fractions containing the desired product were lyophilized to afford compound 81 as a yellow powder (1.4 mg, 1.3 μmol, 6.8%). LC-MS (Method A): $t_R$=2.10 min; MS (m/z) [M+H]$^+$ calc. for $C_{54}H_{57}N_5FO_{19}$ 1098.36, found 1098.51.

Example 56

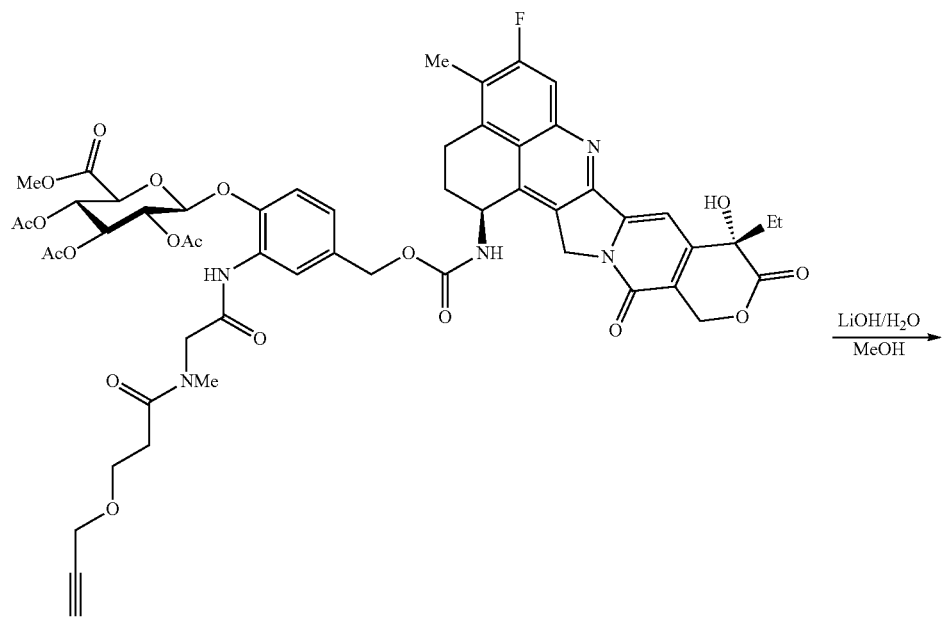

81

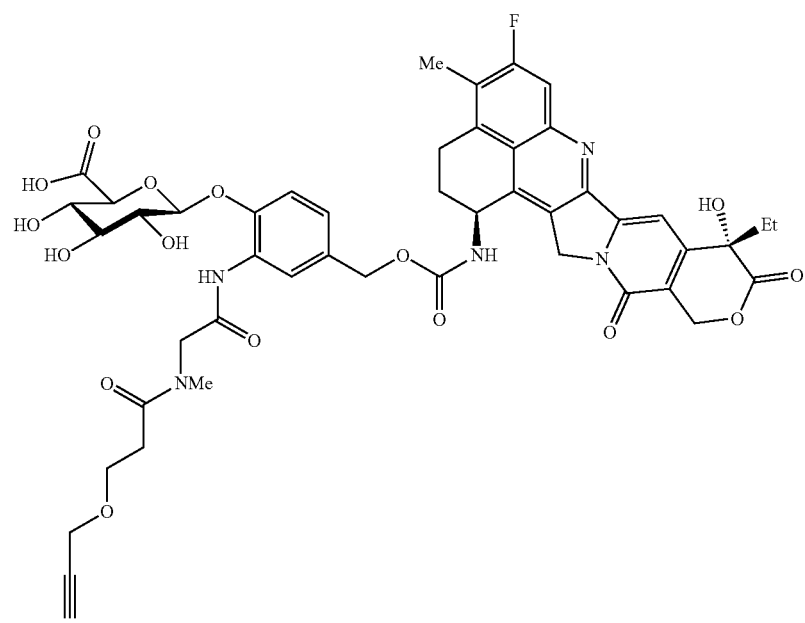

82

Compound 81 (1.4 mg, 1.3 µmol) was dissolved in MeOH (0.5 mL). LiOH (5 mg, 0.209 mmol) was added and the reaction was sonicated to aid dissolution and stirred for 5 mins. $H_2O$ (0.5 mL) was added to the reaction and stirred for 5 minutes, then quenched with AcOH and concentrated in vacuo. The reaction was purified by prep-HPLC 10 mm 5-95% MeCN in $H_2O$. Fractions containing the desired product were lyophilized to afford compound 82 as a yellow powder (0.7 mg, 0.7 µmol, 57%). LC-MS (Method A): $t_R$=1.62 min. MS (m/z) $[M+H]^+$ calc. for $C_{47}H_{49}FN_5O_{16}$ 958.32, found 958.62.

Example 57

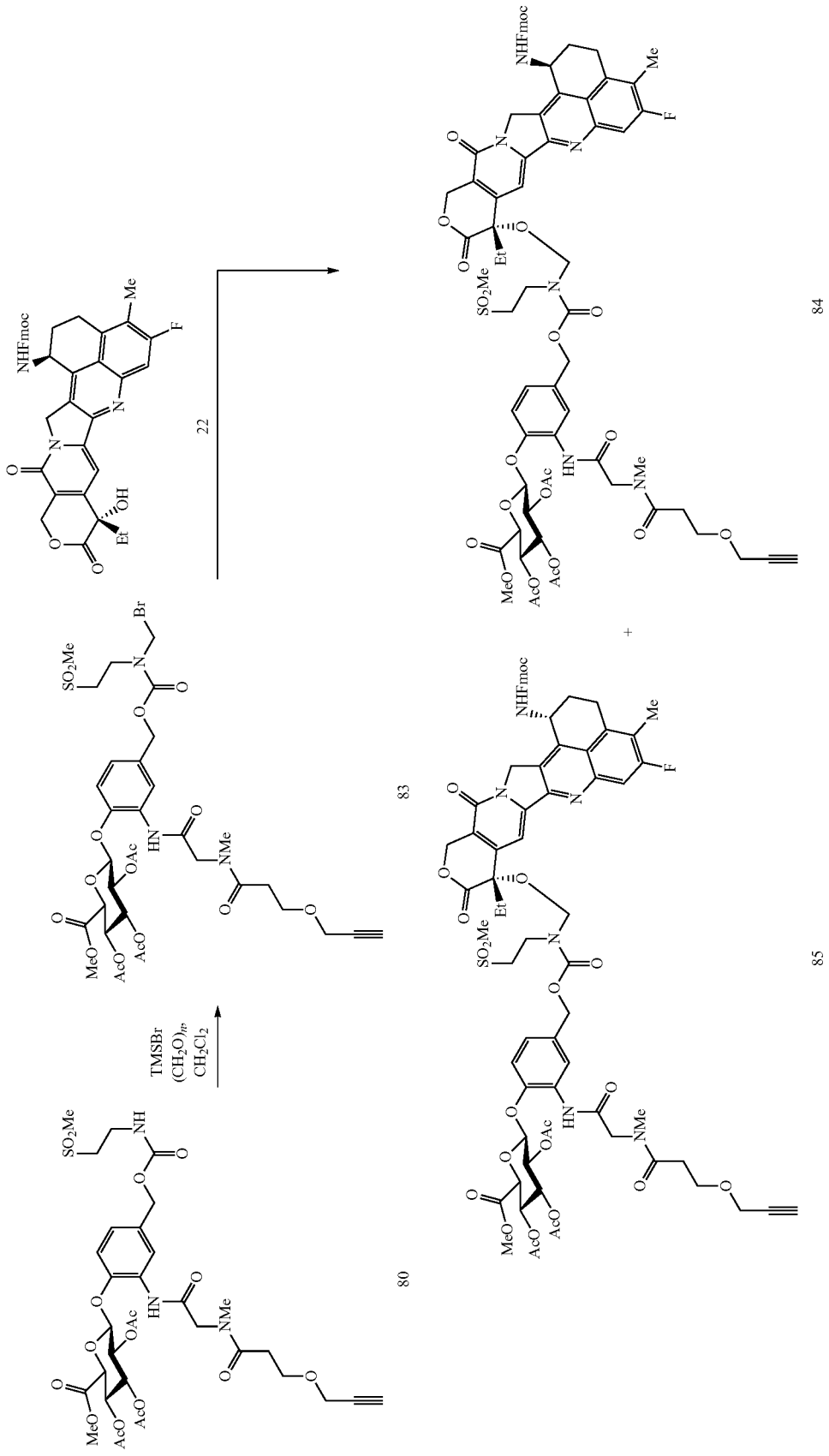

Compound 80 (50.0 mg, 0.0636 mmol) was dissolved in DCM (1 mL). Paraformaldehyde (100 mg, 3.3 mmol) was added to the reaction followed by TMSBr (21 µL, 0.16 mmol). The reaction was stirred for 15 minutes. An aliquot was quenched in MeOH and complete conversion to the MeOH adduct was observed by UPLC-MS. The reaction was filtered through a 0.45 µm PTFE filter, rinsed DCM (2×2 mL), and toluene (2 mL) was added to azeotrope the final mixture. The eluent was concentrated to afford compound 83 as a colorless solid which was used immediately in the next step.

Compound 83 (0.0636 mmol) was dissolved in anhydrous DCM (0.5 mL). 1,2,2,6,6-Pentamethylpiperidine (21 µL, 0.11 mmol) was added to the reaction, and the reaction solution was added directly to the compound 22 solid (12.0 mg, 0.0183 mmol). The reaction was stirred at room temperature for 3.5 h at which time complete conversion was observed by UPLC-MS. The reaction was quenched with AcOH, concentrated and purified by prep-HPLC 21 mm 10-95% MeCN in $H_2O$. Fractions containing the desired product were concentrated to afford compound 84 as a yellow solid (5.4 mg, 3.7 µmol, 20%). LC-MS (Method A): $t_R$=2.30 min; MS (m/z) [M+H]$^+$ calc. for $C_{73}H_{76}FN_6O_{23}S$ 1455.47, found 1455.43. Fractions containing an observed product presumed to be epimerization of the exatecan FMOC protected amine were concentrated in vacuo to afford compound 85 as a yellow solid (2.1 mg, 1.4 µmol, 8%). LC-MS (Method A): $t_R$=152.33 min; MS (m/z) [M+H]$^+$ calc. for $C_{73}H_{76}FN_6O_{23}S$ 1455.47, found 1455.63.

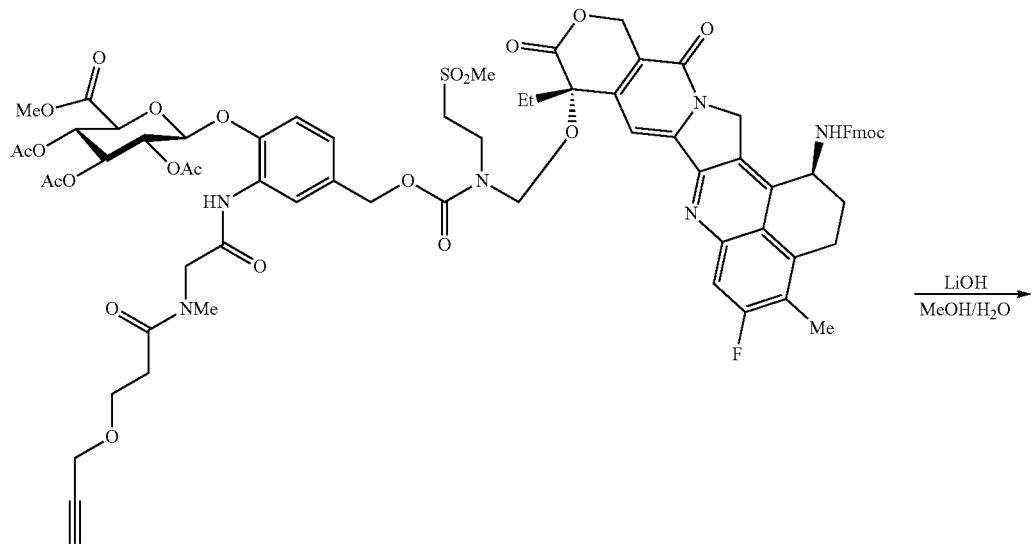

84

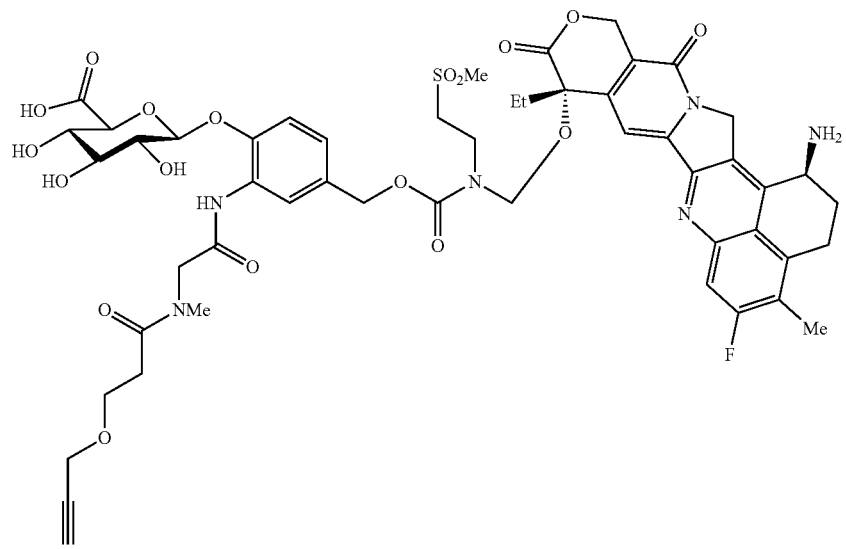

86

Compound 84 (5.4 mg, 3.7 μmol) was dissolved in MeOH (1 ml). LiOH (25 mg) was added and the reaction was sonicated to aid in dissolution. The reaction was stirred for 10 minutes and $H_2O$ (1 mL) was added and stirred for an additional 20 minutes. The reaction was quenched with AcOH, concentrated, and purified by prep-HPLC 10 mm 5-60-95% MeCN in $H_2O$ 0.05% TFA. Fractions containing the desired product were lyophilized to afford compound 86 as a yellow powder (1.96 mg, 1.79 μmol, 48%). LC-MS (Method A): $t_R$=1.22 min; MS (m/z) $[M+H]^+$ calc. for $C_{51}H_{58}FN_6O_{18}S$ 1093.35, found 1093.56.

Example 58

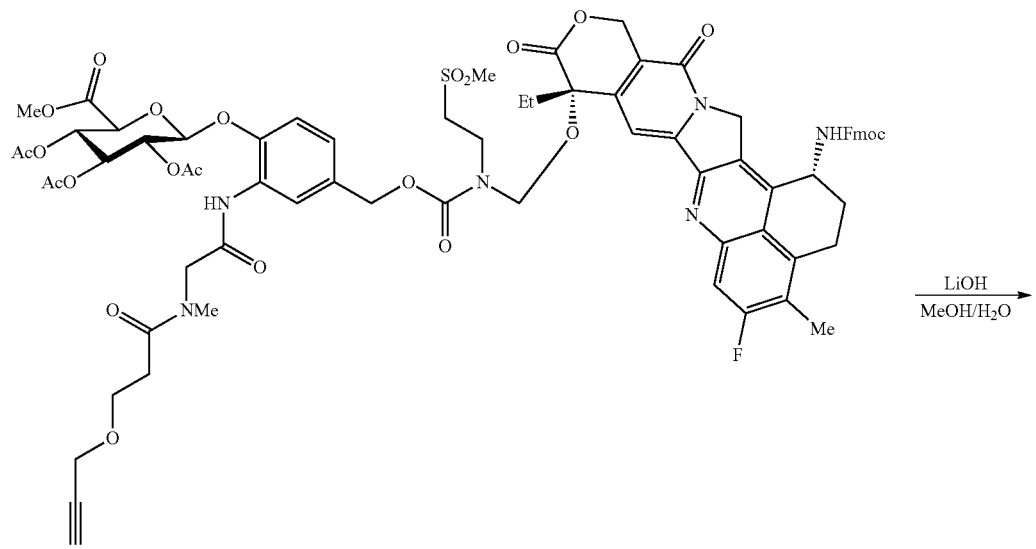

85

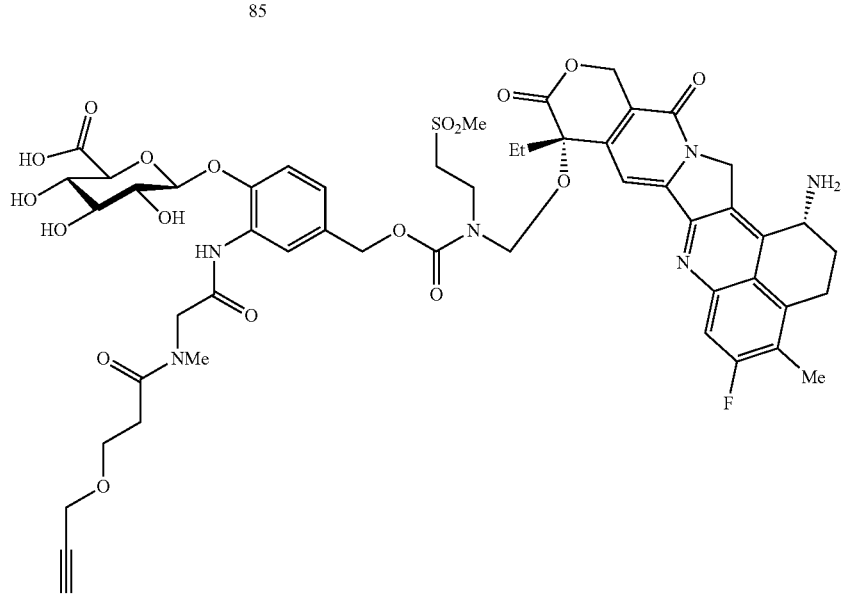

87

Compound 85 from Example 57 (2.1 mg, 1.4 μmol) was dissolved in MeOH (1 mL). LiOH (25 mg) was added and the reaction was sonicated to aid in dissolution. The reaction was stirred for 10 minutes and $H_2O$ (1 mL) was added and stirred for an additional 20 minutes. The reaction was quenched with AcOH, concentrated, and purified by prep-HPLC 10 mm 5-60-95% MeCN in $H_2O$ 0.05% TFA. Fractions containing the desired product were lyophilized to afford compound 87 as a yellow powder (0.98 mg, 0.90 μmol, 62%). LC-MS (Method A): $t_R$=1.40 min; MS (m/z) $[M+H]^+$ calc. for $C_{51}H_{58}FN_6O_{18}S$ 1093.35, found 1093.18.

Example 59

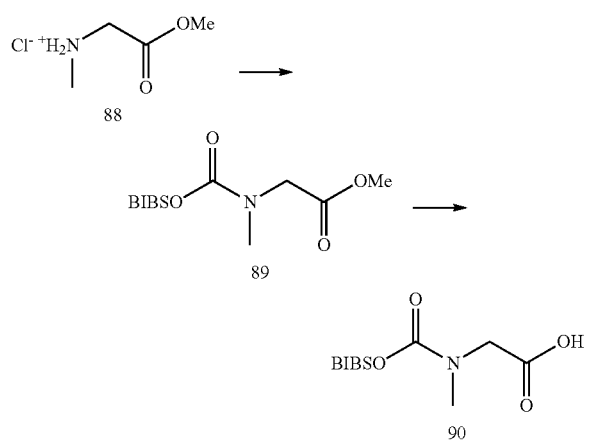

Sarcosine methyl ester HCl (88, 5.00 g, 35.8 mmol) was suspended in anhydrous DCM (100 mL). DIPEA (18.7 mL, 107.5 mmol) was added and the reaction was sonicated and stirred vigorously to solubilize H-Sar-OMe. The solution was slightly opaque. $CO_2$ was bubbled through the reaction for 30 minutes. Di-t-butylisobutylsilyl trifluoromethanesulfonate (BIBSOTf, 20 mL, 72 mmol) purchased from Gelest, Inc. was added to the reaction and stirred for 1 hour. A pellet of dry ice was added to the reaction mixture. After cessation of bubbling, the reaction was concentrated, diluted with Hex (200 mL), washed 1M aq. HCl (3×200 mL), dried $MgSO_4$, filtered and concentrated in vacuo. The crude product was purified by column chromatography 0-10% EtOAc in Hex. $R_f$=0.25 in 9:1 Hex:EtOAc stain $KMnO_4$. Fractions containing the desired product were concentrated in vacuo to afford compound 89 as a colorless oil (10.38 mg, 30.03 mmol, 84%). LC-MS (Method C): $t_R$=1.67 min; MS (m/z) $[M+H]^+$ calc. for $C_{17}H_{36}NO_4Si$ 346.24, found 346.99.

Example 60

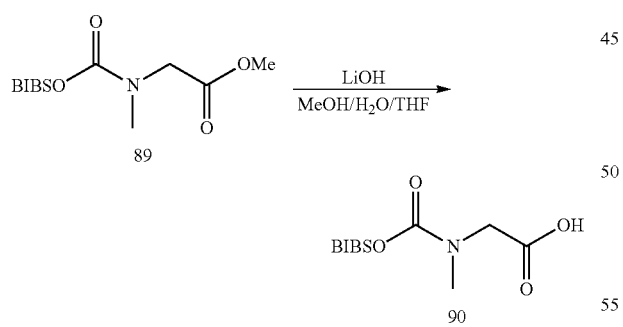

Compound 89 was dissolved in 1:1:1 THF:MeOH:$H_2O$ (60 mL). LiOH (1.80 g, 75.1 mmol) was added and the reaction was stirred for 10 minutes at which point complete conversion was observed by UPLC-MS. The reaction was quenched with AcOH, concentrated in vacuo and purified by column chromatography 0-10% MeOH in DCM. Fractions containing the desired product were concentrated in vacuo to afford compound 90 as a colorless solid (8.79 mg, 26.5 mmol, 88%). LC-MS (Method C): $t_R$=1.50 min; MS (m/z) $[M+H]^+$ calc. for $C_{16}H_{34}NO_4Si$ 332.23, found 331.86.

Example 61

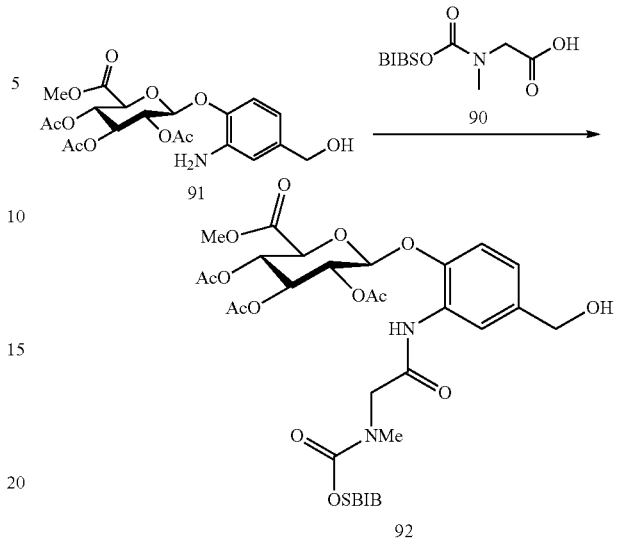

Compound 91 (4.00 g, 8.78 mmol), prepared according to the method of *Bioconjugate Chem.* (2006) 17: 831-840, was dissolved in DCM (10 mL). BIBS-Sar-OH (90, 5.82 g, 17.6 mmol) from Example 60 was added followed by EEDQ (6.52 g, 26.4 mmol). The reaction was stirred for 90 minutes. The reaction was diluted with EtOAc (200 mL), washed with 1M aq. HCL (3×200 mL), sat. $NaHCO_3$ (3×200 mL), water (200 mL), dried $MgSO_4$, filtered and concentrated in vacuo. The crude product was purified by column chromatography 0-60% EtOAc in Hex. Fractions containing the desired product were concentrated in vacuo to afford compound 92 as a colorless solid (5.16, 6.71 mmol, 76%). LC-MS: $t_R$=1.58 min; MS (m/z) $[M+H]^+$ calc. for $C_{36}H_{57}N_2O_{14}Si$ 769.36, found 769.29.

Example 62

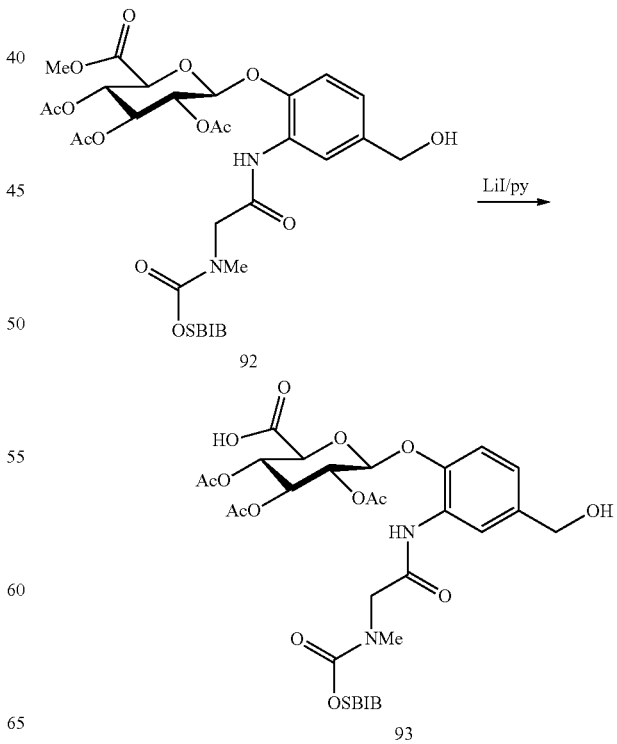

Compound 92 (2.70 g, 3.51 mmol) was dissolved in anhydrous pyridine (10 mL). LiI (2.82 g, 21.1 mmol) was added and the reaction was sealed and heated at 115° C. overnight (~16h). The reaction was diluted with EtOAc (200 mL), washed 1M aq. HCl (3×200 mL), washed H$_2$O, dried MgSO$_4$, filtered and concentrated in vacuo. The crude product was purified by column chromatography 0-60% EtOAc in Hex. Fractions containing the desired product were concentrated in vacuo to afford compound 93 as a colorless solid (2.06 g, 2.73 mmol, 78%). LC-MS (Method C): $t_R$=1.50 min; MS (m/z) [M+H]$^+$ calc. for C$_{35}$H$_{55}$N$_2$O$_{14}$Si 755.34, found 755.32.

Example 63

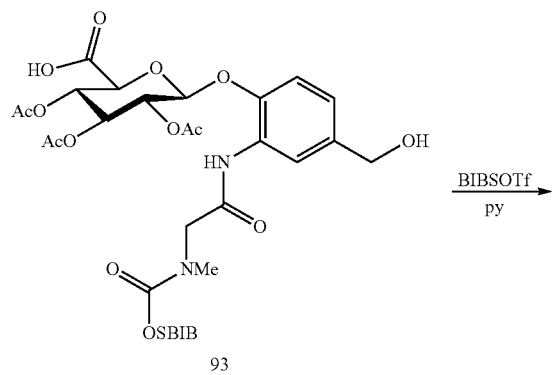

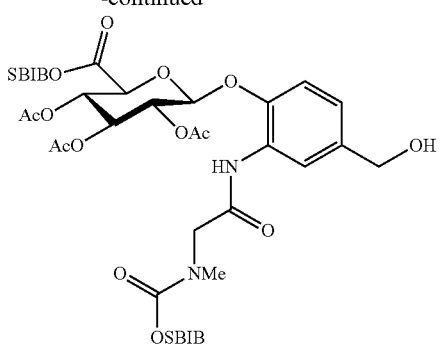

Compound 93 (700 mg, 0.927 mmol) was dissolved in pyridine (2 mL). BIBSOTf (0.78 mL, 2.78 mmol) purchased from Gelest Inc. was added. The reaction was stirred for 30 minutes, diluted with EtOAc (50 mL), washed with 1M HCl (3×50 mL), dried MgSO$_4$, filtered and concentrated in vacuo. The crude product was purified by column chromatography 0-60% EtOAc in Hex. Fractions containing the desired product were concentrated in vacuo to afford compound 94 as a colorless solid (723 mg, 0.758 mmol, 82%). LC-MS (Method C): $t_R$=1.85 min; MS (m/z) [M+H]$^+$ calc. for C$_{47}$H$_{81}$N$_2$O$_{14}$Si$_2$ 953.52, found 953.34.

Example 64

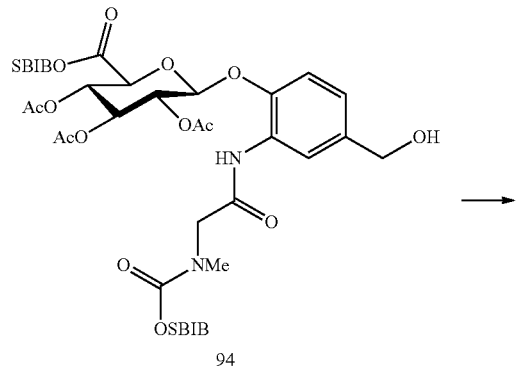

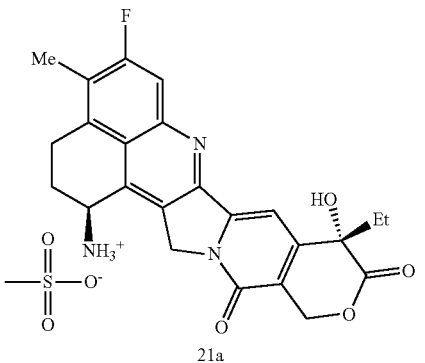

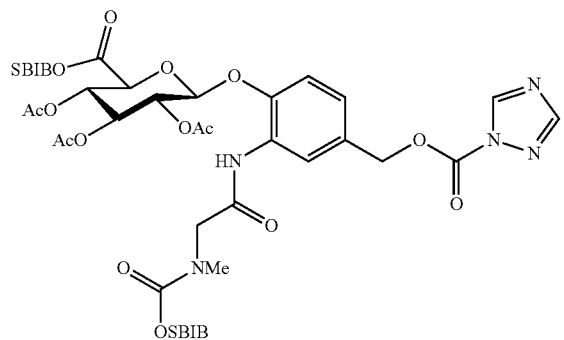

-continued

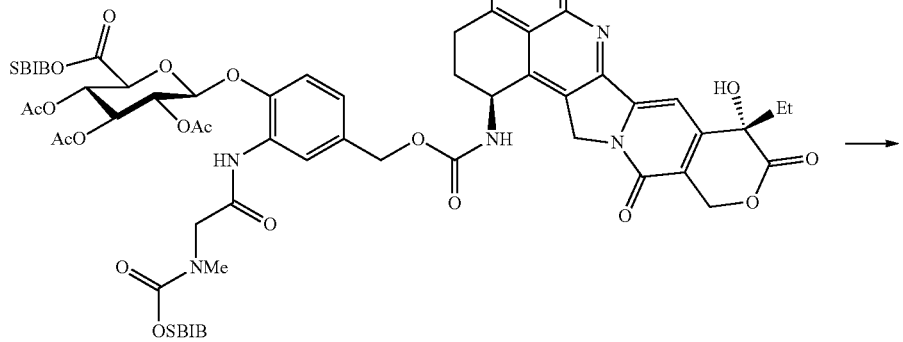

96

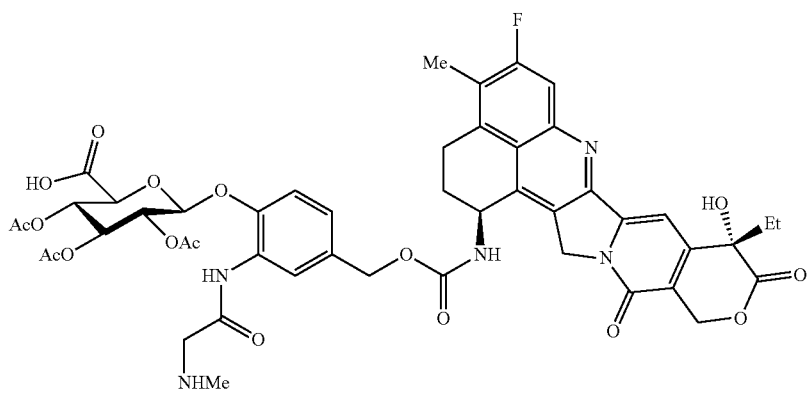

97

Compound 94 (723 mg, 0.758 mmol) was dissolved in DCM (2 mL). CDT (373 mg, 2.28 mmol) was added and the reaction was stirred for 30 minutes. The reaction was diluted with EtOAc (50 mL), washed with $H_2O$ (3×50 mL), dried $MgSO_4$, filtered and concentrated in vacuo to afford compound 95 as a colorless solid (790 mg, 0.753 mmol, 99%), which was used in next step without further purification. LC-MS (Method C): $t_R$=1.86 min; MS (m/z) [M+H]$^+$ calc. for $C_{50}H_{82}N_5O_{15}Si_2$ 1048.53, found 1049.29

Compound 95 (395 mg, 0.376 mmol) was dissolved in 0.5 mL anhydrous DMF and added directly to exatecan mesylate (21-a, 25 mg, 0.047 mmol) solid followed by DIPEA (0.081 mL, 0.47 mmol). The reaction was stirred overnight (approximately 15h). Complete conversion was observed by UPLC-MS. The reaction was diluted with EtOAc (20 mL), washed with sat. $NH_4Cl$ (3×20 mL), dried $MgSO_4$, filtered and concentrated in vacuo to afford compound 96 as a crude product, which was used in the next step without further purification. LC-MS (Method C): $t_R$=1.89 min; MS (m/z) [M+H]$^+$ calc. for $C_{72}H_{101}N_5O_{19}Si_2$ 1414.66, found 1414.71.

Crude compound 96 (0.047 mmol) was dissolved in 1 mL anhydrous DMF. AcOH (200 μL) was added. TBAF 1M in THF (0.28 mL) was added to the reaction. Complete conversion was observed after 45 min. Silica (100 mg) was added to quench fluoride. The reaction was filtered and purified by Prep-HPLC 21 mm 10-95% MeCN in $H_2O$ 0.05% TFA. Fractions containing the desired product were lyophilized to afford compound 97 as a yellow powder (45 mg, 0.046 mmol, 98%). LC-MS (Method A): $t_R$=1.53 min; MS (m/z) [M+H]$^+$ calc. for $C_{47}H_{49}N_5O_{17}$ 974.31, found 974.10.

Example 65

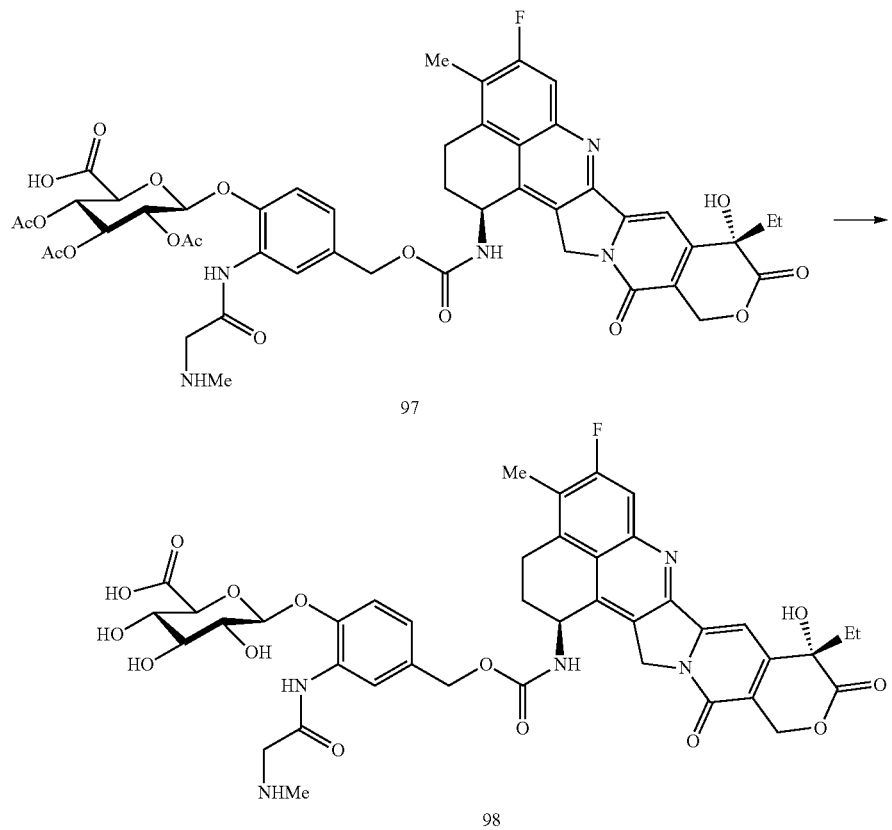

Compound 97 (45 mg, 0.046 mmol) was diluted to form a 10 mM DMSO solution (4.6 mL). PBS 7.4 (10×, 4.6 mL) was added to make a 5 mM solution. A solution of acetyl esterase 800 Units/mL added to form a 2.5 mM drug linker solution (9.2 mL). The reaction was stirred at 40° C. overnight (approximately 15h). Complete conversion was observed. The reaction was diluted into 200 mL cold MeOH, centrifuged, supernatant collected, concentrated, and purified by Prep-HPLC 21 mm 10-95% MeCN in $H_2O$ 0.05% TFA. Fractions containing the desired product lyophilized to afford compound 98 as a yellow powder (30 mg, 0.035 mmol). LC-MS (Method A): $t_R$=1.30 min; MS (m/z) $[M+H]^+$ calc. for $C_{41}H_{43}N_5O_{14}$ 848.28, found 847.97.

Example 66

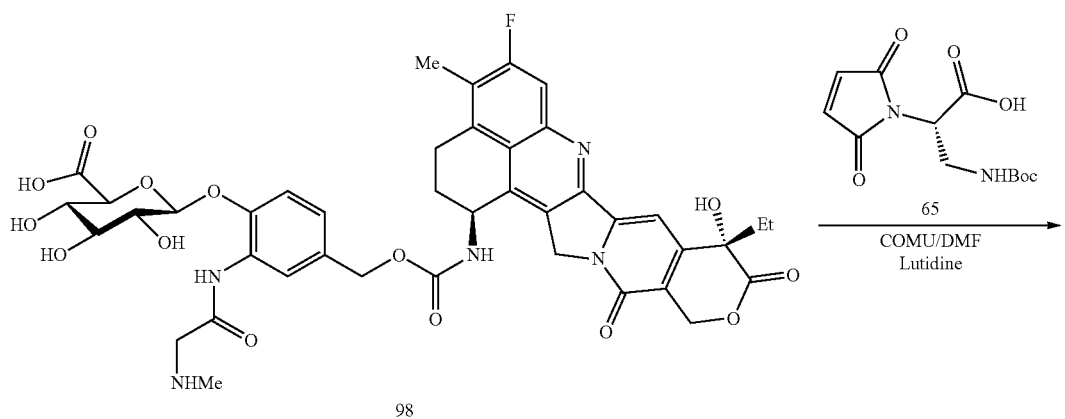

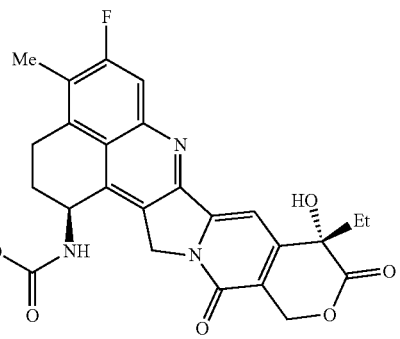
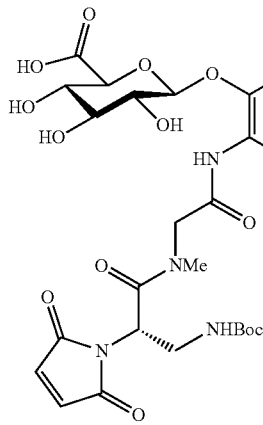

Maleimido-Dpr(Boc)-OH (65, 26.6 mg, 0.0936 mmol), prepared by the procedure of *Nature Biotechnology* (2014) 32: 1059-1062, was dissolved in 0.5 mL anhydrous DMF cooled to 0° C. Lutidine (0.022 mL, 0.19 mmol) was added followed by COMU (38.7 mg, 0.0905 mmol). The reaction was stirred for 30 minutes. The activated Maleimido-DPr (Boc)-OH solution was added directly to compound 98 (30 mg, 0.035 mmol) solid. The reaction was stirred for 60 minutes at which point complete conversion was observed. Reaction was quench with AcOH and purified by Prep-HPLC 21 mm 10-95% MeCN in $H_2O$. Fractions containing the desired product was lyophilized to afford compound 99 as a yellow solid (4.5 mg, 4.0 μmol, 13%). LC-MS (Method A): $t_R$=1.72 min; MS (m/z) $[M+H]^+$ calc. for $C_{53}H_{57}N_7O_{19}$ 1114.37, found 1114.69.

Example 67

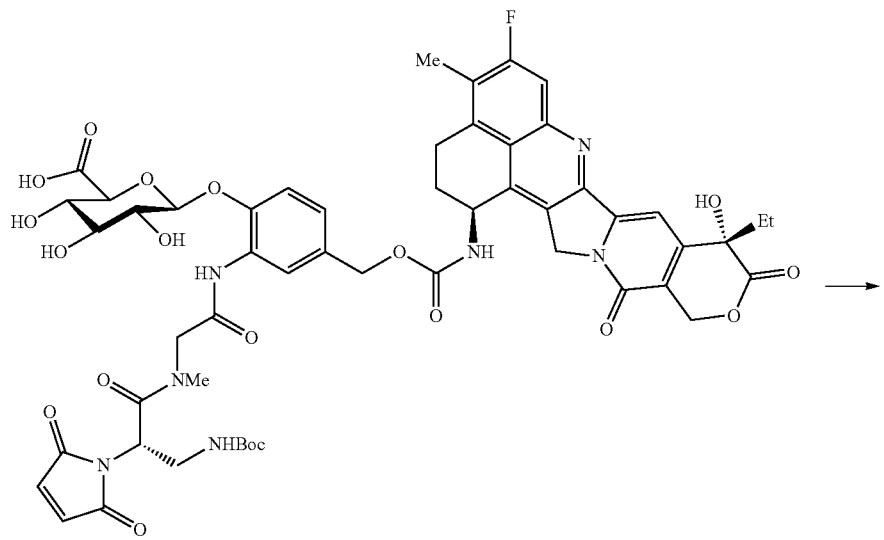

99

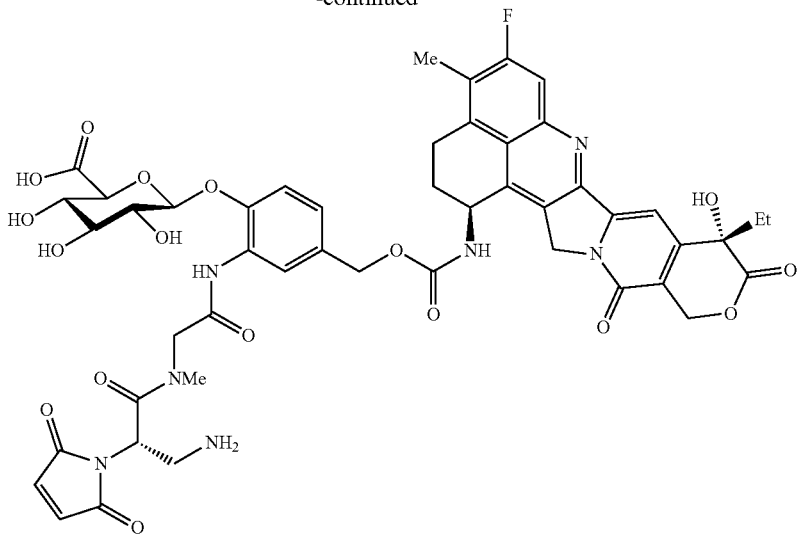

100

Compound 99 (4.5 mg, 4.0 μmol) was dissolved in 20% TFA in DCM. Complete conversion to compound 100 was observed by UPLC-MS after 25 minutes. The reaction was concentrated in vacuo and purified by prep-HPLC 10 mm 10-95% MeCN in H$_2$O 0.05% TFA. Fractions containing the desired product were lyophilized to afford compound 100 as a white powder (3.91 mg, 3.86 μmol, 96%). LC-MS (Method A): t$_R$=1.31 min; MS (m/z) [M+H]$^+$ calc. for C$_{48}$H$_{50}$N$_7$O$_{17}$ 1014.32, found 1014.07.

Example 68

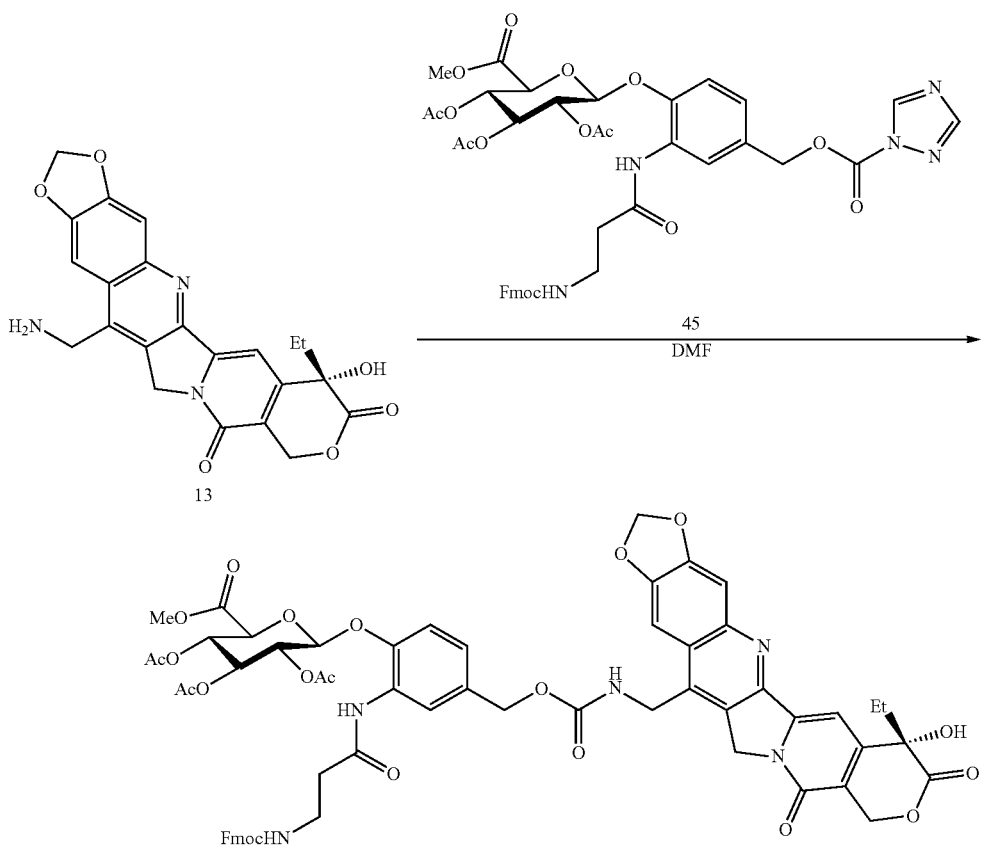

Compound 45 (82 mg, 0.097 mmol), prepared according to the procedure of Example 26, and compound 13 (14 mg, 0.033 mmol), referred to as 7-MAD-MDCPT, were dissolved in DCM (2 mL) followed by DMF (0.5 mL). DCM was evaporated off to concentrate the reaction mixture into DMF. No conversion to product observed after 30 minutes, additionally no hydrolysis of compound 45 was observed. DIPEA (0.1 mL) was added to the reaction mixture whereupon the clear red reaction mixture became opaque. Reaction allowed to stir overnight (~15h) at room temperature. Approximately 50% conversion of drug to the desired drug linker product was observed, ~10% hydrolysis of activated CDT linker remaining. [Note: Using a MeOH diluent for UPLC-MS analysis the Linker-CDT was observed at t=30 min (reaction neutral), Linker-OCOMe observed at t=15h (after base addition)]. Reaction was concentrated slowly at 45° C. under vacuum for 60 minutes. Reaction mixture heated at 60° C. for 4 hours until complete conversion was observed by UPLC-MS. Reaction was concentrated in vacuo, then purified by column chromatography 0-5% MeOH in DCM. Fractions containing the desired product were concentrated to afford compound 101 as a white solid (28 mg, 0.023 mmol, 70%). LC-MS (Method A): $t_R$=2.17 min; MS (m/z) [M+H]$^+$ calc. for $C_{61}H_{58}N_5O_{21}$ 1196.36, found 1196.19.

Example 69

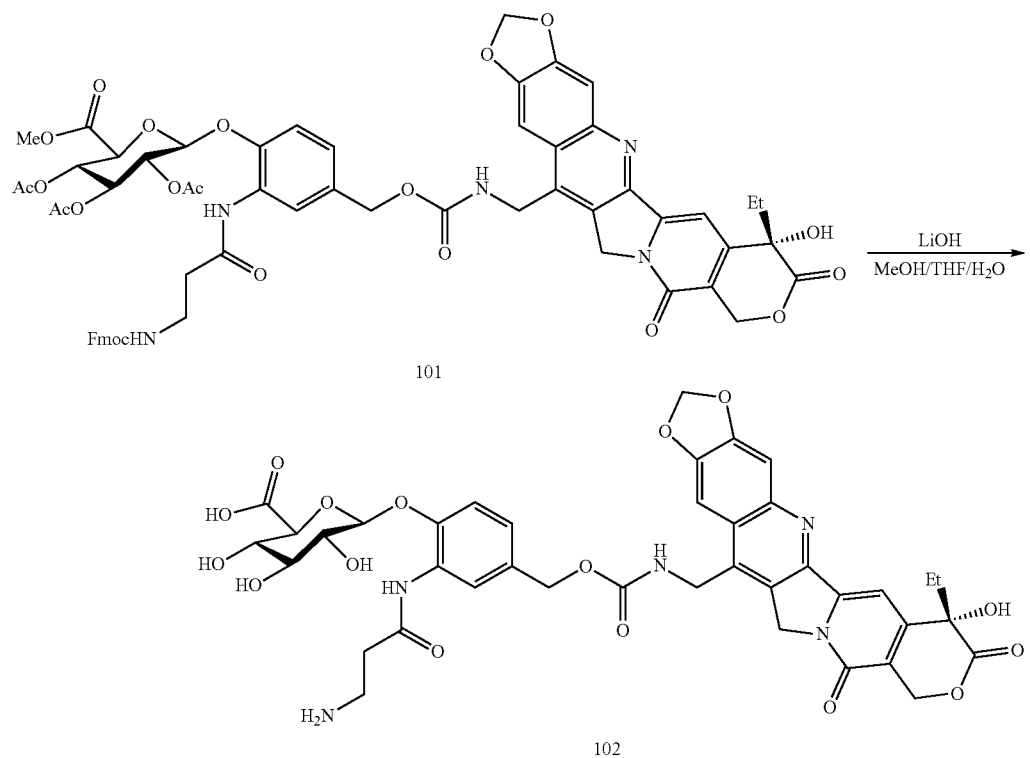

Compound 101, 28 mg, 0.023 mmol) was dissolved in MeOH (0.5 mL) and THF (0.5 mL). LiOH (25 mg, 1.0 mmol) was added. The reaction was sonicated to solubilize LiOH and then stirred. After 10 minutes water was added (0.5 mL). Complete conversion to the deprotected glucuronide was observed by UPLC-MS after 90 minutes. Piperidine (0.05 mL) was added. Complete deprotection of the Fmoc was observed after 60 additional minutes. The reaction was quenched with AcOH (0.2 mL). The reaction was concentrated, then purified by Prep-HPLC using a 10 mm Max-RP with a 5-60-95 MeCN in H2O 0.05% TFA gradient. Fractions containing the desired product were concentrated in vacuo to afford compound 102 as a yellow solid (10.1 mg, 0.0121 mmol, 51.8%). LC-MS (Method A): $t_R$=1.05 min; MS (m/z) [M+H]$^+$ calc. for $C_{39}H_{40}N_5O_{16}$ 834.25, found 833.71.

313
Example 70

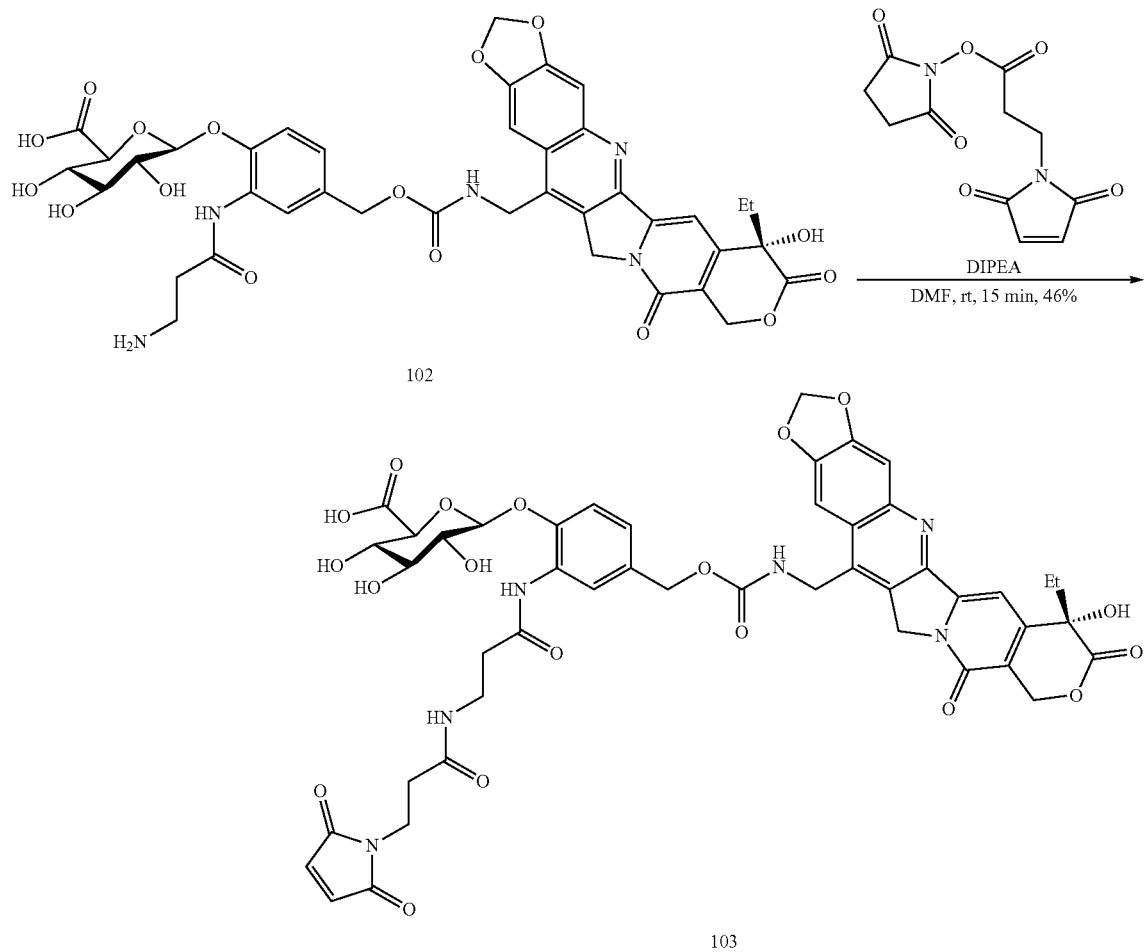

Compound 102 (10.1 mg, 0.0121 mmol) was dissolved in DMF (0.2 mL). 3-(Maleimido)propionic acid N-hydroxysuccinimide ester (9.7 mg, 0.036 mmol) was added. DIPEA (13 µL, 0.073 mmol) was added. The reaction was stirred for 15 minutes at which point complete conversion was observed by UPLC-MS. The reaction was quenched with AcOH (0.05 mL), then purified by Prep-HPLC 10 mm Max RP C125-60-95% MeCN in H$_2$O 0.05% TFA. Fractions containing the desired product were lyophilized to afford compound 103 as a yellow powder (5.53 mg, 0.00561 mmol, 46.4%). LC-MS (Method A) $t_R$=1.24 min; MS (m/z) [M+H]$^+$ calc. for $C_{46}H_{45}N_6O_{19}$ 985.27, found 985.45.

Example 71

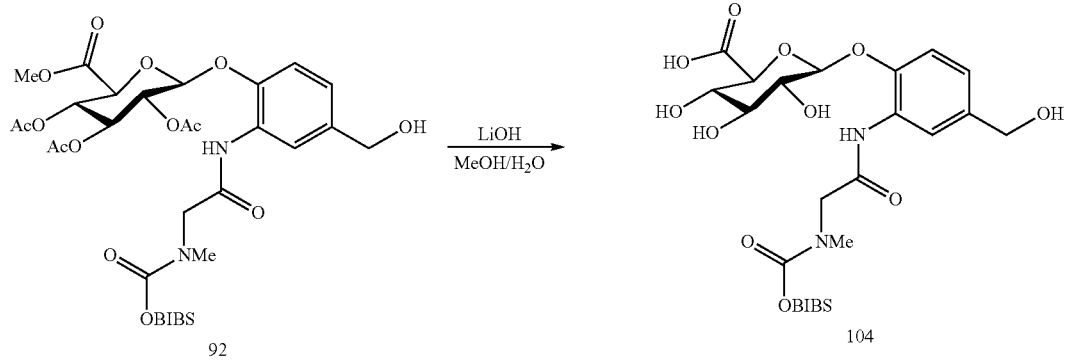

Compound 92 (500 mg, 0.65 mmol), prepared according to the procedure of Example 60, was dissolved in MeOH (10 mL). LiOH (500 mg, 21 mmol) added. The reaction was sonicated, and stirred for 5 min. H₂O added, stir 5 min. Complete conversion observed. The reaction was quench with AcOH, concentrated in vacuo and purified by Prep-HPLC. Fractions containing desired product were concentrated in vacuo to afford compound 104 as a colorless solid (295 mg, 0.469 mmol, 72%). LC-MS (Method C): $t_R$=1.23 min; MS (m/z) [M+H]⁺ calc. for $C_{29}H_{49}N_2O_{11}Si$ 629.31, found 629.01.

Example 72

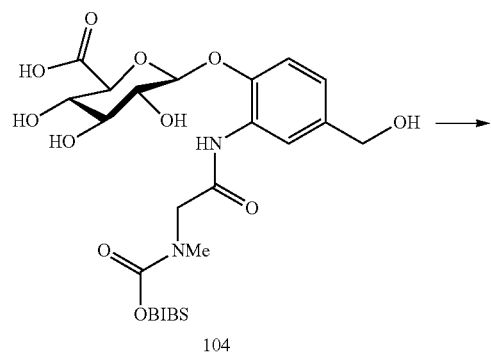

104

-continued

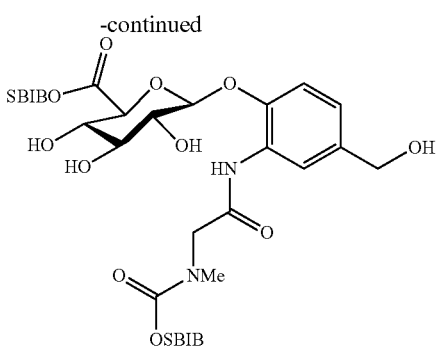

105

Compound 104 (295 mg, 0.469 mmol) was dissolved in anhydrous pyridine (5 mL) and cooled to 0° C. BIBSOTf (0.392 mL, 1.41 mmol) was added dropwise over 15 minutes checking by UPLC-MS for completion after addition of each stoichiometric equivalent. Reaction was diluted with EtOAc (100 mL), washed with 1M HCl (3×100 mL), dried MgSO4, filtered and concentrated in vacuo. The crude product was purified by column chromatography 50G KP-Sil, 10-100% EtOAc in Hex. Fractions containing the desired product concentrated to afford compound 105 as a colorless solid (301 mg, 0.363 mmol, 77%). LC-MS (Method C): $t_R$=1.65 min; MS (m/z) [M+H]⁺ calc. for $C_{41}H_{75}N_2O_{11}Si_2$ 827.49, found 827.31.

Example 73

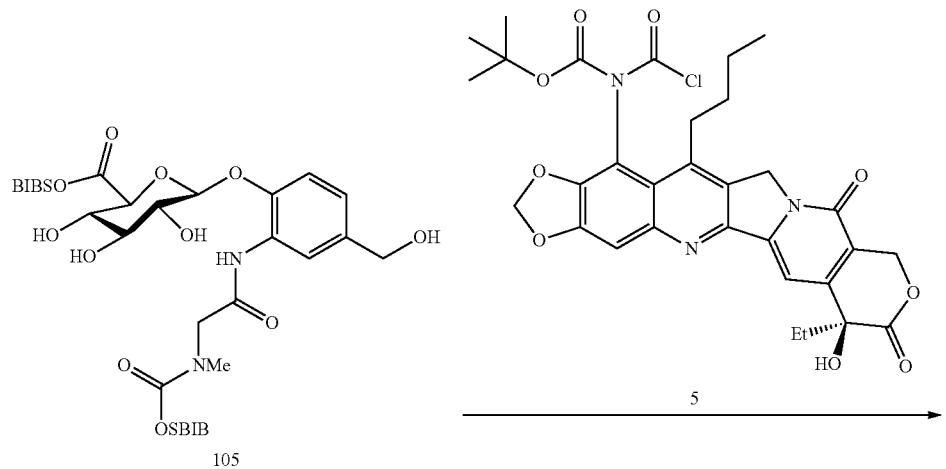

105

-continued

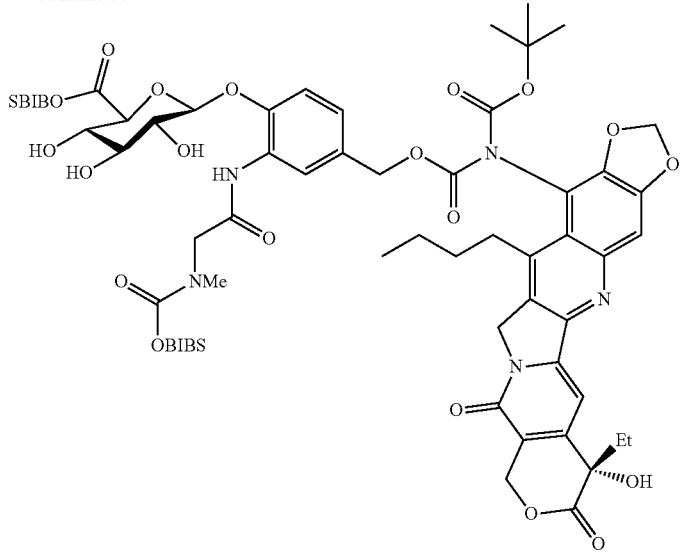

106

Compound 105 (218 mg, 0.264 mmol) was dissolved in anhydrous DCM (1 mL) and cooled to 0° C. The compound 5 (0.087 mmol) reaction solution from Example 2 was added directly to the DCM reaction solution. Reaction mixture allowed to warm to room temperature over 1h. Stirred at room temperature for 16 hours. Reaction quenched with MeOH, then purified by flash chromatography 50G KP-Sil 0-10% MeOH in DCM. Fractions containing the desired product were concentrated in vacuo to afford compound 106 as a yellow solid (66.1 mg, 0.0467 mmol, 53%). LC-MS (Method C): $t_R$=1.76 min; MS (m/z) [M+H]$^+$ calc. for $C_{72}H_{106}N_5O_{20}Si_2$ 1416.70, found 1416.74.

Example 74

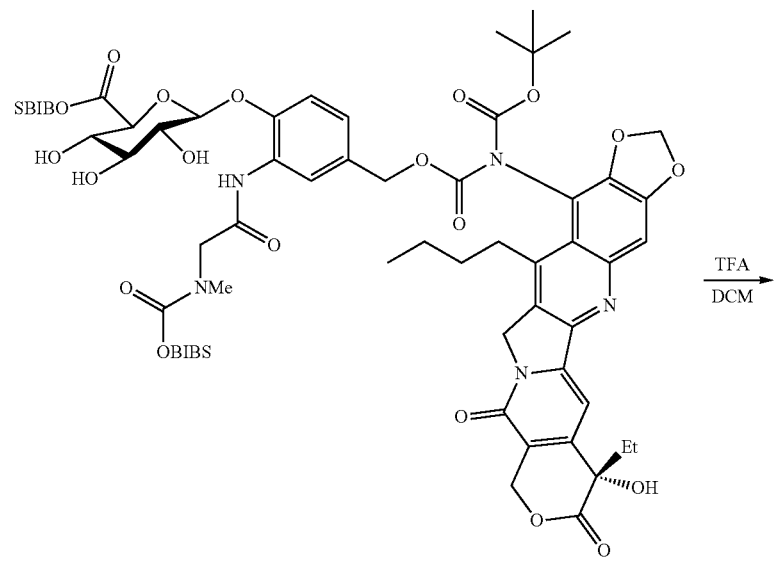

106

-continued

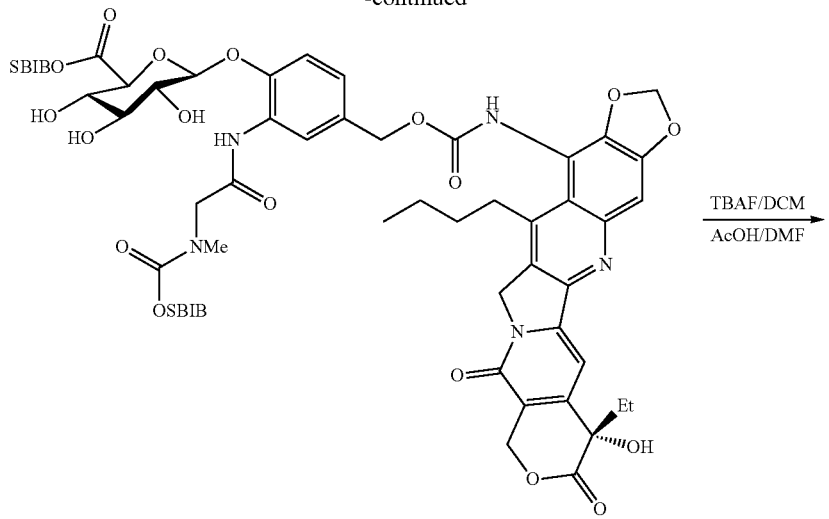

107

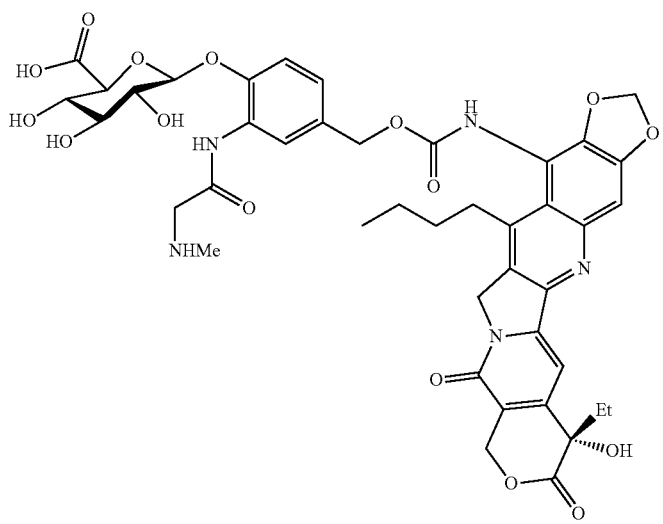

108

Compound 106 (66.1 mg, 0.0467 mmol) was dissolved in DCM (2 mL). TFA (0.4 mL) was added. The reaction was stirred for 20 minutes. Complete conversion observed by UPLC-MS. The reaction was concentrated in vacuo to afford compound 107 as a yellow solid and used in the next step without further purification. LC-MS (Method A): $t_R$=1.68 min; MS (m/z) [M+H]$^+$ calc. for $C_{67}H_{98}N_5O_{18}Si_2$ 1316.64, found 1316.80.

Crude compound 107 (0.0467 mmol) was dissolved in anhydrous DMF (1 mL). AcOH (200 μL) was added followed by TBAF 1M in THF (200 uL). The reaction was stirred at room temperature for 30 minutes. Complete conversion was observed by UPLC-MS. Silica (~100 mg) added to quench fluoride anion. The reaction mixture was filtered through a syringe filter, rinsed 2×1 mL 2:1 DMA:H$_2$O 10% AcOH and purified by prep-HPLC 30 mm 10-95% MeCN in H$_2$O 0.05% TFA. Fractions containing the desired product were lyophilized to afford compound 108 as a yellow powder (33.5 mg, 100.0383 mmol, 82%). LC-MS (Method A): $t_R$=1.16; MS (m/z) [M+H]$^+$ calc. for $C_{42}H_{45}N_5O_{16}$ 875.29, found 875.82.

Example 75

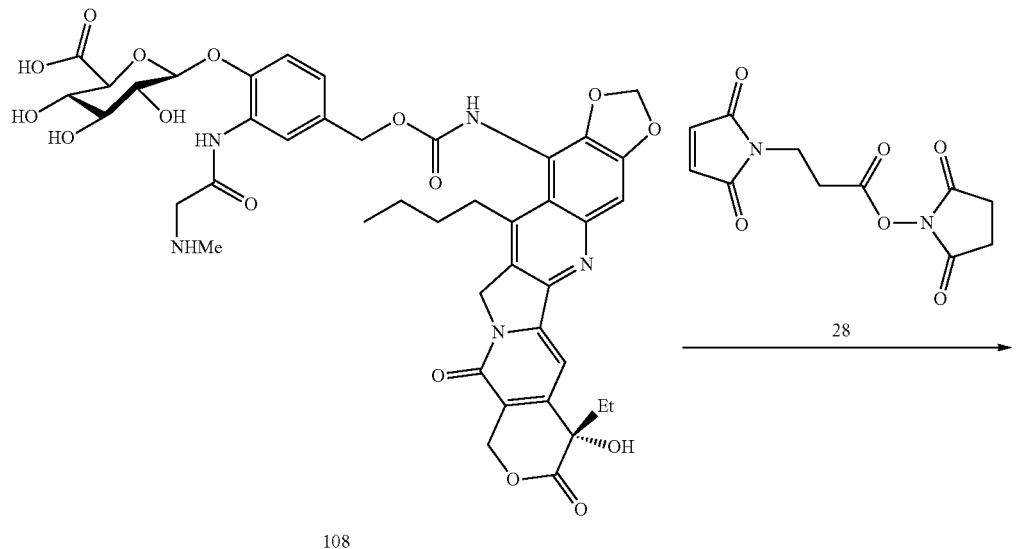

108

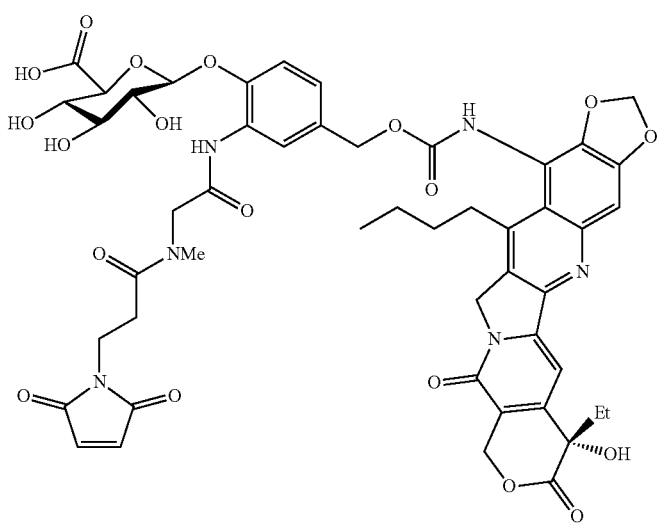

109a

Compound 108 (33.5 mg, 0.0383 mmol) was dissolved in DMF. DIPEA (0.040 mL, 0.23 mmol) was added to the reaction followed by 3-(maleimido)propionic acid N-hydroxysuccinimide ester (28, 30.6 mg, 115 mmol). The reaction was stirred for 90 minutes. Complete conversion was observed by UPLC-MS. The reaction was quenched with AcOH, and purified by Prep-HPLC- 21 mm. Fractions containing the desired product were lyophilized to afford compound 109a as a yellow powder (26.2 mg, 200.0255 mmol, 67%). LC-MS (Method A): $t_R$=1.39 min; MS (m/z) [M+H]$^+$ calc. for $C_{49}H_{51}N_6O_{19}$ 1027.32, found 1026.88.

Similar procedures are used with any of compounds 18a-18p of Example 10 to prepare Drug Linker compounds of general formula 109

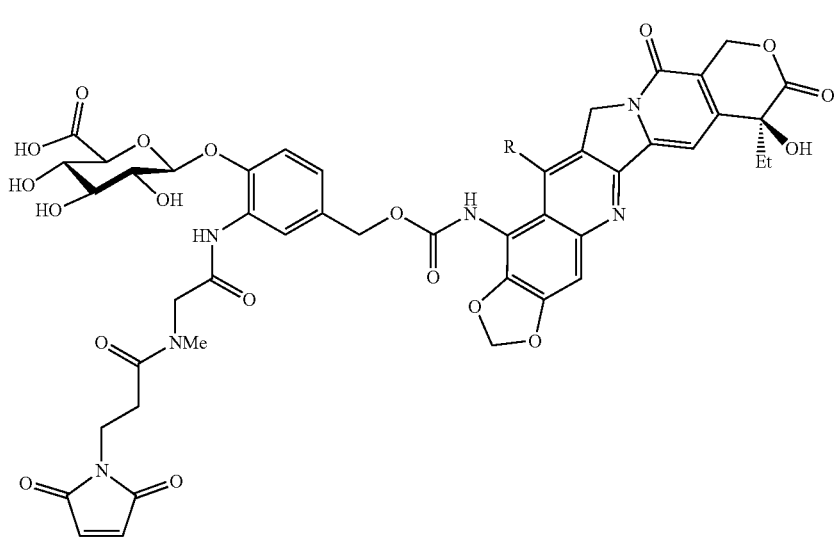
wherein R is any one of the R groups provided in compounds 18a-18p of Example 10, including the synthesized compound in which R is n-pentyl (compound 109b) starting from compound 18q.
Example 76
Compound 113 is prepared according to the following reaction scheme.
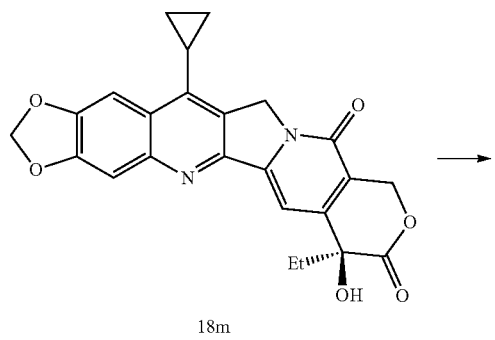
18m
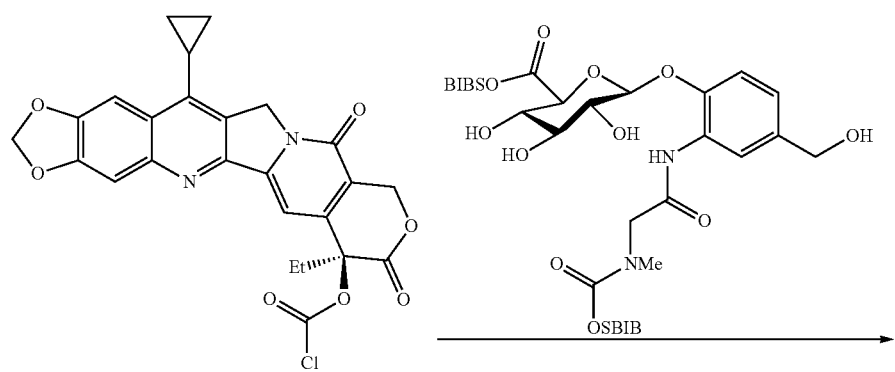
110

-continued
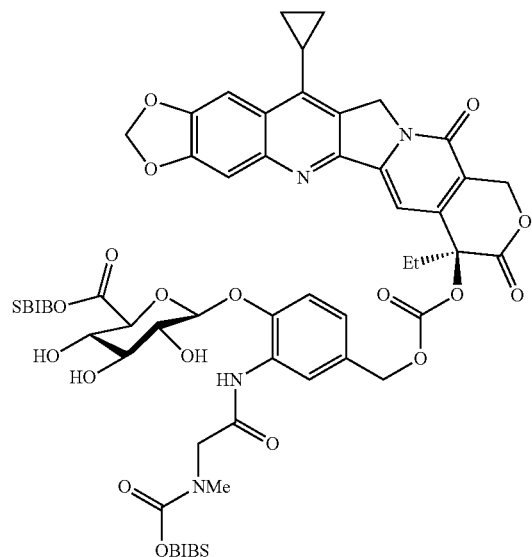
111
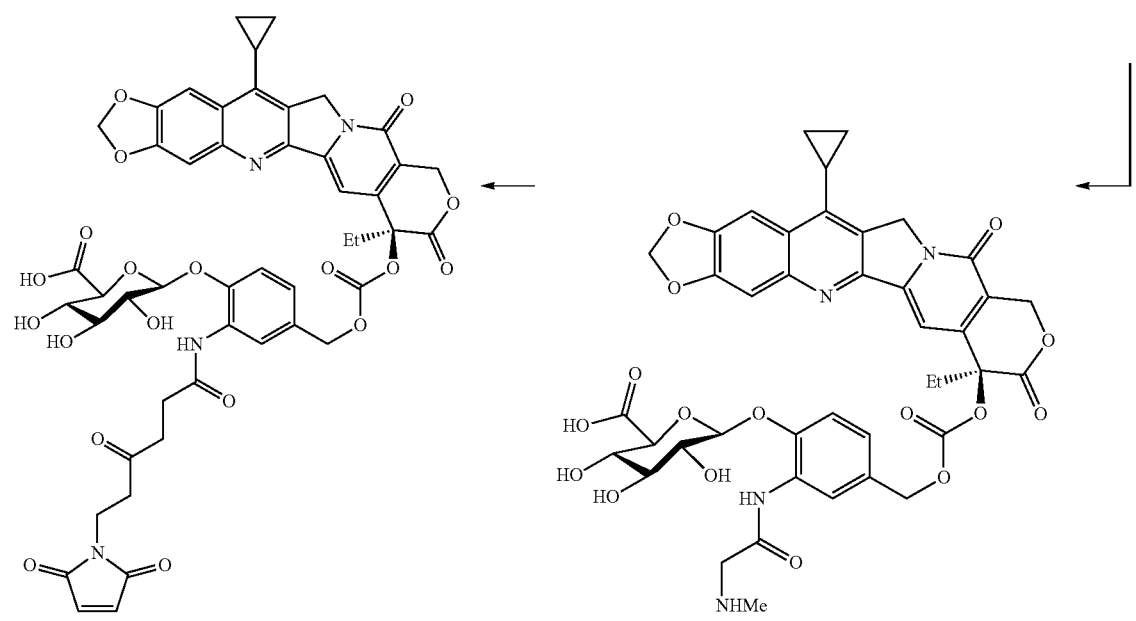
113 112

Similar procedures are used with any of compounds 18a-18p of Example 10 to prepare Drug Linker compounds of general formula 114:

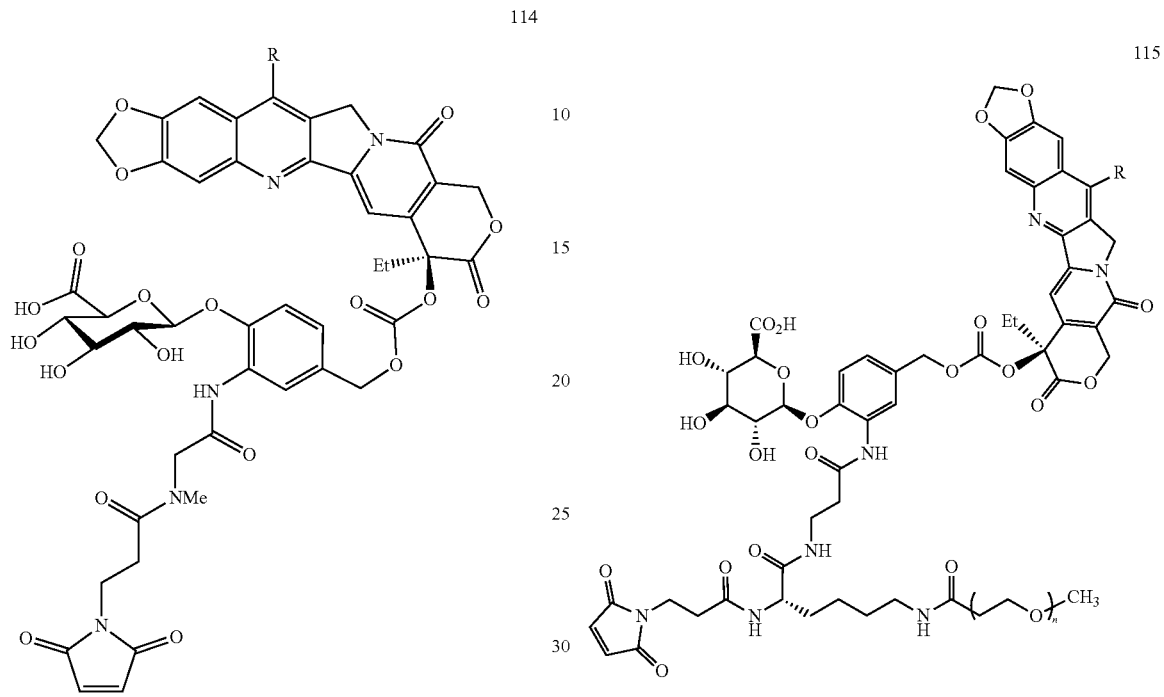

114 wherein R is any one of the R groups provided in compounds 18a-18p of Example 10, including those compounds that were synthesized in which R is n-pentyl (compound 114a) starting from compound 18h and R is n-butyl (compound 114b) starting from compound 6.

Example 77

Following the reaction scheme of Example 76 and Examples 44 and 45 compounds of formula 115 are prepared:

115 wherein subscript n is an integer from 4 to 24 and R is any one of the R groups provided in compounds 18a-18 of Example 10.

Example 78

Following the procedures of Examples 26-28, compounds of formula 116 are prepared:

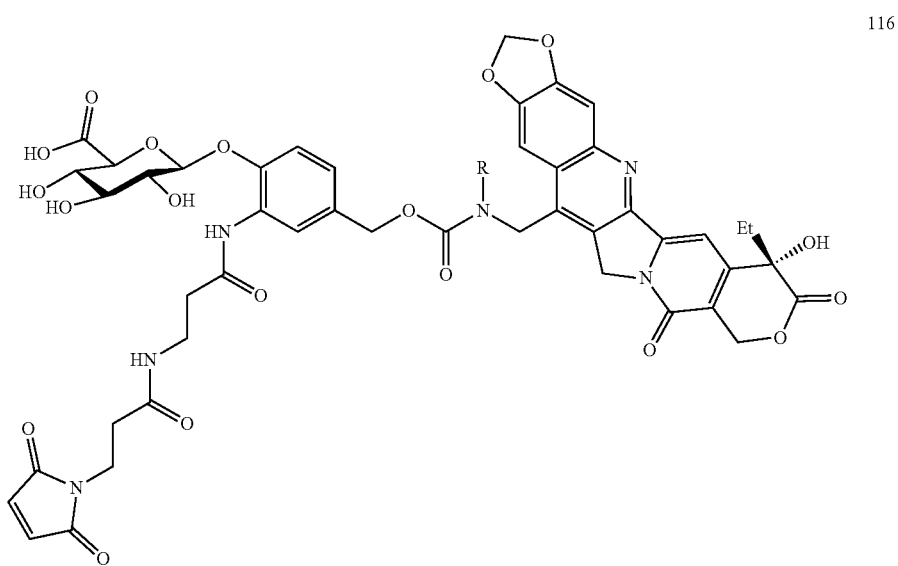

116 wherein R is any of the groups in camptothecin compounds 14a-14z of Example 7 that are compatible with the coupling reaction of compound 45 in so far as no reactive nucleophilic groups are present in the R substituent.

Example 78

Following the procedures of Example 14 and Examples 73-75, the compound of formula 117 is prepared:

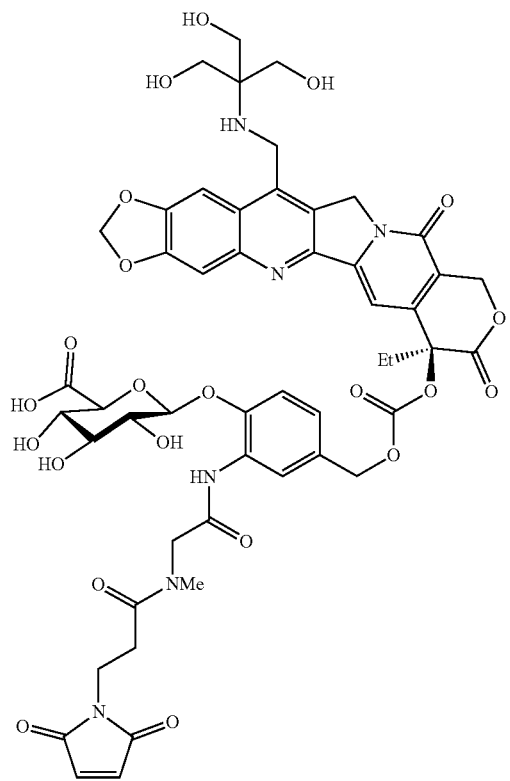

117

Example 79

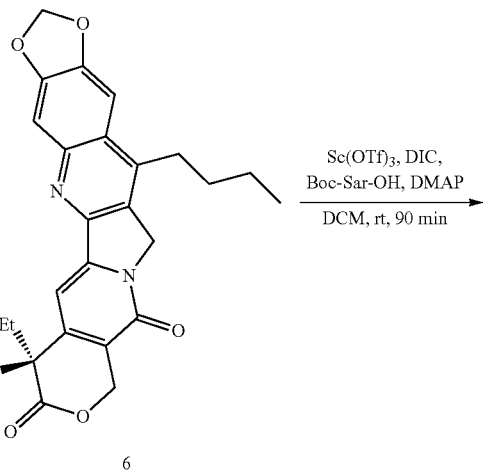

6

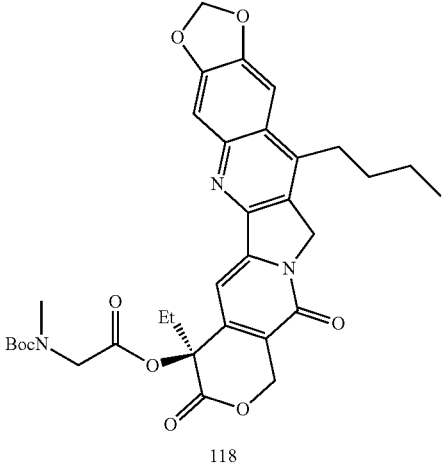

118

Compound 6 (19.0 mg, 0.0424 mmol), prepared according to the procedure of *Bioconjugate Chem.* (2009) 20: 1242-1250, was dissolved in anhydrous DCM (0.5 mL). DMAP (15.4 mg, 0.127 mmol), Sc(OTf)$_3$ (12.5 mg, 0.0254 mmol), Boc-Sar-OH (24.1 mg, 127 mmol) and DIC (21 μL, 136 mmol) were added to the reaction. The reaction was stirred for 90 minutes. The reaction was purified by column chromatography 0-5% MeOH in DCM. Fractions containing the desired product were concentrated in vacuo to afford compound 2 as yellow solid. LC-MS (Method A): t$_R$=1.52 min; MS (m/z) [M+H]$^+$ calc. for C$_{33}$H$_{38}$N$_3$O$_9$ 620.26, found 619.96.

Example 80

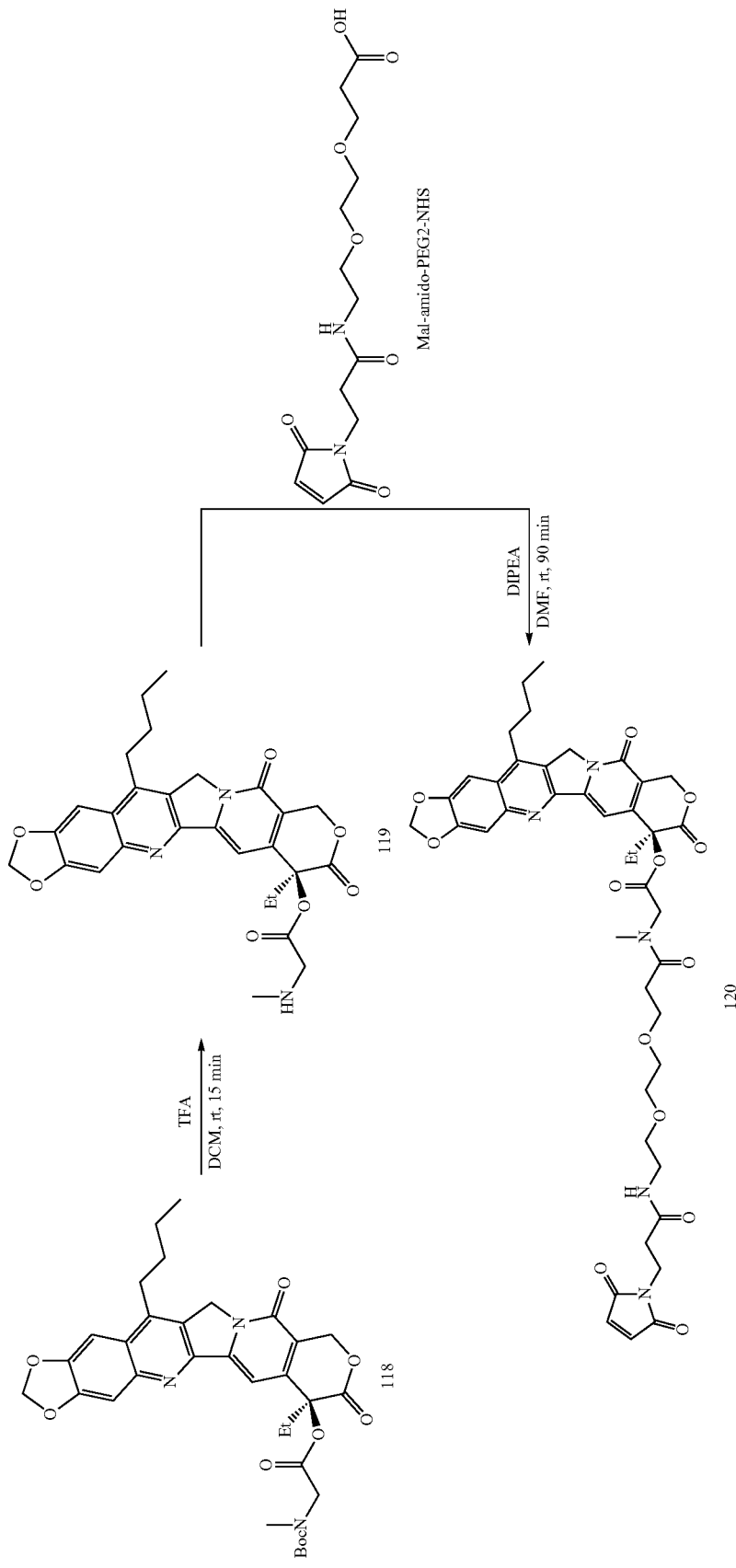

333

Compound 118 (25.2 mg, 0.0407 mmol) was dissolved in 20% TFA in DCM (2 mL). The reaction was stirred for 15 minutes at which point complete conversion was observed by UPLC-MS. The reaction was concentrated in vacuo to afford compound 119 as a yellow solid used in the next step without further purification. LC-MS (Method A): $t_R$=0.93 min; MS (m/z) [M+H]$^+$ calc. for $C_{28}H_{30}N_3O_7$ 520.21, found 519.87.

The crude product 119 (0.0407 mmol) was dissolved in anhydrous DMF (0.5 mL). DIPEA (35 µL, 0.203 mmol) was added followed by Mal-amido-PEG2-NHS (52 mg, 0.122 mmol) obtained from Broadpharm (CAS: 955094-26-5). The reaction was stirred for 90 minutes, quenched with AcOH (50 µL), and purified by Prep-HPLC. Fractions containing the desired product were lyophilized to afford compound 120 as a yellow powder (18.9 mg, 0.0228 mmol, 56%). LC-MS (Method A): $t_R$=1.16 min; MS (m/z) [M+H]$^+$ calc. for $C_{42}H_{48}N_5O_{13}$ 830.32, found 829.86. Compound 120 is an exemplary Drug Linker compound of general formula Z'-A-S*-W-CPT2

Example 81

334

-continued

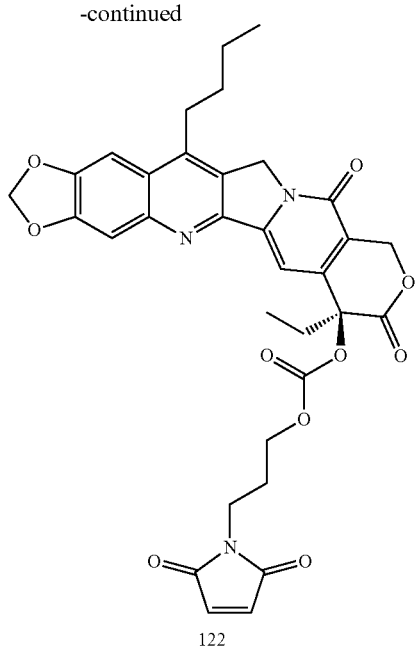

122

N-(3-Hydroxypropyl)maleimide (455 mg, 2.93 mmol) was dissolved in anhydrous DCM (4 mL). Phosgene 20% w/w in toluene was added and reaction was stirred for 60 minutes and then concentrated under flow of nitrogen, followed by concentration in vacuo to provide crude compound 122, which was reconstituted in 50 mg/mL in DCM and used directly in the next step.

Compound 6 (10 mg, 0.022 mmol), prepared according to the procedure of *Bioconjugate Chem.* (2009) 20: 1242-1250, was dissolved in anhydrous DCM (0.5 mL). DMAP (3 mg, 0.02 mmol) was added to the reaction. The compound 64 chloroformate solution (1 mL) prepared in the previous step was added to the reaction. The reaction was stirred for 90 minutes. Approximately 50% conversion to the desired product was observed. The reaction was purified by FCC 10G Biotage Ultra 0-5% MeOH in DCM. Fractions containing the desired product were concentrated in vacuo to afford compound 65 as a yellow solid (7.5 mg, 0.012 mmol, 53%). LC-MS (Method A): $t_R$=2.17 min; MS (m/z) [M+H]$^+$ calc. for $C_{33}H_{32}N_3O_{10}$ 630.21, found 629.98. Compound 122 is an exemplary Drug Linker compound of general formula Z'-A-CPT2

Example 82

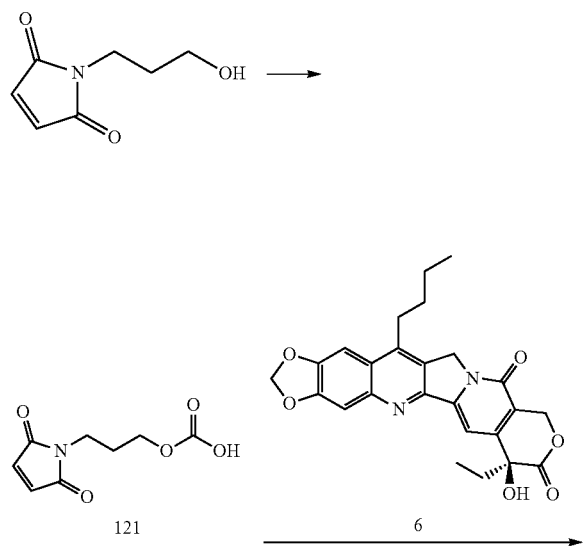

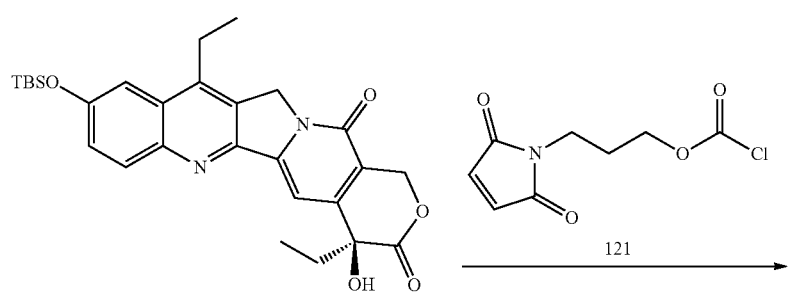

-continued

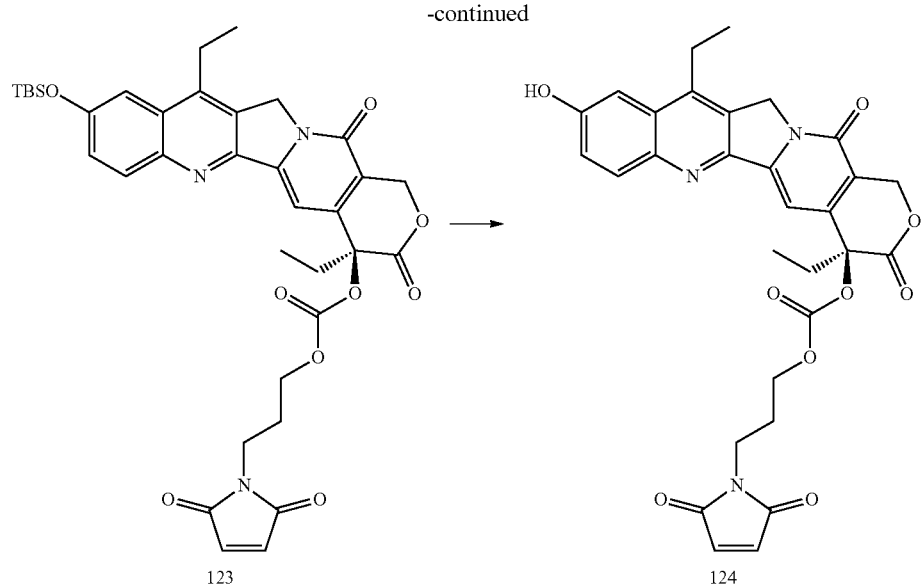

123 → 124

Compound 2 (45 mg, 0.088 mmol), prepared according to the procedure of Example 1, was dissolved in anhydrous DCM (0.5 mL). DIPEA (0.05 mL) and DMAP (11 mg, 0.09 mmol) were added to the reaction. The compound 64 chloroformate solution (1.1 mL) previously described was added to the solution and the reaction was stirred for 60 minutes. Approximately 70% conversion to the desired product was observed. The reaction was quenched with MeOH, then filtered through silica 10% MeOH in DCM. The eluent was concentrated to afford compound 123 as a white solid (0.088 mmol) which was used in the next step without further purification. LC-MS (Method B): $t_R$=1.91 min; MS (m/z) [M+H]$^+$ calc. for $C_{36}H_{42}N_3O_9Si$ 688.27, found 687.99.

Crude compound 123 (0.088 mmol) was dissolved in DMF (2 mL). AcOH (0.5 mL) was added to the reaction mixture followed by TBAF 1M in THF (0.440 mL, 0.444 mmol). The reaction was stirred for 30 minutes, then purified by Prep-HPLC 21 mm 5-95% MeCN in H$_2$O 0.05% TFA. Fractions containing the desired product were lyophilized to afford compound 124 as a yellow powder (10.24, 0.01785 mmol, 20%). LC-MS (Method A): $t_R$=1.24 min; MS (m/z) [M+H]$^+$ calc. for $C_{30}H_{28}N_3O_9$ 574.18, found 573.90. Compound 124 is an exemplary Drug Linker compound of general formula Z'-A-CPT3.

Example 83

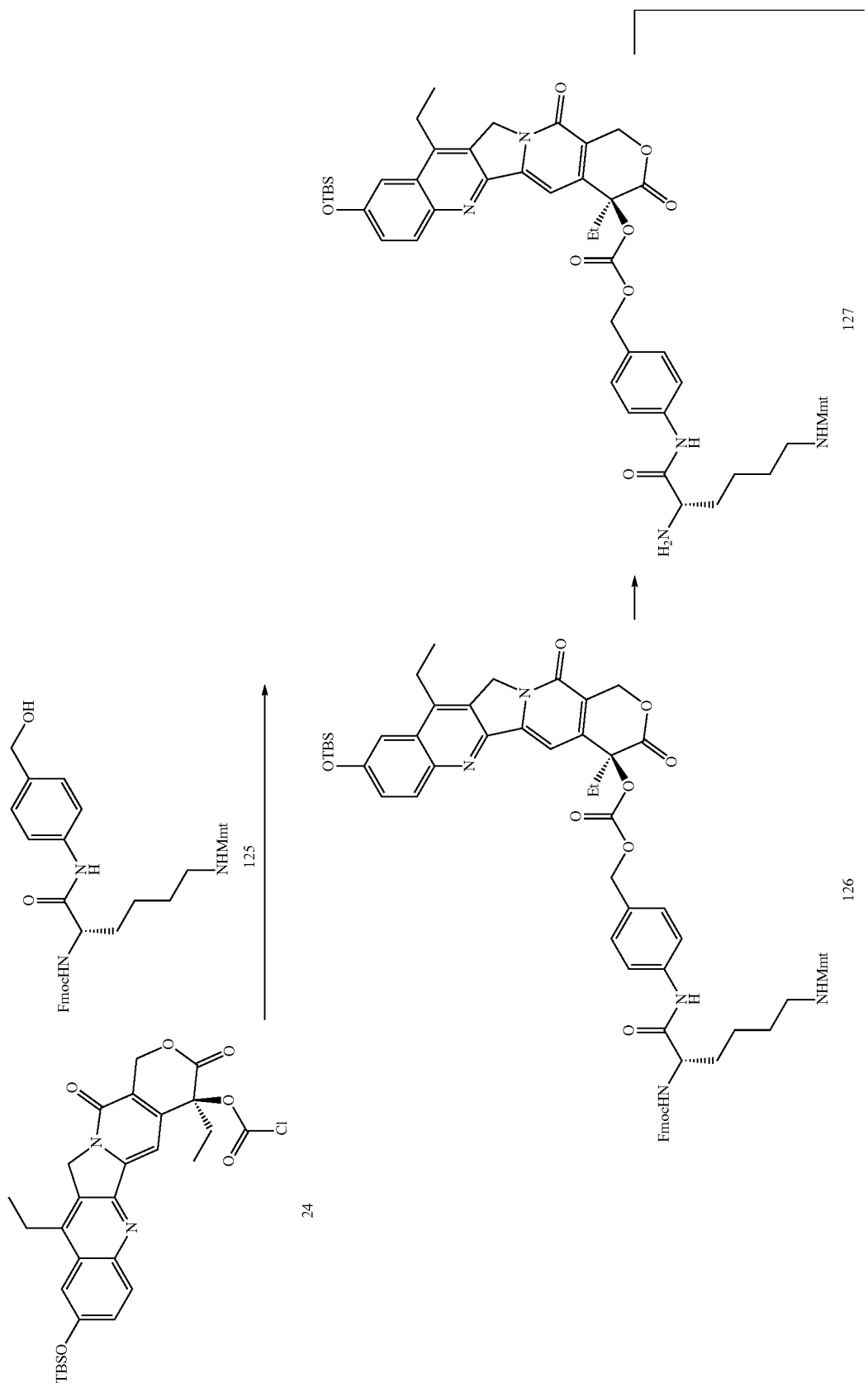

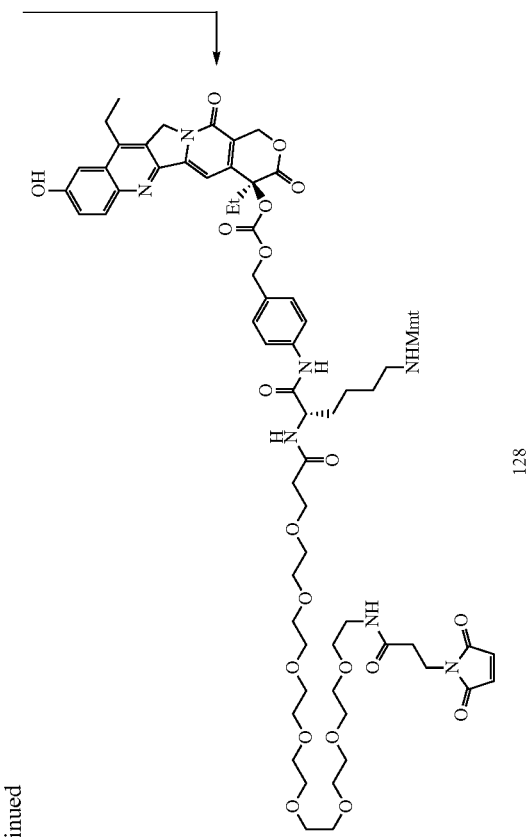
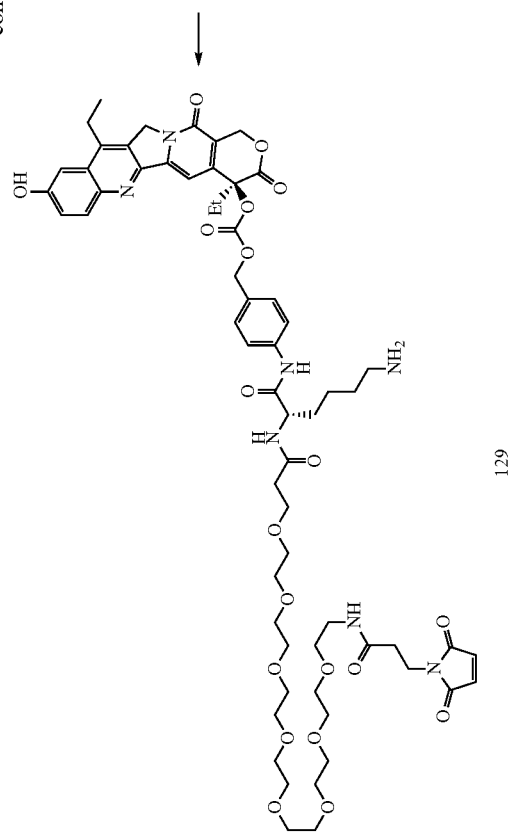

To the compound 24 chloroformate reaction mixture prepared according to Example 14 was added solid compound 125 (291 mg, 0.390 mmol), prepared according to the procedure of Bioorganic & Medicinal Chemistry Letters (2002) 12: 217-219. Conversion to product was observed after 10 minutes by UPLC-MS. The reaction was quenched MeOH, concentrated in vacuo, then roughly purified by column chromatography 0-10% MeOH in DCM. Fractions containing the desired product with impurities (free drug, linker) were concentrated to afford compound 126 as a slight yellow solid, which was used in the next step without further purification. LC-MS (Method C): $t_R$=1.85 min; MS (m/z) $[M+H]^+$ calc. for $C_{77}H_{80}N_5O_{11}Si$ 1278.56, found 1278.09.

Crude compound 126 was dissolved in 50% $Et_2NH$ in DCM. The reaction was stirred for 30 minutes at which time complete Fmoc deprotection was observed by UPLC-MS. The reaction mixture was concentrated in vacuo. After evaporation complete deprotection of the TBS protecting group was observed. The reaction was purified by column chromatography 0-10% MeOH in DCM. Fractions containing the desired product and minor impurities were concentrated in vacuo to afford compound 127 as an off white solid used (100 mg, 0.10 mmol, 41%) in next step without further purification. Rt=1.03 min Hydrophobic Method UPLC. MS (m/z) $[M+H]^+$ calc. for $C_{56}H_{56}N_5O_9$ 942.41, found 942.18.

Crude compound 127 (100 mg, 0.10 mmol) was dissolved in anhydrous DMF (2 mL). DIPEA (0.037 mL, 0.212 mmol) was added followed by MP-PEG8-OSu (81 mg, 117 mmol). Complete conversion was observed by UPLC-MS after 5 minutes. The reaction was quenched with MeOH and AcOH, concentrated in vacuo to provide crude compound 128, which was used in the next step without further purification.

Crude compound 128 was dissolved in 20% TFA in DCM and stirred for 1 hour. The reaction was concentrated in vacuo and purified by prep-HPLC. Fractions containing the desired product were lyophilized to afford compound 129 as an off-white solid (31.0 mg, 0.0249 mmol, 23%). LC-MS (Method A): $t_R$=1.37 min; MS (m/z) $[M+H]^+$ calc. for $C_{62}H_{82}N_7O_{20}$ 1244.56, found 1243.93. Compound 129 is an exemplary Drug Linker compound of general formula Z'-A-S*-W-RL-CPT3

Example 84

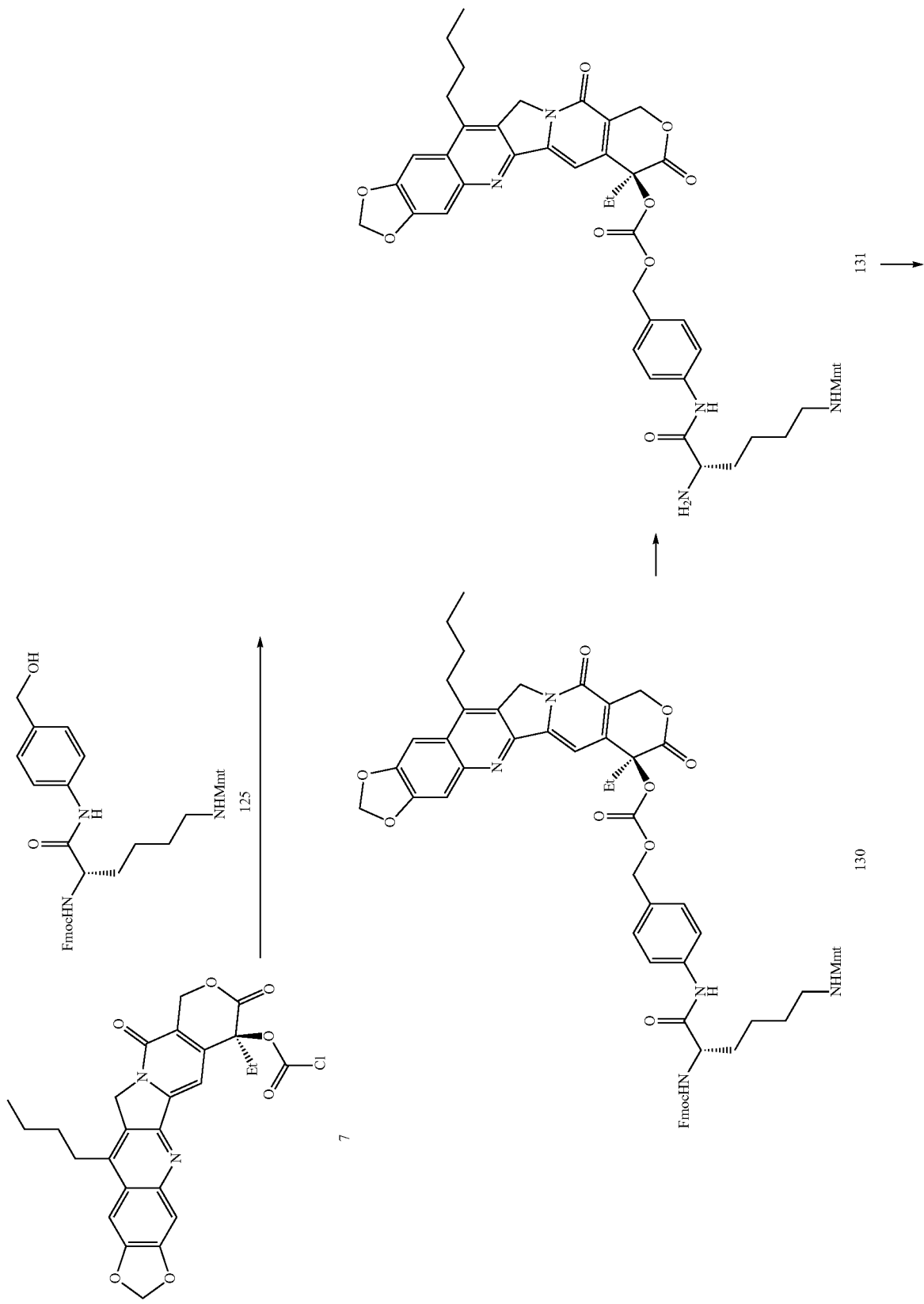

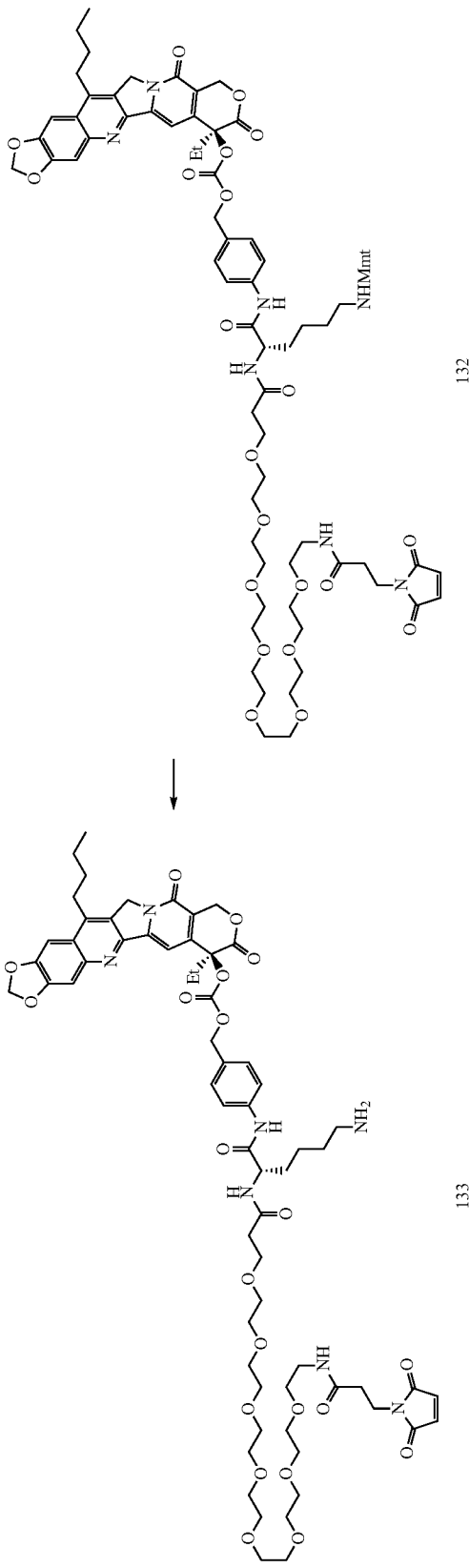

To the compound 7 chloroformate solution (0.334 mmol) from Example 3 was added compound 125 (372 mg, 0.499 mmol), prepared according to the procedure of *Bioorganic & Medicinal Chemistry Letters* (2002) 12: 217-219, in one portion. The reaction was stirred for 45 minutes. Using sample preparation previously described nearly complete conversion of the chloroformate to the desired product was observed. The reaction was quenched with MeOH, concentrated in vacuo and purified by FCC 50G KP-Sil 0-5% MeOH in DCM using a step gradient. Fractions containing the desired product and mixture of impurities concentrated in vacuo to afford compound 130 as a yellow solid (450 mg, ~80% w/w, 0.294 mmol), which was used in next step without further purification. LC-MS (Method A): $t_R$=1.61 min; MS (m/z) [M+H]$^+$ calc. for $C_{74}H_{70}N_5O_{12}$ 1220.50, found 1220.16.

Crude compound 130 (0.294 mmol) was dissolved in 10 mL 50% Et$_2$HN in DCM. The reaction was stirred for 30 minutes at which time nearly complete conversion was observed by UPLC-MS. The reaction was concentrated in vacuo to afford compound 131 as a yellow solid, which was used in next step without further purification. LC-MS (Method A): $t_R$=1.20 min; MS (m/z) [M+H]$^+$ calc. for $C_{59}H_{60}N_5O_{10}$ 998.43, found 998.26.

Crude compound 131 (0.294 mmol) from the previous step was dissolved in anhydrous DCM (5 mL). MP-Peg8-OSu (483 mg, 0.701 mmol) dissolved in DMF (250 mg/mL) was added. DIPEA (0.3 mL) was added and the reaction was stirred for 30 minutes at which time complete conversion to compound 132 was observed by UPLC-MS. The reaction mixture containing compound 132 was used in the next step without further purification. LC-MS (Method A): $t_R$=1.37 min; MS (m/z) [M+H]$^+$ calc. for $C_{85}H_{102}N_7O_{22}$ 1572.71, found 1571.90.

The reaction mixture (compound 57, 0.294 mmol) containing crude compound 132 was quenched and acidified with TFA (1 mL). The reaction was stirred at room temperature for 20 minutes at which time complete conversion was observed. The reaction was concentrated in vacuo and purified by Prep-HPLC 30 mm C1810-95% MeCN in H$_2$O 0.05% TFA. Fractions containing the desired product were lyophilized to afford compound 133 as a yellow solid (107 mg, 0.0823 mmol, 28%). LC-MS (Method A): $t_R$=1.17 min; MS (m/z) [M+H]$^+$ calc. for $C_{65}H_{86}N_7O_{21}$ 1300.59, found 1300.69. Compound 133 is an exemplary Drug Linker compound of general formula Z'-A-S*-W-RL-CPT2.

Example 85

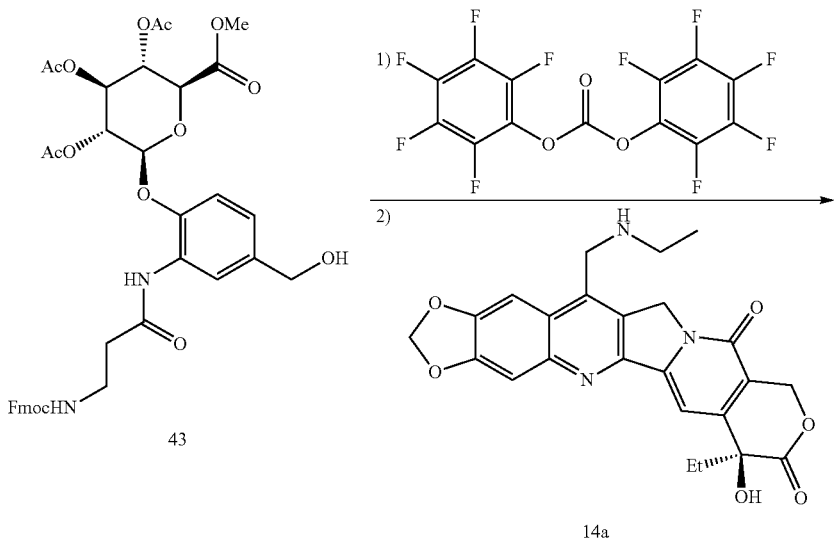

43

14a

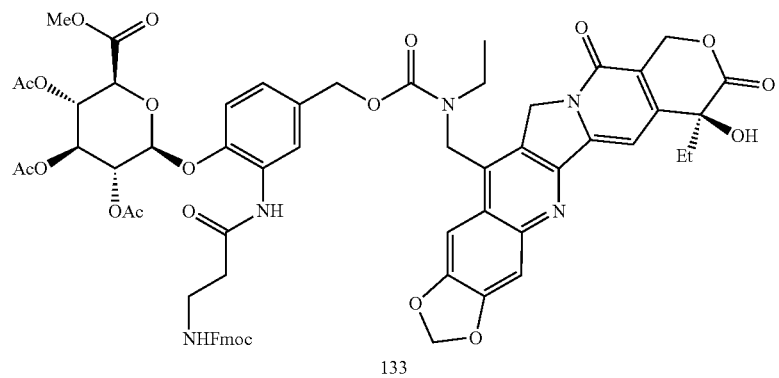

133

Compound 43 (143.4 mg, 0.1916 mmol), prepared according to the procedure *Bioconjugate Chem.* (2006) 17: 831-840 was dissolved in anhydrous DMF (0.5 mL). DIPEA (0.0334 mL, 0.192 mmol). To the DMF solution was added bis-(pentafluorophenyl) carbonate (75.5 mg, 0.192 mmol, purchased form TCI America Product Number B3604). The reaction was stirred for 30 minutes, followed by addition of compound 14a (28.7 mg, 0.0639 mg) from Example 7 in 0.5 mL anhydrous DMF. The reaction was stirred for 2 hours at room temperature. Complete conversion was observed by UPLC-MS. The reaction was quenched with AcOH (0.035 mL), then purified by preparative HPLC on a 21.2×250 mm Max-RP column using a gradient of 30-95% MeCN in H2O 0.05% TFA. Fractions containing the desired product was concentrated in vacuo to afford compound 133 as a yellow solid. (76.6 mg, 0.0623 mmol, 98%). LC-MS (Method F): $t_R$=1.68 min; MS (m/z) [M+H]+ calc. for $C_{63}H_{62}N_5O_{21}$ 1224.39, found 1224.46.

Example 86

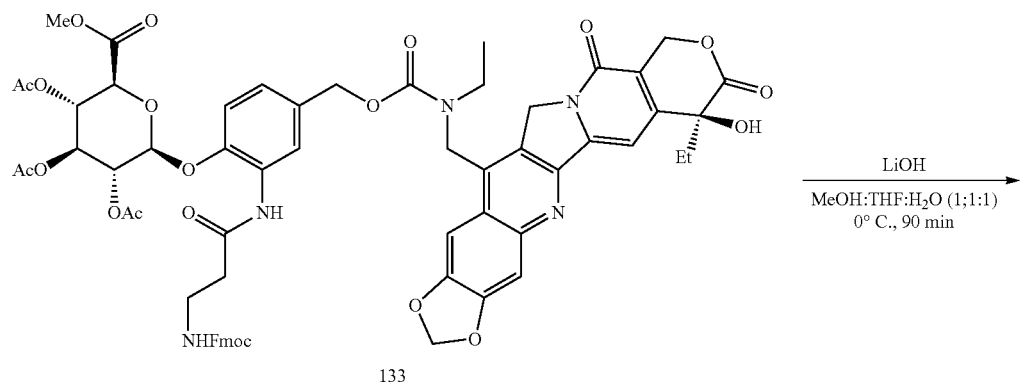

133

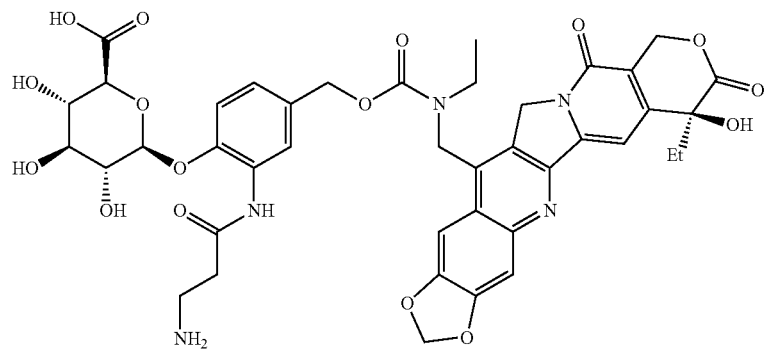

134

Compound 133 (76.6 mg, 0.0623 mmol) was dissolved in THF:MeOH 1:1 (2 mL). The reaction was cooled with an ice/water bath. LiOH (45 mg, 1.9 mmol) was added and the reaction was stirred for 30 minutes. Conversion to the acetate deprotected product observed by UPLC-MS. H2O (1 mL) was added to the reaction mixture. The reaction was stirred for 60 minutes. Complete conversion observed by UPLC-MS. Th reaction was quenched with AcOH (0.2 mL), concentrated in vacuo and purified by preparative HPLC using a 21.2×250 mm Max-RP column eluted with a gradient of 5-40-95% MeCN in H2O 0.05% TFA. Fractions containing the desired compound were concentrated in vacuo to afford compound 134 as a yellow solid (33.3 mg, 0.0386 mmol, 62%). LC-MS (Method D): $t_R$=1.09 min; MS (m/z) [M+H]+ calc. for $C_{41}H_{44}N_5O_{16}$ 862.28, found 862.16.

Example 87

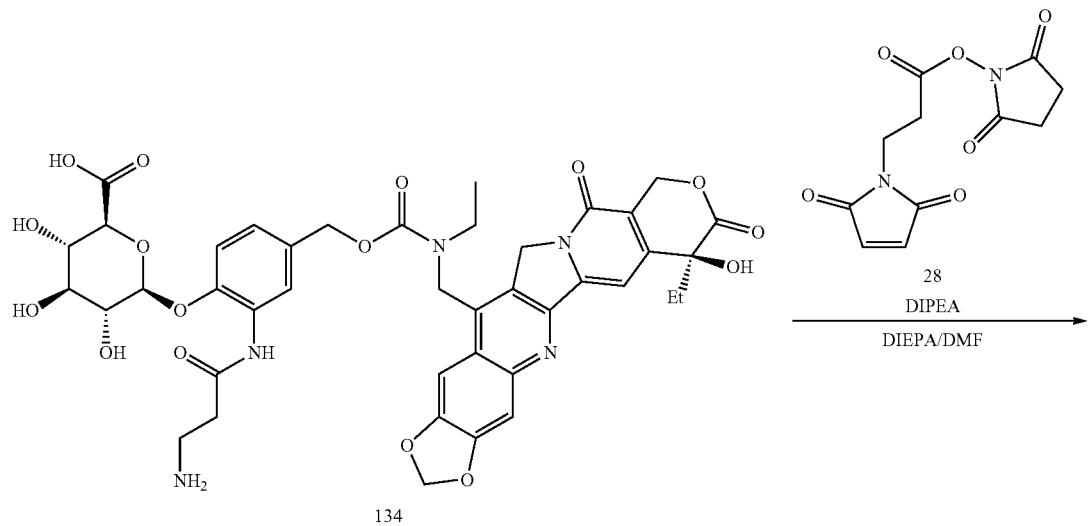

134

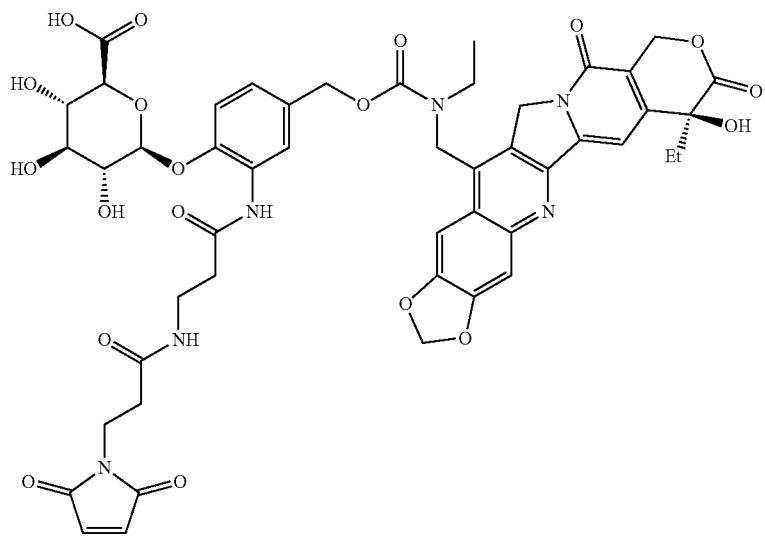

135

To compound 134 (33.3 mg, 0.0386 mmol) dissolved in anhydrous DMF (0.5 mL) and DIPEA (0.020 mL, 0.116 mmol) was added 3-(maleimido)propionic acid N-hydroxysuccinimide ester (28, 15.4 mg, 0.0580 mmol), purchased from TCI America (product number S0427). The reaction was stirred for 30 minutes. Complete conversion was observed after 5 minutes by UPLC-MS. The reaction was quenched with AcOH (0.020 mL) and purified by preparative HPLC eluting with 5-40-95% MeCN in $H_2O$ 0.05% TFA on a 21.2×250 mm Max-RP. Fractions containing the desired product were lyophilized to afford compound 135 as a yellow powder (21.85 mg, 0.02157 mmol, 55.8%). LC-MS (Method D): $t_R$=1.27 min; MS (m/z) [M+H]+ calc. for $C_{48}H_{49}N_6O_{19}$ 1013.30, found 1013.38.

Example 88

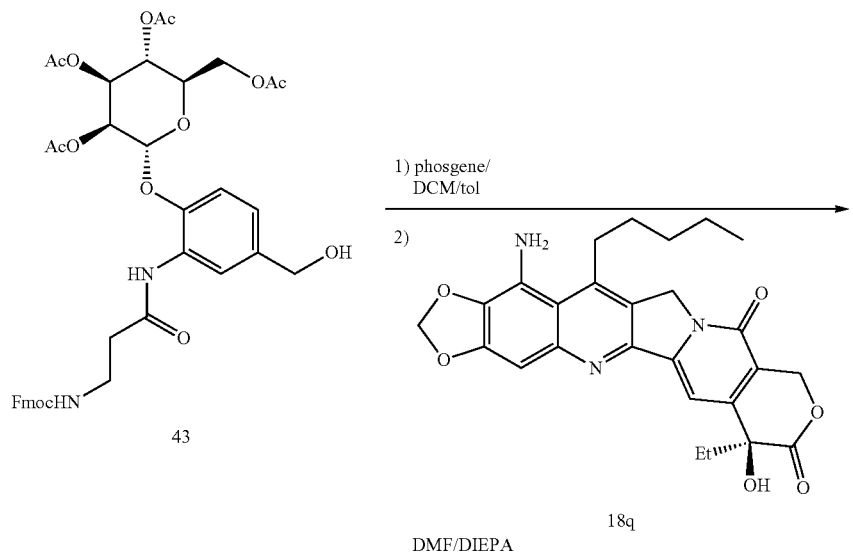

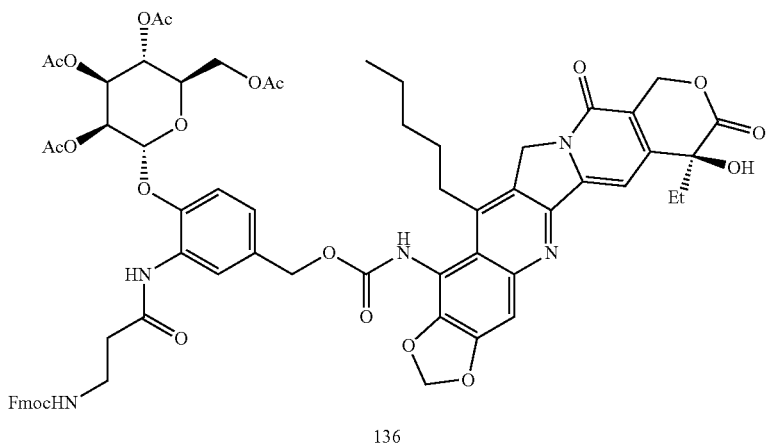

Compound 18q (100.0 mg, 0.2094 mmol) of Example 10 was dissolved in anhydrous DCM (4 mL). Phosgene 20% w/w in Toluene (2 mL, 3.51 mmol) was added to the reaction. The reaction was stirred for 2h at which complete conversion to activated isocyanate intermediate was observed by quenching a 2 μL aliquot of the reaction 98 μL MeOH and observing the formed MeOH adduct by UPLC-MS. The reaction was concentrated under stream of nitrogen, then further dried under high vacuum. Compound 43 (239.6 mg, 0.3141 mmol) was dissolved in anhydrous DMF (1 mL), then added directly to the activated isocyanate solid. DIPEA (0.11 mL, 0.63 mmol) was added and the reaction was stirred to dissolve all components. The reaction was stirred for 30 minutes at which point complete conversion was observed. The reaction was quenched with MeOH, concentrate in vacuo, and purified by column chromatography eluting with 0-6% MeOH in DCM on a 25G KP-Sil column. Fractions containing the desired product and drug related impurities were concentrated to afford compound 113 as a yellow solid (186.6 mg, 0.1474 mmol, 70%). The product was used in the next step without further purification. LC-MS (Method D): $t_R$=2.14 min; MS (m/z) [M+H]+ calc. for $C_{66}H_{68}N_5O_{21}$ 1266.44, found 1266.57.

Example 89

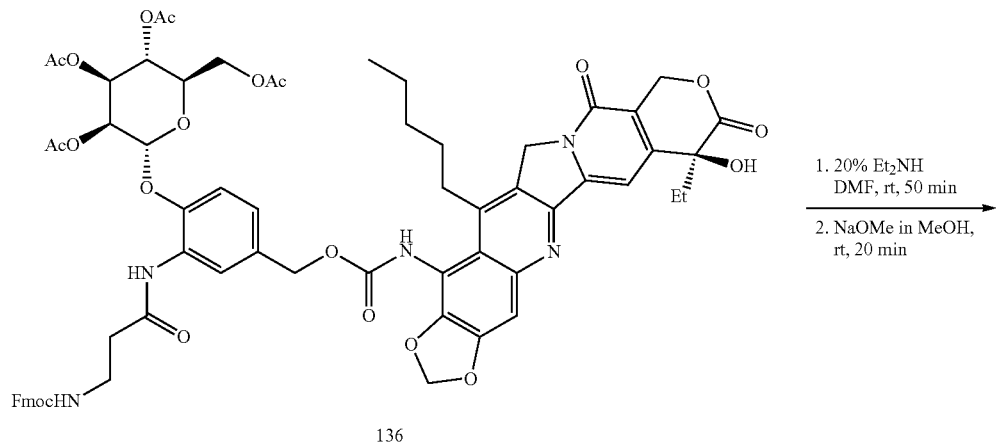

136

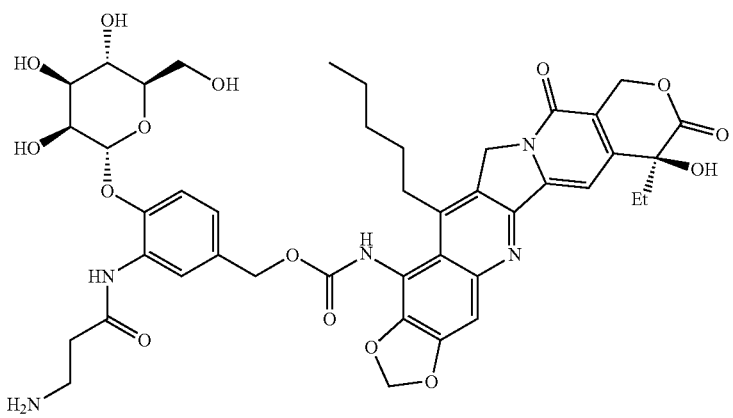

137

Compound 136 (186.6 mg, 0.1474 mmol) was dissolved in 20% diethylamine in DMF (2 mL). The reaction was stirred for 50 minutes at which point nearly complete deprotection of the Fmoc protecting group was observed. The reaction was concentrated in vacuo and re-dissolved in MeOH (2 mL). NaOMe (0.5 M in MeOH, 1.77 mL, 0.884 mmol) was added and the reaction was stirred at room temperature for 20 minutes. Complete conversion was observed by UPLC-MS after 20 minutes. The reaction was neutralized with AcOH, concentrated in vacuo and purified by preparative HPLC eluting with 5-40-95% MeCN in $H_2O$ 0.05% TFA on a 21.2×250 mm Max-RP column. Fractions containing the desired product were concentrated in vacuo to afford compound 137 as a yellow solid (22.5 mg, 0.0257 mmol, 17%). LC-MS (Method D): $t_R$=1.13 min; MS (m/z) [M+H]+ calc. for $C_{43}H_{50}N_5O_{15}$ 876.33, found 876.22.

Example 90

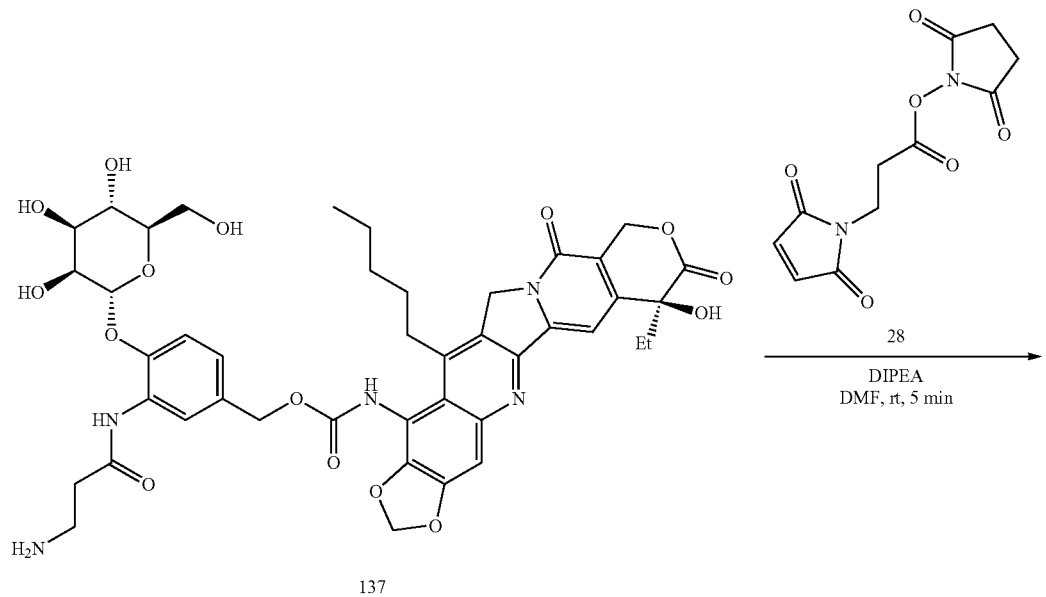

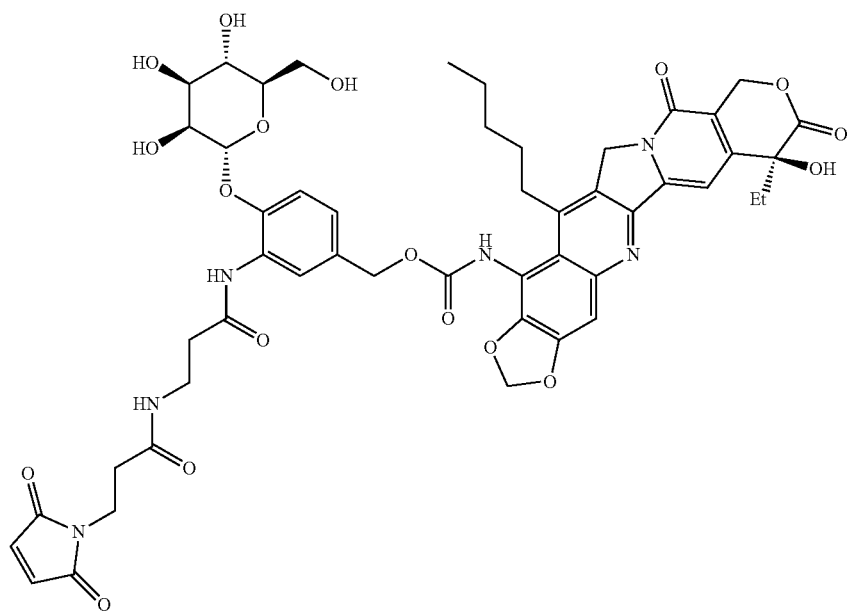

Compound 137 (22.5 mg, 0.0257 mmol) was dissolved in anhydrous DMF (0.5 mL). DIPEA (0.027 mL, 0.15 mmol) was added to the reaction followed by 3-(maleimido)propionic acid N-hydroxysuccinimide ester (28, 20.5 mg, 0.0771 mmol, purchased from TCI America product number S0427). The reaction was stirred for 5 minutes. Complete conversion was observed by UPLC-MS. The reaction was quenched with AcOH (0.030 mL) and purified by preparative HPLC eluting with 5-40-95% MeCN in H2O 0.05% TFA on a 21.2×250 mm MaxRP column. Fractions containing the desired product were lyophilized to afford compound 138a as a yellow powder (11.36 mg, 0.01106 mmol, 43.1%). LC-MS (Method D): $t_R$=1.33 min; MS (m/z) [M+H]+ calc. for $C_{50}H_{55}N_6O_{18}$ 1027.36, found 1027.15.

Example 91

Following the procedures form Examples 88-90 Drug Linker compounds of general formula 138 are prepared:

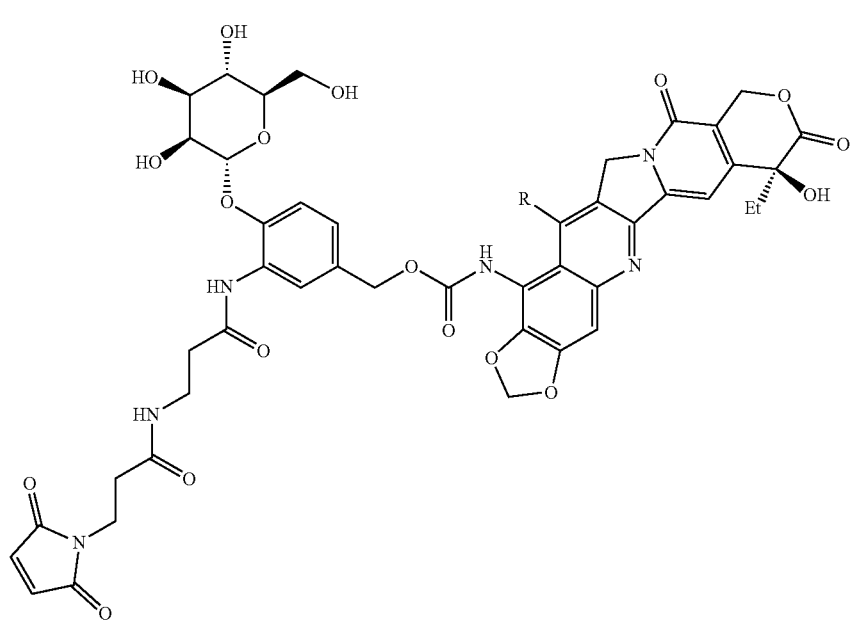

wherein R is any one of the R groups provided in compounds 18a-18p of Example 10, including the synthesized Drug Linker compound in which R is cyclopropyl (compound 138b) starting from compound 18r, except that the mannose residue moiety is replaced by glucuronic acid.

Example 92

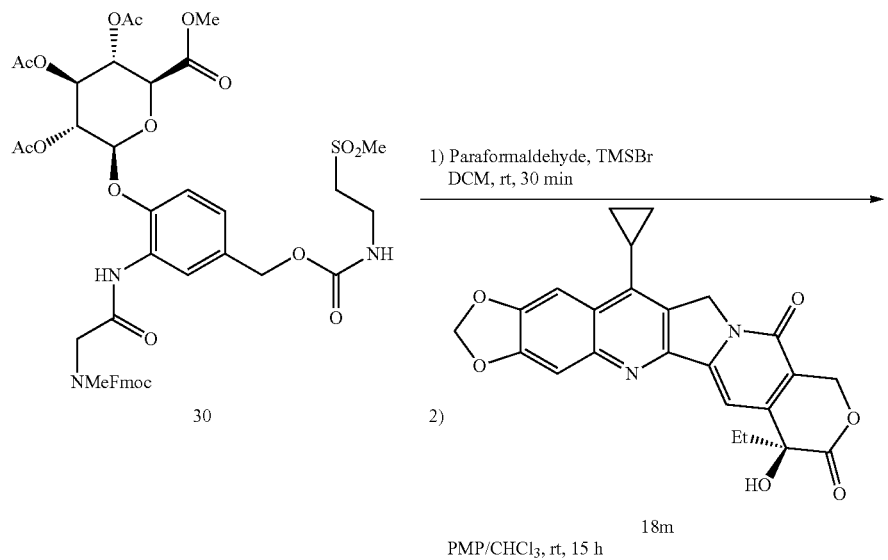

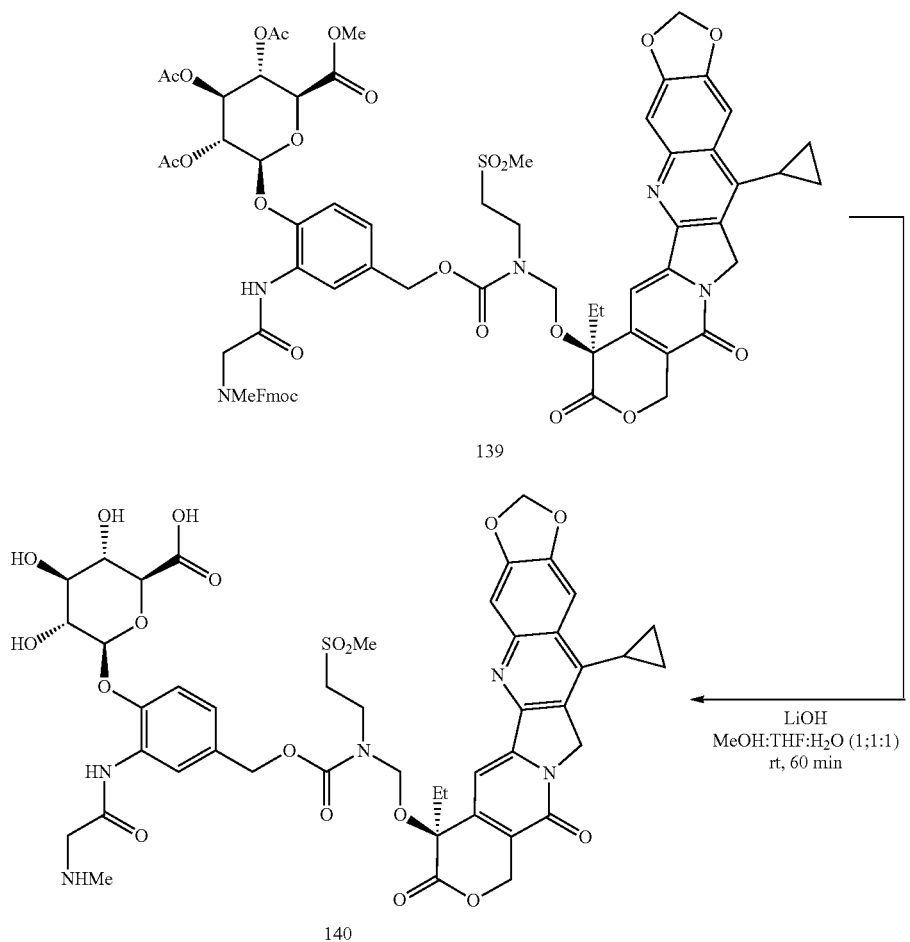

Compound 30 (623 mg, 0.694 mmol), prepared as described by Examples 21 and 22, was dissolved in anhydrous DCM (4 ml). Paraformaldehyde (208 mg, 6.94 mmol) was added to the reaction followed by TMSBr (0.12 mL, 0.925 mmol). The reaction was stirred at room temperature for 30 minutes at which point complete conversion to the activated chloromethyl intermediate was observed by UPLC-MS. The reaction was filtered through a syringe filter, rinsed with DCM 2 mL, and toluene (2 mL) was added to azeotrope the final mixture. The eluent was concentrated in vacuo to afford a colorless solid. Compound 18m (100.0 mg, 0.2313 mmol) from Example 10 was azeotroped with toluene. The chloromethyl intermediate was dissolve in anhydrous CHCl$_3$ (6 mL) and added directly compound 18m followed by 1,2,2,6,6-pentamethylpiperidine (PMP, 0.17 mL, 0.93 mmol). The reaction was stirred at room temperature for 15 hours, quenched MeOH, and concentrated in vacuo. The crude reaction mixture containing compound 139 was used in the next step without purification.

Crude compound 139 (0.2313 mmol) was dissolved in 1:1 MeOH:THF (4 mL). LiOH (55.4 mg, 2.31 mmol) was added and the reaction was stirred for 30 minutes. H$_2$O (2 mL) was added and the reaction was stirred for 30 minutes. The reaction was quenched with AcOH (0.1 mL), concentrated in vacuo and purified by reverse phase flash column chromatography using a Biotage Ultra C1860G column eluting with a gradient of 5-30-95% MeCN in H$_2$O 0.1% formic acid. Fractions containing the desired product and impurities were concentrated and re-purified by preparative HPLC using a 21.2×250 mm Max-RP column with a gradient of 5-30-95% MeCN in H$_2$O 0.1% formic acid. Fractions containing the desired product were concentrated in vacuo to afford compound 140 as a yellow solid (40.9 mg, 0.0417 mmol, 18%). LC-MS (Method D): $t_R$=1.23 min; MS (m/z) [M+H]$^+$ calc. for C$_{45}$H$_{50}$N$_5$O$_{18}$S 980.29, found 980.20.

Example 93

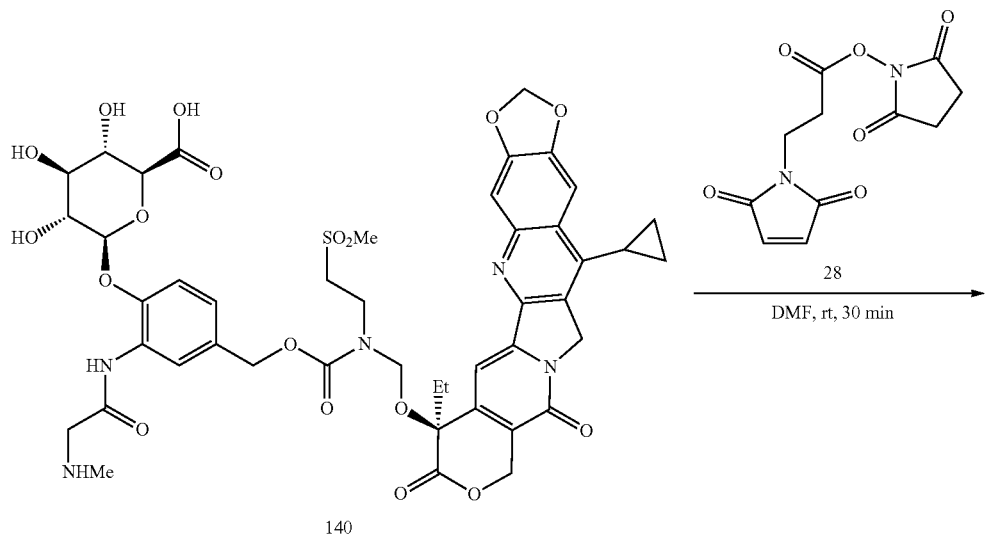

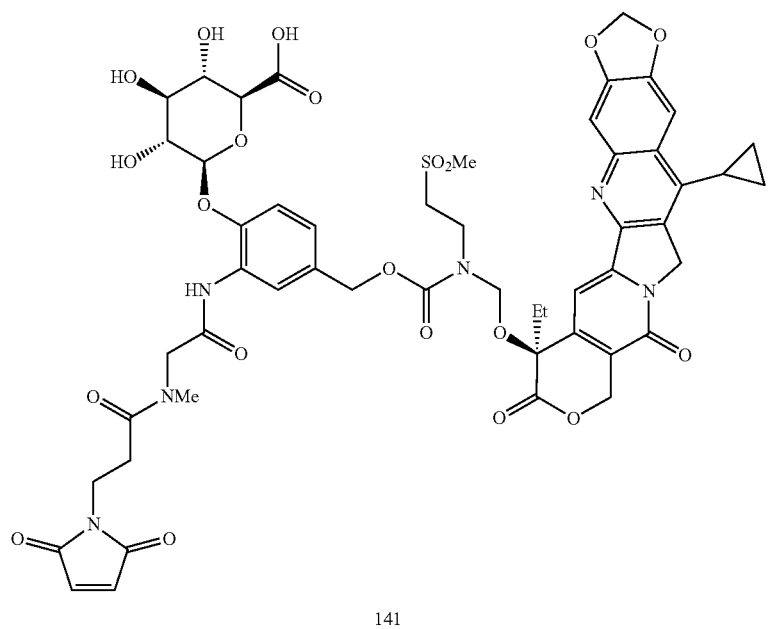

Compound 140 (40.9 mg, 0.0417 mmol) was dissolved in anhydrous DMF (1 mL). DIPEA (43 µL, 0.25 mmol) was added followed by 3-(maleimido)propionic acid N-hydroxysuccinimide ester (28, 33.3 mg, 0.125 mmol), purchased from TCI America product number S0427). The reaction was stirred for 30 minutes. Complete conversion was observed by UPLC-MS. The reaction was quenched with AcOH (5 µL) and purified by preparative HPLC eluting with 5-40-95% MeCN in $H_2O$ 0.1% formic acid on a 21.2×250 mm MaxRP column. Fractions containing the desired product were lyophilized to afford compound 141 as a yellow powder (8.94 mg, 7.90 µmol, 19%). LC-MS (Method D): $t_R$=1.47 min; MS (m/z) $[M+H]^+$ calc. for $C_{52}H_{55}N_6O_{21}S$ 1131.31, found 1131.43.

Example 94

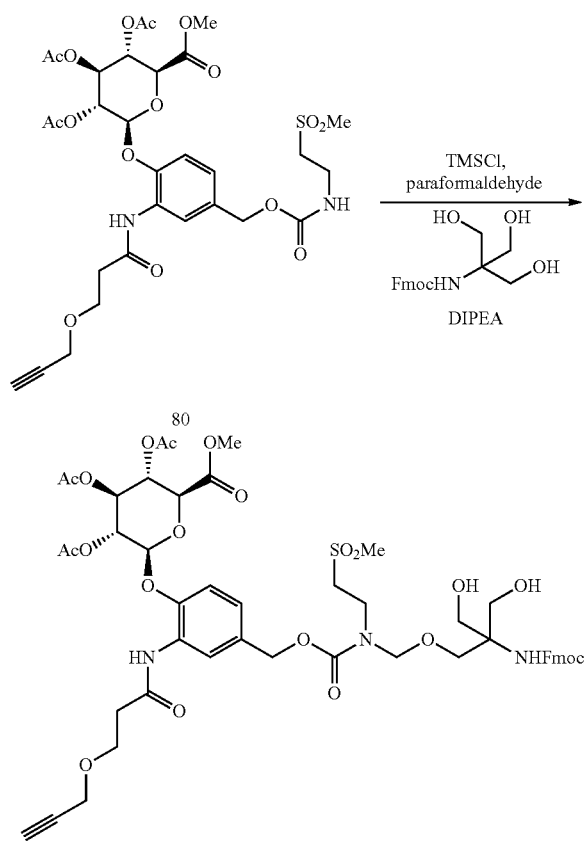

Compound 80 (200 mg, 0.262 mmol) prepared by Example 54 was dissolved in DCM (4 mL). Paraformaldehyde (250 mg) was added followed by TMSCl (2 mL). The reaction was stirred for 20 minutes at which point complete conversion to the activated chloromethyl intermediate observed by quenching a 2 μL aliquot into 98 μL of MeOH to observe the corresponding MeOH adduct by UPLC-MS. The reaction was filtered through a syringe filter, rinse DCM (2 mL), and toluene (2 mL) was added. The solvent was evaporated in vacuo and the final product was placed on high vacuum until ready for use. Fmoc-tris(hydroxymethyl)aminomethane (THAM) was prepared as described in WO 2006/006196. Fmoc-THAM (270 mg, 0.786 mmol) was dissolved in DCM (2 mL) and added directly to the activated intermediate. DIPEA (0.136 mL, 0.786 mmol) was added and the reaction was stirred for 1 hour. Complete conversion was observed by UPLC-MS. The reaction was quenched with MeOH, concentrated in vacuo, and purified by column chromatography using a 50G KP-Sil column with a 20-100% EtOAc in Hex gradient. Fractions containing the desired product were concentrated in vacuo to afford compound 142 as a colorless solid (242.3 mg, 0.2264 mmol, 86%). LC-MS (Method D): $t_R$=2.04 min; MS (m/z) [M+H]$^+$ calc. for $C_{50}H_{60}N_3O_{21}S$ 1070.34, found 1070.42.

Example 95

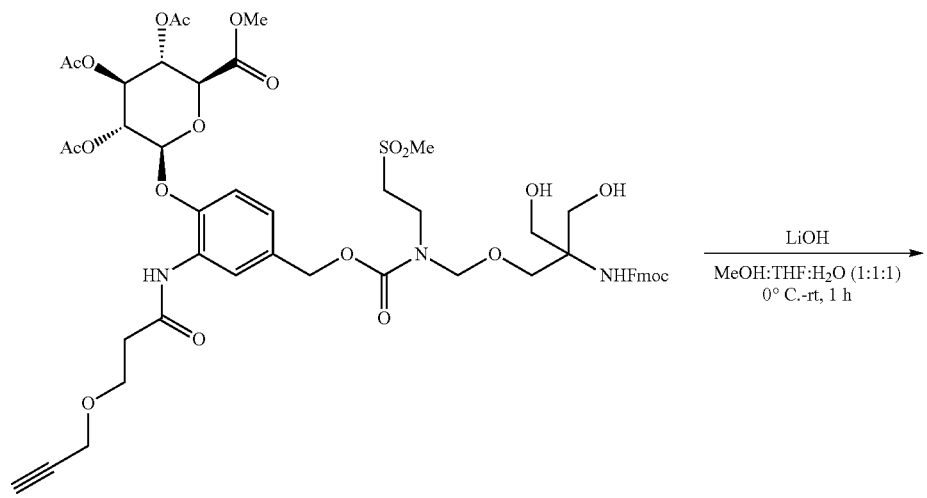

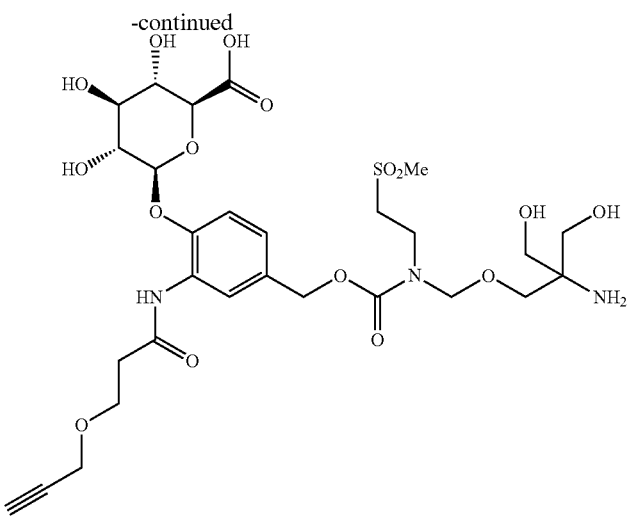

143

Compound 142 (242.3 mg, 0.2264 mmol) was dissolved in MeOH:THF 1:1 (4 mL) and cooled with an ice/water bath. LiOH (54 mg, 2.6 mmol) was added to the reaction and stirred for 30 minutes. $H_2O$ (2 mL) was added to the reaction, allowed to warm to room temperature and stirred for 30 minutes. Complete conversion to the deprotected product was observed. The reaction was neutralized with AcOH, concentrated in vacuo, and purified by reverse phase flash chromatography using a Biotage C18 Ultra 30G column eluting with a gradient of 5-20-95% MeCN in $H_2O$ 0.1% Formic Acid. Fractions containing the desired product were concentrated in vacuo to afford compound 143 as a colorless solid (88.3 mg, 0.125 mmol, 55%). LC-MS (Method D): $t_R$=0.60 min; MS (m/z) [M+H]$^+$ calc. for $C_{28}H_{42}N_3O_{16}S$ 708.23, found 707.84.

Example 96

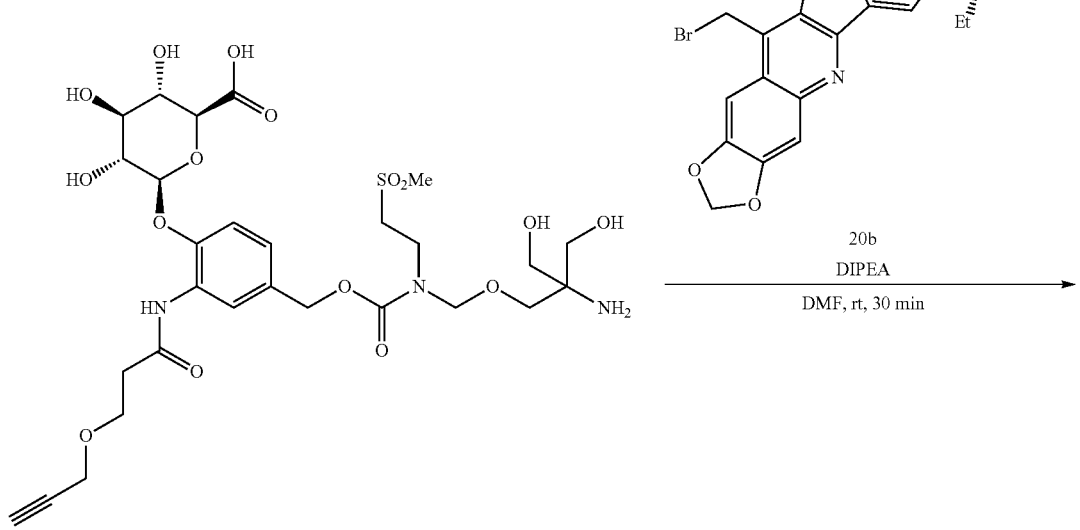

143

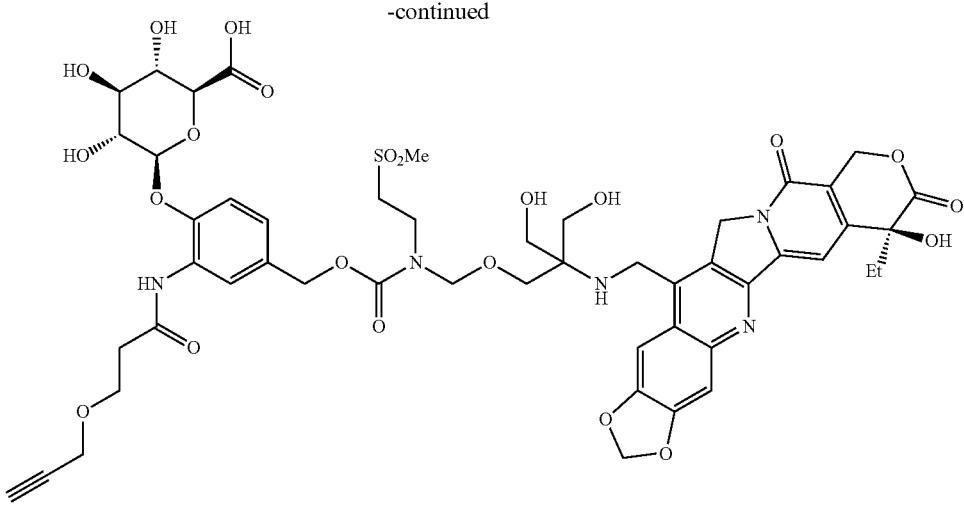

144

Compound 143 (88.3 mg, 0.125 mmol) was dissolved in anhydrous DMF (0.5 mL). Compound 20b (30.0 mg, 0.0618 mmol) was added to the reaction followed by DIPEA (0.032 mL, 0.024 mmol). The reaction was stirred for 30 min, at which point complete conversion to product was observed. The reaction quenched with AcOH (0.050 mL), then purified by preparative HPLC using a 21.2×250 mm Max-RP column eluting with a gradient of 5-40-95% MeCN in H$_2$O 0.1% Formic Acid. Fractions containing the desired product were concentrated in vacuo to afford compound 144 as a yellow solid (1.69 mg, 0.00104 mmol, 1.7%). LC-MS (Method D): t$_R$=1.03 min; MS (m/z) [M+H]$^+$ calc. for C$_{50}$H$_{58}$N$_5$O$_{22}$S 1112.33, found 1112.42.

Example 97

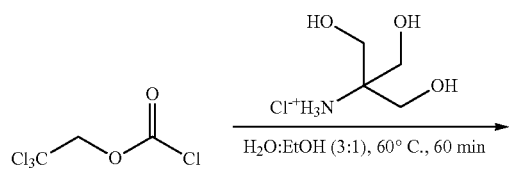

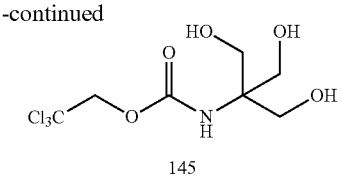

145

Tris(hydroxymethyl)aminomethane hydrochloride (2.00 g, 4.72 mmol) was dissolved in 3:1 water:ethanol (8 mL). 2,2,2-Trichloroethyl chloroformate (1.32 mL, 4.72 mmol) was added to the reaction mixture. The reaction was stirred at 60° C. for 60 minutes. The reaction was cooled to room temperature, diluted with EtOAc (100 mL), washed with 1M HCl (3×100 mL), washed with sat. NaCl (50 mL), dried MgSO4, filtered and concentrated in vacuo to afford the compound 145 as a colorless solid (1.64 g, 5.52 mmol, 58%). LC-MS (Method D): t$_R$=1.06 min; MS (m/z) [M+H]$^+$ calc. for C$_7$H$_{13}$Cl$_3$NO$_5$ 295.99, found 296.12.

Example 98

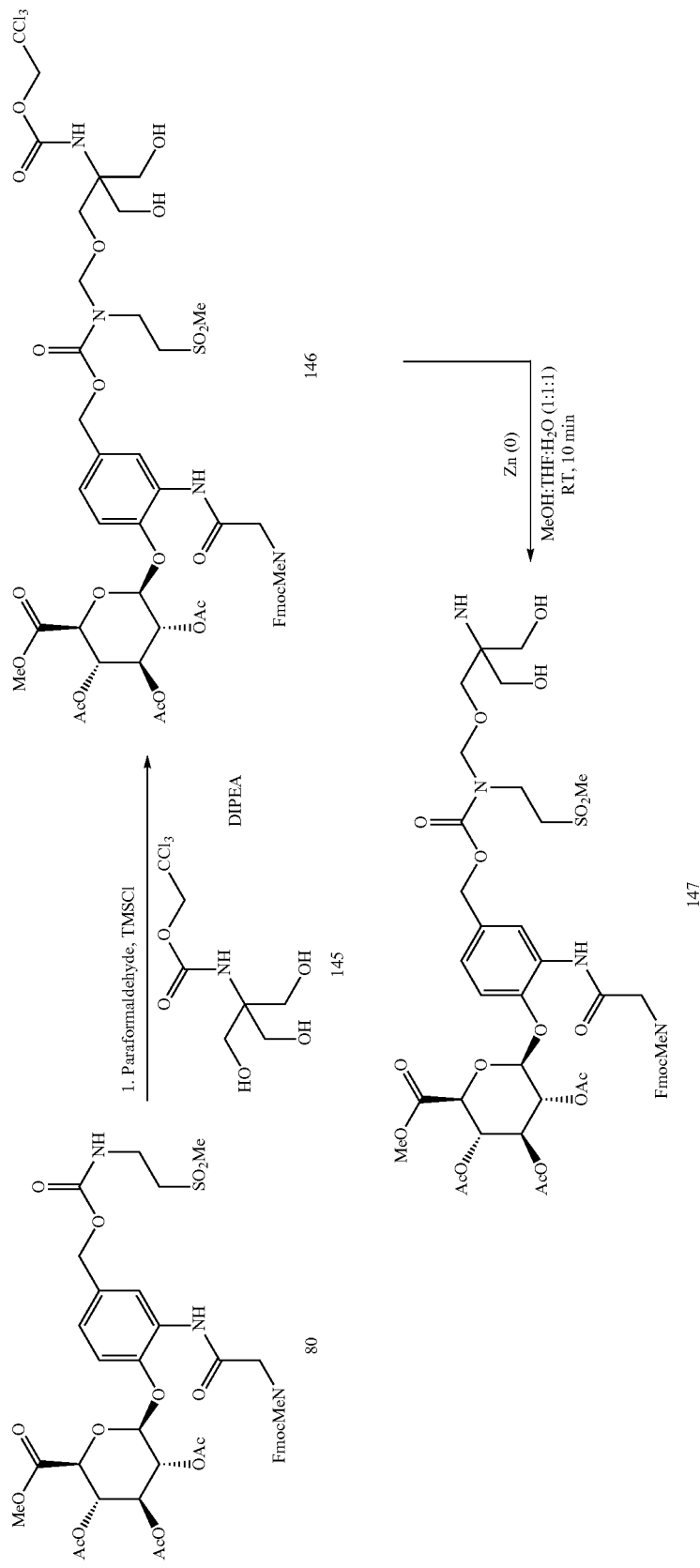

Compound 80 (300 mg, 0.334 mmol) was dissolved in DCM (2 mL). Paraformaldehyde (300 mg, 10.0 mmol) was added followed by TMSCl (1 mL). The reaction was stirred for 10 minutes at which point complete conversion was observed by diluting 2 μL aliquot into 98 μL of MeOH and observing the MeOH adduct by UPLC-MS. The reaction was filtered with a syringe filter, washed with DCM (1 mL), Toluene (2 mL) added to azeotrope final mixture upon concentration. The eluent was concentrated in vacuo to afford a colorless solid. Compound 145 was azeotroped with toluene prior to use. The activated chloromethyl compound was dissolved in anhydrous DCM (1 mL, extra-dry over Mol Sieves). DIPEA (0.23 mL, 1.3 mmol) was added followed by compound 145. The reaction was stirred for 30 minutes at which point complete conversion was observed. The reaction was quenched with MeOH (0.1 mL), concentrated in vacuo to afford compound 146 as a colorless solid which was used in the next step without purification. LC-MS (Method D): $t_R$=2.16 min; MS (m/z) [M+H]$^+$ calc. for $C_{50}H_{60}Cl_3N_4O_{22}S$ 1205.25, found 1205.16.

Crude compound 146 (0.334 mmol) was dissolved in 1:1:1 MeOH:THF:AcOH (3 mL). Zinc dust (218 mg, 3.34 mmol) was added and the reaction was stirred for 10 minutes. Complete conversion to the deprotect product was observed by UPLC-MS. The reaction was filtered, and the eluent concentrated. The crude product was purified by preparative HPLC 5-30-50-95% MeCN in H$_2$O 0.1% formic acid using a 30×250 mm Max-RP column. Fractions containing the desired product were concentrated in vacuo until volume reduced by half, aqueous made basic with sat. NaHCO$_3$, then extracted with CHCl$_3$ (3×50 mL), and EtOAc (3×50 mL). The organics were combined and dried with MgSO$_4$. Filtered and concentrated in vacuo to afford compound 147 as a white solid (103.4 mg, 0.1003 mmol, 30%). LC-MS (Method D): $t_R$=1.65 min; MS (m/z) [M+H]$^+$ calc. for $C_{47}H_{59}N_4O_{20}S$ 1031.34, found 1031.42.

Example 99

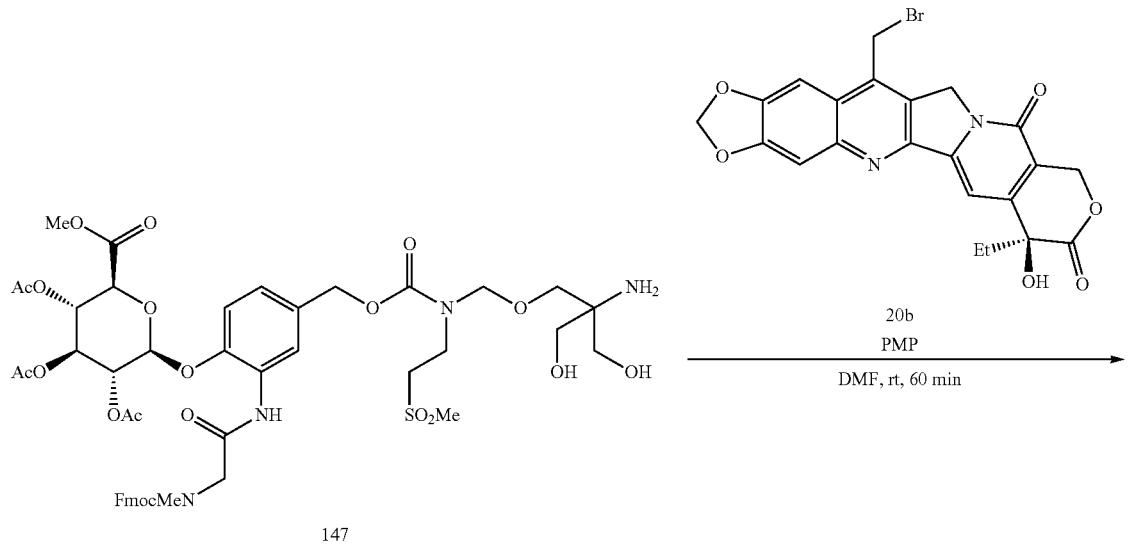

147

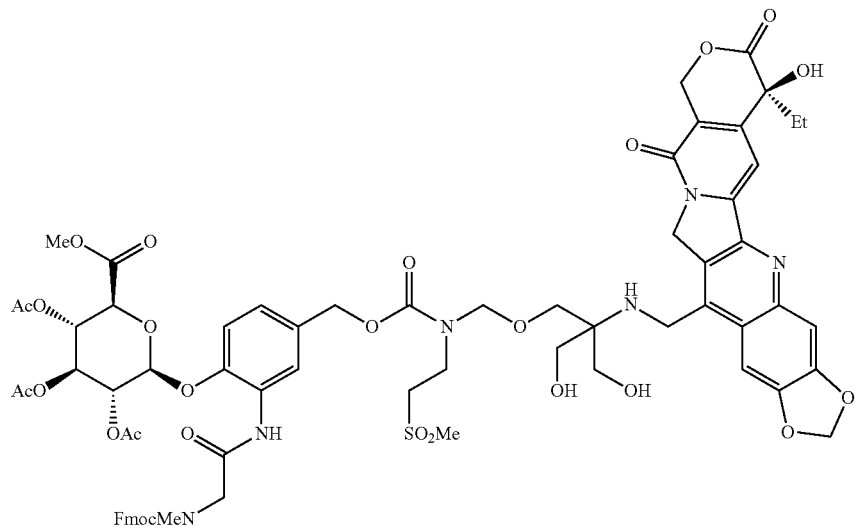

148

Compound 147 (103.4 mg, 0.1003 mmol) was dissolved in anhydrous DMF (0.5 mL). 1,2,2,6,6-Pentamethylpiperidine (PMP, 0.036 mL, 0.20 mmol) was added followed by compound 20b (97.3 mg, 0.201 mmol). The reaction was stirred for 60 minutes at which point complete conversion was observed by UPLC-MS. The reaction was quenched with AcOH (0.030 mL), then purified by reverse phase flash column chromatography using a 50G Biotage C18 ultra column eluting with a gradient of 5-60-95% MeCN IN $H_2O$ 0.1% formic acid. Fractions containing the desired product were concentrated to afford compound 148 as an off white solid (18.7 mg, 0.0130 mmol, 13%). LC-MS (Method D): $t_R$=1.79 min; MS (m/z) $[M+H]^+$ calc. for $C_{69}H_{75}N_6O_{26}S$ 1435.44, found 1435.27.

Example 100

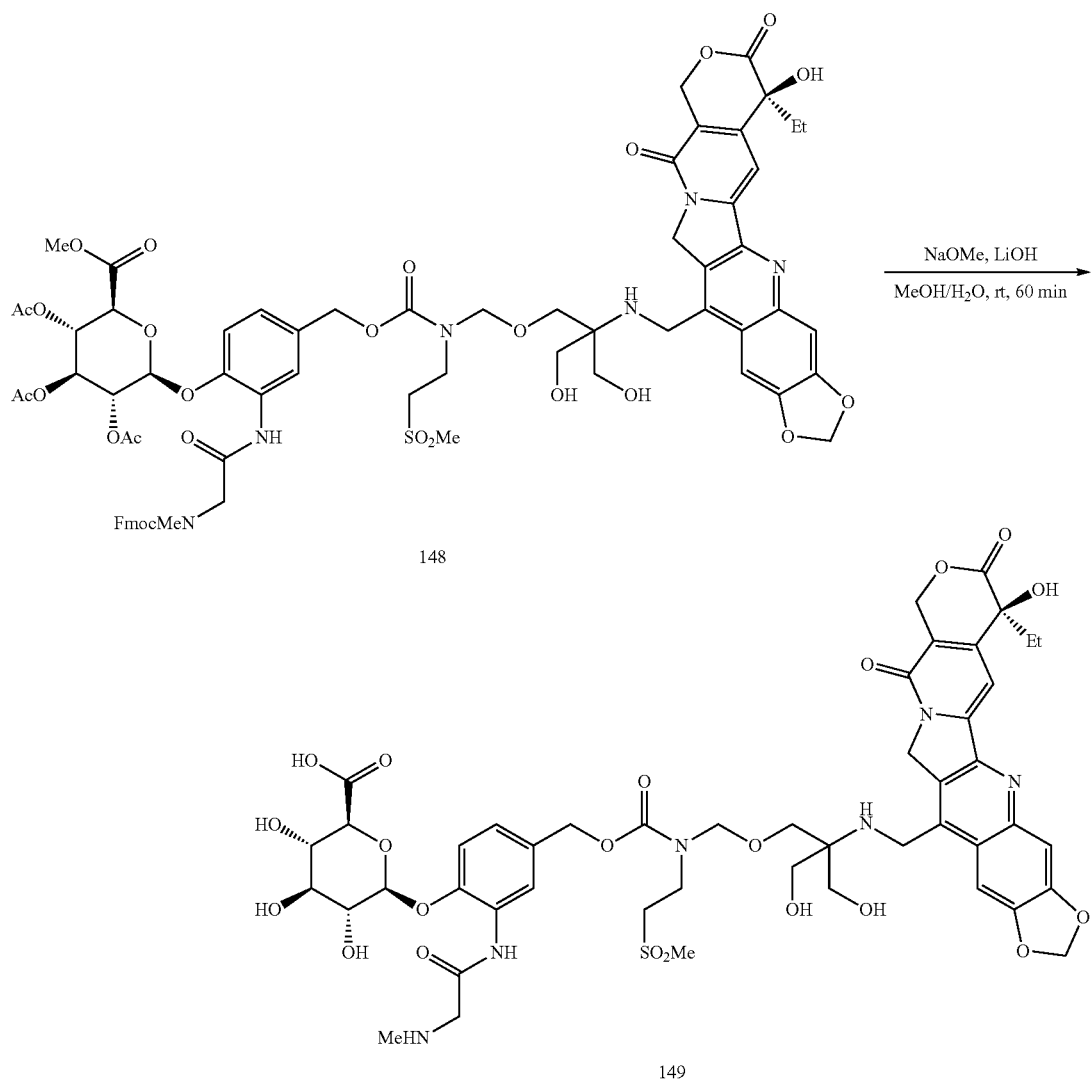

Compound 148 (18.7 mg, 0.0130 mmol) was dissolve in MeOH (1 mL). NaOMe (0.5 M in MeOH, 0.026 mL, 0.013 mmol) was added and the reaction was stirred for 30 minutes. $H_2O$ (1 mL) was added followed by LiOH (1.5 mg, 0.065 mmol) and the reaction was stirred for 30 minutes. Complete conversion to the deprotected product was observe by UPLC-MS. The reaction was neutralized with AcOH, concentrated and purified by preparative HPLC using a 10×250 mm column eluting with a gradient of 5-25-95% MeCN in $H_2O$ 0.1% formic acid. Fractions containing the desired product were concentrated in vacuo to afford compound 149 as a yellow solid (3.9 mg, 0.0036 mmol, 28%). LC-MS (Method D): $t_R$=0.92 min; MS (m/z) $[M+H]^+$ calc. for $C_{47}H_{57}N_6O_{21}$ 1073.33, found 1073.81.

Example 101

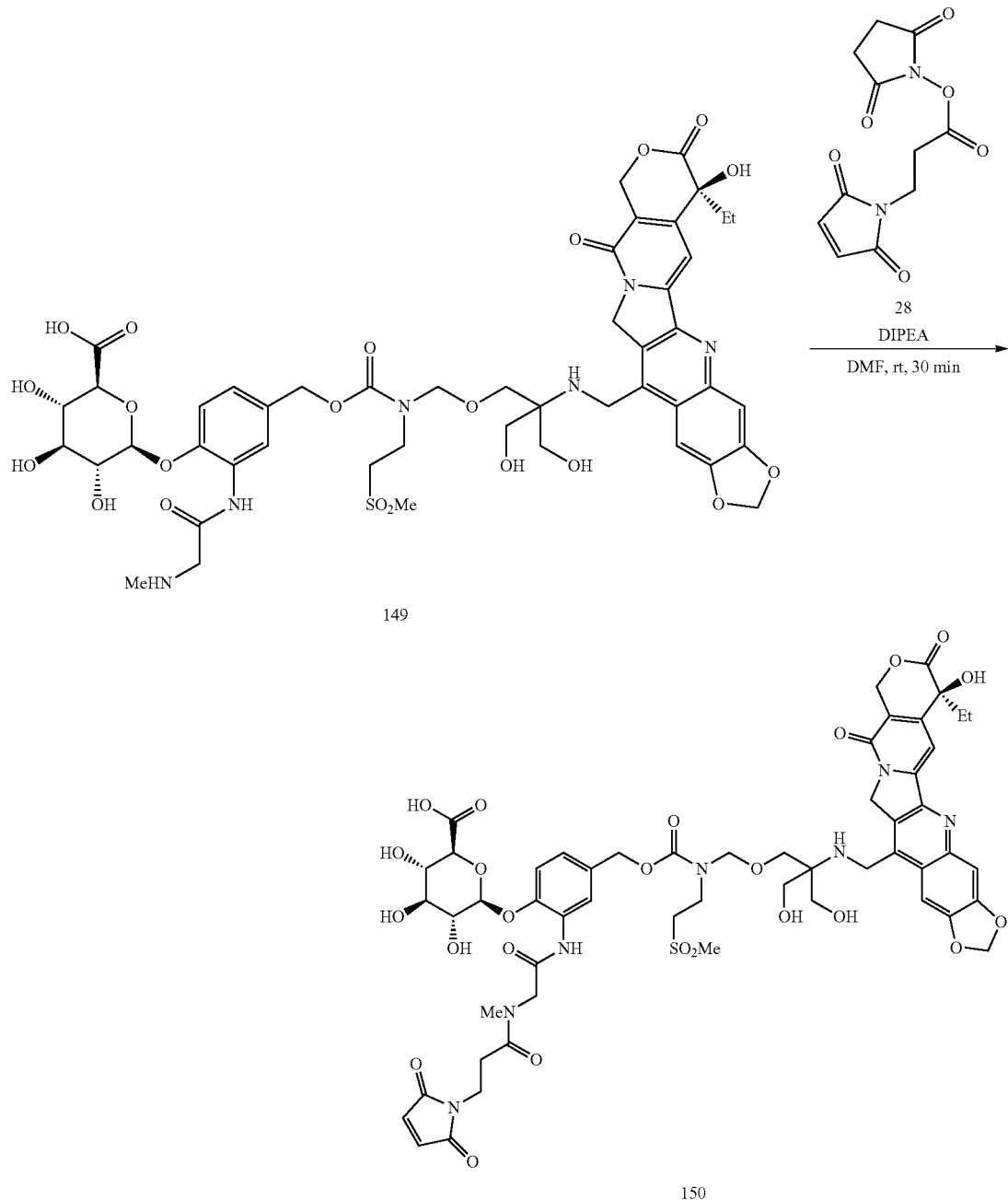 [SMILES: CC[C@@]1(O)C(=O)OCc2c1cc1n(c2=O)Cc2c-1nc1cc3c(cc1c2CNC(CO)(CO)COCN(CCS(C)(=O)=O)C(=O)OCc1ccc(O[C@@H]2O[C@H](C(=O)O)[C@@H](O)[C@H](O)[C@H]2O)c(NC(=O)CNC)c1)OCO3 ; O=C(CCN1C(=O)C=CC1=O)ON1C(=O)CCC1=O ; "DIPEA" ; CC[C@@]1(O)C(=O)OCc2c1cc1n(c2=O)Cc2c-1nc1cc3c(cc1c2CNC(CO)(CO)COCN(CCS(C)(=O)=O)C(=O)OCc1ccc(O[C@@H]2O[C@H](C(=O)O)[C@@H](O)[C@H](O)[C@H]2O)c(NC(=O)CN(C)C(=O)CCN2C(=O)C=CC2=O)c1)OCO3]

Compound 149 (3.9 mg, 0.0036 mmol) was dissolved in anhydrous DMF (0.2 mL). DIPEA (1.3 µL, 0.0073 mmol) was added followed by N-Succinimidyl 3-Maleimidopropionate (1.1 mg, 0.0040 mmol, purchased from TCI America product number S0427). The reaction was stirred for 30 minutes. Complete conversion was observed by UPLC-MS. The reaction was quenched with AcOH (5 µL) and purified by preparative HPLC eluting with 5-30-95% MeCN in H$_2$O 0.1% formic acid on a 10×250 mm MaxRP column. Fractions containing the desired product were lyophilized to afford compound 126 as a yellow powder (0.23 mg, 0.19 µmol, 5%). Rt=1.06 min CORTECS C18 General Method UPLC. MS (m/z) [M+H]$^+$ calc. for C$_{54}$H$_{62}$N$_7$O$_{24}$S 1224.36, found 1224.46.

BIOLOGICAL EXAMPLES

In Vitro Small Molecule and ADC Evaluations

In vitro potency was assessed on multiple cancer cell lines. All cell lines were authenticated by STR profiling at IDEXX Bioresearch and cultured for no more than 2 months after resuscitation. Cells cultured in log-phase growth were seeded for 24 hours in 96-well plates containing 150 µl RPMI 1640 supplemented with 20% FBS. Serial dilutions of antibody-drug conjugates in cell culture media were prepared at 4× working concentrations, and 50 µl of each dilution was added to the 96-well plates. Following addition of test articles, cells were incubated with test articles for 4 days at 37° C. After 96 hours, growth inhibition was assessed by CellTiter-Glo® (Promega, Madison, WI) and luminescence was measured on a plate reader. The $EC_{50}$ value, determined in triplicate, is defined here as the concentration that results in 50% reduction in cell growth relative to untreated controls.

Camptothecin Conjugation Method

Fully or partially reduced ADCs in which one or more of the interchain disulfide bonds have been converted to cysteine residues were prepared in 50% propylene glycol (PG) 1×PBS mixture. A half portion of the PG was added to reduced mAb, and half PG was added to the 1 mM DMSO stock solution of a Camptothecin Drug Linker compound having a Z' component comprised of a maleimide moiety. The PG/drug-linker mix was added to reduced mAb in 25% portions. After the addition of Camptothecin Drug-Linker compound was complete, excess compound was removed by treating with activated charcoal (1 mg of charcoal to 1 mg of mAb). The charcoal was then removed via filtration, and the resulting ADC was buffer exchanged using a NAP5 or PD 10 column, into 5% trehalose in 1×PBS pH 7.4.

For Camptothecin drug linker compounds in which Z' is comprised of a alkyne moiety, the reduced antibody is treated in the same manner with the maleimide-containing compound of $N^6$-diazo-$N^2$-(3-(2,5-dioxo-2,5-dihydro-1H-pyrrol-1-yl)propanoyl)-L-lysine to provide an azido-labeled antibody to which is added 100 mol % excess of the alkyne-containing camptothecin Drug-Linker compound. To the resulting mixture is added a solution prepared from a 1:5 mixture of 100 mM $CuSO_4$ and 100 mM tris-hydroxypropyltriazolylmethylamine (THPTA) so that the final concentration of $CuSO_4$ is 0.5 mM followed by an amount of 100 mM aminoguanidine solution so that the final concentration of aminoguanidine in the solution is 5 mM and an amount of 100 mM solution of sodium ascorbate so that the final concentration of sodium ascorbate is also 5 mM. Additional Camptothecin Drug Linker is added as necessary to complete the conjugation along with sufficient amounts of the 1:5 $CUSO_4$:THPTA and sodium ascorbate solutions in order to maintain their original concentrations. The reaction between the azide and alkyne functional groups result in a Camptothecin ADC having drug linker moieties that are comprised of a triazole ring system.

In Vivo Model Methods

All experiments were conducted in concordance with the Animal Care and Use Committee in a facility fully accredited by the Association for Assessment and Accreditation of Laboratory Animal Care. Efficacy experiments were conducted in the 786-0, L540cy, BXPC3, Colo205 and Caki-1 models. Tumor cells, as a cell suspension, were implanted sub-cutaneous in immune-compromised SCID or nude mice. Upon tumor engraftment, mice were randomized to study groups (5 mice per group) when the average tumor volume reached about 100 mm3. The ADC or controls were dosed once via intraperitoneal injection. Tumor volume as a function of time was determined using the formula (L×W2)/2. Animals were euthanized when tumor volumes reached 750 mm³. Mice showing durable regressions were terminated after 10-12 weeks post implant.

ADC Plasma Stability Determinations

All ADC stocks were normalized to 2.5 mg/mL. The 2.5 mL single use aliquots of citrated mouse (Balb C) were stored at −80 degrees Celsius prior to use. A stock solution in ADC in mouse plasma was made as follows. ADC (50 µg) in 200 µL of plasma (per time point, 0.25 mg/mL) with final PBS concentration at 13.85. Plasma samples were incubated at 37 degrees Celsius for 6h, 1d, 3d, and 7d time points, and were sampled in duplicate. After each time point, the samples were stored at −80 degrees Celsius until they were processes for analysis. A 50% slurry of IgSelect in 1×PBS was prepared. For each time point sample, 50 µL of the IgSelect slurry was added to a 3 µM filter plate, and vacuum was applied to remove supernatant. The resin was washed (2×1 mL 1×PBS), with vacuum applied after each wash. Sample (180 µL) was applied, and the filter plate was shaken (1200 rpm for 1 h at 4 degrees Celsius. Vacuum was then applied to remove plasma. The resin was washed with 1 mL PBS+50 mM NaCl, 1 mL PBS, and with 1 mL water, with vacuum being applied after each wash. The sample plate was then centrifuged at 500×g for 2 mins over a Waters 350 µL collection plate. The ADC was eluted from the resin by treatment with 50 µL Gly pH 3 (2×50 uL), mixing at 500 rpm for 2 min at 4C, centrifuged at 500×g for 3 min into a 350 µL 96 well plate, each well containing 10 µL of 1M Tris pH7.4 buffer. ADC concentration was determined using a UV-Vis plate reader. The samples were deglycosylated using 1 µL of PNGase per sample and incubation for 1 h at 37 degrees Celsius. Each ADC was reduced by adding 12 µL of 100 mM DTT and incubation for 15 min at 37 degrees Celsius. Finally, the samples (10 or 50 µL injection) were analyzed using a 15 min PLRP-MS method to assess light and heavy chain composition.

ADC PK Analysis Experimental Method

This procedure describes a method for the quantification of the total human IgG in rodent $K_2$EDTA plasma.

The method uses a biotin-conjugated murine anti-human light chain kappa mAb (SDIX) as the capture reagent, and the same antibody conjugated to Alexafluor-647 as the detection reagent, for quantification of human antibody and/or antibody-drug conjugate test article as Total Antibody (TAb) in $K_2$EDTA rodent plasma. The assay was carried out using the GyroLab xPlore™ platform, which utilizes a disc containing microfluidic structures with nanoliter scale streptavidin-coated bead columns on which the ligand -binding assay takes place. Briefly, study samples were diluted with naïve pooled rodent $K_2$EDTA plasma as needed, and then, along with calibrators, controls, and a plasma blank, were diluted with Rexxip-HX buffer at a Minimal Required Dilution (MRD) of 1:10 prior to being loaded into a 96-well sample plate. Biotin-anti-human kappa capture reagent at 1 ug/mL in Phosphate Buffered Saline pH 7.4 with Tween-20 (PBS-T), AF647-anti-human kappa detection reagent at 25 nM in Rexxip F buffer, and PBS-T wash buffer was added to a 96-well reagent plate, and both plates were sealed and added to the instrument. A run file was established in the GyroLab Control software, and a sample template was exported to Excel to allow input of sample designations and dilution factors. This template was then imported back into GyroLab Control prior to starting the run. The assay was sequential: the biotinylated capture reagent was applied to the BioAffy1000 CD first, the disc was rinsed with PBS-T, and then the diluted plasma blank, standards, controls, and samples were added. After a subsequent PBS-T rinse, the AF647-conjugated detection reagent was applied. After a final PBS-T rinse, each column of the disc was read with laser-induced fluorescence detection (excitation wavelength: 635 nm). The detected response at 1% PMT was subjected to a 5-parameter logistic regression (5-PL) using GyroLab Evaluator software for conversion of the fluorescence response to ng/mL Total Antibody present in the samples.

The range of the assay for quantitation of total human IgG in rodent $K_2$EDTA plasma was 22.9 ng/mL (LLOQ) to 50,000 ng/mL (ULOQ) for unconjugated antibody test articles and 22.9 ng/mL (LLOQ) to 100,000 ng/mL (ULOQ) for ADCs. The quality control levels were established at 80.0 ng/mL (LQC), 800 ng/mL (MQC), and 8,000 ng/mL (HQC2) and 40,000 ng/mL (HQC1).

This test method applies to the quantitative determination of total human IgG in rodent $K_2$EDTA plasma in support of non-GLP non-clinical studies. This method was not qualified or validated at Seattle Genetics for use in a cGMP- or GLP-compliant manner.

Results:

In the following Tables $IC_{50}$ values for ADCs and CPT free drugs are given in ng/mL and mmol/mL concentrations, respectively, with parenthetic values representing percent cells remaining at the highest concentration tested (1000 ng/mL for ADCs and 1 µM for CPT free compound, unless otherwise indicated) relative to untreated cells. Cell viability was determined by CellTiter-Glo staining after 96h exposure to ADC. ND=Not Determined. Ag1 refers to an antibody targeting a ubiquitous and readily internalizable antigen on cancer cells and h00 is a non-binding control antibody, Ag2 refers to cAC10, which targets the CD30 antigen, Ag3 refers to an antibody that targets a fucosylated peripheral blood antigen found on T-lymphocytes; Ag4 refers to an antibody that targets a surface antigen on activated T and B lymphocytes; and Ag5 refers to an antibody that targets a surface antigen common to peripheral blood lymphocytes.

In vivo data was found to correlated with in vitro data in the following tables, when the Camptothecin Conjugates were found to be active in vitro in one or more of the cells lines that were tested. Unexpectedly, some compounds found to have poor activity in vitro showed good activity in vivo.

The h00 conjugates in general are used to determine if a Camptothecin conjugate has immunological specificity. However, some of the Conjugates tested were designed to have some instability so that once a Conjugate was bound to a targeted antigen is was capable of release free drug within the vicinity of targeted cells without requiring internalization. Therefore, some loss of the Camptothecin Drug Unit is expected in absence of antigen binding for such Conjugates

TABLE 1

In vitro cytotoxicity of glucuronide-based camptothecin DAR 8 ADCs. Values in grey cells correspond to $IC_{50}$ (ng/mL) concentrations. Values in clear cells represent percent cells remaining at highest concentration tested (1000 ng/mL), relative to untreated cells. Cell viability determined by CellTiter-Glo staining after 96 h exposure to ADC.

| CPT-ADC | 786-O | | BxPC3 | | HepG2 | | HL-60 | | HL-60/RV | | L540cy | |
|---|---|---|---|---|---|---|---|---|---|---|---|---|
| Ag1-(51) | >1K | 36 | >1K | 52 | 38 | 40 | >1K | ND | 15 | 10 | 2 | 2 |
| h00-(51) | >1K | 100 | >1K | — | >1K | 92 | >1K | 100 | >1K | 100 | >1K | 100 |
| Ag1-(55) | >1K | 94 | >1K | 44 | 198 | 46 | >1K | 100 | 146 | 40 | 7 | 4 |
| h00-(55) | >1K | — | >1K | 100 | >1K | 87 | >1K | 100 | >1K | 100 | >1K | — |
| Ag1-(61) | >1K | 100 | >1K | ND | >1K | 91 | >1K | 90 | >1K | 96 | 99 | 35 |
| h00-(61) | >1K | 100 | >1K | ND | >1K | ND | >1K | 75 | >1K | 95 | >1K | 89 |
| Ag1-(58) | >1K | ND | >1K | ND | >1K | ND | >1K | 86 | >1K | ND | 2 | 42 |
| h00-(58) | >1K | 100 | >1K | ND | >1K | ND | >1K | ND | >1K | ND | >1K | 92 |
| Ag1-(109a) | 487 | 44 | 61 | 49 | 98 | 35 | >1K | 95 | 164 | 7 | 8 | 2 |
| h00-(109a) | >1K | 96 | >1K | 99 | >1K | ND | >1K | ND | >1K | ND | >1K | ND |
| Ag1-(103) | >1K | 83 | >1K | 51 | >1K | 63 | >1K | ND | >1K | ND | 63 | 5 |
| Ag1-(100) | >1K | 79 | >1K | 64 | >1K | 53 | >1K | ND | 249 | 30 | 16 | 3 |
| h00-(100) | >1K | 100 | >1K | ND | >1K | ND | >1K | 100 | >1K | ND | >1K | 100 |
| Ag1-(42) | >1K | 60 | >1K | 47 | 656 | 45 | 986 | ND | >1K | 84 | 26 | 0 |
| h00-(42) | >1K | 100 | >1K | 100 | >1K | ND | >1K | ND | >1K | 94 | >1K | 86 |
| Ag1-(34) | 915.1 | 43 | 650 | 46 | >1K | 64 | 297 | 37 | >1K | 100 | 31 | 2 |
| Ag1-(67) | 91 | 44 | >1K | 51 | 53 | 37 | >1K | ND | 157 | 4 | 7 | 2 |
| h00-(67) | >1K | 100 | >1K | ND | >1K | ND | >1K | ND | >1K | 100 | >1K | 100 |
| Ag1-(48) | 14 | 18 | 19 | 34 | 36 | 40 | 84 | 0 | >1K | 78 | 2.3 | 2 |
| Ag1-(29) | >1K | 77 | 694 | 45 | >1K | 55 | >1K | 100 | 173 | 41 | 35 | 2 |
| h00-(29) | >1K | 94 | >1K | 90 | >1K | 76 | >1K | 100 | >1K | 100 | >1K | 82 |

| CPT-ADC | 786-O | | BxPC3 | | HepG2 | | HL-60 | | HL60/RV | | L540cy | |
|---|---|---|---|---|---|---|---|---|---|---|---|---|
| Ag1-(114b) | 43 | 6 | 61 | 9 | 41 | 24 | 981 | ND | 61 | 2 | 7 | 2 |
| h00-(114b) | 100 | 7 | 72 | 21 | 112 | 24 | >1K | 78 | 417 | ND | 36 | 2 |
| Ag1-(135) | >1K | ND | >1K | ND | >1K | ND | >1K | ND | >1K | 83 | 35 | 7 |
| h00-(135) | >1K | 100 | >1K | ND | >1K | 89 | >1K | 95 | >1K | ND | >1K | ND |
| Ag1-(109b) | 148 | 36 | 198 | 47 | >1K | 52 | >1K | ND | 51 | 14 | 10 | 3 |
| h00-(109b) | >1K | ND | >1K | ND | >1K | 89 | >1K | ND | >1K | 85 | >1K | ND |
| Ag1-(138b) | 152 | 29 | 85 | 40 | 82 | 36 | >1K | ND | 44 | 5 | 10 | 2 |
| h00-(138b) | >1K | 86 | >1K | 69 | >1K | 48 | >1K | ND | >1K | ND | >1K | ND |
| Ag1-(113) | 38 | 7 | 98 | 15 | 79 | 31 | 873 | ND | 94 | 3 | 7 | 2 |
| h00-(113) | 95 | 2 | 153 | 15 | 261 | 24 | >1K | 84 | 287 | 10 | 34 | 3 |
| Ag1-(138a) | >1K | 60 | >1K | 56 | >1K | 36 | >1K | 87 | 301 | 43 | 15 | 4 |
| Ag1-(144) | 171 | 3 | 405 | 38 | 859 | 38 | >1K | ND | >1K | ND | 250 | 3 |
| Ag1-(114a) | 66 | 3 | 84 | 30 | 57 | 23 | >1K | 83 | 128 | 9 | 15 | 2 |
| h00-(114a) | 138 | 6 | 133 | 21 | 180 | 27 | >1K | ND | >1K | 83 | 67 | 1 |
| Ag1-(141b) | >1K | 52 | >1K | 51 | >1K | 55 | >1K | 109 | 103 | 28 | 10 | 3 |
| h00-(141b) | >1K | ND | >1K | ND | >1K | ND | >1K | ND | >1K | 99 | >1K | 100 |
| Ag1-(67) | 83 | 39 | 165 | 48 | 182 | 43 | >1K | 72 | 104 | 15 | 6 | 2 |

TABLE 1-continued

In vitro cytotoxicity of glucuronide-based camptothecin DAR 8 ADCs. Values in grey cells correspond to $IC_{50}$ (ng/mL) concentrations. Values in clear cells represent percent cells remaining at highest concentration tested (1000 ng/mL), relative to untreated cells. Cell viability determined by CellTiter-Glo staining after 96 h exposure to ADC.

| CPT-ADC | MM.1R | | MOLM13 | | Ramos | | SK-MEL-5 | | SU-DHL-4 | | U266 | |
|---|---|---|---|---|---|---|---|---|---|---|---|---|
| Ag1-(51) | 3 | 3 | 3 | 1 | 1 | 5 | 72 | 32 | 5 | 9 | >1K | 54 |
| h00-(51) | >1K | 75 | >1K | 70 | ND | ND | >1K | 86 | >1K | 97 | >1K | — |
| Ag1-(55) | 6 | 0 | >1K | 44 | ND | ND | >1K | 65 | 27 | 14 | >1K | 100 |
| h00-(55) | >1K | 100 | >1K | 111 | ND | ND | >1K | 100 | >1K | 100 | >1K | 100 |
| Ag1-(61) | >1K | 73 | >1K | 73 | 105 | 19 | >1K | 100 | >1K | 78 | >1K | 89 |
| h00-(61) | >1K | 84 | >1K | 83 | >1K | 98 | >1K | 100 | >1K | 96 | >1K | 85 |
| Ag1-(58) | >1K | 59 | >1K | 65 | 1 | 29 | >1K | ND | >1K | 57 | >1K | 82 |
| h00-(58) | >1K | ND | >1K | 88 | >1K | 98 | >1K | ND | >1K | 99 | >1K | 93 |
| Ag1-(109a) | 6 | 1 | 201 | 12 | 4 | 7 | >1K | 55 | 9 | 6 | 629 | 47 |
| h00-(109a) | >1K | 64 | >1K | 72 | >1K | ND | >1K | ND | >1K | 84 | >1K | 61 |
| Ag1-(103) | 365 | 38 | 261 | 17 | 37 | 8 | >1K | 82 | 347 | 29 | >1K | 63 |
| Ag1-(100) | 18 | 6 | 249 | 31 | 8 | 14 | >1K | 75 | 48 | 20 | >1K | 65 |
| h00-(100) | >1K | ND | >1K | 71 | >1K | 96 | >1K | 94 | >1K | ND | >1K | 24 |
| Ag1-(42) | 13 | 1 | 180 | 0 | 7 | 6 | >1K | 58 | 20 | 4 | 51 | 39 |
| h00-(42) | >1K | 87 | >1K | 83 | >1K | 95 | >1K | 98 | >1K | 92 | >1K | 87 |
| Ag1-(34) | 16 | 4 | 72 | 2 | 1 | 4 | >1K | ND | 12 | 6 | 225 | 33 |
| Ag1-(67) | 7 | 2 | 172 | 13 | 1 | 5 | >1K | 52 | 7 | 5 | >1K | 61 |
| h00-(67) | >1K | 82 | >1K | 73 | >1K | 88 | >1K | 90 | >1K | 66 | >1K | ND |
| Ag1-(48) | 1 | 1 | 21 | 0 | 0.2 | 4 | 536 | 41 | 1 | 3 | 8 | 22 |
| Ag1-(29) | 75 | 18 | 40 | 2 | 37 | 21 | >1K | 78 | 156 | 23 | >1K | 100 |
| h00-(29) | >1K | 81 | >1K | | >1K | 96 | >1K | | >1K | 100 | >1K | 100 |

| CPT-ADC | MM.1R | | MOLM-13 | | Ramos | | SK-MEL-5 | | SU-DHL-4 | | U266 | |
|---|---|---|---|---|---|---|---|---|---|---|---|---|
| Ag1-(114b) | 9 | 1 | 194 | 0 | 7 | 4 | 91 | 5 | 13 | 3 | 181 | 37 |
| h00-(114b) | 49 | 0 | 276 | 12 | 25 | 0 | 108 | ND | 61 | 1 | 483 | 39 |
| Ag1-(135) | 203 | 31 | 251 | 30 | 44 | 25 | >1K | 92 | 110 | 22 | >1K | 85 |
| h00-(135) | >1K | 95 | >1K | ND | >1K | ND | >1K | ND | >1K | 97 | >1K | 99 |
| Ag1-(109b) | 12 | 4 | 227 | 23 | 8 | 12 | >1K | 46 | 17 | 8 | 126 | 49 |
| h00-(109b) | >1K | ND | >1K | ND | >1K | ND | >1K | ND | >1K | 74 | >1K | ND |
| Ag1-(138b) | 10 | 3 | 146 | 8 | 7 | 2 | 634 | ND | 12 | 7 | 164 | 35 |
| h00-(138b) | >1K | ND | >1K | 78 | 614 | ND | >1K | 93 | >1K | ND | >1K | ND |
| Ag1-(113) | 7 | 0.6 | 237 | ND | 12 | 5 | 139 | 2 | 12 | 4 | 56 | 23 |
| h00-(113) | 59 | 0 | 679 | ND | 48 | 4 | 222 | 14 | 68 | 2 | 401 | ND |
| Ag1-(138a) | 14 | 7 | >1K | ND | 10 | ND | >1K | ND | 24 | 17 | >1K | ND |
| Ag1-(144) | 115 | 2 | 413 | ND | 7 | 3 | 221 | ND | 34 | 2 | 293 | 42 |
| Ag1-(114a) | 13 | 1 | 321 | 37 | 9 | 4 | 156 | 11 | 20 | 2 | 401 | 33 |
| h00-(114a) | 78 | 2 | >1K | ND | 46 | 0 | 230 | ND | 79 | 1 | 805 | ND |
| Ag1-(141b) | 10 | 2 | >1K | 60 | 5 | 16 | >1K | 54 | 13 | 8 | 931 | ND |
| h00-(141b) | >1K | ND | >1K | 92 | >1K | 108 | >1K | ND | >1K | 99 | >1K | ND |
| Ag1-(67) | 7 | 3 | 136 | 26 | 14 | 4 | >1K | ND | 10 | 11 | >1K | ND |

TABLE 2

In vitro cytotoxicity of non-glucuronide-based camptothecin DAR 8 ADCs. Values in grey cells correspond to $IC_{50}$ (ng/mL) concentrations. Values in clear cells represent percent cells remaining at highest concentration tested (1000 ng/mL), relative to untreated cells. Cell viability determined by CellTiter-Glo staining after 96 h exposure to ADC.

| CPT ADCs | 786-O | | BxPC3 | | HepG2 | | HL-60 | | HL60/RV | | L540cy | |
|---|---|---|---|---|---|---|---|---|---|---|---|---|
| Ag1-(122) | ++ | + | ++ | ++ | ++ | ++ | + | ++ | ++ | ++ | +++ | + |
| Ag1-(124) | ++ | ND | ++ | ++ | ++ | ++ | + | ++ | ++ | + | +++ | + |
| Ag1-(120) | +++ | + | ++ | ++ | ++ | ++ | + | ++ | ++ | ND | +++ | + |
| Ag1-(133) | +++ | + | +++ | + | +++ | + | ++ | + | +++ | + | +++ | + |
| Ag1-(129) | +++ | + | +++ | + | +++ | + | ++ | + | ++ | + | +++ | + |
| h00-(120) | ++ | + | ++ | ++ | ++ | ++ | + | ND | ++ | ++ | +++ | + |
| h00-(133) | +++ | + | +++ | + | +++ | + | ++ | + | ++ | + | +++ | + |
| h00-(129) | +++ | + | ++ | + | +++ | + | ++ | + | ++ | ND | +++ | + |
| h00-(124) | ++ | ND | ++ | + | ++ | ++ | + | ND | ++ | ND | ++ | + |
| h00-(122) | ++ | ND | ++ | ++ | ++ | ++ | + | ++ | ++ | ++ | +++ | + |

| CPT ADCs | MOLM13 | | Ramos | | SK-MEL-5 | | SU-DHL-4 | | U266 | | MM.1R | |
|---|---|---|---|---|---|---|---|---|---|---|---|---|
| Ag1-(122) | ++ | ++ | ++ | + | ++ | ++ | ++ | + | + | ++ | ++ | ND |
| Ag1-(124) | ++ | + | +++ | + | ++ | + | ++ | + | ++ | ++ | ++ | ND |
| Ag1-(120) | ++ | ND | +++ | + | ++ | +++ | +++ | + | ++ | ND | +++ | + |
| Ag1-(133) | +++ | + | +++ | + | +++ | +++ | +++ | + | +++ | ++ | +++ | + |
| Ag1-(129) | +++ | + | +++ | + | ++ | +++ | +++ | + | +++ | ++ | +++ | + |
| h00-(120) | ++ | + | +++ | + | ++ | +++ | +++ | + | ++ | ++ | +++ | + |

TABLE 2-continued

In vitro cytotoxicity of non-glucuronide-based camptothecin DAR 8 ADCs. Values in grey cells correspond to $IC_{50}$ (ng/mL) concentrations. Values in clear cells represent percent cells remaining at highest concentration tested (1000 ng/mL), relative to untreated cells. Cell viability determined by CellTiter-Glo staining after 96 h exposure to ADC.

| | | | | | | | | | | | | |
|---|---|---|---|---|---|---|---|---|---|---|---|---|
| h00-(133) | ++ | + | +++ | + | +++ | +++ | +++ | + | ++ | ++ | +++ | + |
| h00-(129) | +++ | + | +++ | + | ++ | +++ | +++ | + | ++ | + | +++ | + |
| h00-(124) | ++ | ND | +++ | + | ++ | ++ | ++ | + | ++ | ++ | ++ | ND |
| h00-(122) | ++ | ND | ++ | + | ++ | ++ | ++ | + | + | ND | ++ | ND |

Grey cells, $IC_{50}$ values (ng/mL): + >1K; 100≤ ++ ≤1000; +++ <100.

Clear cells, % maximum inhibition at 1 ug/mL: + <20%; ++ ≥20%.

ND is not determined.

TABLE 3

In vitro cytotoxic potency of glucuronide camptothecin DAR 8 Ag2 and Ag3 ADCs. Concentrations correspond to $IC_{50}$ (ng/mL) values. Values in parenthesis represent percent cells remaining at highest concentration tested (10000 ng/mL), relative to untreated control. Cell viability determined by CellTiter-Glo staining after 96 h exposure to ADC.

| ADCs | H3396 (CellBank) CD30 -Ley + Breast Carcinoma | Ls174T (CellBank) Ley + Colon Carcinoma | RCA (CellBank) Ley + CD30 - Colon Carcinoma | SK-OV-3 (CellBank) Ley + CD30 - Ovarian Carcinoma |
|---|---|---|---|---|
| Ag2-(67) | 5339 (45%) | >10,000 (56%) | 9173 (38%) | >10,000 (100%) |
| Ag2-(72) | >10,000 (63%) | >10,000 (69%) | >10,000 (80%) | >10,000 (100%) |
| Ag3-(67) | 574 (24%) | 1132 (22%) | 5852 (10%) | >10,000 (100%) |
| Ag3-(72) | 1779 (25%) | 2684 (17%) | 9873 (49%) | >10,000 (100%) |

| ADCs | HDLM-2 Ley - CD30 340K HL | Karpas 299 (CellBank) Ley - CD30 290K ALCL | L540cy (CellBank) Ley - CD30 355K HL |
|---|---|---|---|
| Ag2-(67) | 19 (15%) | 13 (23%) | 4 (0%) |
| Ag2-(72) | 7 (26%) | 20 (25%) | 4 (0%) |
| Ag3-(67) | >10,000 (100%) | >10,000 (76%) | 9166 (30%) |
| Ag3-(72) | >10,000 (100%) | >10,000 (100%) | >10,000 (100%) |

TABLE 4A-C

In vitro cytotoxic potency of glucuronide camptothecin DAR 8 ADCs. A. anti-Ag2 ADCs, B. anti-Ag4 ADCs and C. anti-Ag5 ADCs. Concentrations in grey cells correspond to IC50 values (ng/mL) values. Values in clear cells represent percent cells remaining at highest concentration tested (10000 ng/mL), relative to untreated control. Cell viability determined by CellTiter-Glo staining after 96h exposure to ADC.

A

| ADC | 786-O | | DEL | | Karpas 299 | | KM-H2 | | L1236 | | L-428 | | L540cy | |
|---|---|---|---|---|---|---|---|---|---|---|---|---|---|---|
| Ag2-(67) | >10K | ND | 3 | 0 | 9 | 24 | >10K | 71 | >10K | ND | >10K | ND | 4 | 1 |

B

| ADC | 786-O | | ACHN | | Caki-1 | | L540cy | | Raji | | UM-RC-3 | |
|---|---|---|---|---|---|---|---|---|---|---|---|---|
| Ag4-(67) | 4944 | 31 | >10K | ND | >10K | 57 | 46 | 32 | 408 | 32 | 75 | 35 |

TABLE 4A-C-continued

In vitro cytotoxic potency of glucuronide camptothecin DAR 8 ADCs. A. anti-Ag2 ADCs,
B. anti-Ag4 ADCs and C. anti-Ag5 ADCs. Concentrations in grey cells correspond
to IC50 values (ng/mL) values. Values in clear cells represent percent cells remaining
at highest concentration tested (10000 ng/mL), relative to untreated control. Cell
viability determined by CellTiter-Glo staining after 96h exposure to ADC.

C

| ADC | Drug | | | | | | | | | | | |
|---|---|---|---|---|---|---|---|---|---|---|---|---|
| | EJM | | KMM-1 | | MM.1R | | NCI-H929 | | TF-1a | | U-266 | |
| Ag5-(67) | 2213 | 34 | 207 | 40 | 12 | 3 | 8 | 3 | >10K | ND | >10K | ND |

TABLE 5

In vitro cytotoxic potency of select anti-Ag2 glucuronide based DAR8 camptothecin
ADCs against Ag2+ tumor lines with variable Ag2 expression. Values in grey
cells correspond to $IC_{50}$ (ng/mL) concentrations. Values in clear cells represent
percent cells remaining at highest concentration tested (1000 ng/mL), relative
to untreated cells. Cell viability determined by CellTiter-Glo staining
after 96 h exposure to ADC. Each Parenthetic value is the average copy number
of the targeted antigen on the cancer cells.

| ADC | Drug | | | | | | | | | |
|---|---|---|---|---|---|---|---|---|---|---|
| | DEL (285,005) | | Karpas 299 (318,870) | | KM-H2 (74,663) | | L428 (70,324) | | L540cy (408,529) | |
| Ag2-(67) | 7 | 0 | 9 | 37 | >1K | 100 | >1K | 91 | 6 | 1 |
| Ag2-(100) | 10 | 3 | >1K | 59 | >1K | ND | >1K | 98 | 14 | 1 |
| Ag2-(109a) | 7 | 0 | 11 | 46 | >1K | ND | >1K | ND | 9 | 1 |
| Ag2-(34) | 7 | 0 | 174 | 47 | >1K | ND | >1K | 96 | 13 | 1 |
| Ag2-(103) | 7 | 0 | >1K | 51 | >1K | ND | >1K | 93 | 9 | 1 |
| Ag2-(58) | >1K | 59 | >1K | 67 | >1K | 100 | >1K | ND | 48 | 19 |
| Ag2-(61) | >1K | 64 | >1K | 63 | >1K | 100 | >1K | 89 | 81 | 25 |
| h00-(67) | >1K | ND | >1K | ND | >1K | 100 | >1K | 93 | >1K | 100 |
| h00-(100) | >1K | 100 | >1K | 88 | >1K | ND | >1K | 97 | >1K | 97 |
| h00-(109a) | >1K | 92 | >1K | ND | >1K | 75 | >1K | ND | >1K | 94 |
| h00-(34) | >1K | ND | >1K | 80 | >1K | ND | >1K | 92 | >1K | 84 |
| h00-(103) | >1K | 92 | >1K | 97 | >1K | 95 | >1K | 99 | >1K | 67 |
| h00-(58) | >1K | ND | >1K | 95 | >1K | ND | >1K | 97 | >1K | 90 |
| h00-(61) | >1K | ND | >1K | 80 | >1K | 57 | >1K | 97 | >1K | 89 |

TABLE 6

Cytotoxic activity of glucuronide camptothecin ADC Ag2-(67) on
Ag2(+) parental DEL and Ag2(+), MDR(+), DEL-BVR cell
lines. The parental DEL lymphoma cell line was cultured in the
presence of brentuximab vedotin to induce over-expression of the MDR
phenotype, resulting in the DEL brentuximab vedotin resistant line (DEL-
BVR). $IC_{50}$ values (grey cells, ng/mL) were determine for parental
(DEL) and MDR+ (DEL-BVR) lines. Brentuximab vedotin (Ag2-
vcMMAE (8)) ADC was included as a control. Values in clear cells
represent percent cells remaining at the highest dose tested (1000
ng/mL), relative to untreated cells. Cell viability determined
by CellTiter-Glo staining after 96h exposure to ADC.

| ADC/Drug | DEL | | DEL/BVR | |
|---|---|---|---|---|
| Ag2-(67) (8) | 6 | 1 | 4 | 0 |
| Ag2-vcMMAE (8) | 0.5 | 1 | >1000 | 93 |

TABLE 7

Table of $IC_{50}$ values (ng/mL) for Ag5 (anti-Ag5) glucuronide
camptothecin ADCs against MM.1R cells (Ag5-positive) viability
assessed by CellTitre-Glo, a 3:1 co-culture of MM.1R and MM.1R
Ag5 KO luc+ cells, and MM.1R Ag5 KO luc+ cells, viability
assessed by Bright-Glo. Concentrations in gray cells correspond to
$IC_{50}$ values (ng/mL) values. Values in clear cells represent
percent cells remaining at highest concentration tested (10000
ng/mL), relative to untreated control.

| ADC | Drug | | | | | |
|---|---|---|---|---|---|---|
| | MM.1R | | 3:1 co-culture | | MM.1R CD48- Luc+ | |
| Ag5-(34) | 90 | 0 | 1592 | 0 | 2477 | 3 |
| Ag5-(103) | 91 | 0 | 2886 | 15 | >10K | ND |
| Ag5-(48) | 5 | 2 | >10K | ND | >10K | ND |
| Ag5-(109a) | 18 | 3 | 82 | 12 | >10K | ND |
| Ag5-(67) | 14 | 1 | 75 | 11 | >10K | ND |
| Ag5-(141b) | 7.5 | 2 | 11.5 | 3 | >10K | ND |
| Ag5-(135) | 37 | 9 | 1190 | ND | >10K | ND |

TABLE 8

Figure 1B:
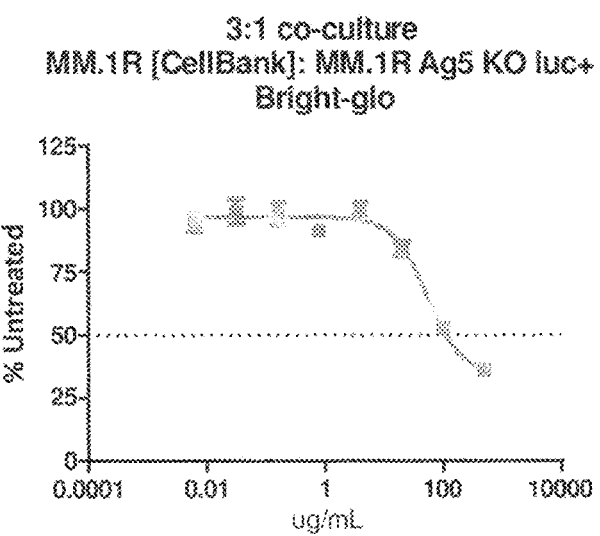

IC$_{50}$ values (ng/mL) for Ag5-(67) treated MM.1R, 3:1 co-culture and MM.1R Ag5 KO luc+, and MM.1R Ag5 KO luc+ cells. Concentrations in gray cells correspond to IC$_{50}$ values (ng/mL) values. Values in clear cells represent percent cells remaining at highest concentration tested (10000 ng/mL), relative to untreated control (see FIG. 1).

| Antibody-(Drug) (DAR) | MM.1R | 3:1 co-culture | | MM.1R CD48 KO luc+ | |
|---|---|---|---|---|---|
| Ag5-(67) (8) | 15 | 16 | 112 | 34 | >500 | 94 |

TABLE 9

Figure 2:
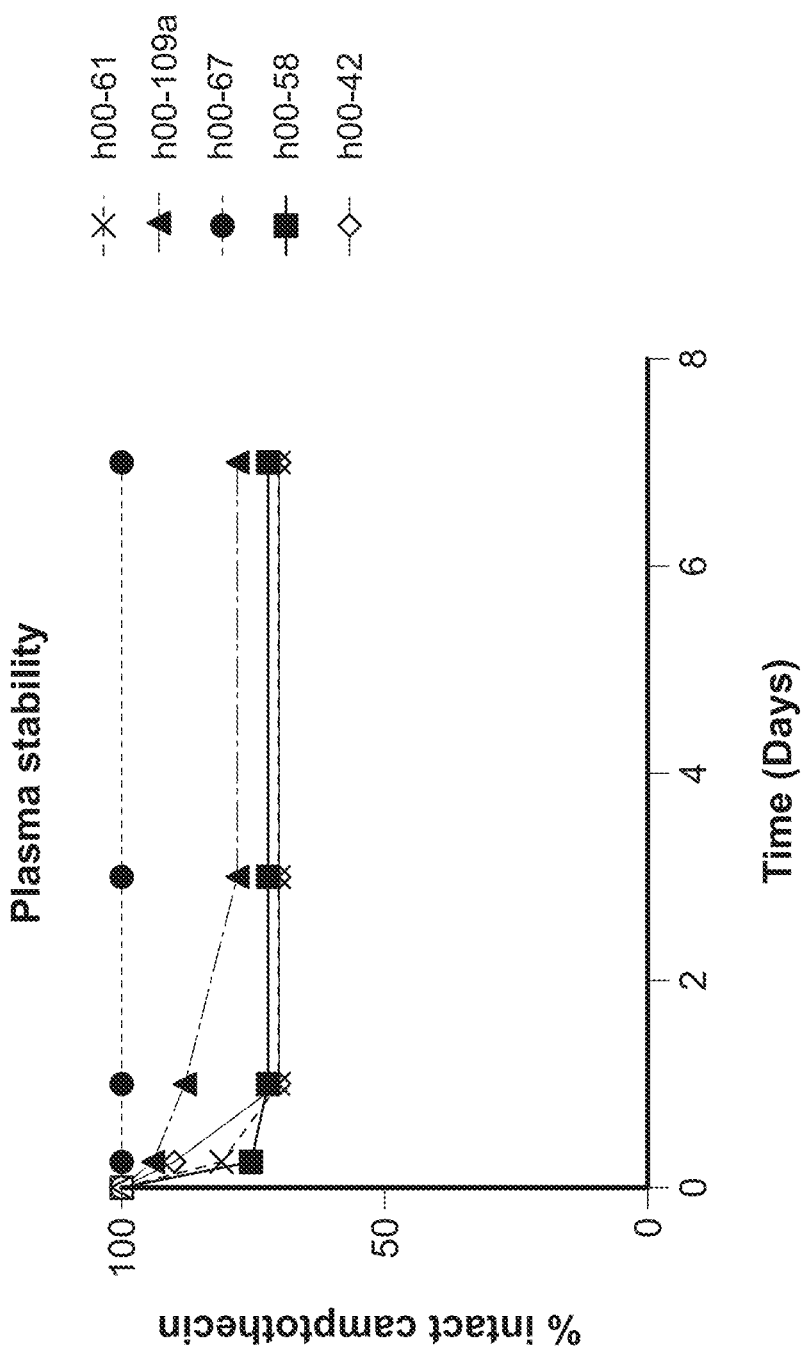
FIG. 2 shows the results of an ADC stability study in mouse plasma. A. Camptothecin DAR8 ADCs were incubated at 37 degrees Celsius in mouse plasma (Balb C). The plasma was sampled at 6 h, 24 h, 72 h, and 7 days. The ADCs were isolated from plasma with IgSelect, deglycosylated with PNGase and reduced with dithiothreitol. Both ADC heavy and light chains were assessed by PLRP-MS to quantify drug-loading at each timepoint.
Figure 3:
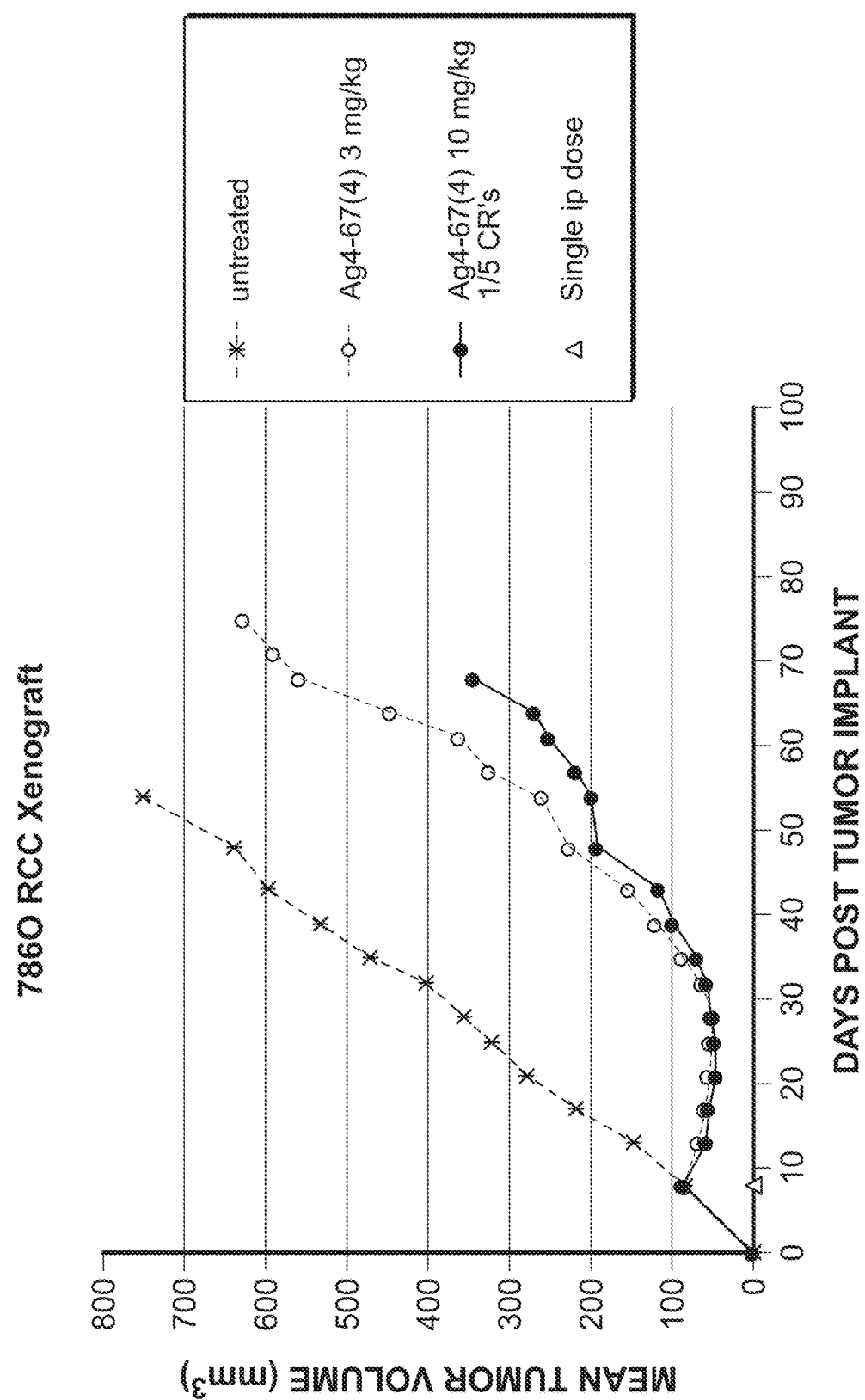
FIG. 3 shows mean tumor volume graph for a 786O renal cell carcinoma subcutaneous mouse xenograft model with an anti-Ag4 camptothecin DAR4 ADC ((Ag4-(67)). Animals were implanted with 786O cells. On day 7, the animals were sorted into groups with an average tumor size of 100 mm³, and then treated with a single dose of the camptothecin ADC at 3 and 10 mg/Kg. Animals were evaluated for tumor size and in-life signs during the course of the study.
Figure 4:
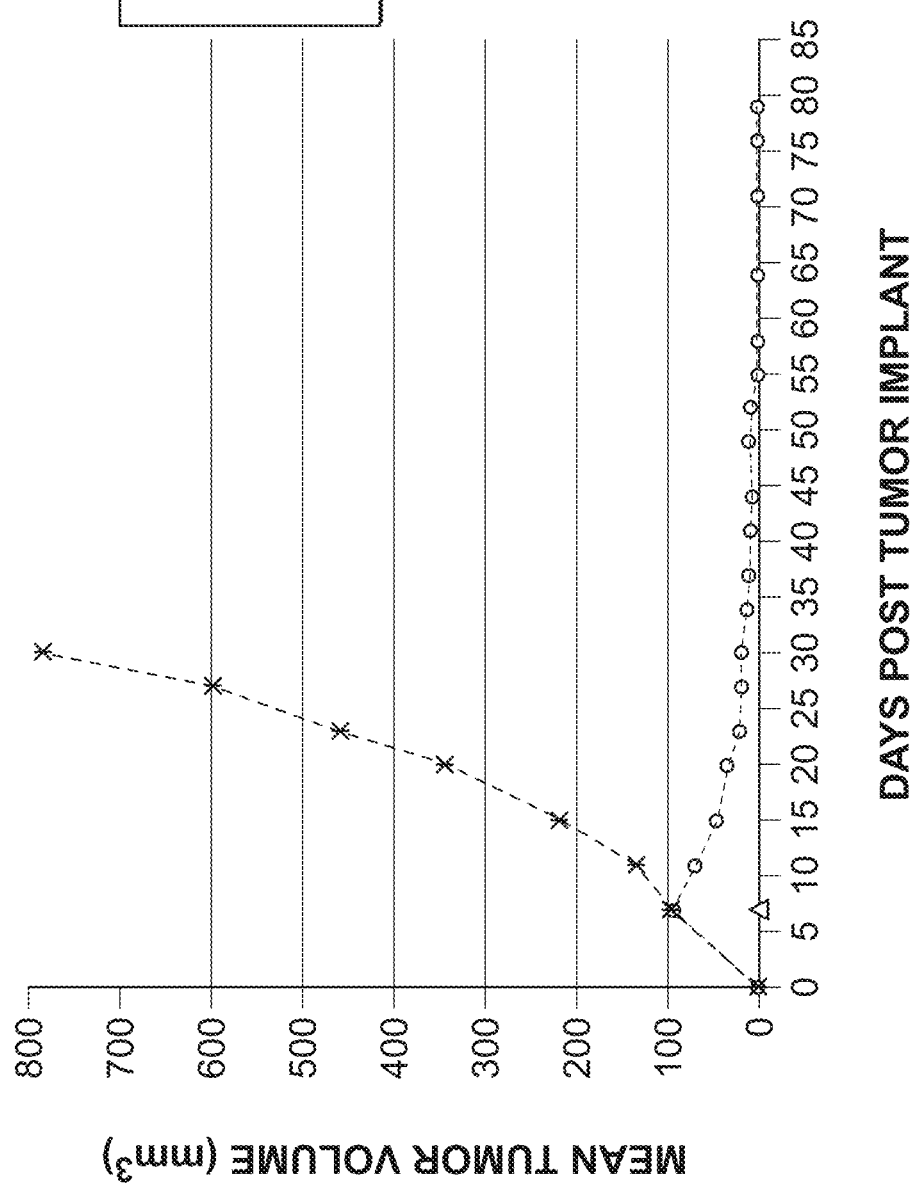
FIG. 4 shows a mean tumor volume graph for an L540cy subcutaneous mouse xenograft model of Hodgkin lymphoma treated with an anti-Ag2 camptothecin DAR4 ADC (Ag2-(67)). Animals were implanted with L540cy cells. After 7 days, the animals were sorted into groups with an average tumor size of 100 mm³, and then treated with a single dose of the camptothecin ADC at 3 mg/Kg. Animals were evaluated for tumor size and in-life signs during the course of the study.
Figure 5:
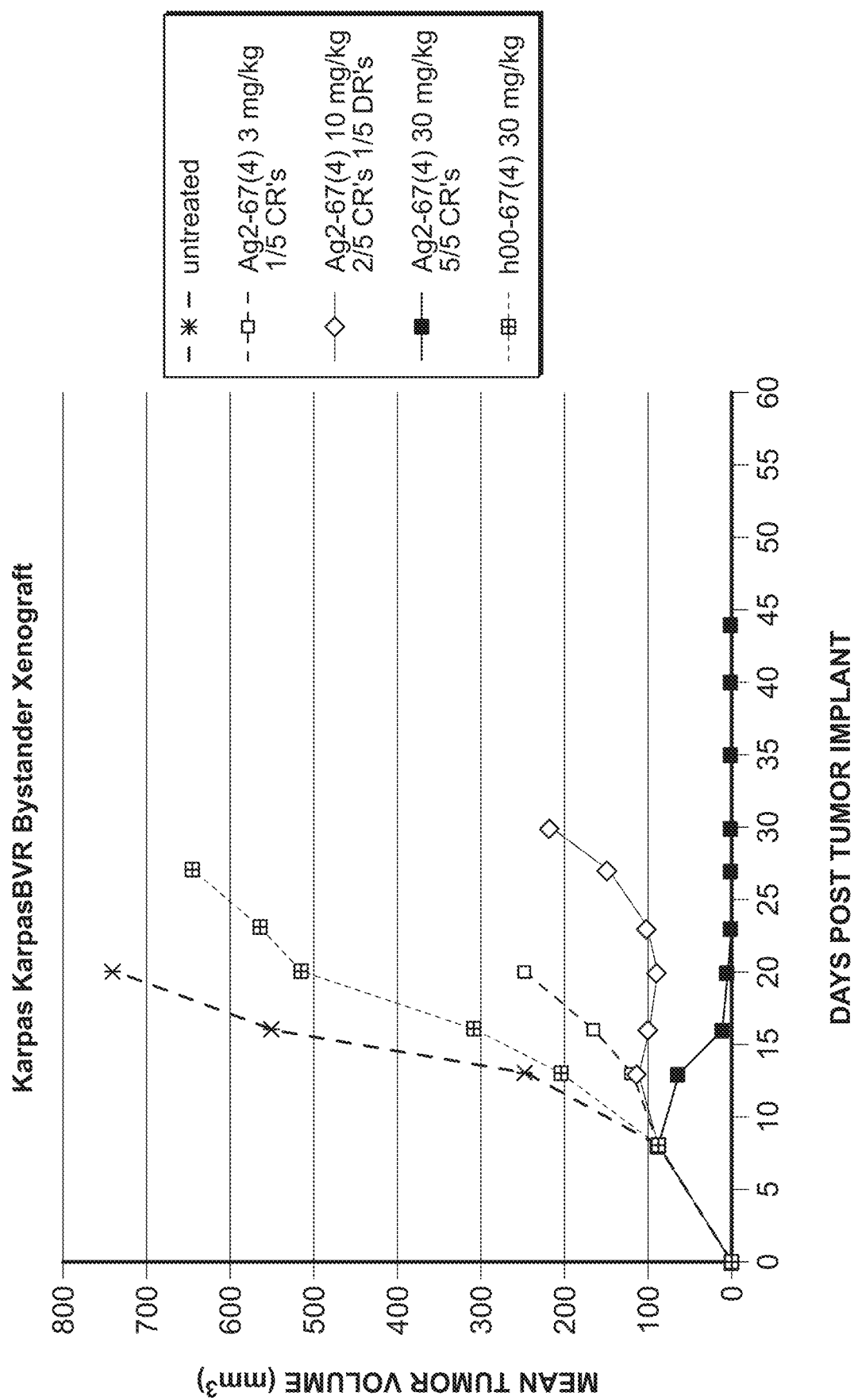
FIG. 5 shows the results of Karpas 299/Karpas299-BVR anaplastic large cell lymphoma bystander subcutaneous xenograft tumor model treated with camptothecin ADCs. The graph shows mean tumor volume for an anti-Ag2 camptothecin DAR4 ADC (Ag2-(67)), and non-binding DAR4 ADC (h00-(67)). Animals were implanted with a 1:1 mixture of Ag2(+) Karpas299 and Ag2(−) Karpas299-brentuximab vedotin resistant (Karpas299-BVR) cells. After 8 days, the animals were sorted into groups with an average tumor size of 100 mm³, and then treated with a single dose of the camptothecin ADC at 3, 10 and 30 mg/Kg. The non-binding h00 camptothecin ADC was dosed at 30 mg/Kg. Animals were evaluated for tumor size and in-life signs during the course of the study.
Figure 6:
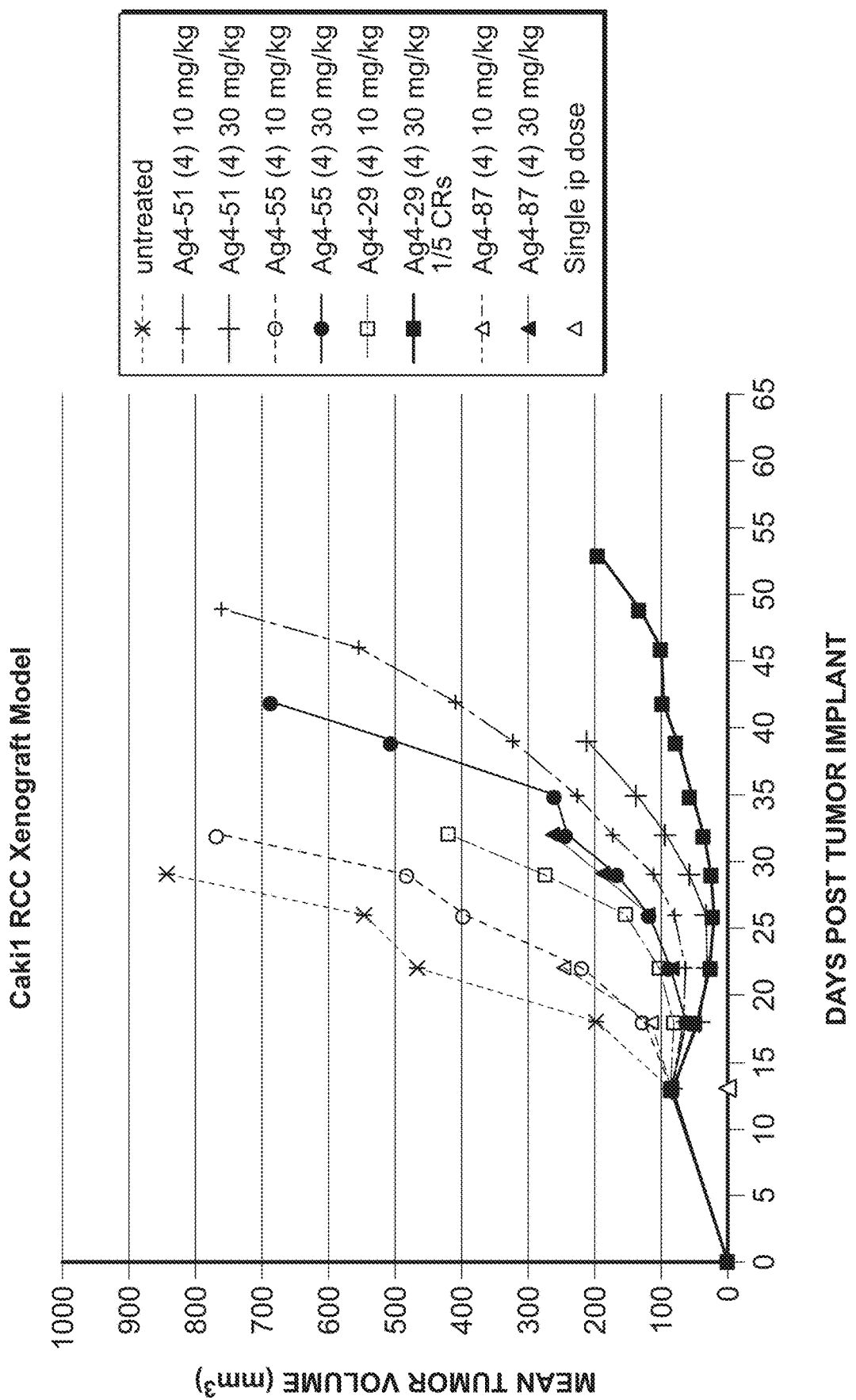
FIG. 6 shows mean tumor volume for a caki-1 renal cell carcinoma subcutaneous mouse xenograft model with glucuronide camptothecin DAR4 ADCs. Animals were implanted with solid caki-1 tumors, via trocar. On day 13, the animals were sorted into groups with an average tumor size of 100 mm³, and then treated with a single dose of a camptothecin ADC at 10 and 30 mg/Kg. Animals were evaluated for tumor size and in-life signs during the course of the study.
Figure 7:
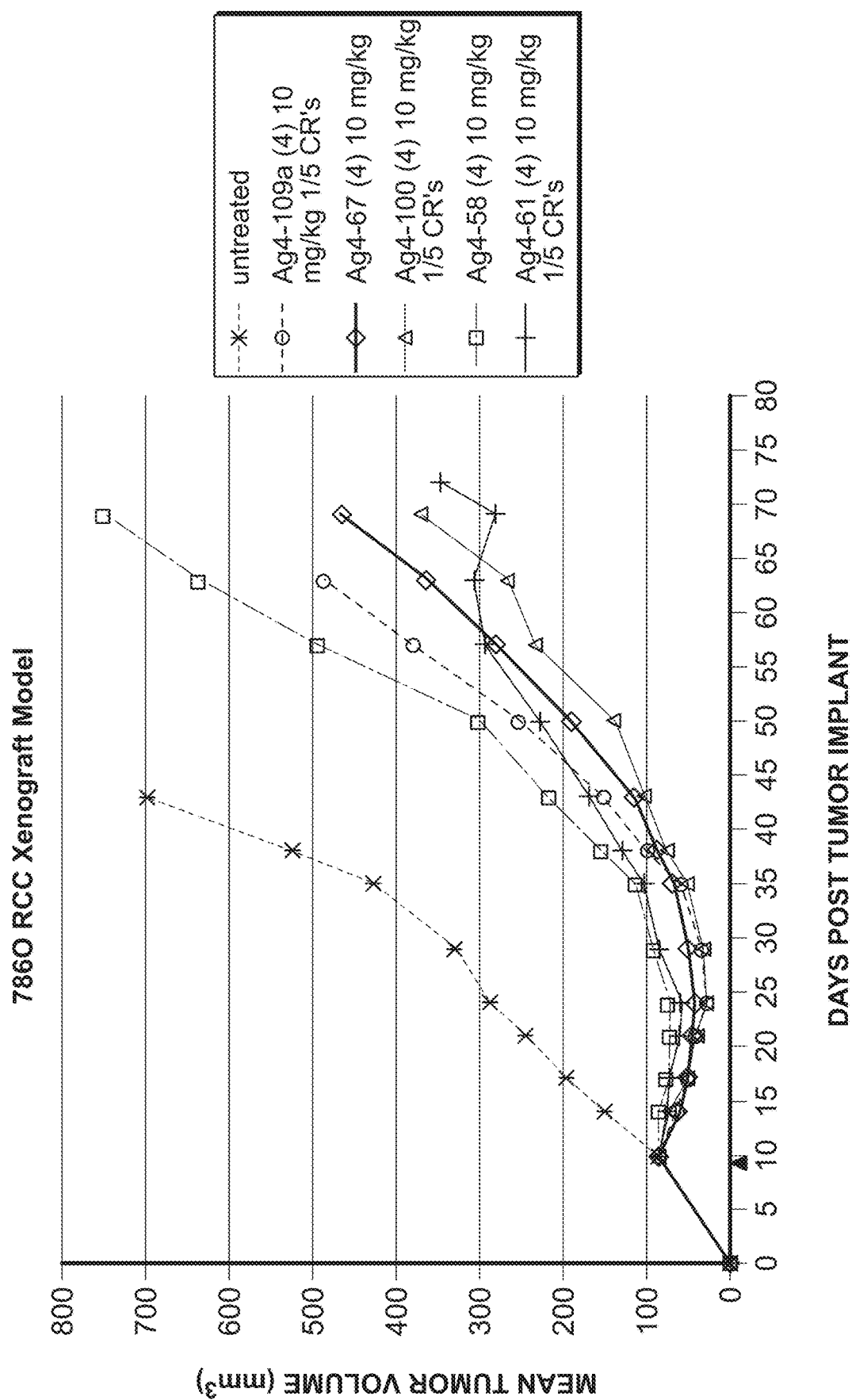
FIG. 7 shows mean tumor volume for a 786O renal cell carcinoma subcutaneous mouse xenograft model with glucuronide camptothecin DAR4 ADCs. Animals were implanted with 786O cells. On day 7, the animals were sorted into groups with an average tumor size of 100 mm³, and then treated with a single dose of a camptothecin ADC at 10 mg/Kg. Animals were evaluated for tumor size and in-life signs during the course of the study.
Figure 8:
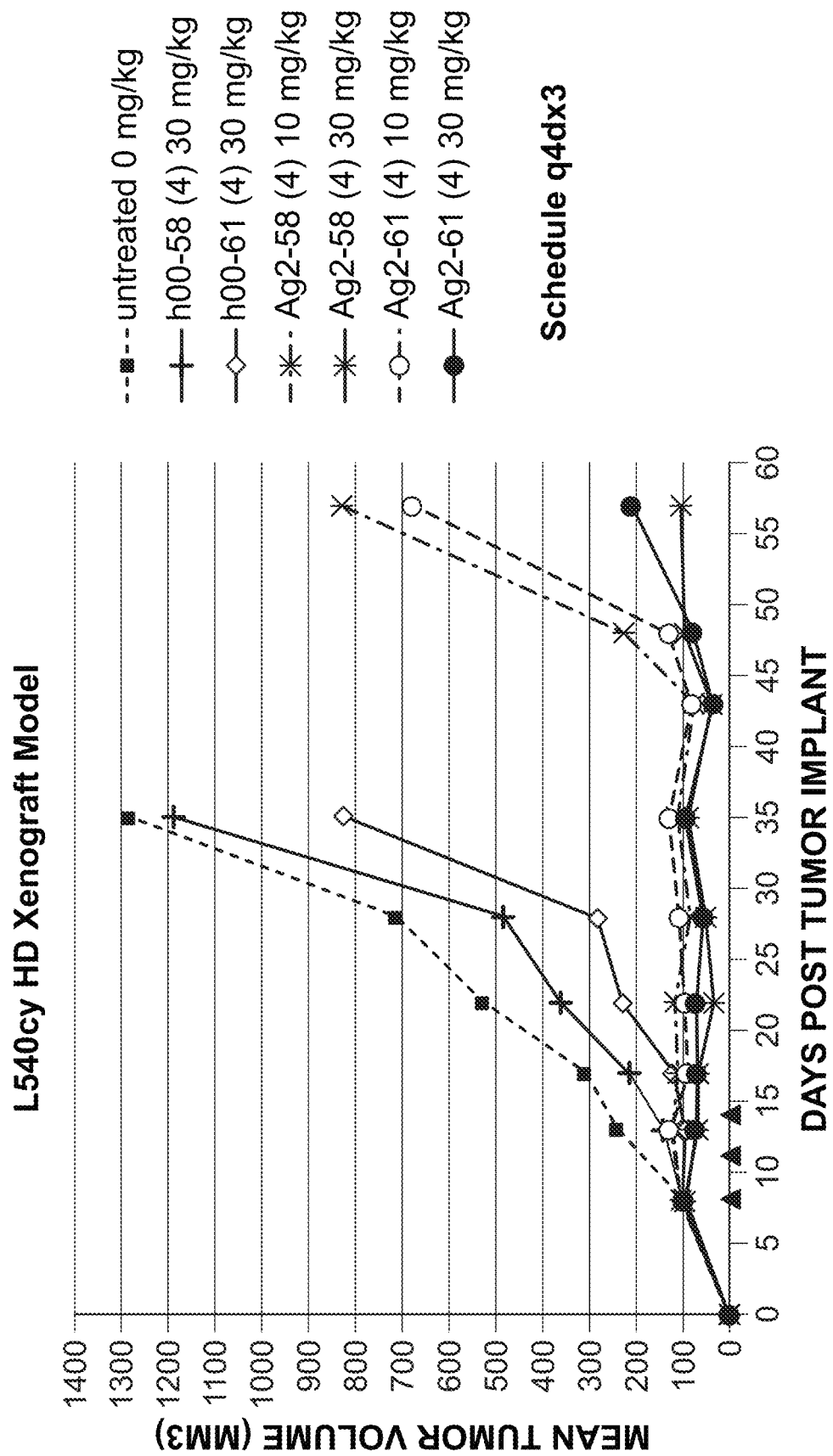
FIG. 8 shows a mean tumor volume graph for a L540cy subcutaneous mouse xenograft model of Hodgkin lymphoma treated with anti-Ag2 and non-binding h00 glucuronide camptothecin ADCs. Animals were implanted subcutaneously with L540cy cells. After 7 days, the animals were sorted into groups with an average tumor size of 100 mm³, and were then treated q4 d×3 with Ag2-(58) or Ag2-(61) DAR4 camptothecin ADC at 10 and 30 mg/kg. The corresponding non-binding h00 ADCs were dosed q4 d×3 at 30 mg/Kg. Animals were evaluated for tumor size and in-life signs during the course of the study.
Figure 9:
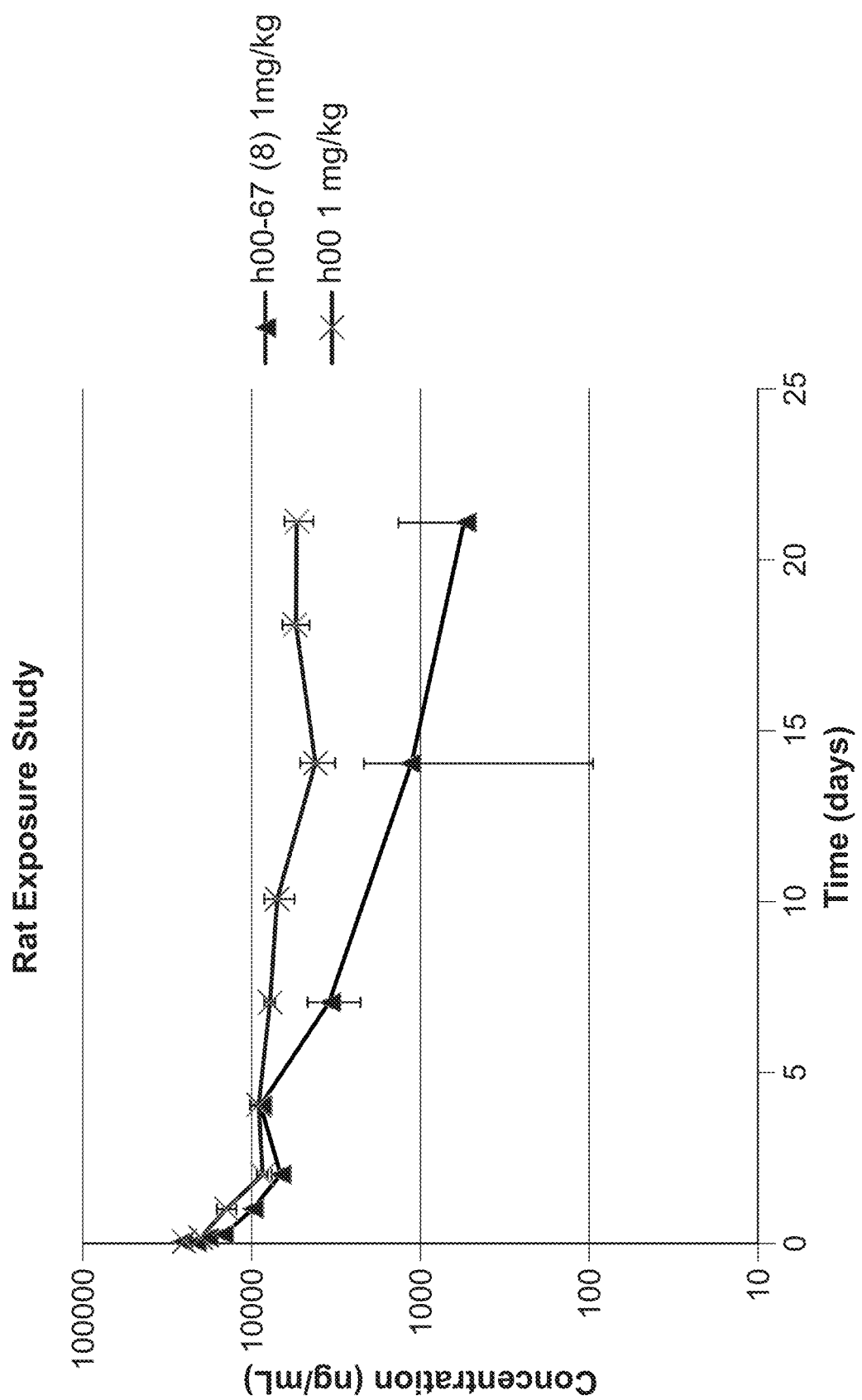
FIG. 9 shows the pharmacokinetic profile of a h00 mAb, and h00-camptothecin ADC in Sprague-Dawley rat. Rats were injected with 1 mg/kg of parental non-binding humanized antibody (h00) or h00-(67) DAR8 camptothecin ADC. Samples from scheduled blood draws were processed and h00 parental antibody and ADC were captured from plasma via a biotin-conjugated murine anti-human light chain kappa mAb and streptavidin-coated beads. The h00 antibody and ADC were quantified via ELISA using a AF647-anti-human kappa detection reagent.
Figure 10:
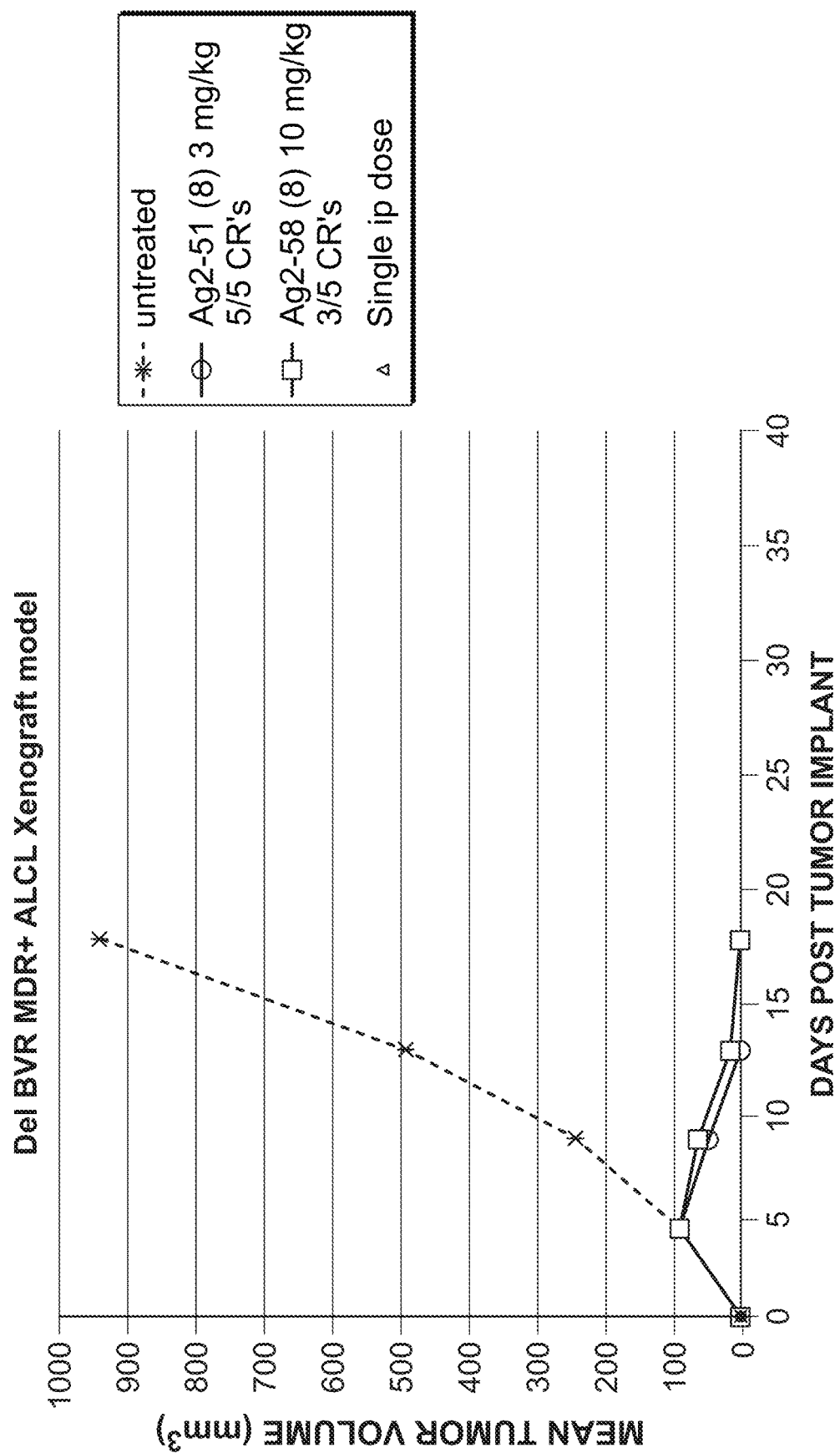
FIG. 10 shows mean tumor volume graph for glucuronide campothecin DAR8 ADCs in a Del-BVR (brentuximab vedotin resistant, MDR+) xenograft model. Animals were implanted subcutaneously with Del-BVR cells. After 4 days, the animals were sorted into groups with an average tumor size of 100 mm³, and were treated with a single dose of a camptothecin DAR8 ADC. Animals were evaluated for tumor size and in-life signs during the course of the study.
Figure 11:
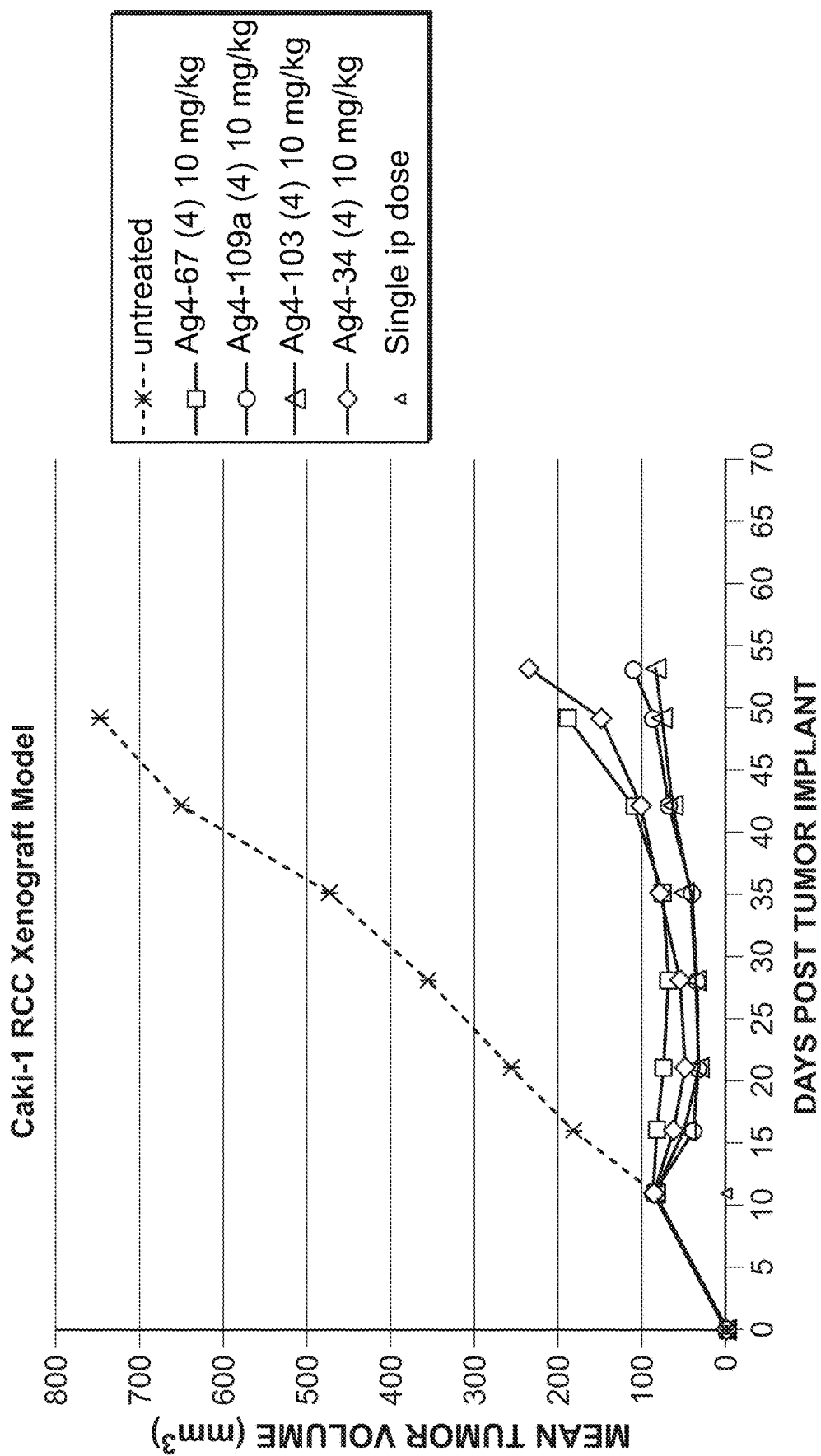
FIG. 11 shows mean tumor volume graph for a Caki-1 renal cell carcinoma subcutaneous mouse xenograft model with DAR4 glucuronide camptothecin ADCs. Animals were implanted with Caki-1 cells. On day 11, the animals were sorted into groups with an average tumor size of 100 mm³, and then treated with a single dose of a camptothecin ADC at 10 mg/Kg. Animals were evaluated for tumor size and in-life signs during the course of the study.
Figure 12:
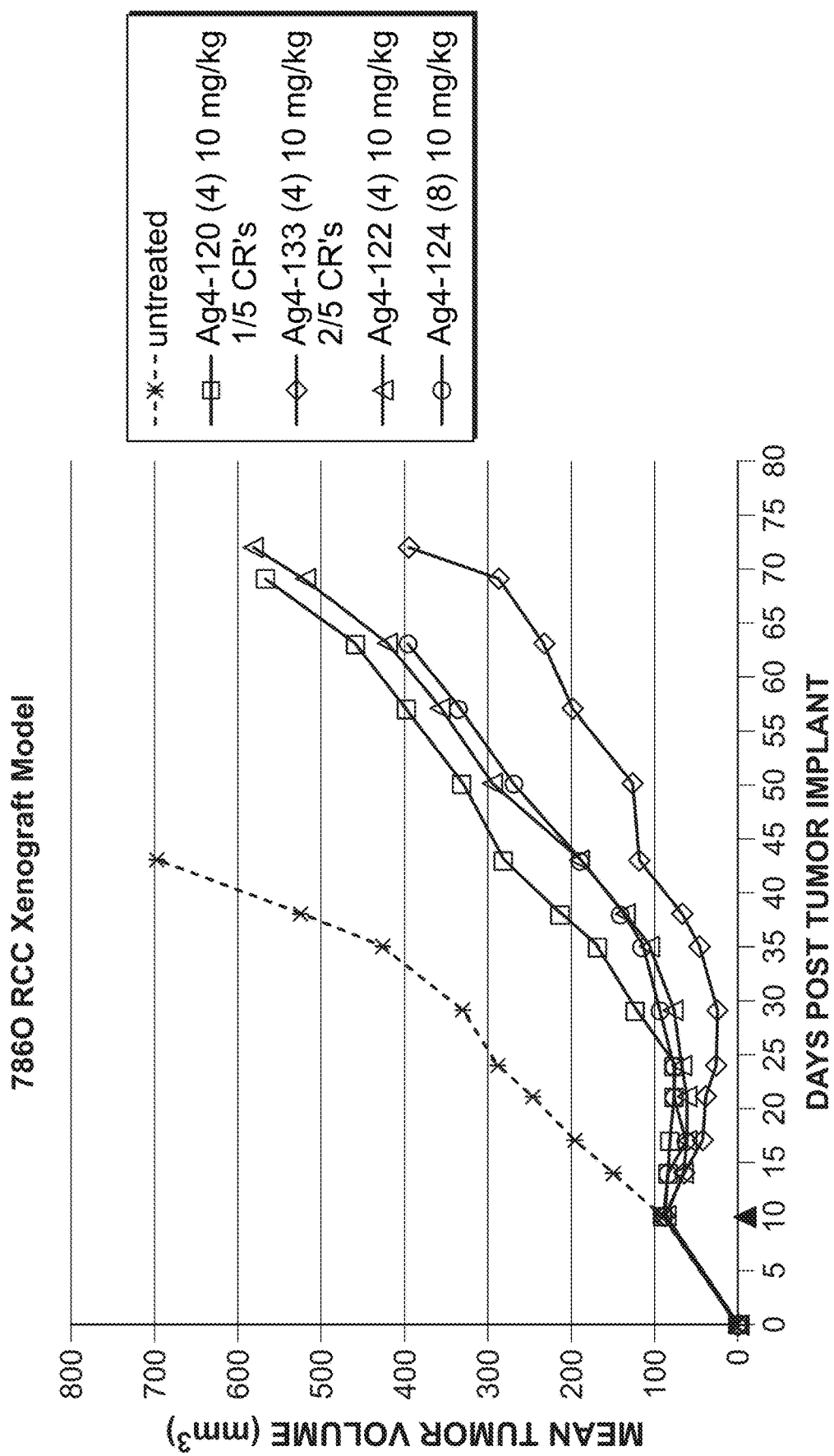
FIG. 12 is a graph showing the activity of selected camptothecin ADCs in a nude mouse RCC xenograft model.
Figure 13:
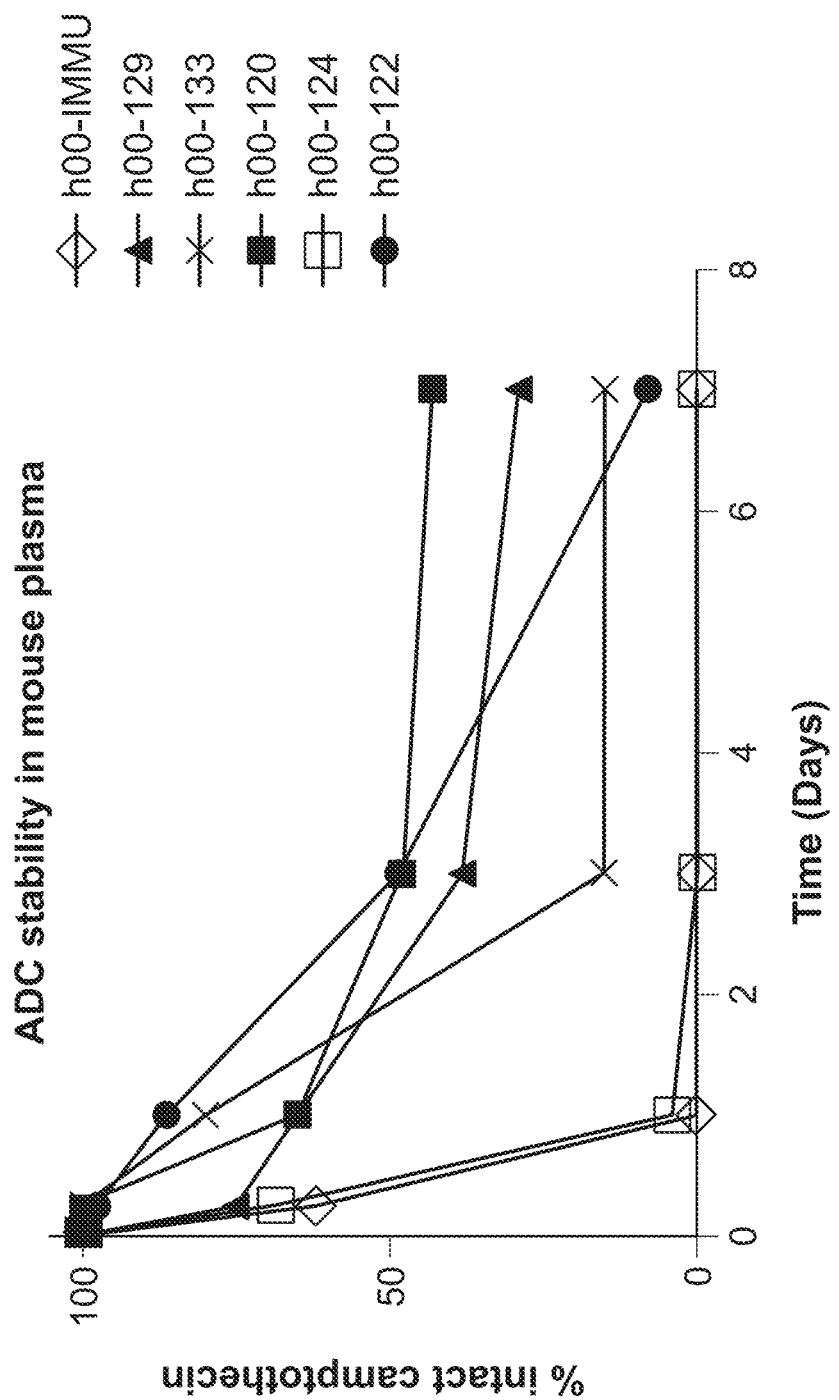
FIG. 13 is a graph and table illustrating plasma stability of selected camptothecin ADCs in a mouse model.
Figure 14:
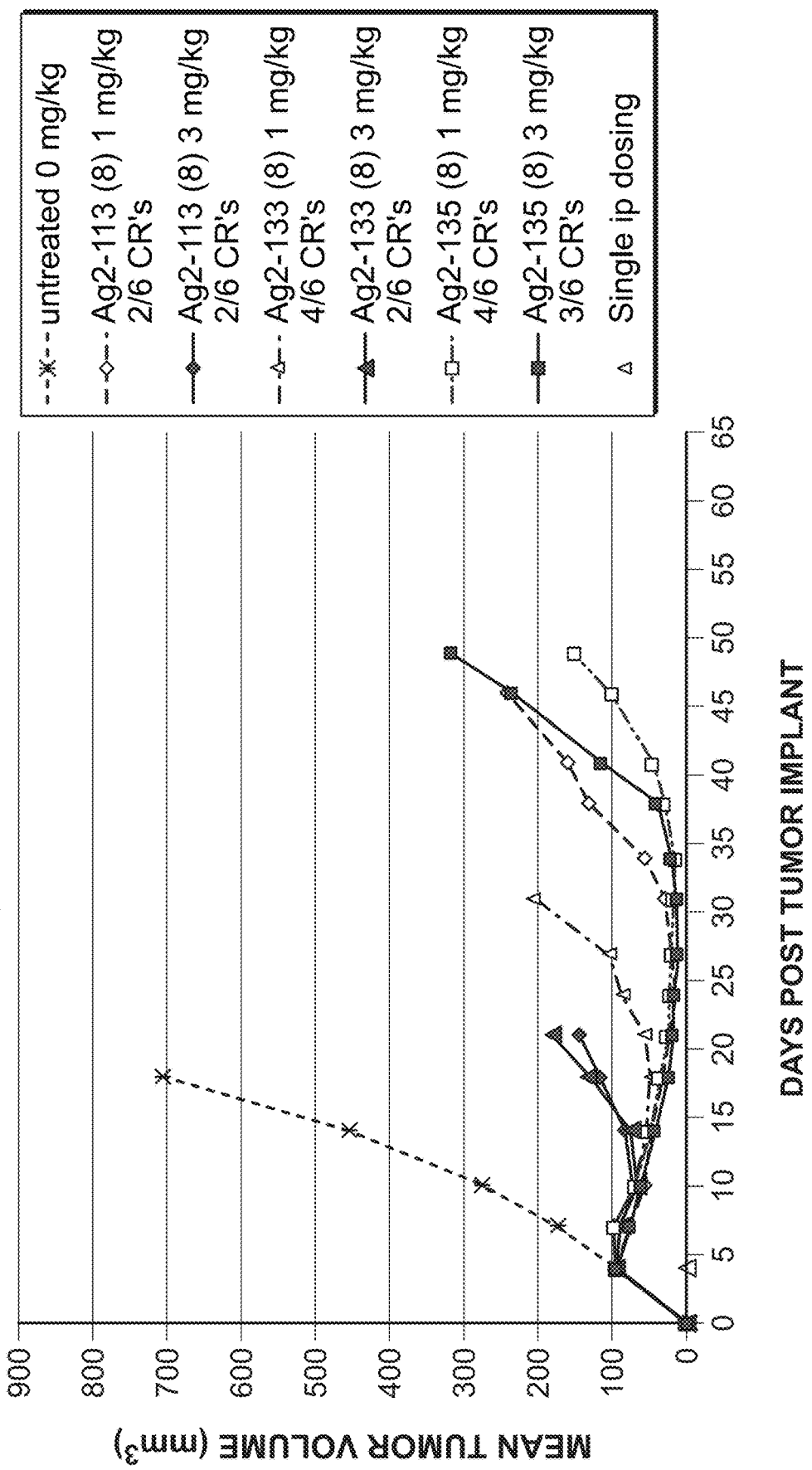
FIG. 14 shows additional results from a Karpas 299/Karpas299-BVR anaplastic large cell lymphoma bystander subcutaneous xenograft tumor model treated with camptothecin ADCs.
Figure 15:
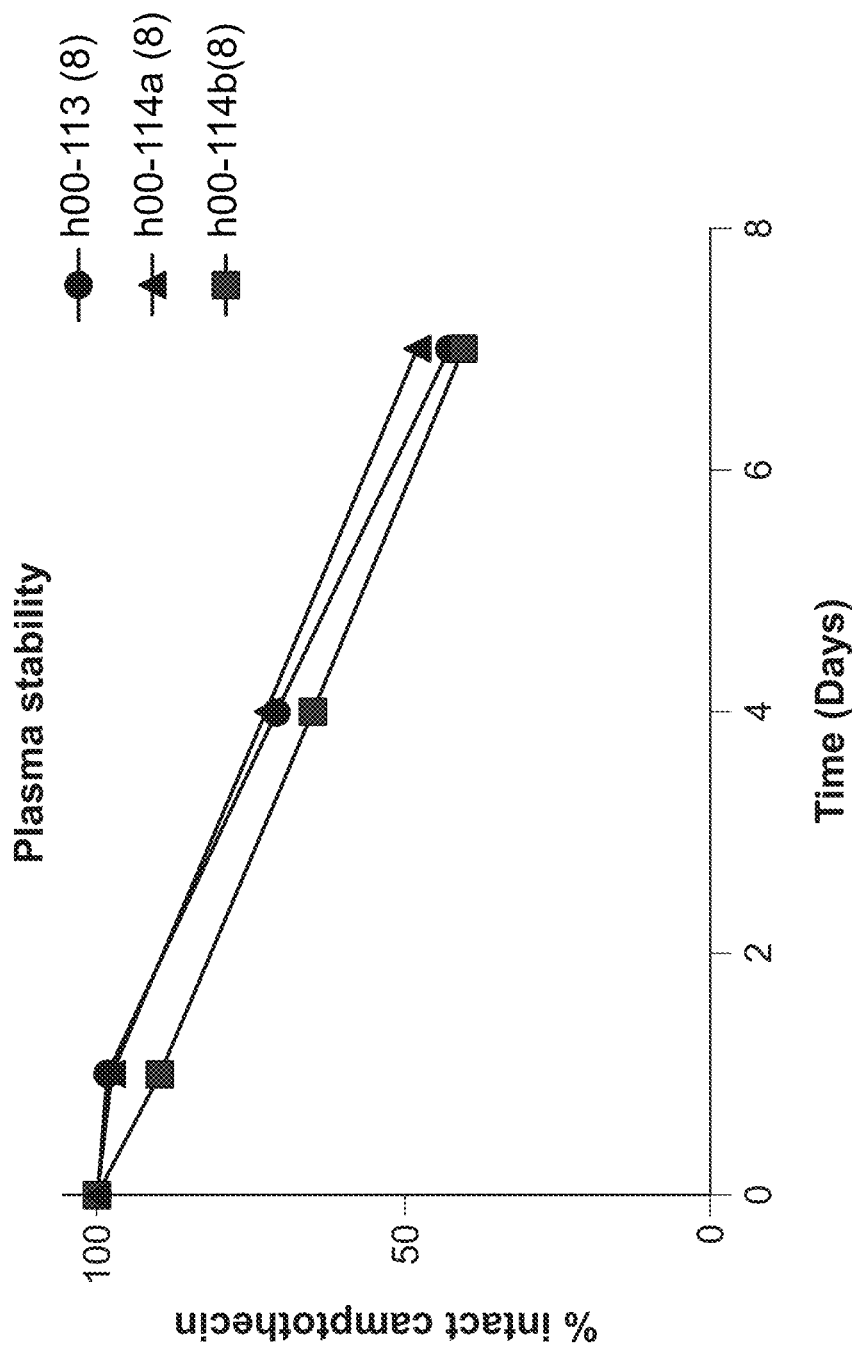
FIG. 15 shows unexpected stability of Camptothecin Conjugates in which conjugation is through the C20 hydroxy group that substitutes the lactone ring

Stability of Camptothecin DAR8 ADCs incubated at 37 degrees Celsius in mouse plasma as determined by PLRP-MS to quantify drug-loading (see FIGS. 2 and 13).

| Conjugate | Starting dr/Ab | Ending dr/Ab | Final % intact drug |
|---|---|---|---|
| h00-(61) | 7.2 | 5.05 | 70 |
| h00-(109a) | 8 | 6.2 | 78 |
| h00-(67) | 8 | 8 | 100 |
| h00-(58) | 6.1 | 4.39 | 72 |
| h00-(42) | 7.8 | 5.65 | 72 |
| h00-(120) | 8 | 3.4 | 43 |
| h00-(133) | 8 | 1.2 | 15 |
| h00-(129) | 4.8 | 1.4 | 29 |
| h00-IMMU* | 6.8 | 0 | 0 |
| h00-(124) | 6.8 | 0 | 0 |

*IMMU is the Camptothecin Conjugate targeting CL2A described by *European Journal of Medicinal Chemistry* (2019) 167: 583-593

What is claimed is:

1. A Camptothecin Conjugate having the formula:

L-(Q-D)$_p$ or a salt thereof, wherein

L is a Ligand Unit, wherein the Ligand Unit is an antibody that selectively binds to a cancer cell antigen or antigen-binding fragment thereof;

subscript p is an integer ranging from 1 to 16;

-Q-D is

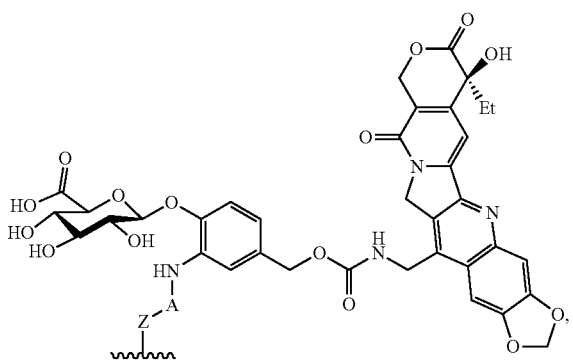

wherein
the wavy line indicates the site of covalent attachment to L;
Z is a Stretcher Unit, wherein Z is

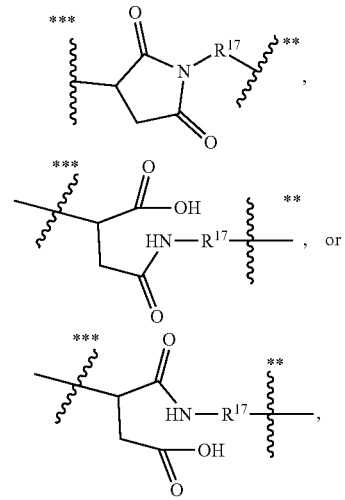

wherein:
the wavy line marked with a double asterisk (**) indicates the site of covalent attachment to A;
the wavy line marked with a triple asterisk (***) indicates the point of covalent attachment to a sulfur atom of L; and
R$^{17}$ is —C$_1$-C$_{10}$ alkylene-C(=O)—, optionally substituted by —(CH$_2$)$_x$NH$_2$, wherein x is an integer from 1 to 4; and
A is a bond or a Connector Unit having the formula:

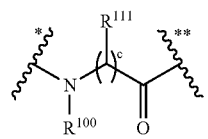

wherein
the wavy line marked with a single asterisk (*) indicates the point of covalent attachment to Z;
the wavy line marked with a double asterisk (**) indicates the site of covalent attachment to the remainder of Q-D;
R$^{100}$ and R$^{111}$ are each independently hydrogen or —C$_1$-C$_3$ alkyl; and
c is an integer from 1 to 5.

2. The Camptothecin Conjugate of claim 1, or a salt thereof, wherein R$^{17}$ is —(CH$_2$)$_{2-5}$—C(=O)—.

3. The Camptothecin Conjugate of claim 1, or a salt thereof, wherein Z is

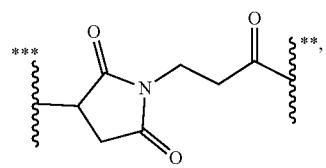 [SMILES: *C(=O)CCN1C(=O)CC(*)C1=O]

optionally having the succinimide ring in hydrolyzed form as a succinic acid amide moiety, wherein the wavy line marked with a double asterisk () indicates the site of covalent attachment to A; and the wavy line marked with a triple asterisk (*) indicates the point of covalent attachment to a sulfur atom of L.

4. The Camptothecin Conjugate of claim 3, or a salt thereof, wherein Z is

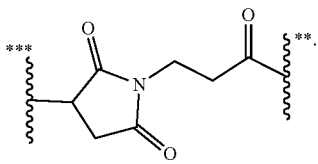 [SMILES: *C(=O)CCN1C(=O)CC(*)C1=O]

5. The Camptothecin Conjugate of claim 3, or a salt thereof, wherein Z is

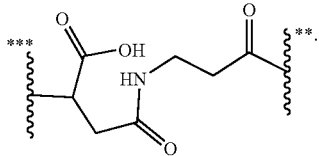 [SMILES: *C(=O)CCNC(=O)CC(*)C(=O)O]

6. The Camptothecin Conjugate of claim 3, or a salt thereof, wherein Z is

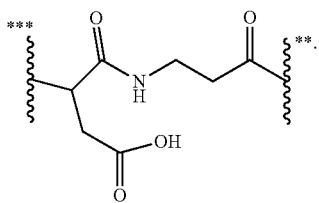 [SMILES: *C(=O)CCNC(=O)C(*)CC(=O)O]

7. The Camptothecin Conjugate of claim 1, or a salt thereof, wherein A is a Connector Unit.

8. The Camptothecin Conjugate of claim 1, or a salt thereof, wherein A has the formula:

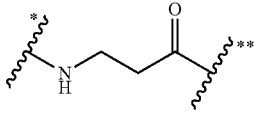

wherein
the wavy line marked with a double asterisk (**) indicates the site of covalent attachment to the remainder of Q-D; and
the wavy line marked with a single asterisk (*) indicates the point of covalent attachment to Z.

9. The Camptothecin Conjugate of claim 1, or a salt thereof, wherein —Z-A- has the formula:

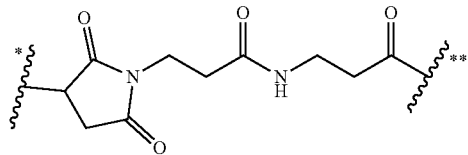 [SMILES: *C(=O)CCNC(=O)CCN1C(=O)CC(*)C1=O]

wherein
the wavy line marked with a double asterisk (**) indicates the site of covalent attachment to the remainder of Q-D; and
the wavy line marked with a single asterisk (*) indicates the point of covalent attachment to L.

10. The Camptothecin Conjugate of claim 1, or a salt thereof, having the formula of:

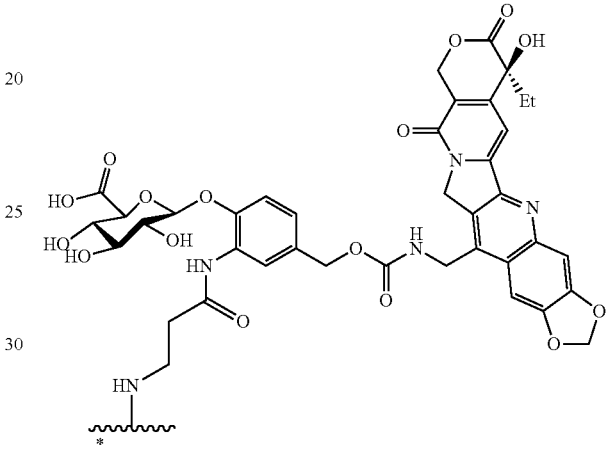

wherein
the wavy line marked with a single asterisk (*) indicates the point of covalent attachment to Z.

11. A Camptothecin Conjugate having the formula:

L-(Q-D)$_p$ or a salt thereof, wherein
L is a Ligand Unit, wherein the Ligand Unit is an antibody that selectively binds to a cancer cell antigen or antigen-binding fragment thereof;
subscript p is an integer ranging from 1 to 16; and
wherein Q-D has the formula:

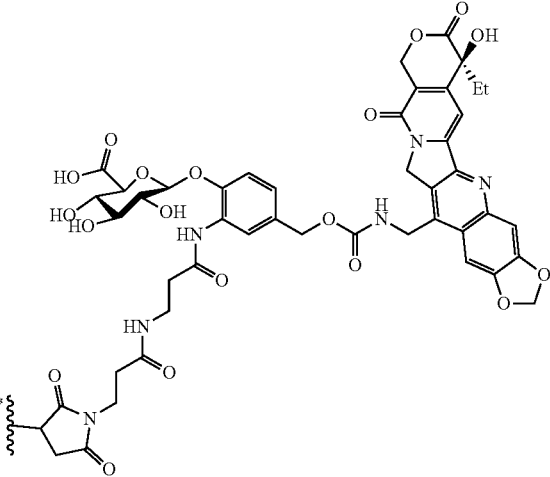

wherein
the wavy line marked with a single asterisk (*) indicates the point of covalent attachment to L.

12. A Camptothecin Conjugate having the formula:

L-(Q-D)$_p$ or a salt thereof, wherein
L is a Ligand Unit, wherein the Ligand Unit is an antibody that selectively binds to a cancer cell antigen or antigen-binding fragment thereof;
subscript p is an integer ranging from 1 to 16; and
wherein -Q-D has the formula:

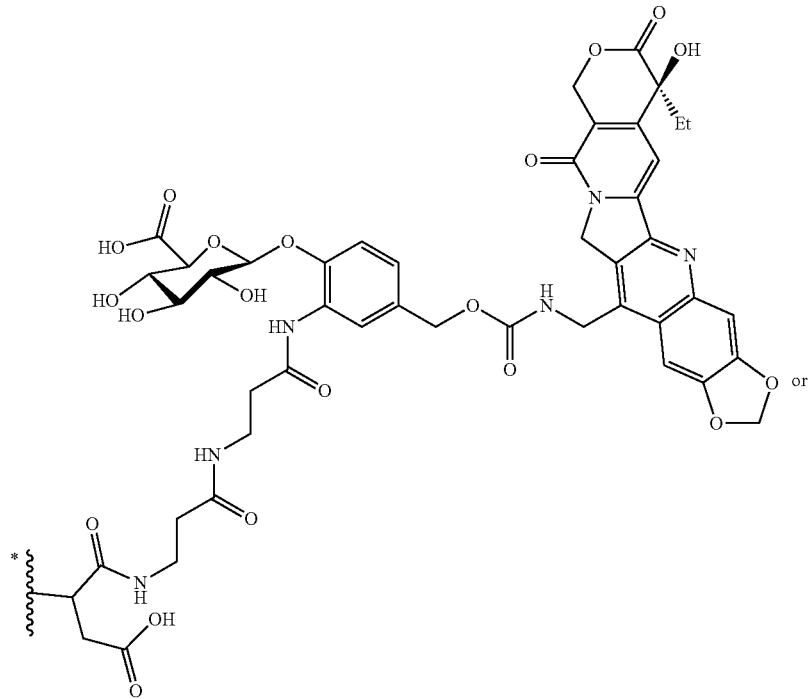

or

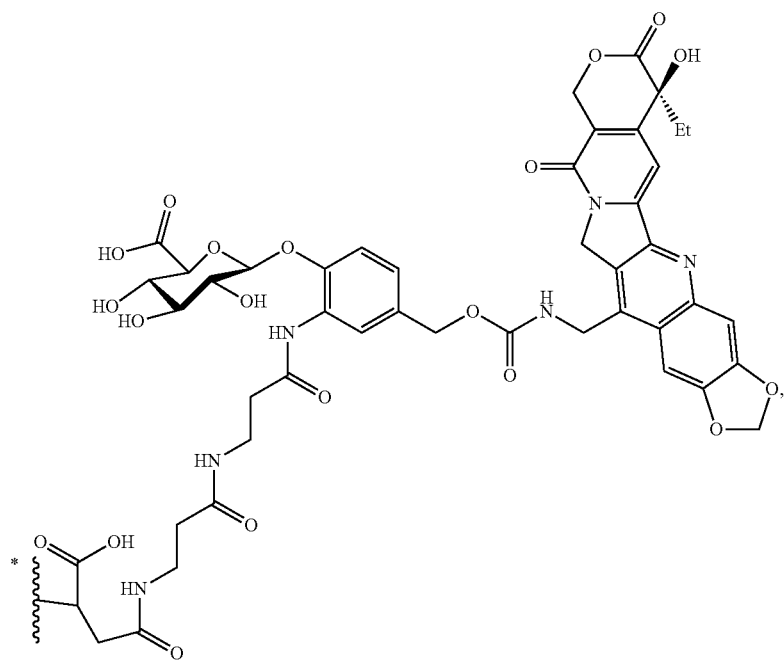

wherein the wavy line marked with a single asterisk (*) indicates the point of covalent attachment to L.

13. A Camptothecin-Linker compound, or a salt thereof, having the structure of:

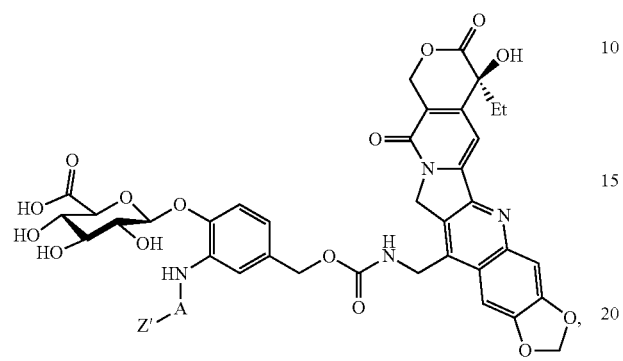

wherein

Z' is a Stretcher Unit precursor, wherein Z' is

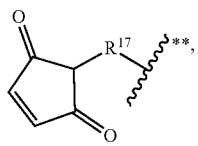

wherein:

the wavy line marked with a double asterisk (**) indicates the site of covalent attachment to A;

$R^{17}$ is —$C_1$-$C_{10}$ alkylene-C(=O)—, optionally substituted by —(CH$_2$)$_x$NH$_2$, wherein x is an integer from 1 to 4;

A is a bond or a Connector Unit having the formula:

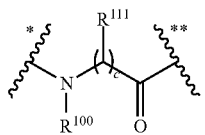

wherein the wavy line marked with a single asterisk (*) indicates the point of covalent attachment to Z';

the wavy line marked with a double asterisk (**) indicates the site of covalent attachment to the remainder of the Camptothecin-Linker structure;

$R^{100}$ and $R^{111}$ are each independently hydrogen or —$C_1$-$C_3$ alkyl; and c is an integer from 1 to 5.

14. The Camptothecin-Linker compound of claim 13, or a salt thereof, wherein $R^{17}$ is —(CH$_2$)$_{2-5}$—C(=O)—.

15. The Camptothecin-Linker compound of claim 13, or a salt thereof, wherein Z' is

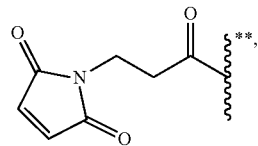 [SMILES: *C(=O)CCN1C(=O)C=CC1=O]

wherein the wavy line marked with a double asterisk (**) indicates the site of covalent attachment to A.

16. The Camptothecin-Linker compound of claim 13, or a salt thereof, wherein A is a Connector Unit.

17. The Camptothecin-Linker compound of claim 13, or a salt thereof, wherein A has the formula:

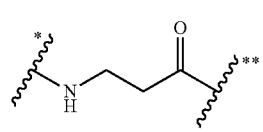 [SMILES: *NCCC(*)=O]

wherein the wavy line marked with a double asterisk (**) indicates the site of covalent attachment to the remainder of the Camptothecin-Linker structure; and the wavy line marked with a single asterisk (*) indicates the point of covalent attachment to Z'.

18. The Camptothecin-Linker compound of claim 13, or a salt thereof, wherein Z'-A- has the formula:

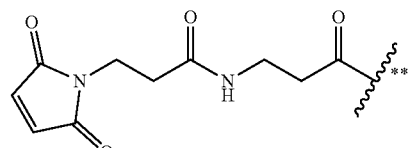

wherein the wavy line marked with a double asterisk (**) indicates the site of covalent attachment to the remainder of the Camptothecin-Linker structure.

19. The Camptothecin-Linker compound of claim 13, or a salt thereof, having the formula of:

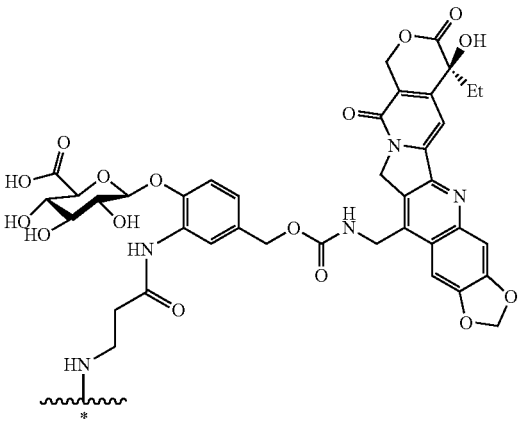

wherein the wavy line marked with a single asterisk (*) indicates the point of covalent attachment to Z'.

20. A Camptothecin-Linker compound, or a salt thereof, having the formula:

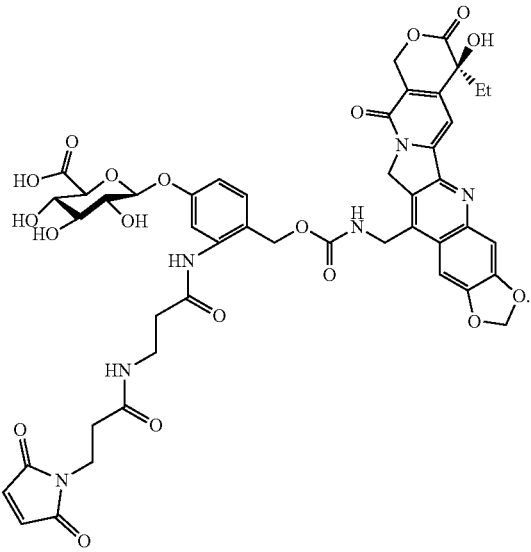

21. A pharmaceutically acceptable composition comprising a Camptothecin Conjugate of claim 1, or a salt thereof, and at least one pharmaceutically acceptable excipient.

22. A pharmaceutically acceptable composition comprising a Camptothecin Conjugate of claim 11, or a salt thereof, and at least one pharmaceutically acceptable excipient.

23. A pharmaceutically acceptable composition comprising a Camptothecin Conjugate of claim 12, or a salt thereof, and at least one pharmaceutically acceptable excipient.

24. A method of treating cancer in a subject in need thereof comprising administering to the subject an effective amount of a Camptothecin Conjugate of claim 1, or a salt thereof.

25. A method of treating cancer in a subject in need thereof comprising administering to the subject an effective amount of a Camptothecin Conjugate of claim 11, or a salt thereof.

26. A method of treating cancer in a subject in need thereof comprising administering to the subject an effective amount of a Camptothecin Conjugate of claim 12, or a salt thereof.

27. The method of claim 24, wherein the cancer is selected from the group consisting of lymphomas, leukemias, and solid tumors.

28. The method of claim 27, wherein the cancer is a lymphoma or a leukemia.

29. The method of claim 25, wherein the cancer is selected from the group consisting of lymphomas, leukemias, and solid tumors.

30. The method of claim 29, wherein the cancer is a lymphoma or a leukemia.

31. The method of claim 26, wherein the cancer is selected from the group consisting of lymphomas, leukemias, and solid tumors.

32. The method of claim 31, wherein the cancer is a lymphoma or a leukemia.

33. A method of preparing a Camptothecin Conjugate of claim 1, or a salt thereof, said method comprising the step of contacting an antibody or antigen-binding fragment thereof having a functional group reactive towards Z' of a Camptothecin-Linker Compound of claim 13, or a salt thereof, thereby forming a covalent bond between the Ligand Unit and Stretcher Unit (Z) of the Camptothecin Conjugate, which corresponds in structure to the antibody or antigen-binding fragment thereof and Z', respectively.

34. The method of claim 33, wherein the antibody or antigen-binding fragment thereof is an antibody having at least one cysteine residue in which the reactive functional group is thiol.

35. The Camptothecin Conjugate of claim 1, wherein L is an antibody that specifically binds to an antigen selected from the group consisting of CD19, CD30, CD33, CD70, and LIV-1.

36. The Camptothecin Conjugate of claim 1, wherein L is an antibody that specifically binds to an antigen of CD30.

37. The Camptothecin Conjugate of claim 36, wherein the antibody is cAC10.

38. The Camptothecin Conjugate of claim 11, wherein L is an antibody that specifically binds to an antigen selected from the group consisting of CD19, CD30, CD33, CD70, and LIV-1.

39. The Camptothecin Conjugate of claim 11, wherein L is an antibody that specifically binds to an antigen of CD30.

40. The Camptothecin Conjugate 103, wherein the antibody is cAC10.

41. The Camptothecin Conjugate of claim 12, wherein L is an antibody that specifically binds to an antigen selected from the group consisting of CD19, CD30, CD33, CD70, and LIV-1.

42. The Camptothecin Conjugate of claim 12, wherein L is an antibody that specifically binds to an antigen of CD30.

43. The Camptothecin Conjugate of claim 42, wherein the antibody is cAC10.

* * * * *